United States Patent
Tasaki et al.

(10) Patent No.: US 11,739,061 B2
(45) Date of Patent: *Aug. 29, 2023

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD, Tokyo (JP)

(72) Inventors: Satomi Tasaki, Sodegaura (JP); Masahiro Kawamura, Sodegaura (JP); Toshinari Ogiwara, Sodegaura (JP); Hitoshi Kuma, Sodegaura (JP); Kei Yoshida, Sodegaura (JP); Keiji Okinaka, Sodegaura (JP)

(73) Assignee: IDEMITSU KOSAN CO., LTD, Tokyo (JP)

( * ) Notice: Subject to any disclaimer, the term of this patent is extended or adjusted under 35 U.S.C. 154(b) by 31 days.

This patent is subject to a terminal disclaimer.

(21) Appl. No.: 17/343,035

(22) Filed: Jun. 9, 2021

(65) Prior Publication Data

US 2022/0363637 A1    Nov. 17, 2022

Related U.S. Application Data

(63) Continuation of application No. 17/015,410, filed on Sep. 9, 2020, now Pat. No. 11,059,781, which is a (Continued)

(30) Foreign Application Priority Data

Jun. 26, 2013  (JP) ................ 2013-134020
Feb. 28, 2014  (JP) ................ 2014-038262
May 16, 2014  (JP) ................ 2014-102875

(51) Int. Cl.
*H01L 51/54*      (2006.01)
*C07D 209/80*   (2006.01)
(Continued)

(52) U.S. Cl.
CPC ......... *C07D 209/80* (2013.01); *C07D 209/82* (2013.01); *C07D 209/94* (2013.01); (Continued)

(58) Field of Classification Search
None
See application file for complete search history.

(56) References Cited

U.S. PATENT DOCUMENTS 10,590,080 B2 *   3/2020  Tasaki ............... H01L 51/0072
2009/0072727 A1   3/2009  Takeda
(Continued)

FOREIGN PATENT DOCUMENTS

CN    101321755 A    12/2008
CN    101372615 A    2/2009
(Continued)

OTHER PUBLICATIONS

Third Party Observation issued Aug. 26, 2019 in European Patent Application No. 14818191.0.
(Continued)

*Primary Examiner* — Andrew K Bohaty
(74) *Attorney, Agent, or Firm* — Oblon, McClelland, Maier & Neustadt, L.L.P.

(57) ABSTRACT

A compound is represented by a formula (1) below, in which k is an integer of 0 or more, m is an integer of 1 or more, n is an integer of 2 or more. L is a substituted or unsubstituted aromatic hydrocarbon ring having 6 to 30 ring carbon atoms, CN is a cyano group, and $D_1$ and $D_2$ are each independently represented by one of a formula (2), a formula (3) and formula (3x) below, $D_1$ and $D_2$ being optionally mutually the same or different.

[Formula 1]

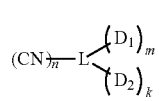

(1)

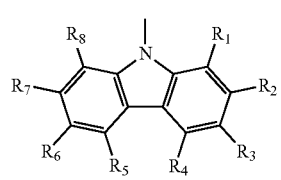

(2)

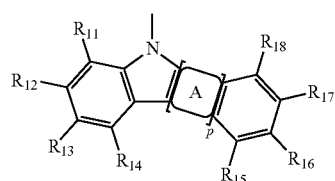

(3)

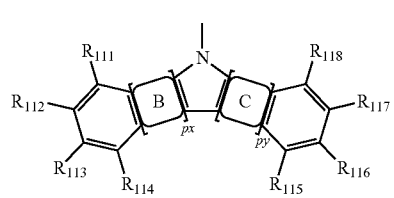

(3x)

15 Claims, 3 Drawing Sheets

Figure 1:
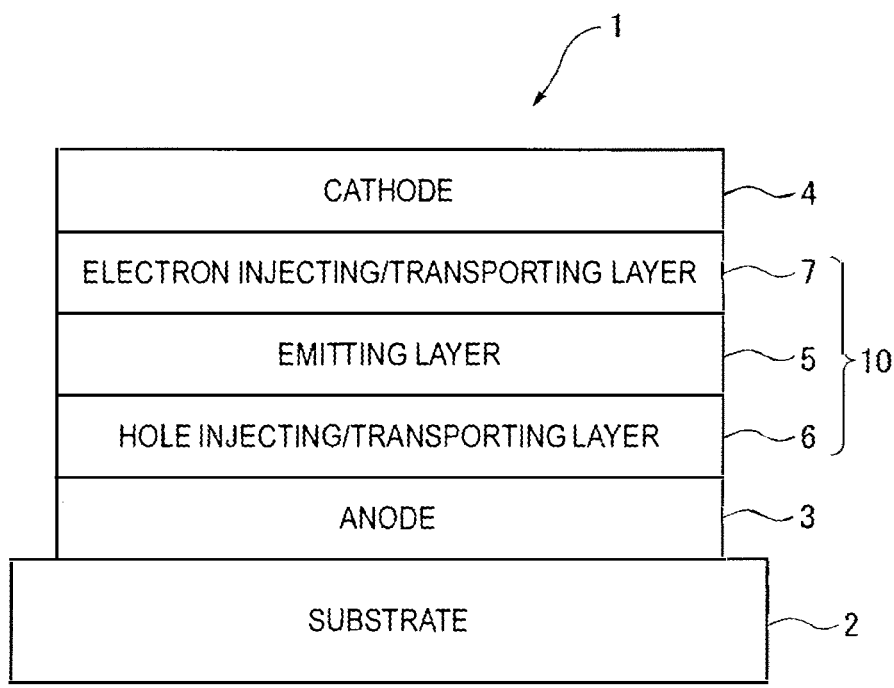

Related U.S. Application Data continuation of application No. 16/739,157, filed on Jan. 10, 2020, now Pat. No. 10,851,055, which is a continuation of application No. 14/894,028, filed as application No. PCT/JP2014/067065 on Jun. 26, 2014, now Pat. No. 10,590,080.

(51) Int. Cl.

| | | |
|---|---|---|
| *C07D 209/82* | (2006.01) | |
| *C07D 209/94* | (2006.01) | |
| *C07D 491/048* | (2006.01) | |
| *C07D 491/147* | (2006.01) | |
| *C09K 11/06* | (2006.01) | |
| *H10K 85/60* | (2023.01) | |
| *H10K 50/11* | (2023.01) | |

(52) U.S. Cl.
CPC ..... *C07D 491/048* (2013.01); *C07D 491/147* (2013.01); *C09K 11/06* (2013.01); *H10K 85/657* (2023.02); *H10K 85/6572* (2023.02); *H10K 50/11* (2023.02)

(56) References Cited

U.S. PATENT DOCUMENTS

| | | |
|---|---|---|
| 2009/0096356 A1 | 4/2009 | Murase et al. |
| 2009/0302742 A1 | 12/2009 | Kormori et al. |
| 2012/0241732 A1 | 9/2012 | Endo et al. |
| 2016/0046563 A1 | 2/2016 | Stoessel et al. |
| 2016/0072076 A1 | 3/2016 | Stoessel et al. |

FOREIGN PATENT DOCUMENTS

| | | |
|---|---|---|
| EP | 1 956 022 A1 | 8/2008 |
| EP | 2 039 737 A2 | 3/2009 |
| JP | 2009-094486 | 4/2009 |
| JP | 2012-033663 A | 2/2012 |
| JP | 5802854 B2 | 11/2015 |
| JP | 5802862 B2 | 11/2015 |
| KR | 10-2012-0032572 A | 4/2012 |
| TW | 201114773 | 5/2011 |
| TW | 201309778 A1 | 3/2013 |
| WO | 2012/014696 A1 | 2/2012 |
| WO | 2013/081088 A1 | 6/2013 |
| WO | 2013/084881 A1 | 6/2013 |
| WO | 2013/154064 A | 10/2013 |
| WO | 2014/128945 A1 | 8/2014 |
| WO | 2014/146750 A1 | 9/2014 |
| WO | 2014/146752 A1 | 9/2014 |

OTHER PUBLICATIONS

Combined Office Action and Search Report dated Apr. 17, 2017 in Chinese Patent Application No. 201480027397.1 (with English translation and English translation of categories of cited documents).

Notice of Reason(s) for Rejection dated Jan. 24, 2017 in Japanese Patent Application No. 2015-524123 (with English translation).

Combined Chinese Office Action and Search Report dated Sep. 14, 2016 in Patent Application No. 201480027397.1 (with English translation and English translation of categories of cited documents).

Extended European Search Report dated Oct. 14, 2016 in Patent Application No. 14818191.0.

Uoyama, H. et al., "Highly efficient organic light-emitting diodes from delayed fluorescence", Nature, vol. 492, pp. 234-238 (Dec. 13, 2012).

File Registry on STN, RN 1289558-72-0, Entered STN: May 3, 2011.

File Registry on STN, RN 274924-75-3, Entered STN: Jul. 6, 2000.

International Search Report dated Jul. 22, 2014 in PCT/JP2014/067065.

Satoh, K. et al, Eds. "Expression of Highly-Efficient Thermally-Activated Delayed-Fluorescence and Application Thereof to OLED", Organic EL Symposium, Proceeding for the Tenth Meeting, 6 pages (Jun. 17-18, 2010).

Tokumaru, K., Ed. "Organic Ph0tochemical Reaction Theory", Tokyo Kagaku Dojin Co., Ltd., vol. 1, Issue 1, 9 pages (Mar. 31, 1973).

Office Action dated Aug. 11, 2020, in corresponding Korean patent Application No. 10-2015-7033384.

Office Action as received in the corresponding Chinese patent application No. 201810978179.6 dated Sep. 1, 2020.

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

TECHNICAL FIELD

The present invention relates to a compound, a material for an organic electroluminescence device, an organic electroluminescence device, and electronic equipment.

BACKGROUND ART

When voltage is applied to an organic electroluminescence device (hereinafter, occasionally referred to as an organic EL device), holes are injected from an anode to an emitting layer while electrons are injected from a cathode to the emitting layer. The injected holes and electrons are recombined in the emitting layer to form excitons. At this time, singlet excitons and triplet excitons are generated at a ratio of 25%:75% according to statistics of electron spin. In the classification according to the emission principle, in a fluorescent EL device which uses emission caused by singlet excitons, an internal quantum efficiency of the organic EL device is believed to be limited to 25%. On the other hand, it has been known that the internal quantum efficiency can be improved up to 100% under efficient intersystem crossing from the singlet excitons in a phosphorescent EL device which uses emission caused by triplet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, an organic EL device using TTF (Triplet-Triplet Fusion) mechanism that is one of mechanisms for delayed fluorescence has been proposed. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the fluorescent emission is still problematic on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap (ΔST) between the singlet level and the triplet level. An organic EL device with use of the TADF mechanism is disclosed, for instance, in non-Patent Literature 1.

Non-Patent Literature 1 describes carbazolyl dicyanobenzene (CDCB) as a luminescent material for TADF. Non-Patent Literature 1 describes that CDCB includes carbazole as a donor and dicyanobenzene as an electron acceptor and emits light in a range from a blue color (473 nm) to an orange color (577 nm).

CITATION LIST

Non-Patent Literature(s)

Non-Patent Literature 1: Hiroki Uoyama et al. NATURE. vol. 492, pp. 234-238, Dec. 13, 2012

SUMMARY OF THE INVENTION

Problem(s) to be Solved by the Invention

In order to practically use an organic EL device, a compound that emits light in a long wavelength region with use of the TADF mechanism has been desired.

An object of the invention is to provide a compound that emits light in a long wavelength region. Another object of the invention is to provide a material for an organic electroluminescence device containing the above compound, an organic electroluminescence device containing the above compound, and electronic equipment including the organic electroluminescence device.

Means for Solving the Problem(s)

According to an aspect of the invention, a compound represented by a formula (1) below is provided.

[Formula 1]

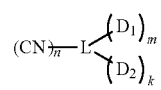

(1)

In the formula (1), k is an integer of 0 or more, m is an integer of 1 or more, and n is an integer of 2 or more. L is a substituted or unsubstituted aromatic hydrocarbon ring having 6 to 30 ring carbon atoms. CN is a cyano group. $D_1$ and $D_2$ are each independently represented by one of a formula (2), a formula (3) and formula (3x) below. $D_1$ and $D_2$ may be the same or different. A plurality of $D_1$ may be the same or different. A plurality of $D_2$ may be the same or different.

[Formula 2]

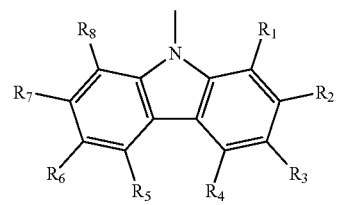

(2)

[Formula 3]

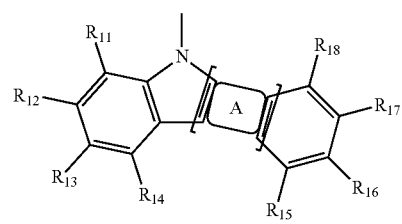

(3)

[Formula 4]

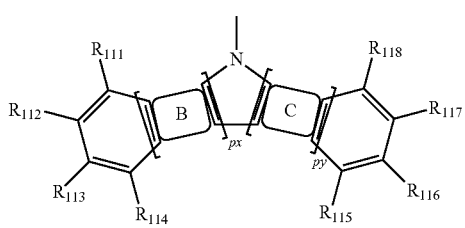

(3x)

$R_1$ to $R_8$ of the formula (2), $R_{11}$ to $R_{18}$ of the formula (3), and $R_{111}$ to $R_{118}$ of the formula (3x) each independently represent a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

In the formula (2), at least one of combinations of substituents selected from $R_1$ to $R_8$ is mutually bonded to form a cyclic structure.

In the formula (3), at least one of combinations of substituents selected from $R_{11}$ to $R_{18}$ is optionally mutually bonded to form a cyclic structure.

In the formula (3x), at least one of combinations of substituents selected from $R_{111}$ to $R_{118}$ is optionally mutually bonded to form a cyclic structure.

In the formulae (3) and (3x): A, B and C each independently represent a cyclic structure represented by one of a formula (31) and a formula (32) below, each of the cyclic structure A, cyclic structure B, and cyclic structure C being fused with its adjacent cyclic structures at any positions; p, px and py are each independently an integer of 1 to 4; when p is an integer of 2 or more, a plurality of cyclic structures A are the same or different; when px is an integer of 2 or more, a plurality of cyclic structures B are the same or different; and when py is an integer of 2 or more, a plurality of cyclic structures C are the same or different.

[Formula 5]

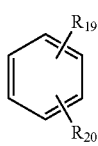

(31)

(32)

In the formula (31), $R_{19}$ and $R_{20}$ each independently represent the same as $R_1$ to $R_8$ and are optionally mutually bonded to form a cyclic structure.

In the formula (32): $X_1$ represents $CR_{30}R_{31}$, $NR_{32}$, a sulfur atom, or an oxygen atom and $R_{30}$ to $R_{32}$ each independently represent the same as $R_1$ to $R_8$ described above. At least one of combinations of substituents selected from $R_{19}$, $R_{20}$ and $R_{30}$ to $R_{32}$ are optionally mutually bonded to form a cyclic structure.

A material for an organic electroluminescence device according to another aspect of the invention contains the compound in the above aspect of the invention.

An organic electroluminescence device according to still another aspect of the invention includes: an anode; a cathode; and one or more organic layers interposed between the anode and the cathode, at least one of the organic layers contains the compound according to the above aspect of the invention.

Electronic equipment includes the organic electroluminescence device according to the above aspect of the invention.

A compound according to the aspect of the invention emits light in a long wavelength region. In the above aspect, a material for an organic electroluminescence device containing the above compound, an organic electroluminescence device containing the above compound, and electronic equipment including the organic electroluminescence device can be provided.

BRIEF DESCRIPTION OF DRAWING(S)

FIG. 1 schematically shows an exemplary arrangement of an organic EL device according to an exemplary embodiment.

Figure 2:
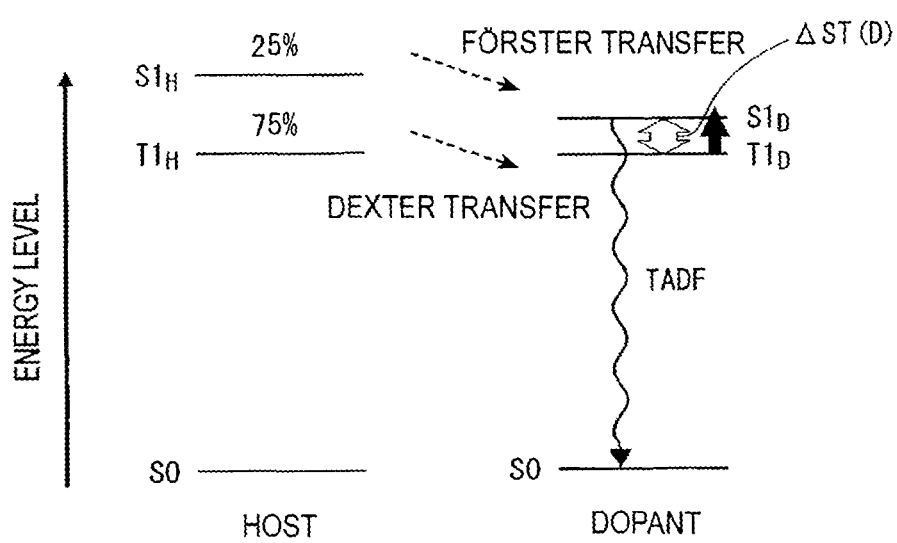

FIG. 2 shows a relationship in energy level and energy transfer between the host material and the dopant material in the emitting layer.

Figure 3:
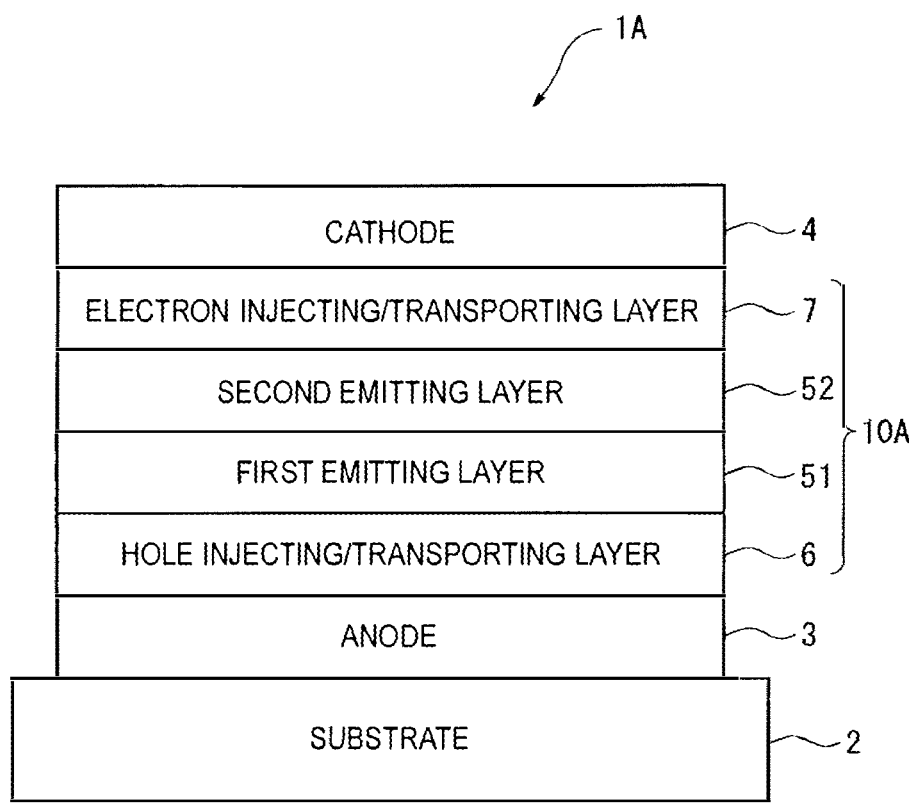

FIG. 3 schematically shows an exemplary arrangement of an organic EL device according to a modification.

DESCRIPTION OF EMBODIMENT(S)

Exemplary embodiment(s) will be described below.

First Exemplary Embodiment

Compound(s)

A compound in the first exemplary embodiment is represented by a formula (1) below.

[Formula 1]

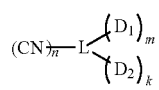

(1)

In the formula (1), k is an integer of 0 or more, m is an integer of 1 or more, and n is an integer of 2 or more. L is a substituted or unsubstituted aromatic hydrocarbon ring having 6 to 30 ring carbon atoms. CN is a cyano group.

$D_1$ and $D_2$ are each independently represented by one of a formula (2), a formula (3) and formula (3x) below. $D_1$ and $D_2$ may be mutually the same or different. When m is 2 or more, a plurality of $D_1$ may be mutually the same or different. When k is 2 or more, a plurality of $D_2$ may be mutually the same or different.

[Formula 7]

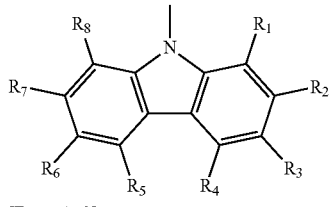

(2)

[Formula 8]

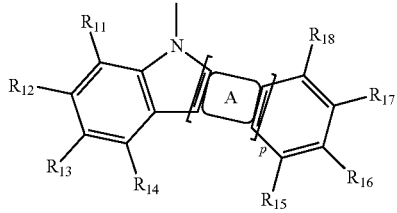

(3)

[Formula 9]

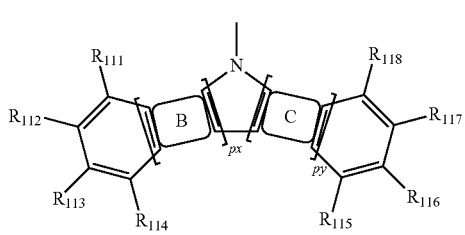

(3x)

R₁ to R₈ of the formula (2), R₁₁ to R₁₈ of the formula (3), and R₁₁₁ to R₁₁₈ of the formula (3x) each independently represent a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

In the formula (2), at least one of combinations of substituents selected from $R_1$ to $R_8$ is mutually bonded to form a cyclic structure. Specifically, in the formula (2), substituents selected from $R_1$ to $R_8$ that are respectively bonded to adjacent ones of the carbon atoms of the six-membered rings to which $R_1$ to $R_8$ are respectively bonded form a cyclic structure. Specifically, in the formula (2), at least one of combinations of substituents, namely, a combination of $R_1$ and $R_2$, a combination of $R_2$ and $R_3$, a combination of $R_3$ and $R_4$, a combination of $R_4$ and $R_5$, a combination of $R_5$ and $R_6$, a combination of $R_6$ and $R_7$, and a combination of $R_7$ and $R_8$ is mutually bonded to form a cyclic structure. In the first exemplary embodiment, the cyclic structure formed by bonding the substituents is preferably a fused ring. When the cyclic structure is formed in the formula (2), the formed structure is preferably a fused six-membered cyclic structure.

In the formula (3), at least one of combinations of substituents selected from $R_{11}$ to $R_{18}$ may be mutually bonded to form a cyclic structure.

In the formula (3x), at least one of combinations of substituents selected from $R_{111}$ to $R_{118}$ may be mutually bonded to form a cyclic structure.

In the formulae (3) and (3x), A, B and C each independently represent a cyclic structure represented by one of a formula (31) and a formula (32) below. Each of the cyclic structure A, cyclic structure B, and cyclic structure C is fused with its adjacent cyclic structures at any positions. p, px and py are each independently an integer of 1 to 4. When p is an integer of 2 or more, a plurality of cyclic structures A may be the same or different. When px is an integer of 2 or more, a plurality of cyclic structures B may be the same or different. When py is an integer of 2 or more, a plurality of cyclic structures C may be the same or different.

[Formula 10]

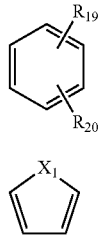

(31)

(32)

In the formula (31), $R_{19}$ and $R_{20}$ each independently represent the same as $R_1$ to $R_8$ described above and may be mutually bonded to form a cyclic structure. $R_{19}$ and $R_{20}$ are respectively bonded to carbon atoms forming the benzene ring of the formula (31).

In the formula (32), $X_1$ represents $CR_{30}R_{31}$, $NR_{32}$, a sulfur atom, or an oxygen atom and $R_{30}$ to $R_{32}$ each independently represent the same as $R_1$ to $R_8$ described above. At least one of combinations of substituents selected from $R_{19}$, $R_{20}$ and $R_{30}$ to $R_{32}$ may be mutually bonded to form a cyclic structure.

In the first exemplary embodiment, $D_1$ and $D_2$ represented by one of the formula (2), the formula (3) and the formula (3x) is a compound having an extended carbazol skeleton. Accordingly, in the compound in the first exemplary embodiment, conjugation is extended, an energy gap is reduced, and an emission wavelength is closer to a long wavelength. Moreover, since the compound in the first exemplary embodiment has two or more cyano groups, the energy gap is reduced and the emission wavelength is closer to a long wavelength. Here, it is not sufficient to simply extend the conjugation. It is further required to extend the conjugation so that ΔST is reduced. As for this point, a method of extending the conjugation by extending the carbazole skeleton is useful in a molecular design. Moreover, in a later-described exemplary embodiment, the emission wavelength can be further lengthened by further introducing a donating substituent or a conjugated substituent to a terminal of the carbazole skeleton.

In the first exemplary embodiment, when L has a substituent, the substituent is preferably a halogen atom, a substituted or unsubstituted aryl group having 6 to 30 ring carbon atoms, a substituted or unsubstituted heterocyclic group having 6 to 30 ring atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms. When L has a plurality of substituents, the plurality of substituents may be the same or different.

In the first exemplary embodiment, L is preferably a substituted or unsubstituted aromatic hydrocarbon ring having 6 to 14 ring carbon atoms. Examples of the aromatic hydrocarbon ring having 6 to 14 ring carbon atoms include benzene, naphthalene, fluorene and phenanthrene. The aromatic hydrocarbon ring having 6 to 10 ring carbon atoms is more preferable.

In the first exemplary embodiment, in the formula (1), it is preferable that $D_1$ or $D_2$ is bonded to a first one of the carbon atoms forming the aromatic hydrocarbon ring represented by L and CN is bonded to a second one of the carbon atoms adjacent to the first one. For instance, in the compound of the first exemplary embodiment, it is preferable that D is bonded to the first carbon atoms $C_1$ and a cyano group is bonded to the second carbon atoms $C_2$ adjacent to the first carbon atoms $C_1$ as shown in a partial structure represented by a formula (1a) below. D in the formula (1a) below represents $D_1$ or $D_2$ described above. In the formula (1a), a wavy line represents a bonding position with another structure or an atom.

[Formula 11]

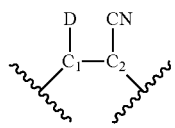

(1a)

Since $D_1$ or $D_2$ having a skeleton represented by the formula (2), (3) or (3x) and the cyano group are adjacently bonded to the aromatic hydrocarbon ring represented by L, a value of ΔST of the compound can be reduced.

In the first exemplary embodiment, m is preferably an integer of 2 or more. When 2 or more $D_1$ are bonded to the aromatic hydrocarbon ring represented by L, the plurality of $D_1$ may be the same or different in the structure.

In the first exemplary embodiment, the compound is preferably represented by a formula (40) below.

[Formula 12]

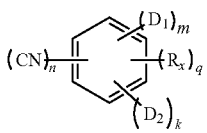

(40)

In the formula (40), k is an integer of 0 to 3, m is an integer of 1 to 4, n is an integer of 2 to 5, q is an integer of 0 to 3, and k+m+n+q=6.

In the formula (40), $R_X$ represents a hydrogen atom, a halogen atom, a substituted or unsubstituted aryl group having 6 to 30 ring carbon atoms, a substituted or unsubstituted heterocyclic group having 6 to 30 ring atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms. A plurality of $R_X$ may be the same or different.

In the formula (40), $D_1$ and $D_2$ each independently represent the same as $D_1$ and $D_2$ of the formula (1). A plurality of $D_1$ may be mutually the same or different. A plurality of $D_2$ may be mutually the same or different.

In the formula (40), $R_X$, $D_1$, $D_2$ and CN are respectively bonded to carbon atoms forming the benzene ring.

In the first exemplary embodiment, the compound is preferably represented by a formula (40a) below.

[Formula 13]

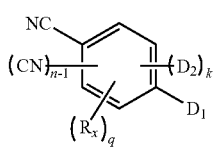

(40a)

In the formula (40a), k is an integer of 0 to 3, n is an integer of 2 to 5, q is an integer of 0 to 3, and k+n+q=5.

In the formula (40a), $R_X$ represents the same as $R_X$ in the formula (40). A plurality of $R_X$ may be the same or different.

In the formula (40a), $D_1$ and $D_2$ each independently represent the same as $D_1$ and $D_2$ in the formula (1). A plurality of $D_2$ may be the same or different.

In the formula (40a), $R_X$, $D_2$ and CN are respectively bonded to carbon atoms forming the benzene ring.

For instance, the compound represented by the formula (40a) has a skeleton in which $D_1$ is bonded at a para-position to the cyano group bonded to the benzene ring. The compound having such a skeleton is preferable since having a higher fluorescence quantum yield.

In the first exemplary embodiment, the compound is also preferably represented by a formula (40b) or a formula (40c) below.

[Formula 14]

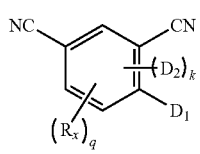

(40b)

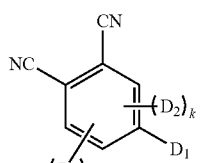

(40c)

In the formulae (40b) and (40c), k is an integer of 0 to 3, q is an integer of 0 to 3, and k+q=3.

In the formulae (40b) and (40c), $R_X$ represents the same as $R_X$ in the formula (40). A plurality of $R_X$ may be the same or different.

In the formulae (40b) and (40c), $D_1$ and $D_2$ each independently represent the same as $D_1$ and $D_2$ in the formula (1). A plurality of $D_2$ may be the same or different.

In the formulae (40b) and (40c), $R_X$ and $D_2$ are respectively bonded to carbon atoms forming the benzene ring.

In the first exemplary embodiment, the compound is also preferably represented by a formula (40d) or a formula (40e) below.

[Formula 15]

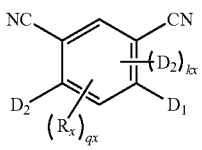

(40d)

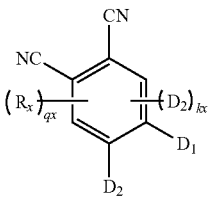

(40e)

In the formulae (40d) and (40e), kx is an integer of 0 to 2, qx is an integer of 0 to 2, and kx+qx=2.

In the formulae (40d) and (40e), $R_X$ represents the same as $R_X$ in the formula (40). A plurality of $R_X$ may be the same or different.

In the formulae (40d) and (40e), $D_1$ and $D_2$ each independently represent the same as $D_1$ and $D_2$ in the formula (1). A plurality of $D_2$ may be the same or different.

In the formulae (40d) and (40e), $R_X$ and $D_2$ are respectively bonded to carbon atoms forming the benzene ring.

In the first exemplary embodiment, the compound is also preferably represented by a formula (40f) below.

[Formula 16]

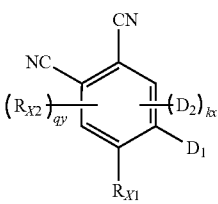

(40f)

In the formula (40f), kx is an integer of 0 to 2, qy is an integer of 0 to 2, and kx+qy=2.

In the formula (40f), $R_{X1}$ represents a halogen atom, a substituted or unsubstituted aryl group having 6 to 30 ring carbon atoms, a substituted or unsubstituted heterocyclic group having 6 to 30 ring atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms. $R_{X2}$ represents the same as $R_X$ in the formula (40). $R_{X1}$ and $R_{X2}$ may be the same or different. A plurality of $R_{X2}$ may be the same or different.

In the formula (40f), $D_1$ and $D_2$ each independently represent the same as $D_1$ and $D_2$ in the formula (1). A plurality of $D_2$ may be the same or different.

In the formula (40f), $R_{X2}$ and $D_2$ are respectively bonded to carbon atoms forming the benzene ring.

For instance, in the compound represented by the formula (40e) and the compound represented by the formula (40f), $D_1$ is bonded to the first carbon atom of the benzene ring and $D_2$ or $R_{X1}$ is bonded to the second carbon atom adjacent to the first carbon atom as described in relation to the formula (1a). The compounds having such a skeleton are preferable since exhibiting a shorter delayed fluorescence lifetime.

In the first exemplary embodiment, the compound is preferably represented by a formula (40g) below.

[Formula 17]

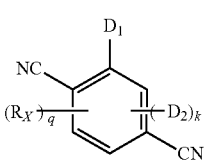

(40g)

In the formula (40g), k is an integer of 0 to 3, q is an integer of 0 to 3, and k+q=3.

In the formula (40g), $R_X$ each independently represents the same as $R_X$ in the formula (40). A plurality of $R_X$ may be the same or different.

In the formula (40g), $D_1$ and $D_2$ each independently represent the same as $D_1$ and $D_2$ in the formula (1). A plurality of $D_2$ may be the same or different.

In the formula (40g), $R_X$ and $D_2$ are respectively bonded to carbon atoms forming the benzene ring.

For instance, the compound represented by the formula (40g) has a skeleton in which the cyano groups are bonded to the benzene ring at para-positions. The compound having such a skeleton is preferable since exhibiting a shorter fluorescence quantum yield.

A compound in the first exemplary embodiment is preferably represented by a formula (4) below.

[Formula 18]

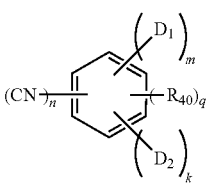

(4)

In the formula (4), k is an integer of 0 to 3, m is an integer of 1 to 4, n is an integer of 2 to 5, q is an integer of 0 to 3, and k+m+n+q=6. In the first exemplary embodiment, x is preferably an integer of 2 to 4 and m is preferably an integer of 2 to 4.

In the formula (4), $R_{40}$ each independently represents a hydrogen atom, a halogen atom, a substituted or unsubstituted aryl group having 6 to 30 ring carbon atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms. A plurality of $R_{40}$ may be the same or different.

In the formula (4), $D_1$ and $D_2$ each independently represent the same as $D_1$ and $D_2$ of the formula (1). A plurality of $D_1$ may be mutually the same or different. A plurality of $D_2$ may be mutually the same or different.

In the formula (4), $R_{40}$, $D_1$, $D_2$ and CN are respectively bonded to carbon atoms forming the benzene ring.

In the first exemplary embodiment, the compound represented by the formula (4) is preferably represented by one of formulae (41) to (47) below.

[Formula 19]

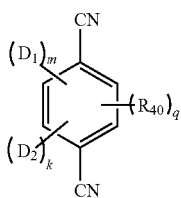

(41)

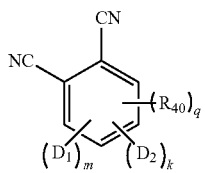

(42)

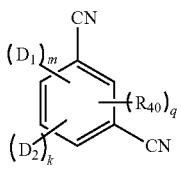

(43)

[Formula 20]

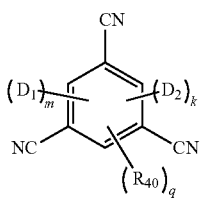

(44)

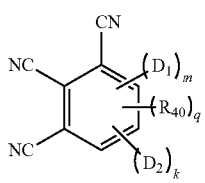

(45)

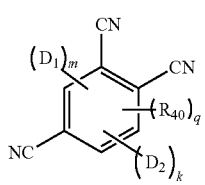

(46)

[Formula 21]

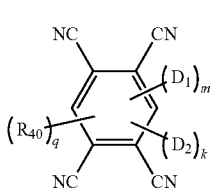

(47)

In the formulae (41) to (43), $D_1$ and $D_2$ each independently represent the same as $D_1$ and $D_2$ in the formula (1) and $R_{40}$ each independently represents the same as $R_{40}$ in the formula (4).

In the formulae (41) to (43), k is an integer of 0 to 3, m is an integer of 1 to 4, q is an integer of 0 to 3, and k+m+q=4.

In the formulae (44) to (46), k is an integer of 0 to 2, m is an integer of 1 to 3, q is an integer of 0 to 2, and k+m+q=3.

In the formula (47), k is 0 or 1, m is 1 or 2, and q is 0 or 1, and k+m+q=2.

In the first exemplary embodiment, in the formulae (41) to (46), it is preferable that $D_1$ or $D_2$ is bonded to the carbon atom (second carbon atom) adjacent to the carbon atom (the first carbon atom) of the benzene ring to which CN is bonded in the same manner as in the formula (47). The value of ΔST of the compound can be reduced when $D_1$ or $D_2$ and CN are adjacently bonded to the benzene ring.

In the first exemplary embodiment, m of the formulae (41) to (47) is preferably 2. Moreover, it is more preferable that m is 2 and k is 0. A plurality of $D_1$ may be mutually the same or different in the structure.

In the first exemplary embodiment, the compound is preferably represented by a formula (4x) below.

[Formula 22]

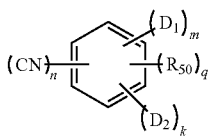

(4x)

In the formula (4x), k is an integer of 0 to 3, m is an integer of 1 to 4, n is an integer of 2 to 5, q is an integer of 0 to 3, and k+m+n+q=6.

In the formula (4x), $R_{50}$ each independently represents a substituted or unsubstituted heterocyclic group having 6 to 30 ring atoms. A plurality of $R_{50}$ may be the same or different.

In the formula (4x), $D_1$ and $D_2$ each independently represent the same as $D_1$ and $D_2$ of the formula (1). A plurality of $D_1$ may be mutually the same or different. A plurality of $D_2$ may be mutually the same or different.

In the formula (4x), $R_{50}$, $D_1$, $D_2$ and CN are respectively bonded to carbon atoms forming the benzene ring.

$R_{50}$ is preferably each independently a group selected from the group consisting of a substituted or unsubstituted 1-carbazolyl group, a substituted or unsubstituted 2-carbazolyl group, a substituted or unsubstituted 3-carbazolyl group, a substituted or unsubstituted 4-carbazolyl group, and a substituted or unsubstituted 9-carbazolyl group.

In the first exemplary embodiment, the compound represented by the formula (4x) is preferably represented by one of formulae (51) to (57) below.

[Formula 23]

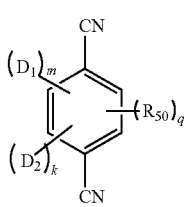

(51)

-continued

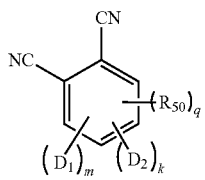
(52)

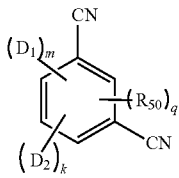
(53)

[Formula 24]

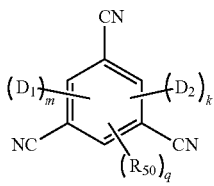
(54)

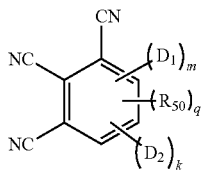
(55)

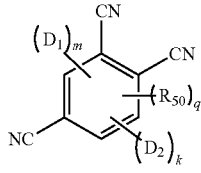
(56)

[Formula 25]

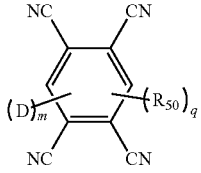
(57)

In the formulae (51) to (53), $D_1$ and $D_2$ each independently represent the same as $D_1$ and $D_2$ in the formula (1) and $R_{50}$ each independently represents the same as $R_{50}$ in the formula (4x).

In the formulae (51) to (53), k is an integer of 0 to 3, m is an integer of 1 to 4, q is an integer of 0 to 3, and k+m+q=4.

In the formulae (54) to (56), k is an integer of 0 to 2, m is an integer of 1 to 3, q is an integer of 0 to 2, and k+m+q=3.

In the formula (57), k is 0 or 1, m is 1 or 2, and q is 0 or 1, and k+m+q=2.

In the first exemplary embodiment, in the formulae (51) to (56), it is preferable that $D_1$ or $D_2$ is bonded to the carbon atom (second carbon atom) adjacent to the carbon atom (the first carbon atom) of the benzene ring to which CN is bonded in the same manner as in the formula (57). The value of ΔST of the compound can be reduced when $D_1$ or $D_2$ and CN are adjacently bonded to the benzene ring.

In the first exemplary embodiment, m of the formulae (51) to (57) is preferably 2. Moreover, it is more preferable that m is 2 and k is 0. A plurality of $D_1$ may be mutually the same or different in the structure. It is more preferable that a first one of $D_1$ is bonded to the benzene ring and a second one of $D_1$ is bonded to the benzene ring at a para-position or a meta-position relative to the first one of $D_1$.

A compound in the first exemplary embodiment is preferably represented by one of formulae (48) to (50) below.

[Formula 26]

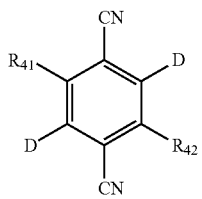
(48)

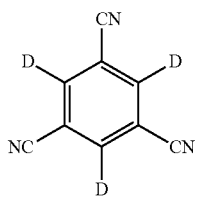
(49)

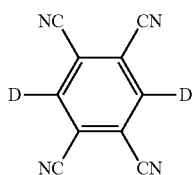
(50)

In the formula (48), $R_{41}$ and $R_{42}$ each independently represent the same as $R_1$ to $R_8$ described above.

In the formulae (48) to (50), D each independently represents the same as $D_1$ or $D_2$ of the formula (1).

In the first exemplary embodiment, in the formula (2), it is preferable that one or two of combinations of substituents selected from $R_1$ to $R_8$ are mutually bonded to form a cyclic structure. Specifically, as $D_1$ or $D_2$ represented by the formula (2), it is preferable that one or two of combinations of substituents, namely, a combination of $R_1$ and $R_2$, a combination of $R_2$ and $R_3$, a combination of $R_3$ and $R_4$, a combination of $R_4$ and $R_5$, a combination of $R_5$ and $R_6$, a combination of $R_6$ and $R_7$, and a combination of $R_7$ and $R_8$ are mutually bonded to form a cyclic structure. It is more preferable that at least one of the combination of $R_2$ and $R_3$, the combination of $R_3$ and $R_4$, the combination of $R_5$ and $R_6$, and the combination of $R_6$ and $R_7$ is mutually bonded to form a cyclic structure. In this arrangement, since the cyclic structure is formed including at least one of a carbon atom at a position 3 and a carbon atom at a position 6 of the carbazole skeleton of the formula (2), it is inferred that an active site of the carbazole skeleton is modified by this cyclic structure, thereby improving the stability of the compound in the first exemplary embodiment.

In the first exemplary embodiment, at least one of $D_1$ and $D_2$ represented by the formula (2) is preferably represented by one of formulae (21) to (26) below.

[Formula 27]

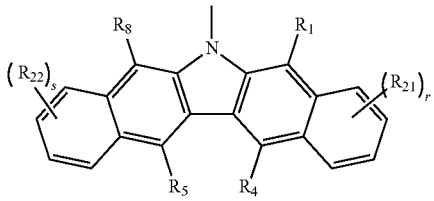
(21)

[Formula 28]

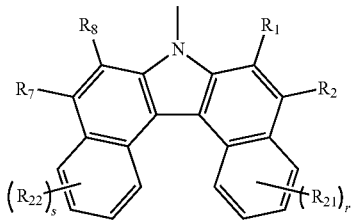
(22)

[Formula 29]

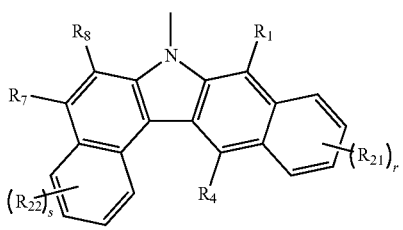
(23)

[Formula 30]

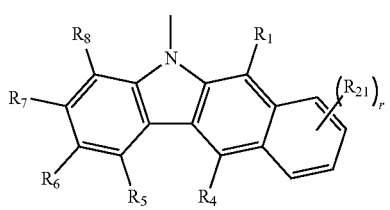
(24)

[Formula 31]

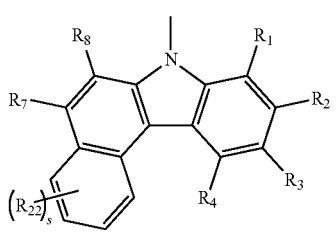
(25)

[Formula 32]

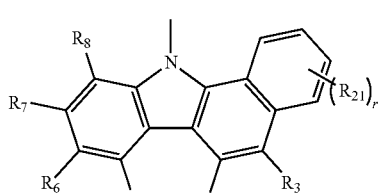
(26)

In the formulae (21) to (26), $R_1$ to $R_8$, $R_{21}$ and $R_{22}$ each independently represent the same as $R_1$ to $R_8$ described above, r and s are each 4, and $R_{21}$ and $R_{22}$ are each bonded to a carbon atom of a six-membered ring. A plurality of $R_{21}$ may be mutually the same or different. A plurality of $R_{22}$ may be mutually the same or different.

In the formulae (21) to (26), at least one of combinations of substituents selected from $R_1$ to $R_8$, $R_{21}$ and $R_{22}$ may be mutually bonded to form a cyclic structure.

In the first exemplary embodiment, at least one of $D_1$ and $D_2$ represented by the formula (2) is preferably represented by one of formulae (201) to (203) below.

[Formula 33]

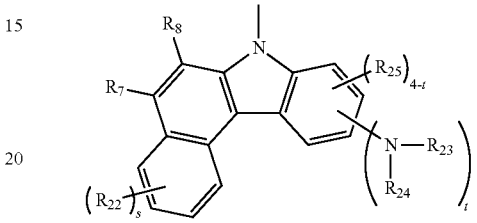
(201)

[Formula 34]

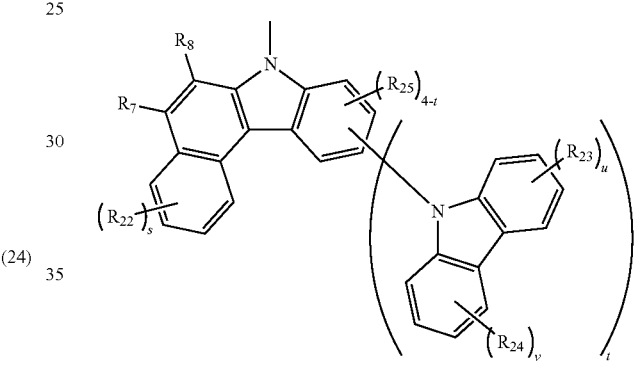
(202)

[Formula 35]

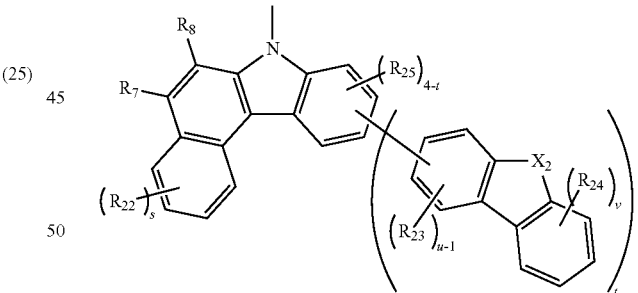
(203)

In the formulae (201) to (203), $R_7$, $R_8$, $R_{22}$ to $R_{25}$ each independently represent the same as $R_1$ to $R_8$ described above. $X_2$ represents $CR_{26}R_{27}$, $NR_{28}$, a sulfur atom, or an oxygen atom. $R_{26}$ to $R_{28}$ each independently represent the same as $R_1$ to $R_8$ described above. s is 4. t is an integer of 1 to 4. u and v are each 4. A plurality of $R_n$ may be mutually the same or different. A plurality of $R_{23}$ may be mutually the same or different. A plurality of $R_{24}$ may be mutually the same or different. A plurality of $R_{25}$ may be mutually the same or different.

It is inferred that, since a particular substituent is further bonded to the carbazole skeleton fused with a ring as shown in the formulae (201) to (203), an emission wavelength of the compound in the first exemplary embodiment is shifted toward a longer wavelength as compared with an arrangement in which the substituent is not bonded.

In the formulae (201) to (203), at least one of combinations of substituents selected from $R_7$, $R_8$, and $R_{22}$ to $R_{25}$ may be mutually bonded to form a cyclic structure.

In the formulae (201) to (203), t is preferably 1.

A compound represented by a formula (201a) is preferable among the compound represented by the formula (201). A compound represented by a formula (202a) is preferable among the compound represented by the formula (202). A compound represented by a formula (203a) is preferable among the compound represented by the formula (203).

[Formula 36]

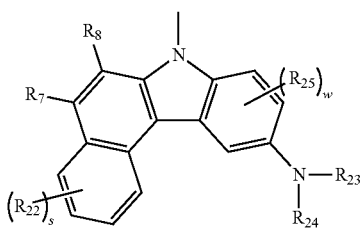

(201a)

[Formula 37]

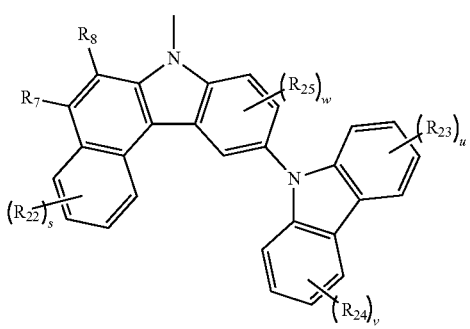

(202a)

[Formula 38]

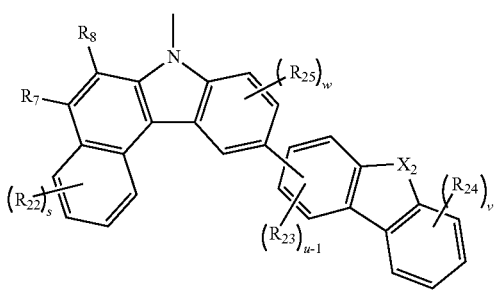

(203a)

In the formulae (201a), (202a) and (203a); $R_7$, $R_8$, and $R_{22}$ to $R_{25}$ each independently represent the same as $R_1$ to $R_8$ described above; $X_2$ represents $CR_{26}R_{27}$, $NR_{28}$, a sulfur atom, or an oxygen atom; $R_{26}$ to $R_{28}$ each independently represent the same as $R_1$ to $R_8$ described above; s is 4; w is 3; and u and v are each 4. A plurality of $R_{22}$ may be mutually the same or different. A plurality of $R_{23}$ may be mutually the same or different. A plurality of $R_{24}$ may be mutually the same or different. A plurality of $R_{25}$ may be mutually the same or different.

When the compound in the first exemplary embodiment includes at least one of the structures represented by the formulae (201a), (202a) and (203a), at least one of the carbon atoms at the position 3 and the carbon atom at the position 6 of the carbazole skeleton is substituted by a predetermined substituent. Accordingly, it is inferred that, since the carbon atoms at the positions 3 and 6 of the carbazole skeleton are modified by the fused ring or are substituted by the substituent, the stability of the compound in the first exemplary embodiment is further improved. Consequently, when the compound in the first exemplary embodiment is used in an organic electroluminescence device, the lifetime of the organic electroluminescence device can be prolonged.

In the first exemplary embodiment, it is preferable that p is 2, in other words, two cyclic structures A are present in the formula (3). In this arrangement, the formula (3) is represented by a formula (3a) below.

[Formula 39]

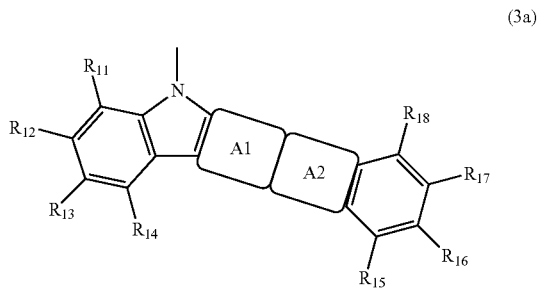

(3a)

In the formula (3a), $R_{11}$ to $R_{18}$ represent the same as $R_{11}$ to $R_{18}$ of the formula (3).

In the formula (3a), a cyclic structure A1 and a cyclic structure A2 each independently represent the same as the cyclic structure A represented by the formula (31) or (32).

In the formula (3a), it is preferable that the cyclic structure A1 is the cyclic structure represented by the formula (31) and the cyclic structure A2 is the cyclic structure represented by the formula (32).

In the first exemplary embodiment, at least one of $D_1$ and $D_2$ represented by the formula (3) is preferably represented by one of formulae (33) to (38) below.

[Formula 40]

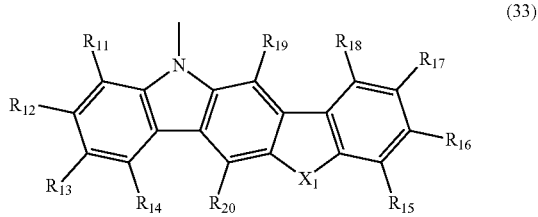

(33)

[Formula 41]

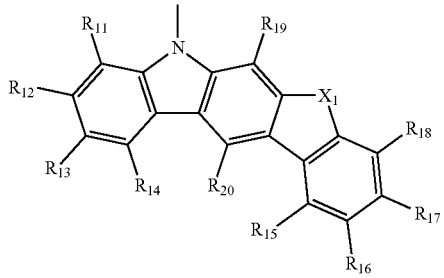

(34)

[Formula 42]

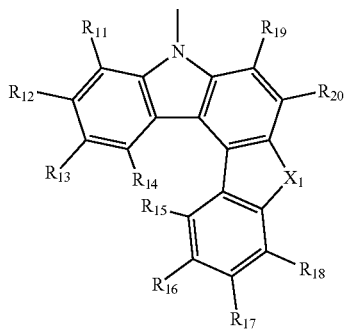

(35)

[Formula 43]

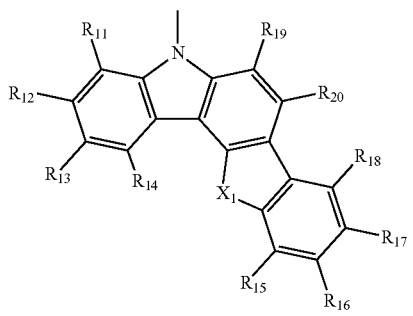

(36)

[Formula 44]

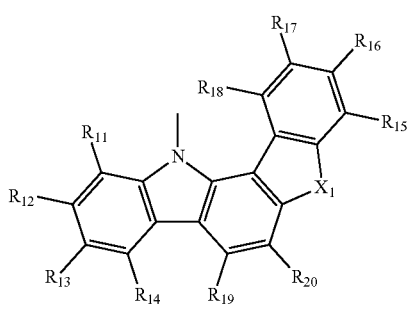

(37)

[Formula 45]

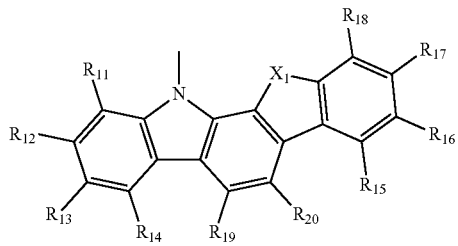

(38)

In the formulae (33) to (38), $R_{11}$ to $R_{18}$ each independently represent the same as $R_{11}$ to $R_{18}$ in the formula (3), and $R_{19}$ and $R_{20}$ each independently represent the same as $R_{19}$ and $R_{20}$ in the formula (31), and $X_1$ represents the same as $X_1$ in the formula (32).

In the formulae (33) to (38), at least one of combinations of substituents selected from $R_{11}$ to $R_{20}$ may be mutually bonded to form a cyclic structure.

In the first exemplary embodiment, at least one of $D_1$ and $D_2$ represented by the formula (3) is preferably represented by one of the formulae (33) to (36).

Since the cyclic structure represented by the formula (31) is fused to the cyclic structure represented by the formula (32) as shown in the formulae (33) to (36), the cyclic structure includes at least one of the carbon atoms at the positions 3 and 6 of the carbazole skeleton. Accordingly, it is inferred that the active site of the carbazole skeleton is modified by the cyclic structure to improve the stability of the compound in the first exemplary embodiment.

In the first exemplary embodiment, at least one of $D_1$ and $D_2$ represented by the formula (3) is also preferably the structure represented by one of the formulae (33) and (34), in which $X_1$ is $CR_{30}R_{31}$. In this arrangement, the formula (33) is represented by a formula (33a) below and the formula (34) is represented by a formula (34a) below.

[Formula 46]

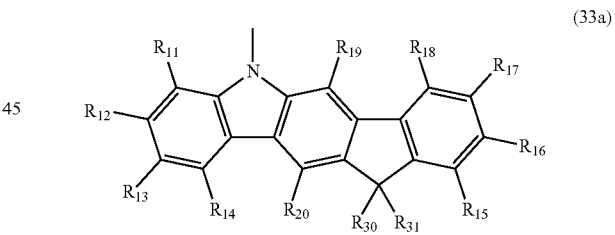

(33a)

[Formula 47]

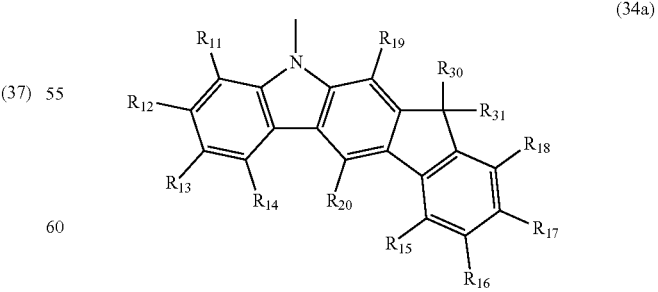

(34a)

In the formulae (33a) and (34a), $R_{11}$ to $R_{18}$ each independently represent the same as $R_{11}$ to $R_{18}$ in the formula (3) and $R_1$ and $R_2$ each independently represent the same as $R_{30}$ and $R_{31}$ in the formula (32).

In the formulae (33a) and (34a), at least one of combinations of substituents selected from $R_{11}$ to $R_{18}$, $R_{30}$ and $R_{31}$ may be mutually bonded to form a cyclic structure.

In the first exemplary embodiment, $R_{30}$ and $R_{20}$ in the formula (33a) are preferably mutually bonded to form a cyclic structure. Moreover, in the formula (34a), $R_{30}$ and $R_{19}$ are preferably mutually bonded to form a cyclic structure.

In the first exemplary embodiment, at least one of $D_1$ and $D_2$ represented by the formula (3) is preferably represented by one of formulae (27) and (28) below.

[Formula 48]

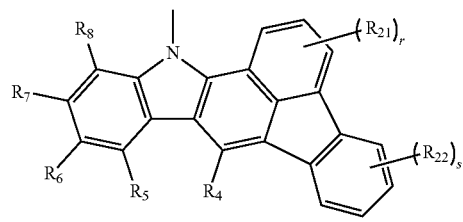

(27)

[Formula 49]

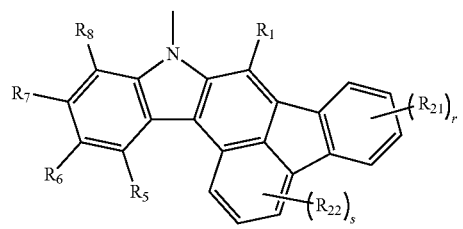

(28)

In the formulae (27) and (28), $R_1$, $R_4$ to $R_8$, $R_{21}$ and $R_{22}$ each independently represent the same as $R_1$ to $R_8$ described above, r and s are each 4, and $R_{21}$ and $R_{22}$ are each bonded to a carbon atom of the six-membered ring. A plurality of $R_{21}$ may be mutually the same or different. A plurality of $R_n$ may be mutually the same or different.

In the formulae (27) and (28), at least one of combinations of substituents selected from $R_1$, $R_4$ to $R_8$, $R_{21}$ and $R_{22}$ may be mutually bonded to form a cyclic structure. In this arrangement, since the cyclic structure is formed including at least one of the carbon atom at the position 3 and the carbon atom at the position 6 of the carbazole skeleton as described above, it is inferred that the stability of the compounds represented by the formulae (27) and (28) is improved. Consequently, also when the compounds represented by the formulae (27) and (28) are used in an organic electroluminescence device, a lifetime of the organic electroluminescence device can be prolonged.

In the first exemplary embodiment, it is also preferable that $D_1$ and $D_2$ are each independently represented by a formula (5) below.

[Formula 50]

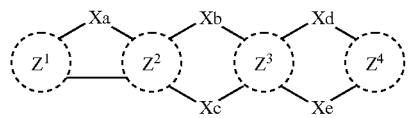

(5)

In the formula (5), Xa represents an oxygen atom, a sulfur atom, $NR^{100}$ or $CR^{103}R^{104}$.

Xb, Xc, Xd and Xe each independently represent a single bond, an oxygen atom, a sulfur atom, $NR^{100}$, $CR^{103}R^{104}$ or a nitrogen atom to be bonded to L of the formula (1).

At least one of Xa, Xb, Xc, Xd and Xe is $NR^1$. At least one of Xa, Xb, Xc, Xd and Xe is a nitrogen atom to be bonded to L of the formula (1). Xb and Xc are not simultaneously single bonds. Xd and Xe are not simultaneously single bonds.

$R^{100}$ is selected from the group consisting of a hydrogen atom, a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, a substituted or unsubstituted heterocyclic group having 5 to 30 ring atoms, and a group represented by $-L^1-R^{102}$.

When a plurality of $R^{100}$ are present, the plurality of $R^{100}$ may be mutually the same or different.

$L^1$ represents a single bond or a linking group. When $L^1$ is a linking group, the linking group is selected from the group consisting of a substituted or unsubstituted aromatic hydrocarbon group having 6 to 30 ring carbon atoms and a substituted or unsubstituted heterocyclic group having 5 to 30 ring atoms. When a plurality of $L^1$ are present, the plurality of $L^1$ may be mutually the same or different.

$R^{102}$ to $R^{104}$ are each selected from the group consisting of a hydrogen atom, a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, and a substituted or unsubstituted heterocyclic group having 5 to 30 ring atoms.

When a plurality of $R^{102}$ are present, the plurality of $R^{102}$ may be mutually the same or different.

When a plurality of $R^{103}$ are present, the plurality of $R^{103}$ may be mutually the same or different.

When a plurality of $R^{104}$ are present, the plurality of $R^{104}$ may be mutually the same or different.

$Z^1$, $Z^2$, $Z^3$ and $Z^4$ each independently represent a cyclic structure selected from the group consisting of a substituted or unsubstituted aromatic hydrocarbon ring having 6 to 30 ring carbon atoms, and a substituted or unsubstituted heterocyclic ring having 5 to 30 ring atoms.

It should be noted that Xe does not represent an element symbol of xenon in the present specification.

In the formula (5), Xa and a single bond connecting $Z^1$ and $Z^2$ are respectively bonded to adjacent atoms of the cyclic structure represented by $Z^1$ and respectively bonded to adjacent atoms of the cyclic structure represented by $Z^2$. Xb and Xc are respectively bonded to adjacent atoms of the cyclic structure represented by $Z^2$ and respectively bonded to adjacent atoms of the cyclic structure represented by $Z^3$. Xd and Xe are respectively bonded to adjacent atoms of the cyclic structure represented by $Z^3$ and respectively bonded to adjacent atoms of the cyclic structure represented by $Z^4$.

When $Z^1$ is, for instance, a benzene ring in the formula (5), a bonding pattern of $Z^1$, Xa and a single bond is represented by a formula (5-1) below in which a wavy part represents a bonding position to $Z^2$.

[Formula 51]

(5-1)

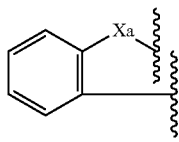

When both of $Z^1$ and $Z^2$ are, for instance, benzene rings in the formula (5), a bonding pattern of $Z^1$, Xa, a single bond and $Z^2$ is represented by one of formulae (5-2), (5-3) and (5-4) below in which a wavy part represents a bonding position to Xb and Xc.

[Formula 52]

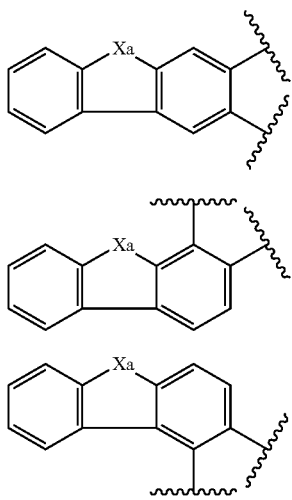

(5-2)

(5-3)

(5-4)

In the first exemplary embodiment, $Z^1$, $Z^2$, $Z^3$ and $Z^4$ are preferably each independently a substituted or unsubstituted aromatic hydrocarbon ring having 6 to 30 ring carbon atoms, more preferably a substituted or unsubstituted aromatic hydrocarbon ring having 6 to 20 ring carbon atoms, further preferably an aromatic hydrocarbon ring selected from the group consisting of a benzene ring, naphthalene ring, phenanthrene ring, and triphenylenylene ring, particularly preferably a benzene ring.

In the first exemplary embodiment, it is preferable that one of Xb and Xc is a single bond and one of Xd and Xe is a single bond.

When one of Xb and Xc is a single bond and one of Xd and Xe is a single bond, $D_1$ and $D_2$ represented by the formula (5) is represented by one of formulae (5A) to (5D) below.

[Formula 53]

(5A)

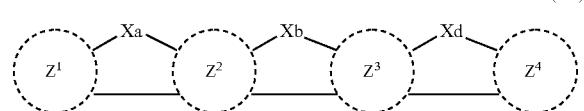

(5B)

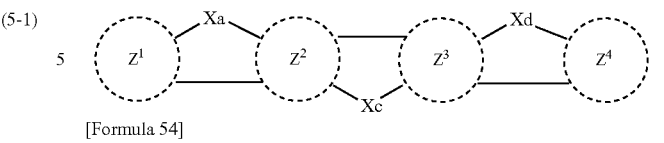

[Formula 54]

(5C)

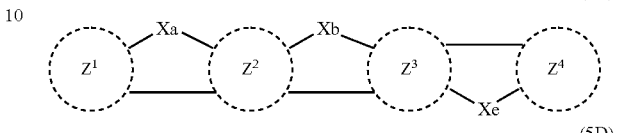

(5D)

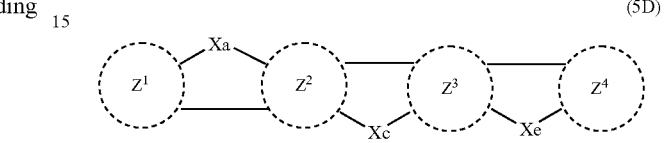

In $D_1$ and $D_2$ represented by the formula (5A) or (5B), it is preferable that Xa is $NR^{100}$ and Xd is a nitrogen atom to be bonded to L in the formula (1). In this arrangement, Xb and Xc are preferably an oxygen atom or a sulfur atom, more preferably an oxygen atom.

In $D_1$ and $D_2$ represented by the formula (5C) or (5D), it is preferable that Xa is $NR^{100}$ and Xe is a nitrogen atom to be bonded to L in the formula (1). In this arrangement, Xb and Xc are preferably an oxygen atom or a sulfur atom, more preferably an oxygen atom.

An organic compound for expressing thermally activated delayed fluorescence is exemplified by a compound in which a donor moiety (a moiety having electron donating performance) is bonded to an acceptor moiety (a moiety having electron accepting performance) in a molecule. When the number of a nitrogen atom included in the skeleton represented by the formula (5) is increased, the electron donating performance of the donor moiety of a first compound is enhanced, thereby providing a suitable balance between the electron donating performance of the donor moiety and the electron accepting performance of the acceptor moiety in the first compound. Consequently, the first compound exhibits suitable characteristics as a material for exhibiting delayed fluorescence.

In the first exemplary embodiment, at least one of $R^{100}$ is preferably a group represented by $-L^1-R^{102}$.

In the first exemplary embodiment, px and py of the formula (3x) are preferably the same integer, more preferably 2. In this arrangement, the formula (3x) is represented by a formula (3y) below.

[Formula 55]

(3y)

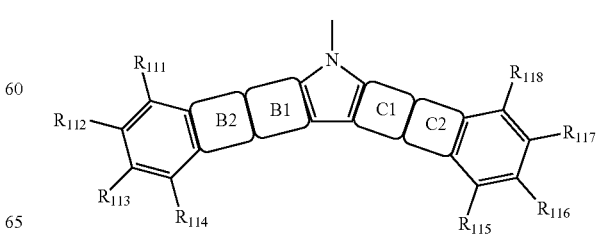

In the formula (3y), $R_{111}$ to $R_{118}$ each independently represent the same as $R_{111}$ to $R_{118}$ described in the formula (3x).

The cyclic structure B1 and the cyclic structure B2 each independently represent the same as the cyclic structure B. The cyclic structure C1 and the cyclic structure C2 each independently represent the same as the cyclic structure C.

In the formula (3y), it is preferable that the cyclic structure B1 and the cyclic structure C1 are each independently the cyclic structure represented by the formula (31) and the cyclic structure B2 and the cyclic structure C2 are each independently the cyclic structure represented by the formula (32).

In the first exemplary embodiment, it is also preferable that $D_1$ and $D_2$ are each independently represented by a formula (10) below.

$D_1$ and $D_2$ represented by the formula (10) below each have a ring in a bonding pattern allowing a high triplet energy to be maintained. Accordingly, $D_1$ and $D_2$ represented by the formula (10) below are preferable since $D_1$ and $D_2$ can effectively confine a high emission energy in a wavelength region from blue to green.

[Formula 56]

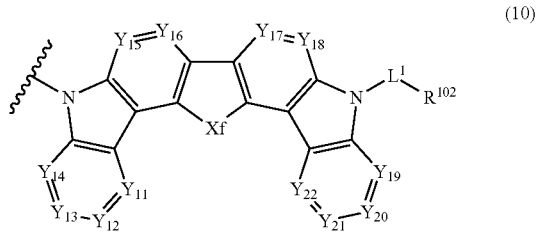

(10)

In the formula (10), Xf represents an oxygen atom, a sulfur atom, $NR^{100}$ or $CR^{103}R^{104}$.

$R^{100}$ is selected from the group consisting of a hydrogen atom, a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, a substituted or unsubstituted heterocyclic group having 5 to 30 ring atoms, and a group represented by $-L^1-R^{102}$.

$L^1$ represents a single bond or a linking group. When $L^1$ is a linking group, the linking group is selected from the group consisting of a substituted or unsubstituted aromatic hydrocarbon group having 6 to 30 ring carbon atoms and a substituted or unsubstituted heterocyclic group having 5 to 30 ring atoms. When a plurality of $L^1$ are present, the plurality of $L^1$ may be mutually the same or different.

$Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$ and $Y_{22}$ each independently represent a nitrogen atom or $CR^{105}$.

$R^{102}$ to $R^{105}$ are each independently selected from the group consisting of a hydrogen atom, a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, and a substituted or unsubstituted heterocyclic group having 5 to 30 ring atoms.

When a plurality of $R^{102}$ are present, the plurality of $R^{102}$ may be mutually the same or different.

When a plurality of $R^{105}$ are present, the plurality of $R^{105}$ may be mutually the same or different. When at least two of the plurality of $R^{105}$ are substituents, $R^{105}$ of the substituents may be mutually bonded to form a cyclic structure.

A wavy part in the formula (10) shows a bonding position to L in the formula (1) and the like.

In the first exemplary embodiment, $R^{102}$ is preferably each independently a substituent selected from the group consisting of a substituted or unsubstituted aromatic hydrocarbon group having 6 to 30 ring carbon atoms and a substituted or unsubstituted heterocyclic group having 5 to 30 ring atoms.

In the first exemplary embodiment, $R^{102}$ is preferably each independently a substituted or unsubstituted aromatic hydrocarbon group having 6 to 30 ring carbon atoms, more preferably a substituted or unsubstituted aromatic hydrocarbon group having 6 to 20 ring carbon atoms, further preferably an aromatic hydrocarbon group selected from the group consisting of a phenyl group, biphenyl group, terphenyl group, naphthyl group, phenanthryl group and triphenylenyl group.

In the first exemplary embodiment, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$ and $Y_{22}$ are preferably $CR^{105}$, in which $R^{105}$ is more preferably a hydrogen atom. In this arrangement, for instance, the formula (10) is represented by a formula (10B) below.

[Formula 57]

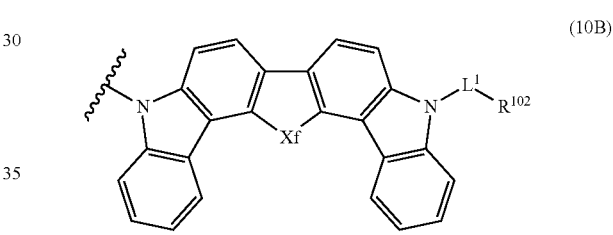

(10B)

In the formula (10B), Xf, $L^1$ and $R^{102}$ each independently represent the same as Xf, $L^1$ and $R^{102}$ in the formula (10). A wavy part in the formula (10B) shows a bonding position to L in the formula (1) and the like.

In the formulae (10) and (10B), Xf is preferably an oxygen atom or a sulfur atom, more preferably an oxygen atom.

In the first exemplary embodiment, when m is 2 or more, $D_1$ and $D_2$ are preferably different from each other. When a plurality of $D_1$ are present, the plurality of $D_1$ may be mutually the same or different. When a plurality of $D_2$ are present, the plurality of $D_2$ may be mutually the same or different. When a plurality of $D_1$ and a plurality of $D_2$ are present, the plurality of $D_1$ and the plurality of $D_2$ may be mutually the same or different.

The compound in the first exemplary embodiment may have: the structures represented by the formulae (2) and (3); the structures represented by the formulae (2) and (3x); the structures represented by the formulae (3) and (3x); a plurality of structures represented by the formula (2) that are mutually different in details; a plurality of structures represented by the formula (3) that are mutually different in details; or a plurality of structures represented by the formula (3x) that are mutually different in details.

In the first exemplary embodiment, at least one of $R_3$ and $R_6$ is preferably substituted by a substituent. In the first exemplary embodiment, at least one of $R_{13}$ and $R_{16}$ is preferably substituted by a substituent.

In the first exemplary embodiment, it is preferable that $R_1$ to $R_8$, $R_{11}$ to $R_{18}$ and $R_{111}$ to $R_{118}$ are each independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, or a substituted or unsubstituted arylamino group having 6 to 60 ring carbon atoms.

In the first exemplary embodiment, it is more preferable that $R_1$ to $R_8$, $R_{11}$ to $R_{18}$ and $R_{111}$ to $R_{118}$ are each independently a hydrogen atom, a substituted or unsubstituted aryl group having 6 to 30 ring carbon atoms, a substituted or unsubstituted heterocyclic group having 5 to 30 ring atoms, a substituted or unsubstituted arylamino group having 6 to 40 ring carbon atoms, or a substituted or unsubstituted alkyl group having 1 to 30 carbon atoms.

In the first exemplary embodiment, it is further preferable that $R_1$ to $R_8$, $R_{11}$ to $R_{18}$ and $R_{111}$ to $R_{118}$ are each independently a hydrogen atom, a substituted or unsubstituted aryl group having 6 to 12 ring carbon atoms, a substituted or unsubstituted heterocyclic group having 5 to 14 ring atoms, or a substituted or unsubstituted alkyl group having 1 to 6 carbon atoms.

In the first exemplary embodiment, it is preferable that $R_X$ is each independently a hydrogen atom, a substituted or unsubstituted heterocyclic group having 6 to 30 ring atoms, a substituted or unsubstituted alkyl group having 1 to 30 carbon atoms, or a substituted or unsubstituted alkylsilyl group having 3 to 30 carbon atoms.

In the first exemplary embodiment, it is preferable that $R_X$ is each independently a hydrogen atom, a substituted or unsubstituted heterocyclic group having 6 to 14 ring atoms, a substituted or unsubstituted alkyl group having 1 to 6 carbon atoms, or a substituted or unsubstituted alkylsilyl group having 3 to 18 carbon atoms.

In the first exemplary embodiment, carbon atoms forming a ring (also referred to as "ring carbon atoms") indicates the number of carbon atoms in atoms forming a ring of a compound in which the atoms are bonded to each other to form a cyclic structure (e.g., monocyclic compound, fused cyclic compound, cross-linking compound, carbon ring compound, and heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

In the first exemplary embodiment, atoms forming a ring (also referred to as "ring atoms") indicates the number of atoms forming a ring of a compound (e.g., monocyclic compound, fused cyclic compound, cross-linking compound, carbon ring compound, and heterocyclic compound) in which the atoms are bonded to each other to form a cyclic structure (e.g., monocyclic ring, fused ring, and ring system). Atom(s) not forming the ring (e.g., a hydrogen atom for terminating the atoms forming the ring) and atoms included in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms and atoms forming the substituents respectively bonded to carbon atoms of the pyridine ring or the quinazoline ring are not counted in the number of the ring atoms. When a fluorene ring is substituted by, for instance, a fluorene ring (e.g., a spirofluorene ring), the number of atoms of the fluorene ring as a substituent is not included in the number of the ring atoms for the fluorene ring.

Next, each of substituents described in the above formulae will be described.

In the first exemplary embodiment, examples of the aryl group (occasionally referred to as an aromatic hydrocarbon group) having 6 to 30 ring carbon atoms include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 12 ring carbon atoms. Among the above aryl group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

In the first exemplary embodiment, the heterocyclic group having 5 to 30 ring atoms (occasionally referred to as a heteroaryl group, heteroaromatic cyclic group or an aromatic heterocyclic group) includes, as a hetero atom, preferably at least one atom selected from the group consisting of nitrogen, sulfur, oxygen, silicon, selenium and germanium, more preferably at least one atom selected from the group consisting of nitrogen, sulfur and oxygen.

Examples of the heterocyclic group having 5 to 30 ring atoms in the exemplary embodiment include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazole group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

The alkyl group having 1 to 30 carbon atoms in the exemplary embodiment is preferably linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group, and neopentyl group are particularly preferable.

Examples of the cycloalkyl group in the exemplary embodiment include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the above cycloalkyl group, a cyclopentyl group and a cyclohexyl group are particularly preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkylsilyl group having 3 to 30 carbon atoms in the exemplary embodiment is exemplified by a trialkylsilyl group having the above alkyl group having 1 to 30 carbon atoms. Specific examples of the trialkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and tri-isopropylsilyl group. Three alkyl groups in the trialkylsilyl group may be mutually the same or different.

Examples of the arylsilyl group having 6 to 60 ring carbon atoms in the exemplary embodiment include a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms.

The alkyldiarylsilyl group is exemplified by an alkyldiarylsilyl group having one of the examples of the alkyl group having 1 to 30 carbon atoms and two of the aryl group having 6 to 30 ring carbon atoms. The dialkylarylsilyl group preferably has 13 to 30 carbon atoms.

The triarylsilyl group is exemplified by a triarylsilyl group having three of the aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $-OZ_1$ is exemplified by the above alkyl group having 1 to 30 carbon atoms. Examples of the alkoxy group include a methoxy group, ethoxy group, propoxy group, butoxy group, pentyloxy group and hexyloxy group.

A halogenated alkoxy group provided by substituting the alkoxy group with a halogen atom is exemplified by a halogenated alkoxy group provided by substituting the alkoxy group having 1 to 30 carbon atoms with one or more halogen groups.

The aryloxy group having 6 to 30 ring carbon atoms in the exemplary embodiment is represented by $-OZ_2$. $Z_2$ is exemplified by the above aryl group having 6 to 30 ring carbon atoms. The aryloxy group is exemplified by a phenoxy group.

The alkylamino group having 2 to 30 carbon atoms is represented by $-NHR_V$ or $-N(R_V)_2$. $R_V$ is exemplified by the alkyl group having 1 to 30 carbon atoms.

The arylamino group having 6 to 60 ring carbon atoms is represented by $-NHR_W$ or $-N(R_W)_2$. $R_W$ is exemplified by the above aryl group having 6 to 30 ring carbon atoms.

The alkylthio group having 1 to 30 carbon atoms is represented by $-SR_V$. $R_V$ is exemplified by the alkyl group having 1 to 30 carbon atoms.

The arylthio group having 6 to 30 ring carbon atoms is represented by $-SR_W$. $R_W$ is exemplified by the above aryl group having 6 to 30 ring carbon atoms.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

In the invention, a "hydrogen atom" means isotopes having different neutron numbers and specifically encompasses protium, deuterium and tritium.

Examples of the substituents in the first exemplary embodiment ("substituted or unsubstituted") and the substituent in the cyclic structures A, A1, A2, B, B1, B2, C, C1, C2, $Z^1$ to $Z^4$ and the like are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

In the above-described substituents, the aryl group, heterocyclic group, alkyl group, halogen atom, alkylsilyl group, arylsilyl group and cyano group are preferable. The preferable ones of the specific examples of each substituent are further preferable.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$—$Z_4$. $Z_3$ is exemplified by an alkylene group derived from the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom are fluorine, chlorine, bromine and iodine, among which a fluorine atom is preferable.

"Unsubstituted" in "substituted or unsubstituted" herein means that a group is not substituted by the above-described substituents but bonded with a hydrogen atom.

Examples of a substituent in "substituted or unsubstituted" herein include the above-described substituents. The substituent may be further substituted by the above-described substituents. The substituent in "substituted or unsubstituted" herein may be provided by a plurality of substituents. The plurality of substituents may be mutually bonded to form a ring.

In the exemplary embodiment, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX." "XX" and "YY" each mean an integer of 1 or more.

In the exemplary embodiment, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX." "XX" and "YY" each mean an integer of 1 or more.

The same description as the above applies to "substituted or unsubstituted" in the following compound or a partial structure thereof.

In the first exemplary embodiment, when the substituents are mutually bonded to form a cyclic structure, the cyclic structure is a saturated ring, unsaturated ring, aromatic hydrocarbon ring, or heterocyclic ring.

In the first exemplary embodiment, the aryl group and the heteroaryl group as the linking group are exemplified by a divalent or multivalent group obtained by removing at least one atom from the above-described monovalent group.

In the first exemplary embodiment, the aromatic hydrocarbon ring and the heterocyclic ring are exemplified by a cyclic structure from which the above-described monovalent group is derived.

Specific examples of the compound represented by the formula (1) are shown below, but the invention is not limited thereto.

[Formula 58]

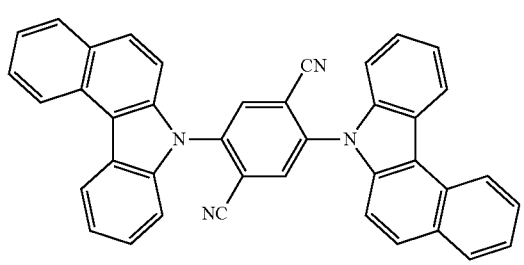

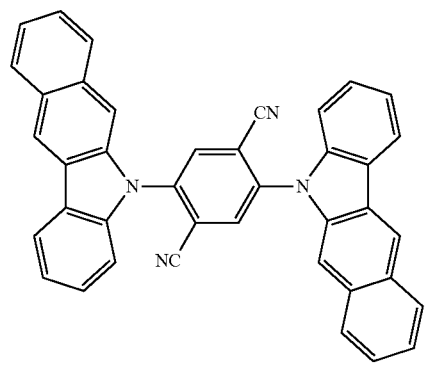

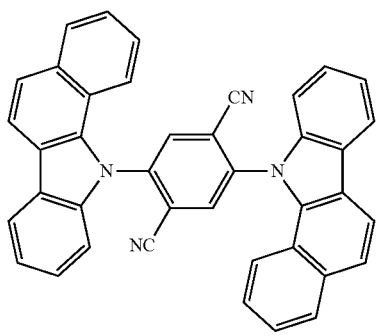
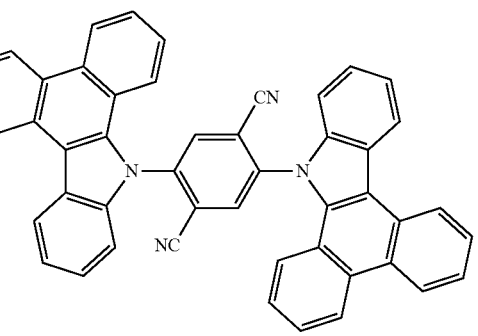
[Formula 59]
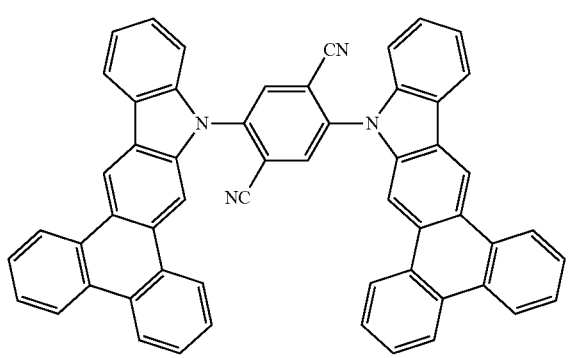
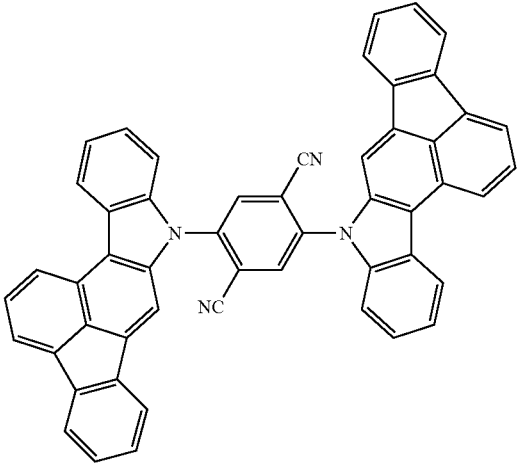
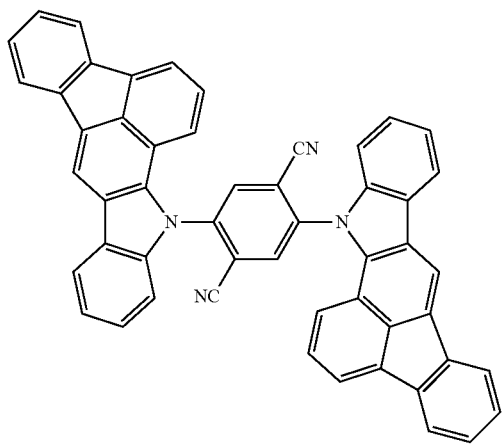
[Formula 60]
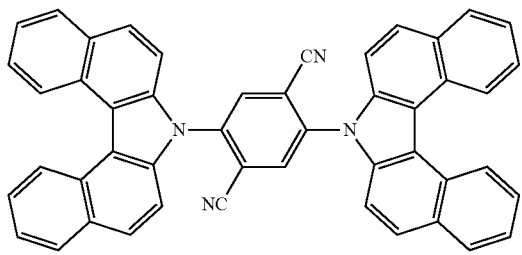

[Formula 61]
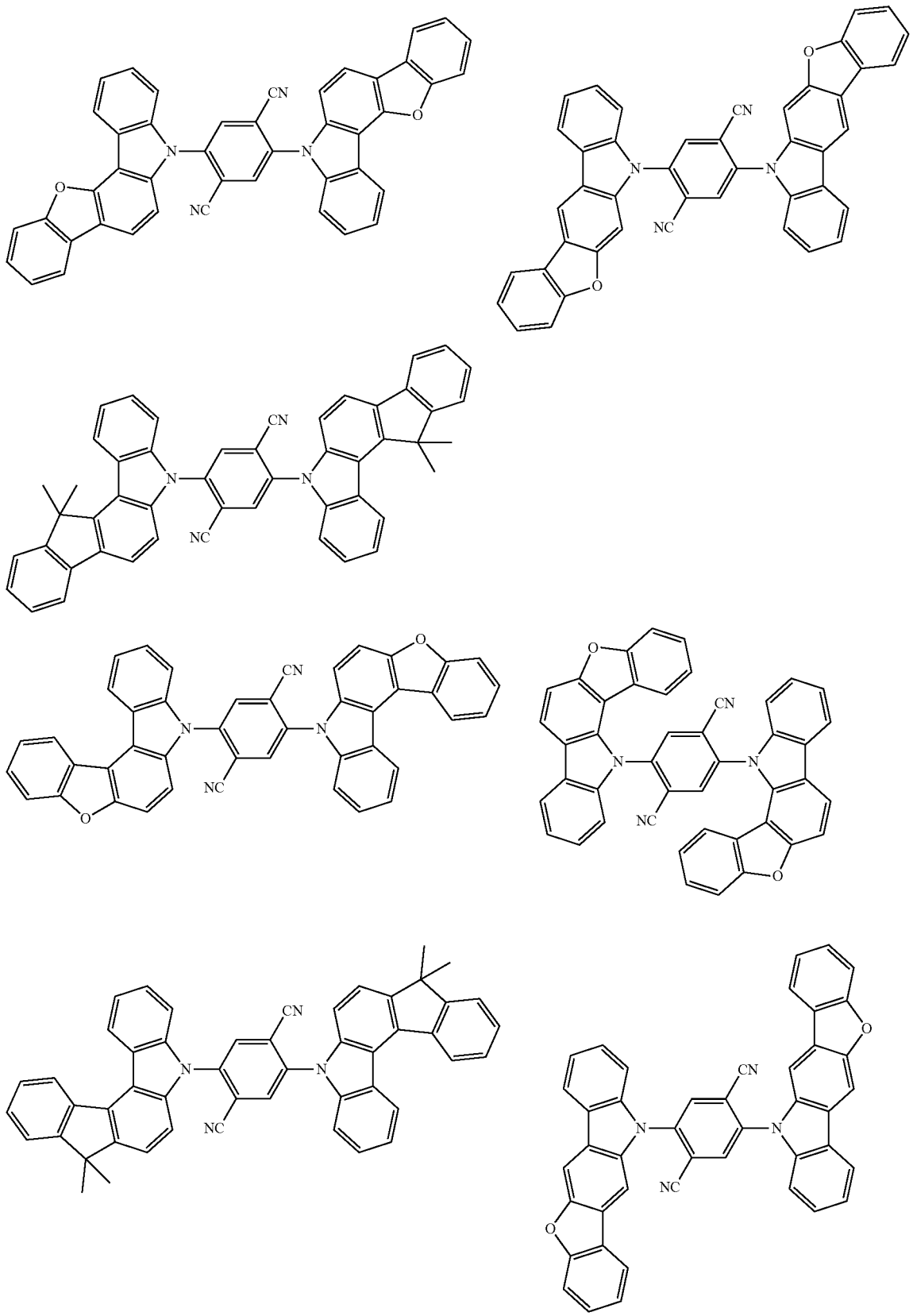

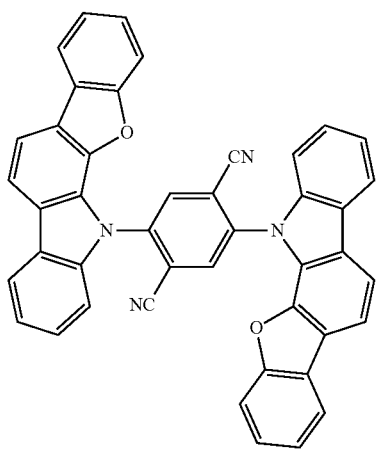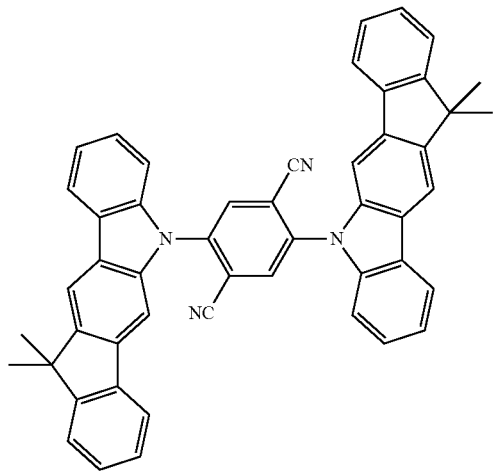
[Formula 62]
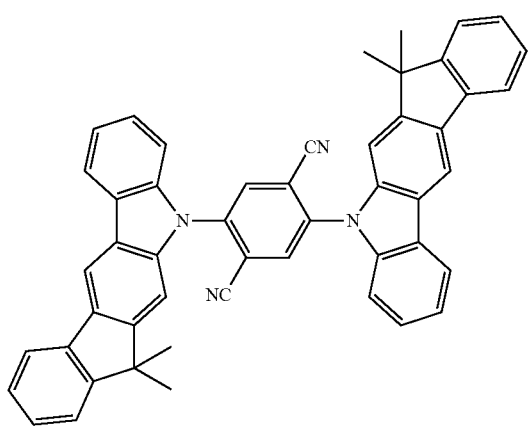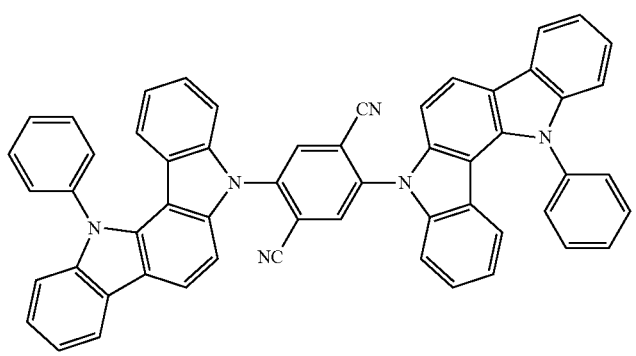

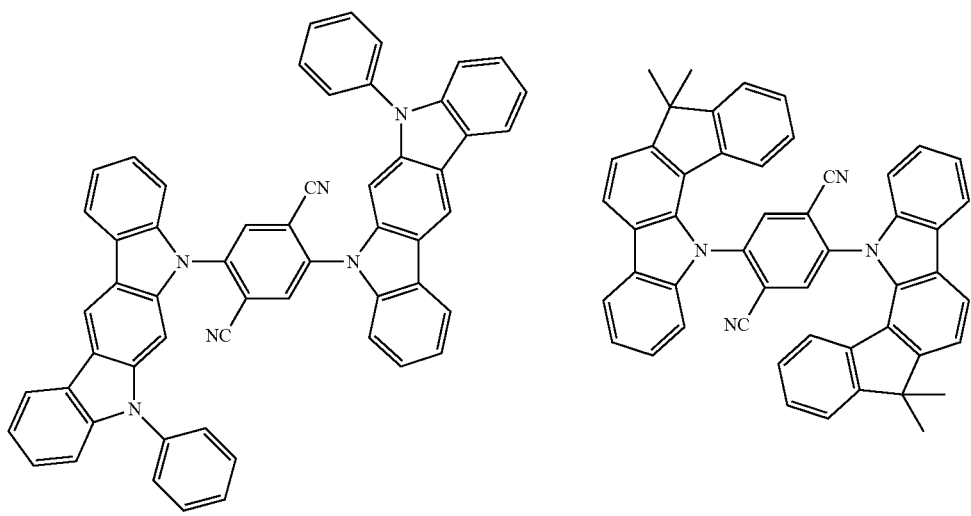
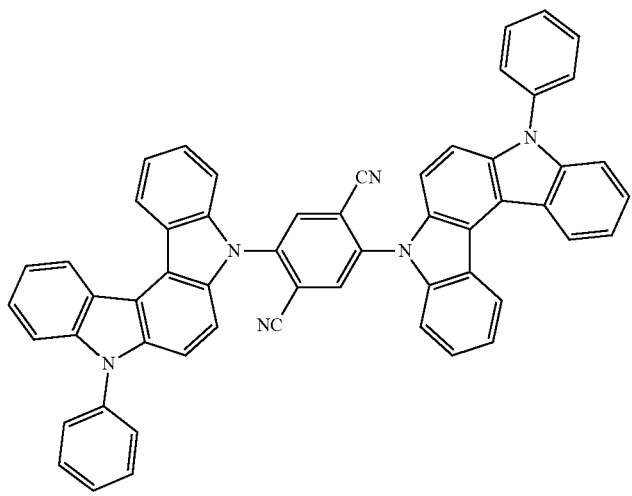
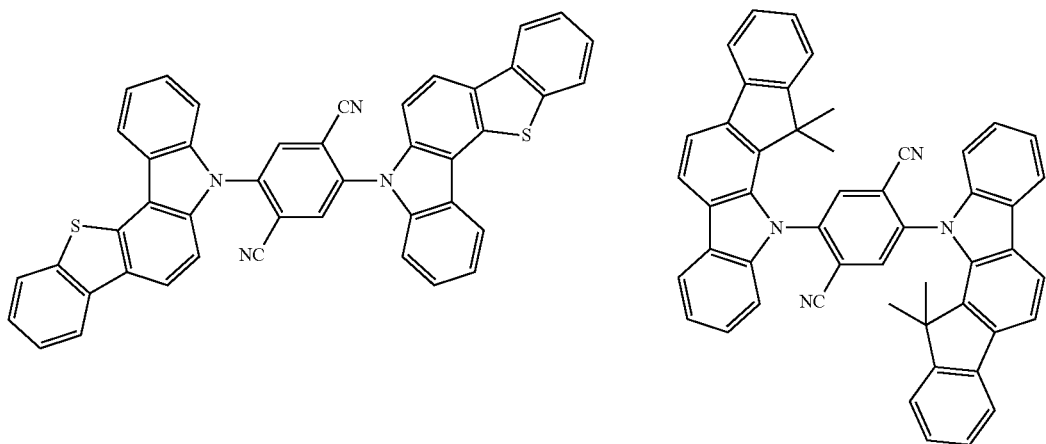

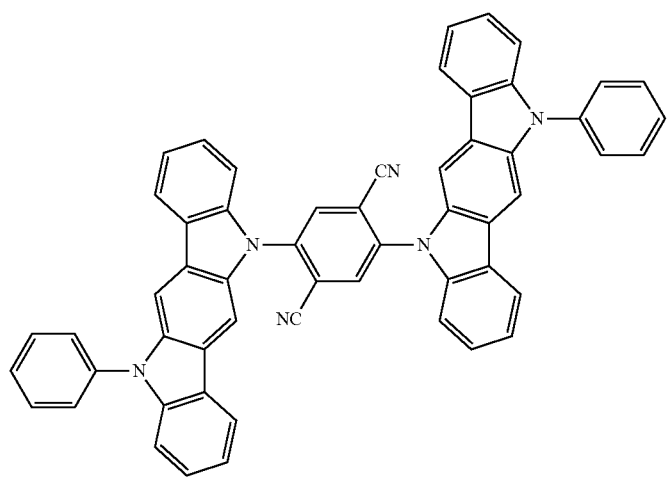
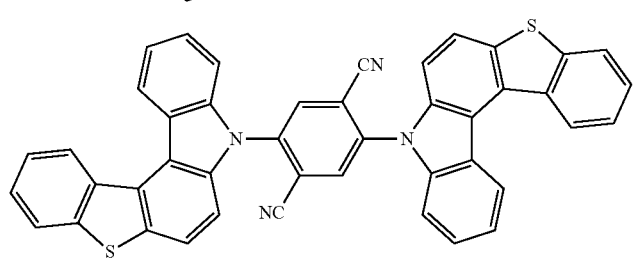
[Formula 63]
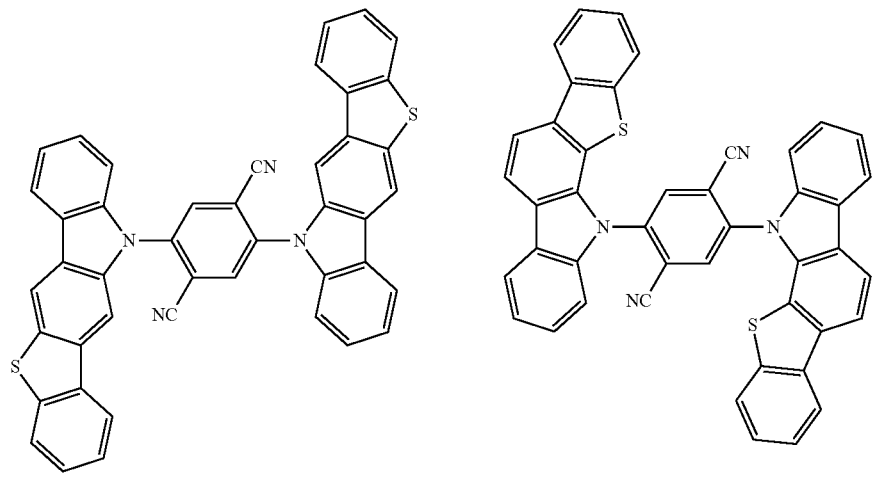
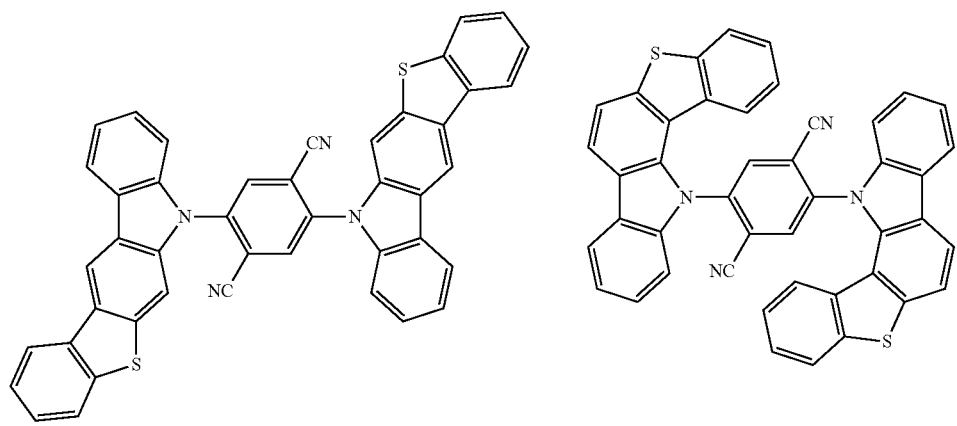

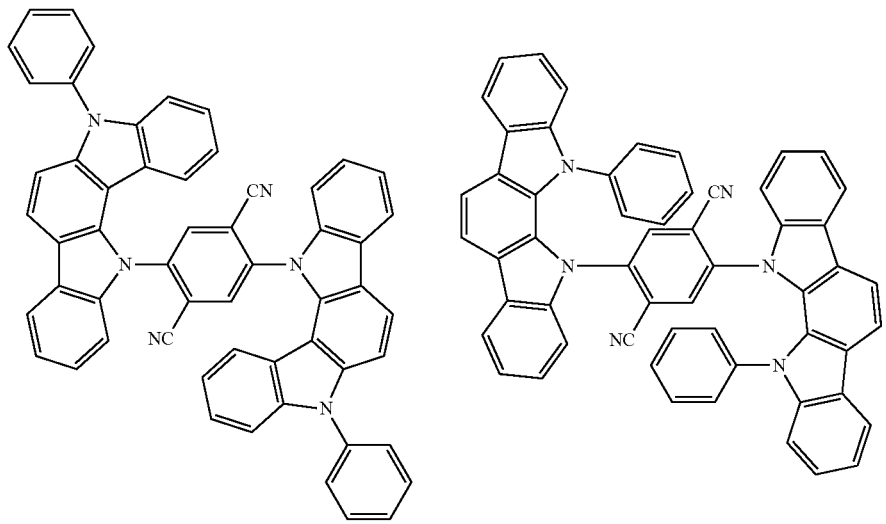
[Formula 64]
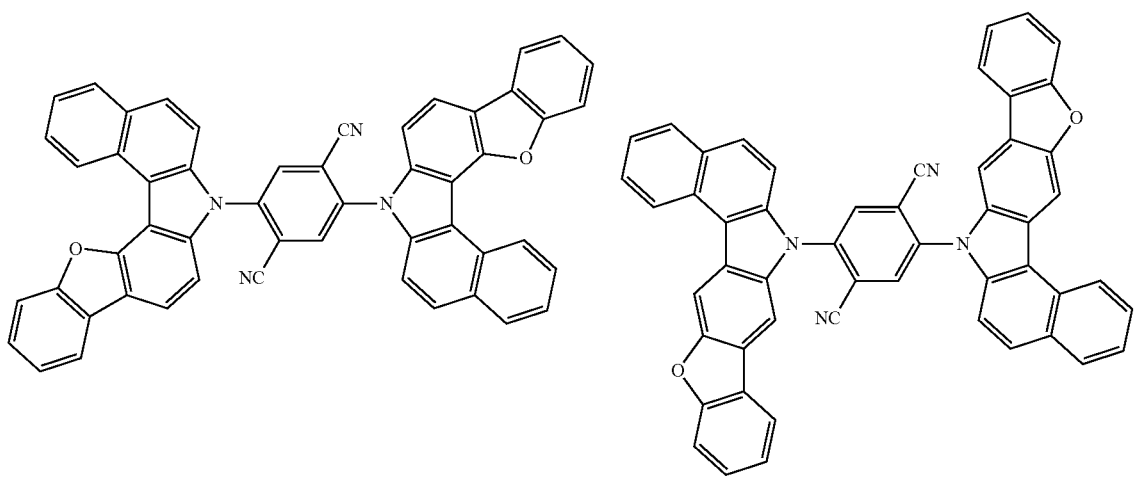
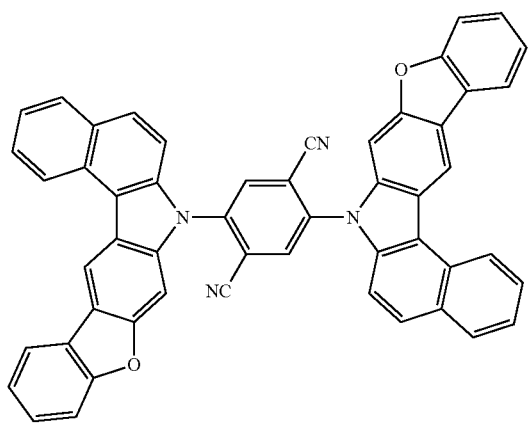

45
46
-continued
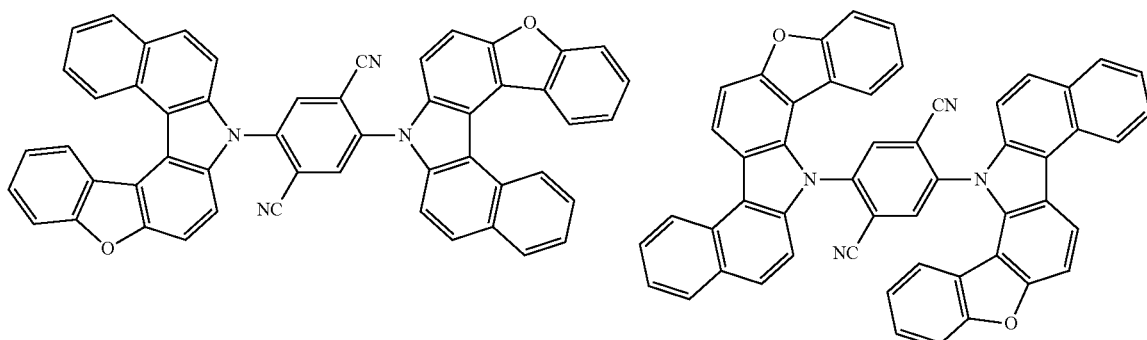
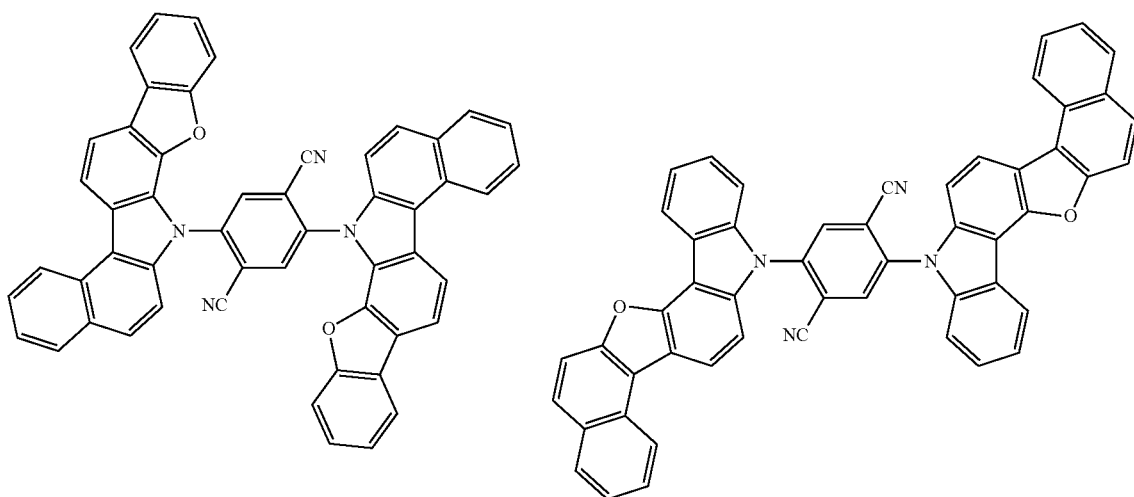
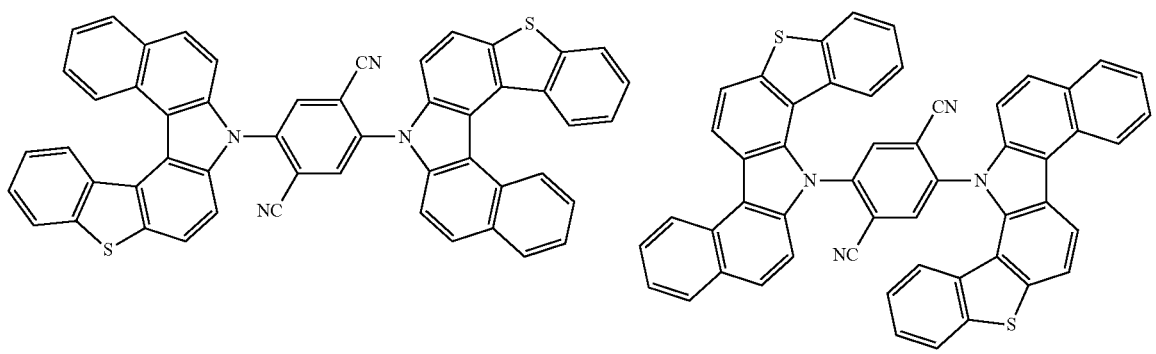
[Formula 65]
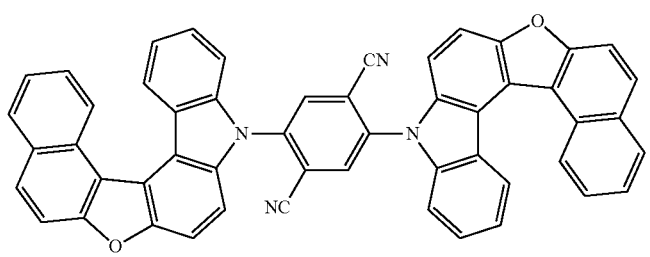

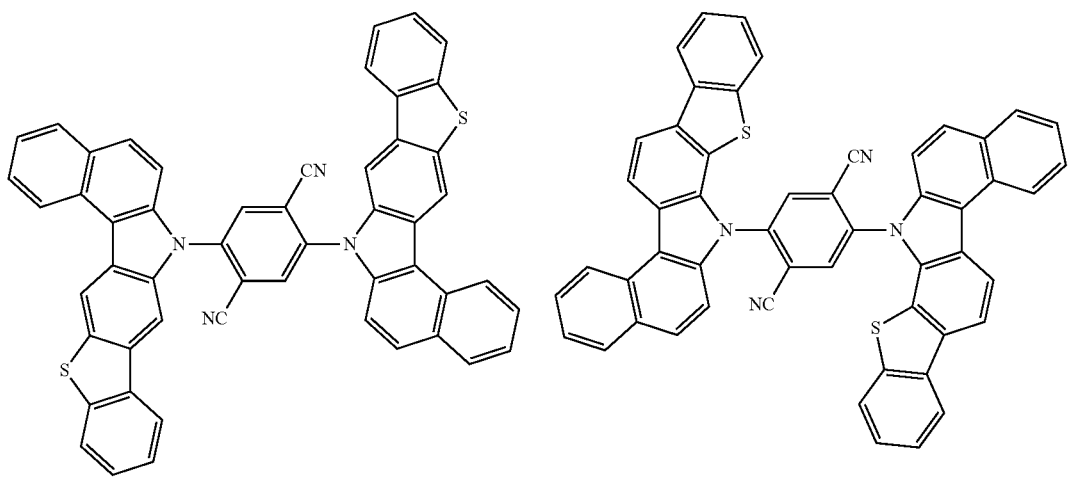
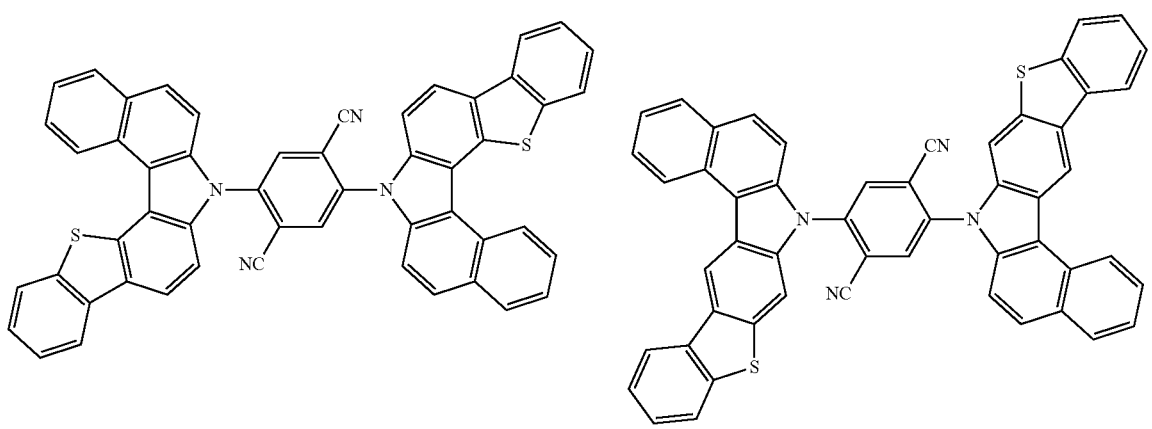
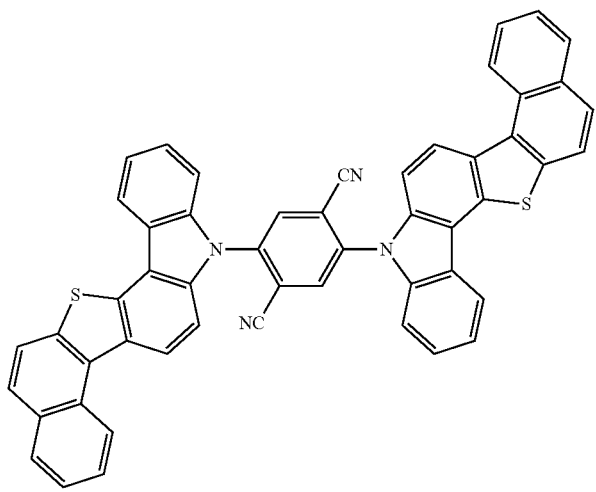

-continued
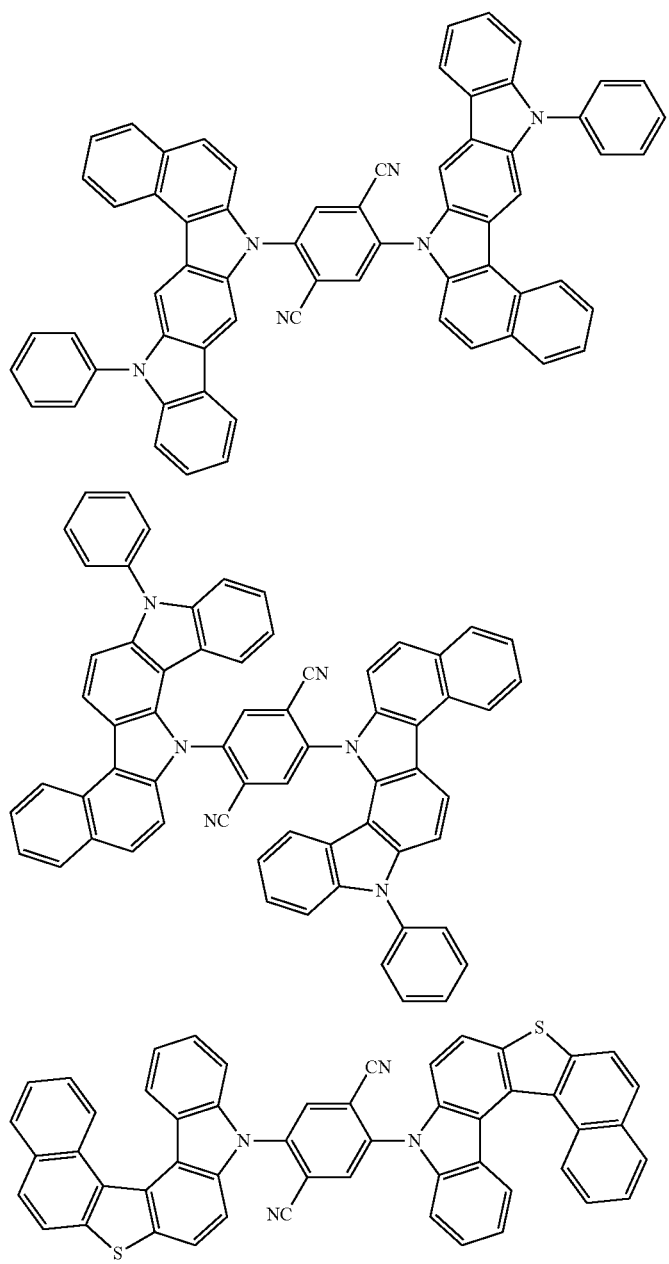
[Formula 66]
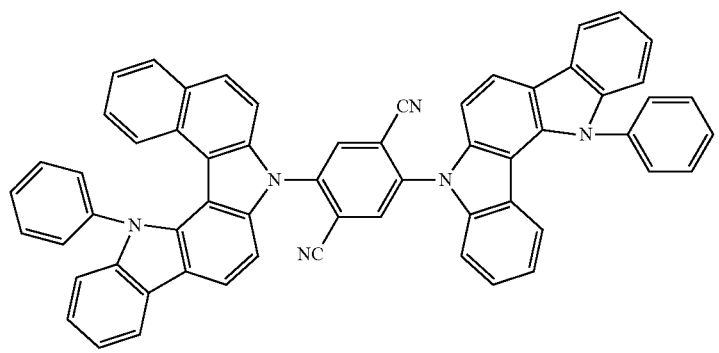

-continued
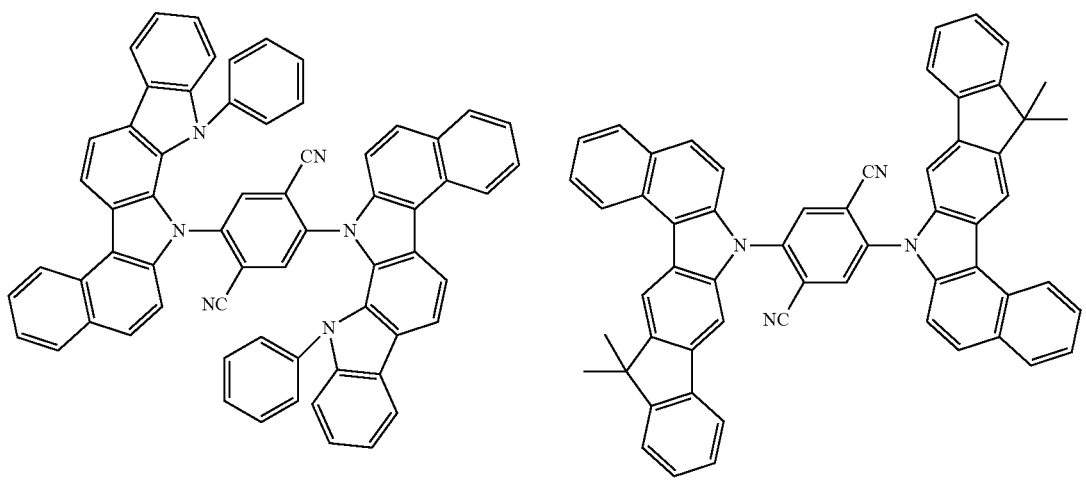
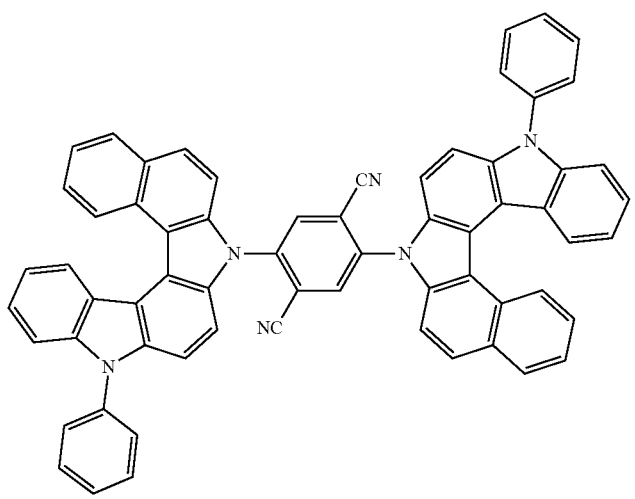
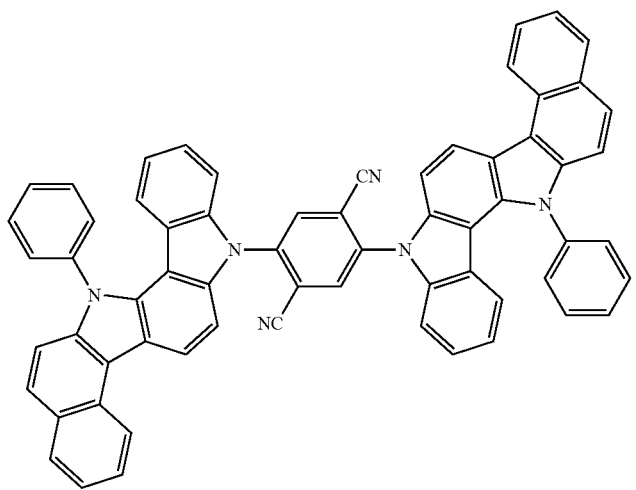

-continued
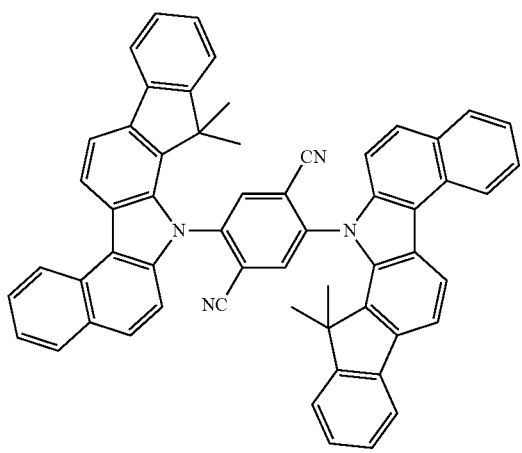 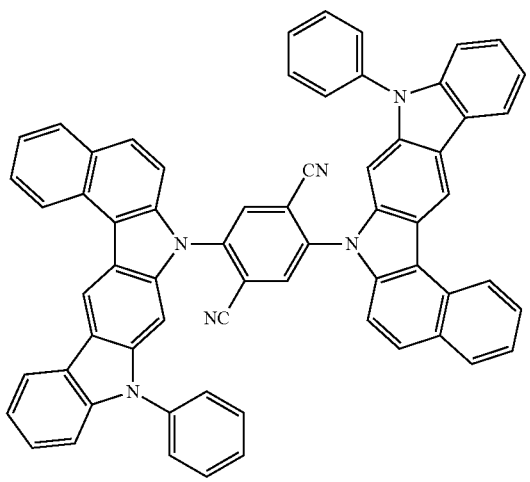
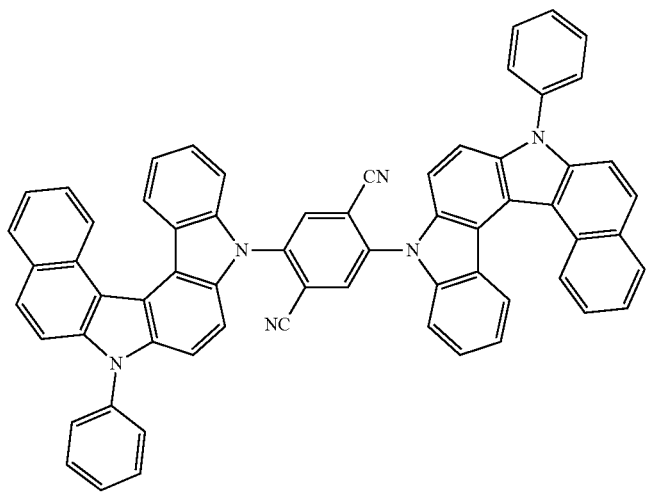
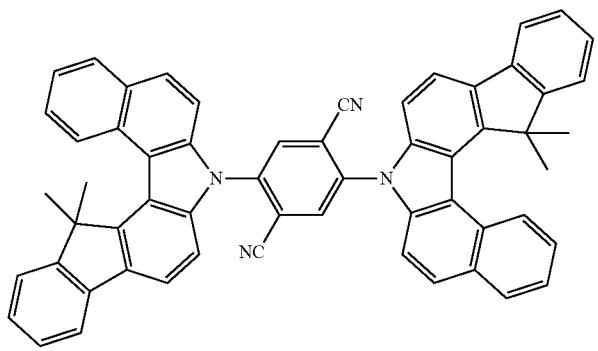

[Formula 67]
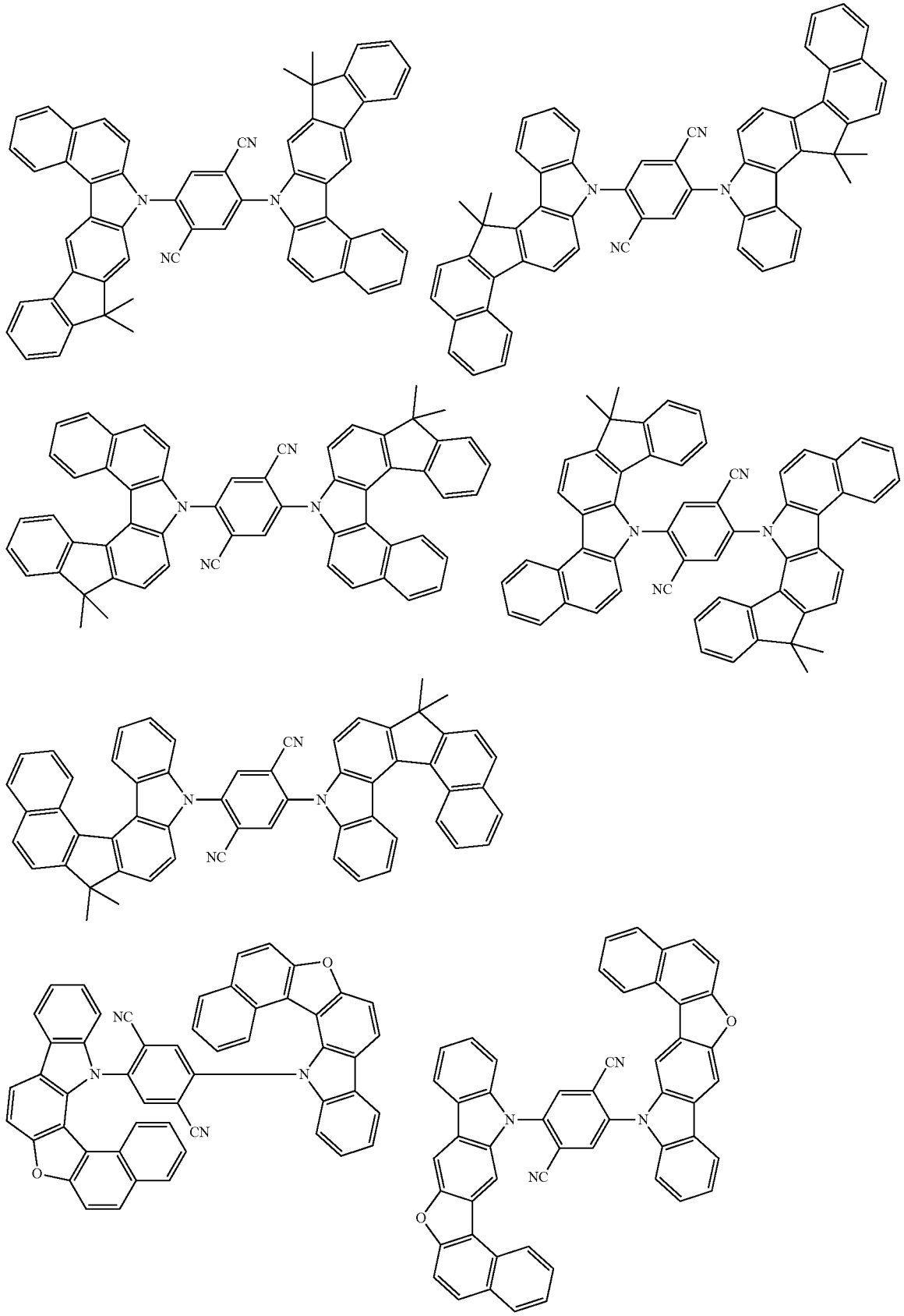

-continued
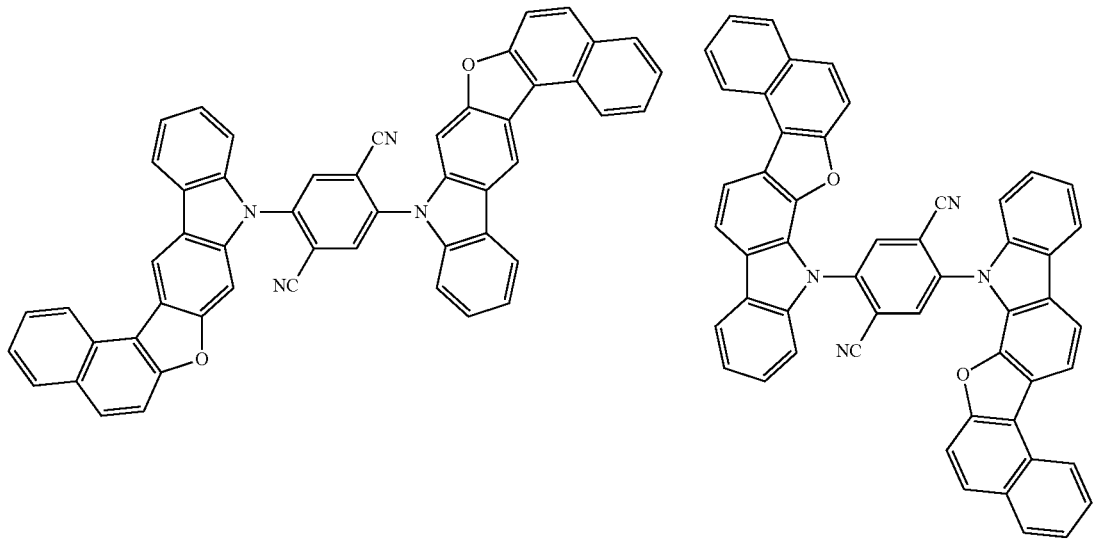
[Formula 68]
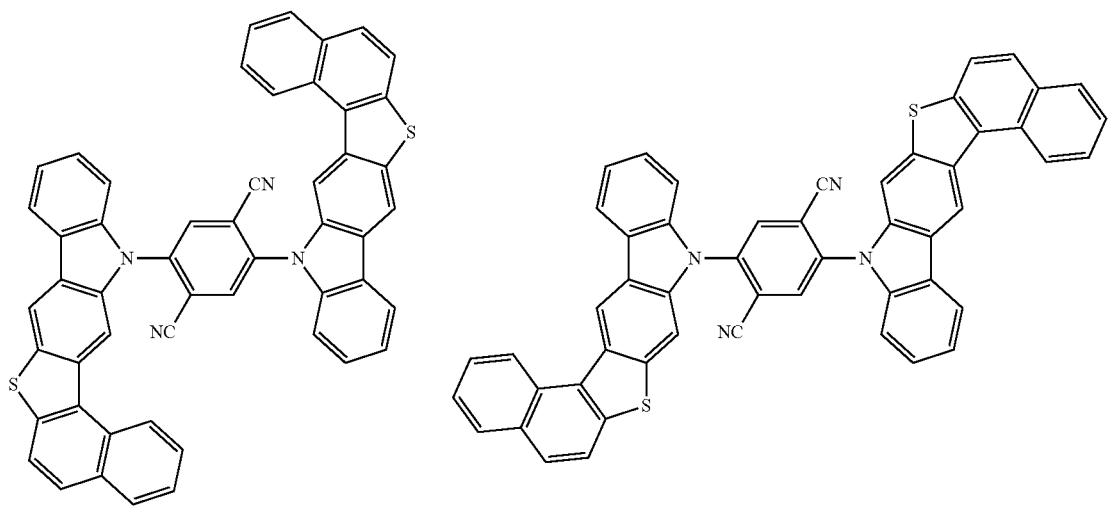
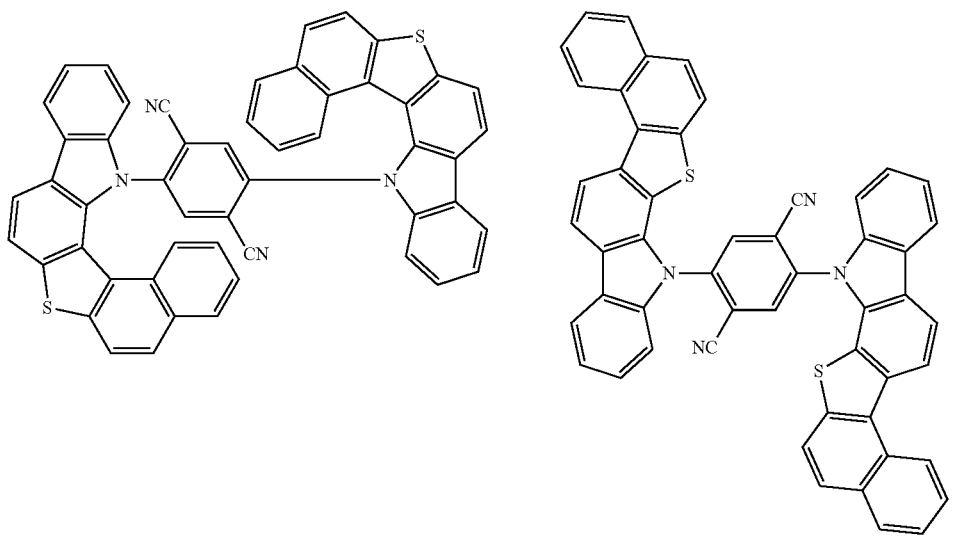

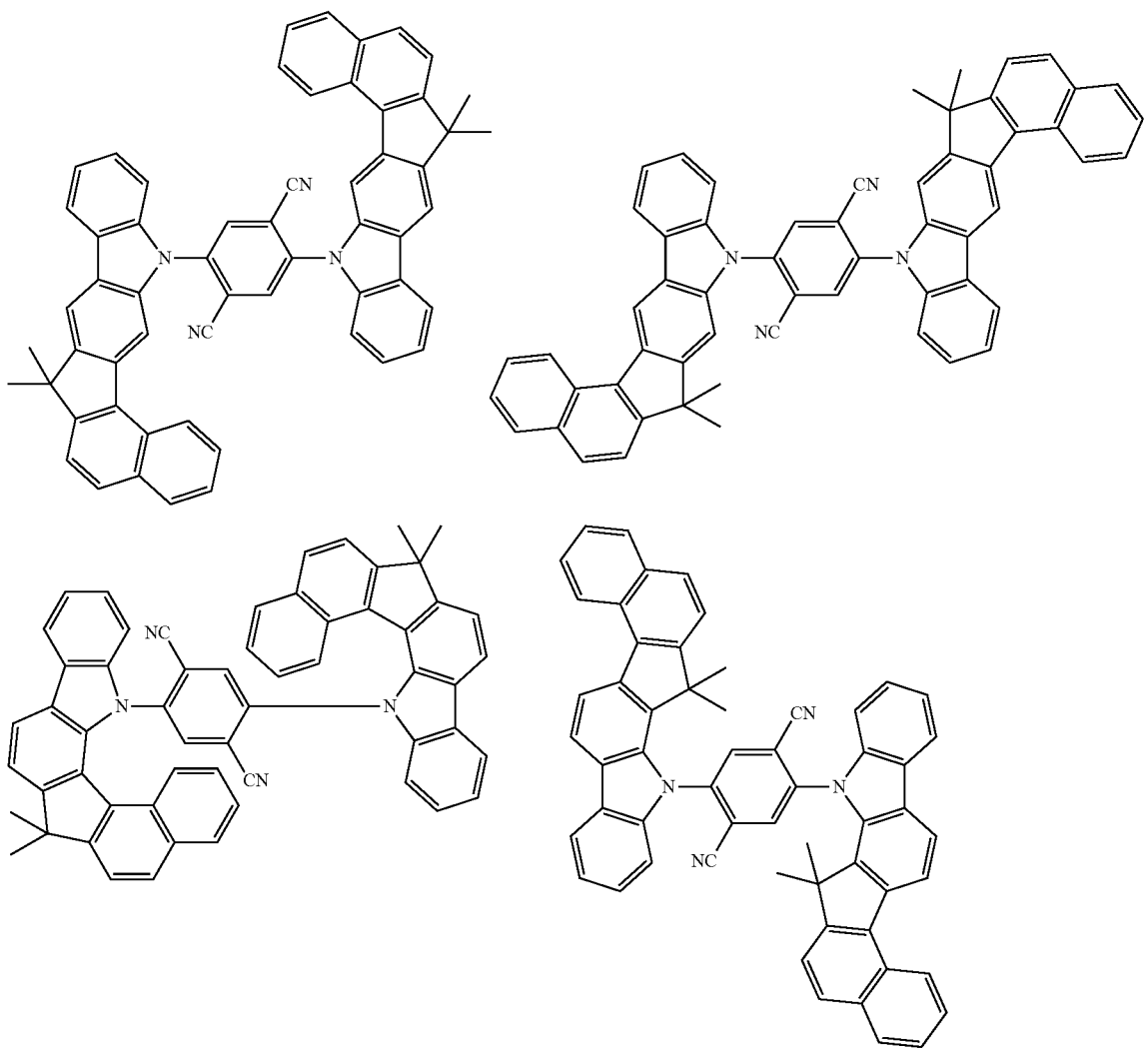
[Formula 69]
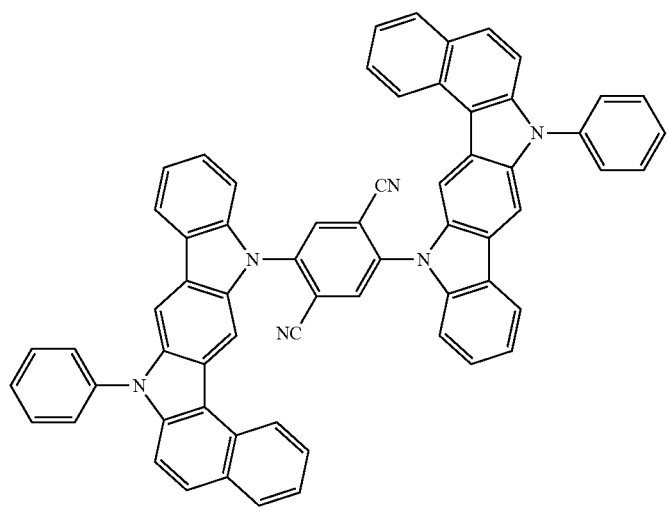

-continued
61 62
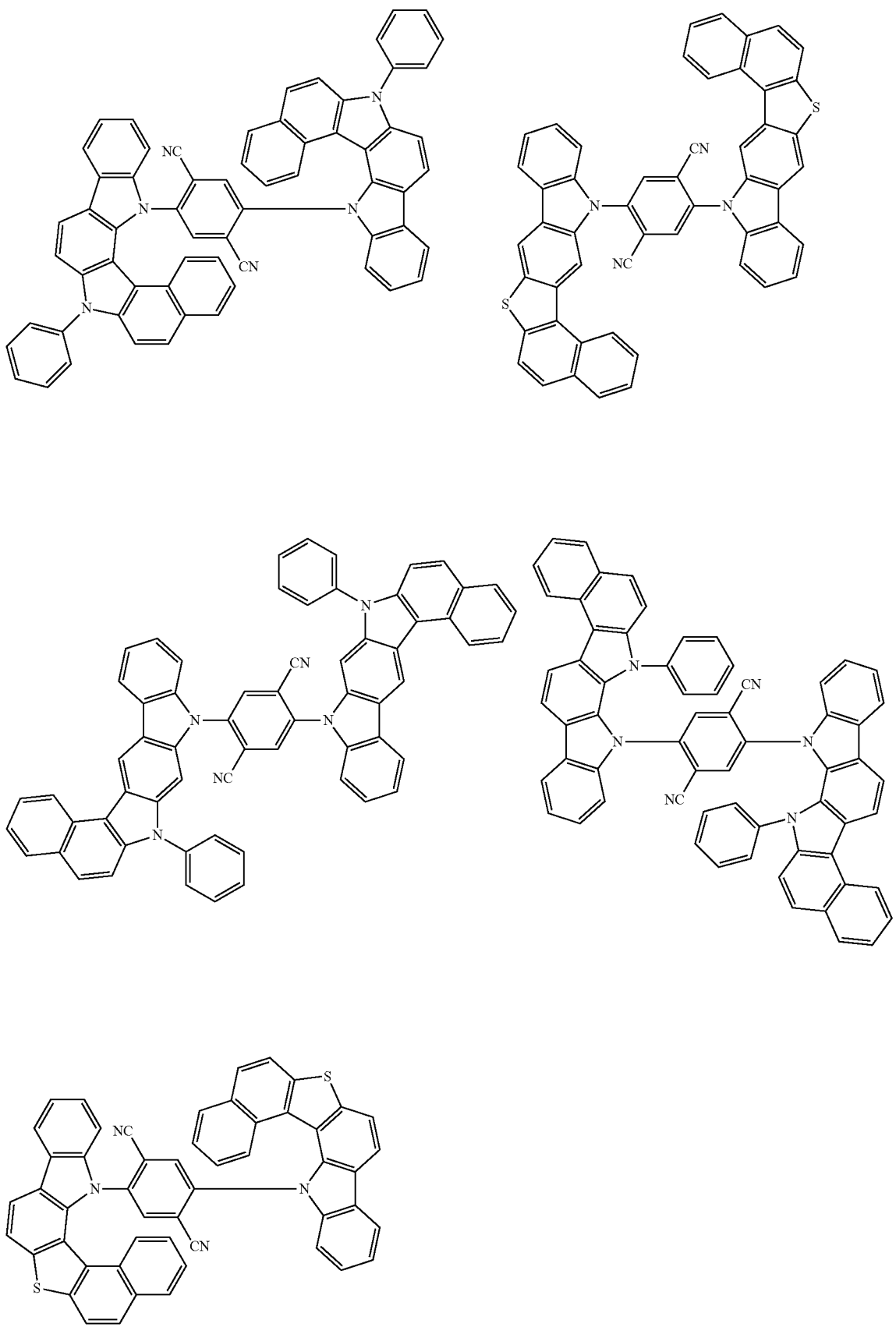

-continued
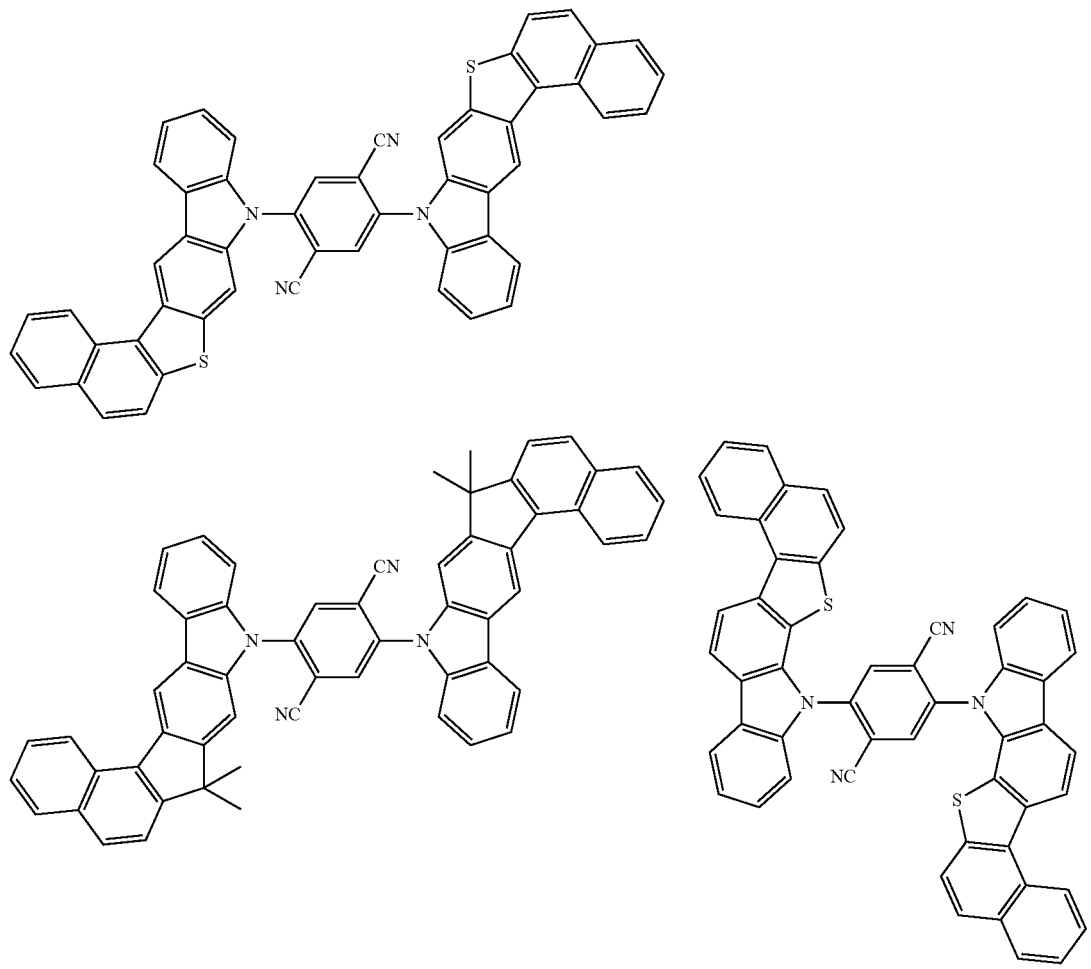
[Formula 70]
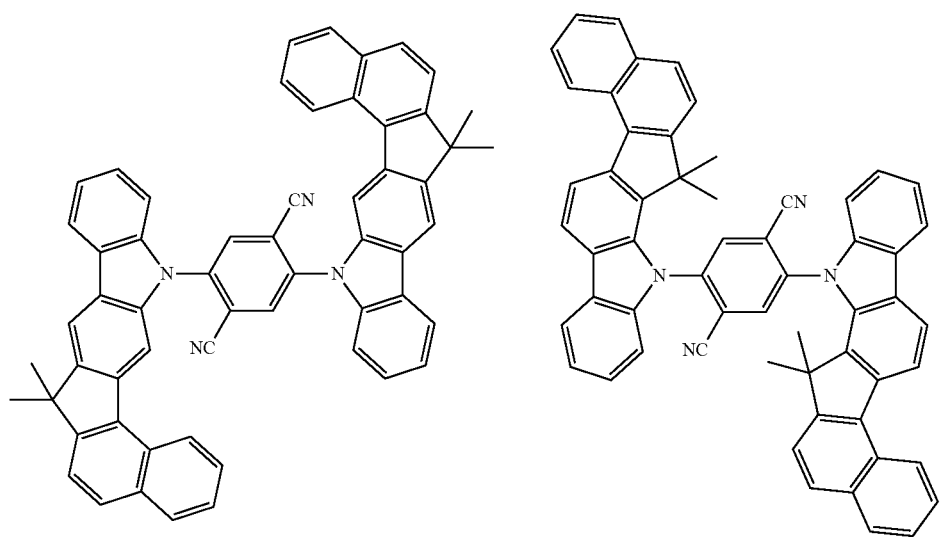

-continued
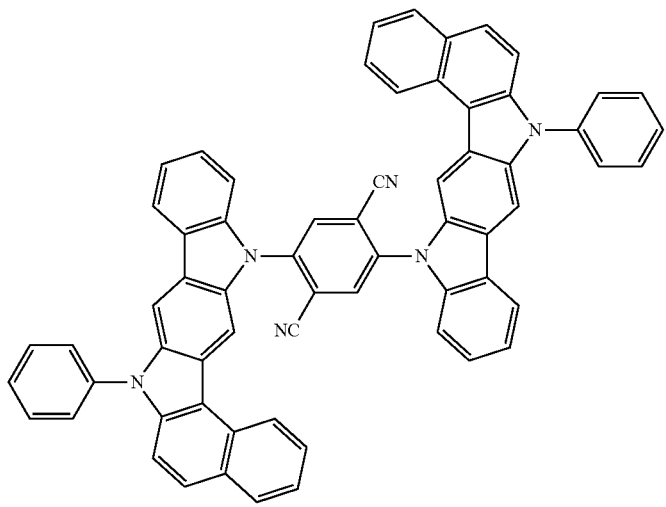
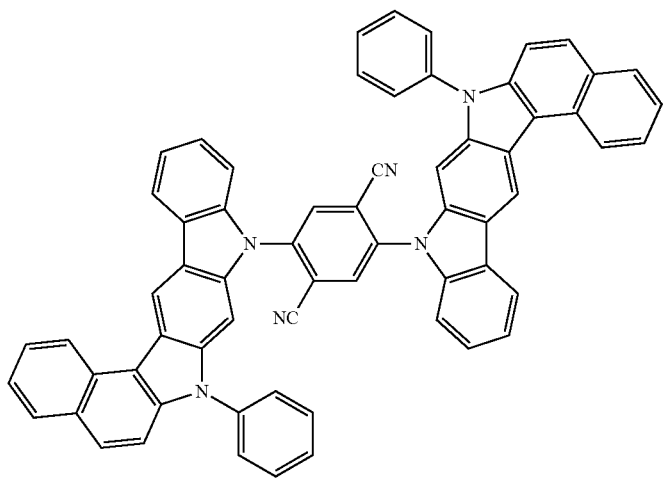
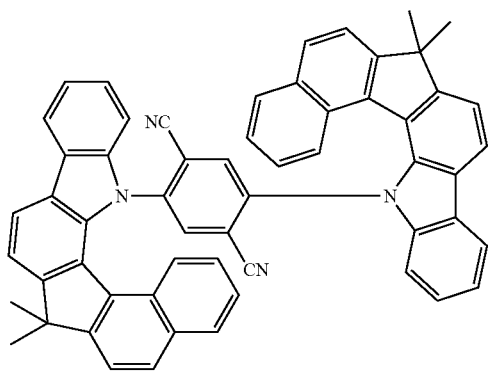

-continued
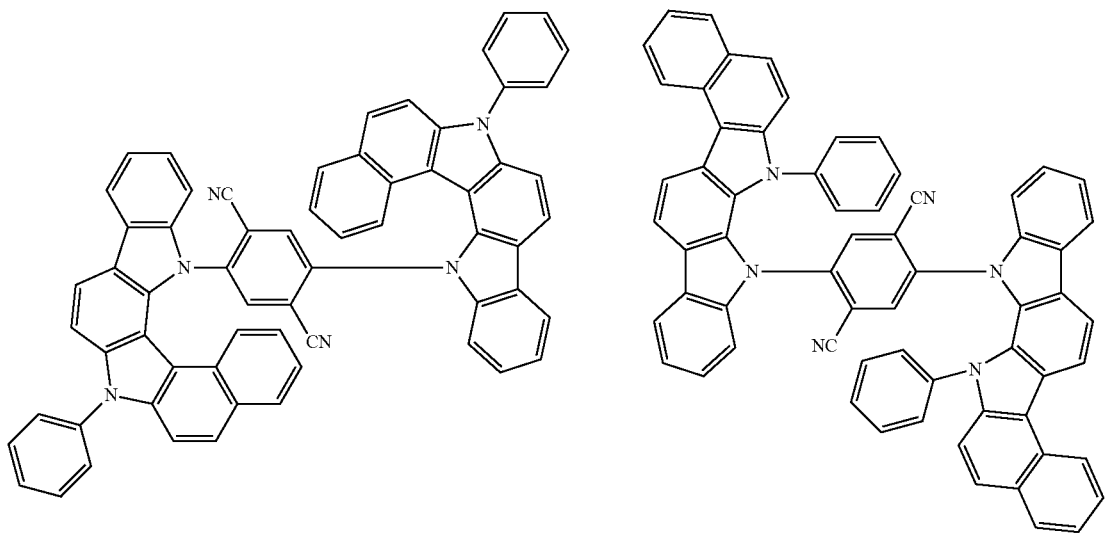
[Formula 71]
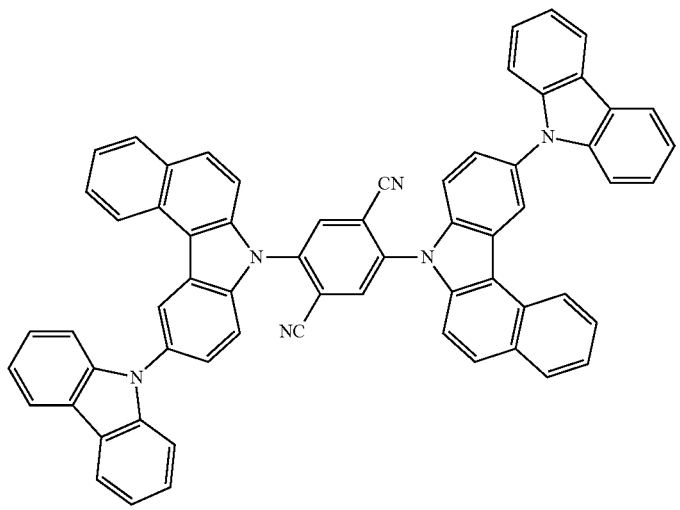
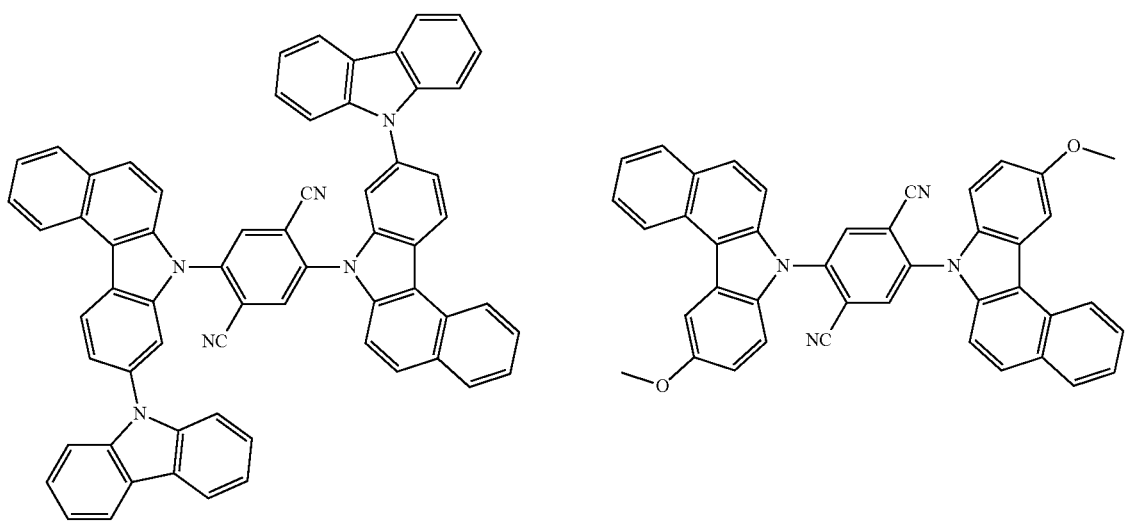

-continued
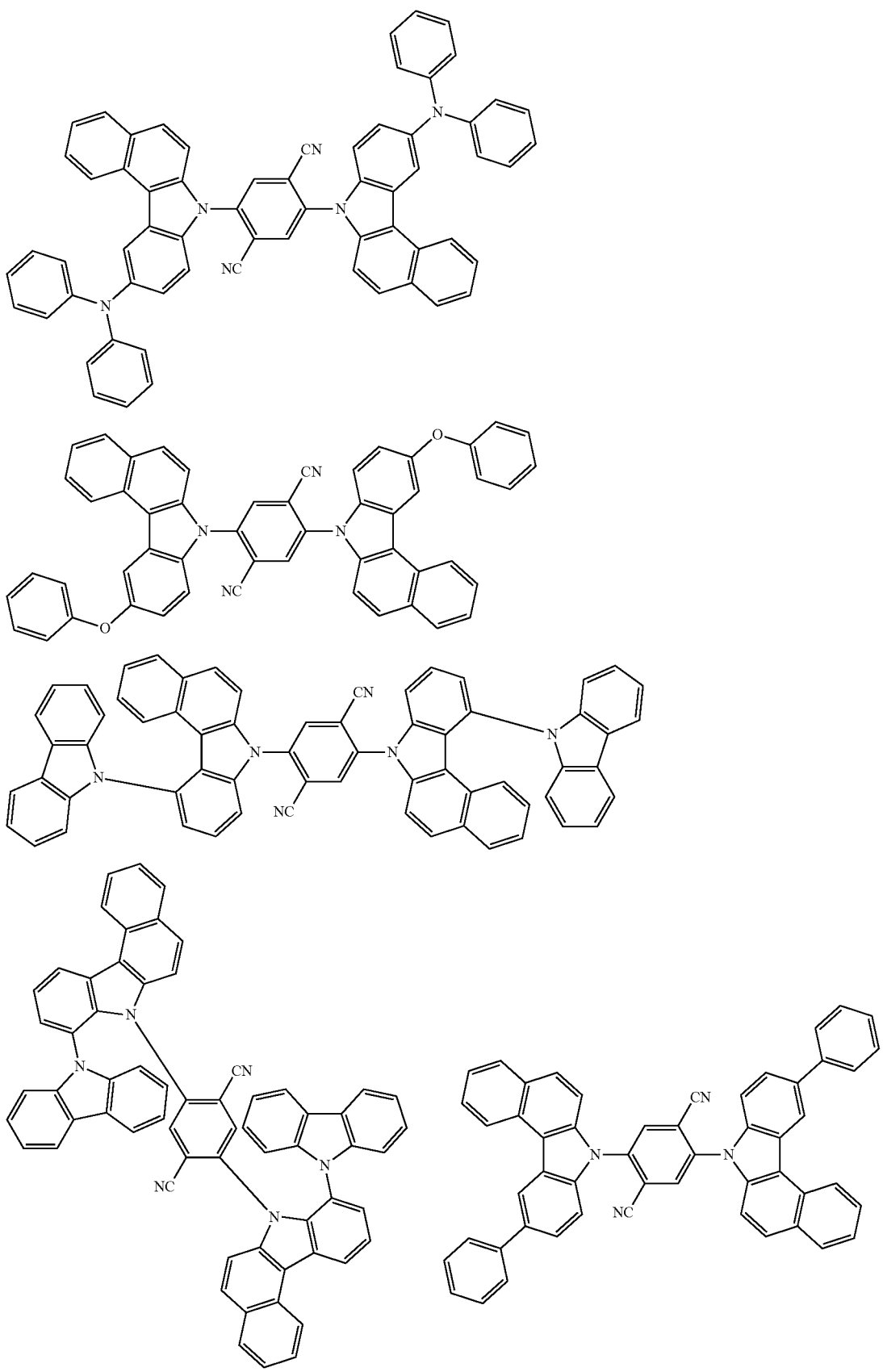

[Formula 72]
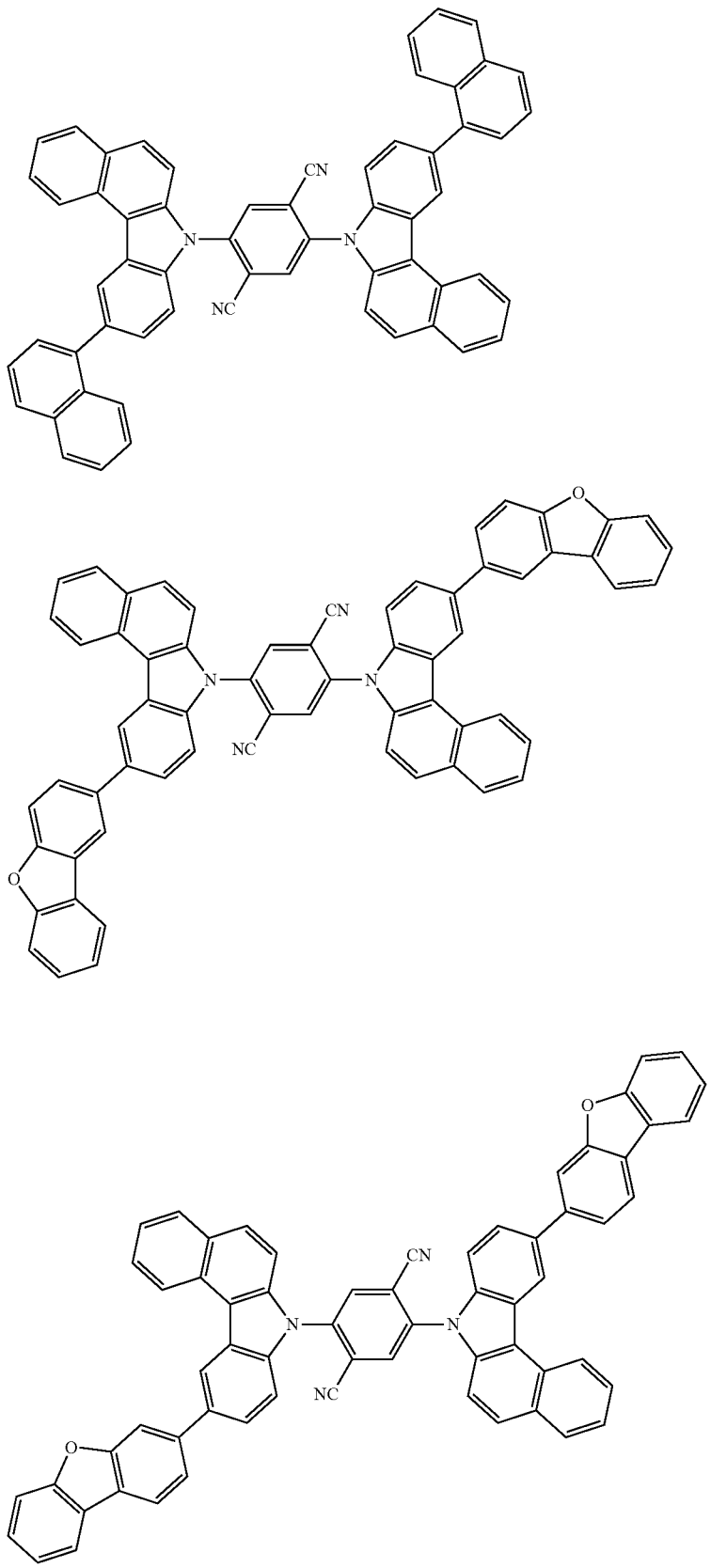

73 74
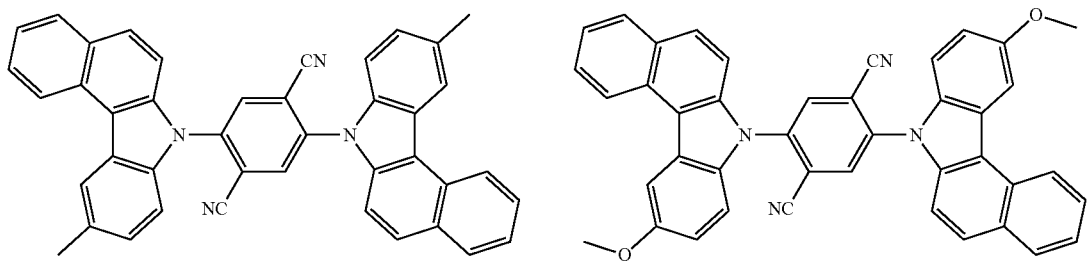
-continued
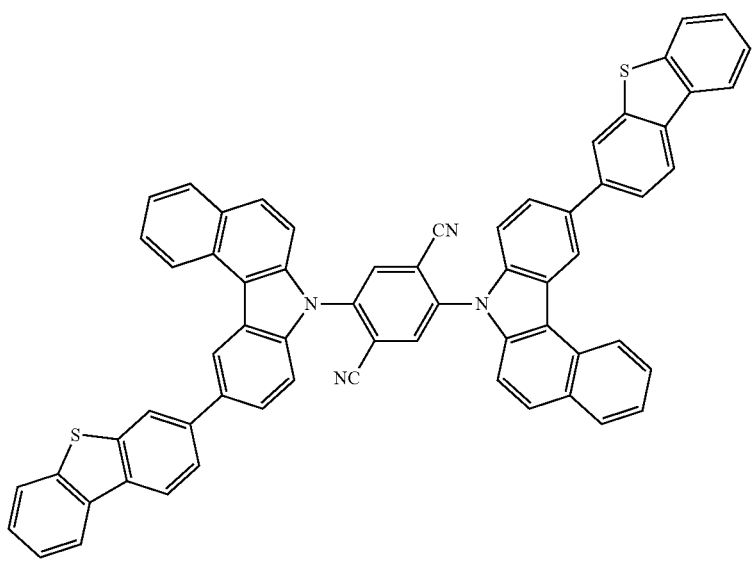
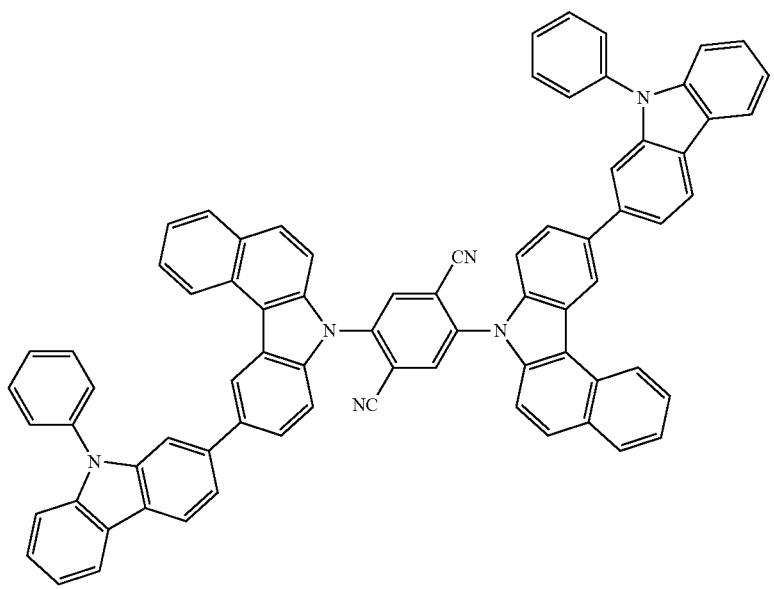

[Formula 73]
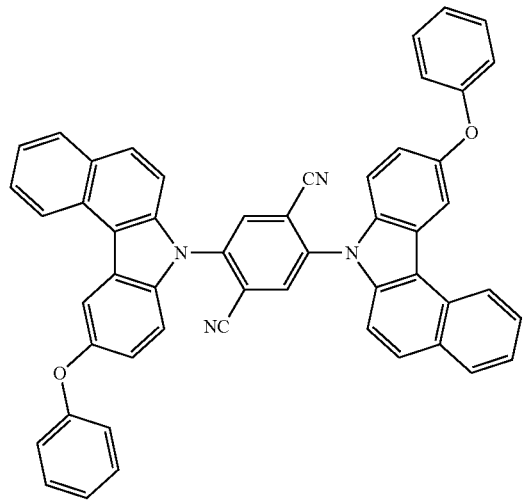
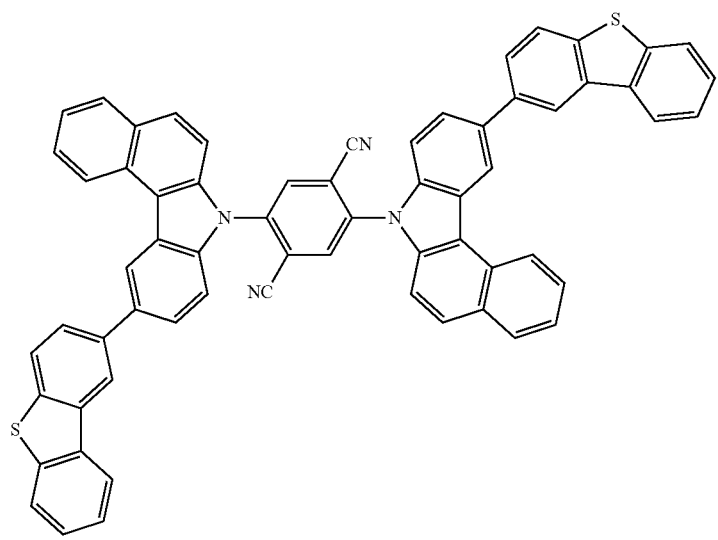
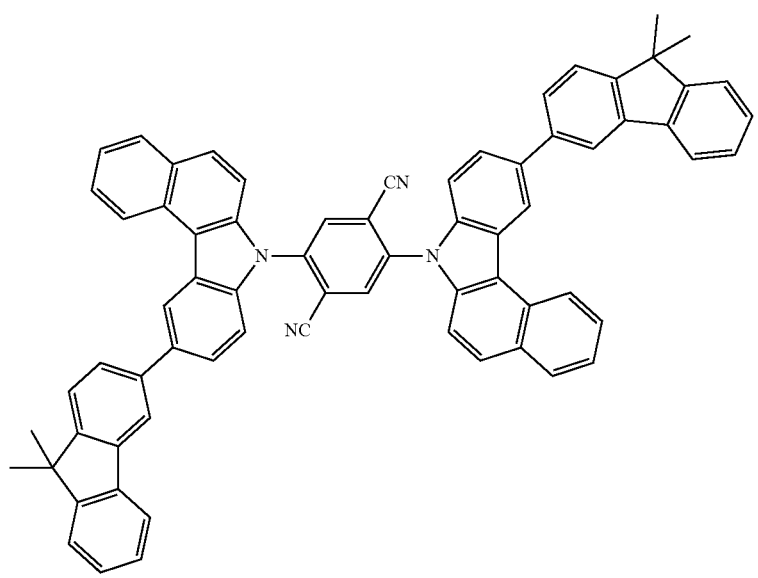

-continued
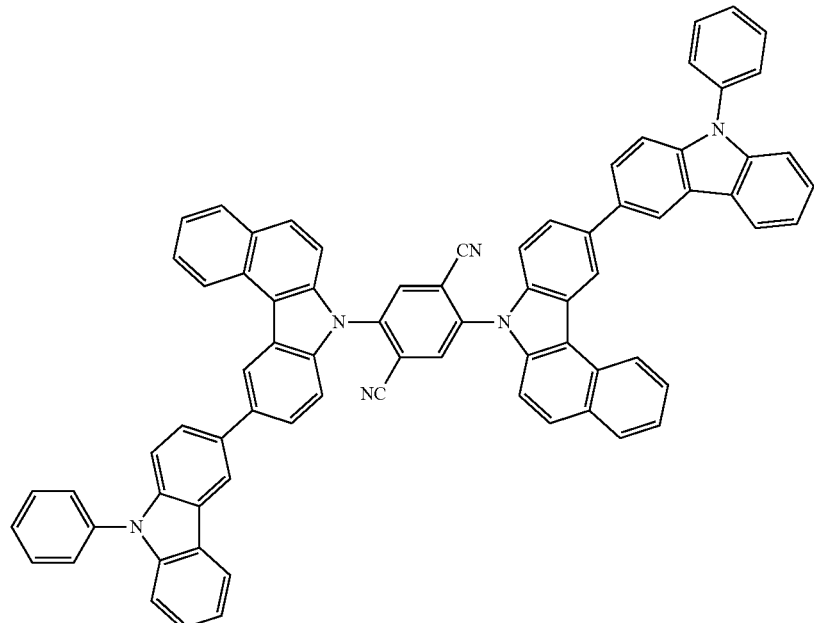
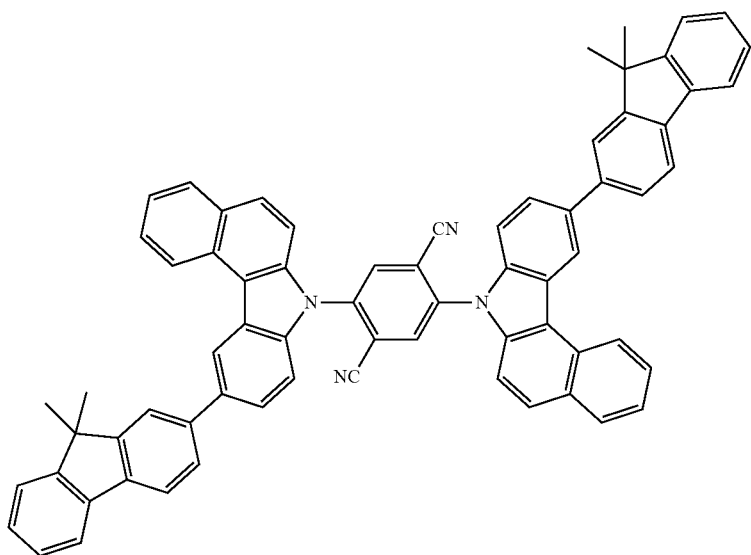
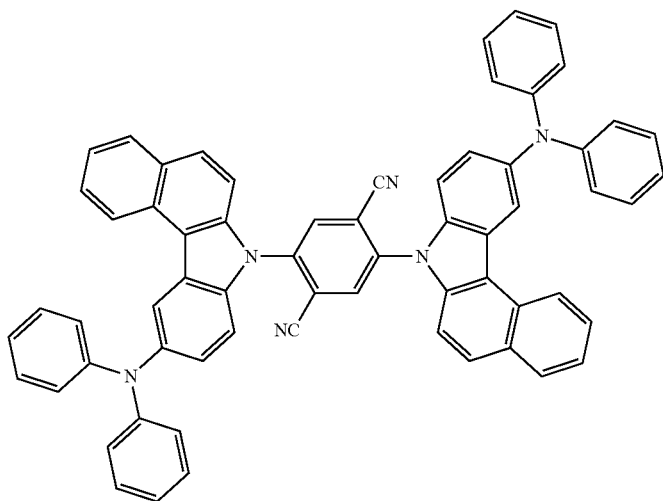

[Formula 74]
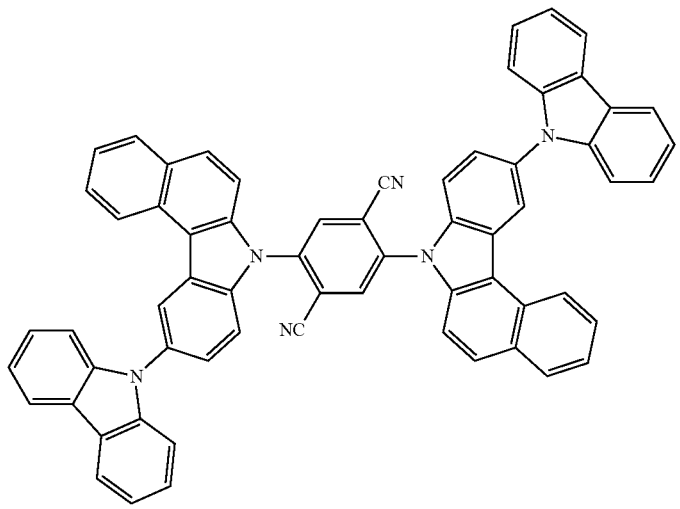
[Formula 75]
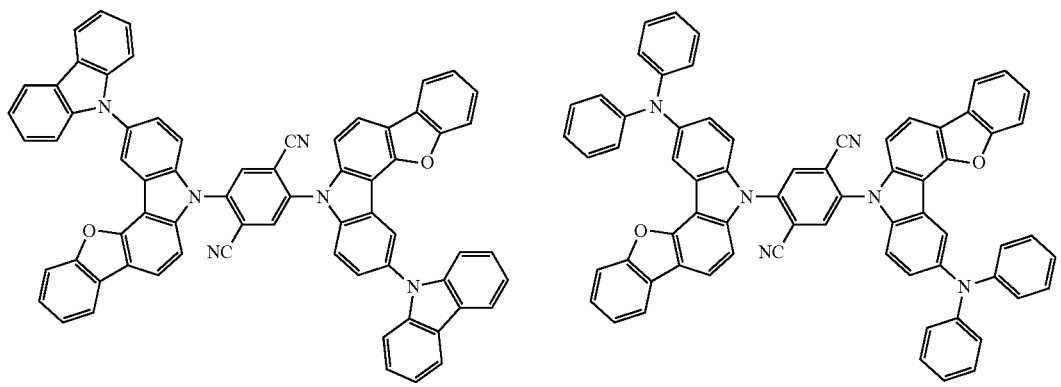
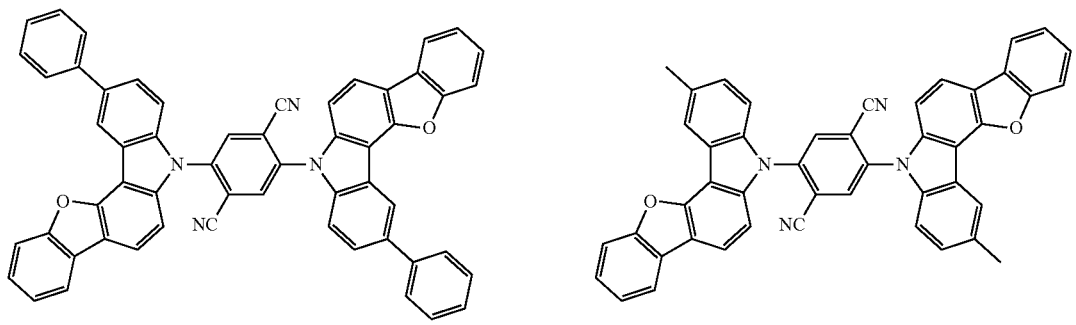

-continued
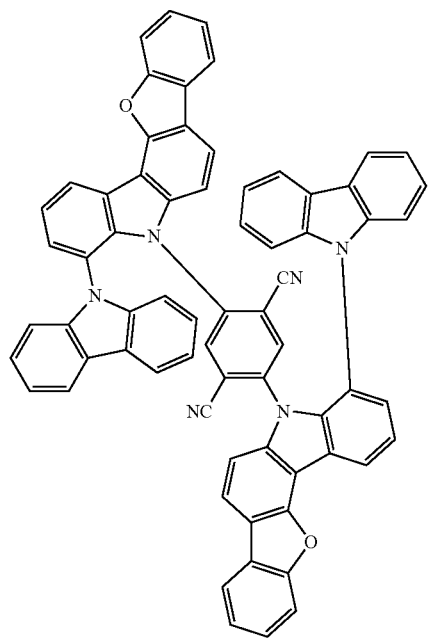
[Formula 76]
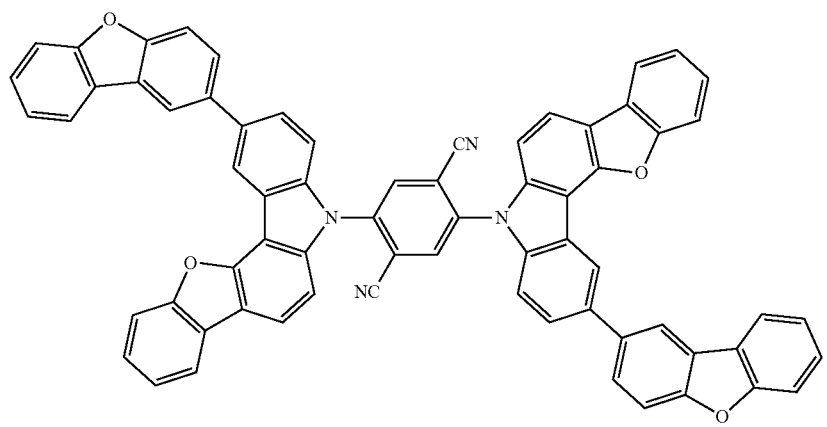
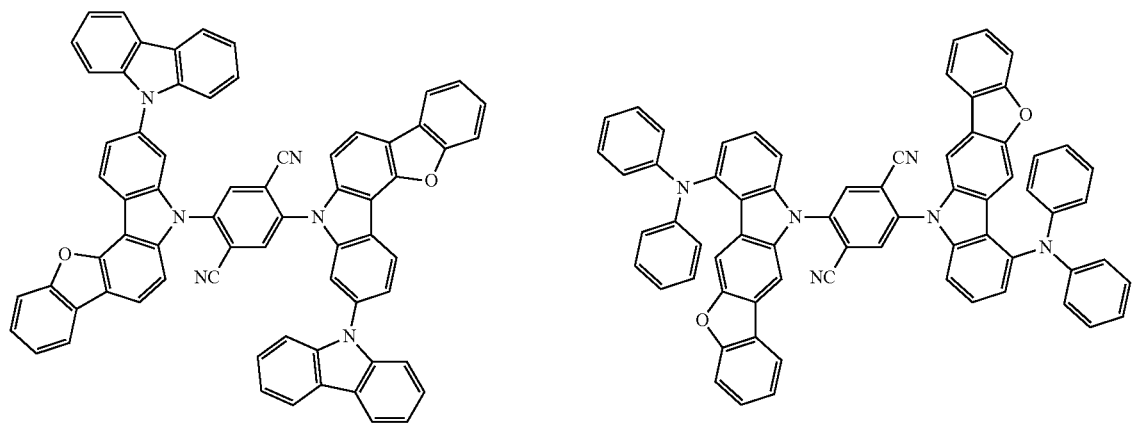

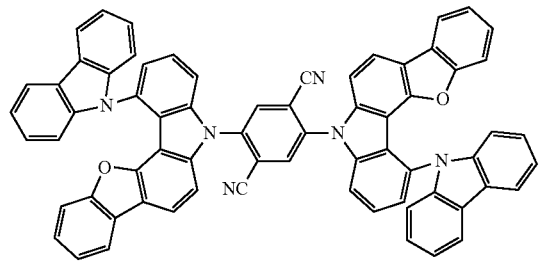
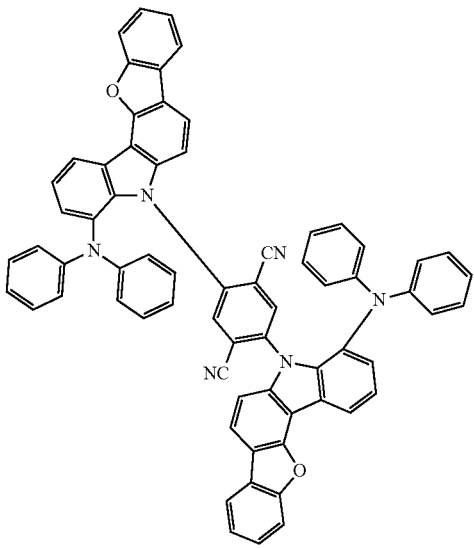
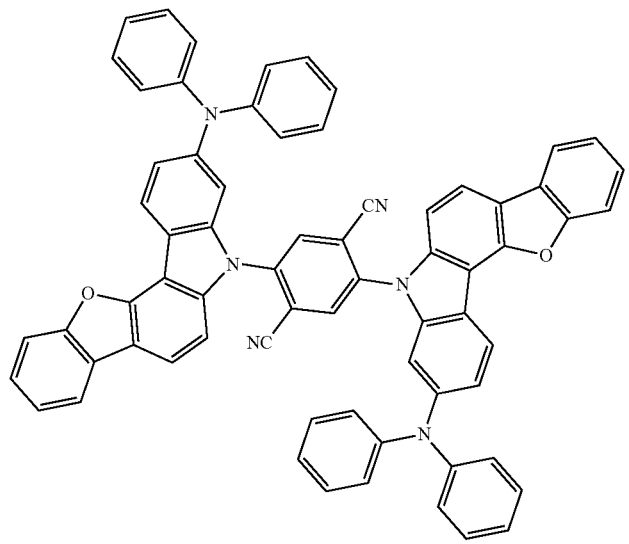
[Formula 77]
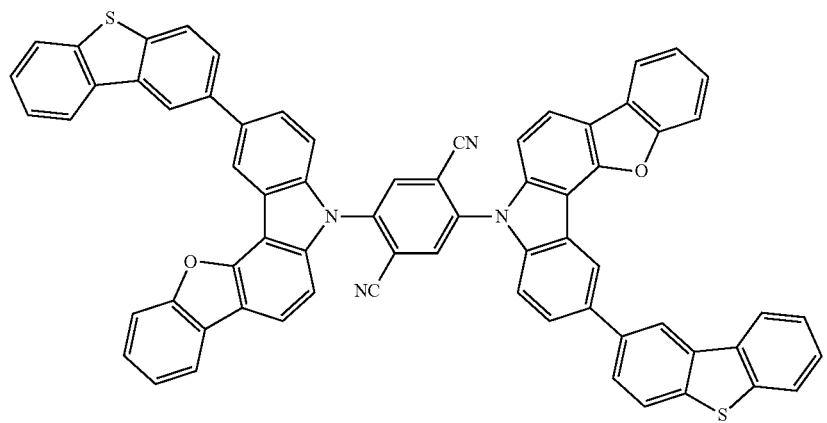

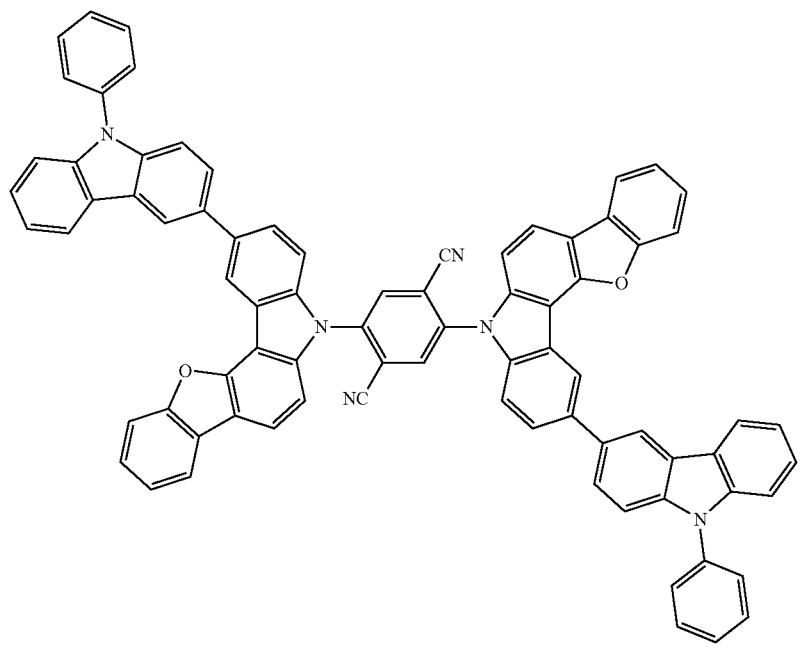
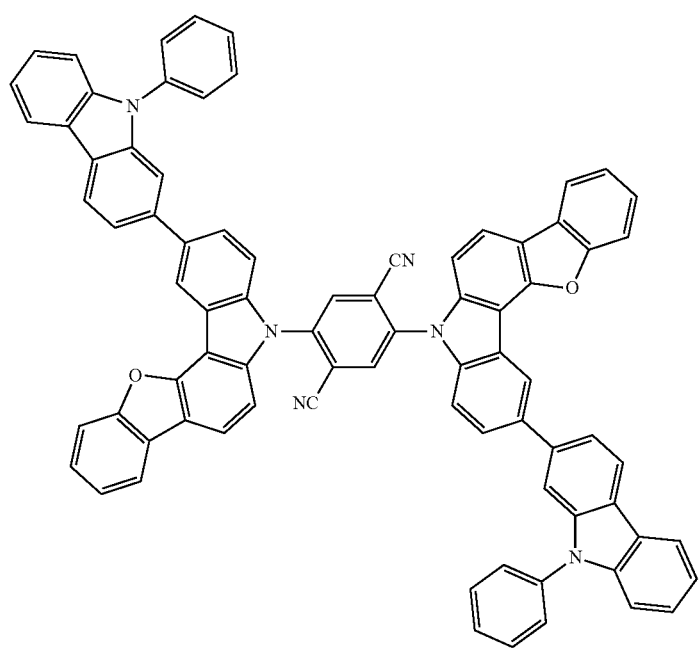

[Formula 78]
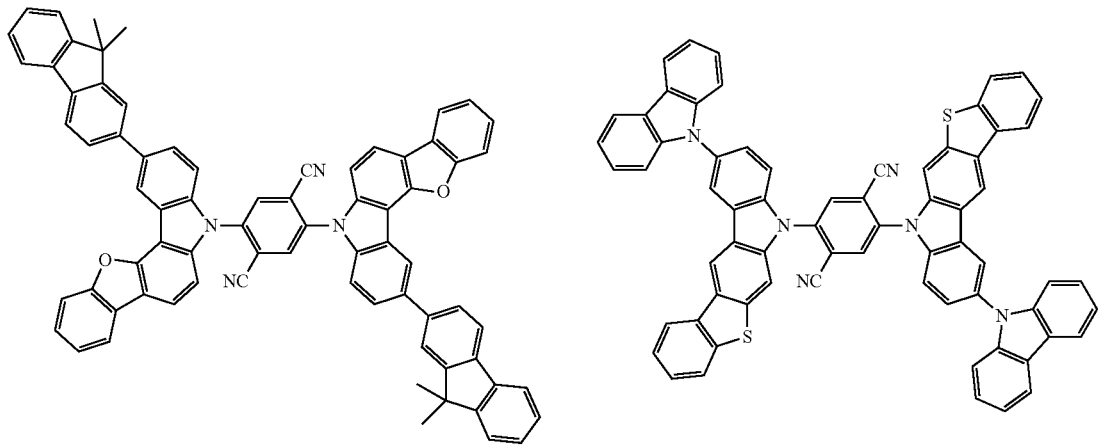
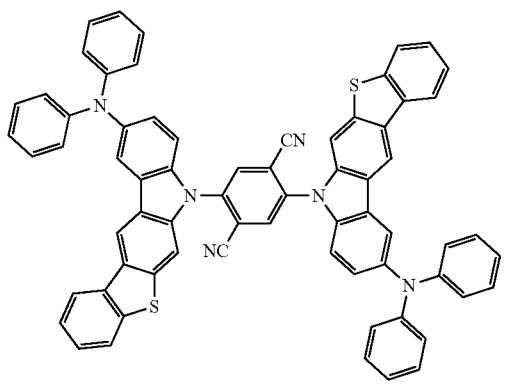
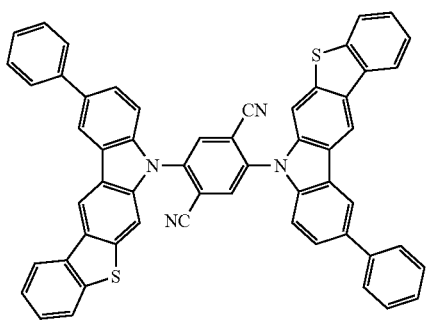
[Formula 79]
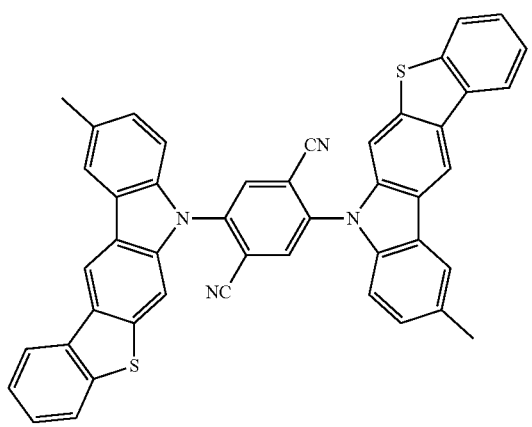

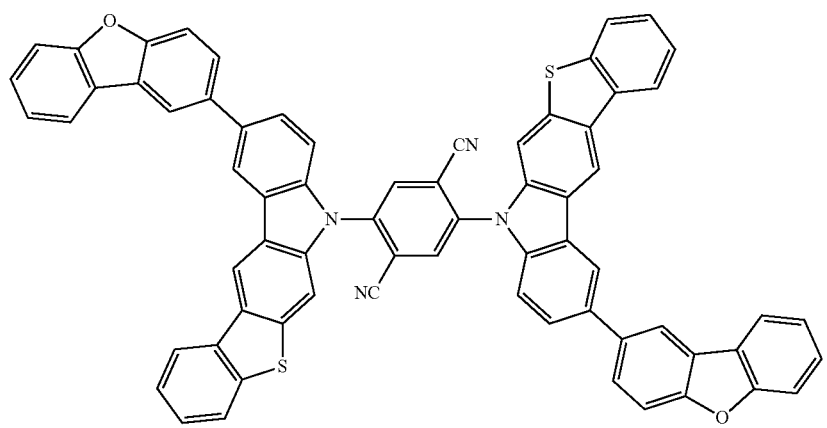
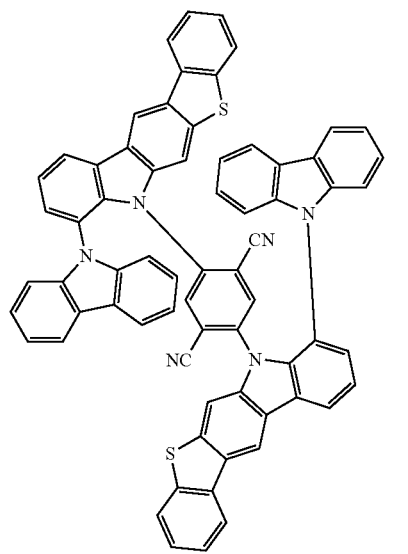
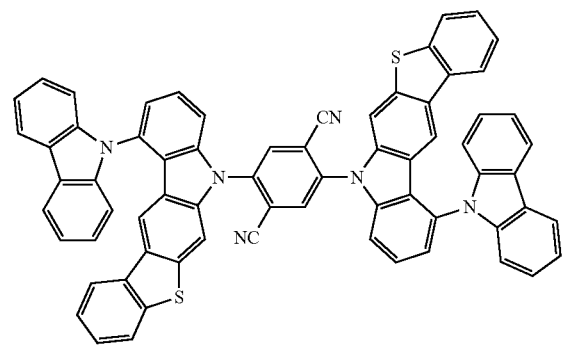
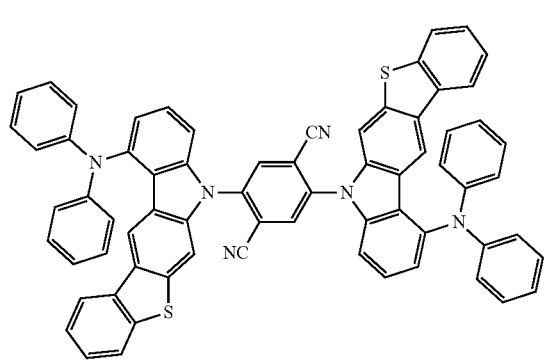
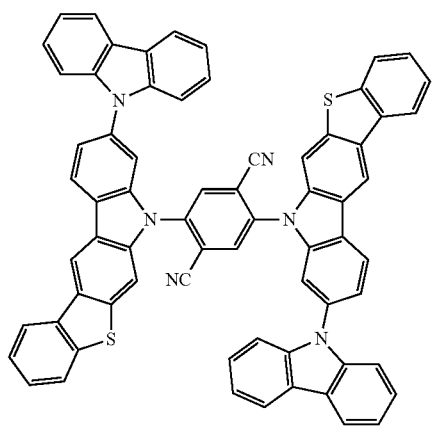

[Formula 80]
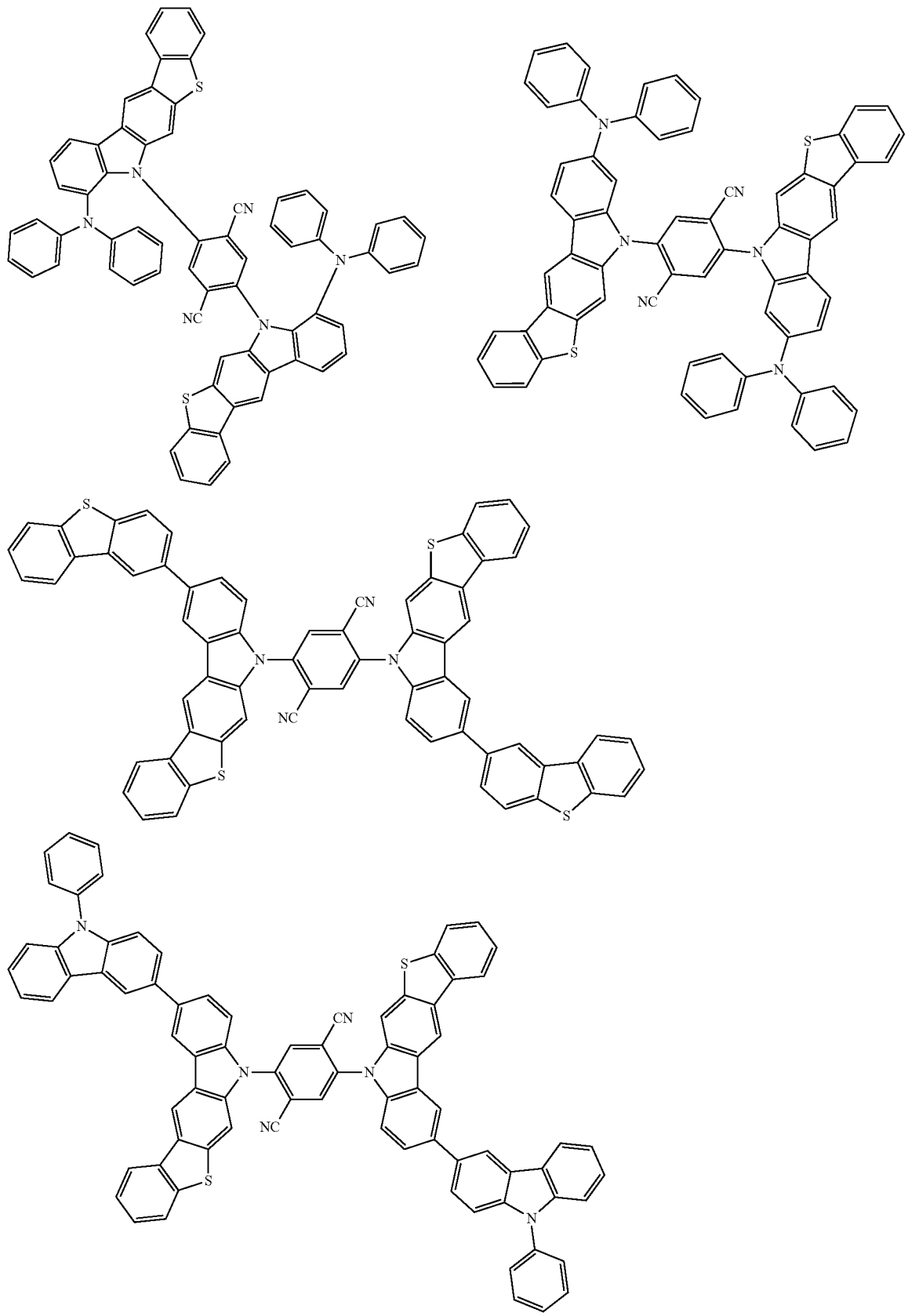

-continued
[Formula 81]
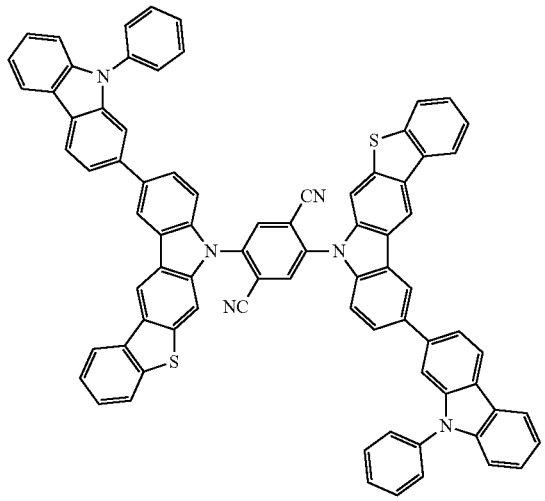
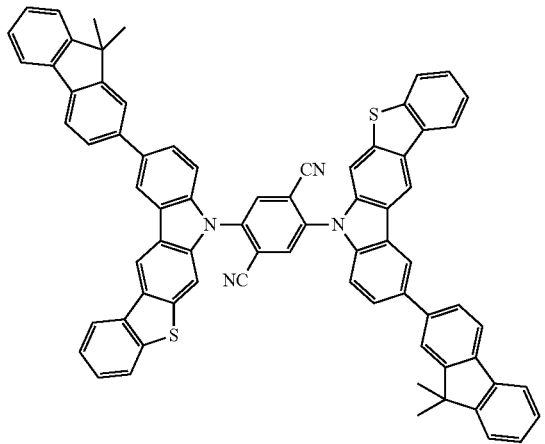
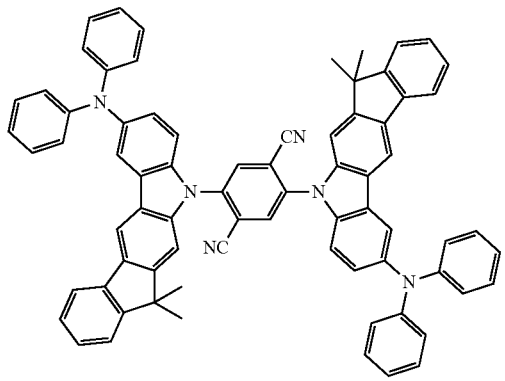
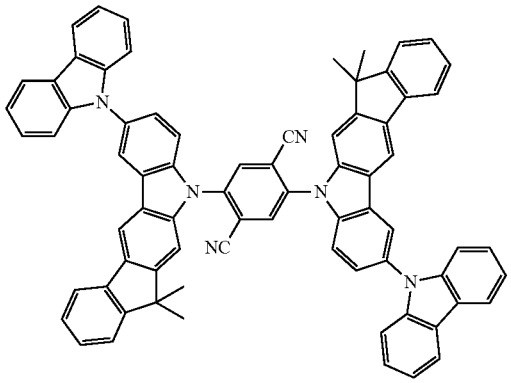
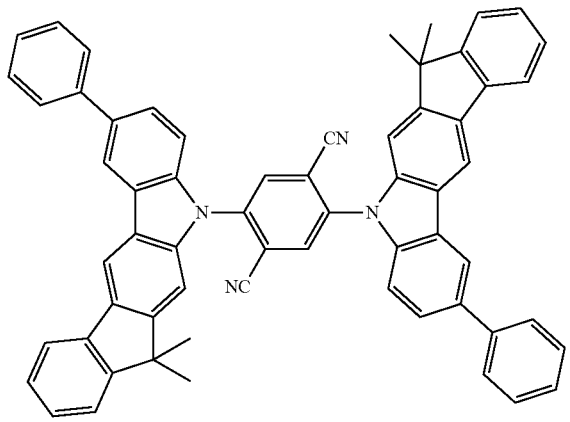

-continued
[Formula 82]
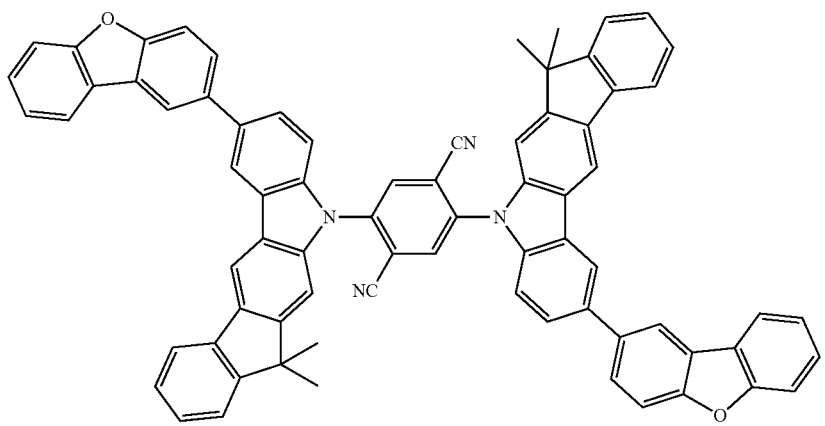
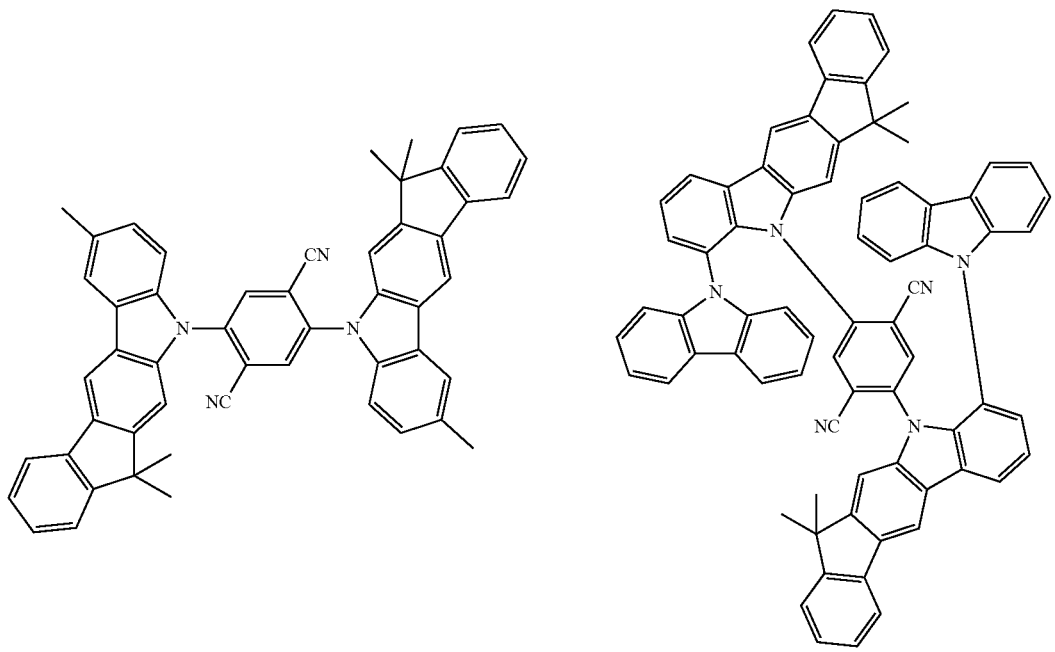
[Formula 83]
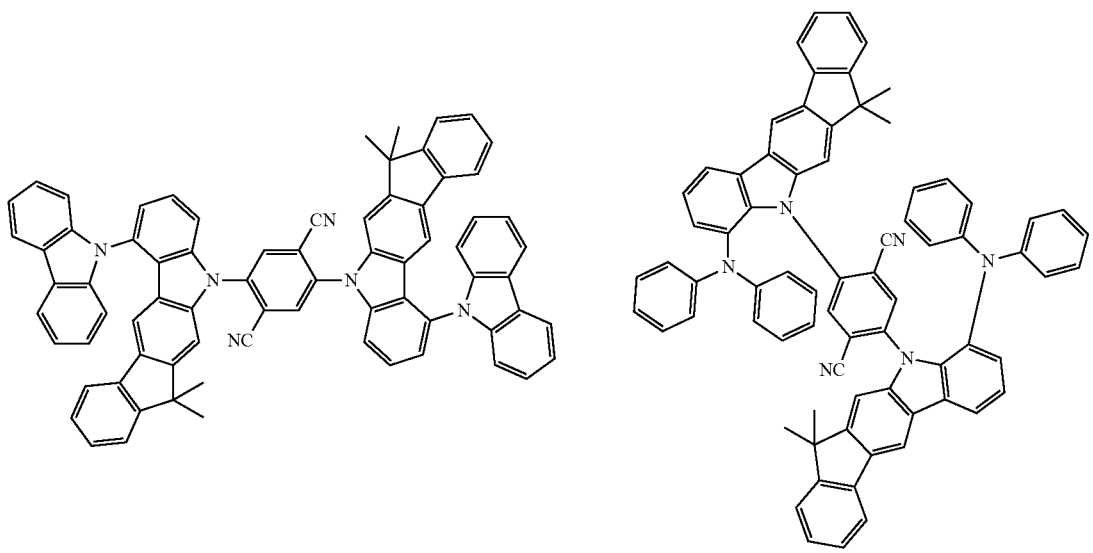

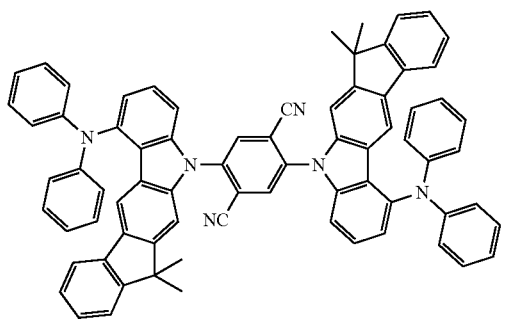
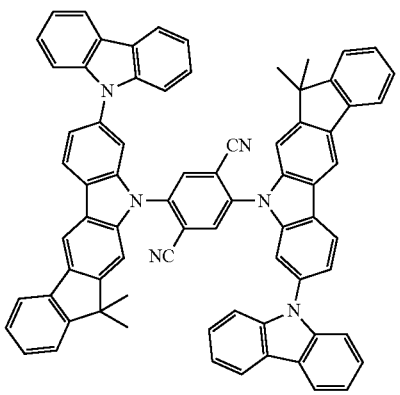
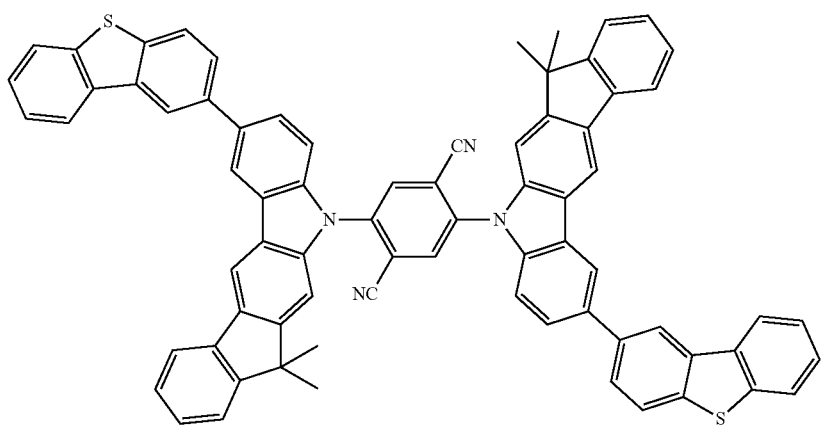
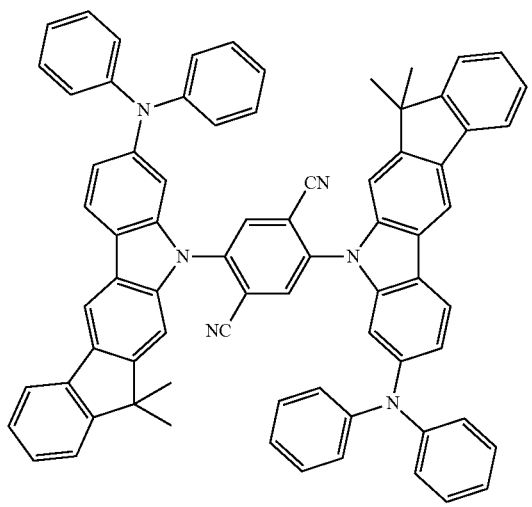

[Formula 84]
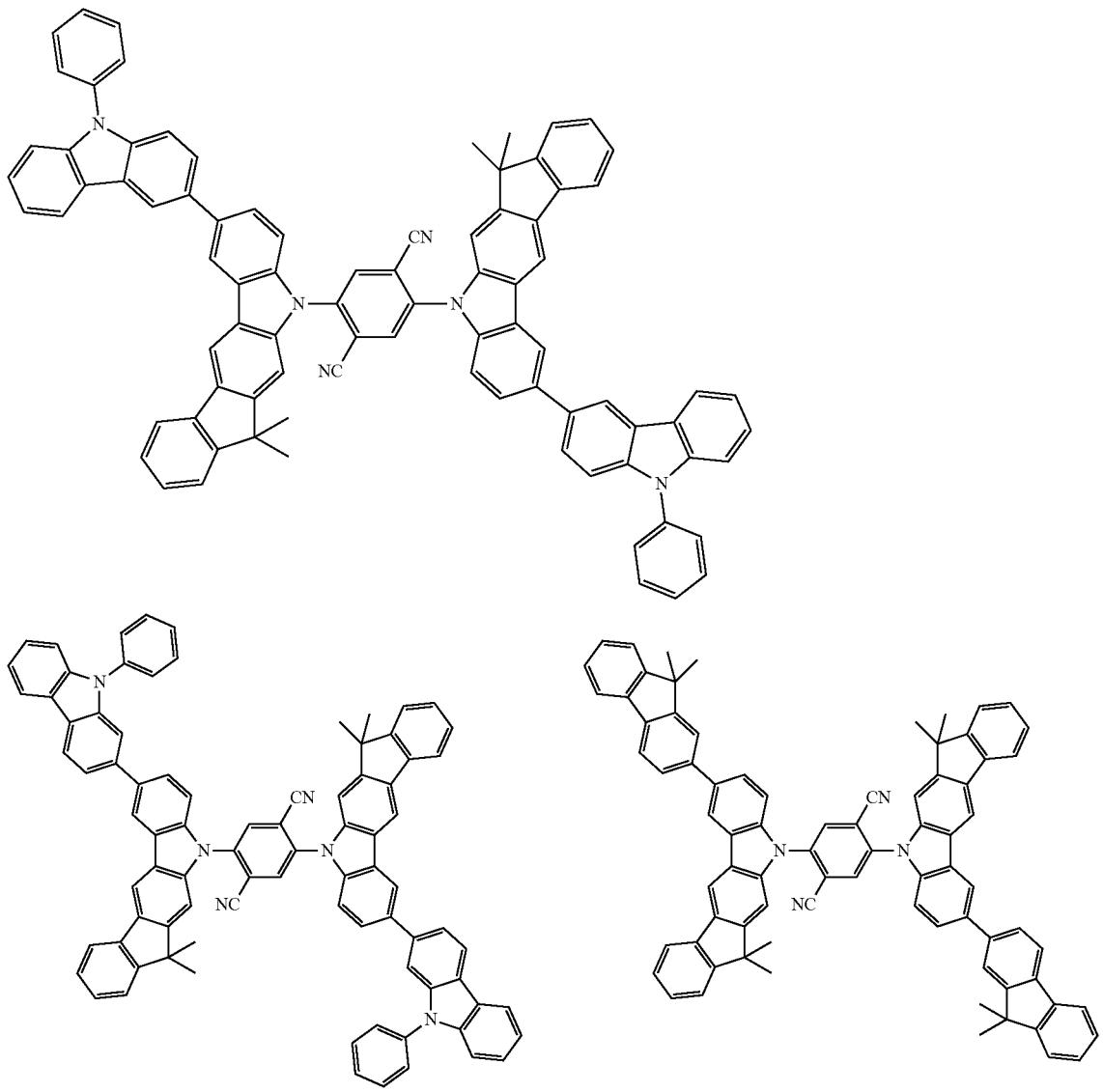
[Formula 85]
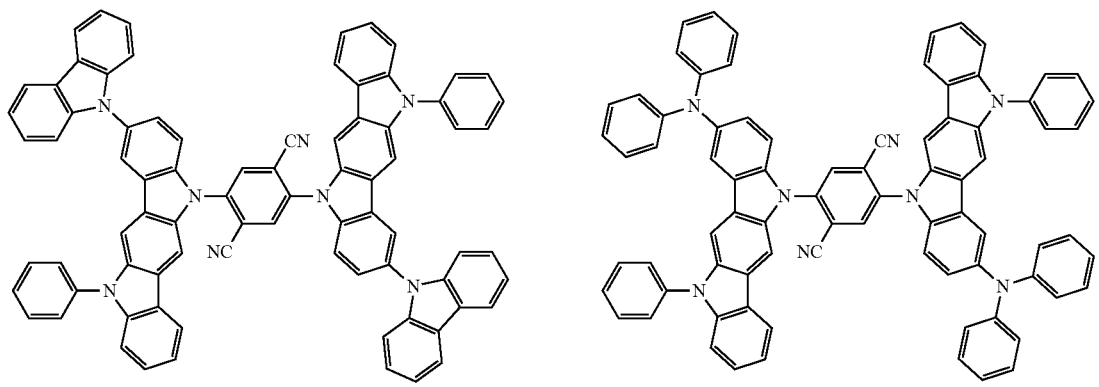

-continued
101
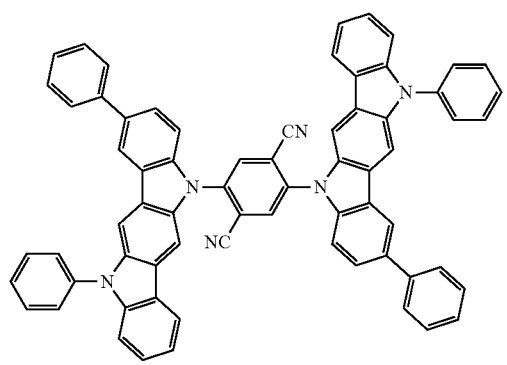
102
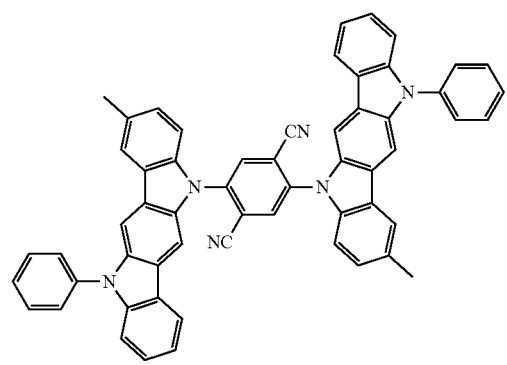
[Formula 86]
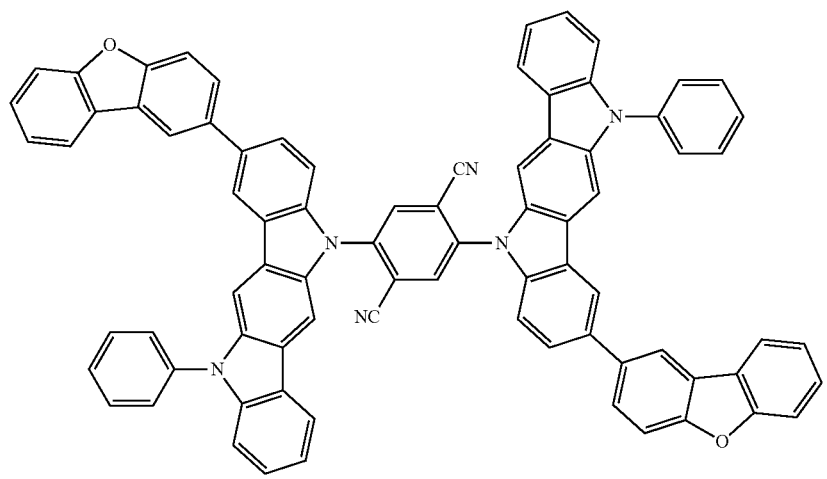
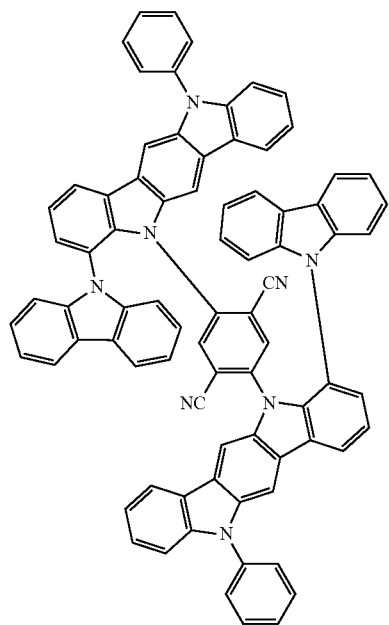
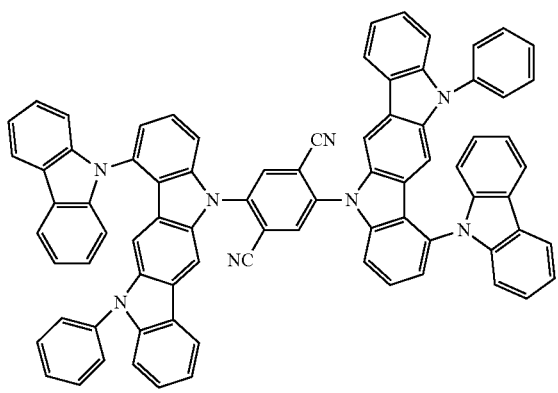

-continued
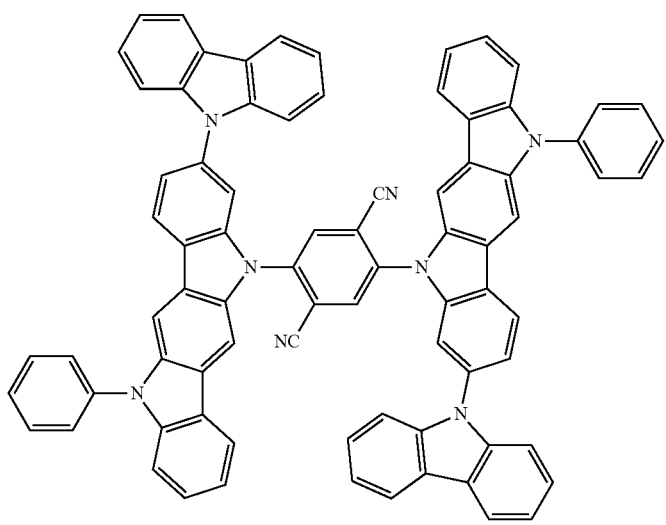
[Formula 87]
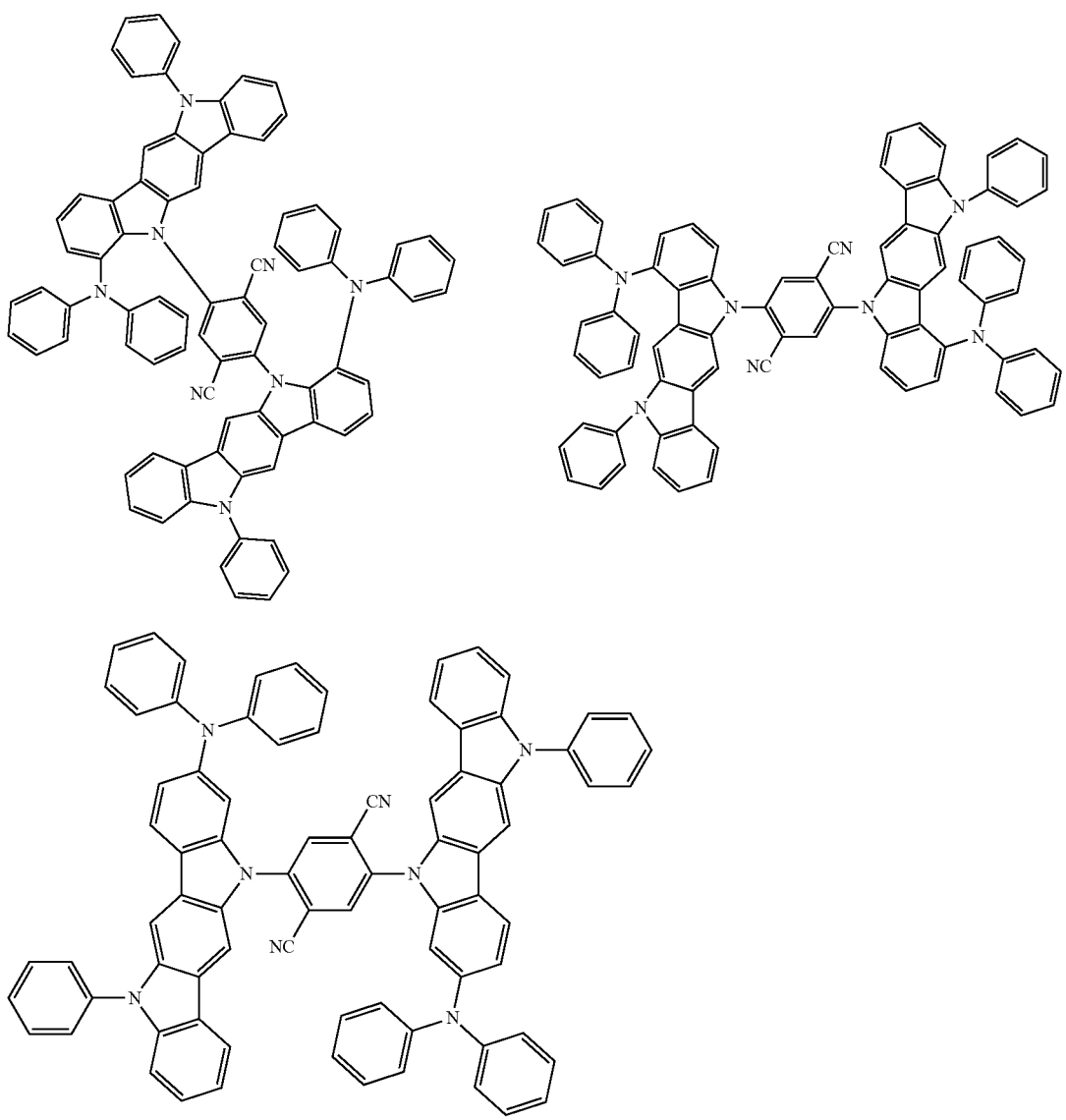

-continued
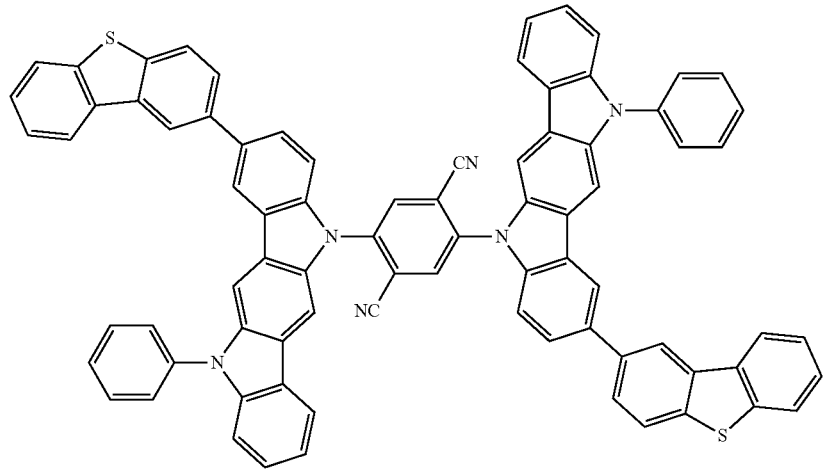
[Formula 88]
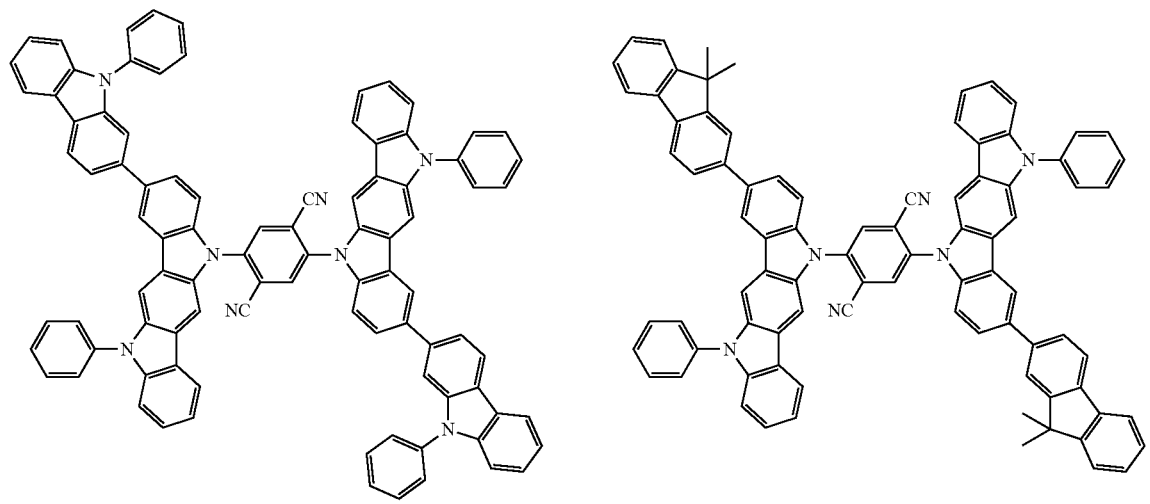
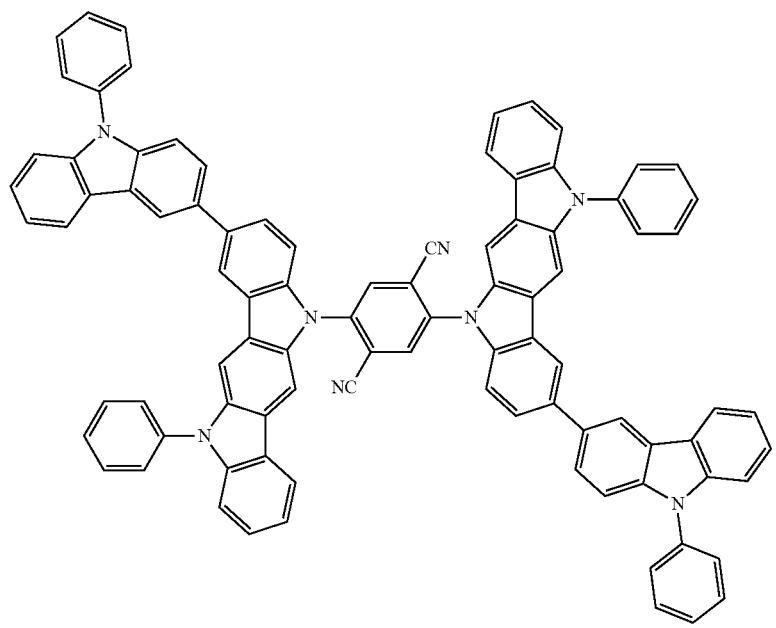

[Formula 89]
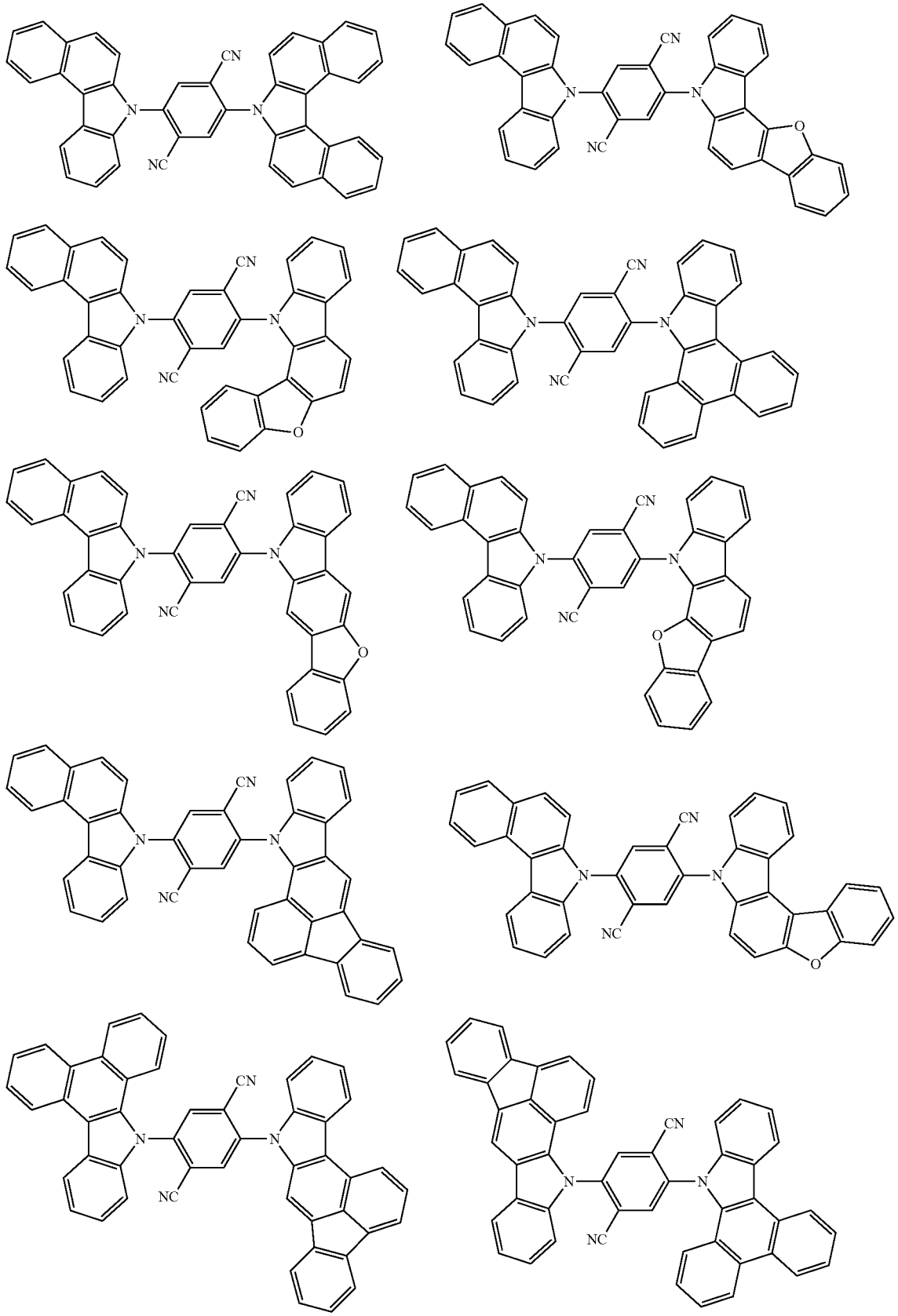

-continued
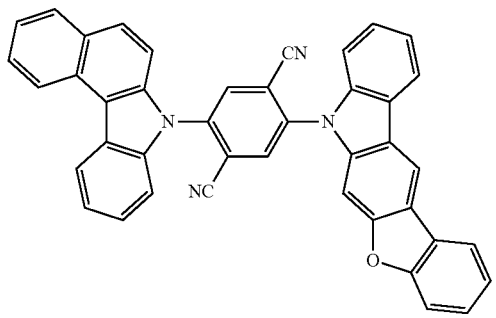
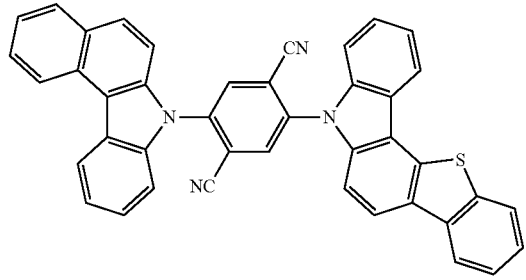
[Formula 90]
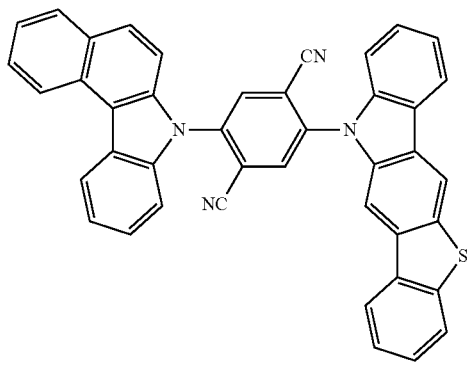
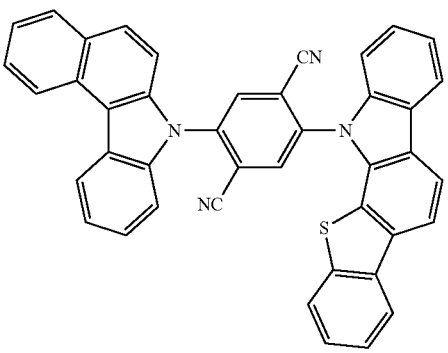
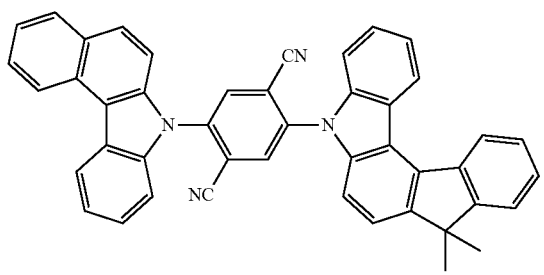
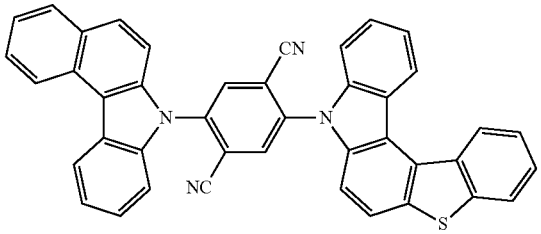
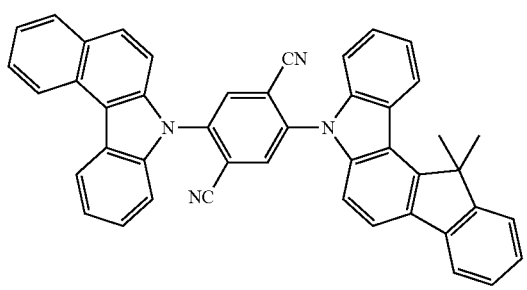
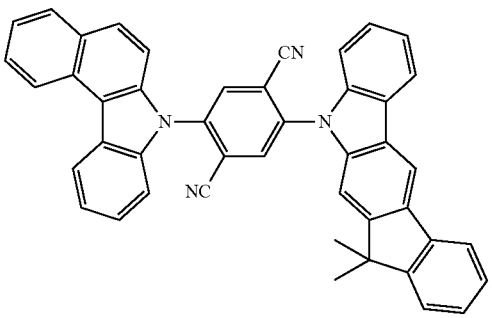
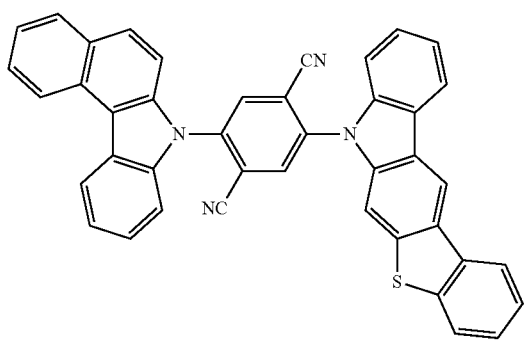
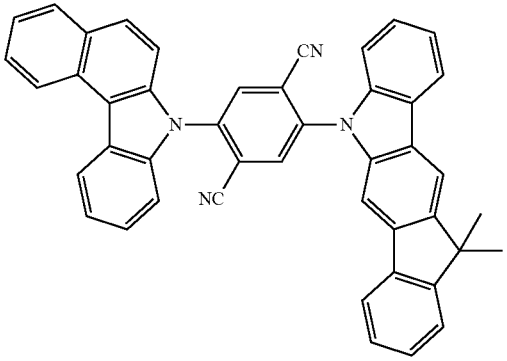

111
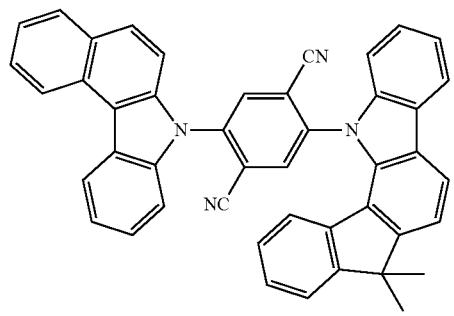
112
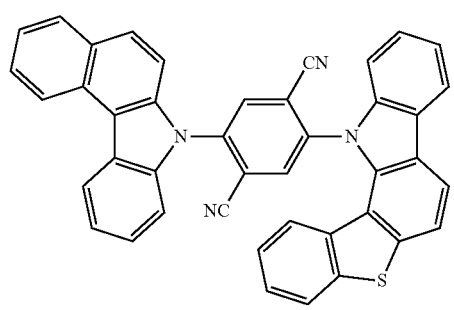
[Formula 91]
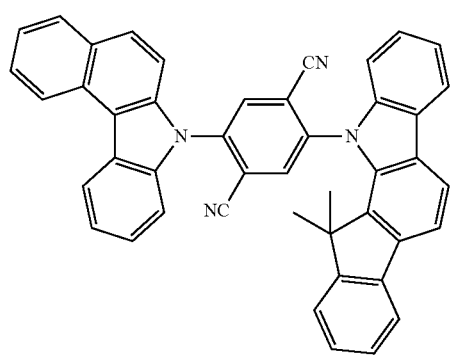
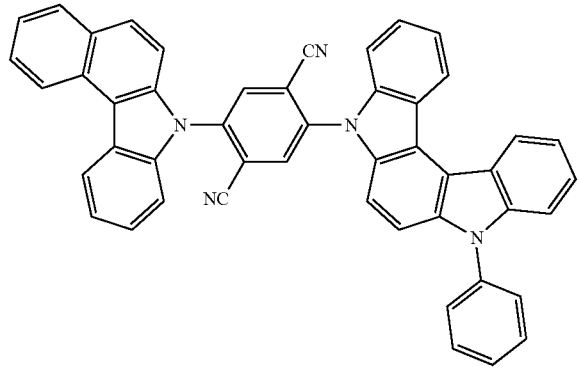
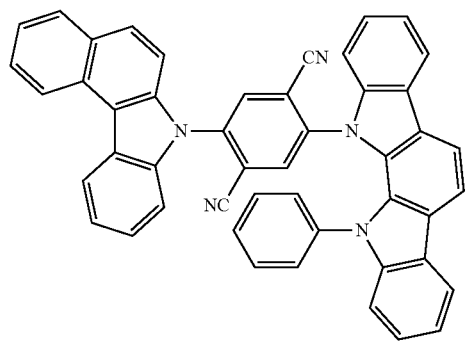
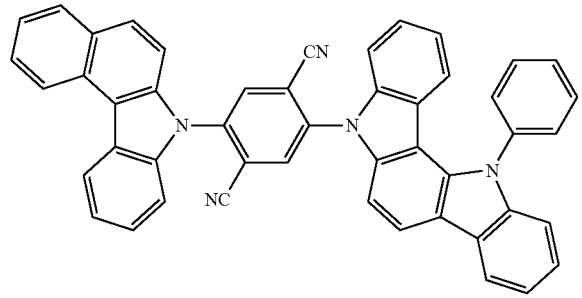
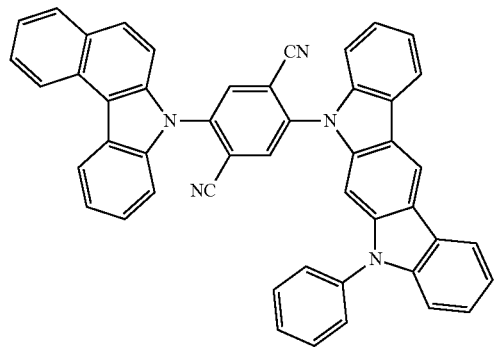
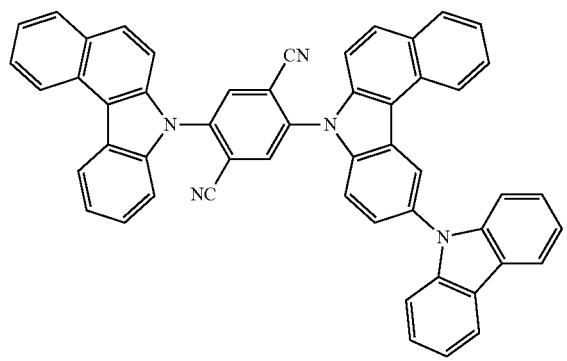

113
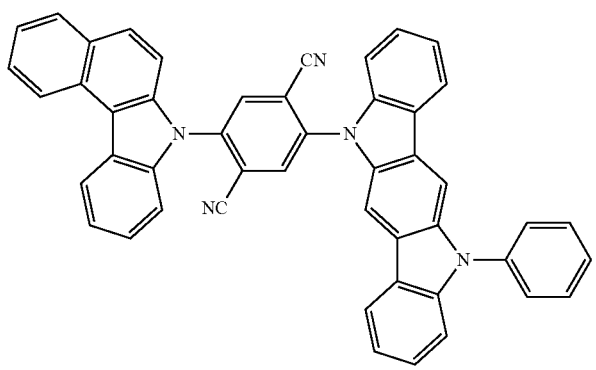
114
-continued
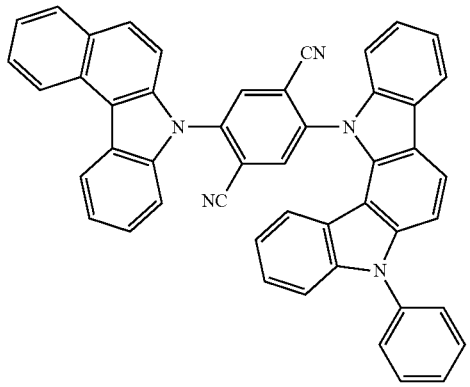
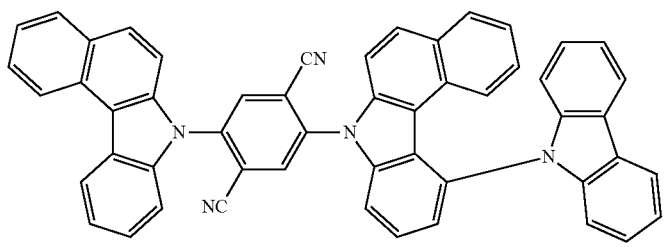
[Formula 92]
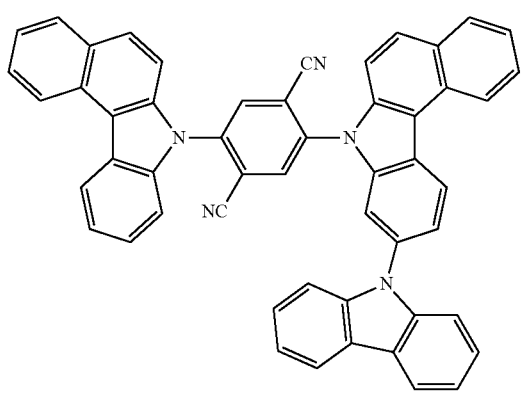
-continued
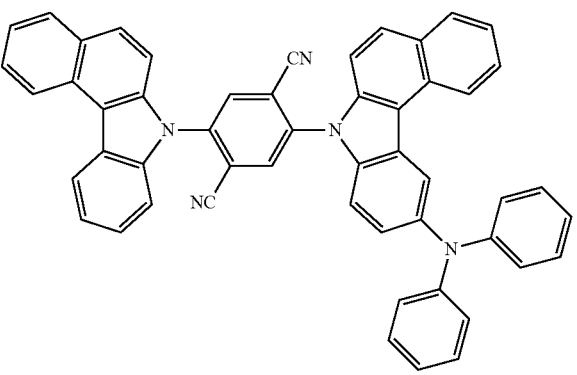
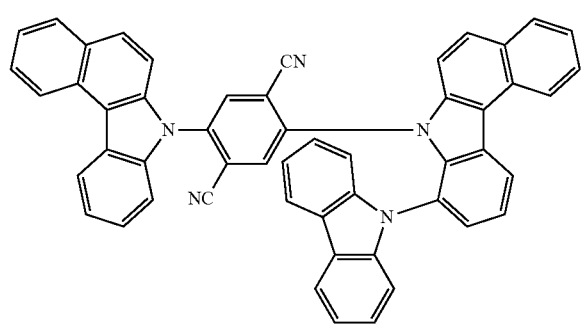
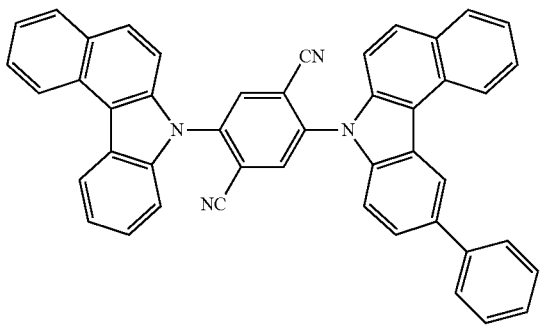

115
-continued
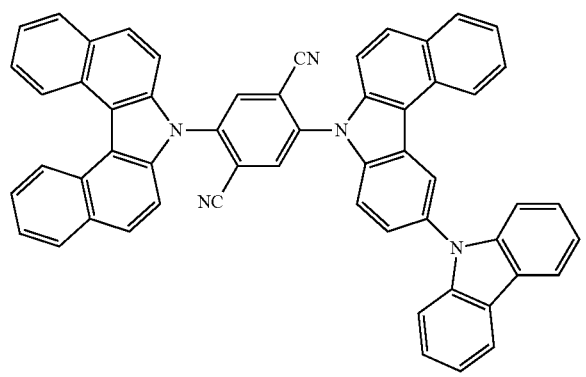
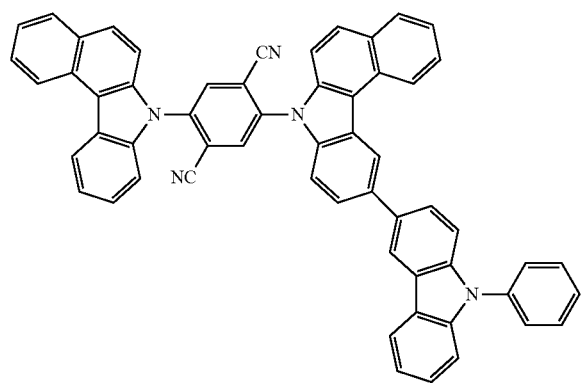
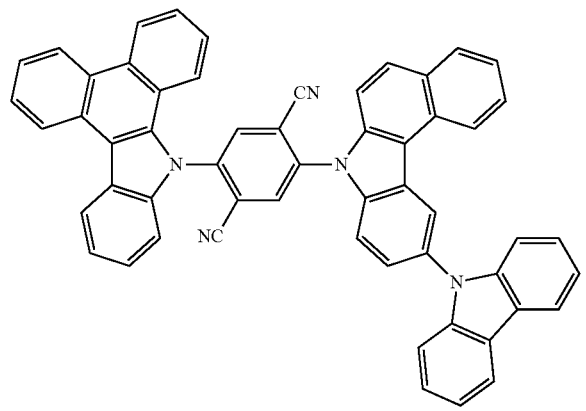
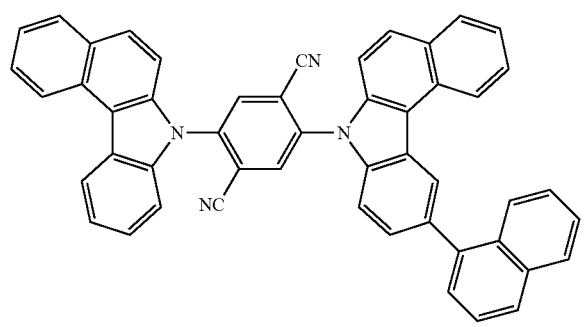
116
-continued
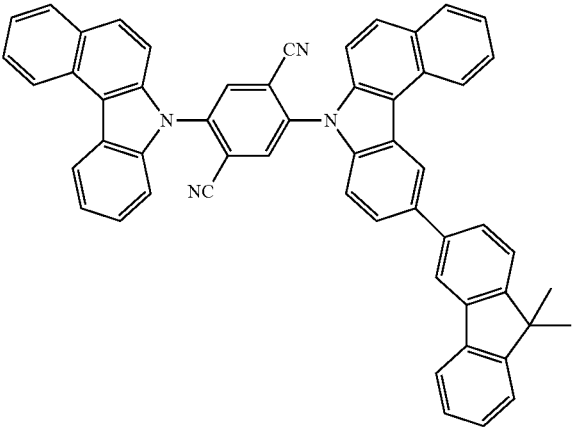
[Formula 93]
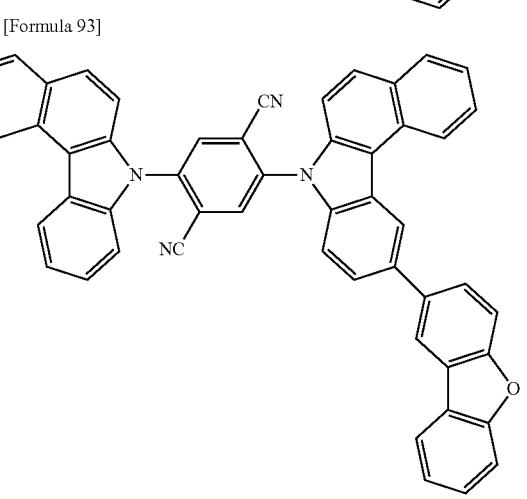

117
-continued
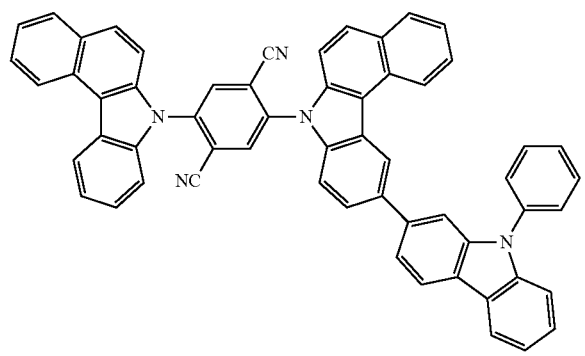
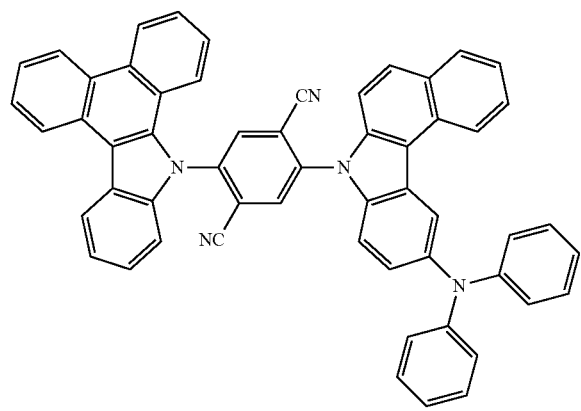
[Formula 94]
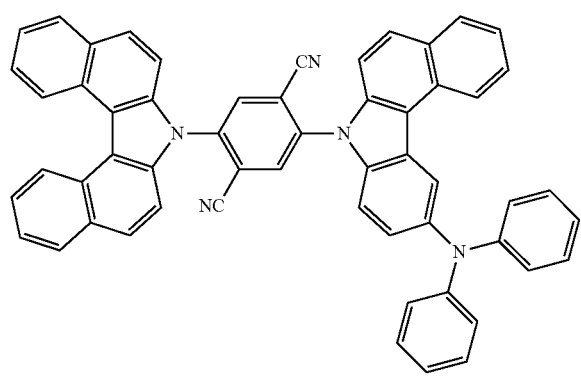
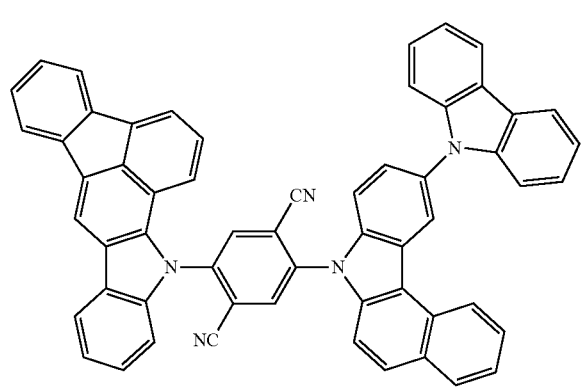
118
-continued
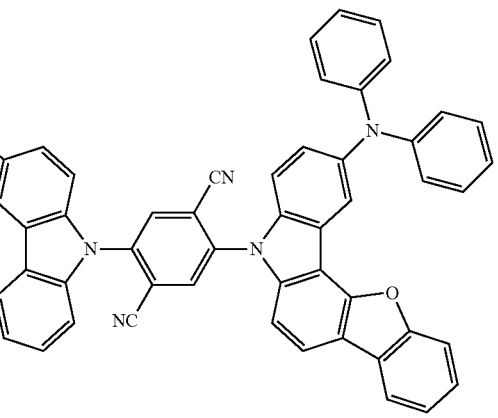
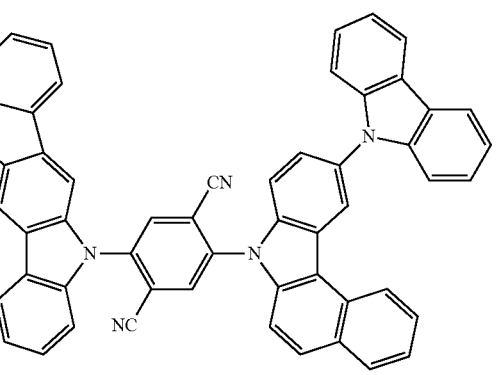
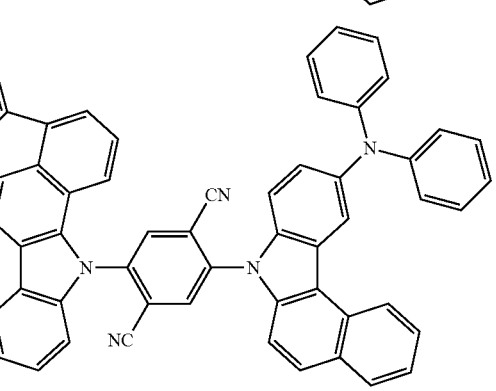
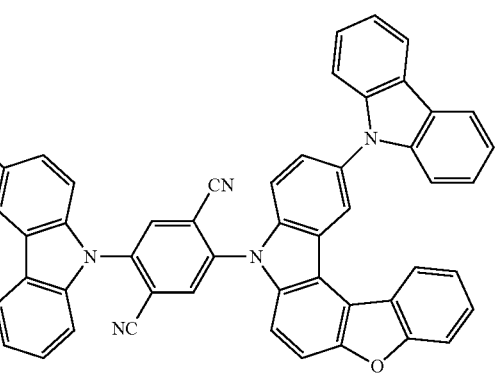

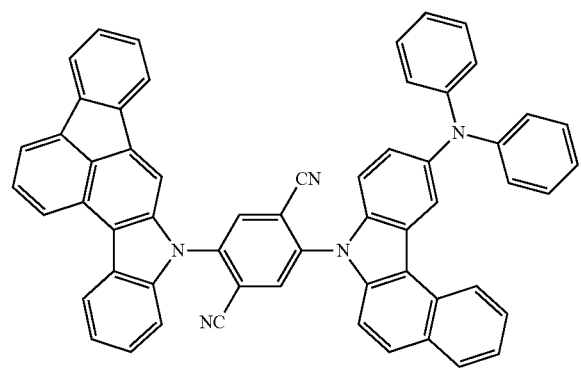
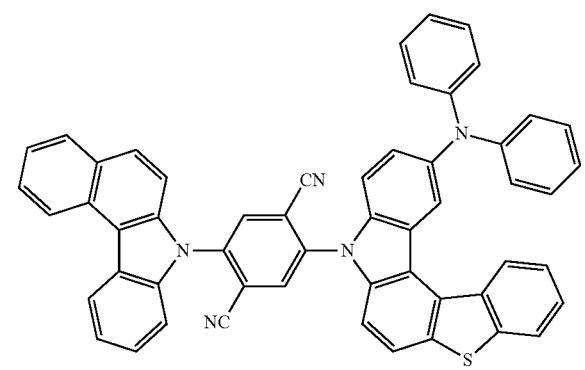
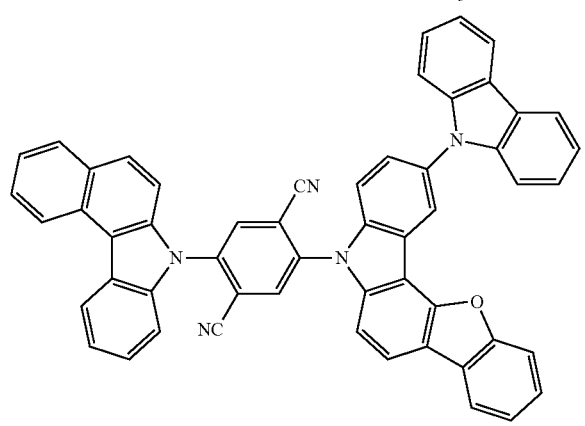
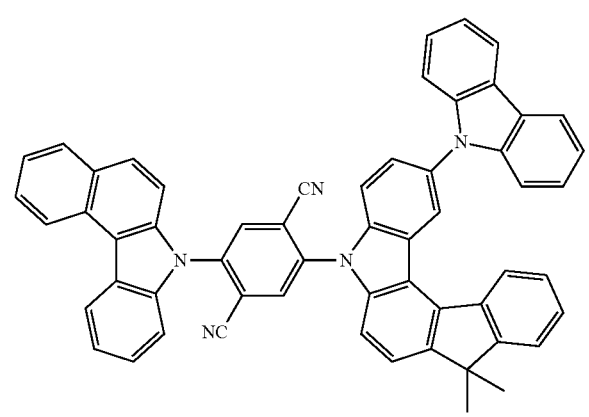
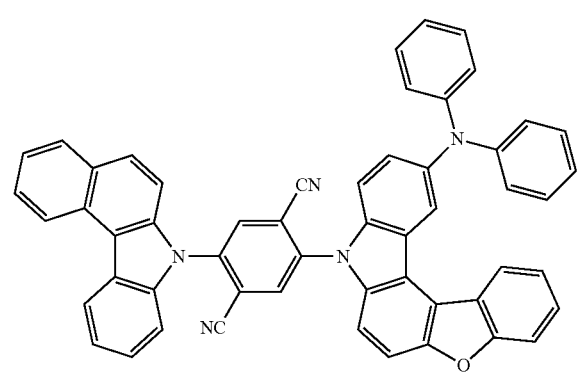
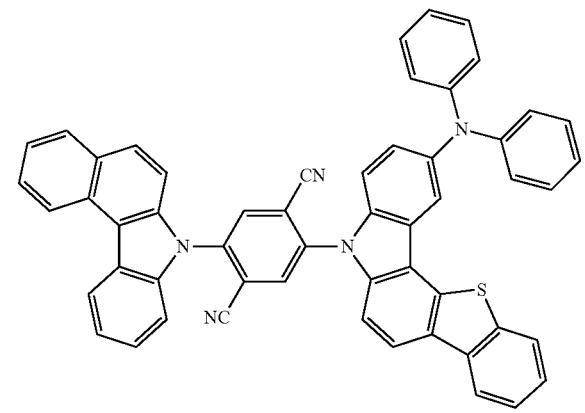
[Formula 95]
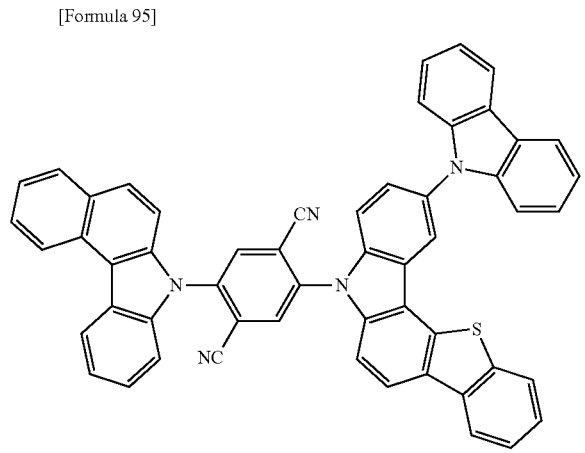
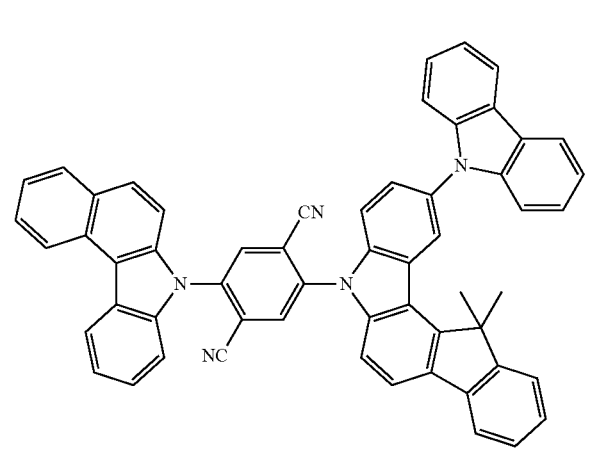

121
-continued
122
-continued
[Formula 96]
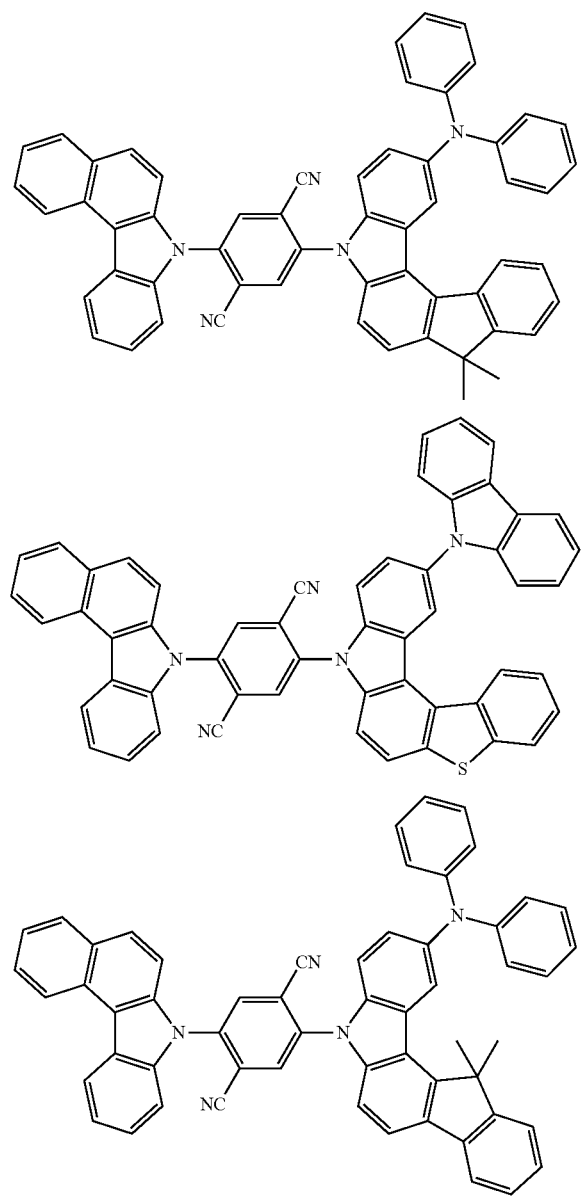
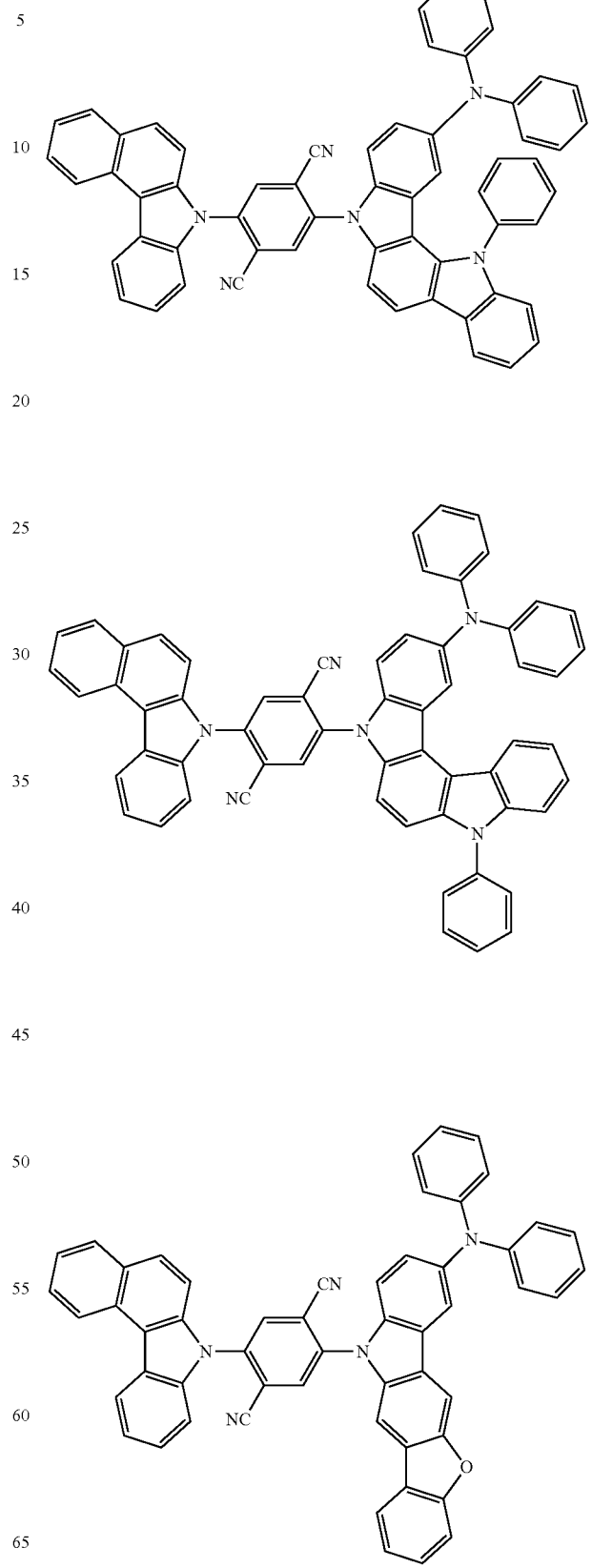

123
-continued
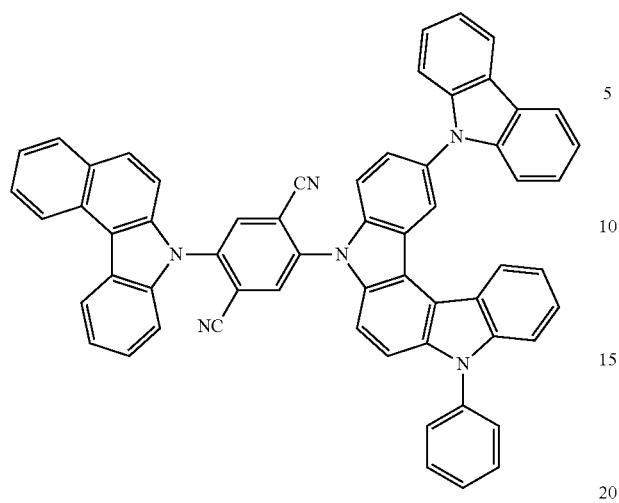
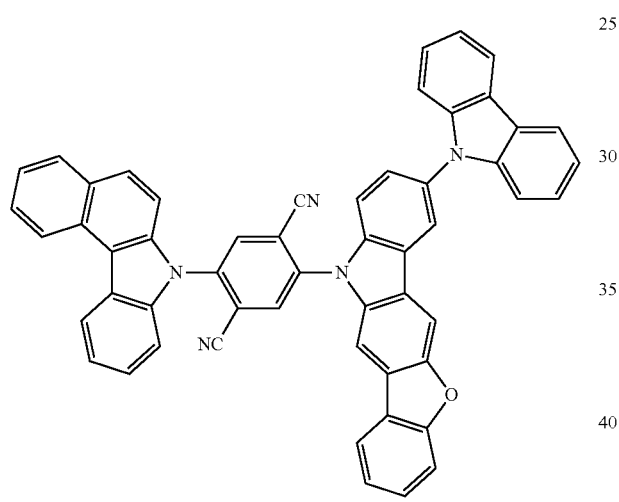
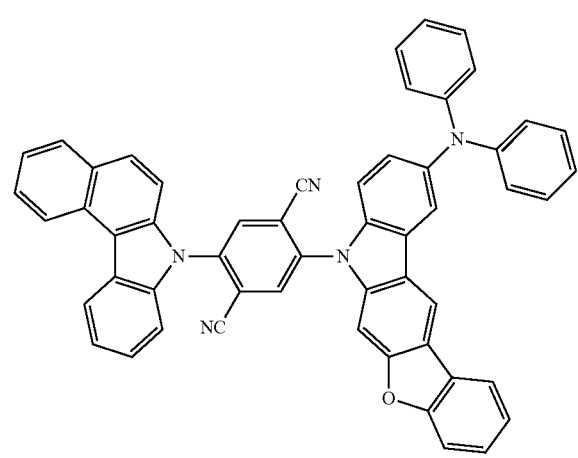
124
-continued
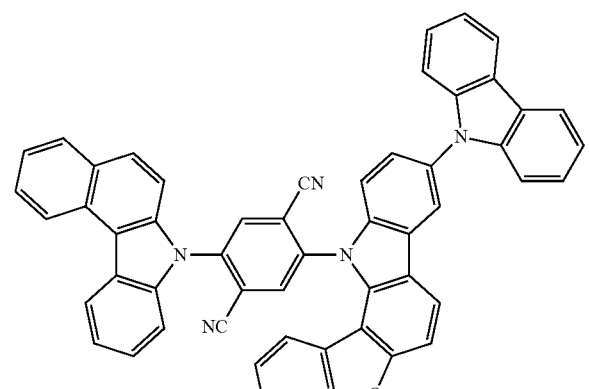
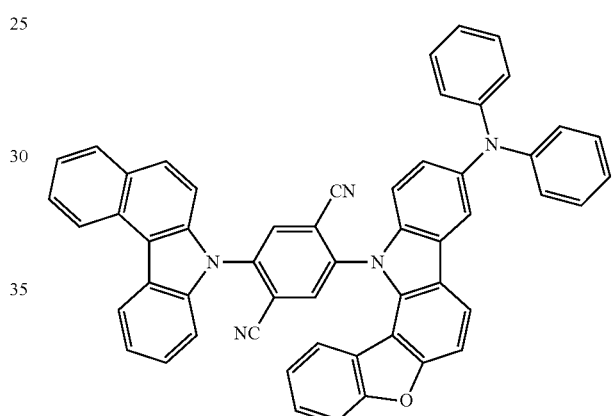
[Formula 97]
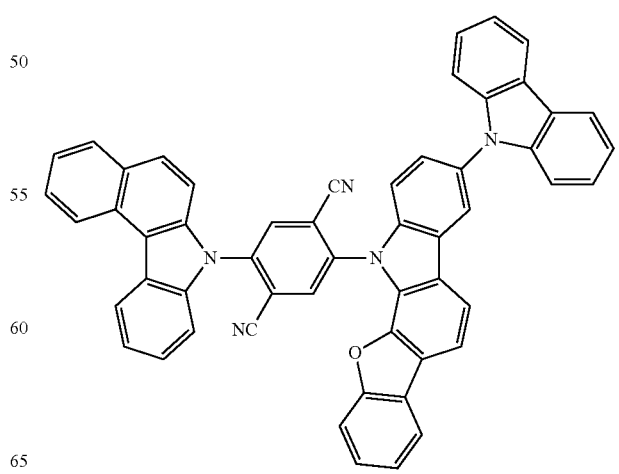

125 126
-continued -continued

127
-continued
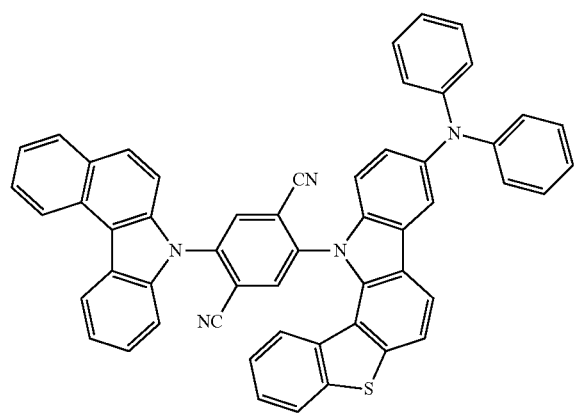
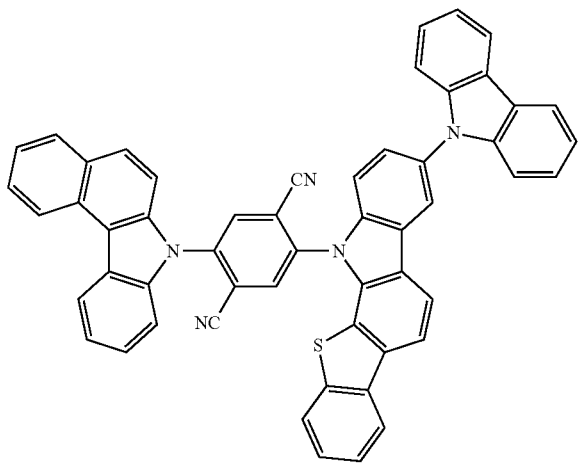
[Formula 98]
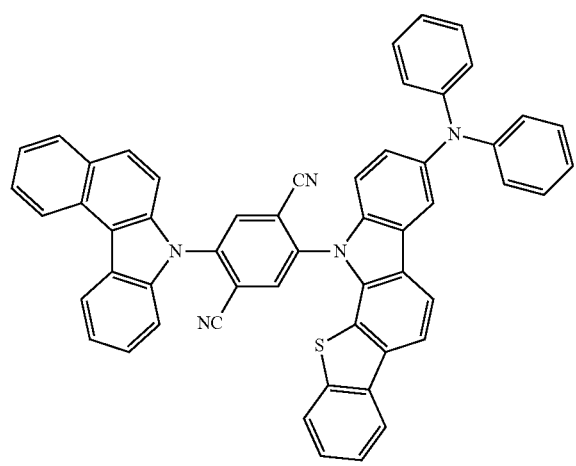
128
-continued
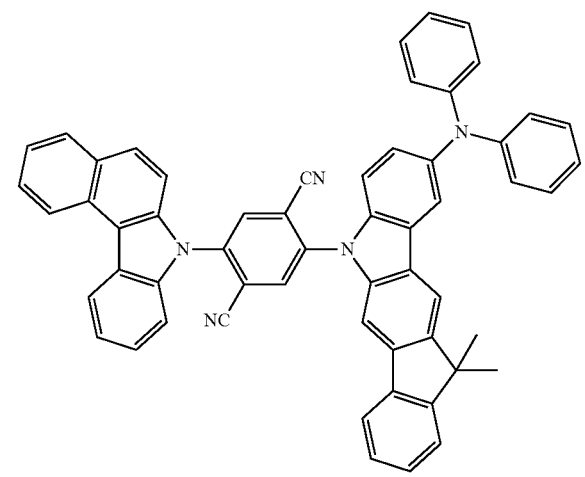
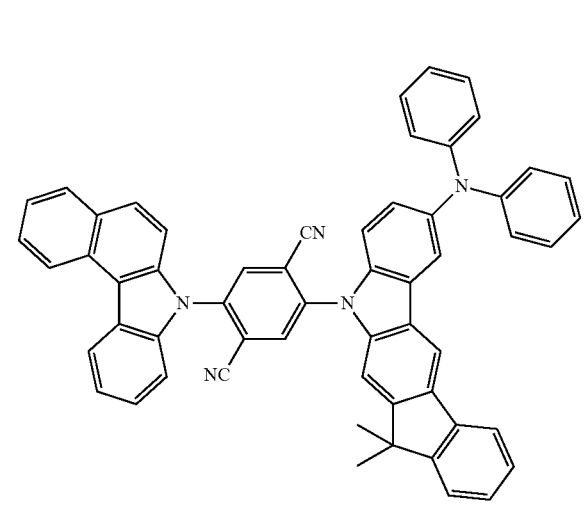
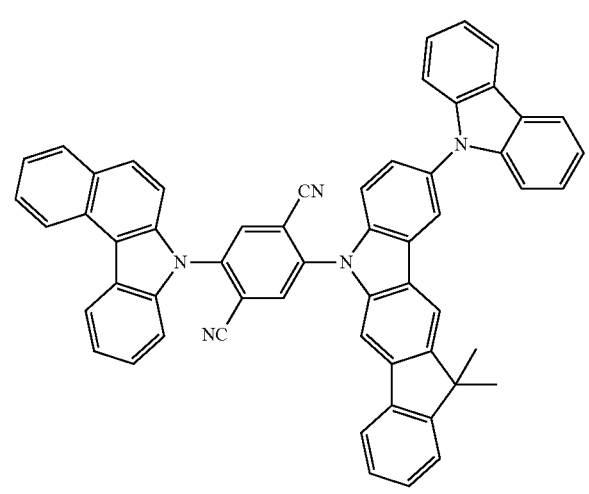

129
-continued
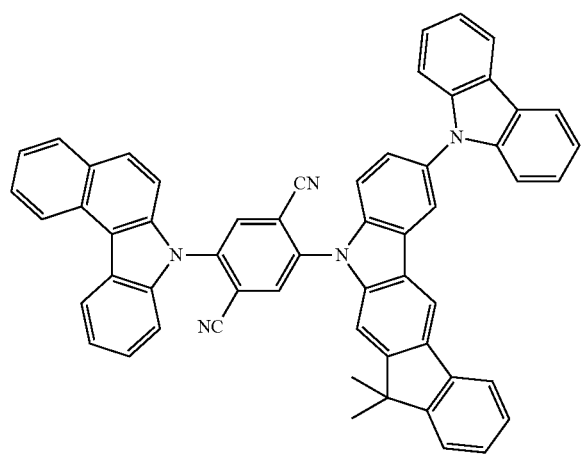
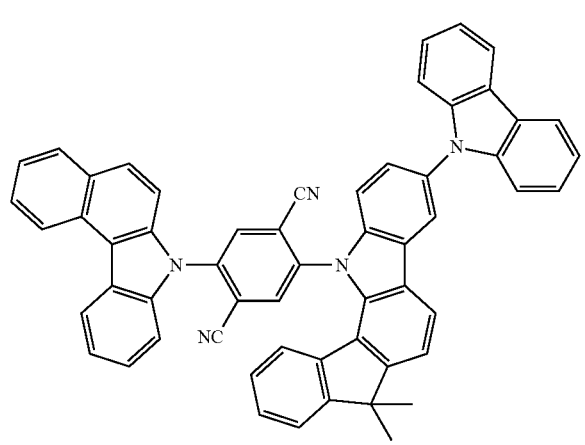
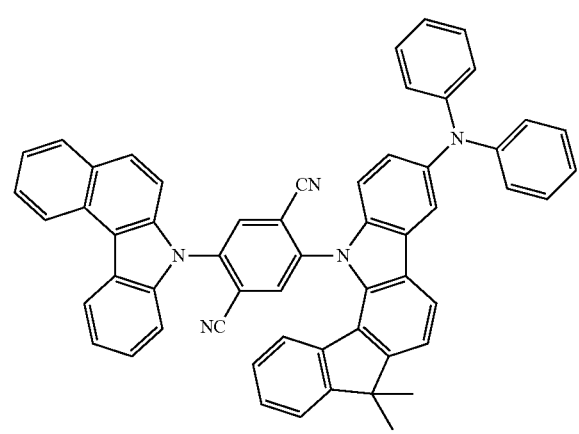
130
-continued
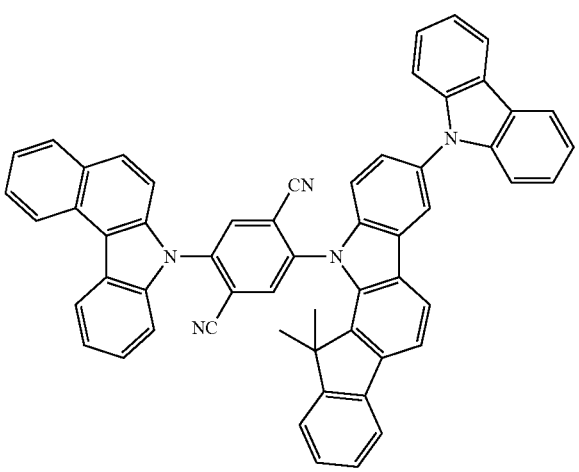
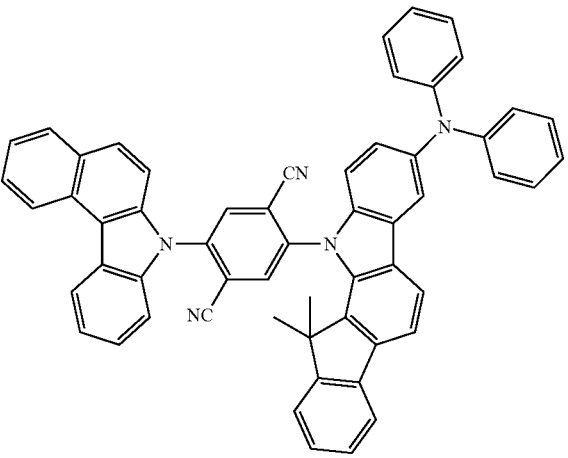
[Formula 99]
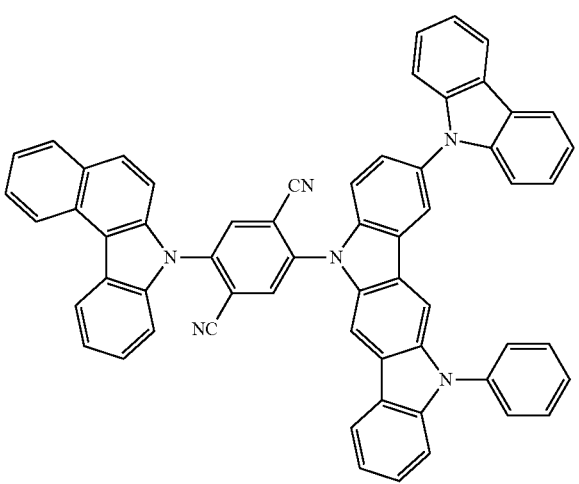

131
-continued
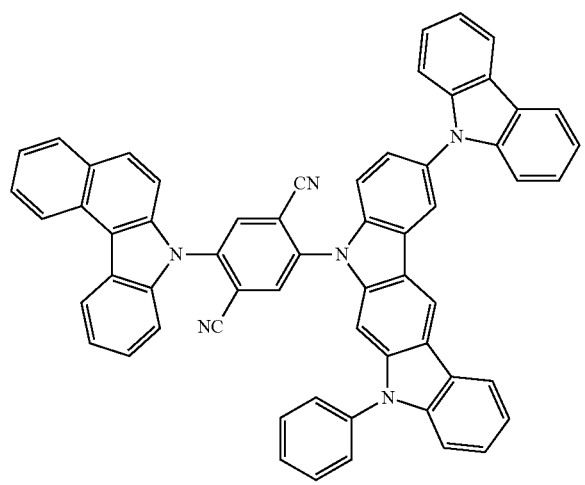
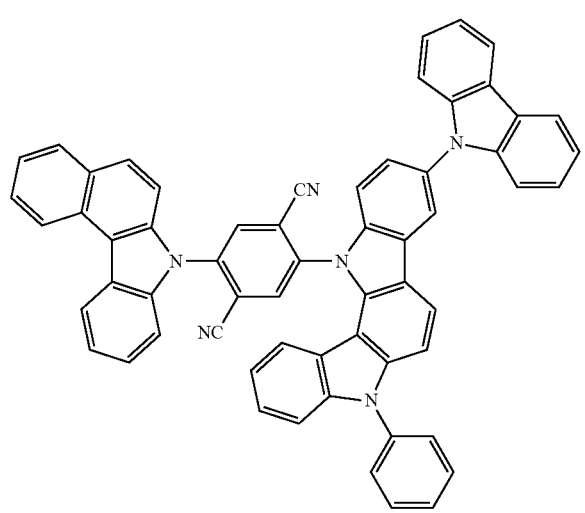
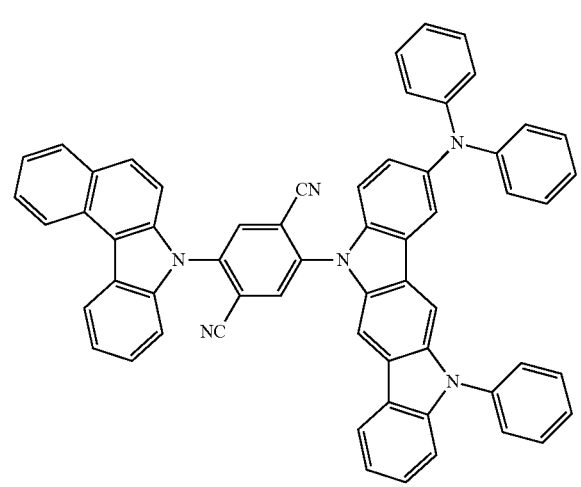
132
-continued
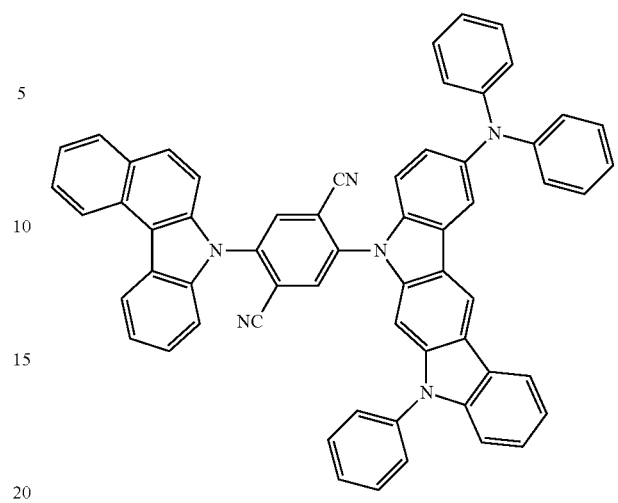
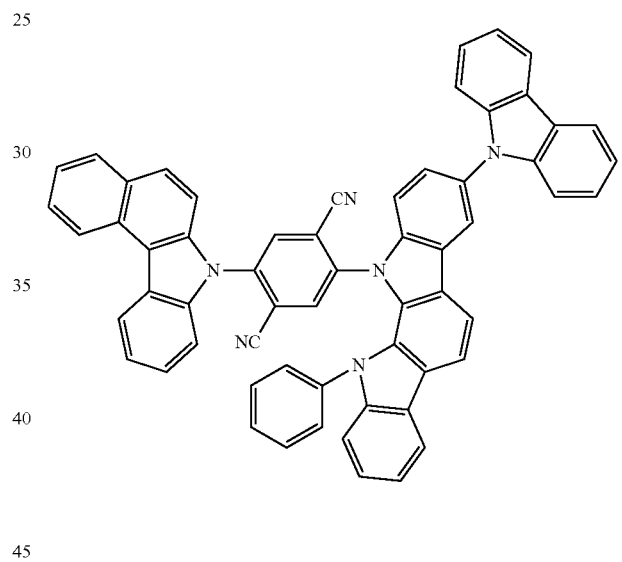
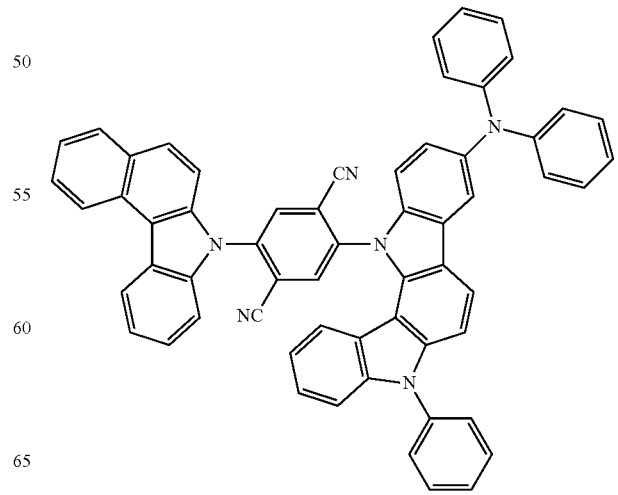

133
-continued
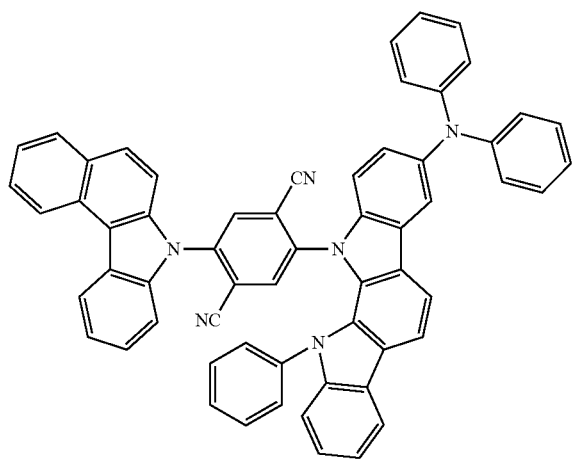
[Formula 100]
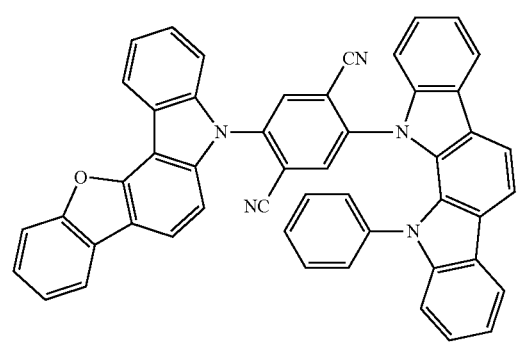
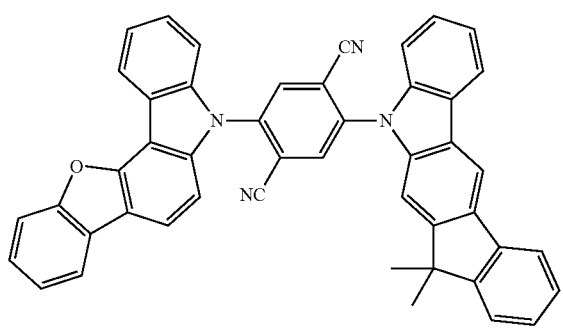
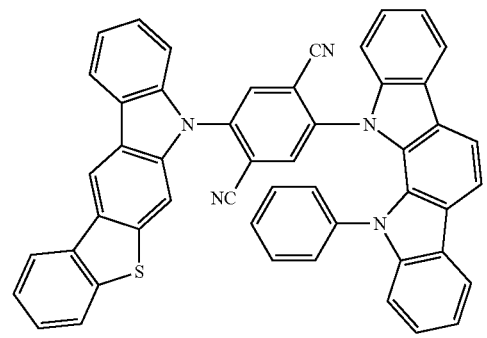
134
-continued
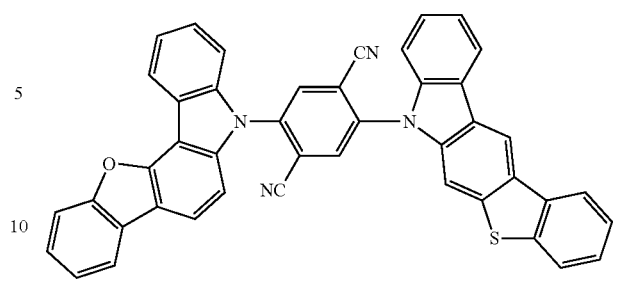
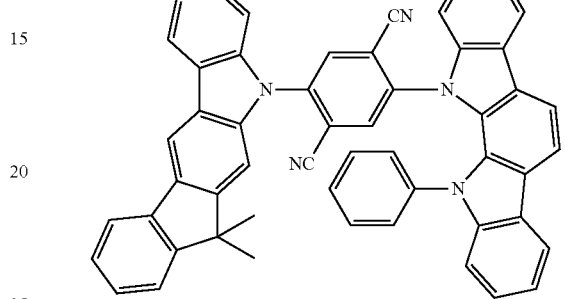
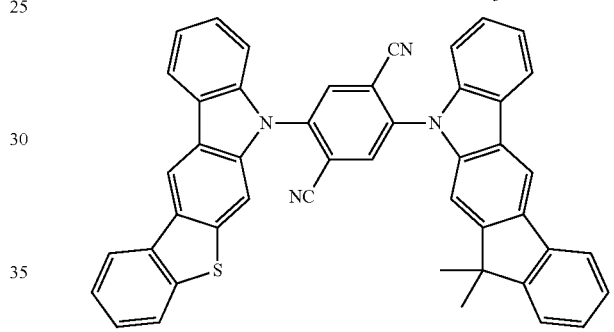
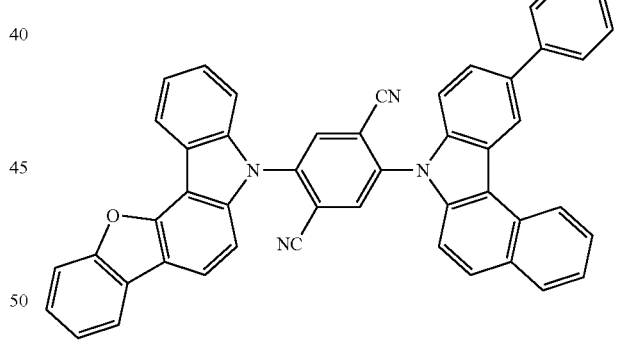
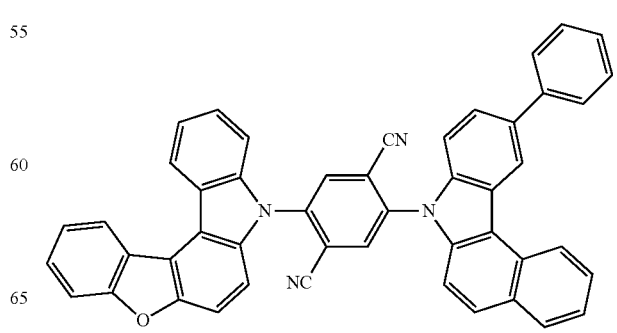

[Formula 101]
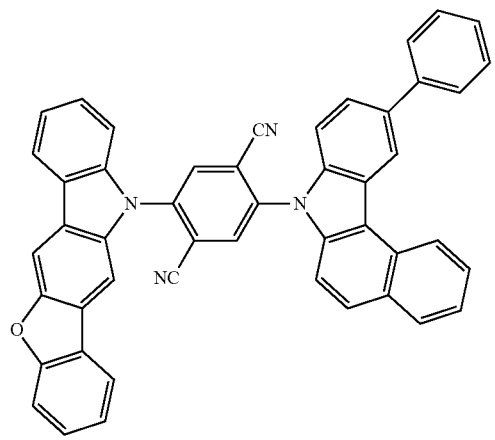
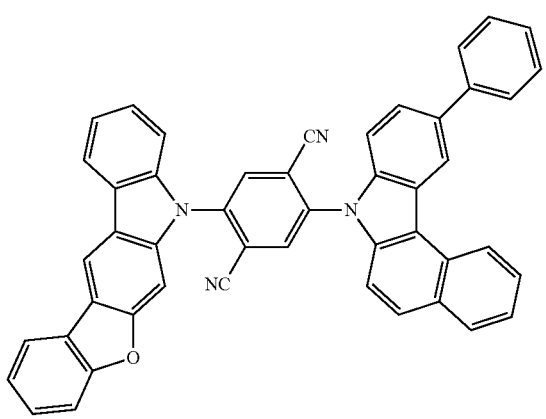
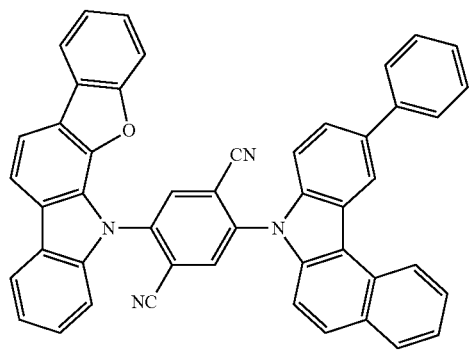
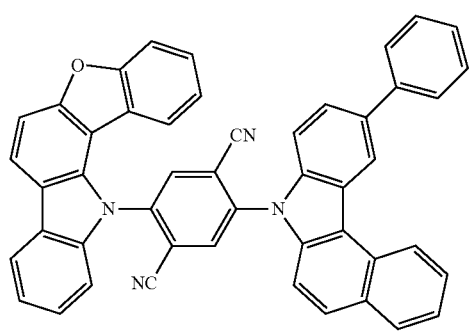
[Formula 102]
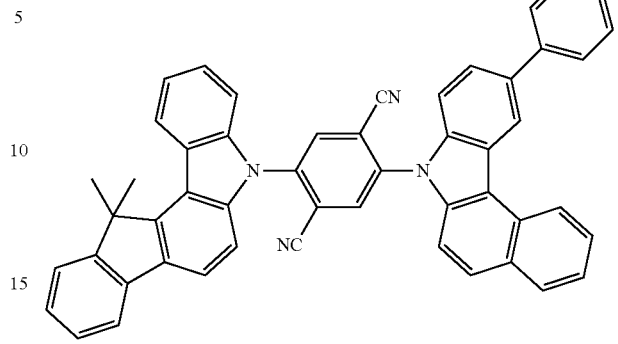
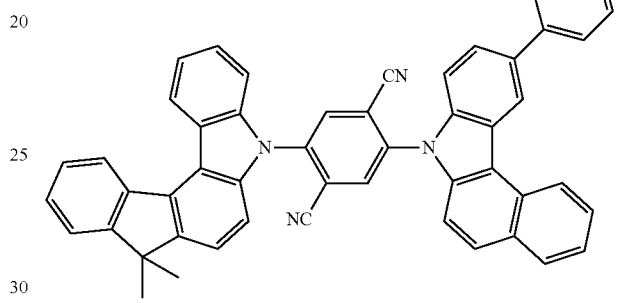
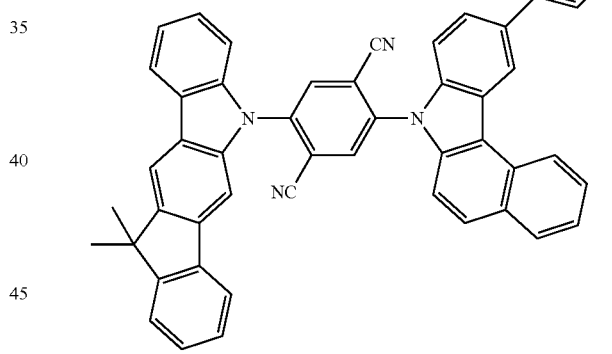
[Formula 103]
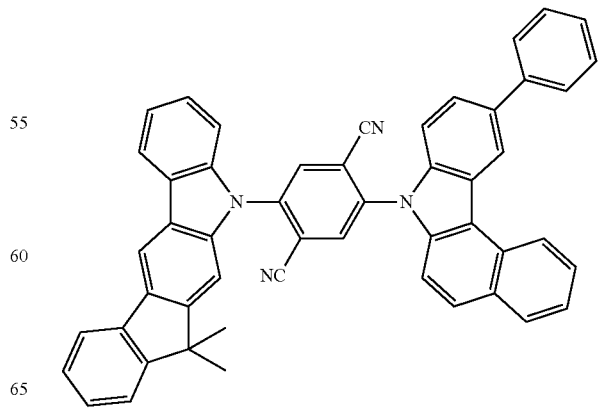

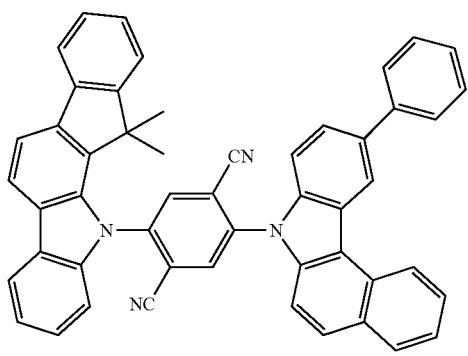
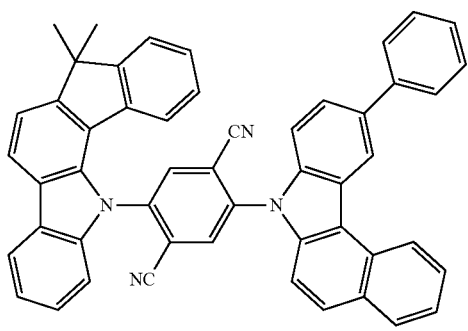
[Formula 104]
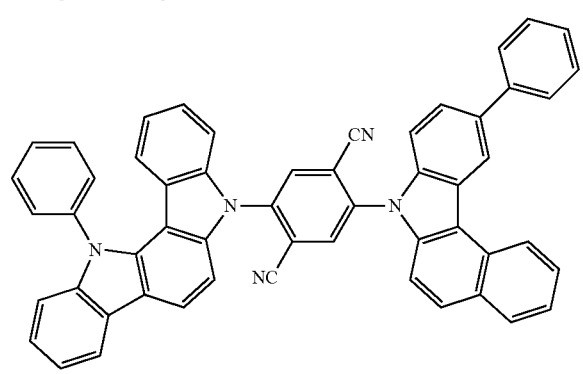
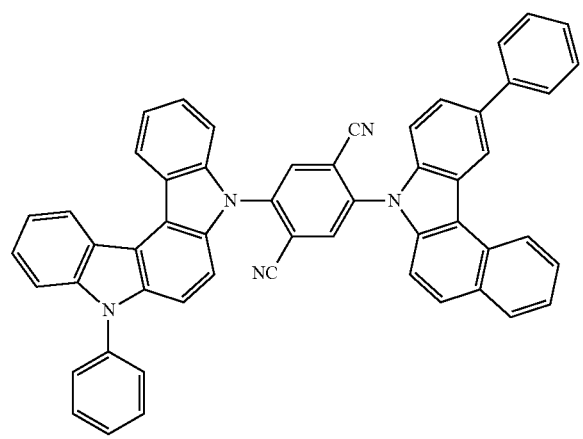
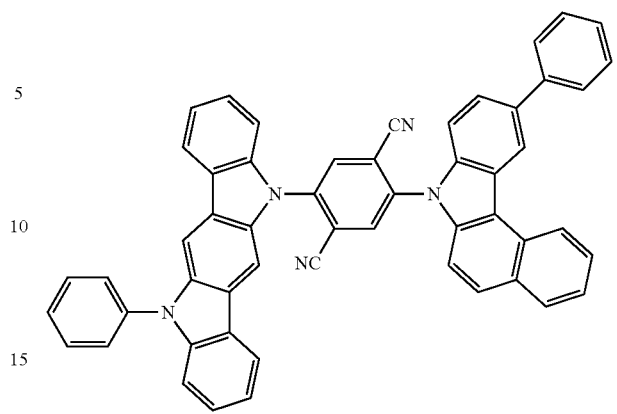
[Formula 105]
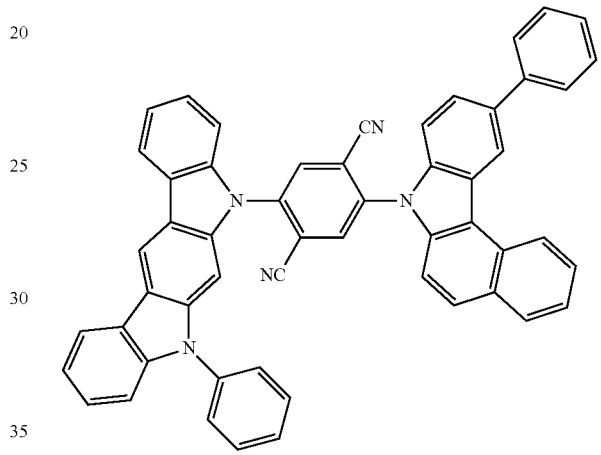
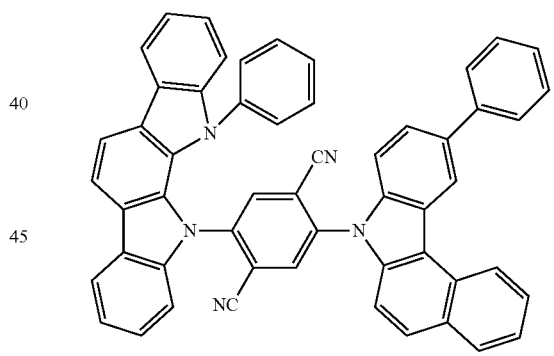
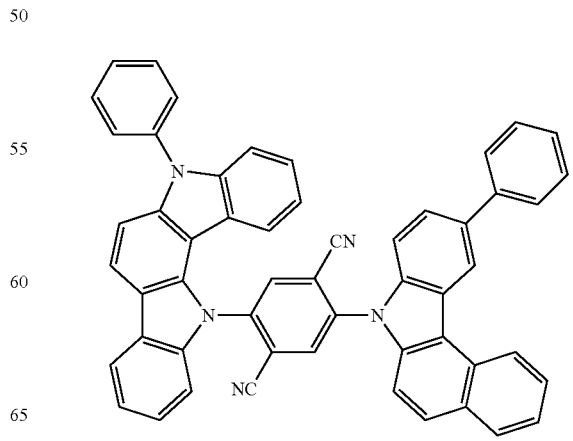

[Formula 106]
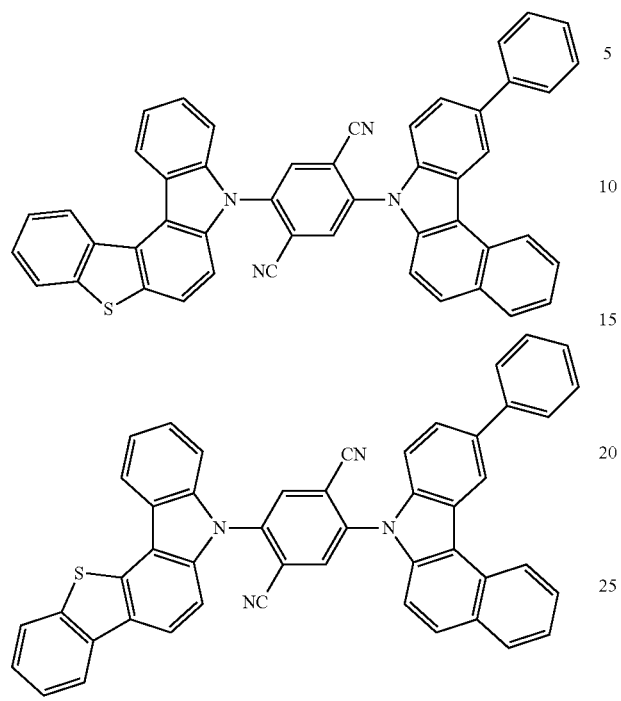
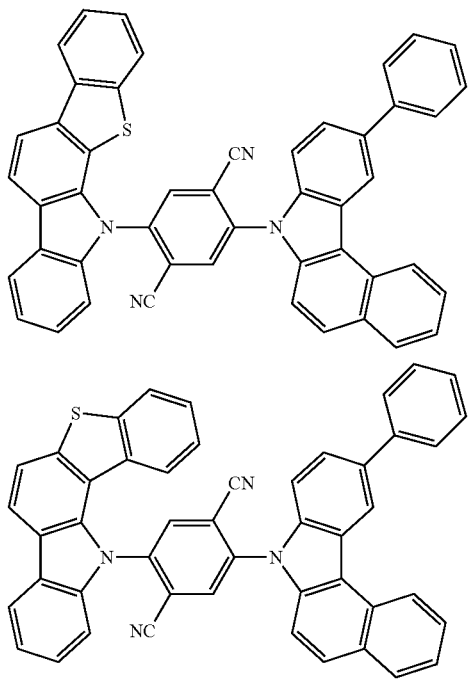
[Formula 107]
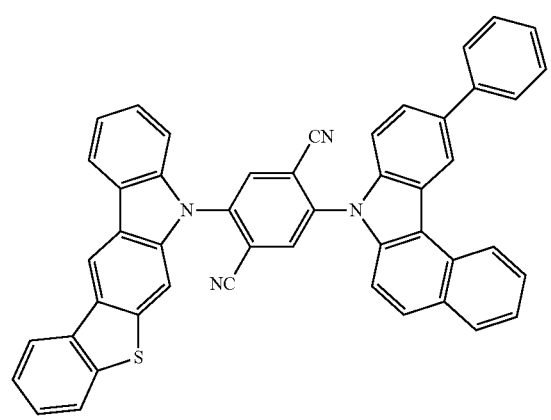
[Formula 108]
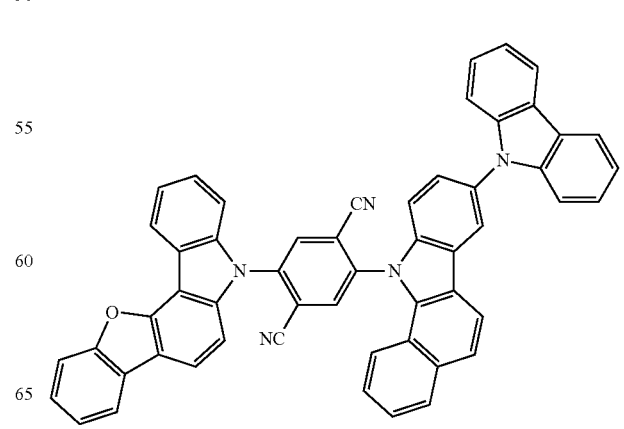
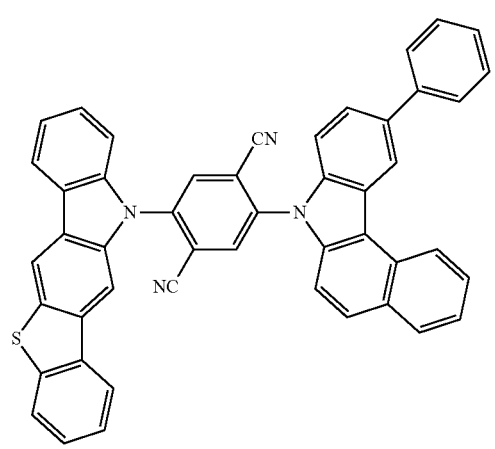

[Formula 109]
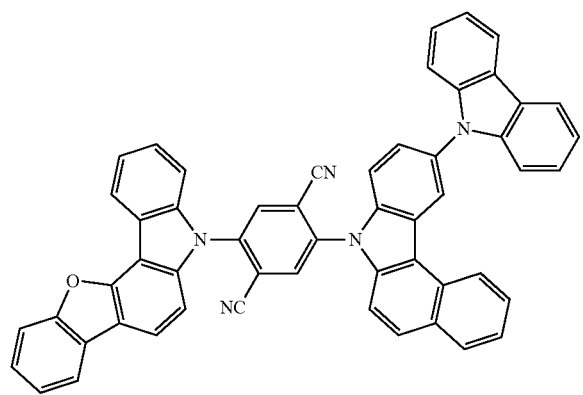
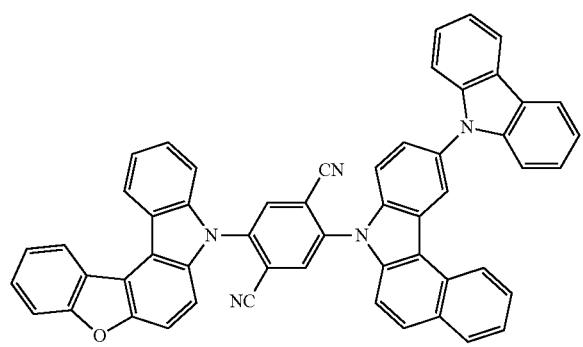
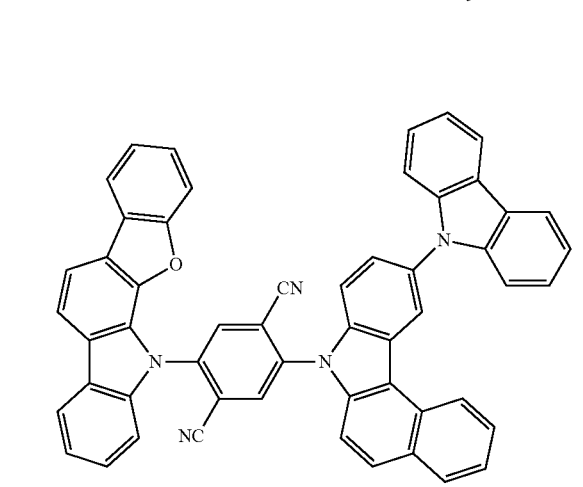
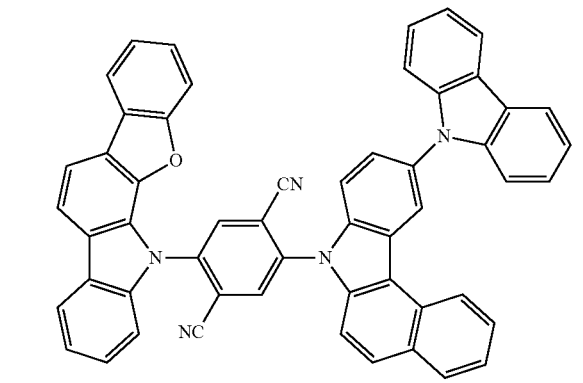
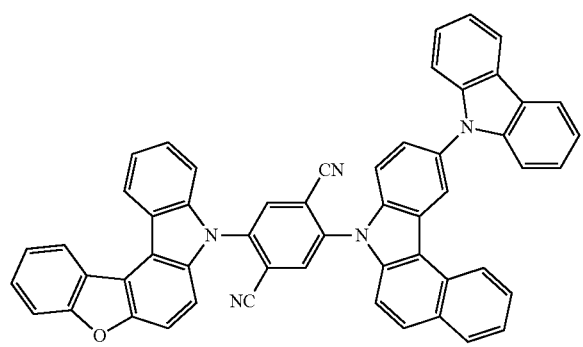
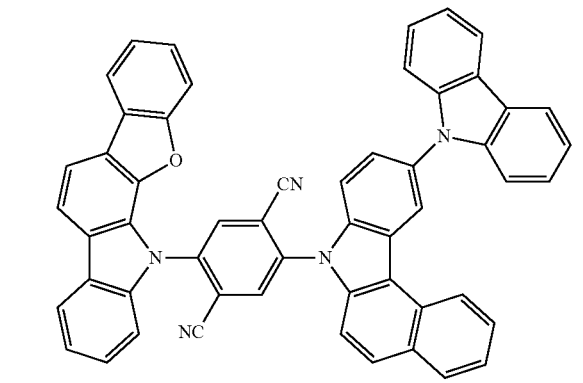

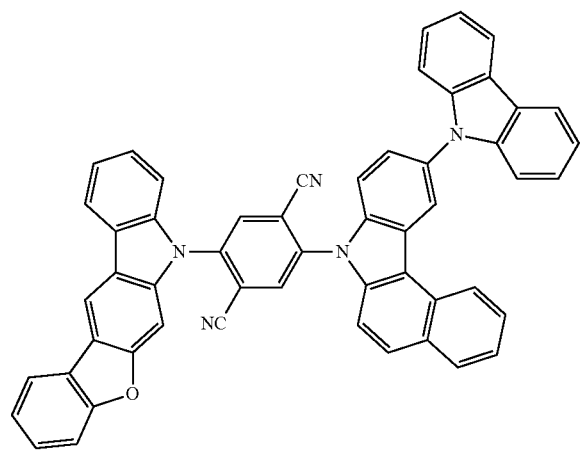
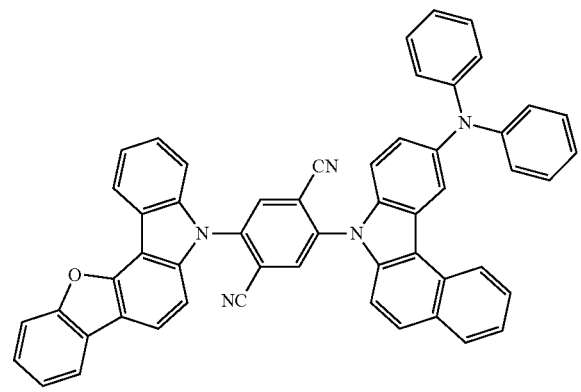
[Formula 110]
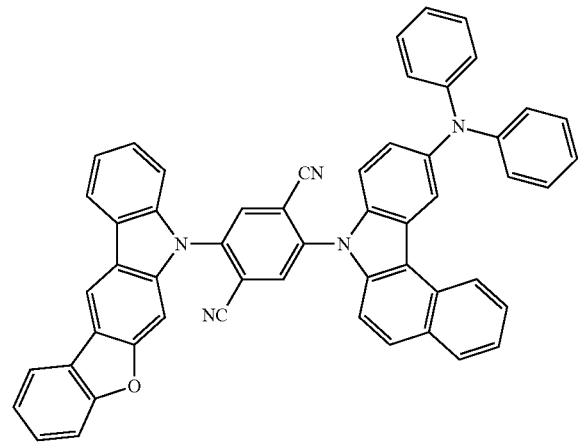
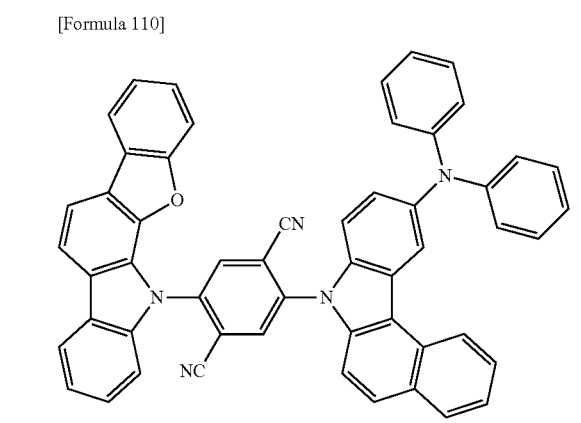
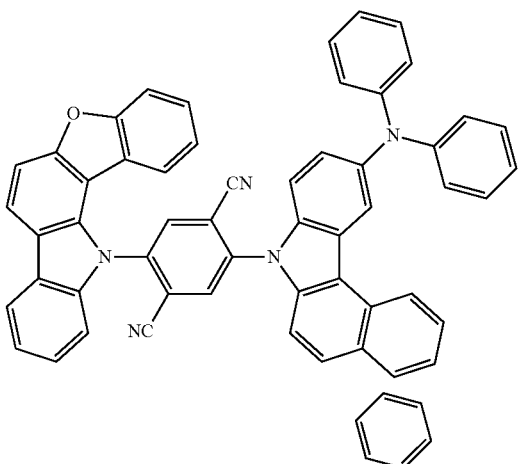
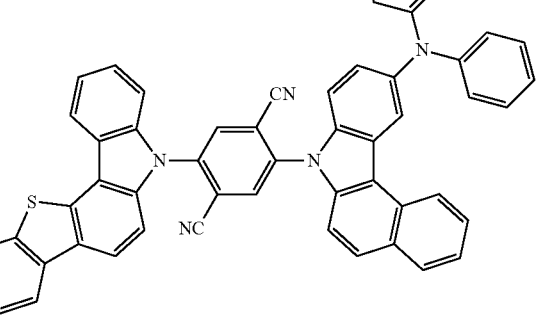
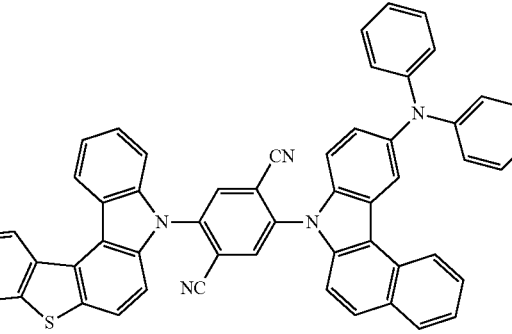
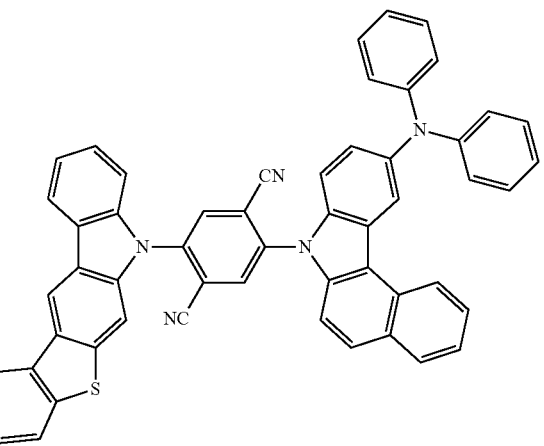

145
-continued
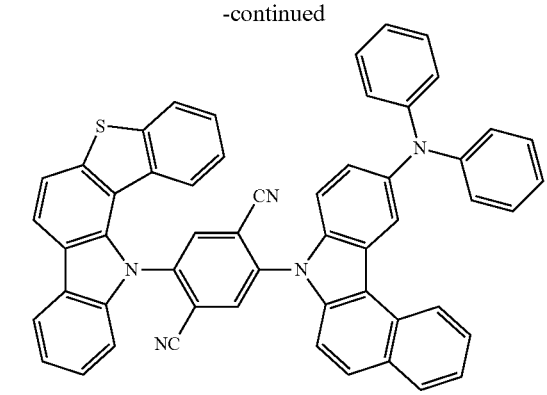
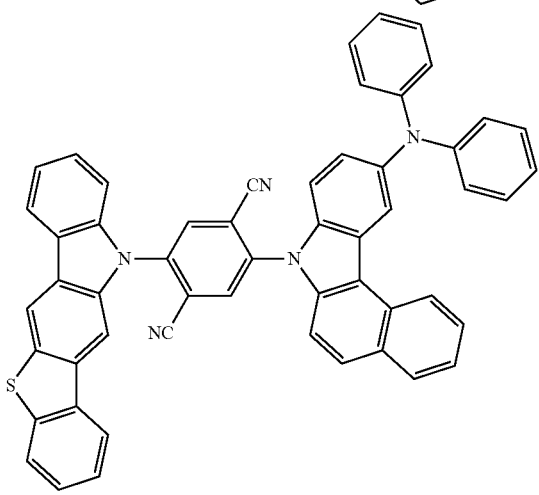
146
-continued
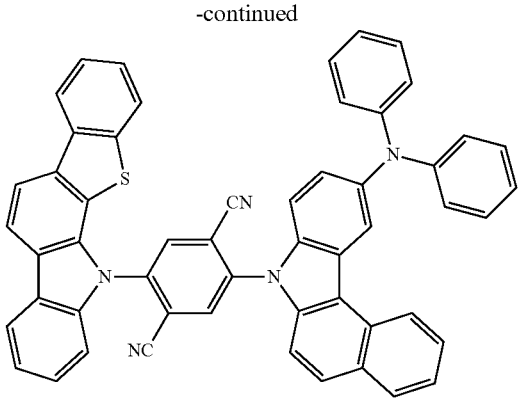
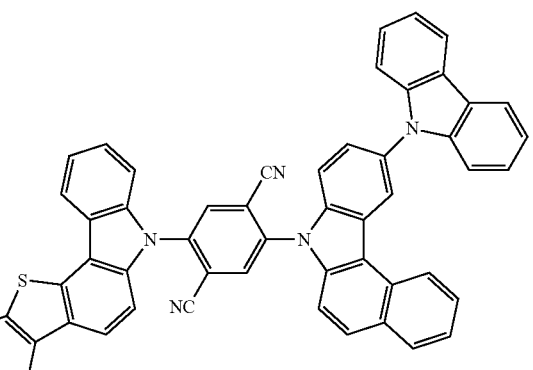
[Formula 111]
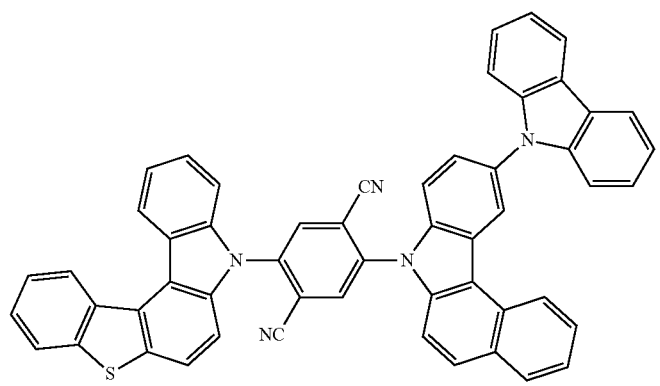
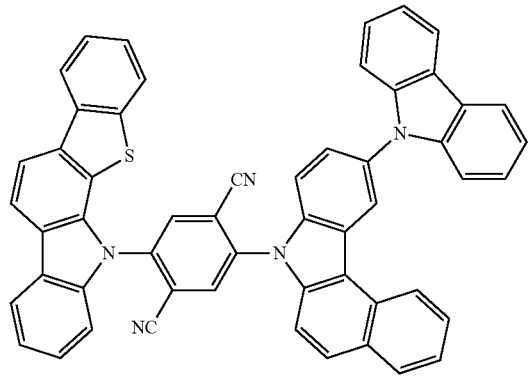

-continued
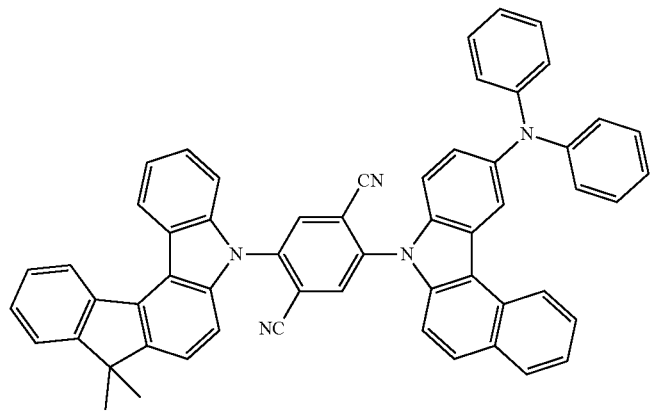
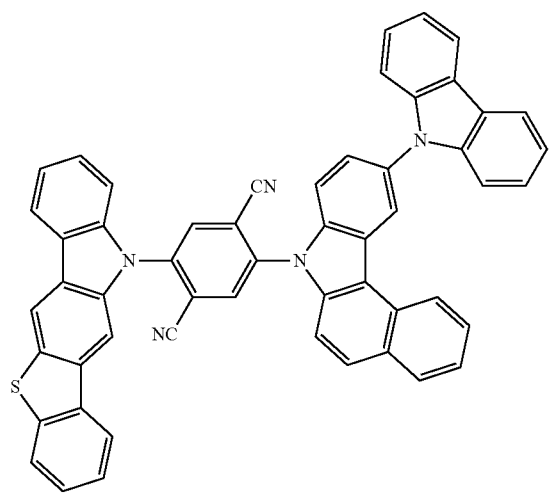
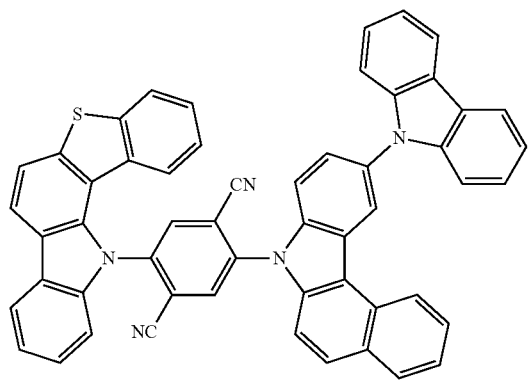

-continued
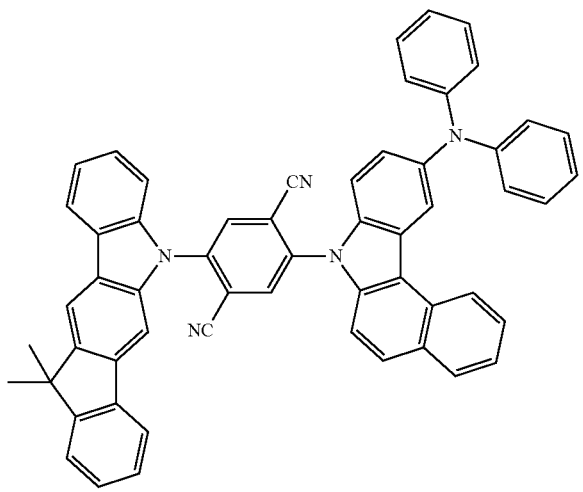
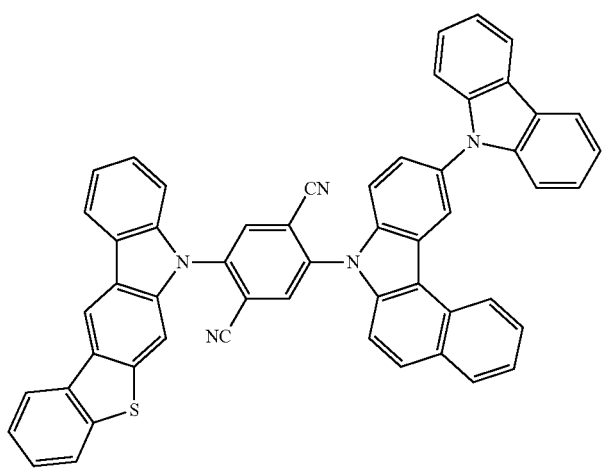
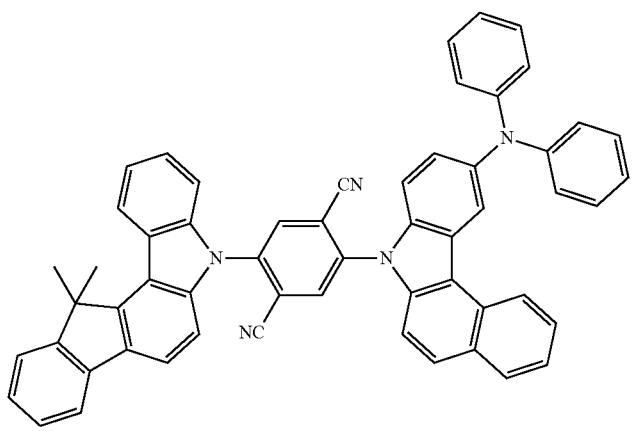

-continued
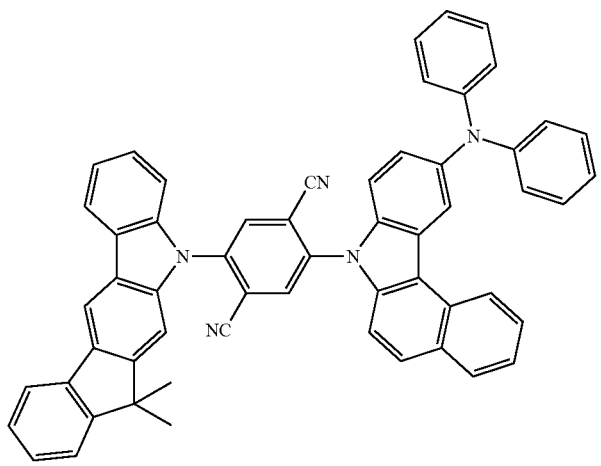
[Formula 112]
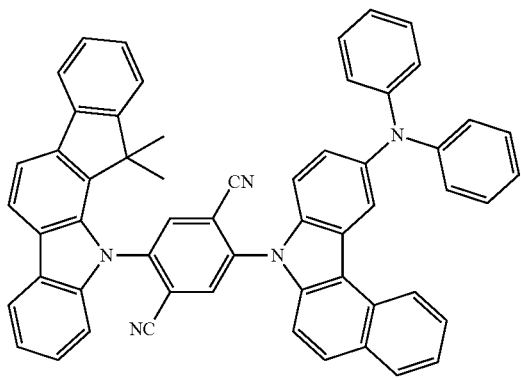
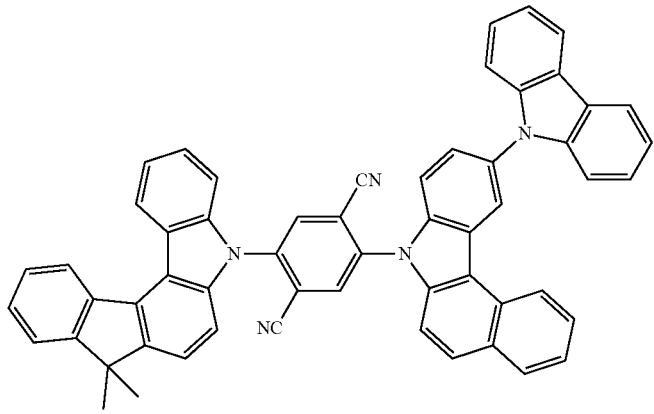
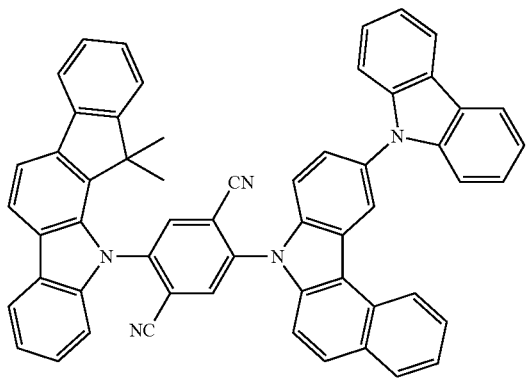

-continued
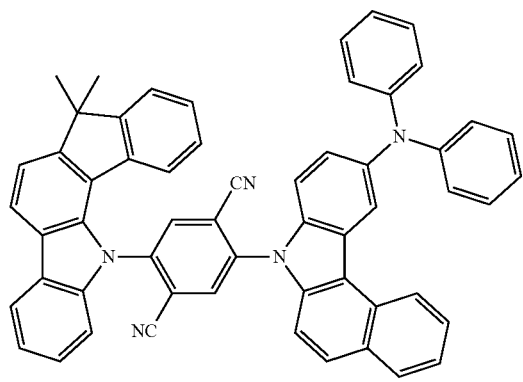
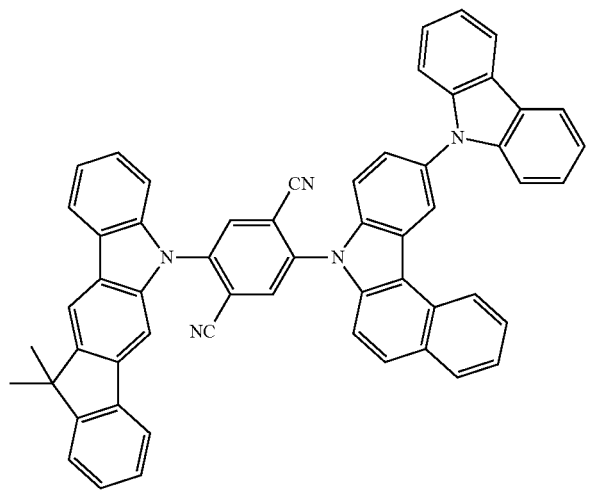
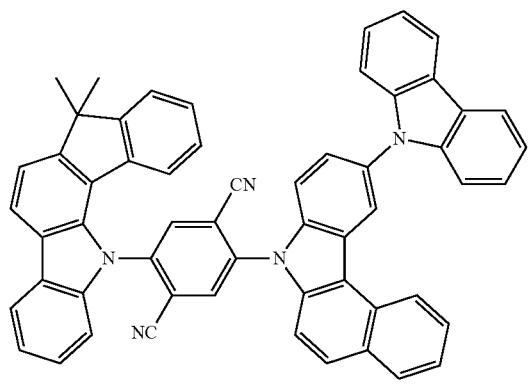
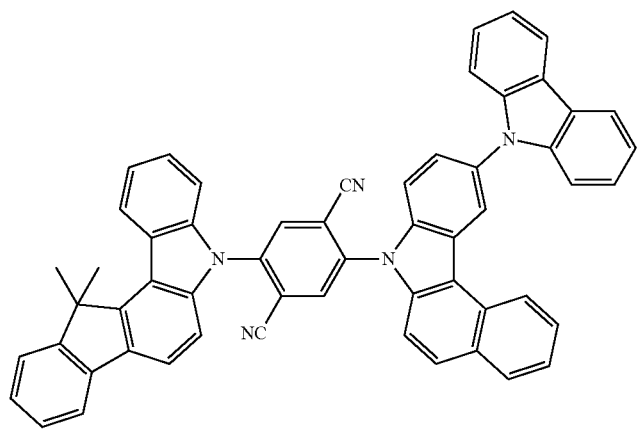

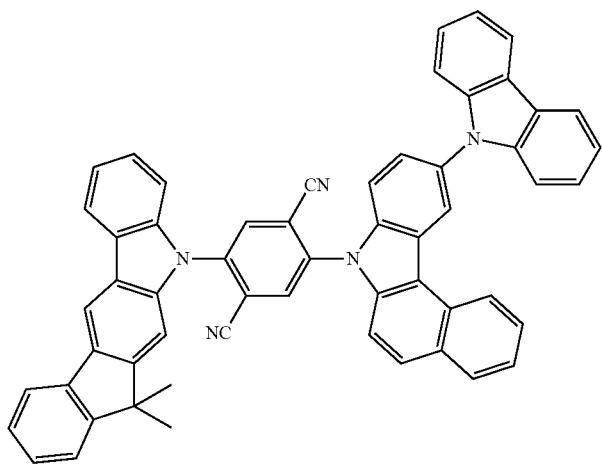
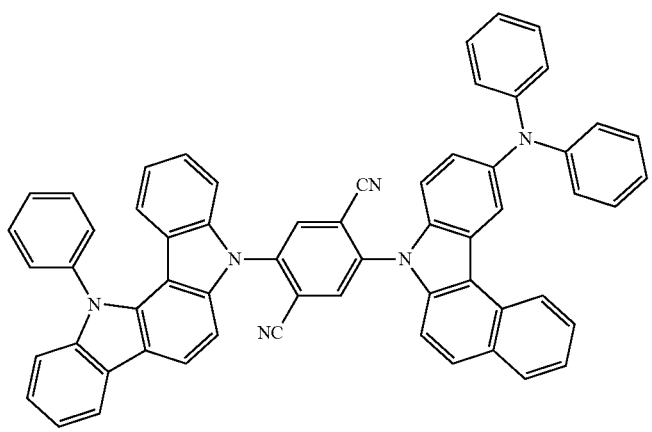
[Formula 113]
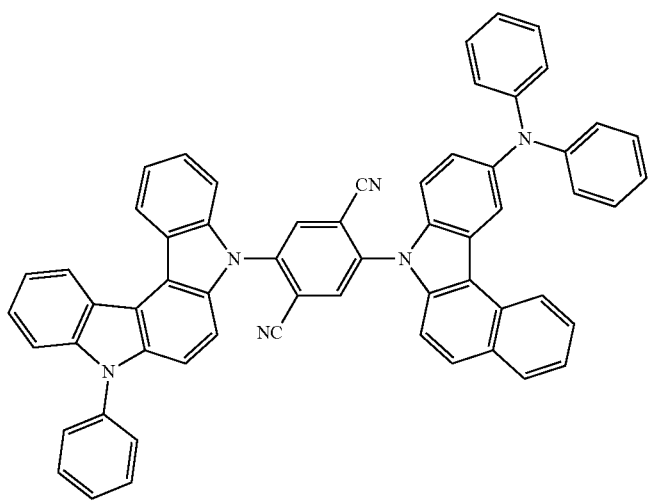

-continued
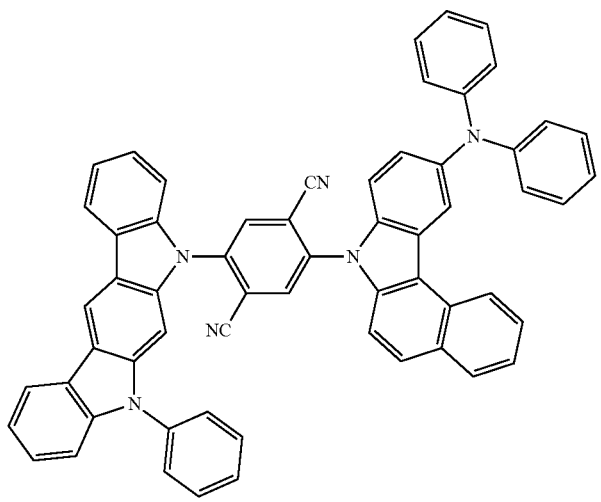
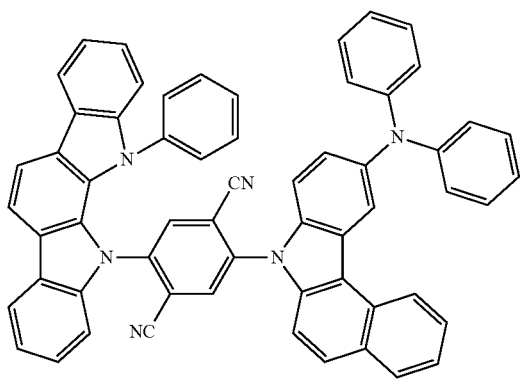
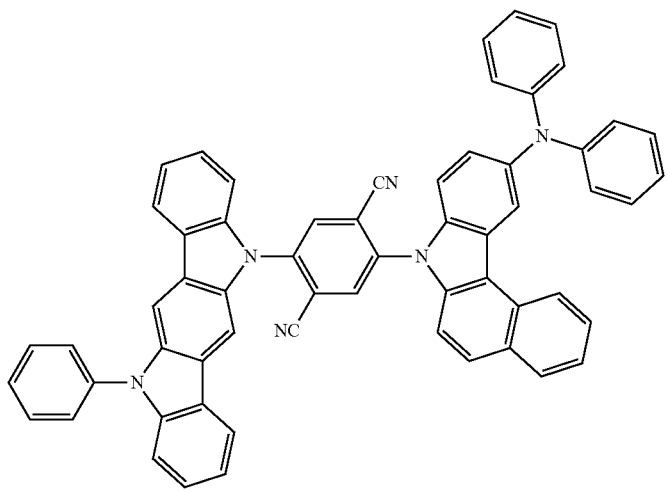

-continued
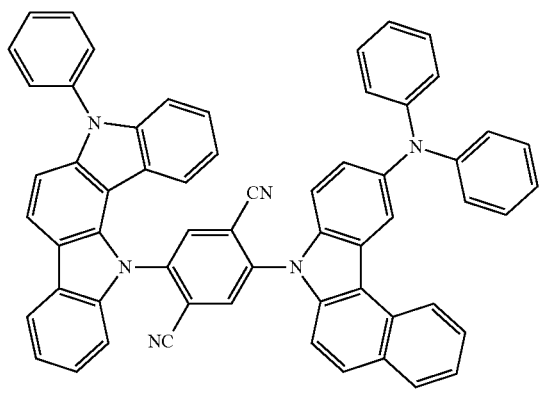
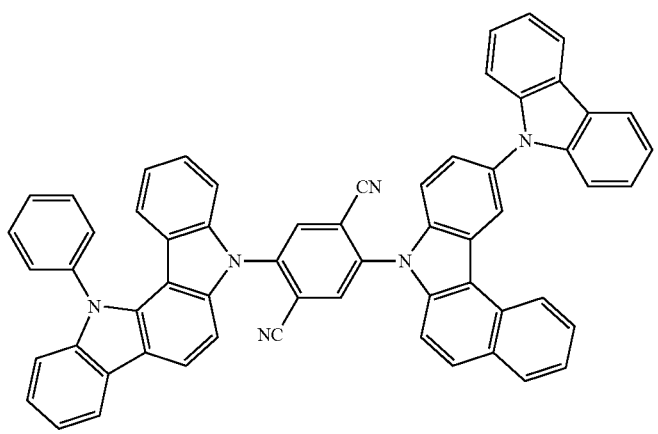
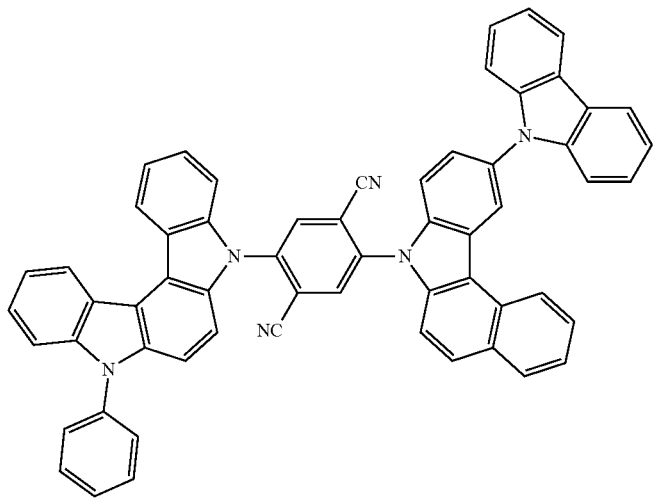

-continued
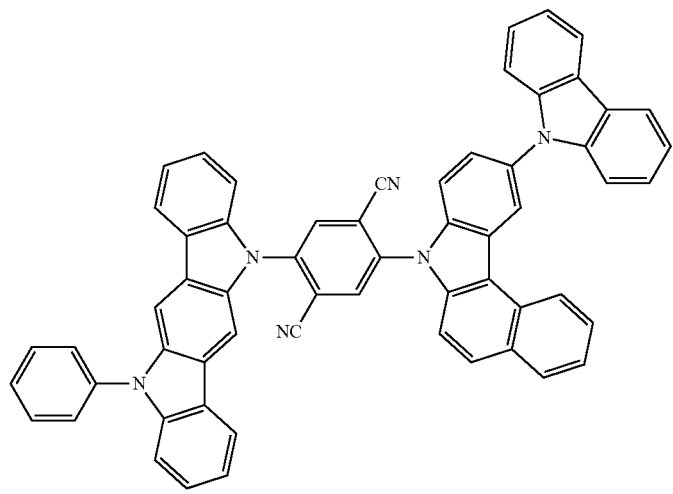
[Formula 114]
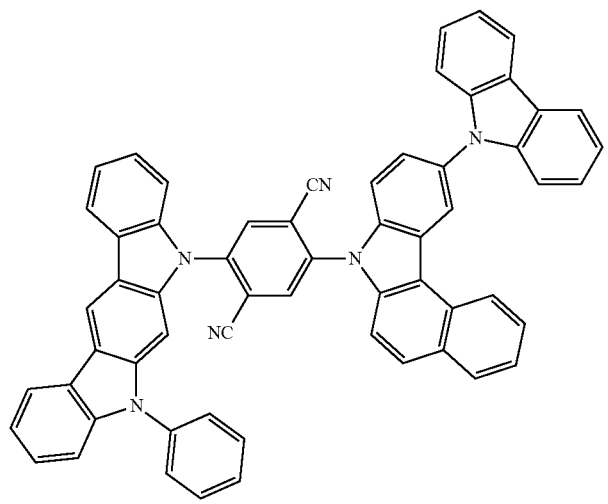
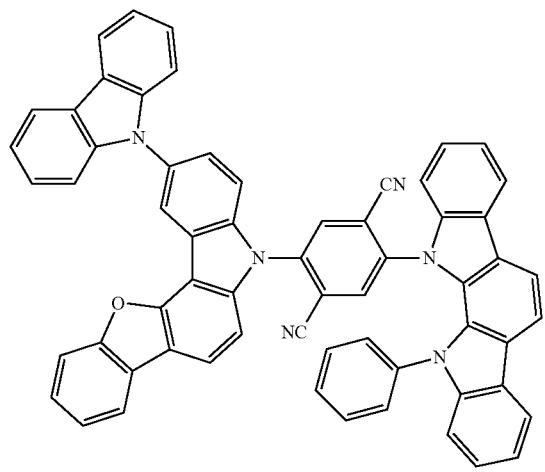

-continued
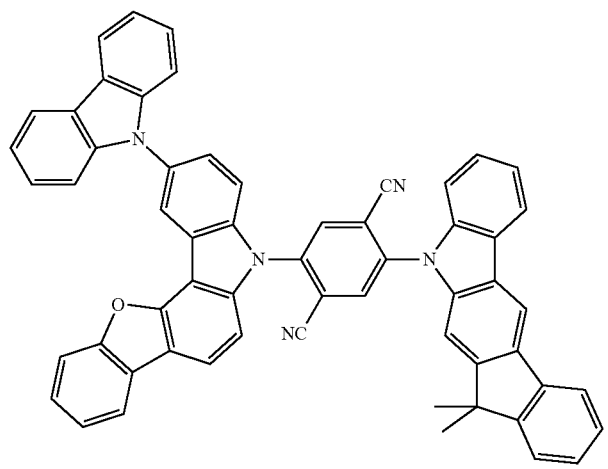
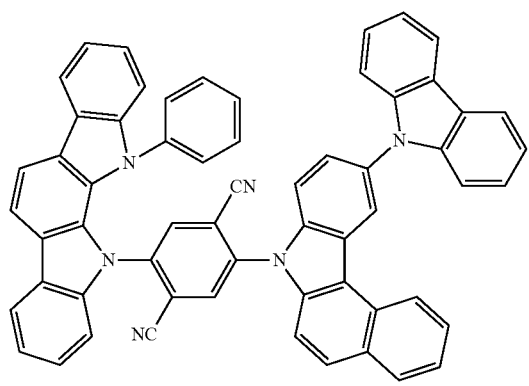
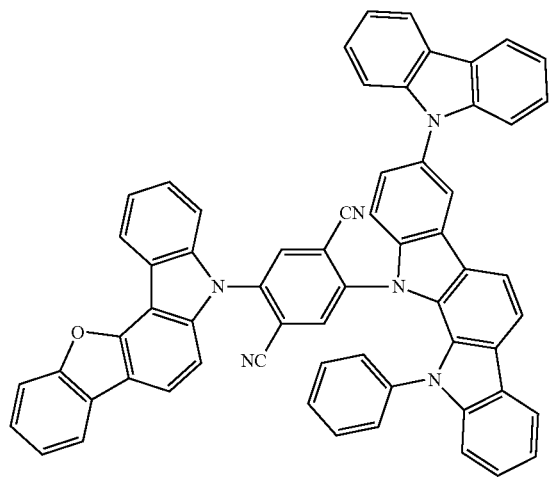

-continued
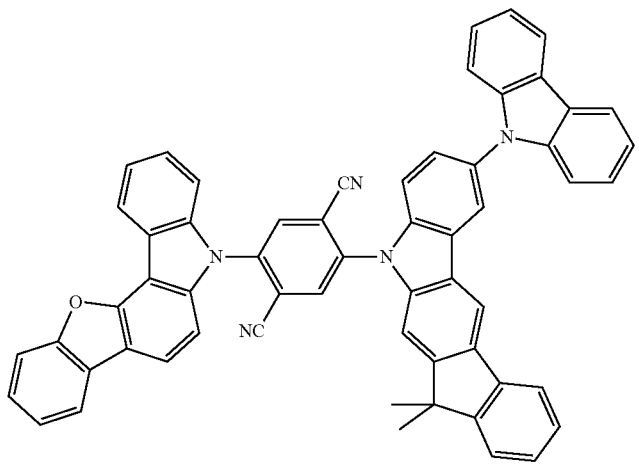
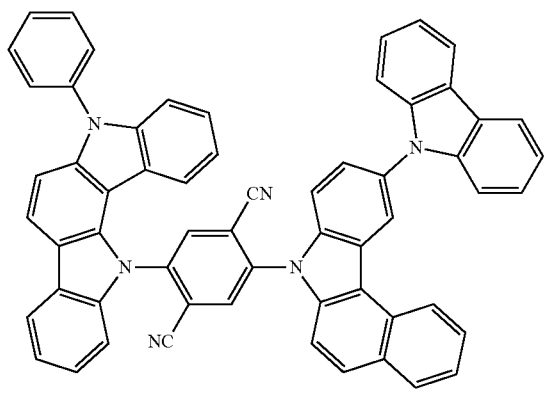
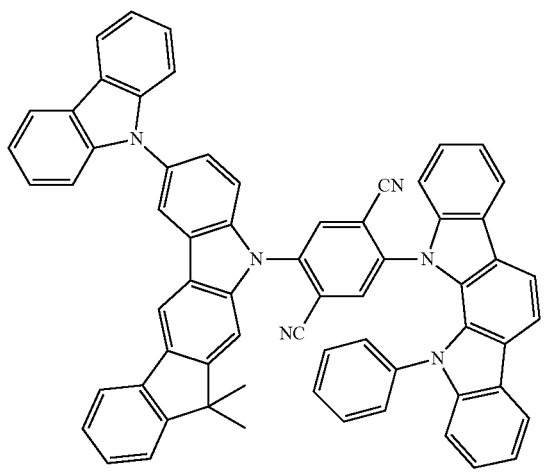

[Formula 115]
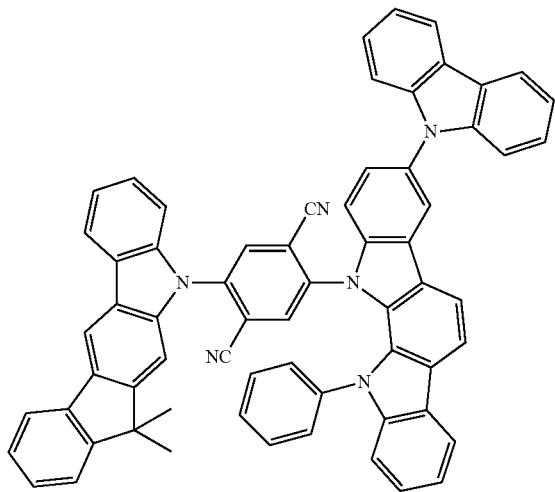
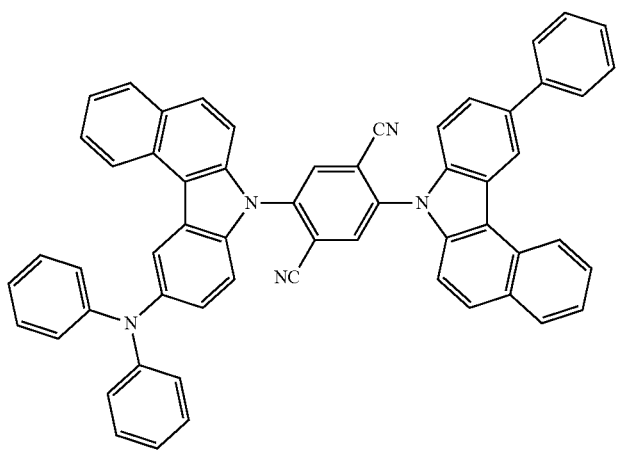
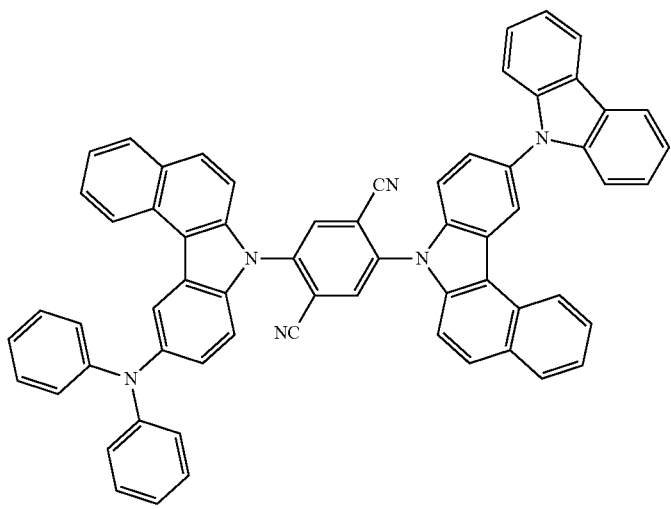

-continued
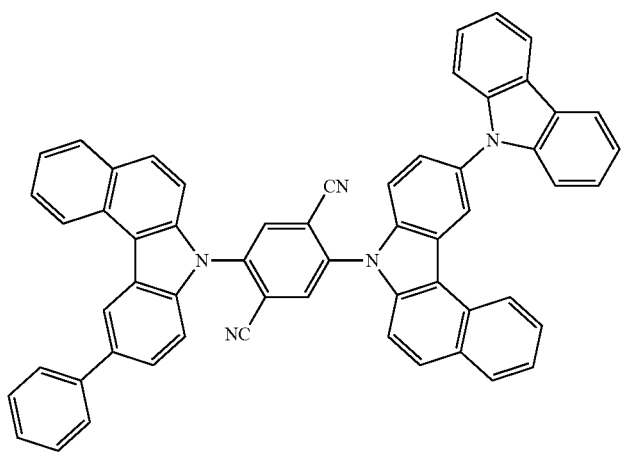
[Formula 116]
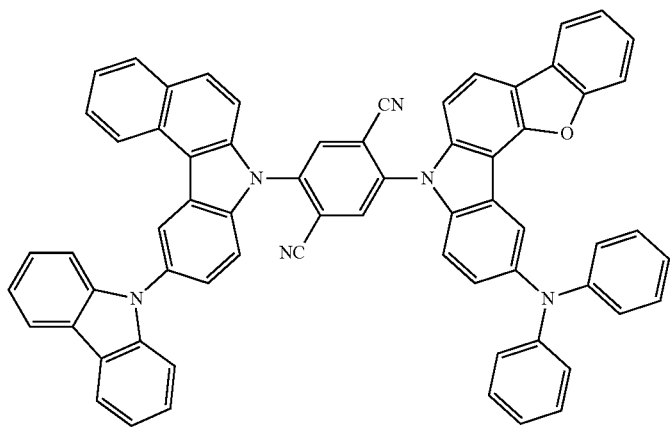
[Formula 117]
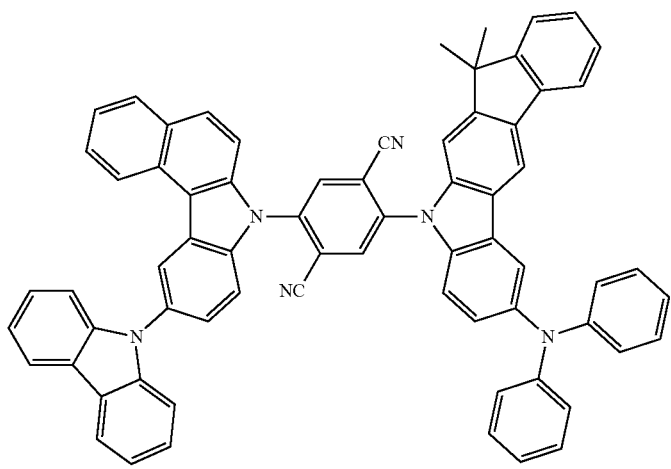

-continued
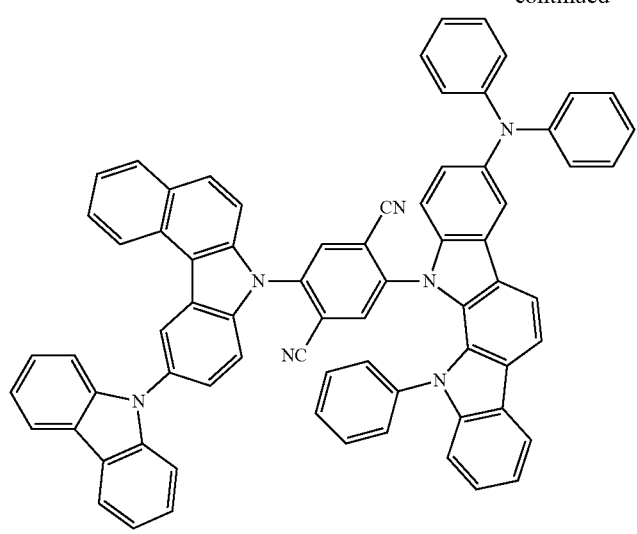
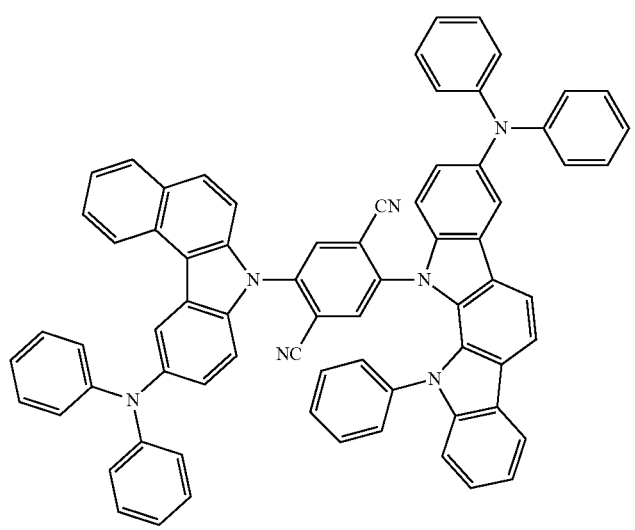
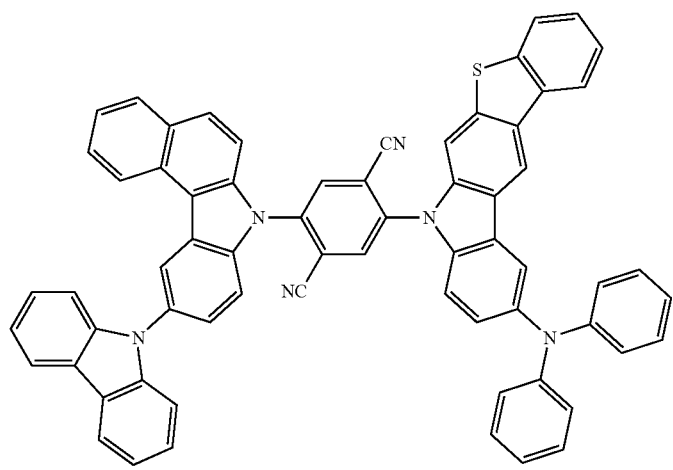

-continued
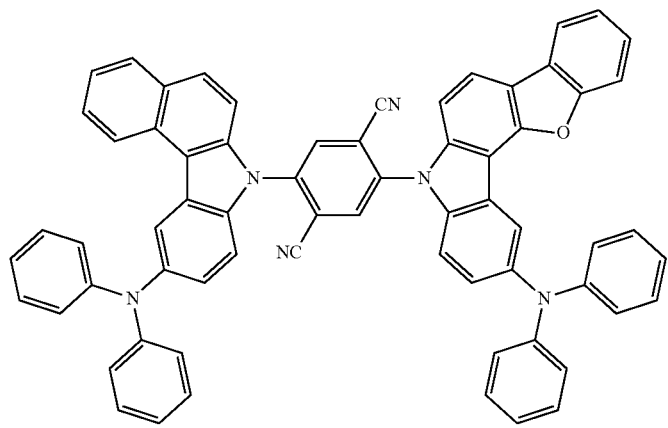
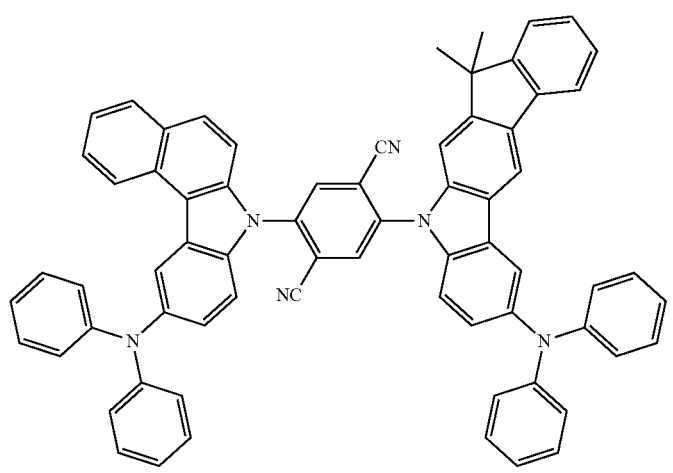
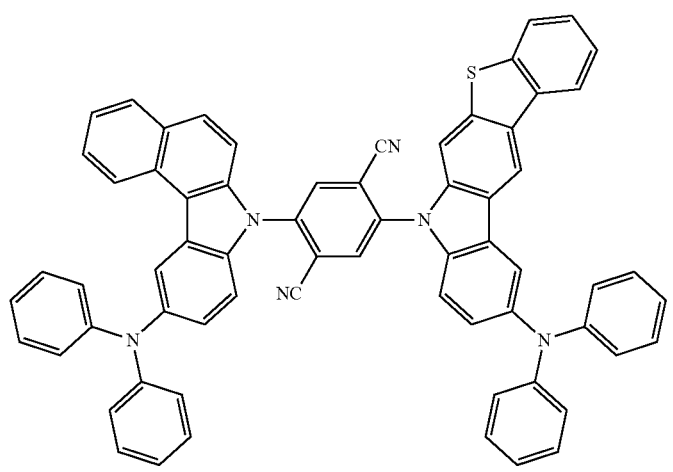

[Formula 118]
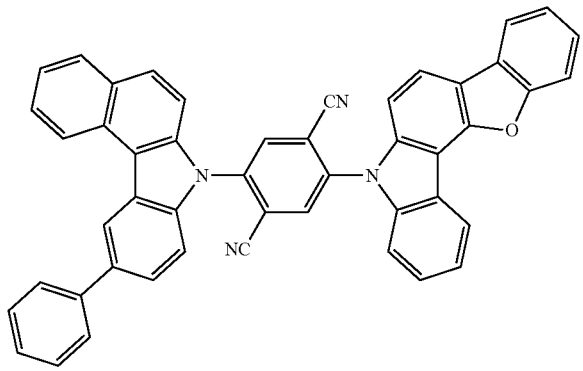
[Formula 119]
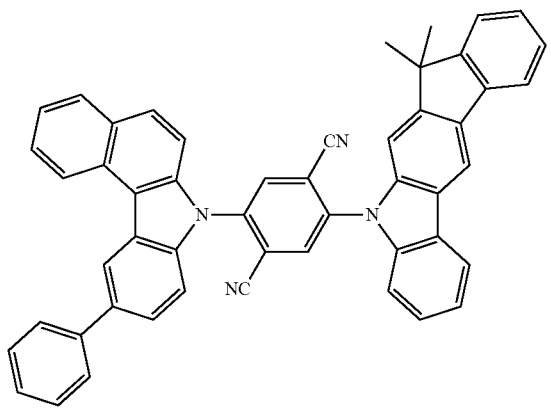
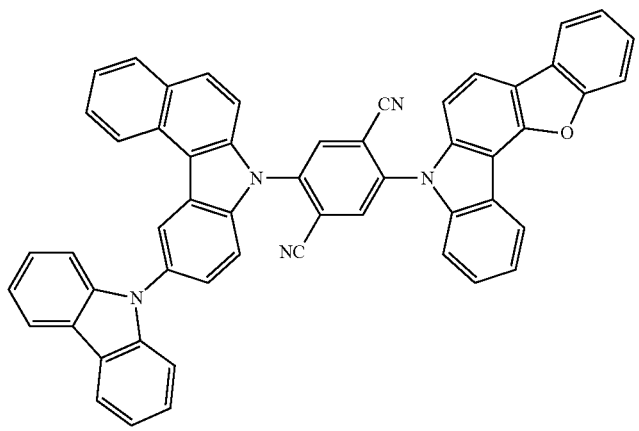
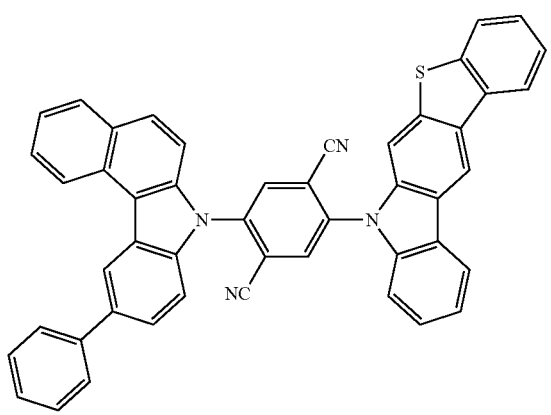

177 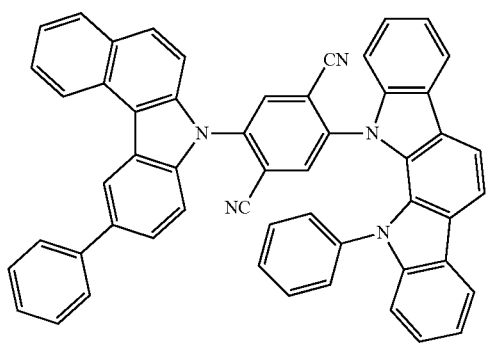
178 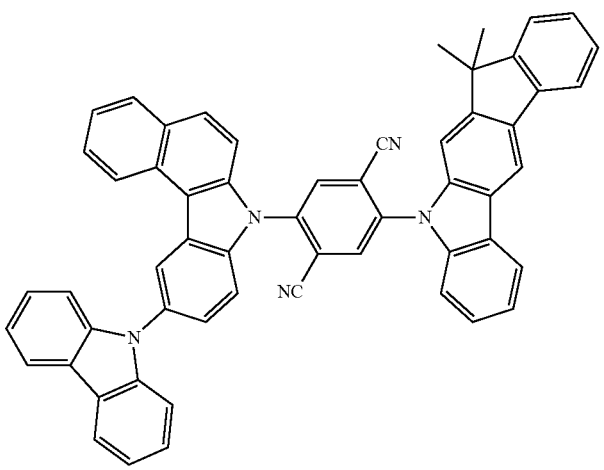
[Formula 120]
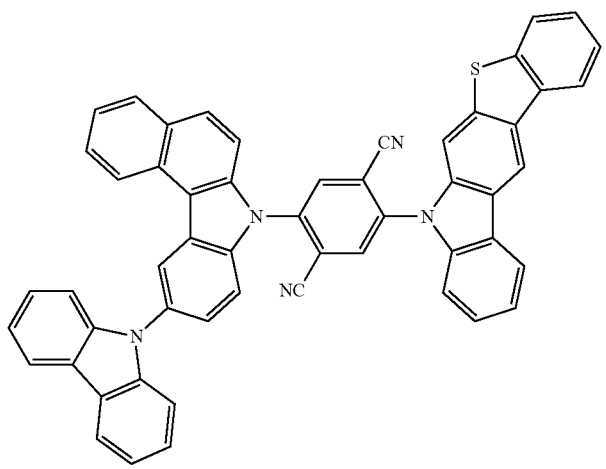
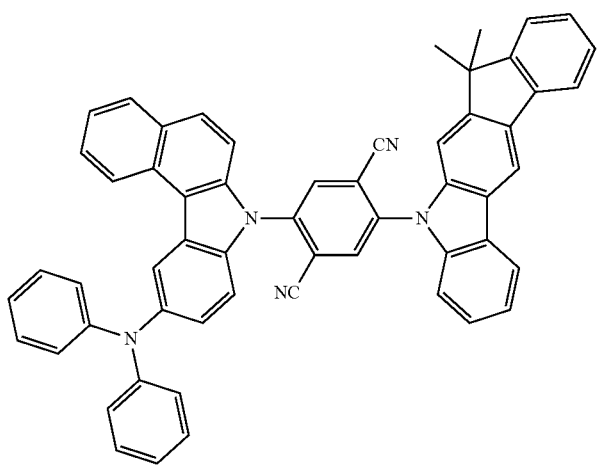

179 180
-continued
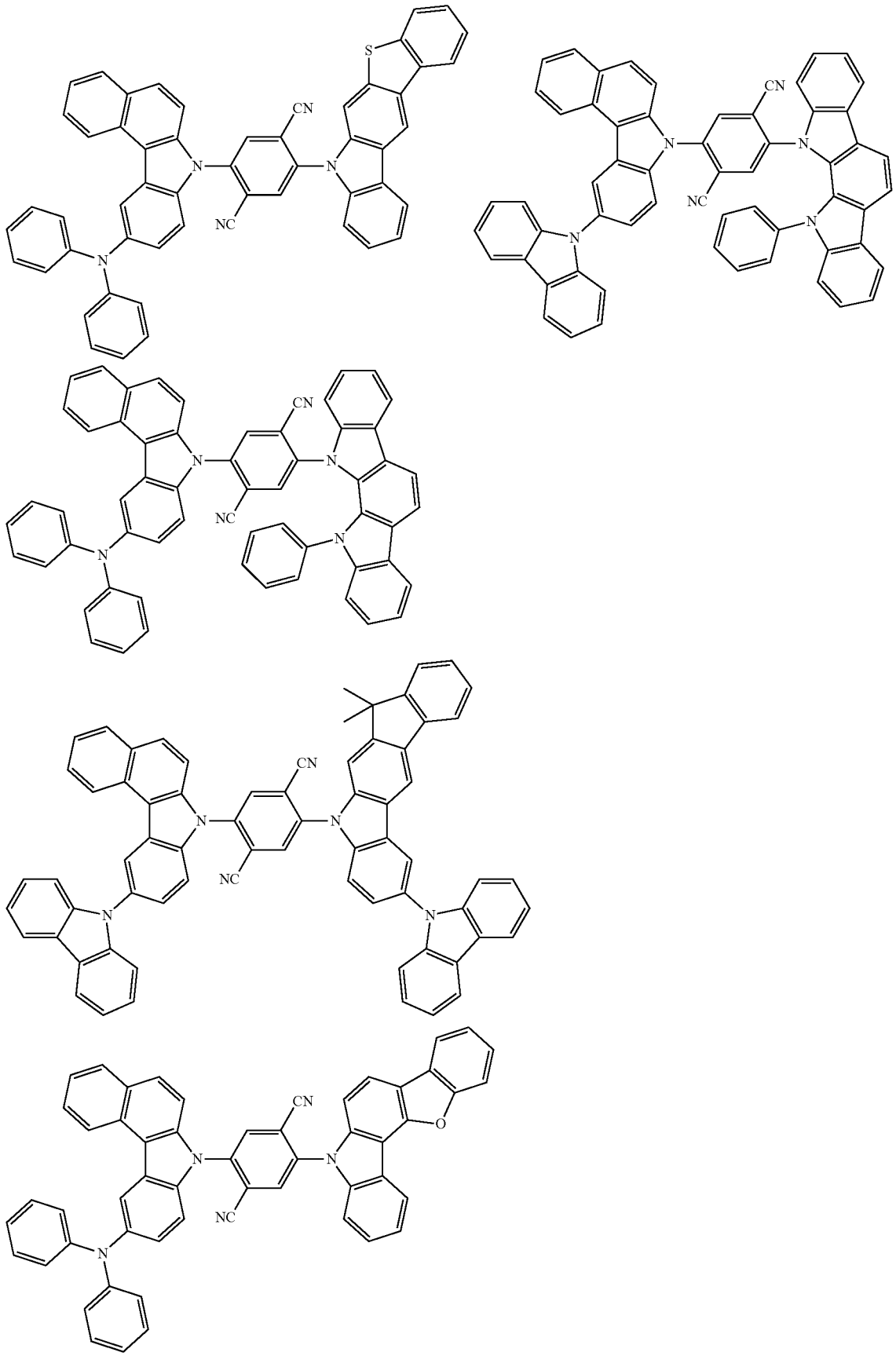

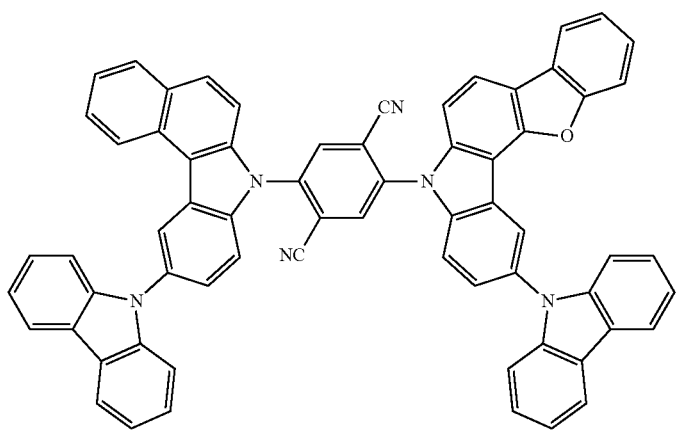
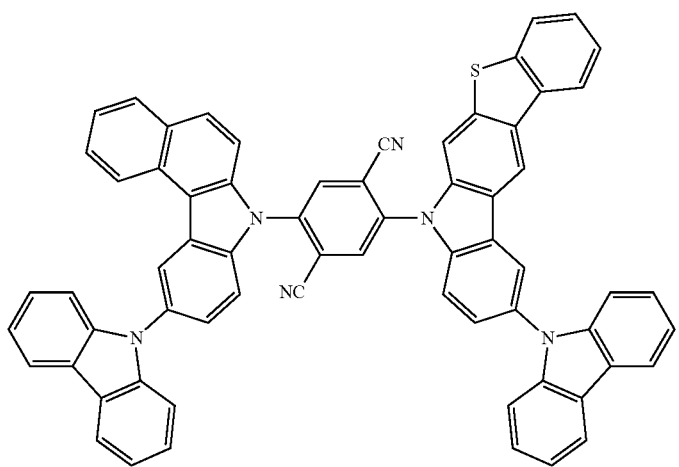
[Formula 121]
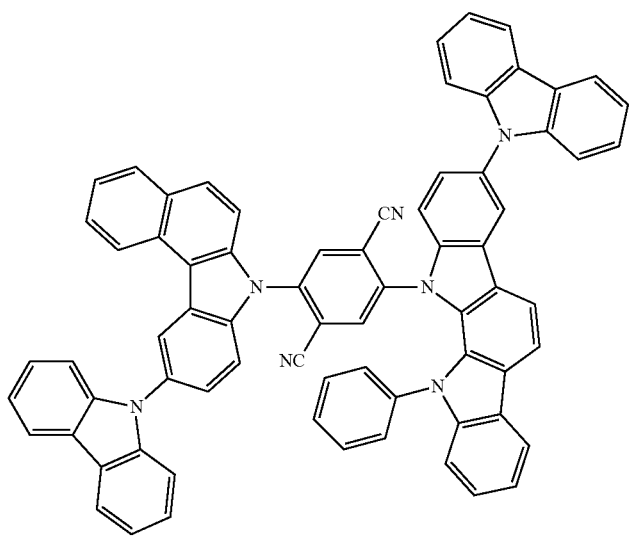

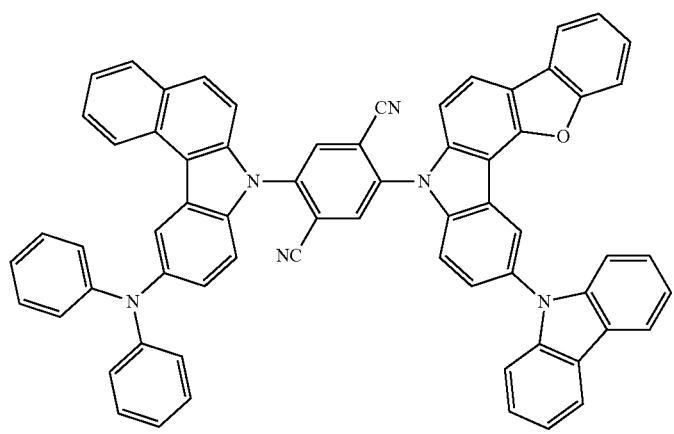
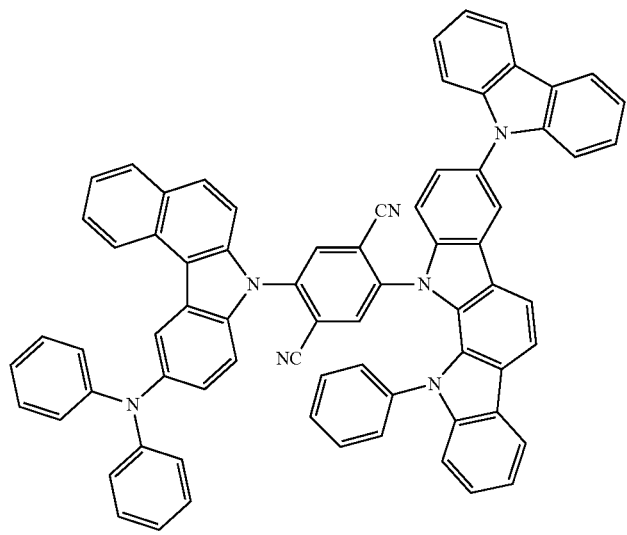
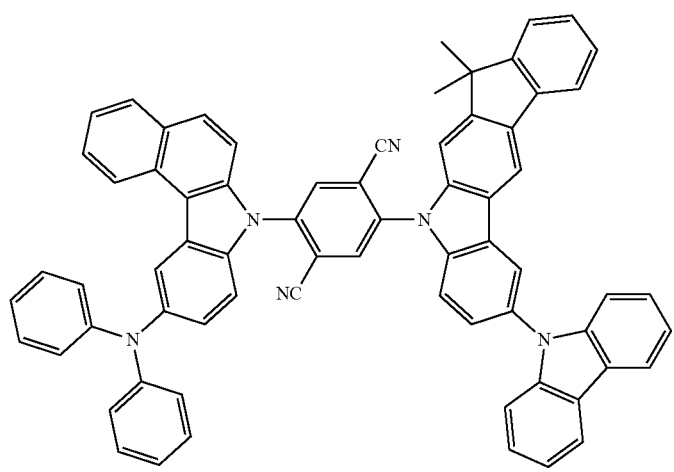

-continued
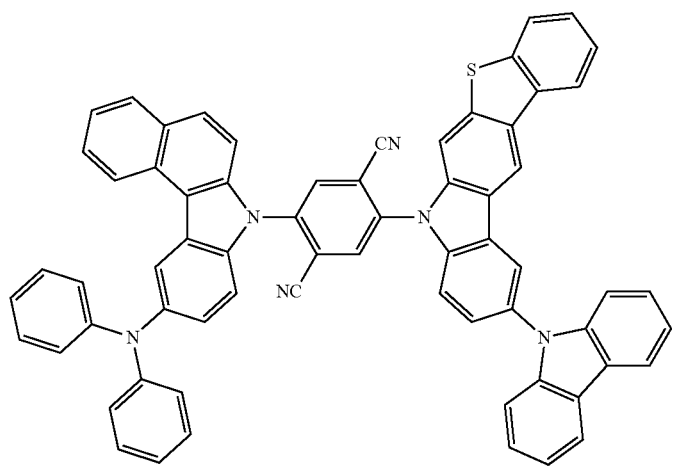
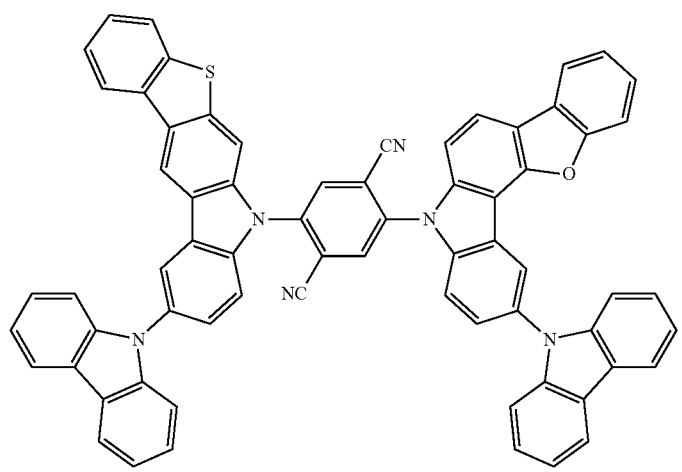
[Formula 122]
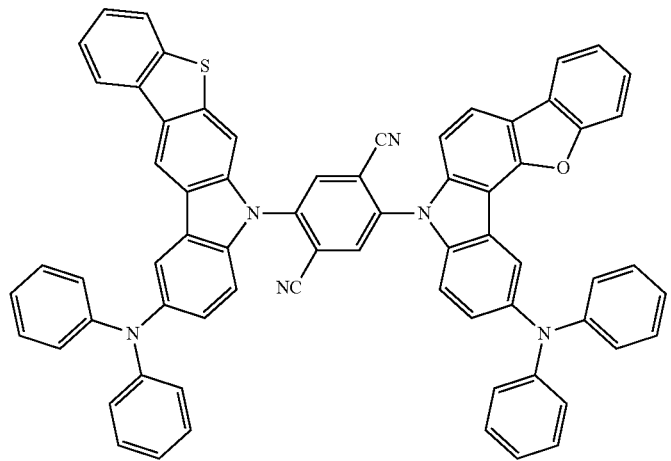

-continued
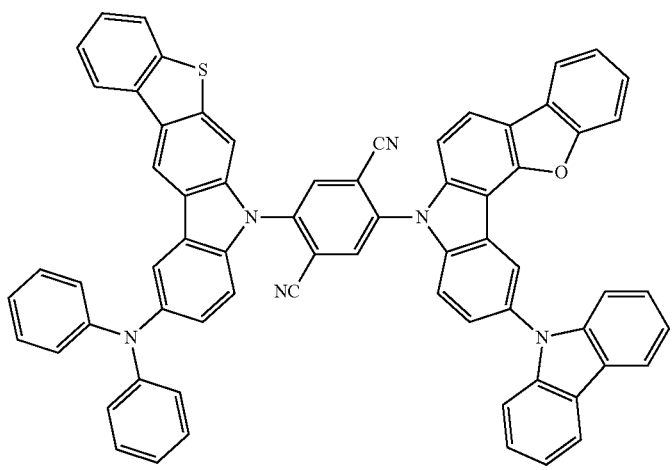
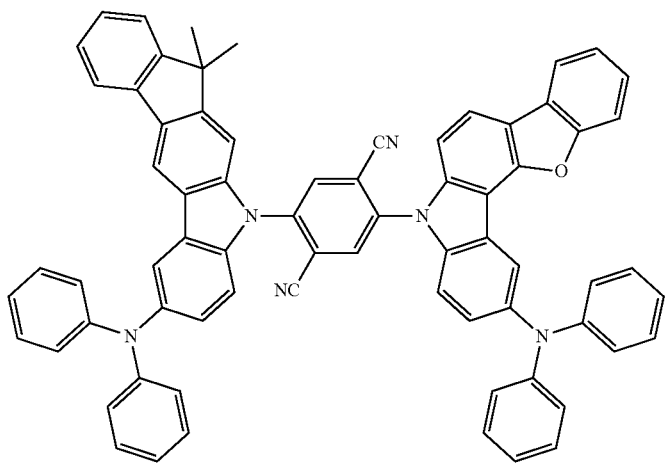
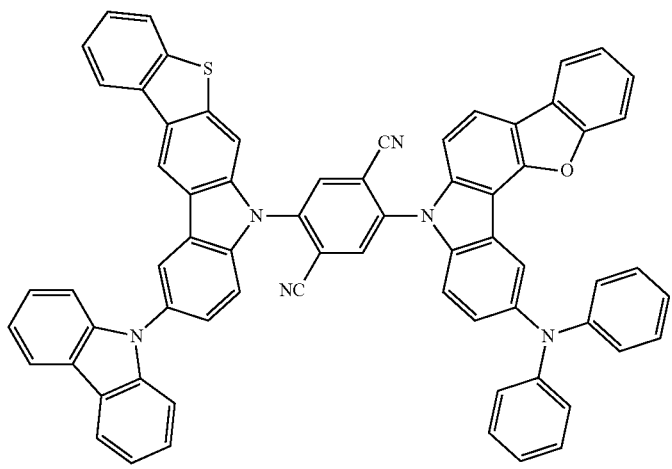

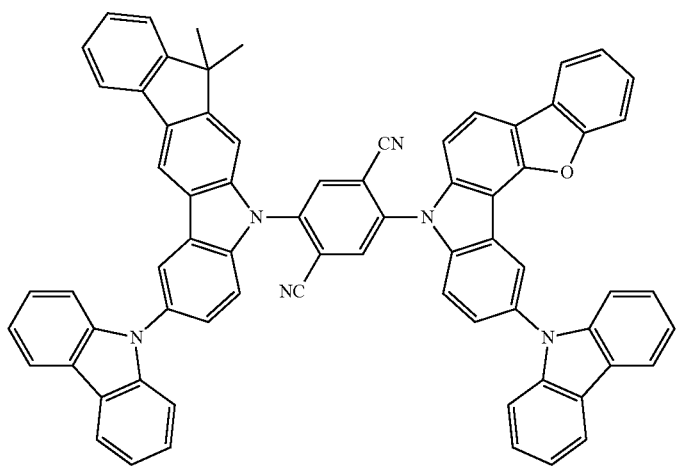
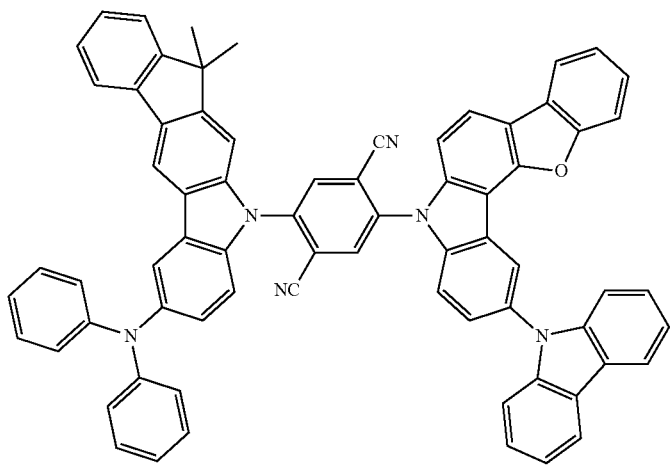
[Formula 123]
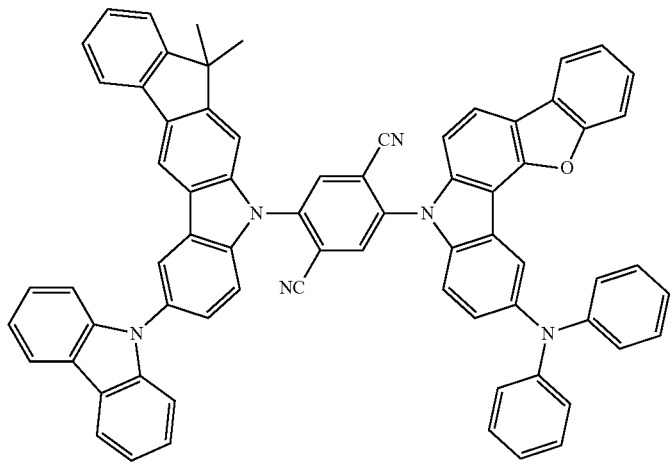

-continued
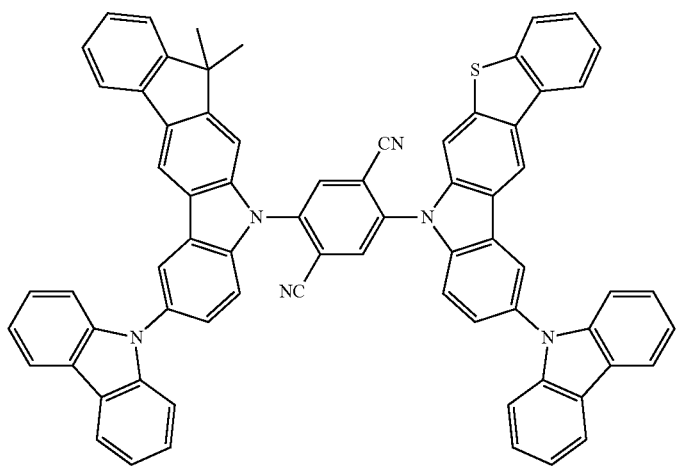
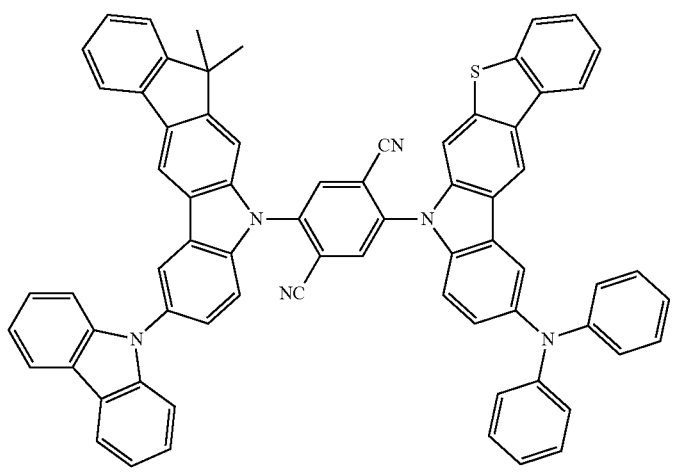
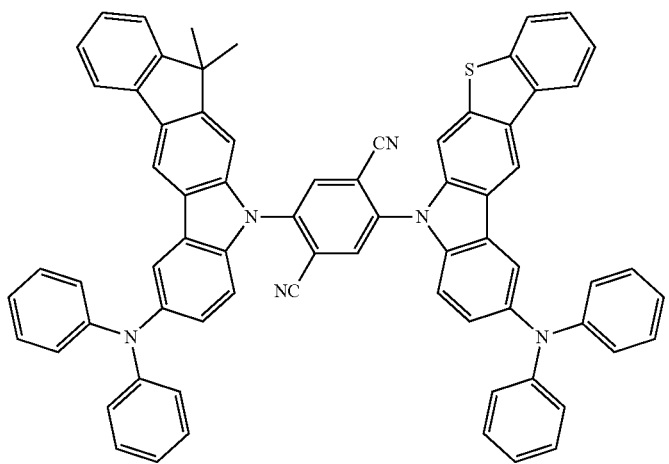

-continued
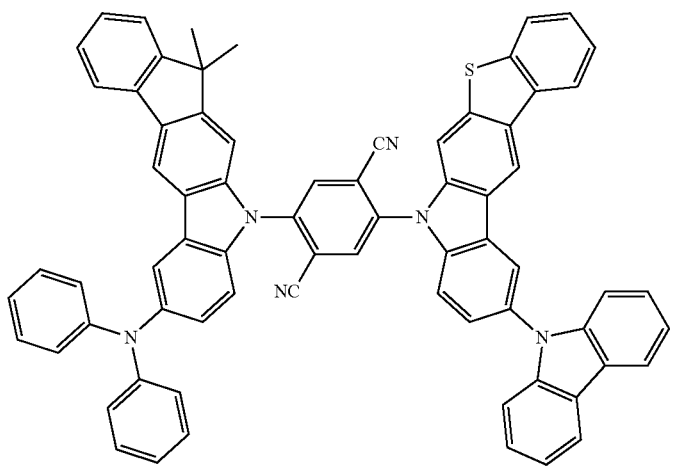
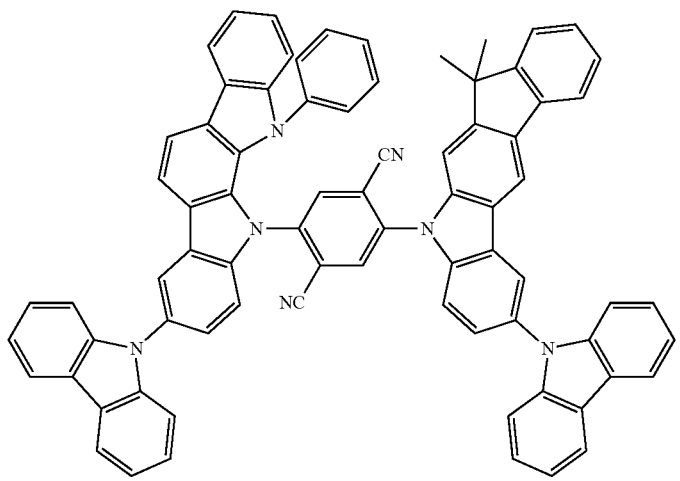
[Formula 124]
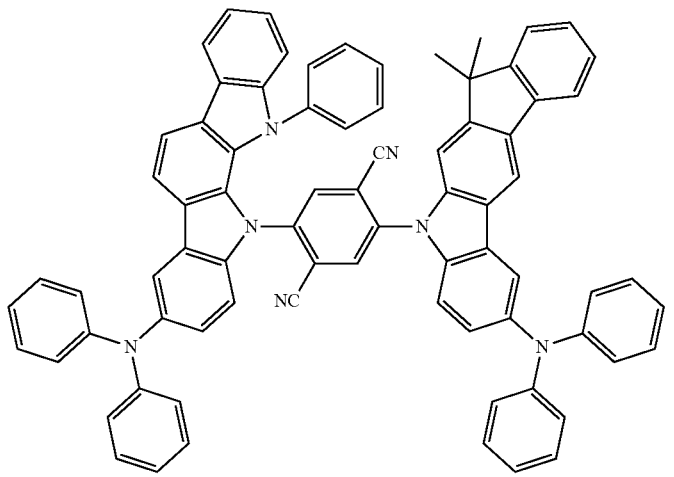

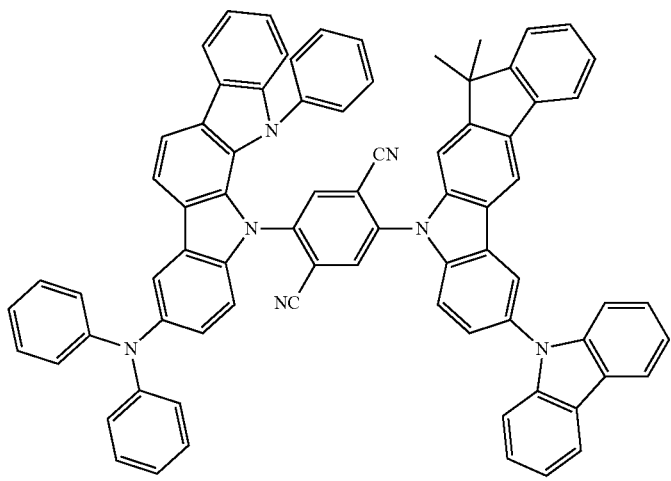
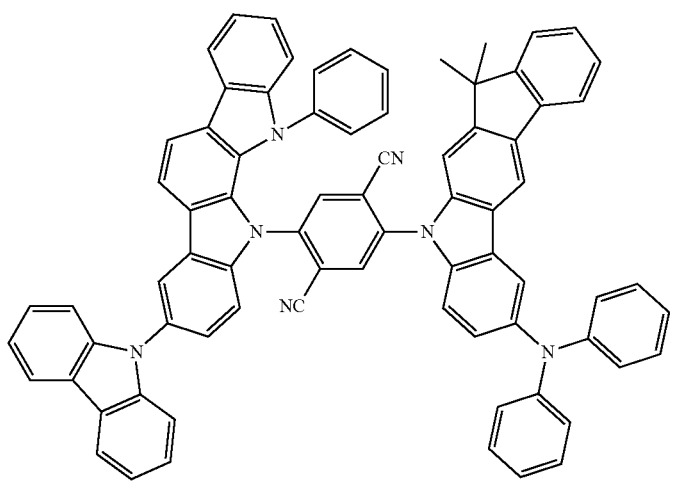
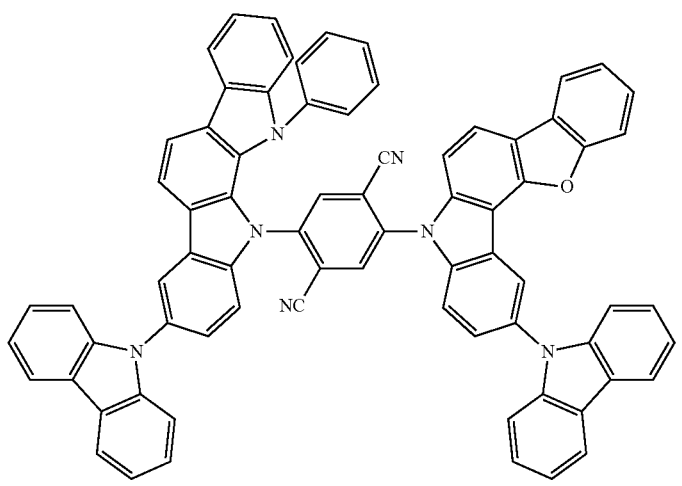

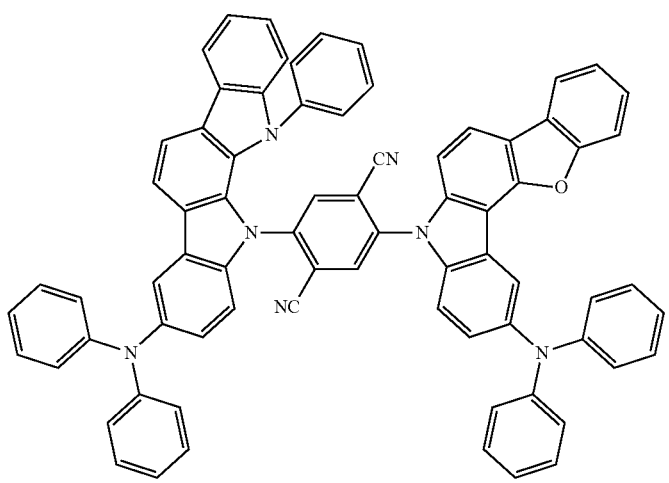
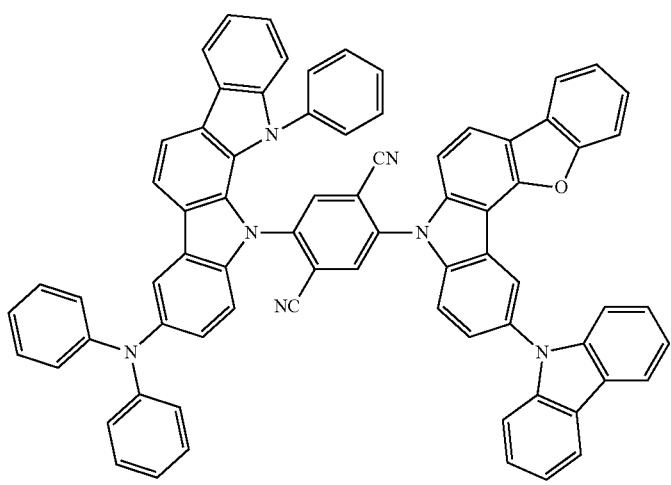
[Formula 125]
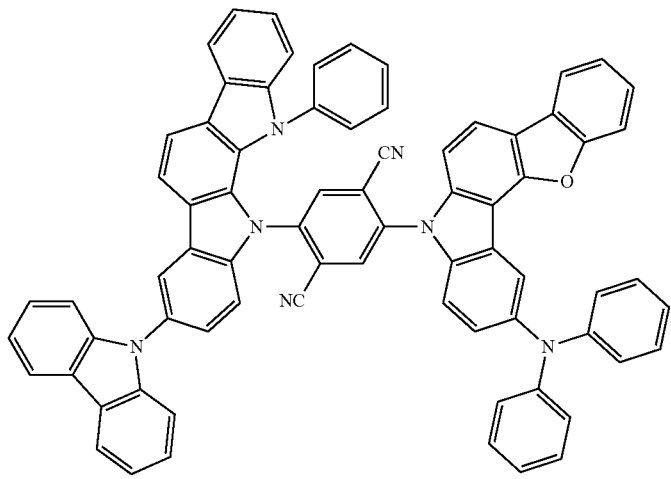

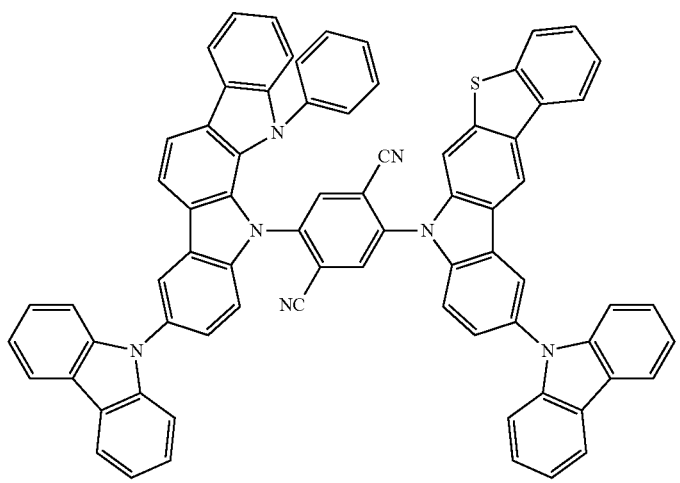
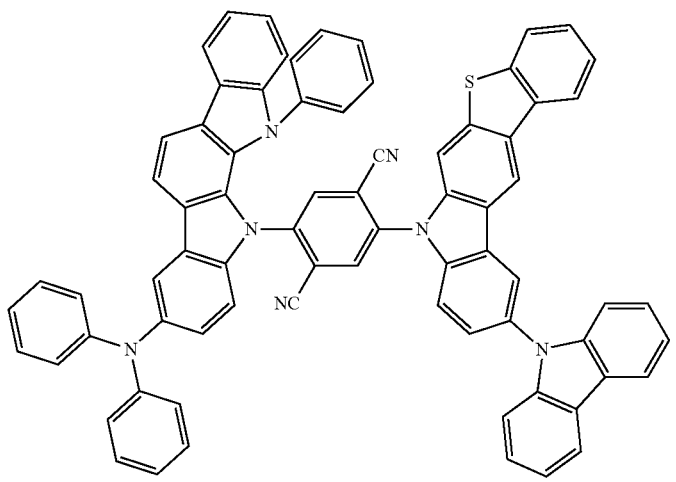
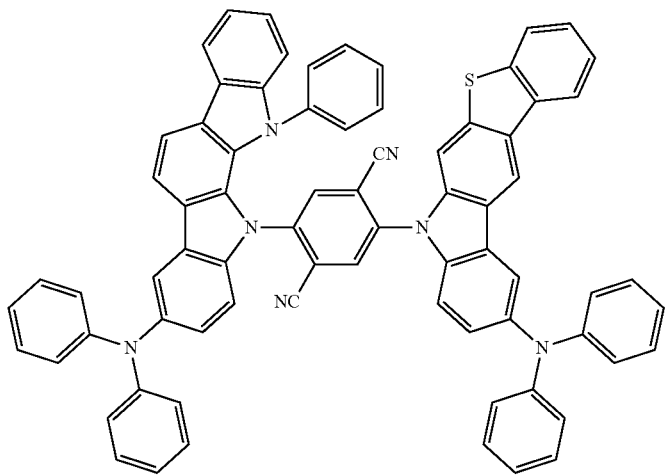

201
202
-continued
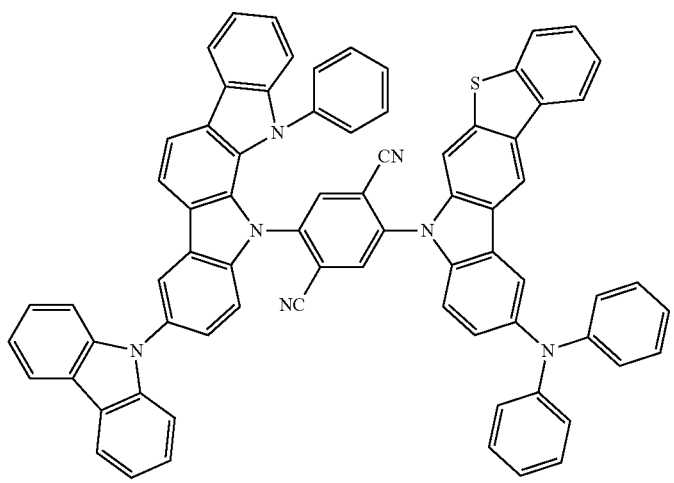
[Formula 126]
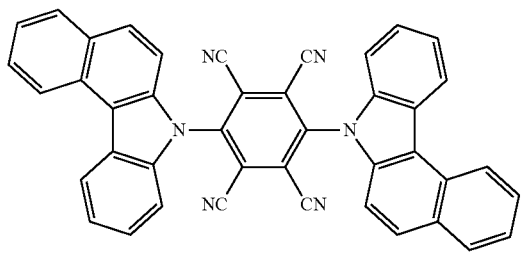
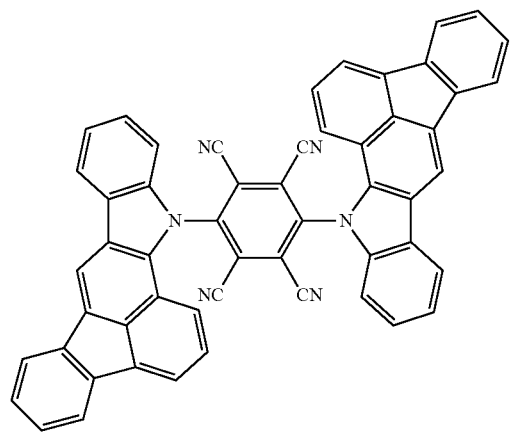
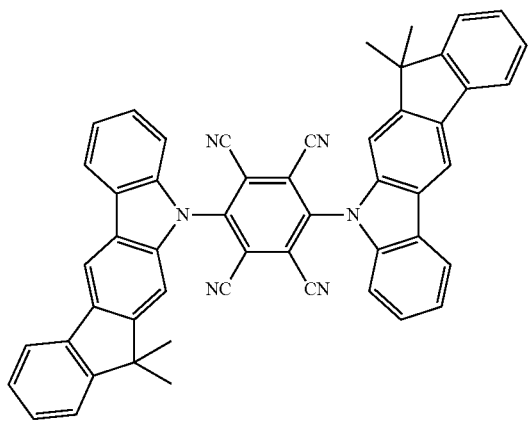
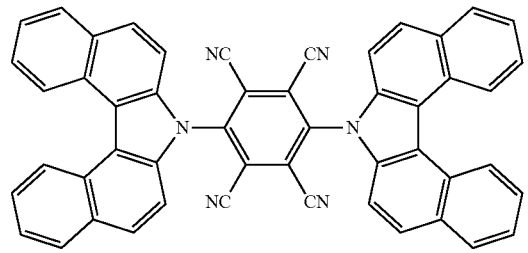

-continued
203
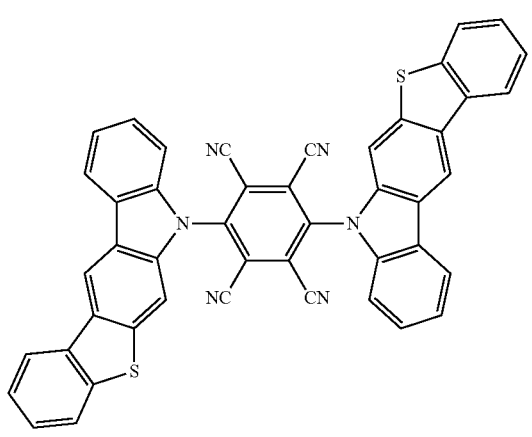
204
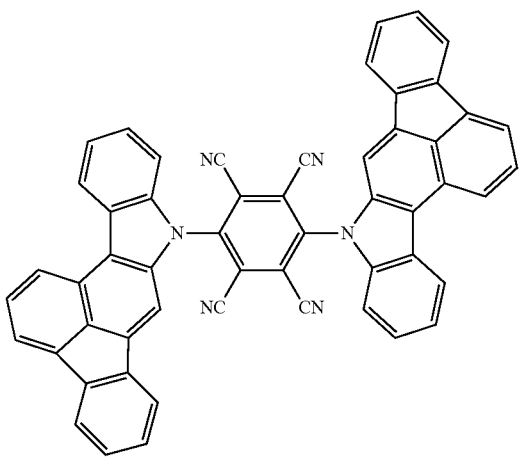
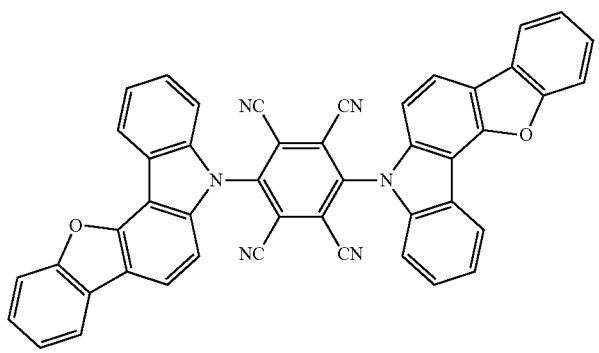
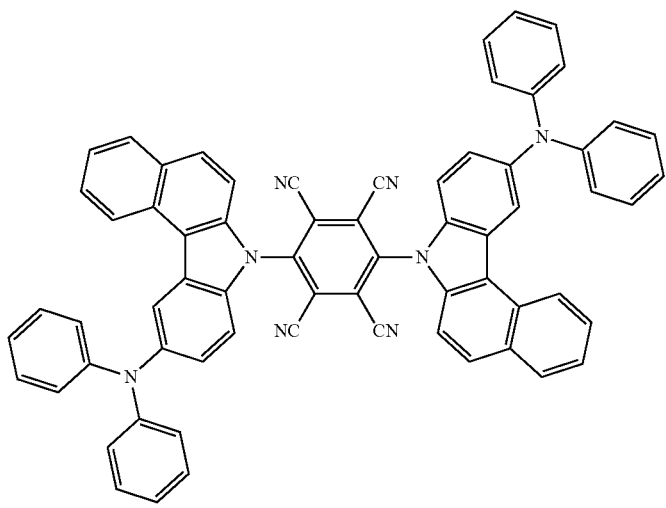

[Formula 127]
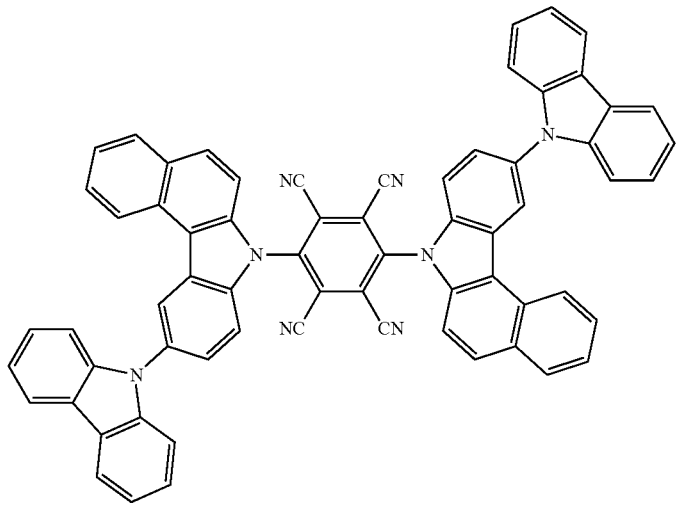
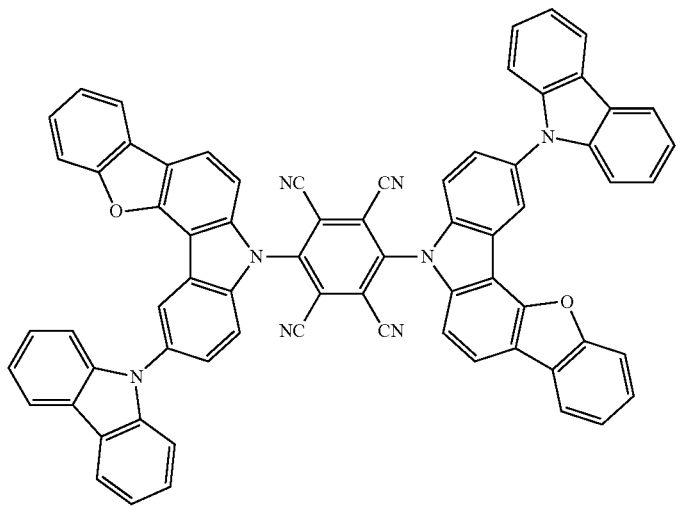
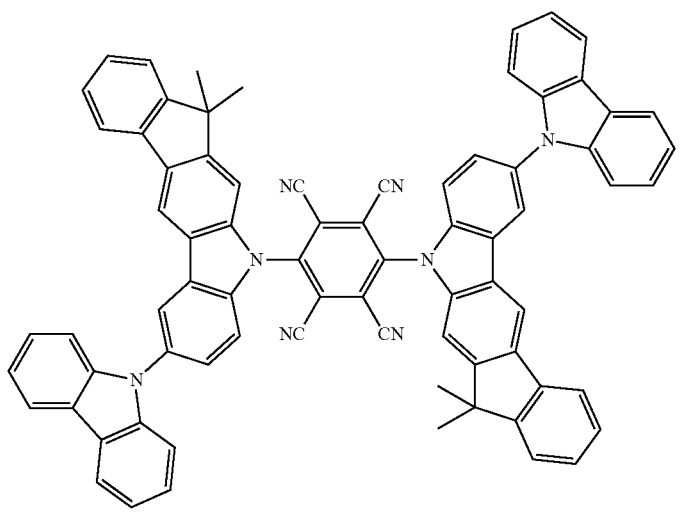

-continued
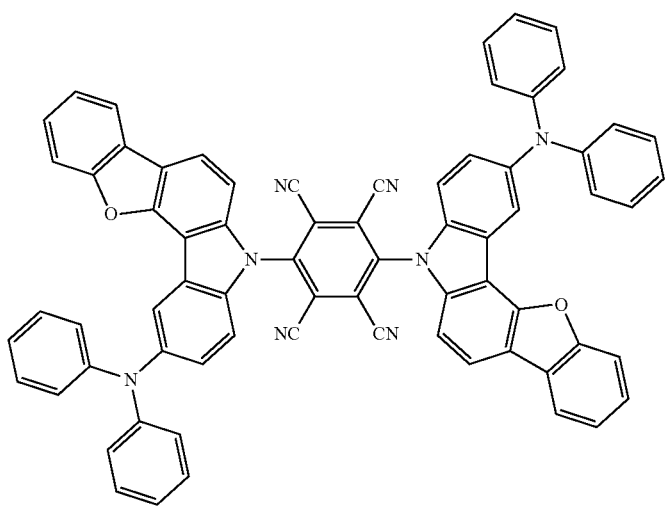
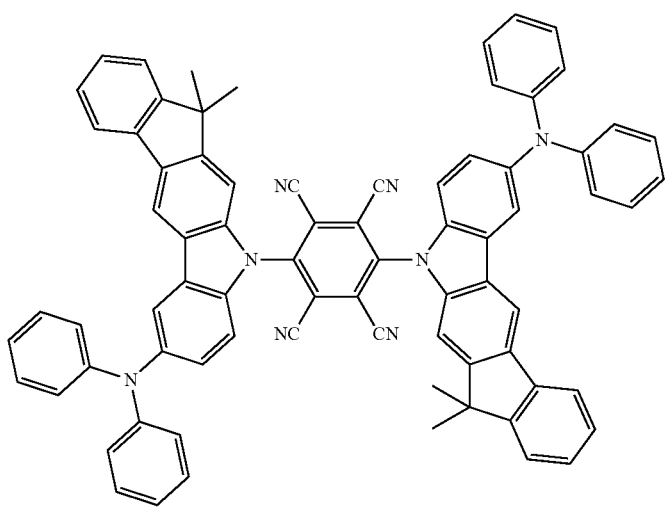
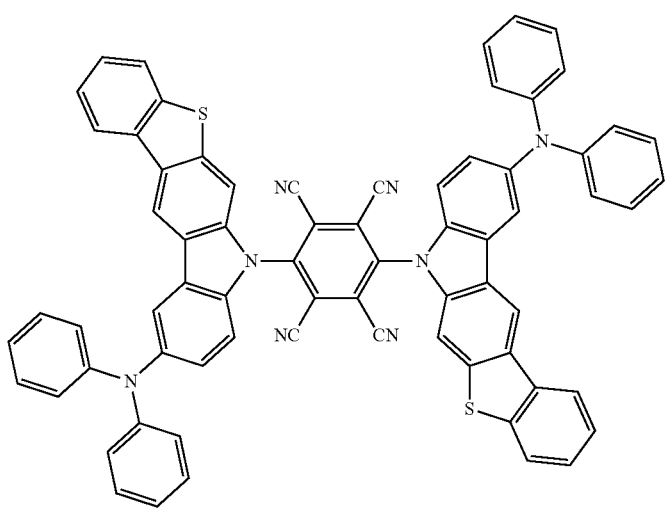

[Formula 128]
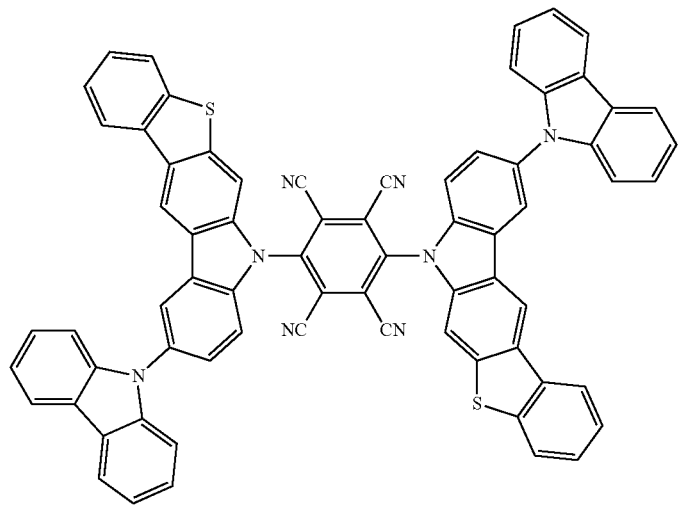
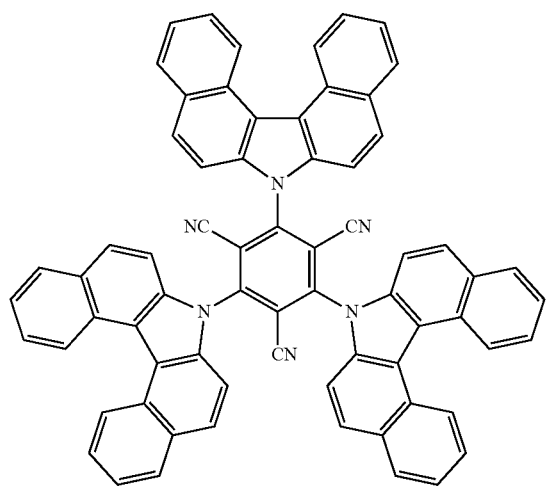
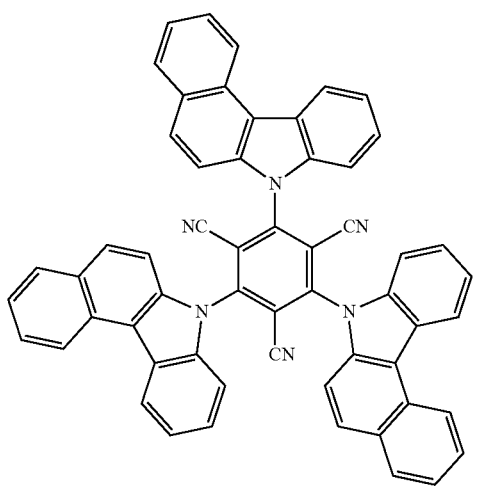
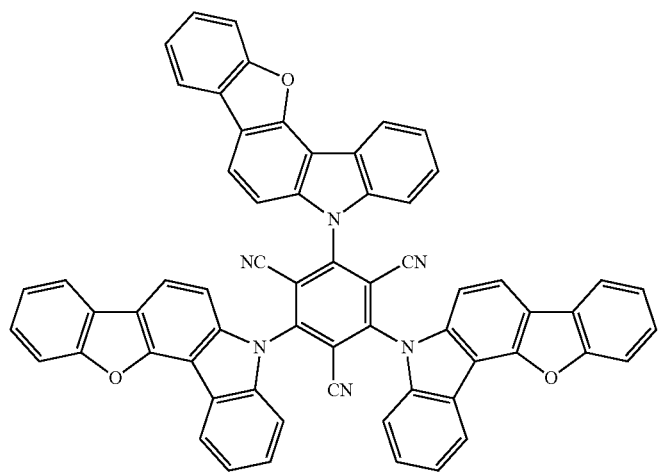

-continued
211
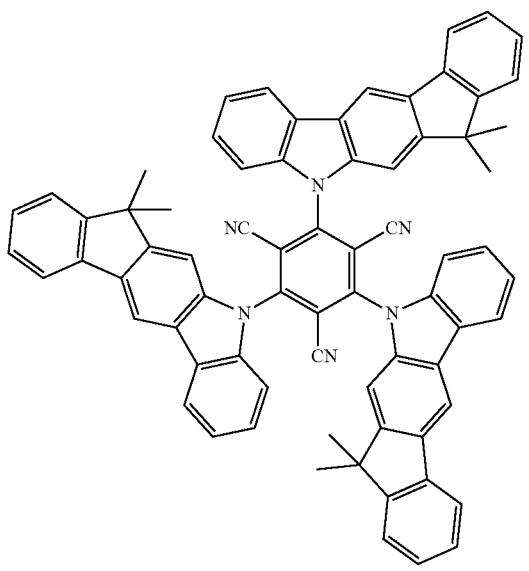
[Formula 129]
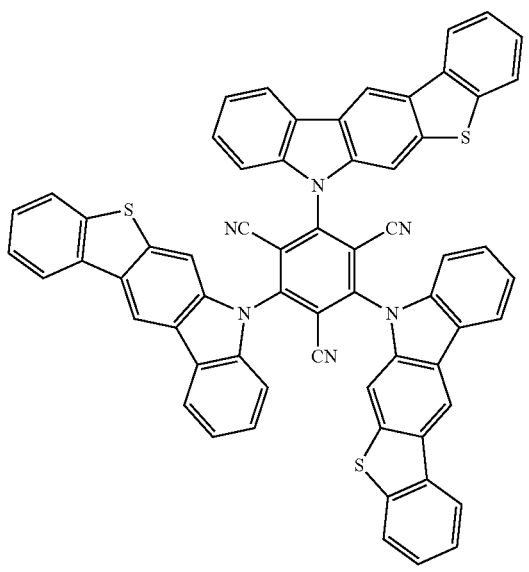
[Formula 130]
212
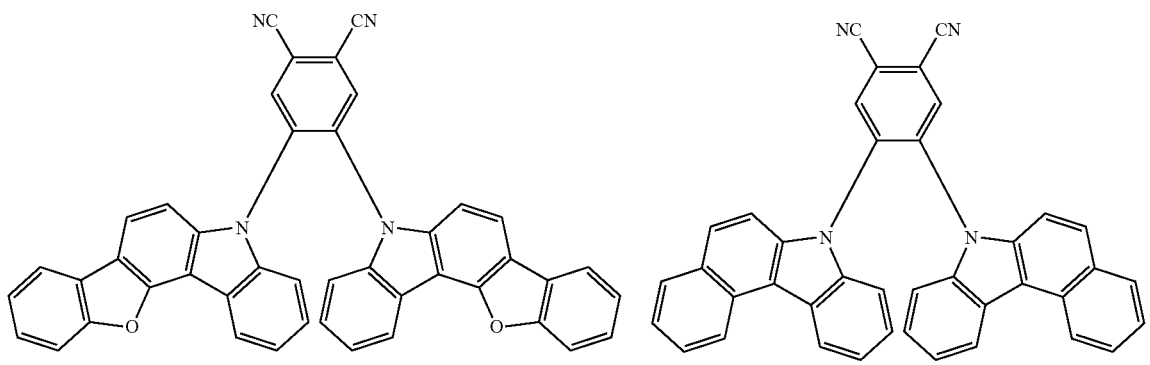

213 214
-continued
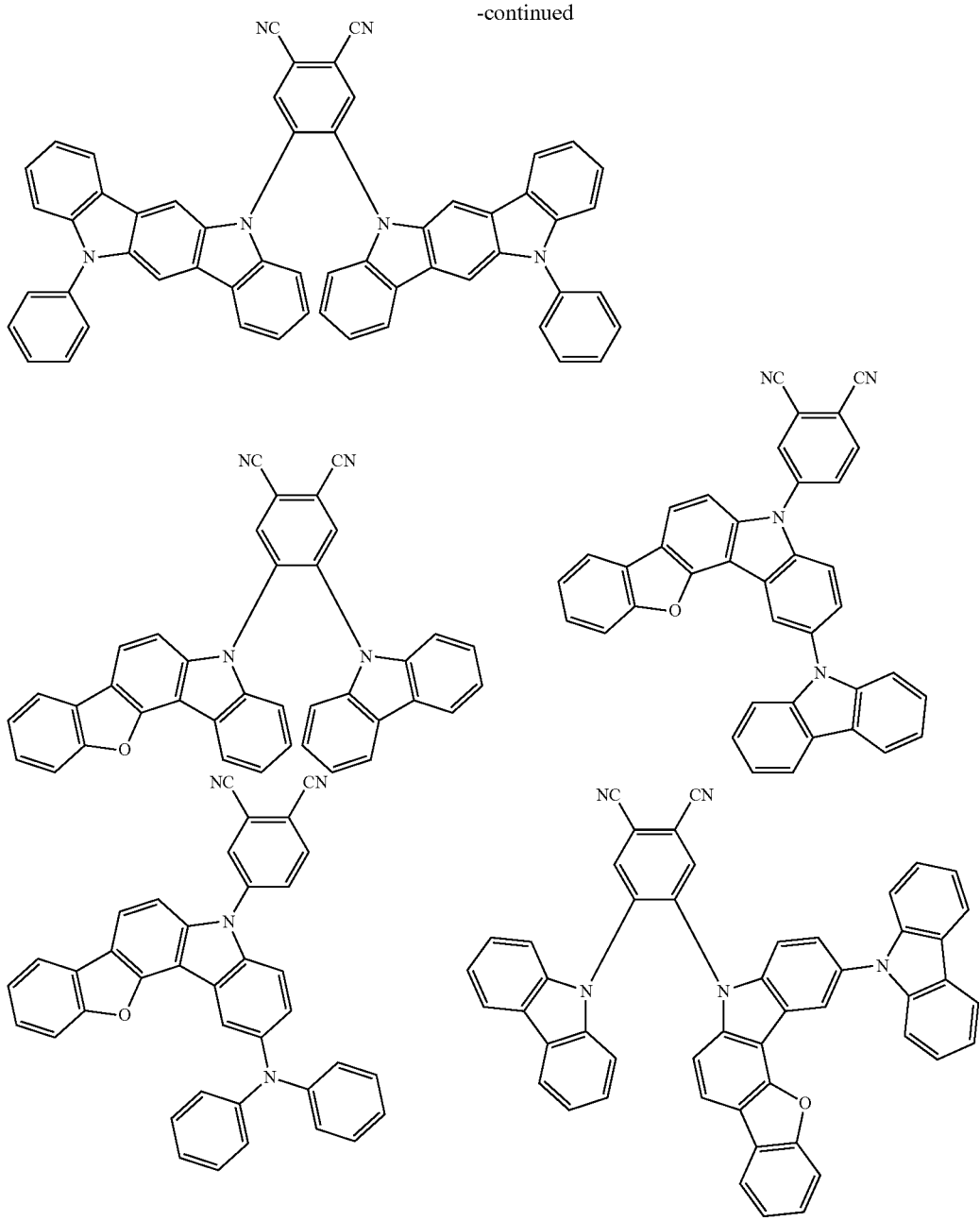
[Formula 131]
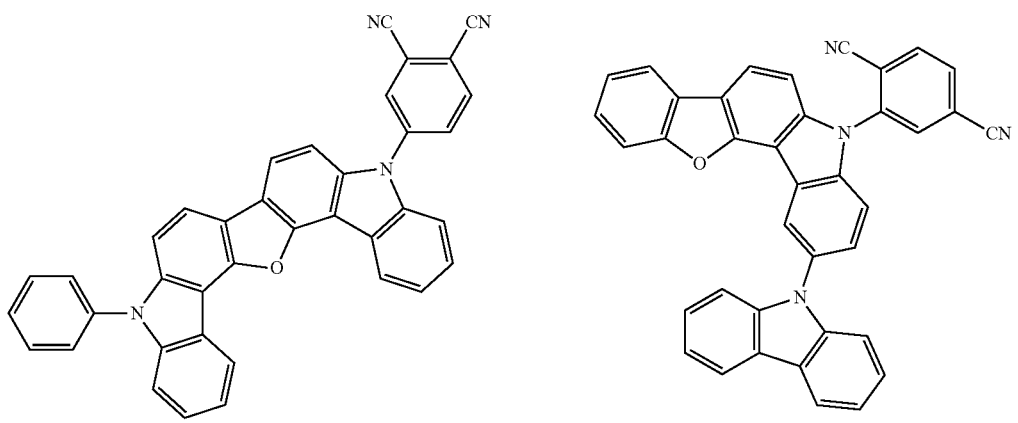

-continued
215
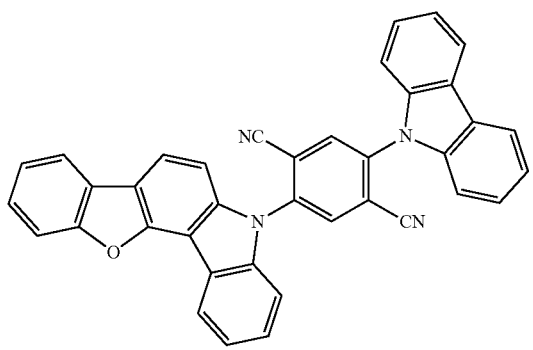
216
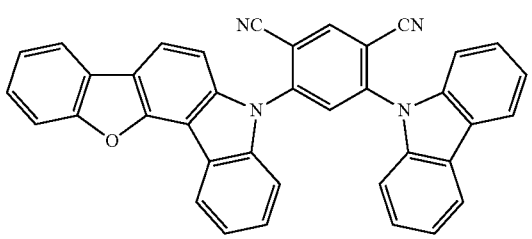
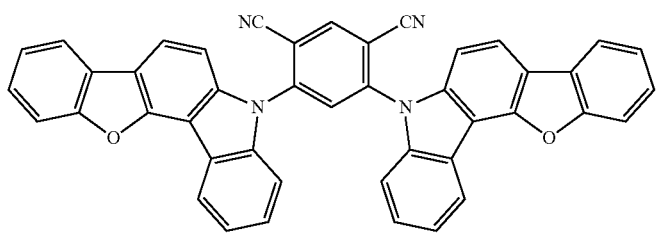
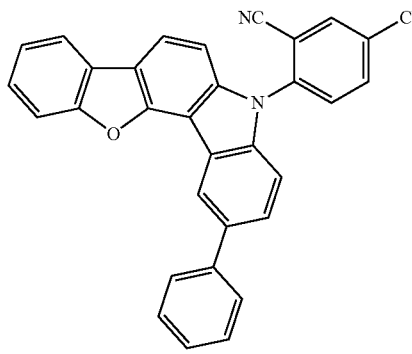
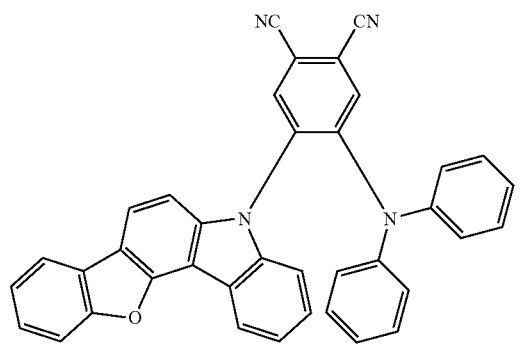
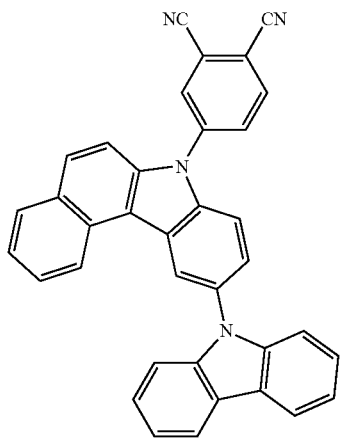

[Formula 132]
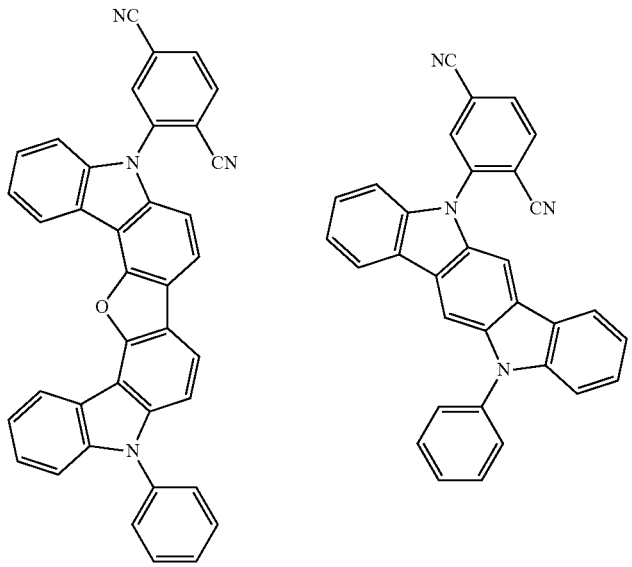
[Formula 133]
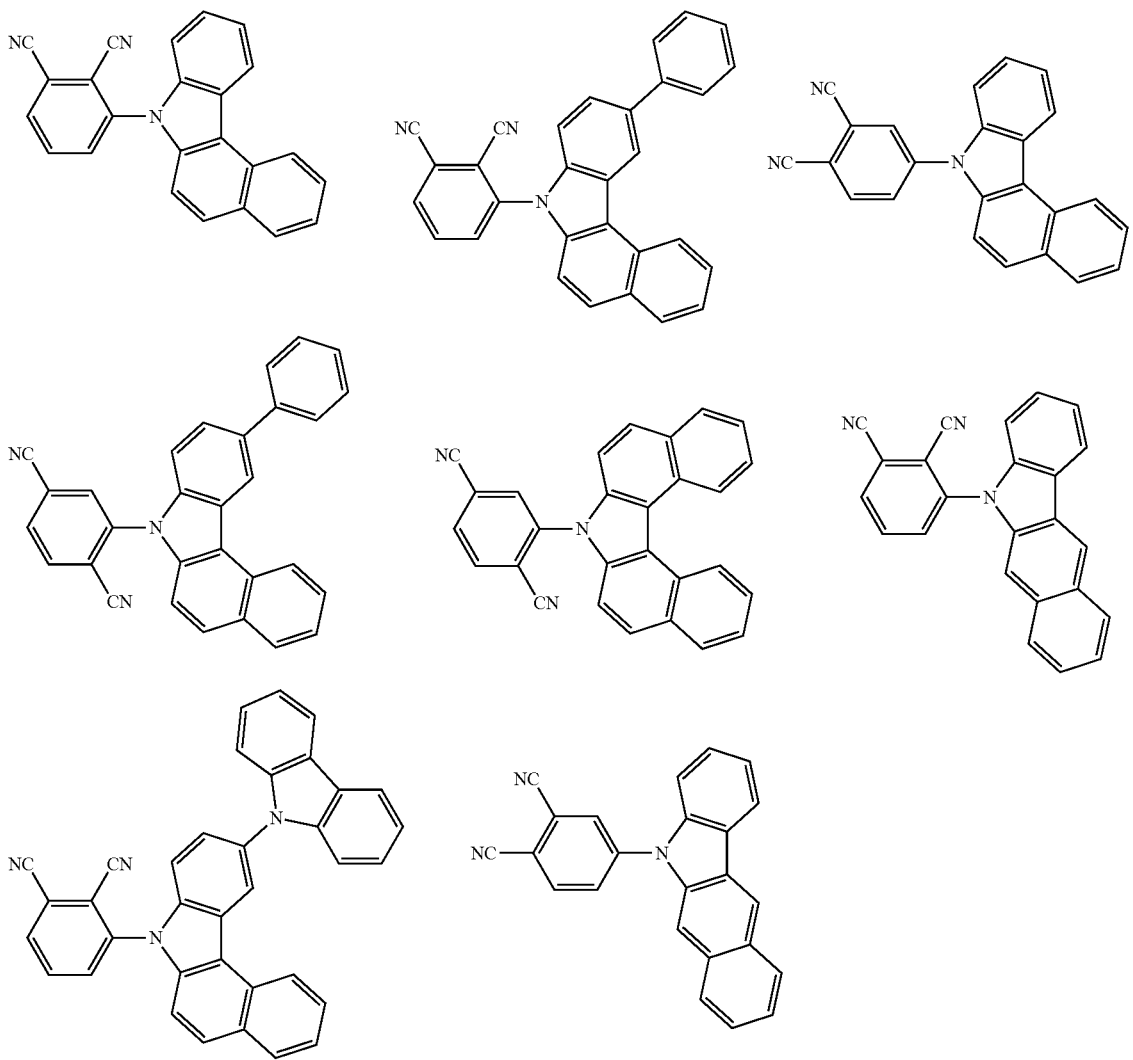

219
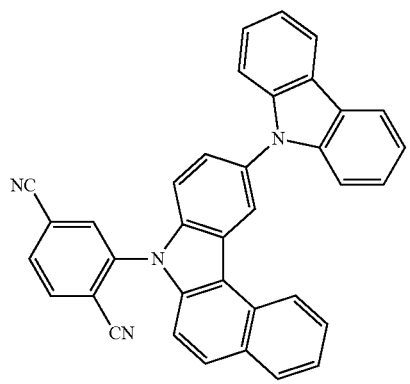
220
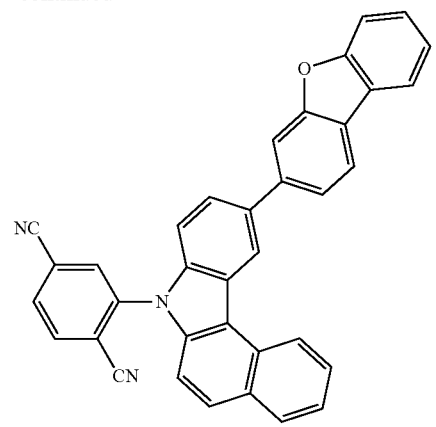
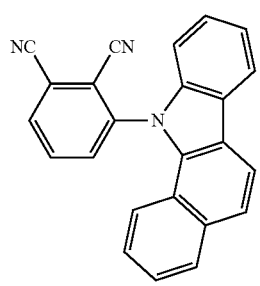
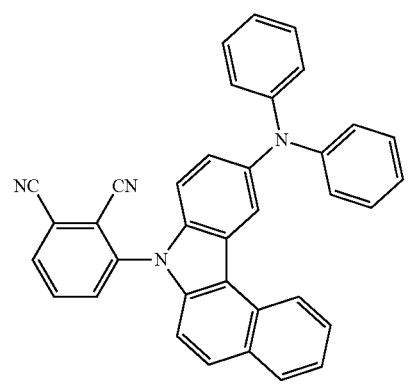
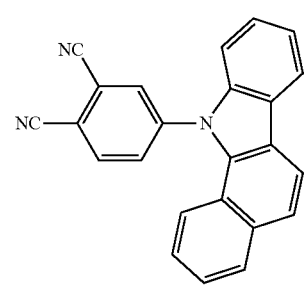
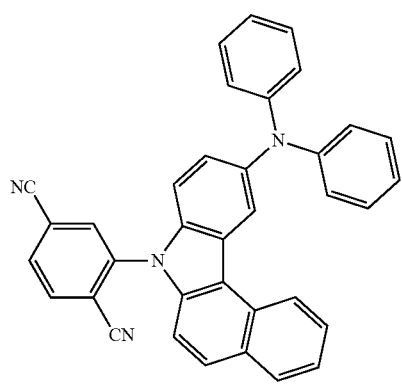
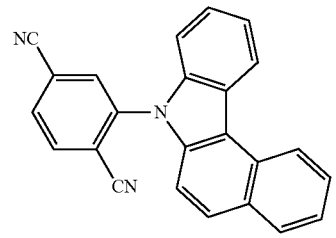
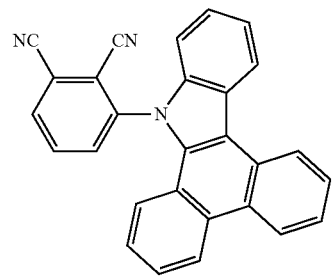
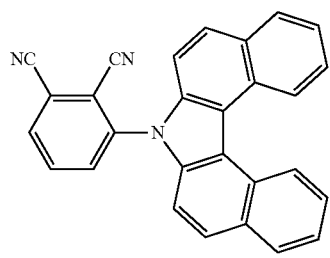
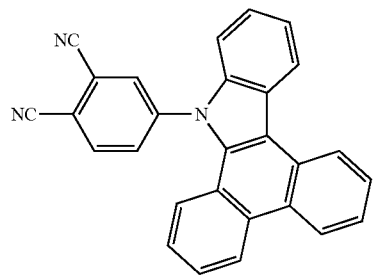
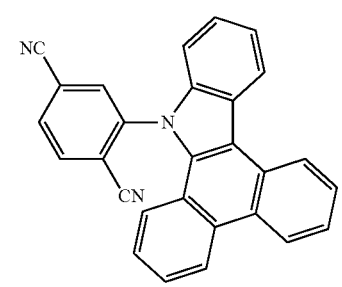

-continued
221
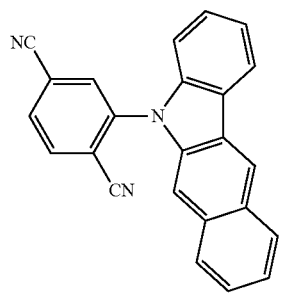
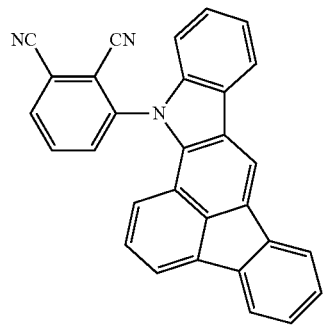
222
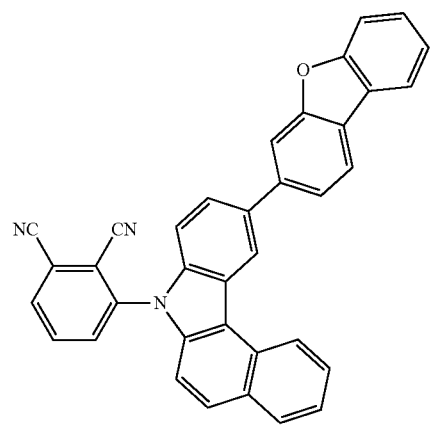
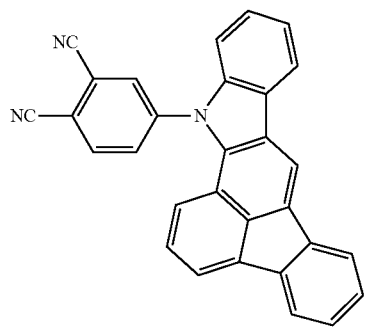
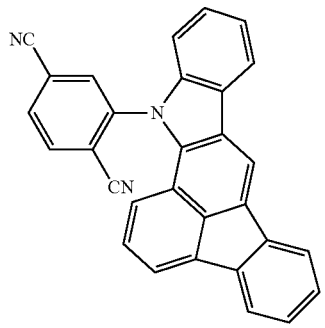
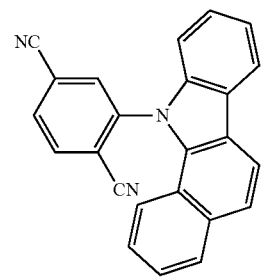
[Formula 134]
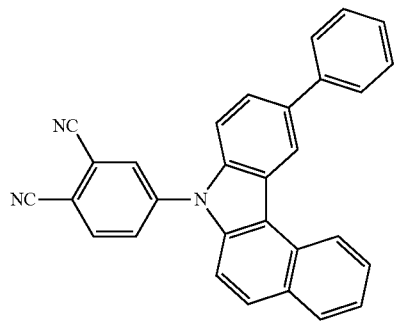
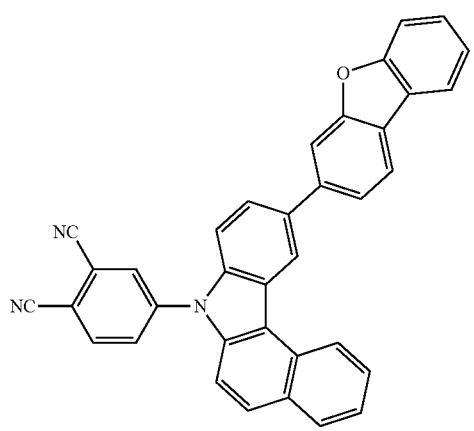
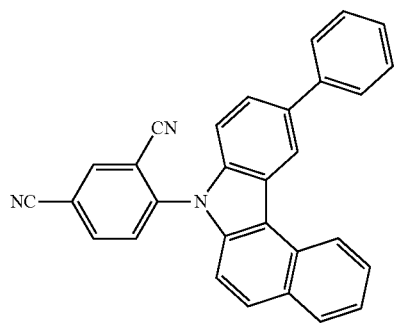
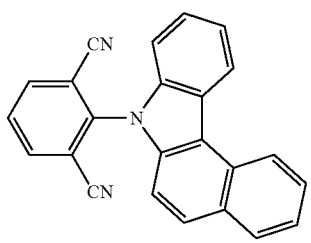
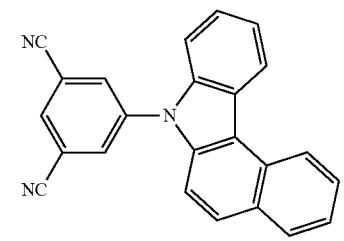

-continued
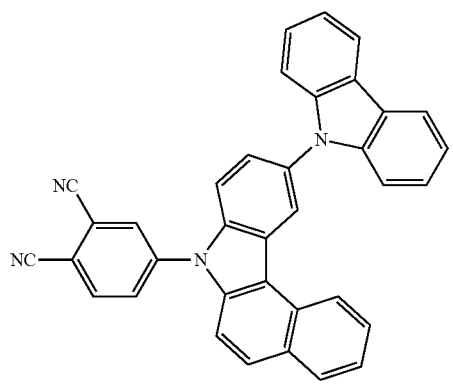
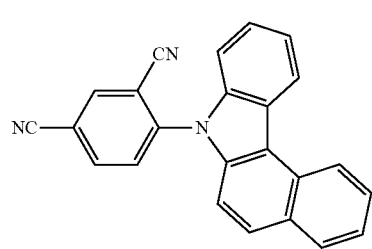
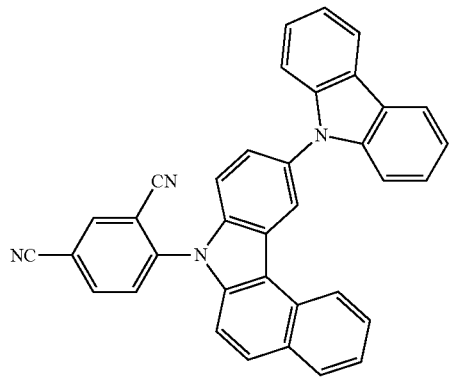
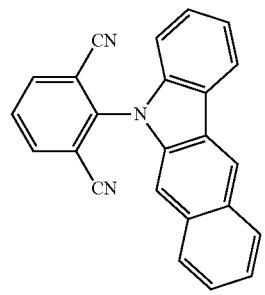
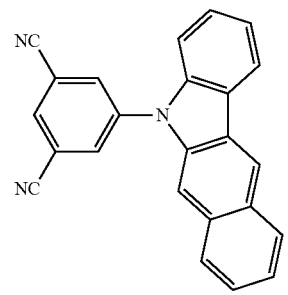
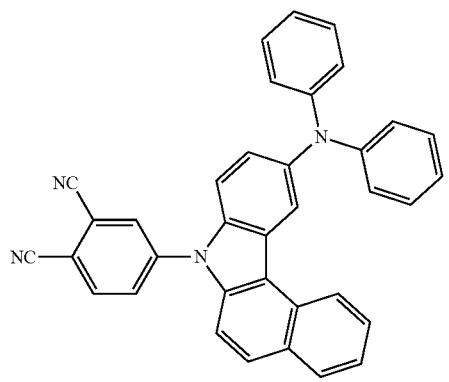
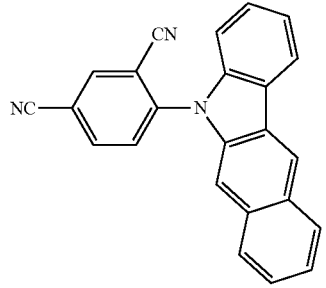
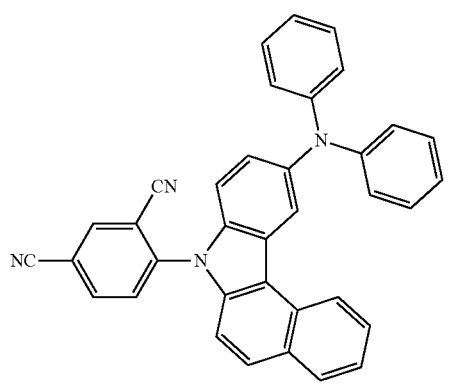
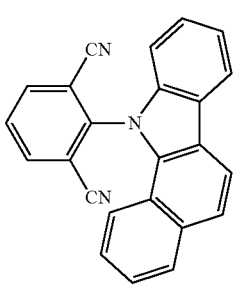
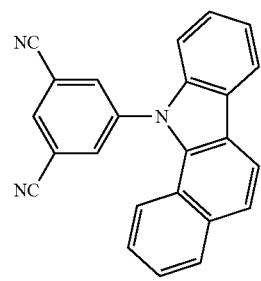

-continued
225
226
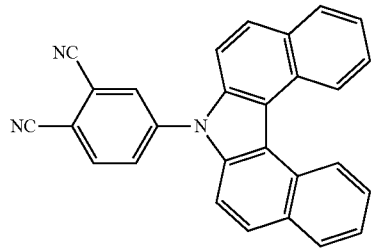
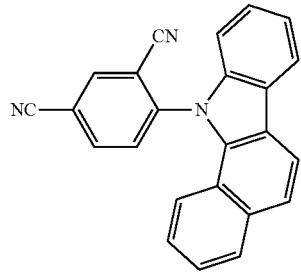
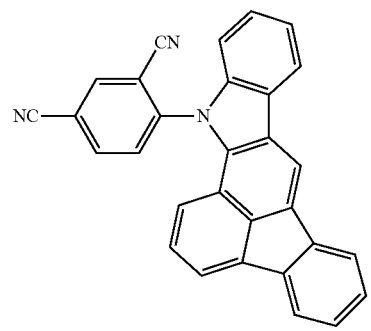
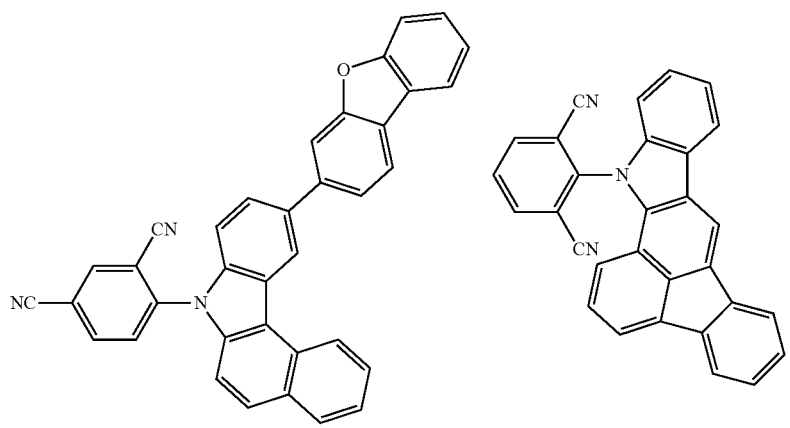
[Formula 135]
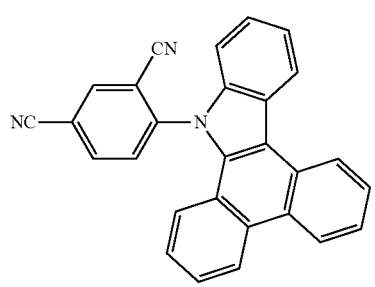
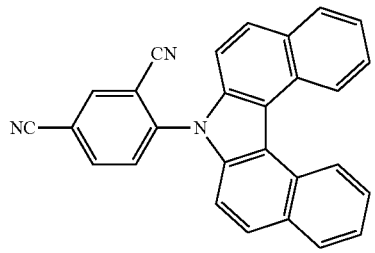
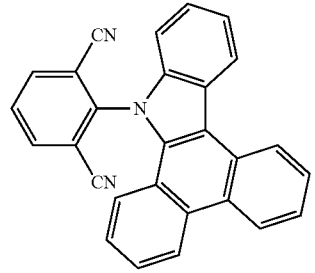
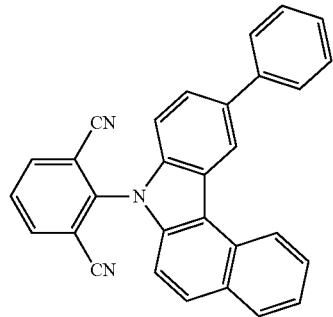
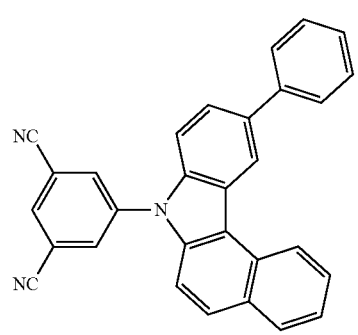
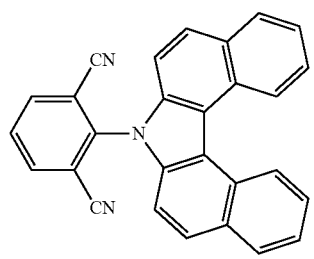

-continued
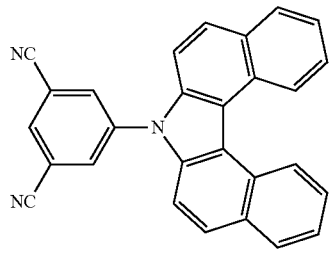
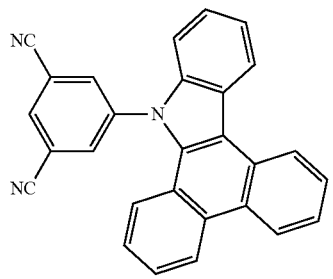
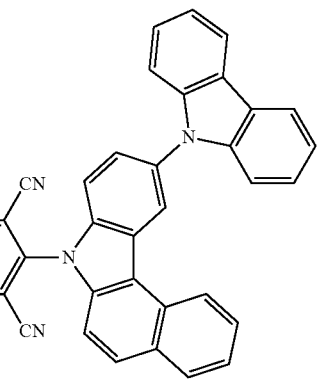
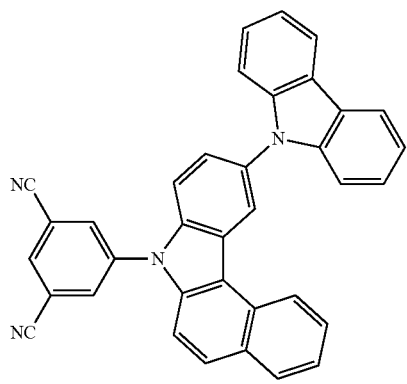
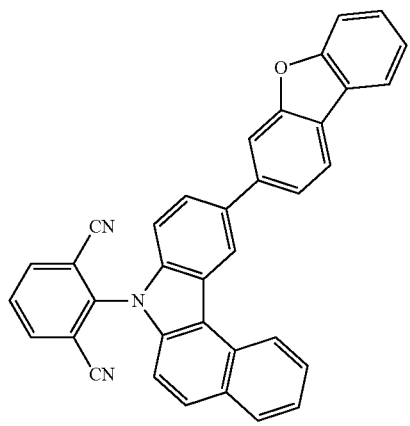
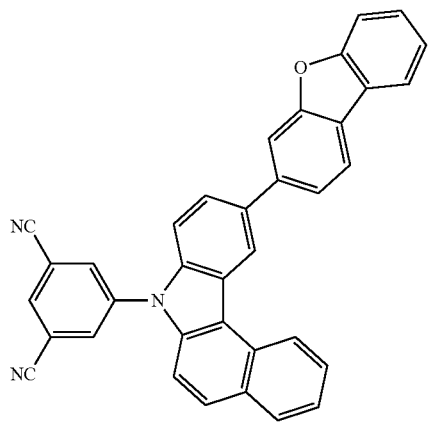
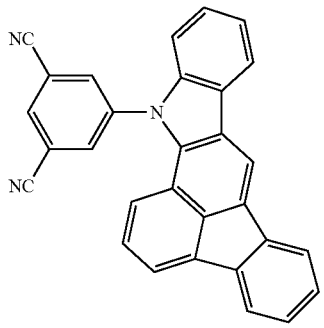
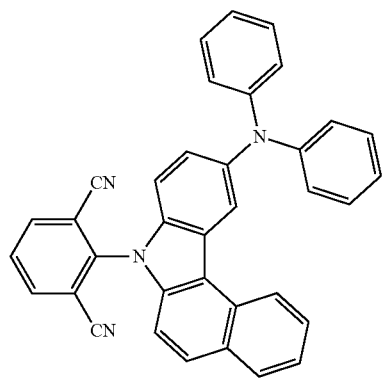
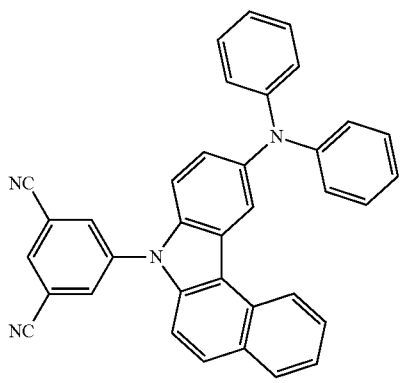

229 230
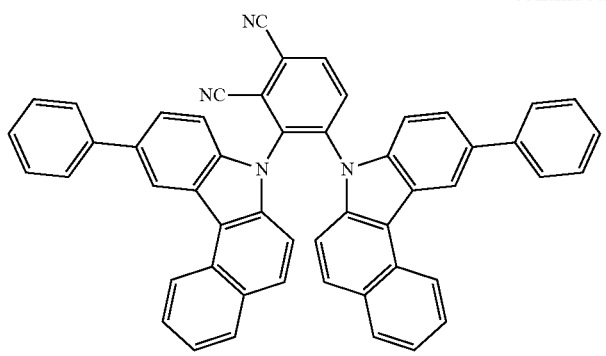
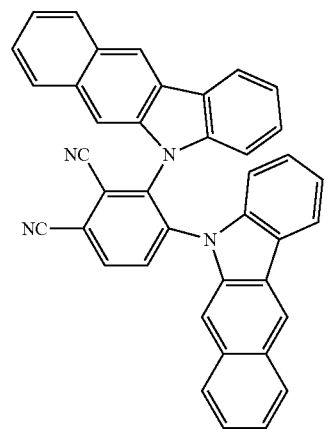
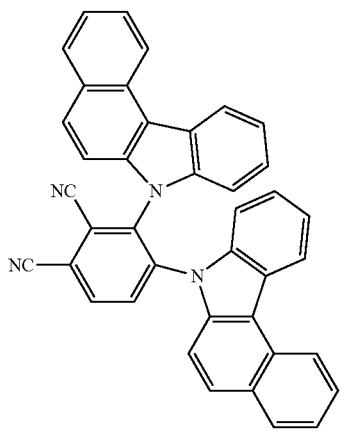
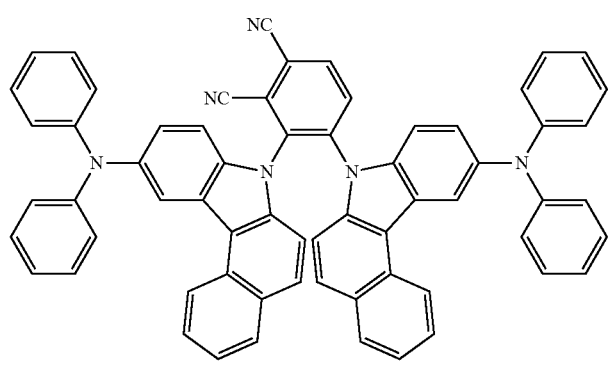
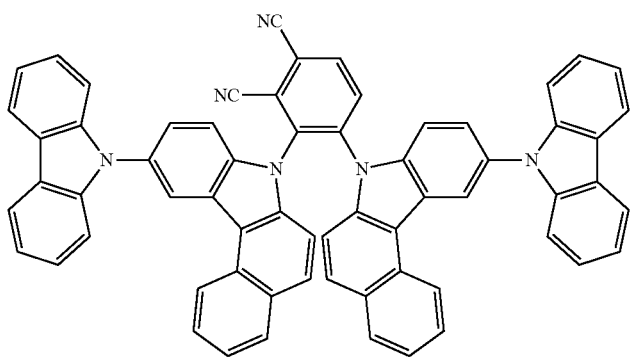
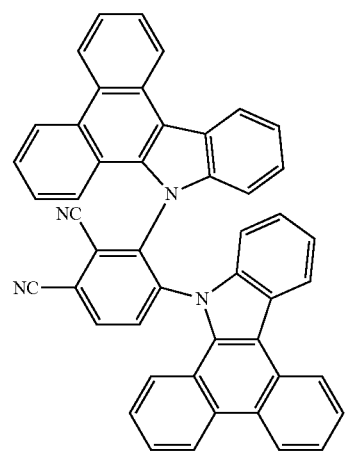

-continued
231
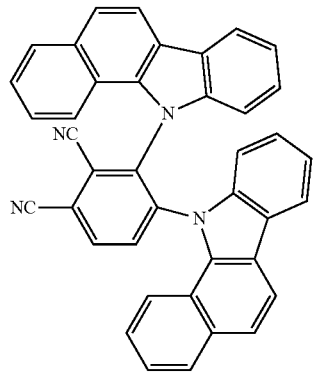
232
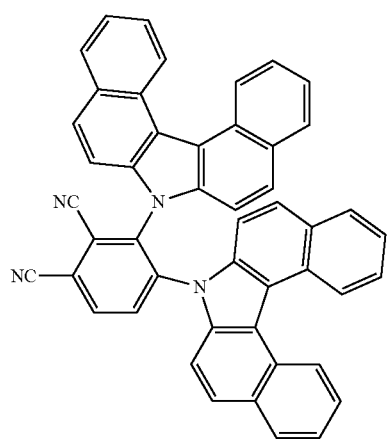
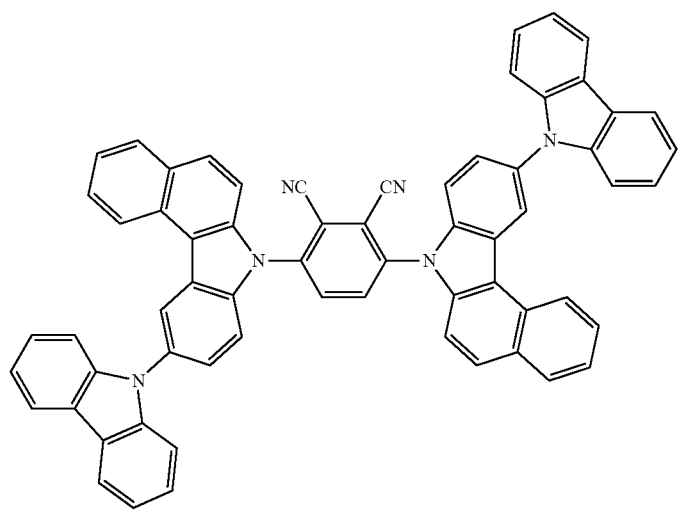
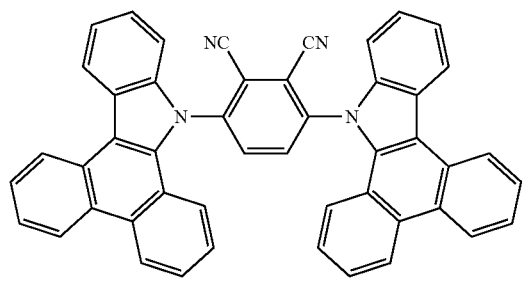
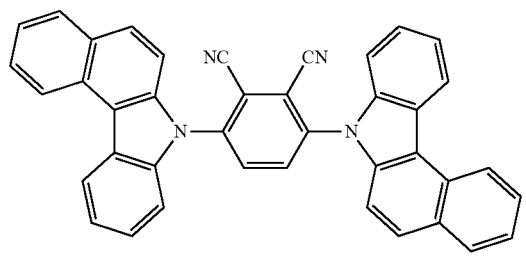

-continued
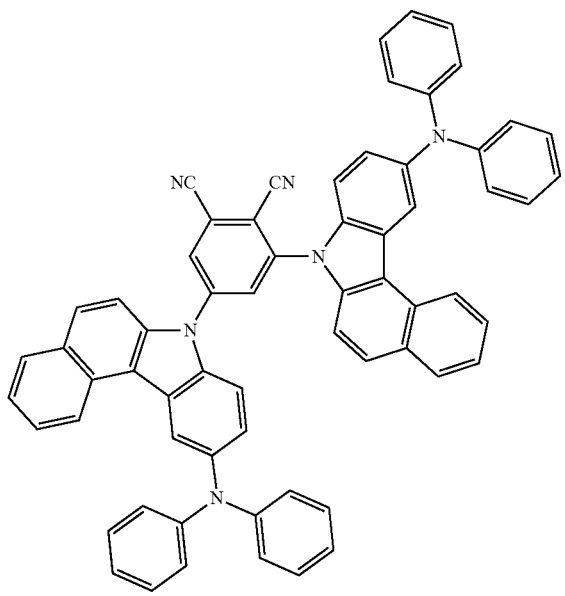
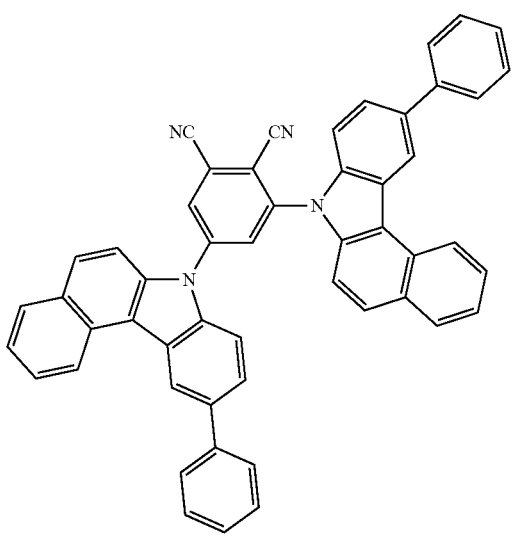
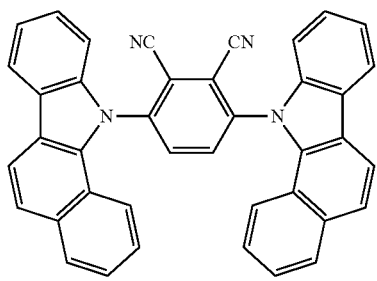
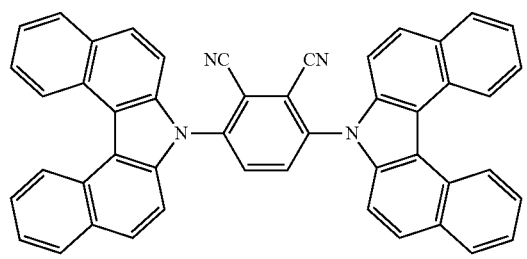
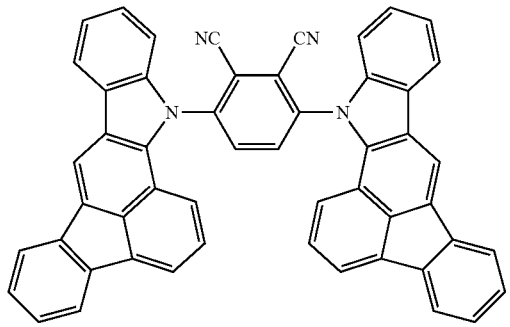
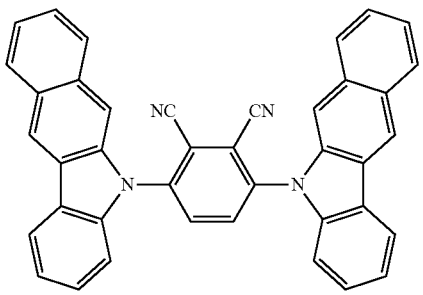
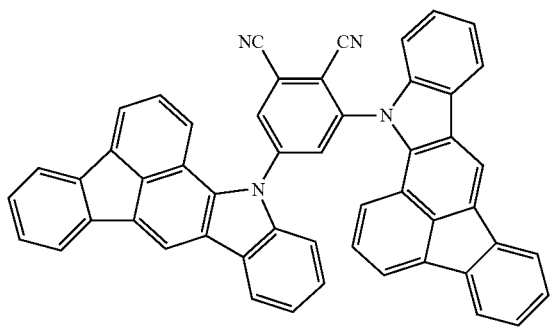
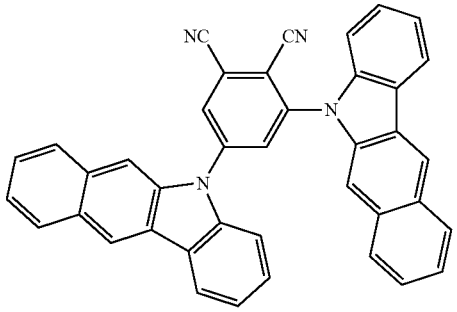

-continued
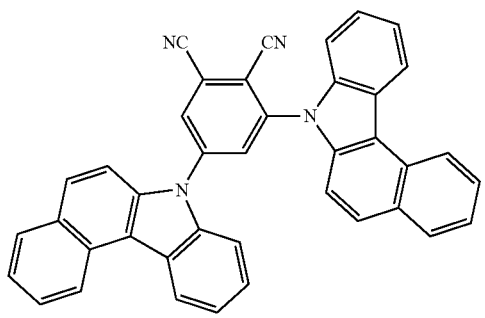
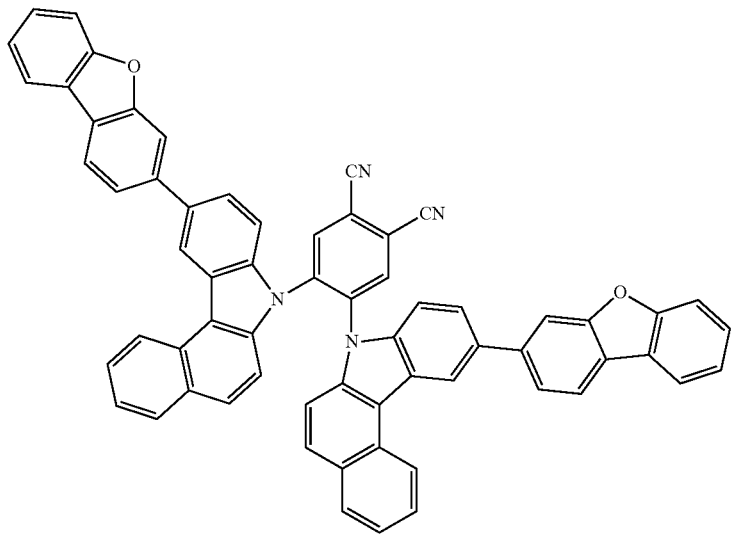
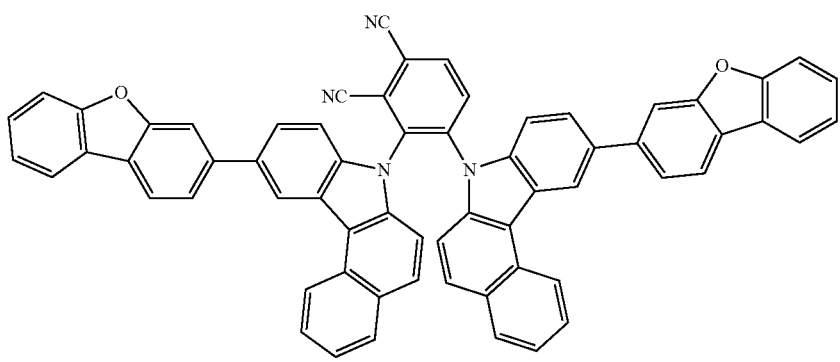
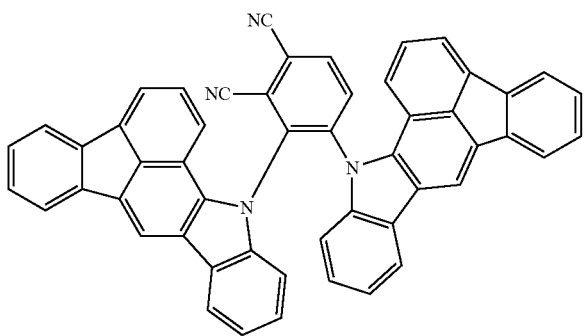

[Formula 137]
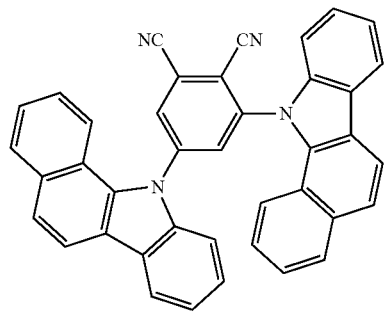
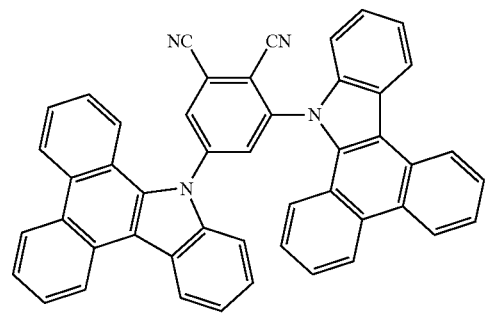
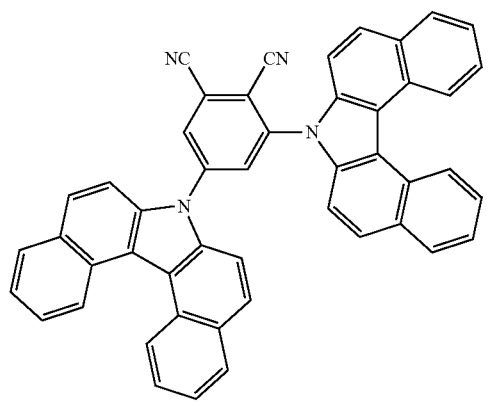
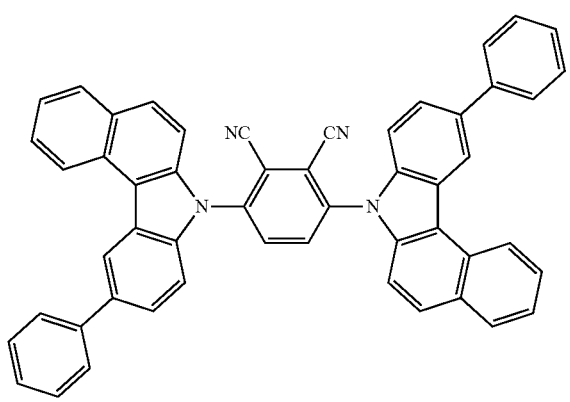
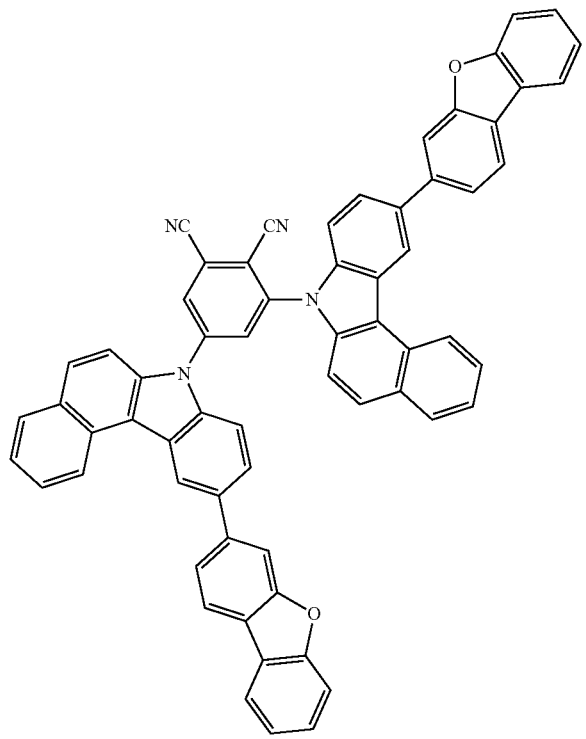

-continued
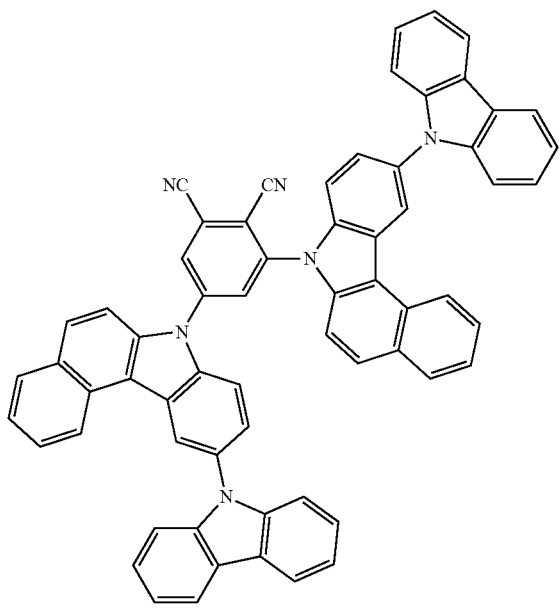
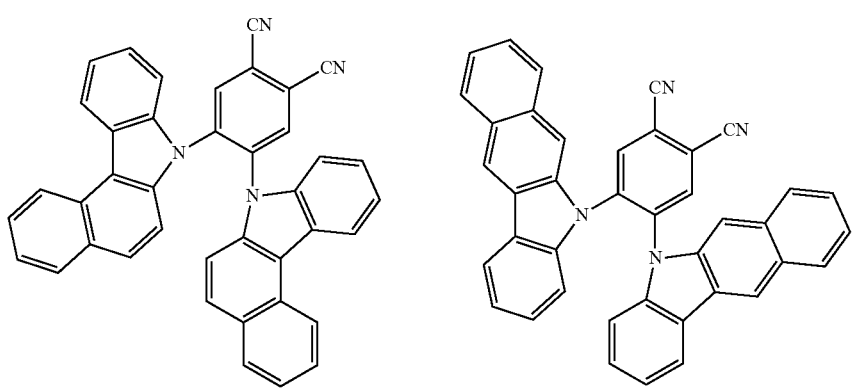
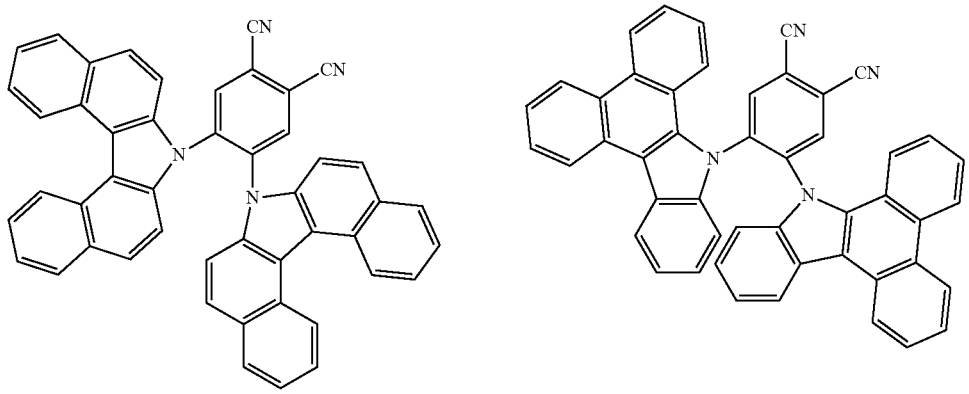

-continued
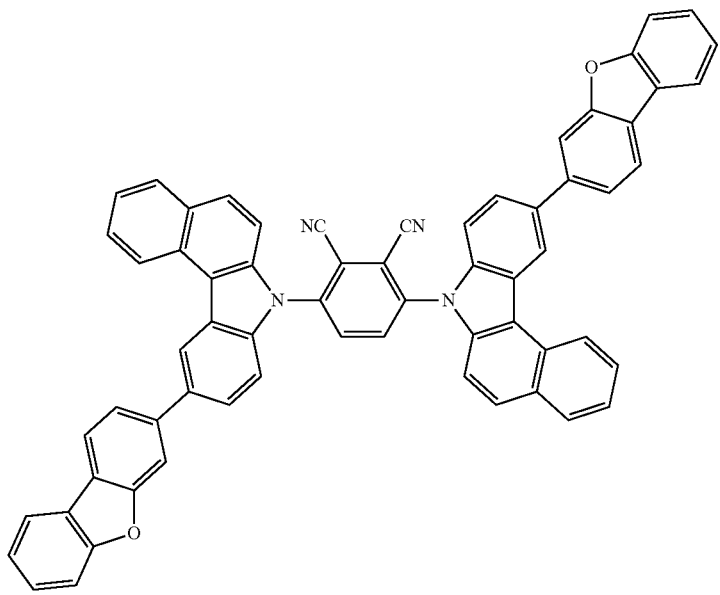
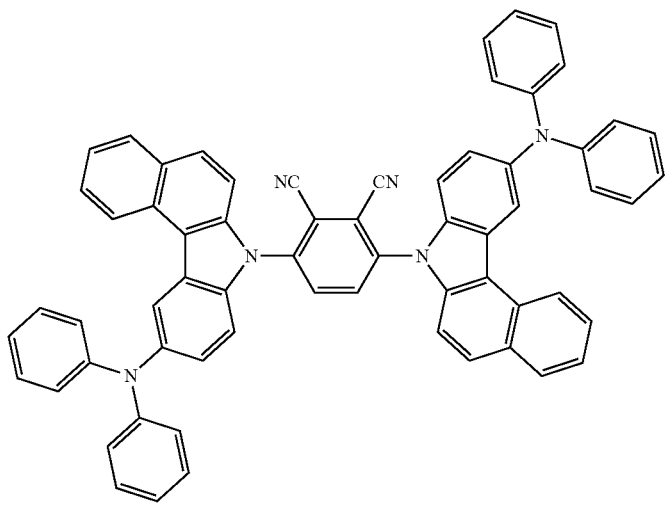
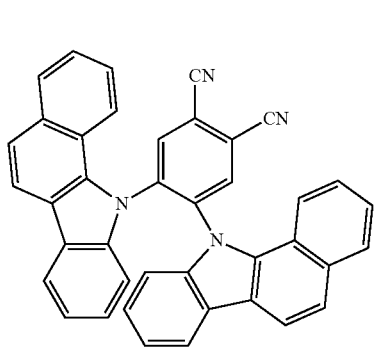
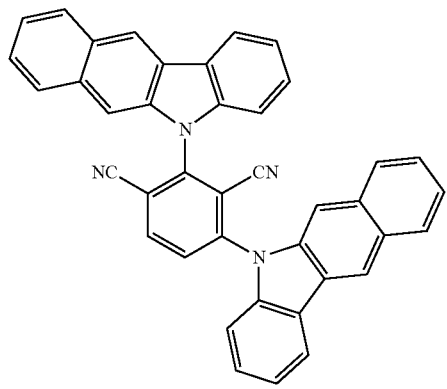

[Formula 138]
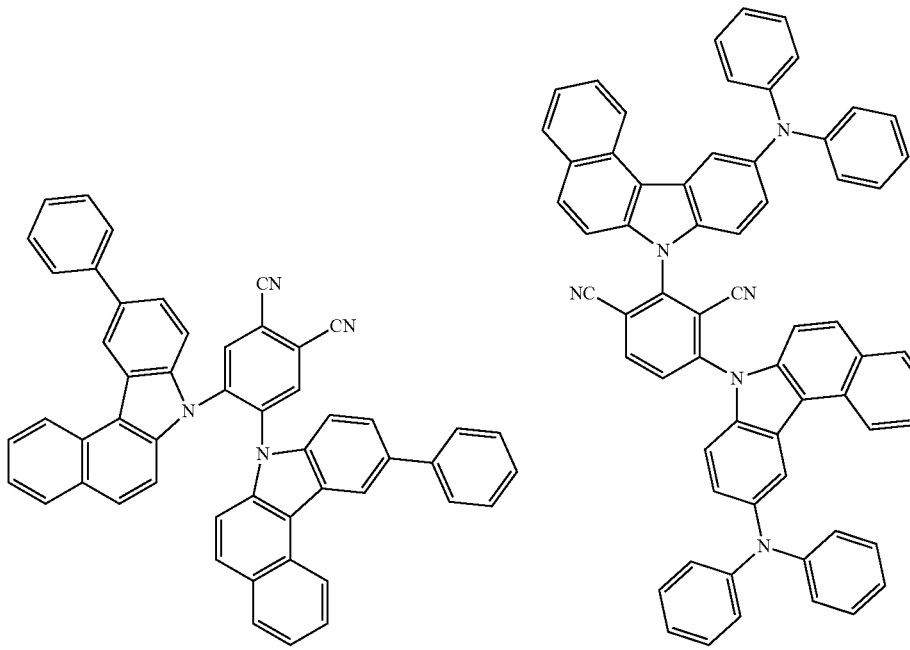
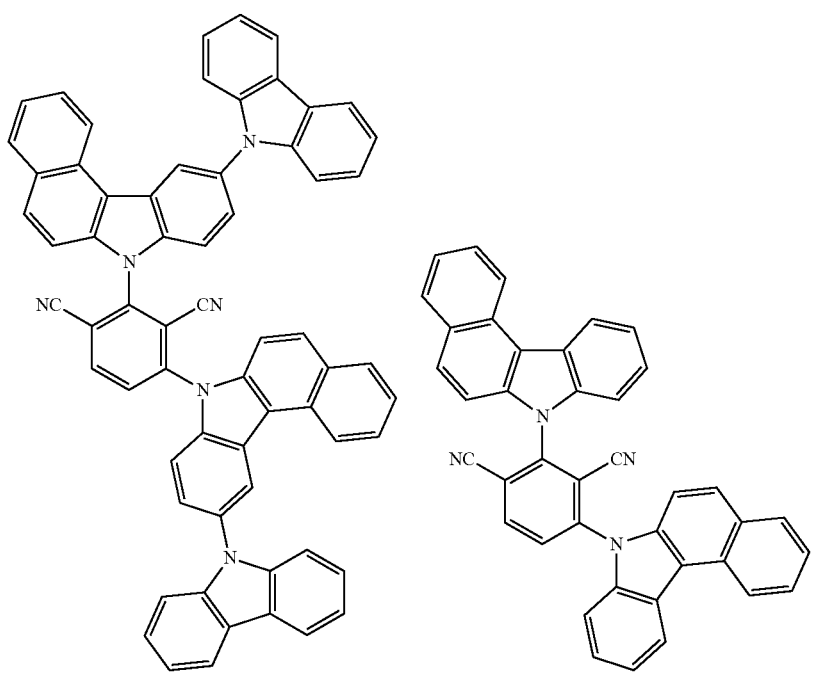

245 246
-continued
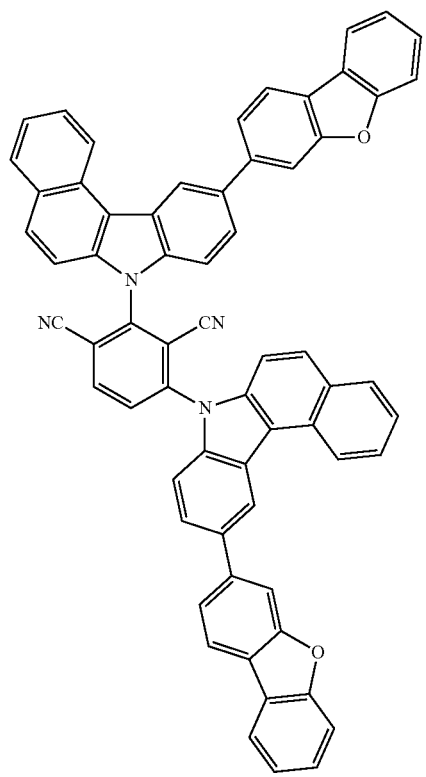
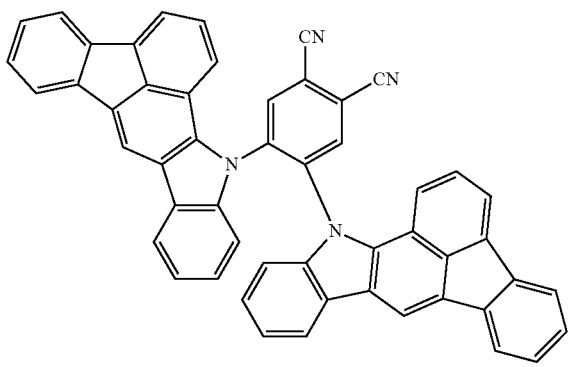
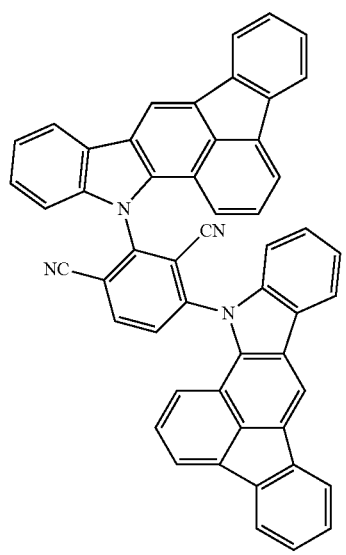
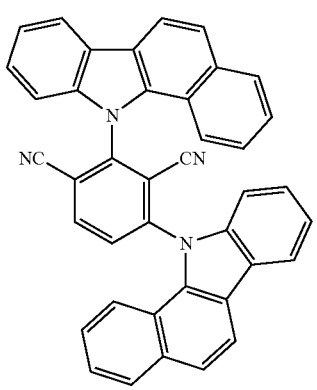
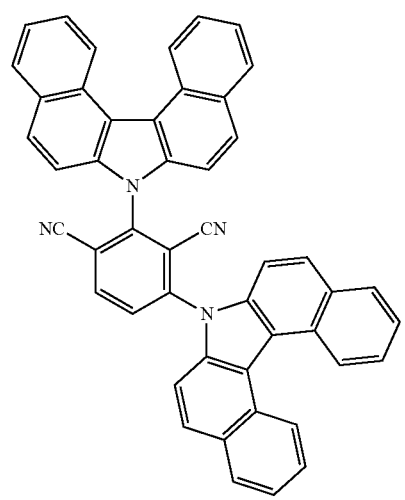

-continued
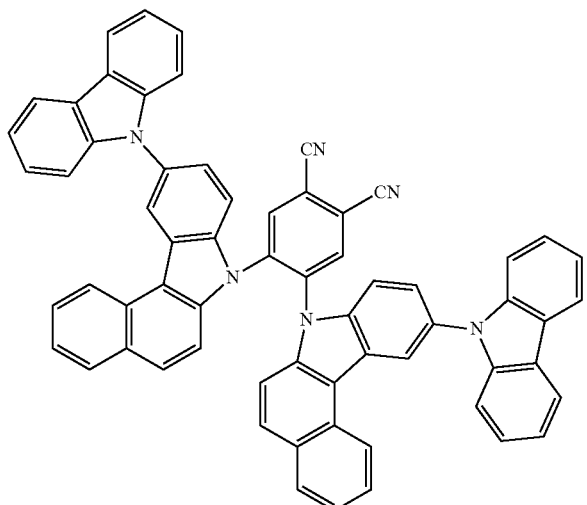
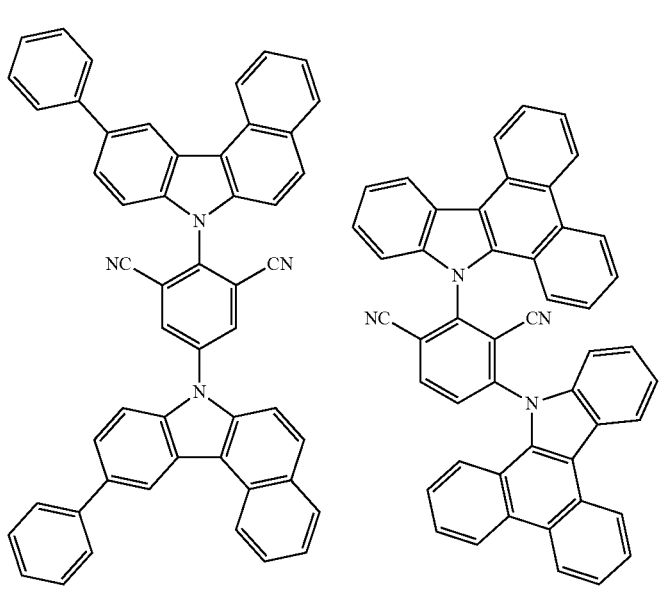
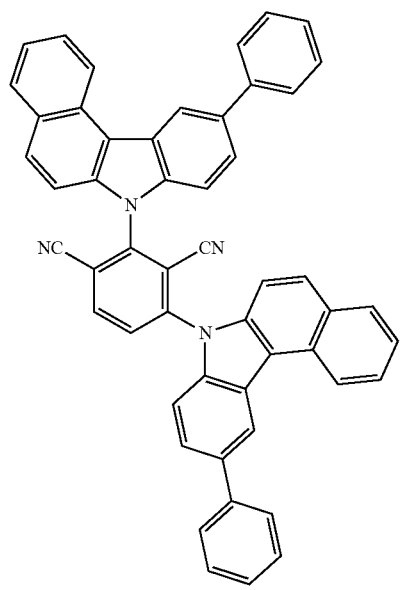
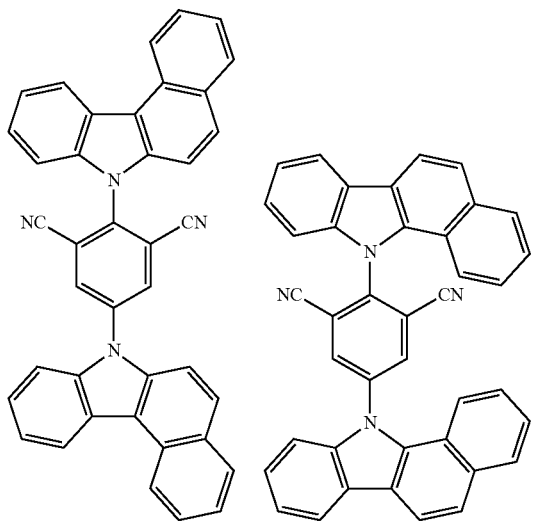

[Formula 139]
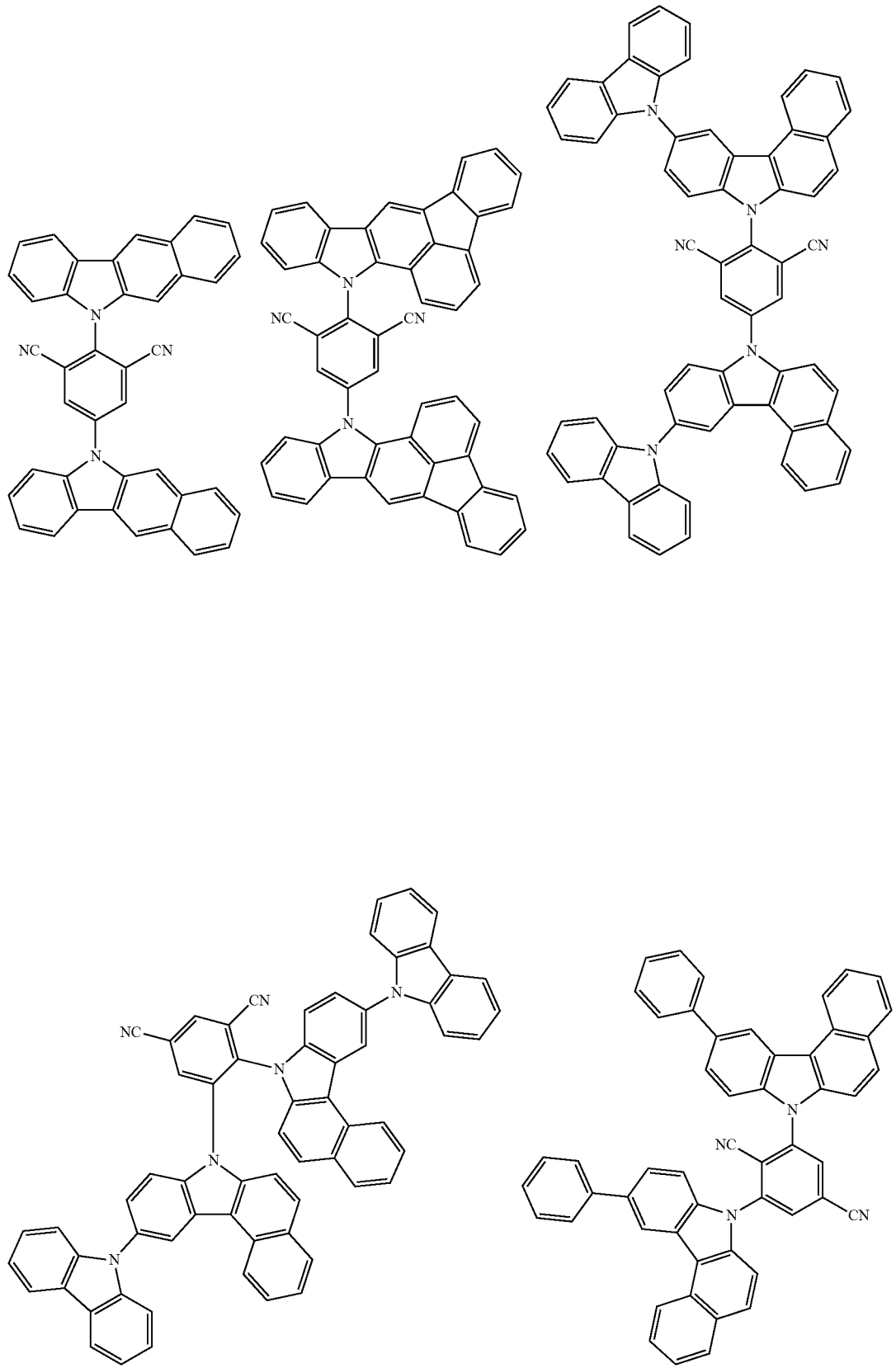

251 252
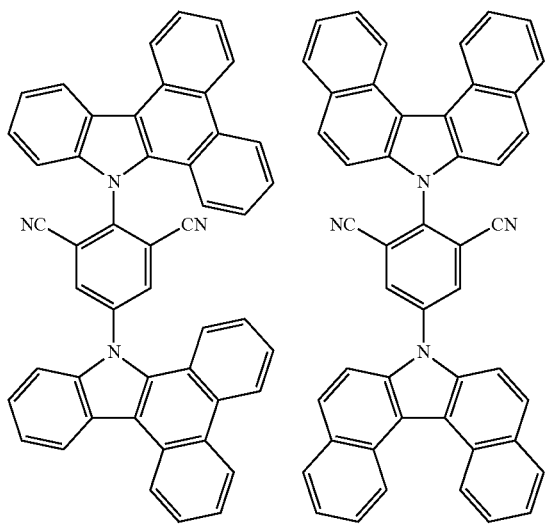
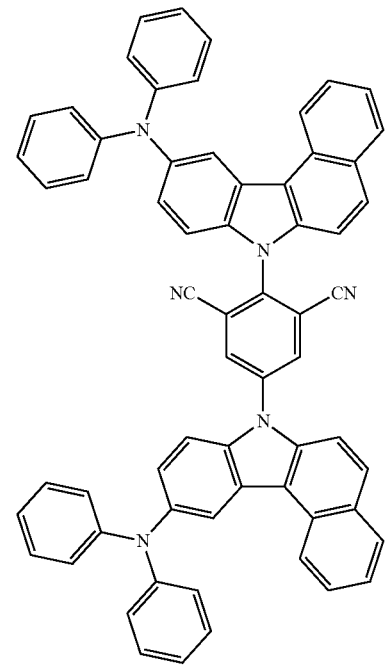
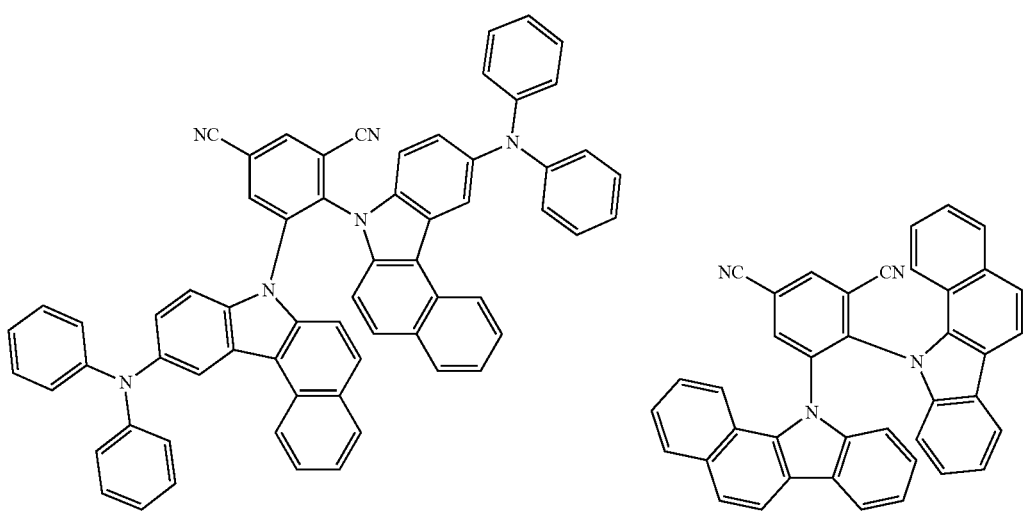

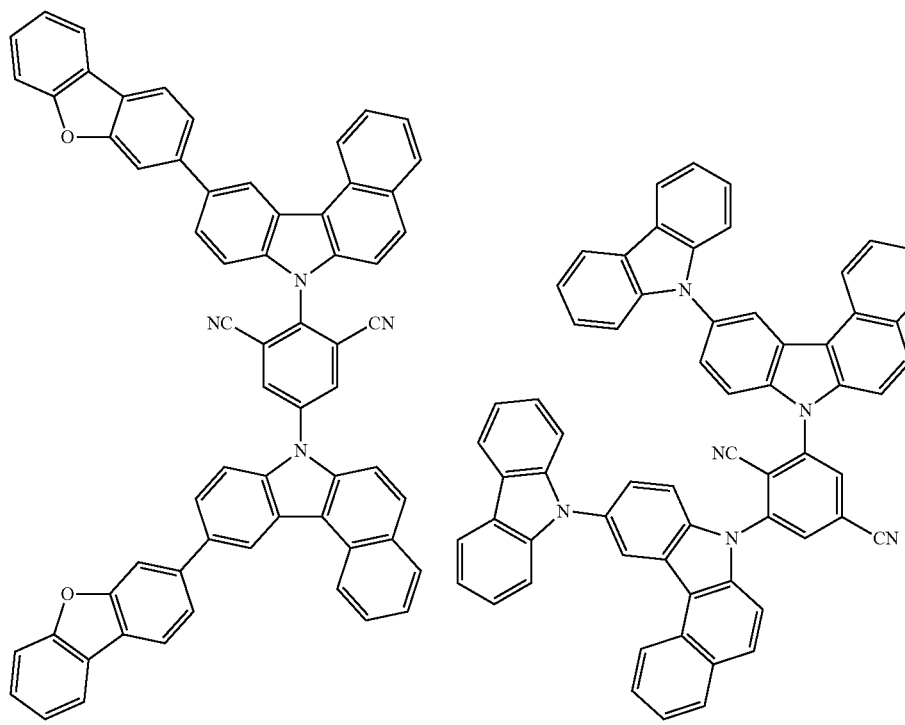
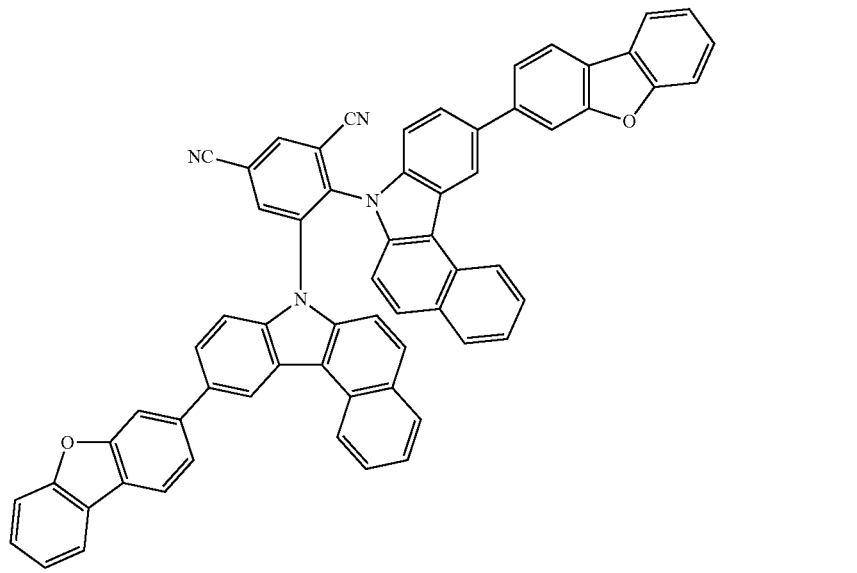
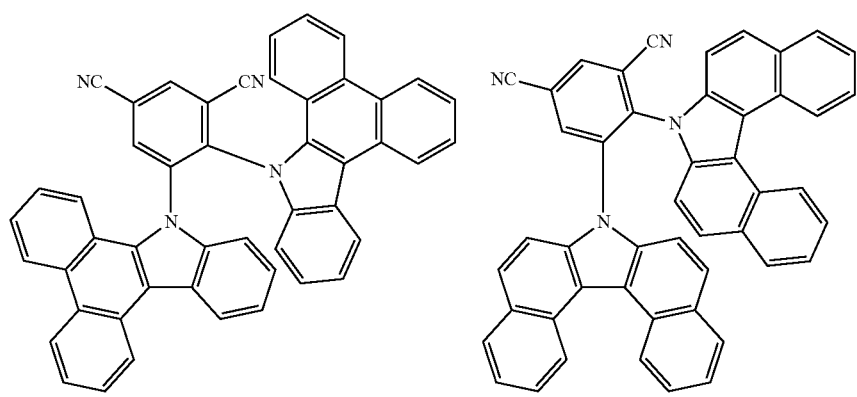

-continued
[Formula 140]
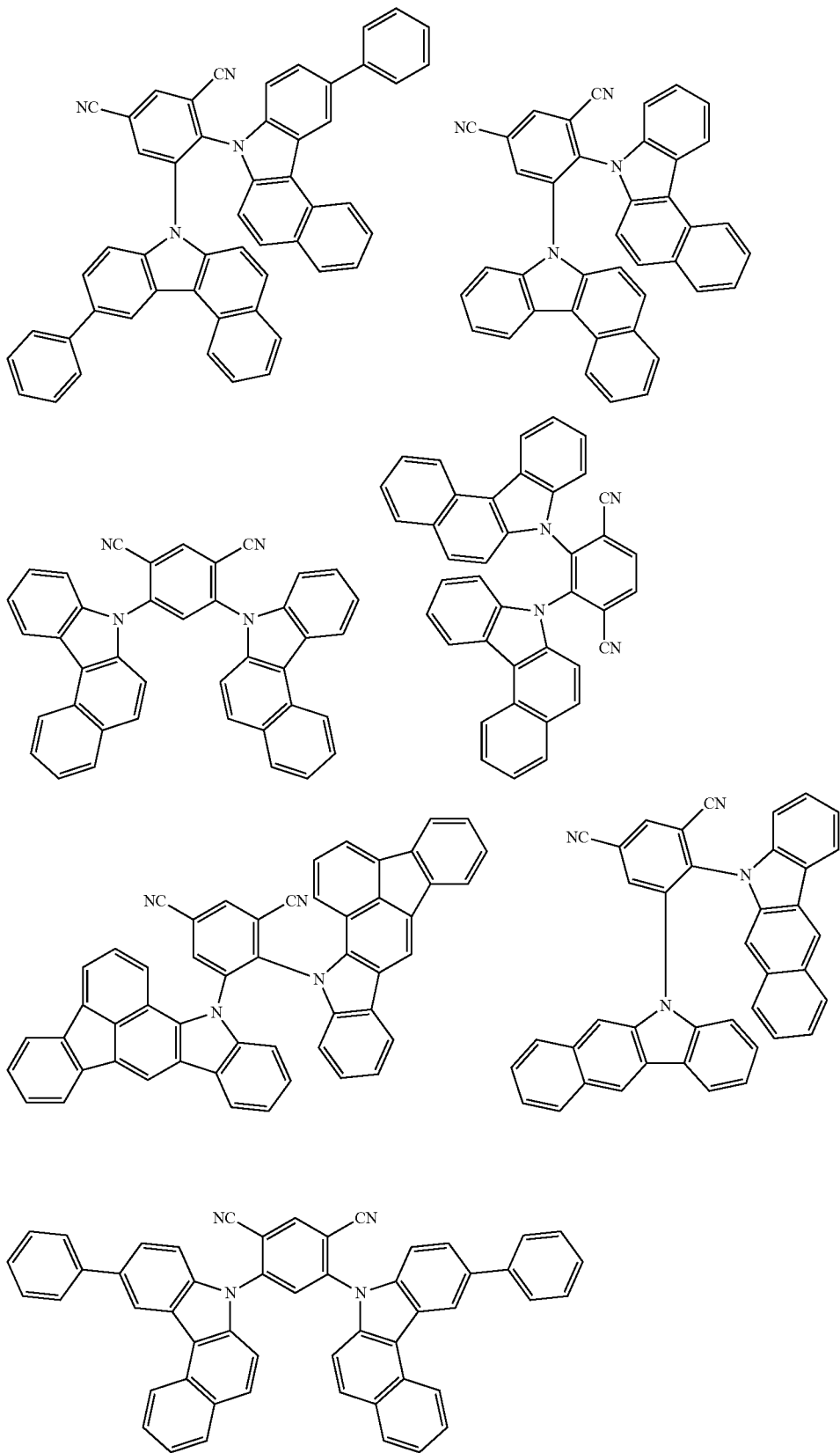

-continued
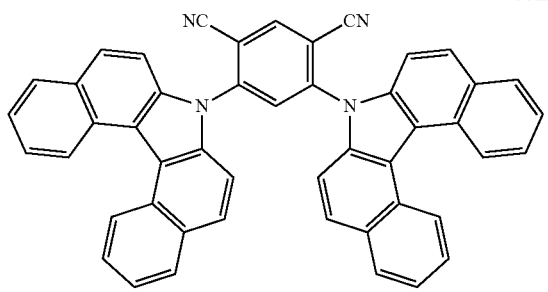
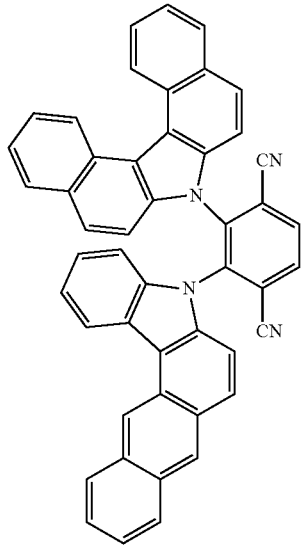
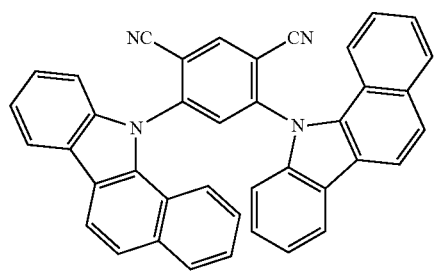
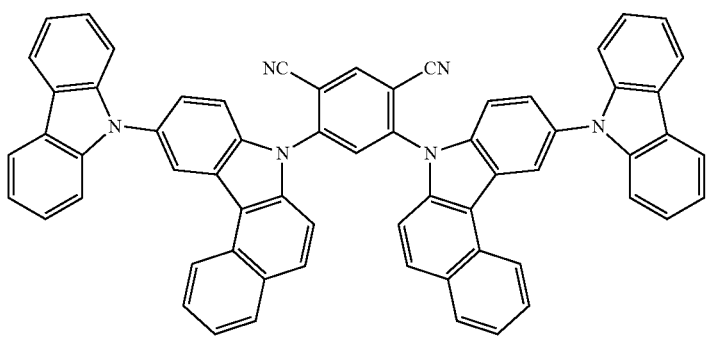
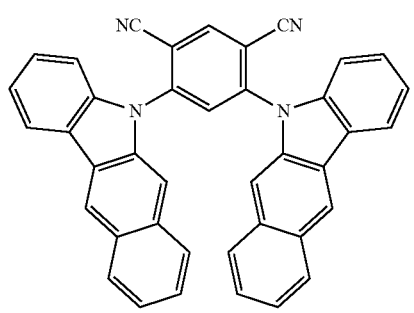
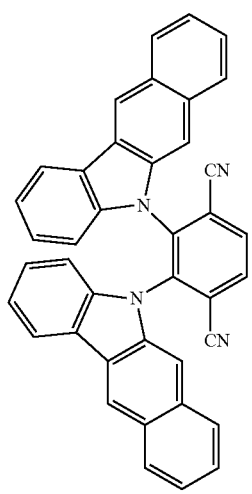
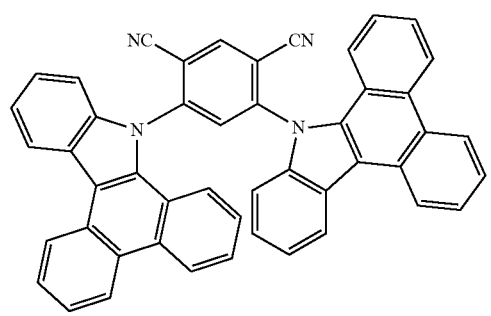

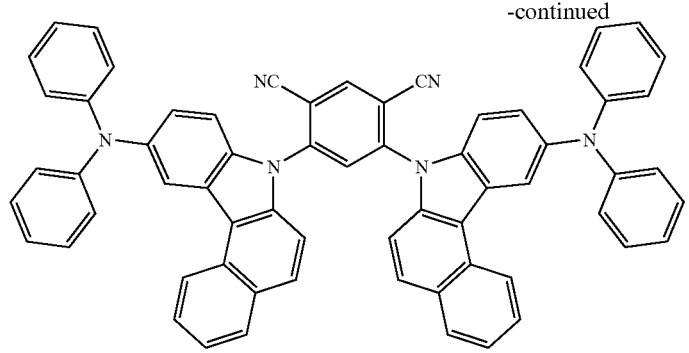
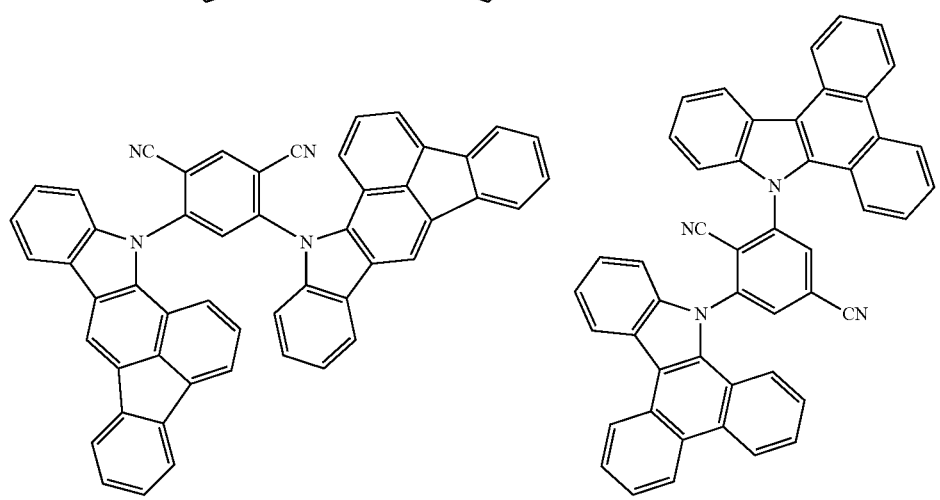
[Formula 141]
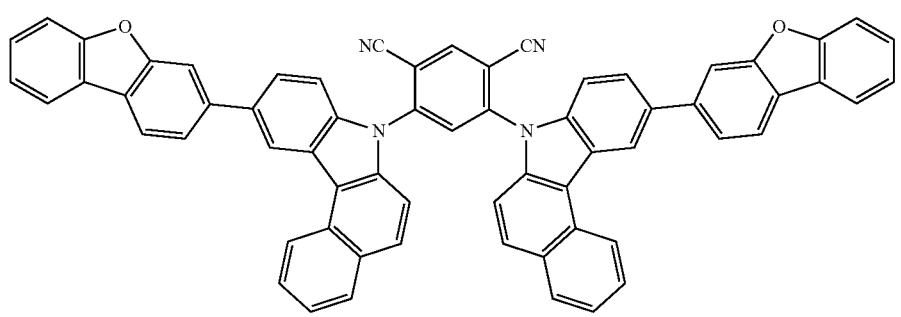
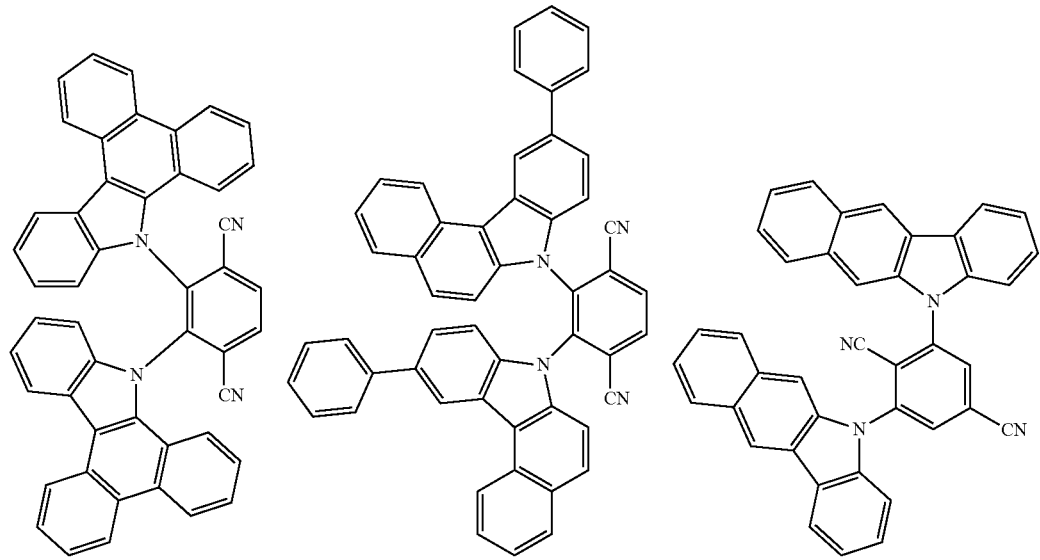

261 262
-continued
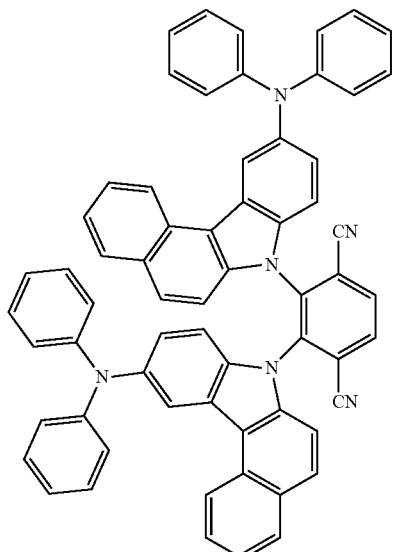
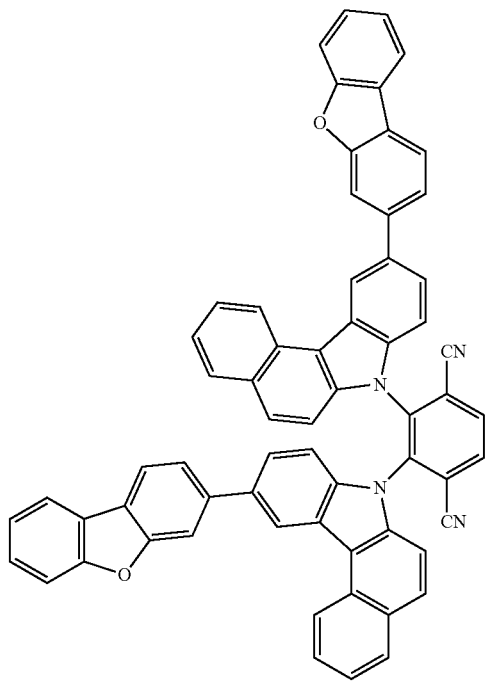
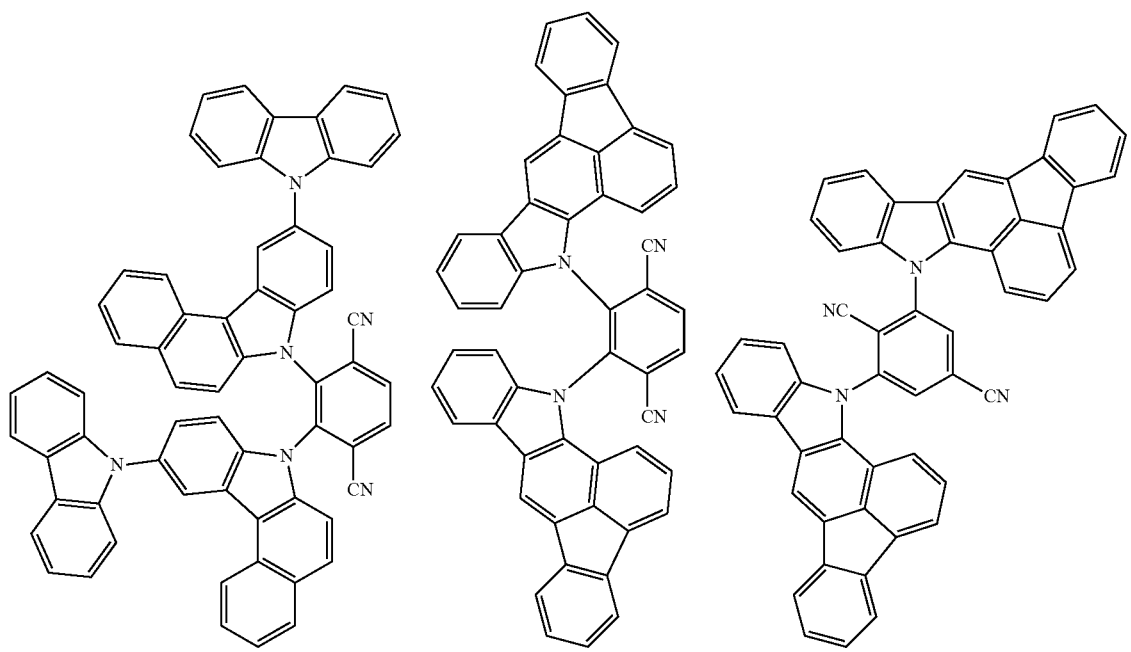

-continued
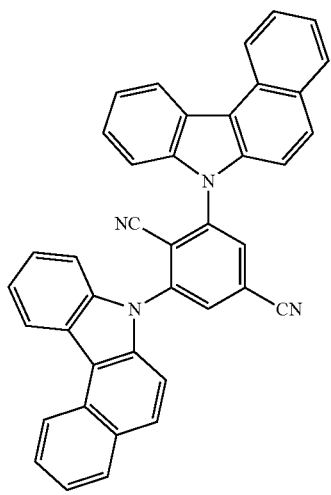
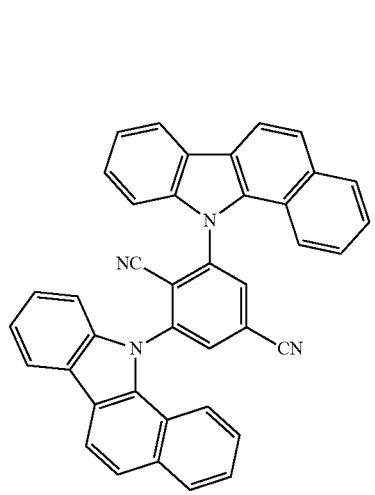
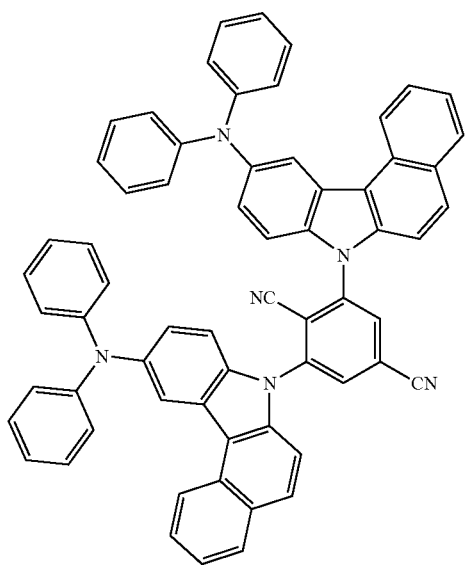
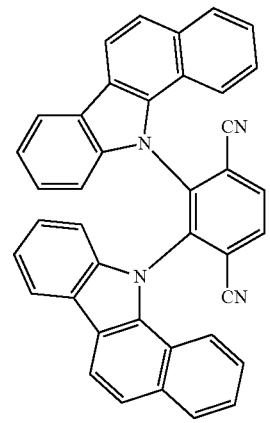
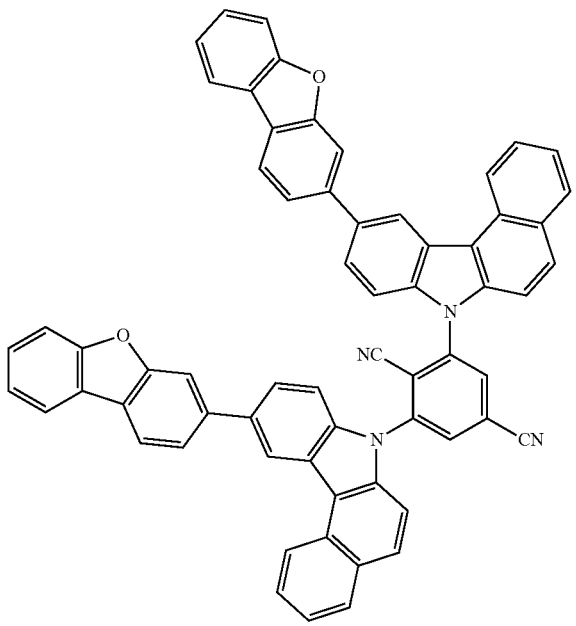
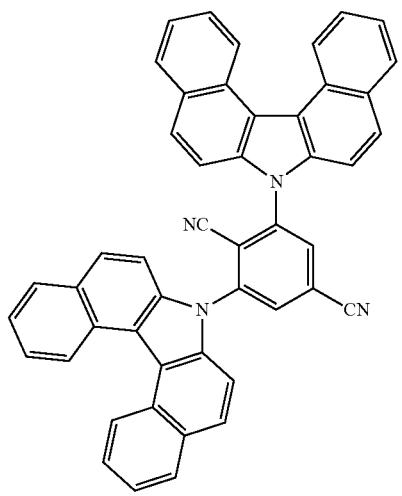

[Formula 142]
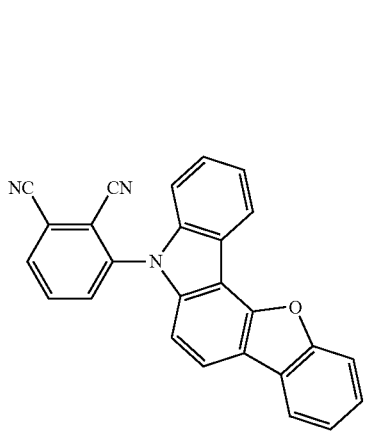
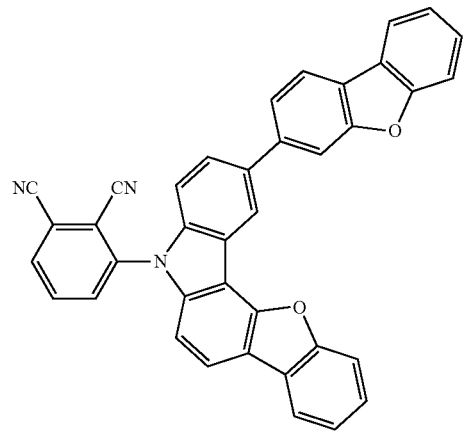
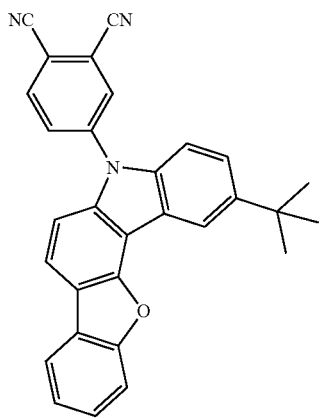
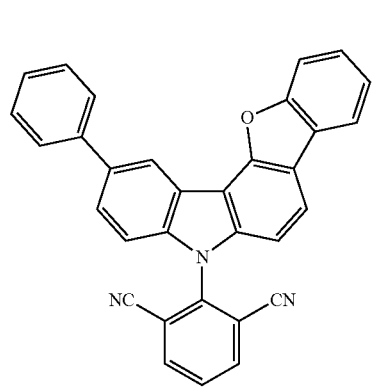
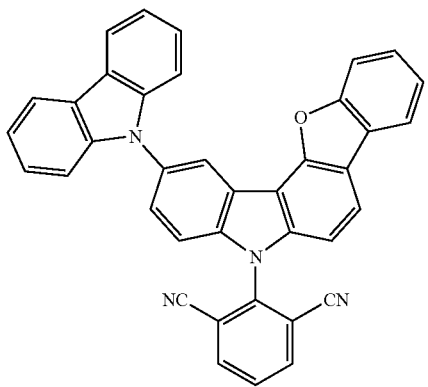
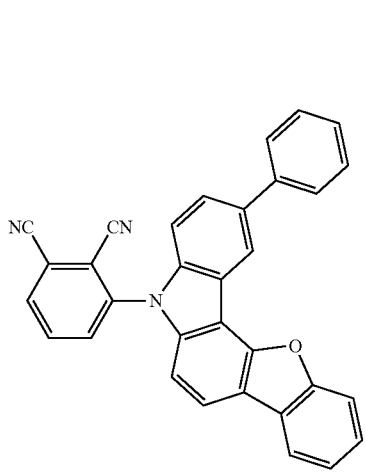
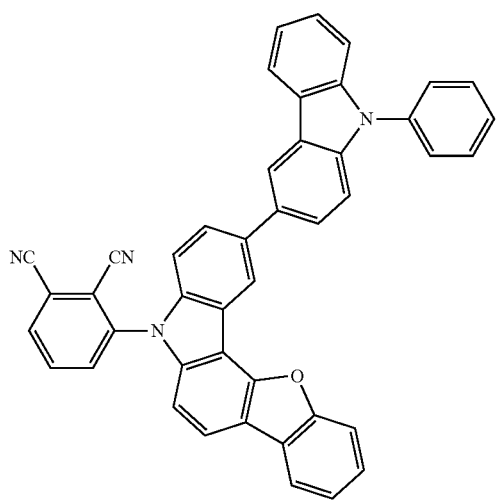

-continued
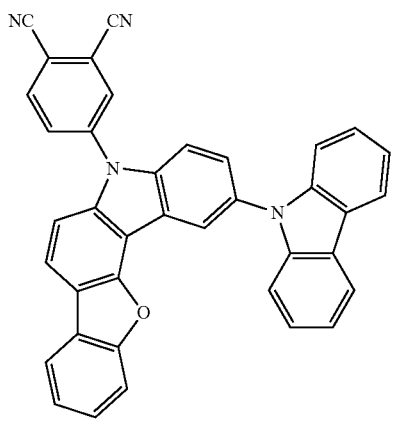
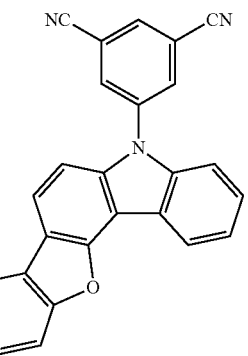
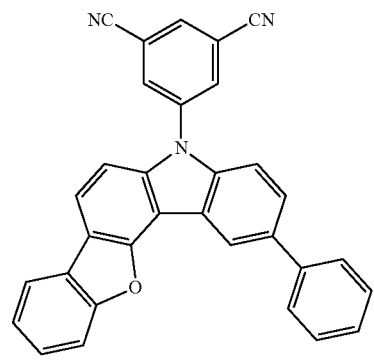
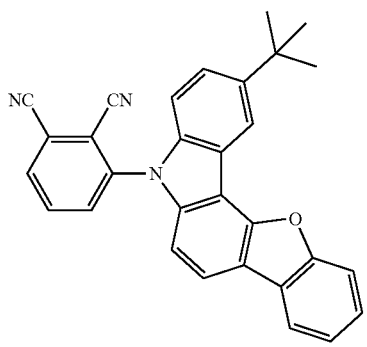
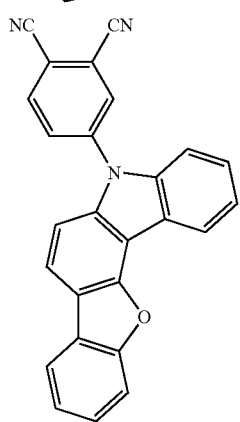
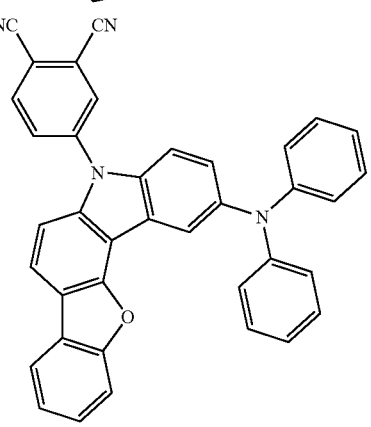
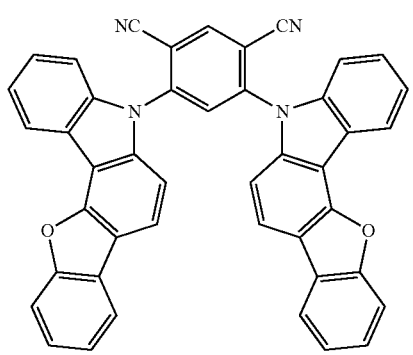
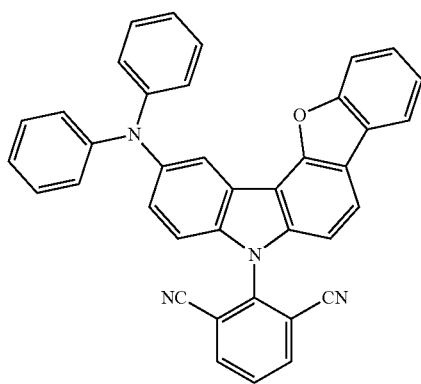
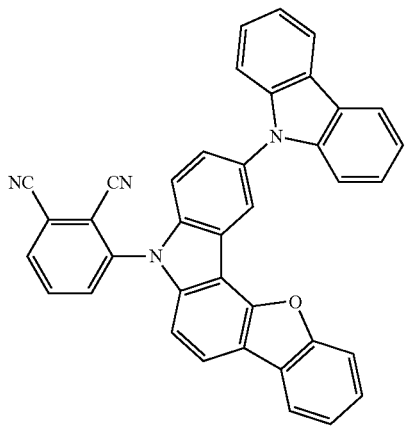

-continued
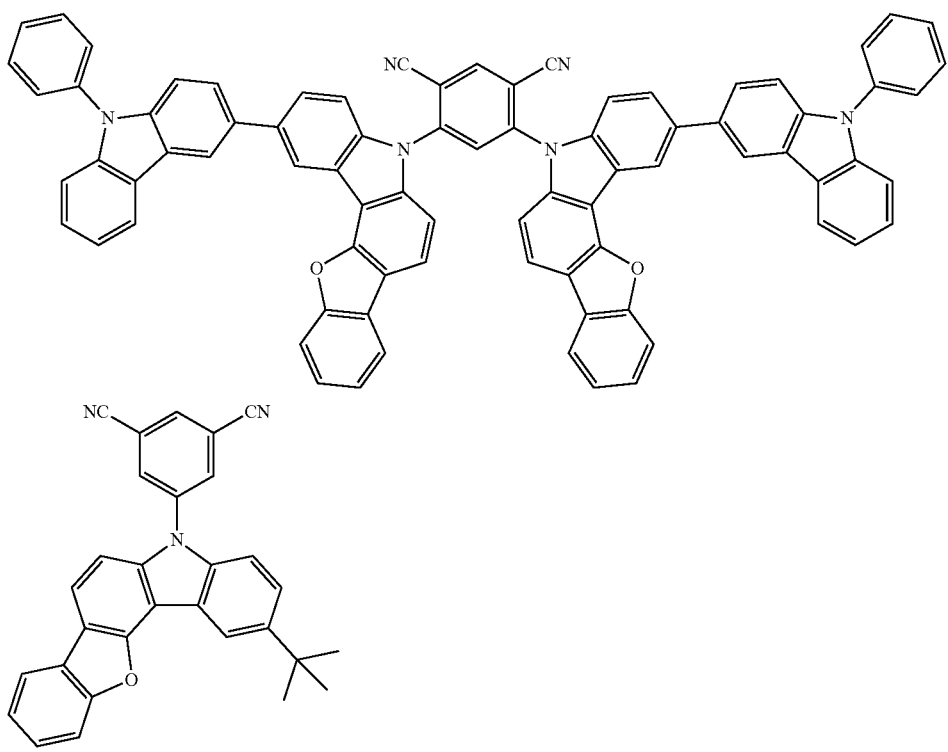
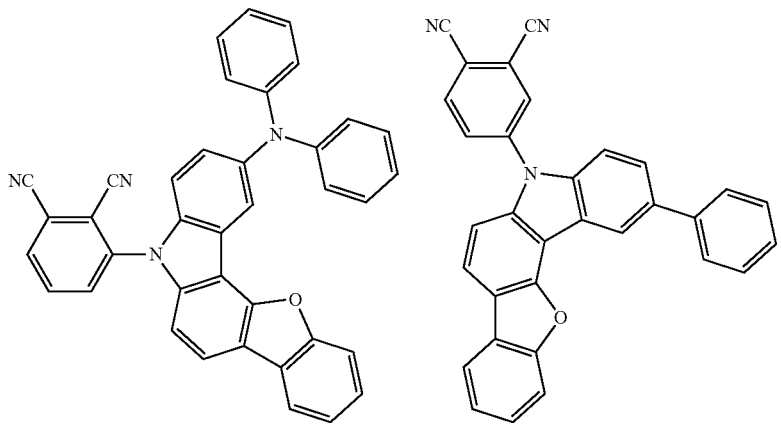
[Formula 143]
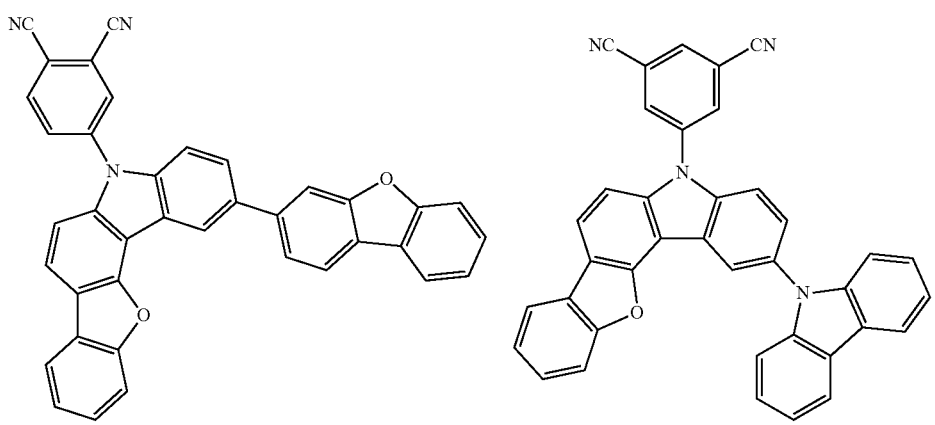

-continued
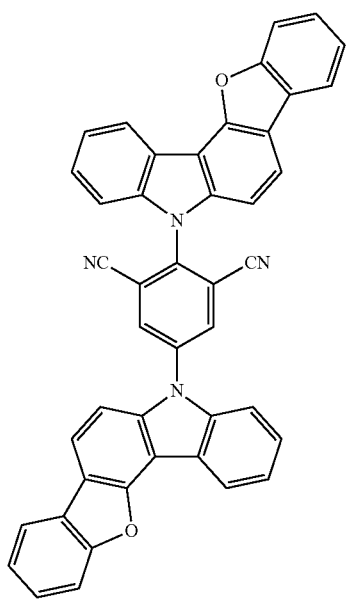
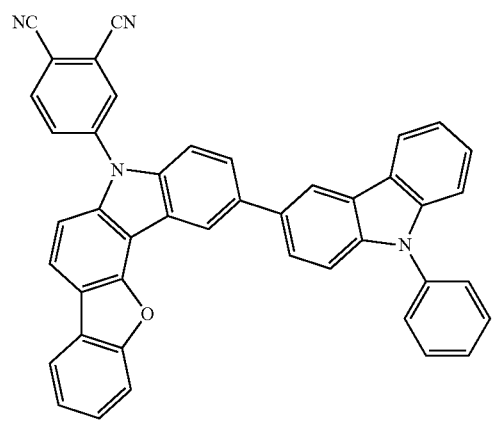
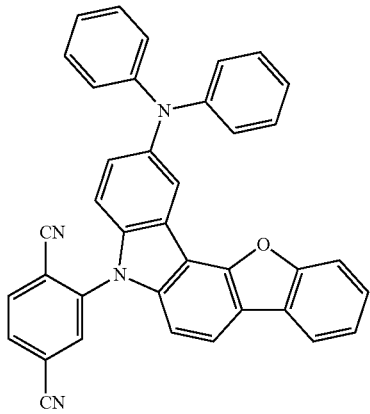
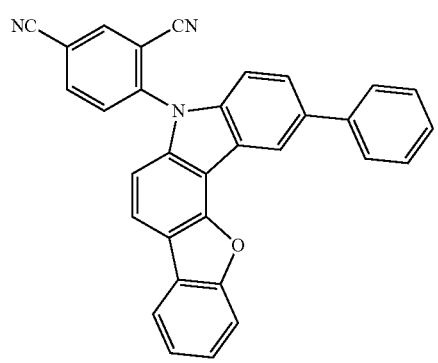
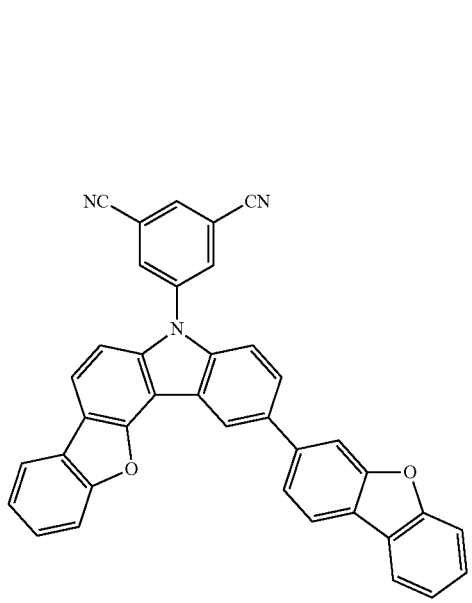
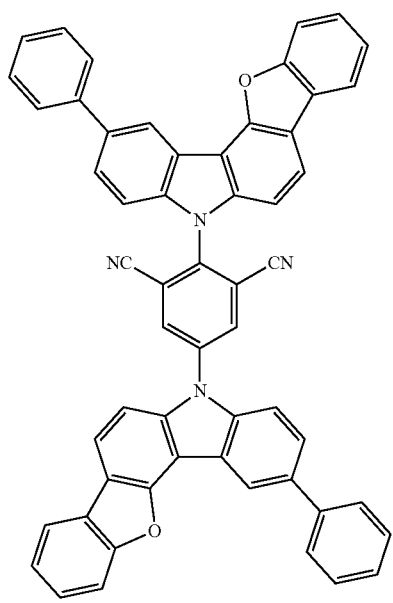

-continued
273
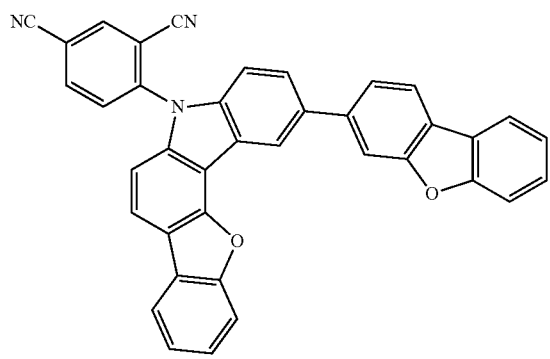
274
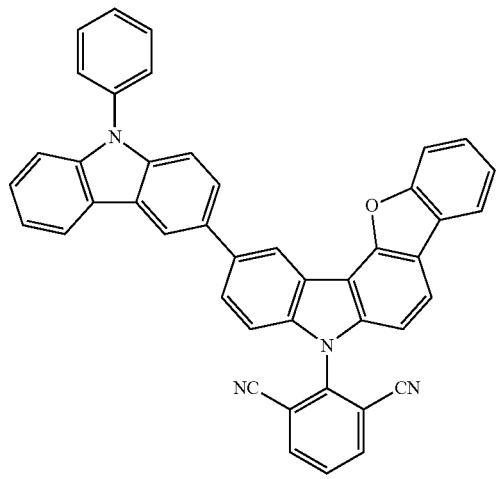
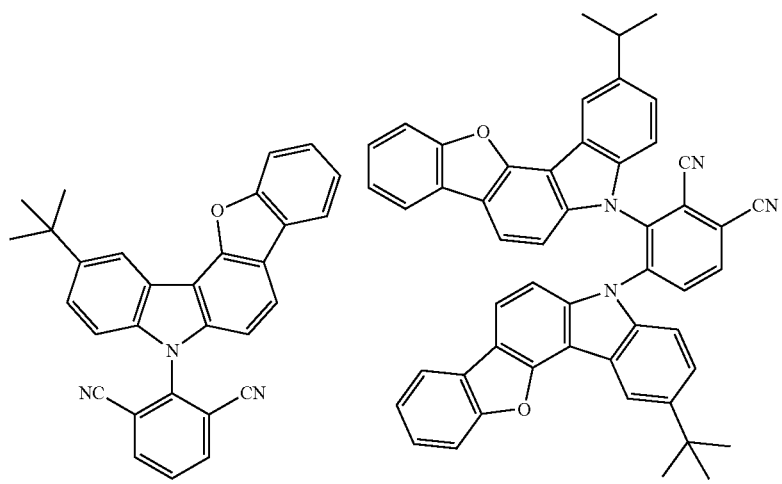
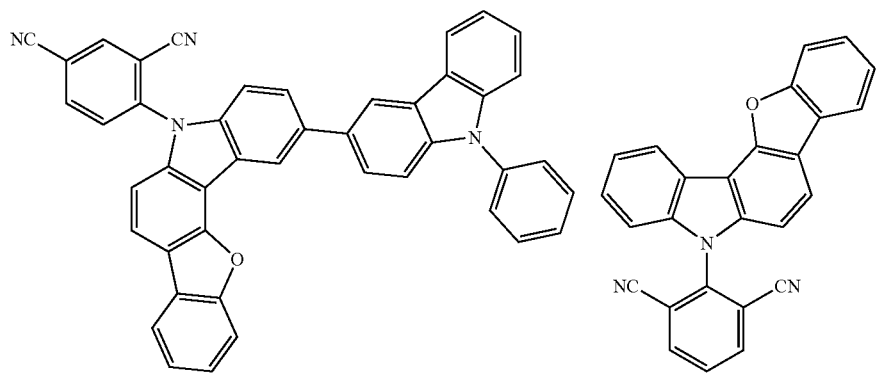

-continued
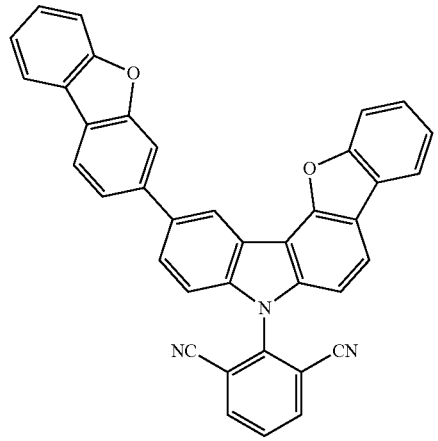
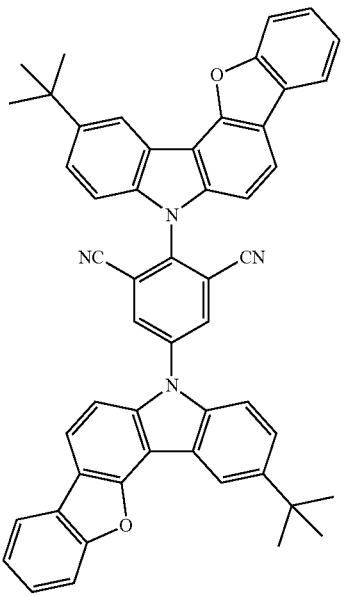
[Formula 144]
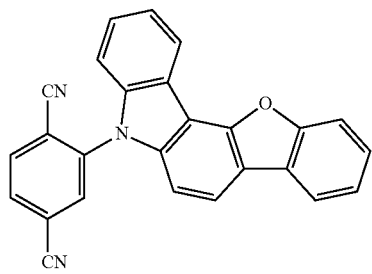
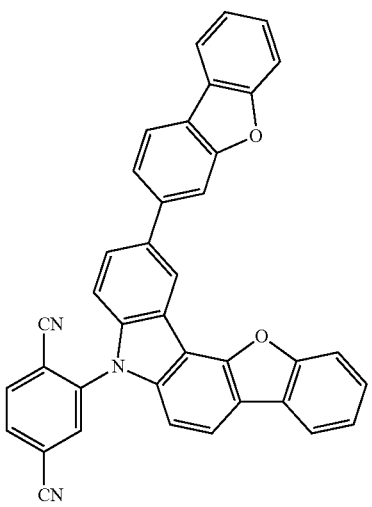
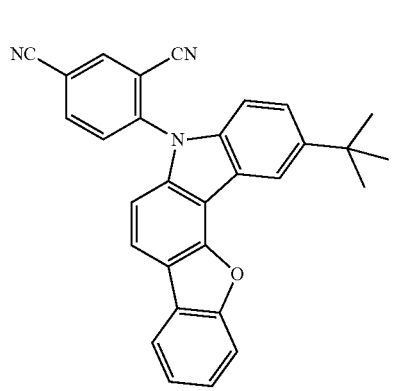
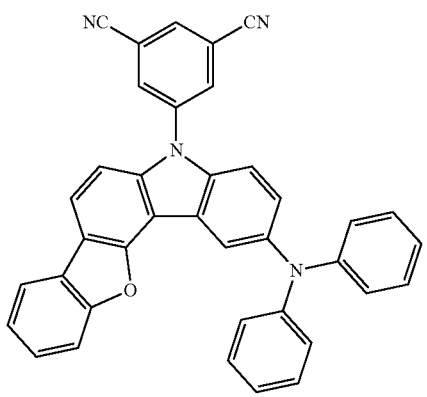

-continued
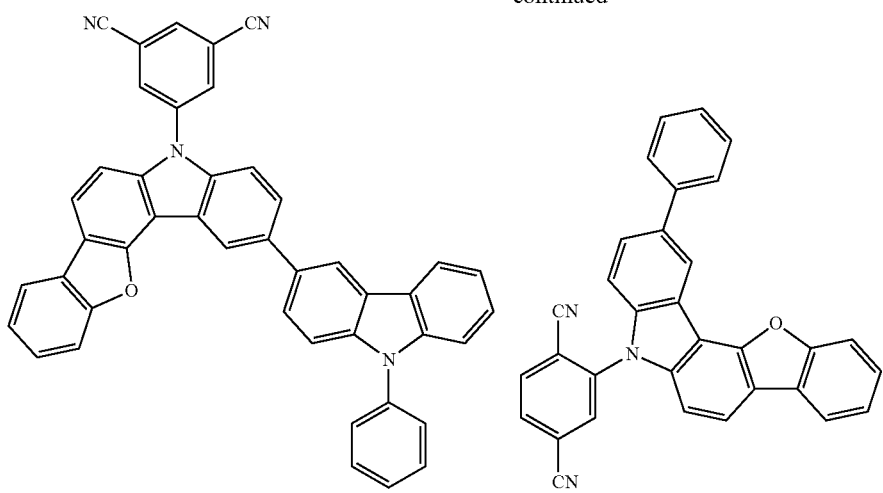
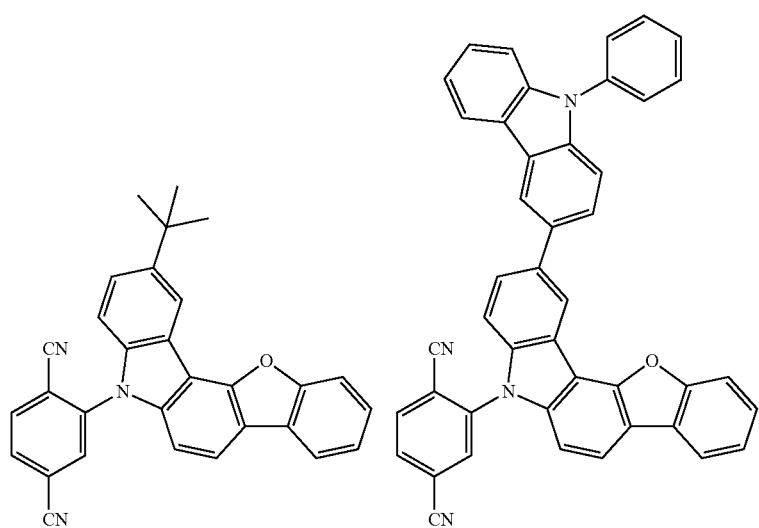
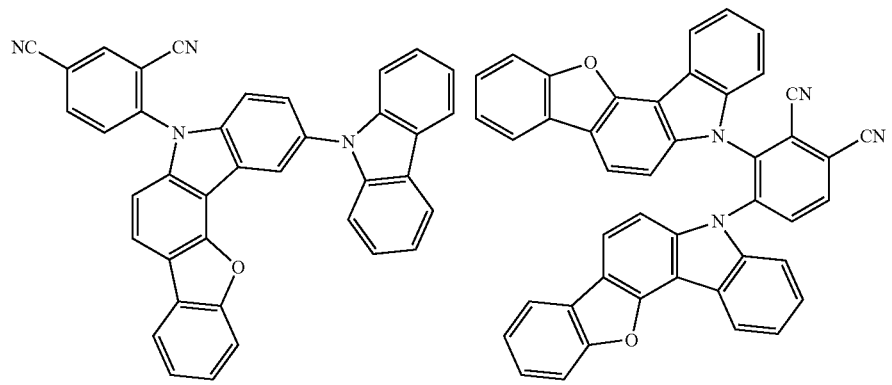

-continued
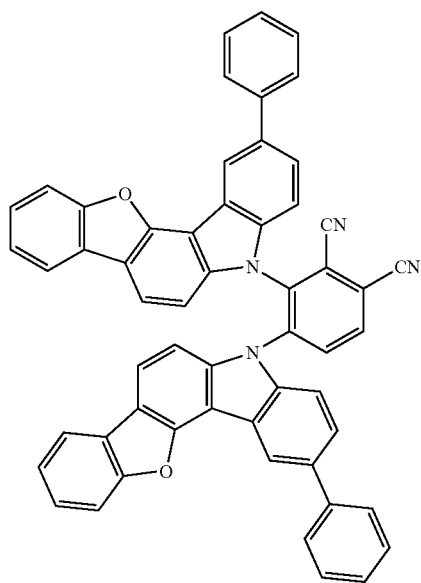
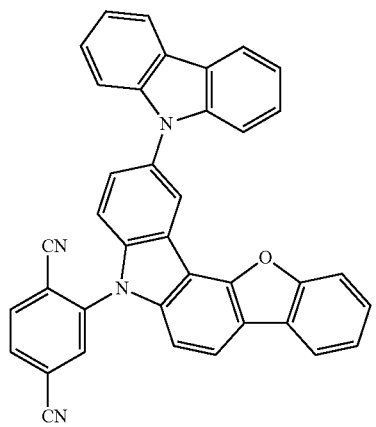
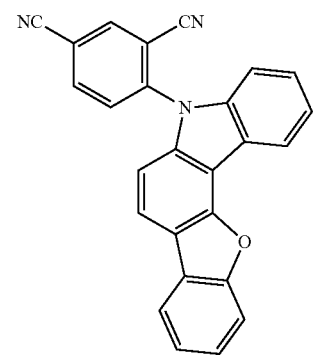
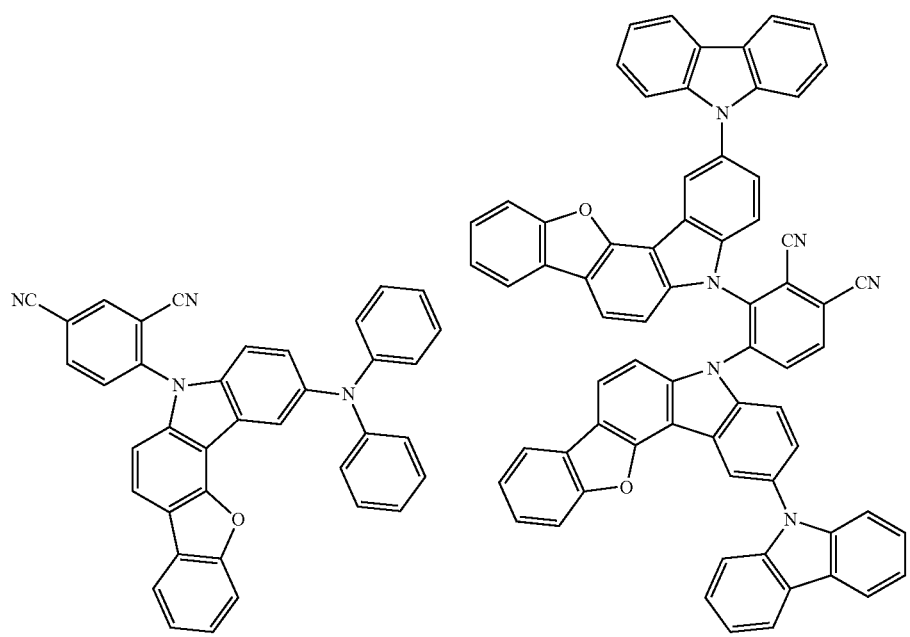

281
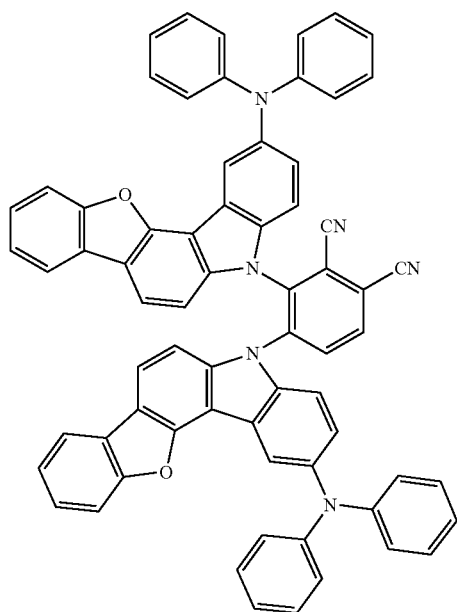
-continued
282
[Formula 145]
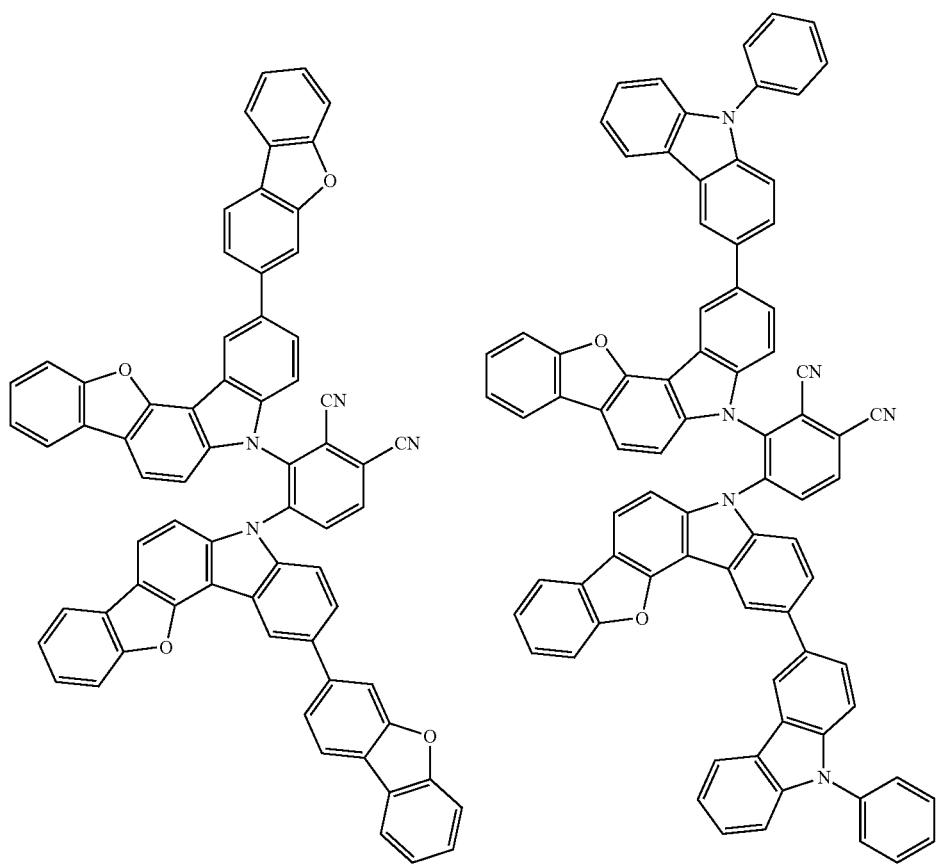

283
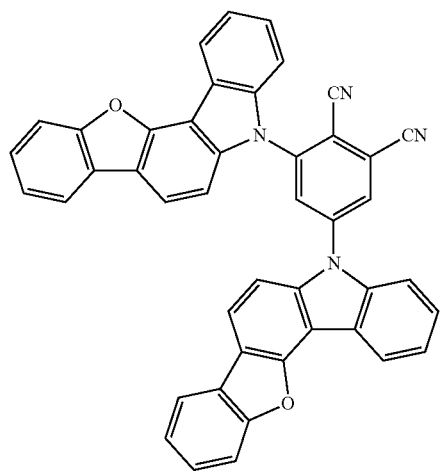
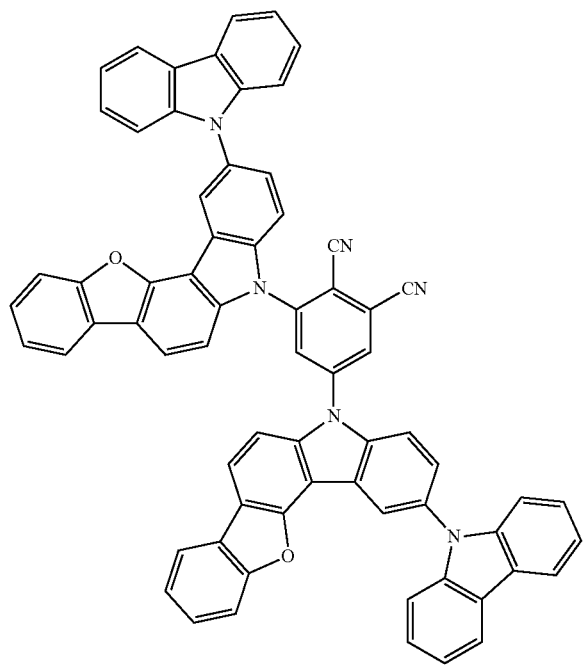
284
-continued
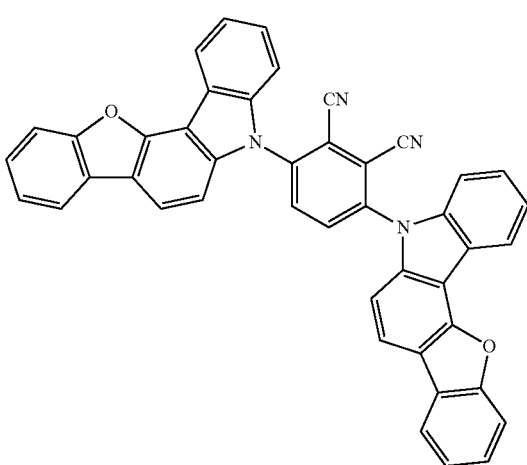
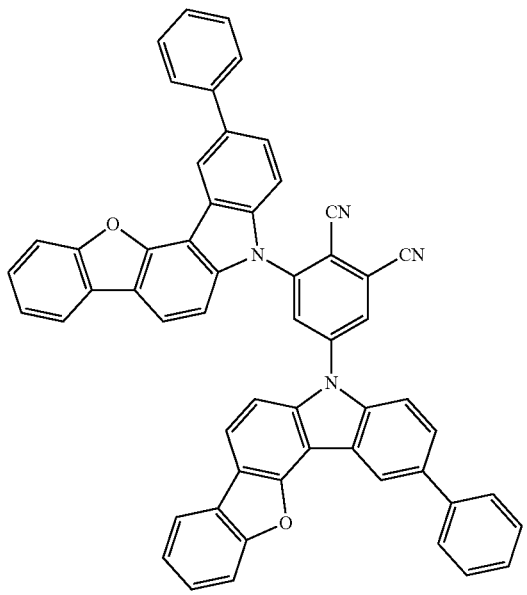
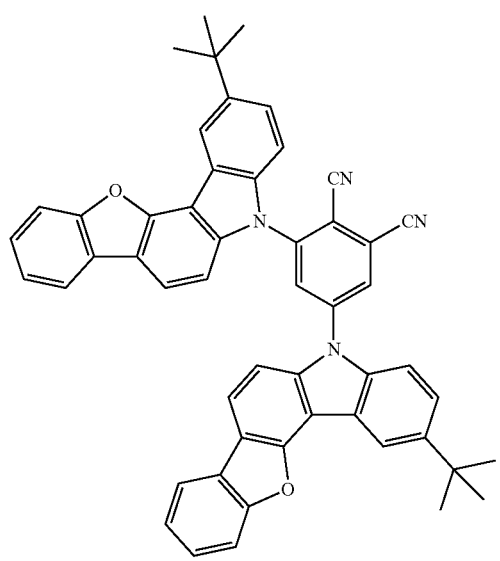

-continued
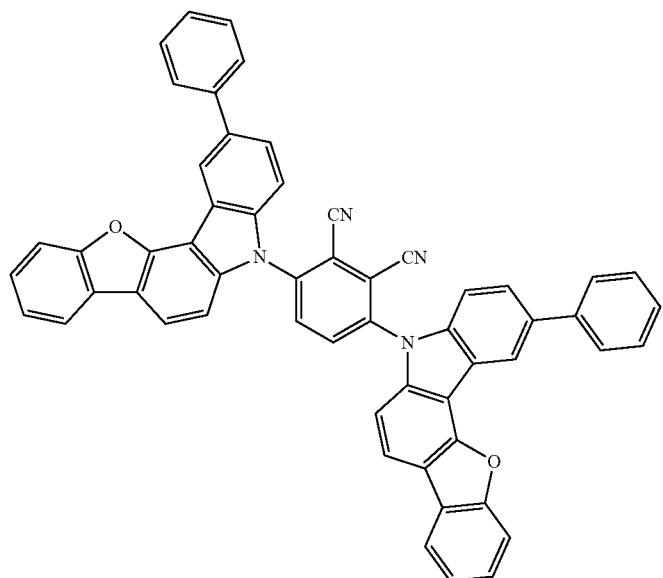
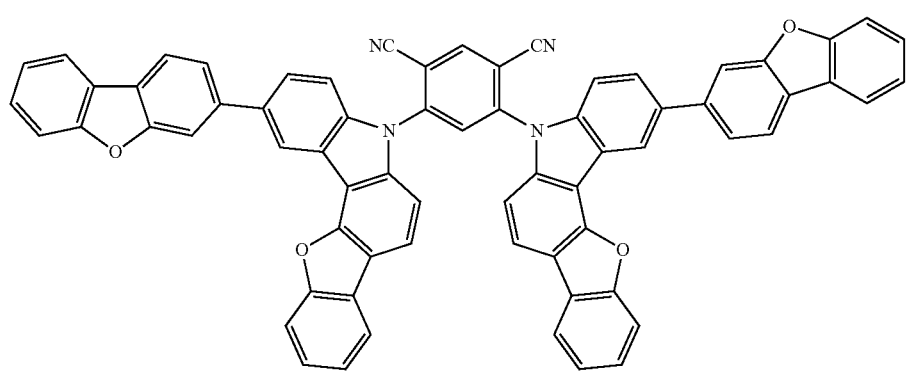
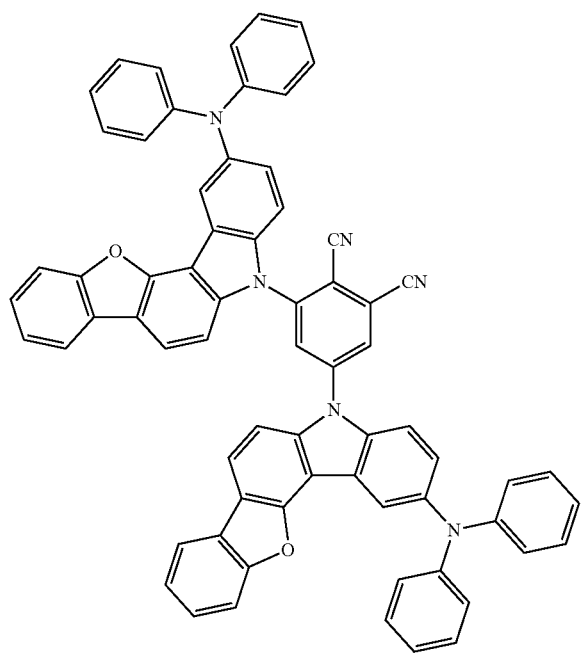

-continued
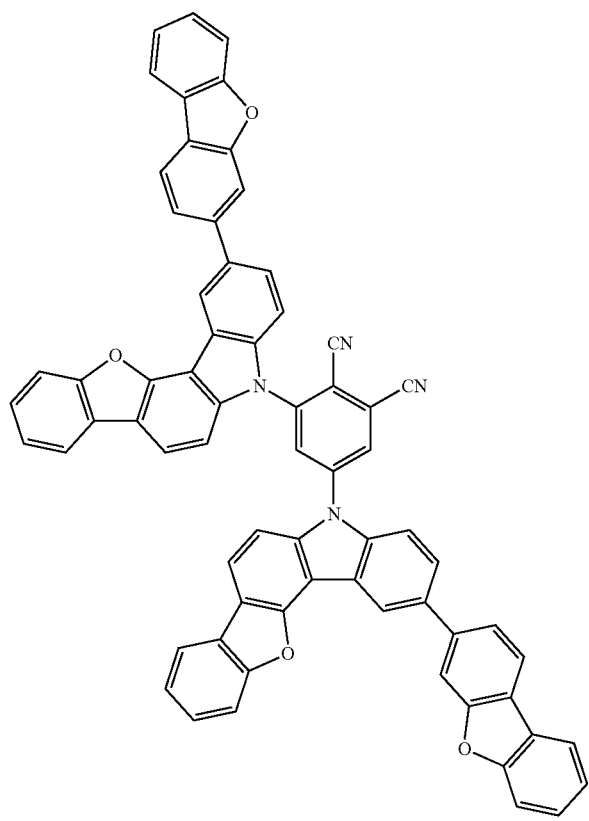
[Formula 146]
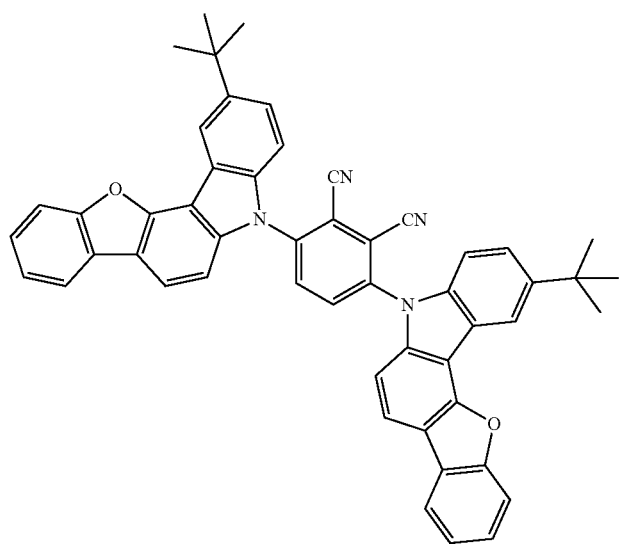

-continued
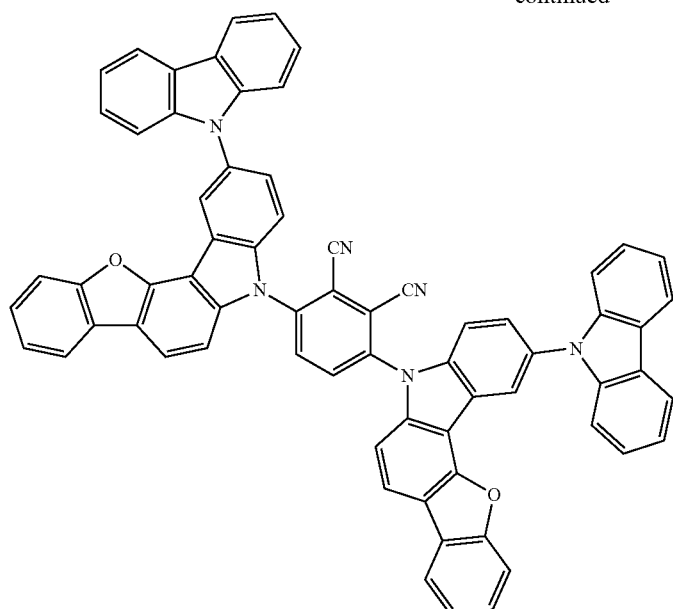
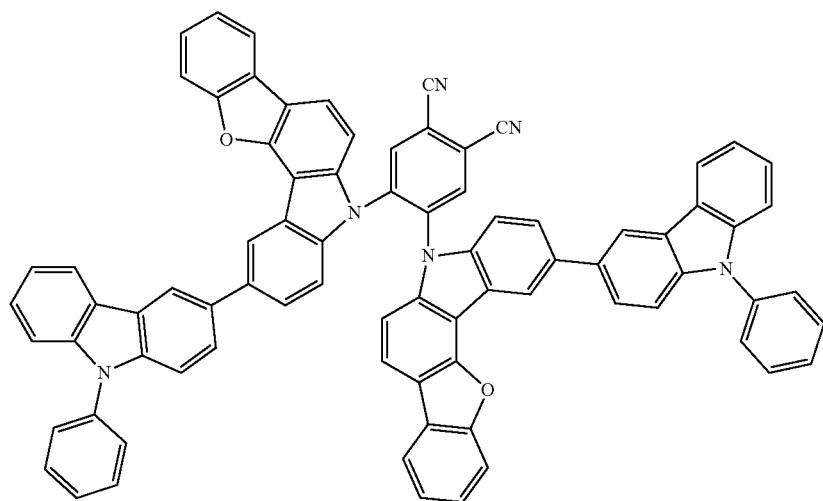
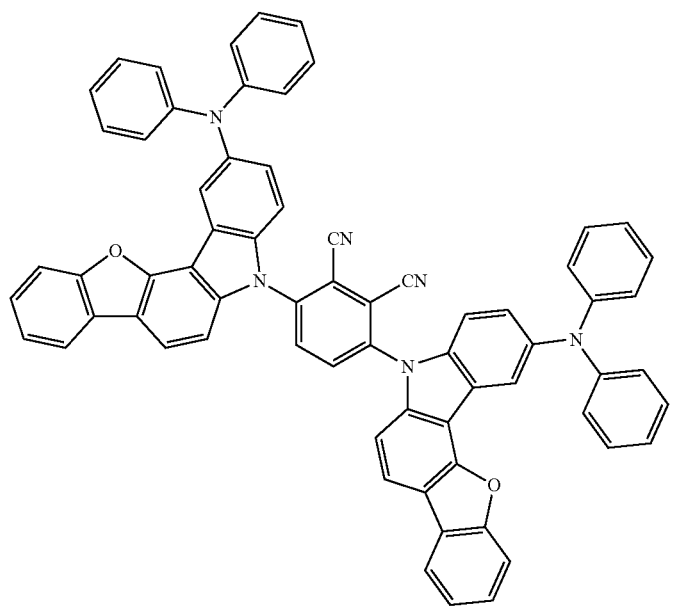

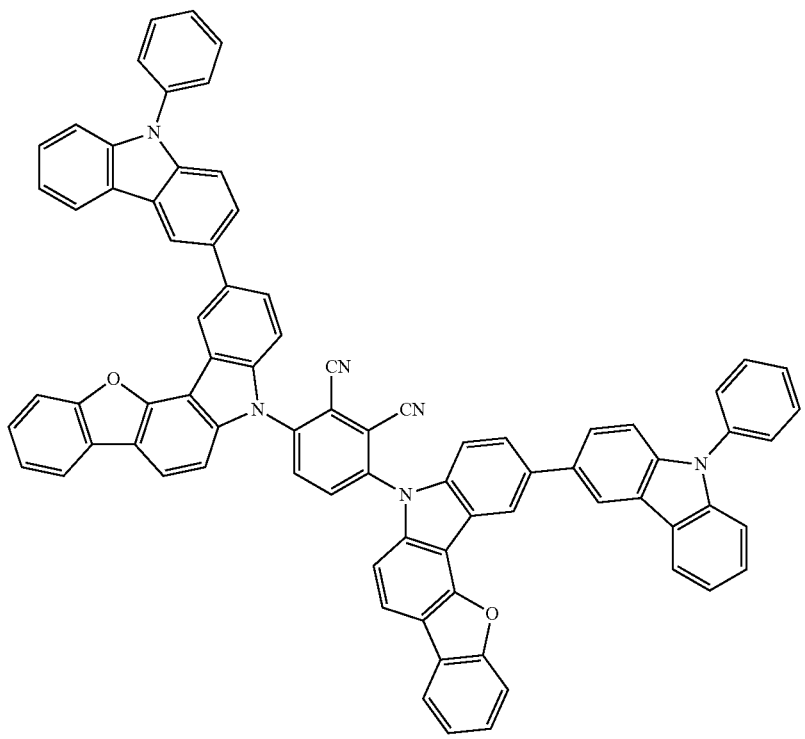
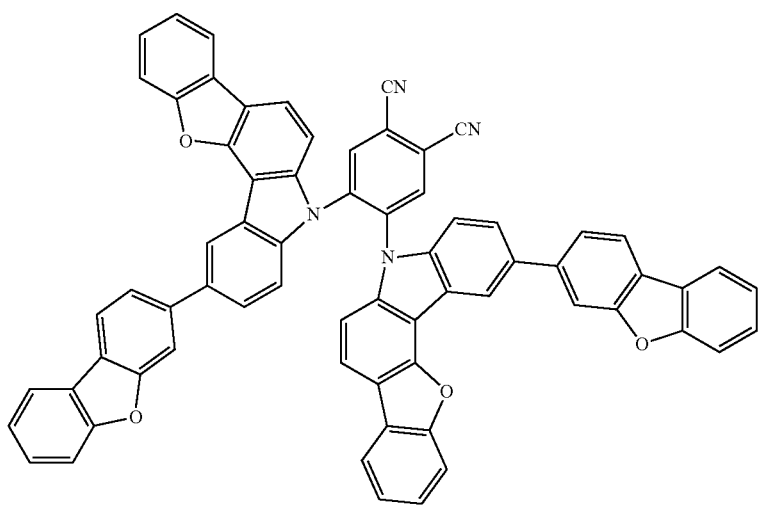

-continued
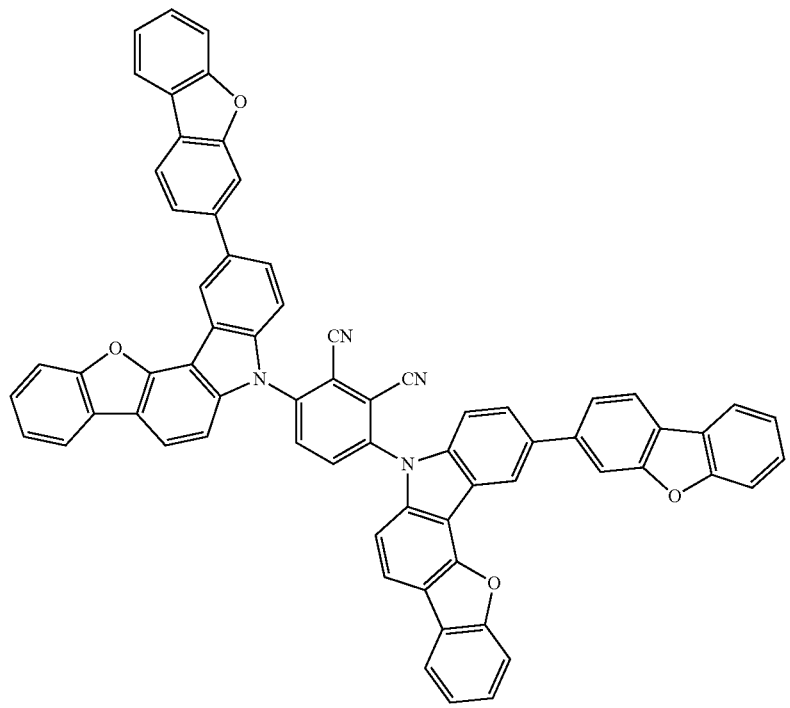
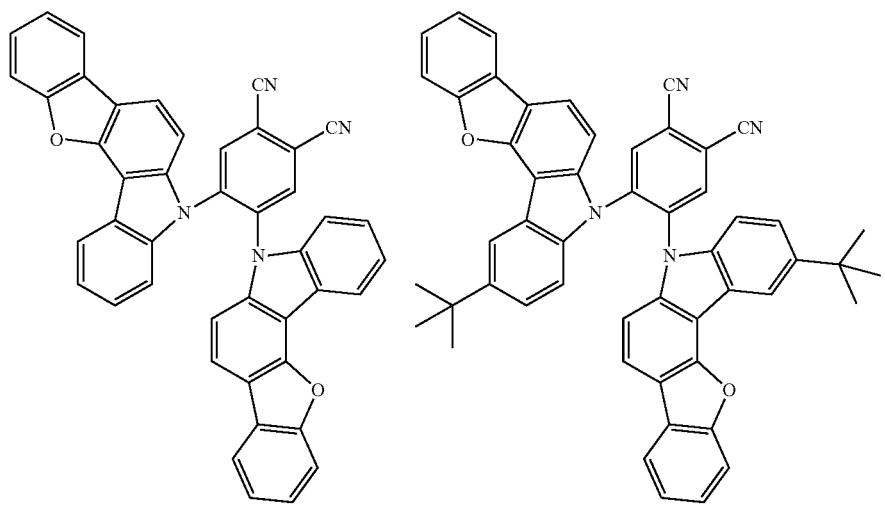
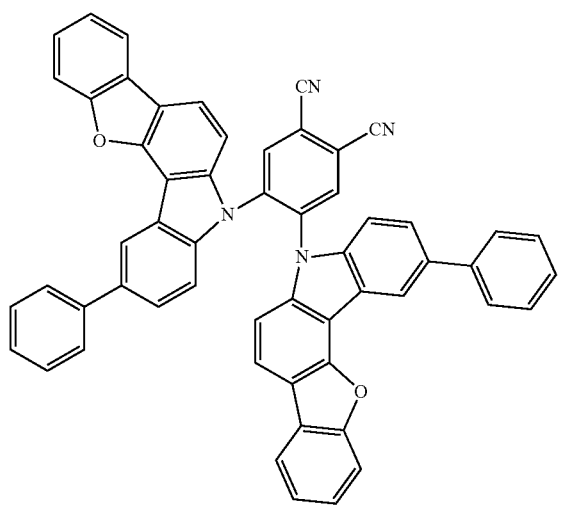

[Formula 147]
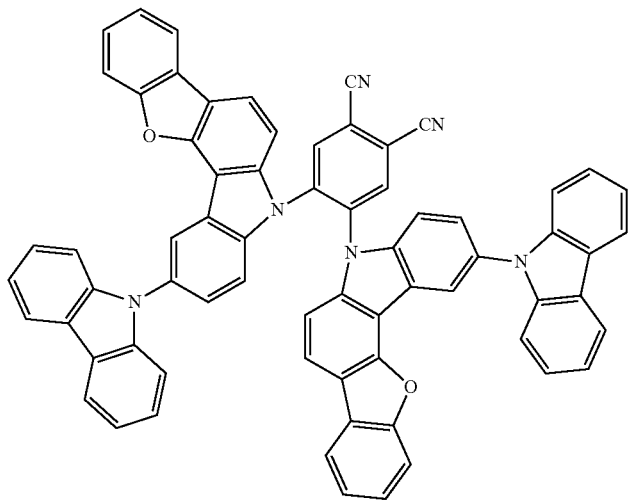
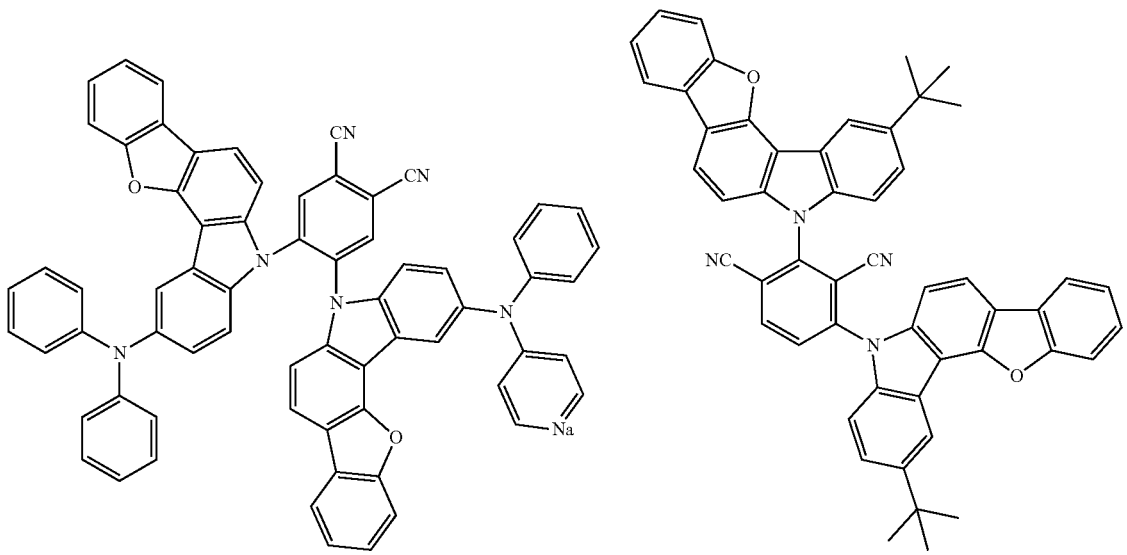

297
298
-continued
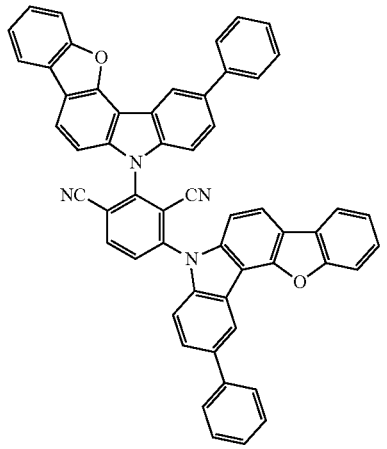
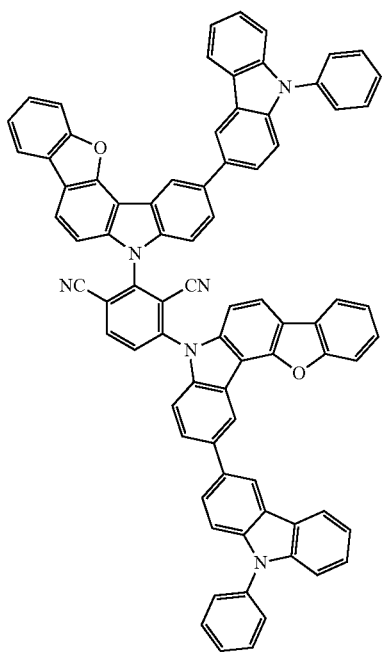
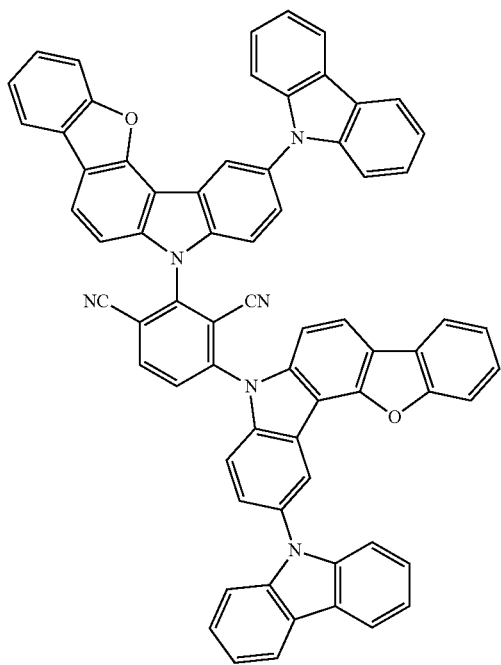
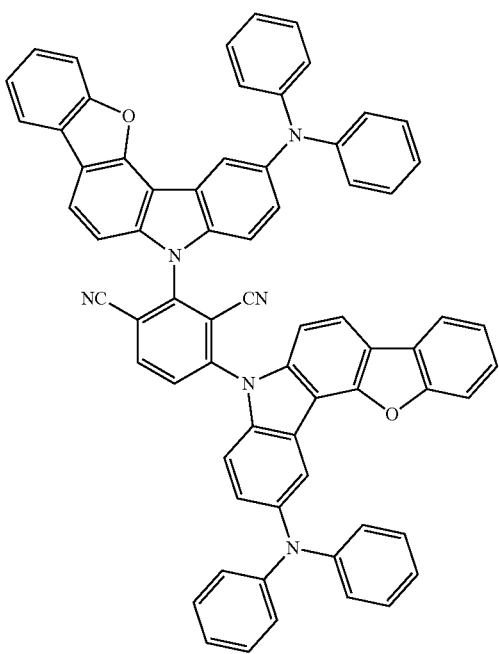

-continued
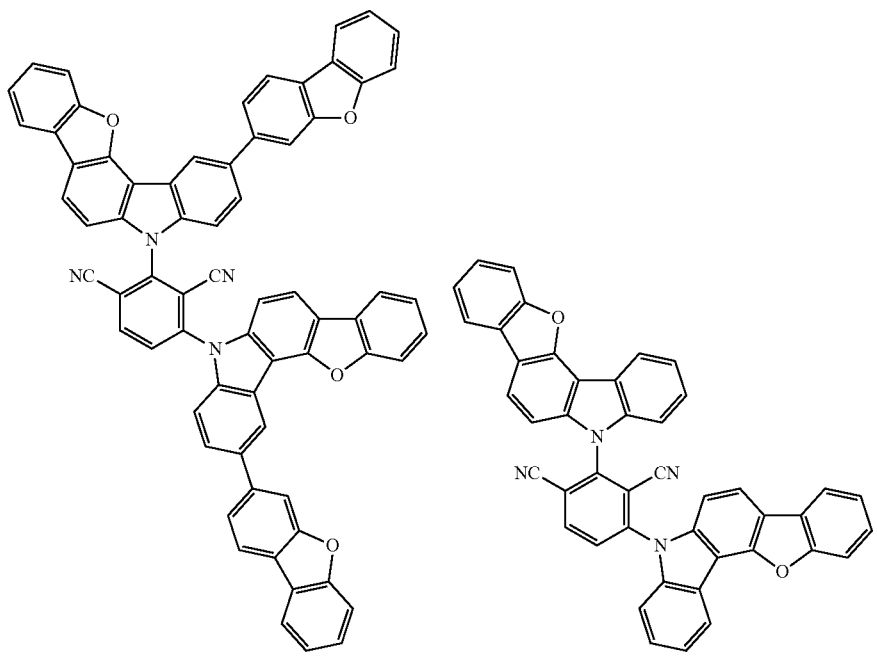
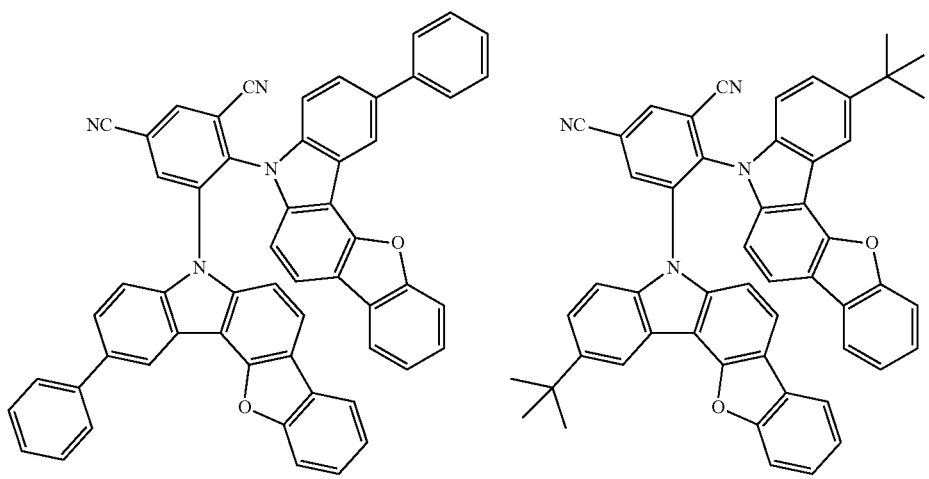
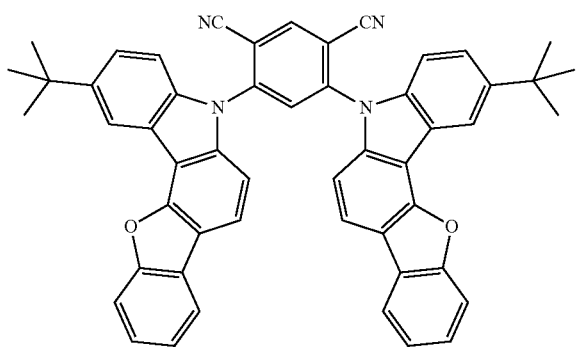

[Formula 148]
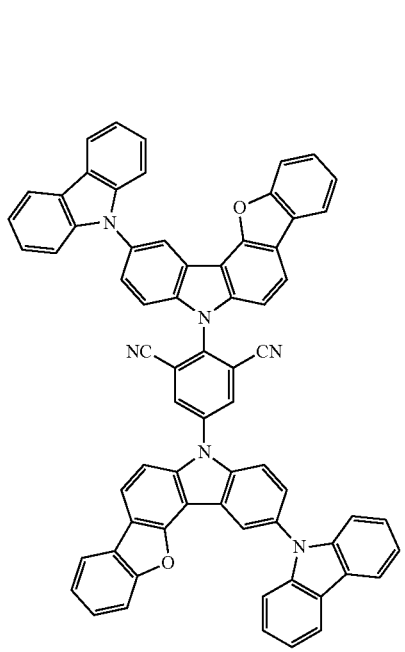
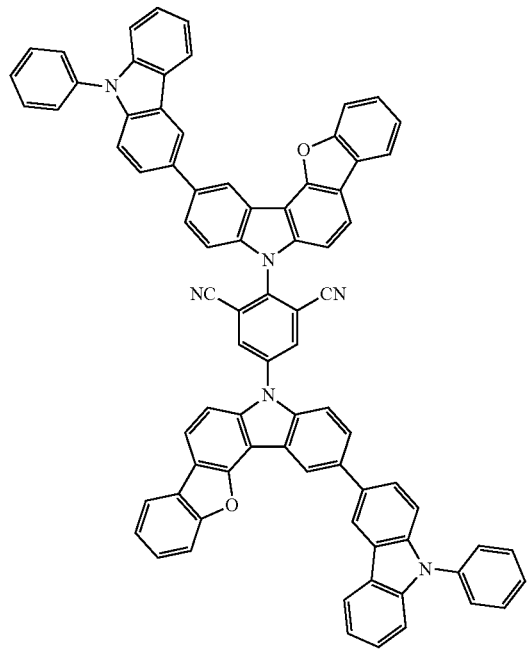
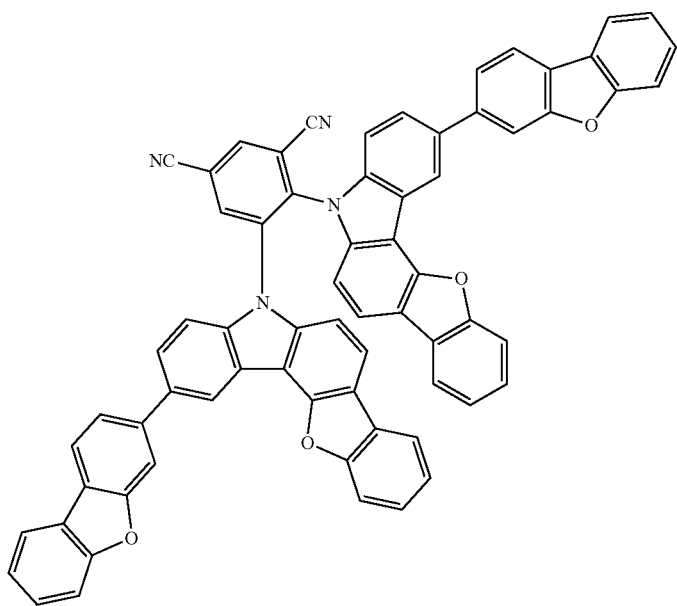

303
-continued
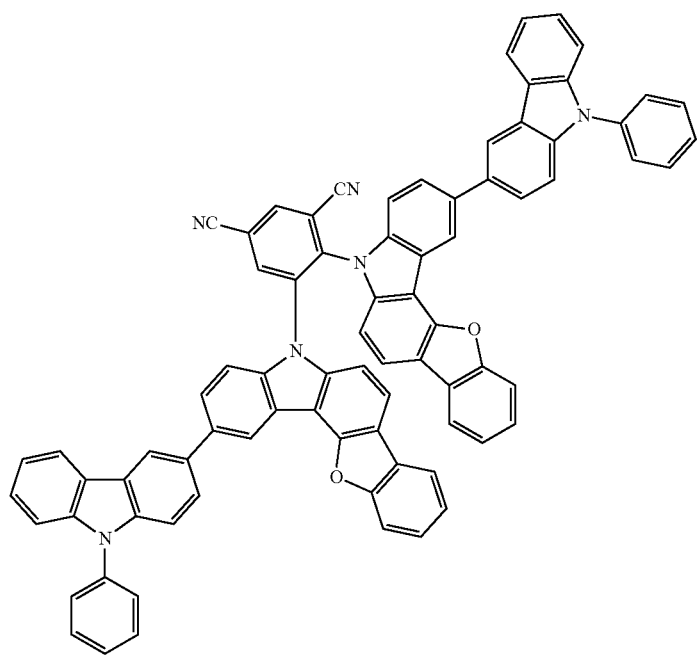
304
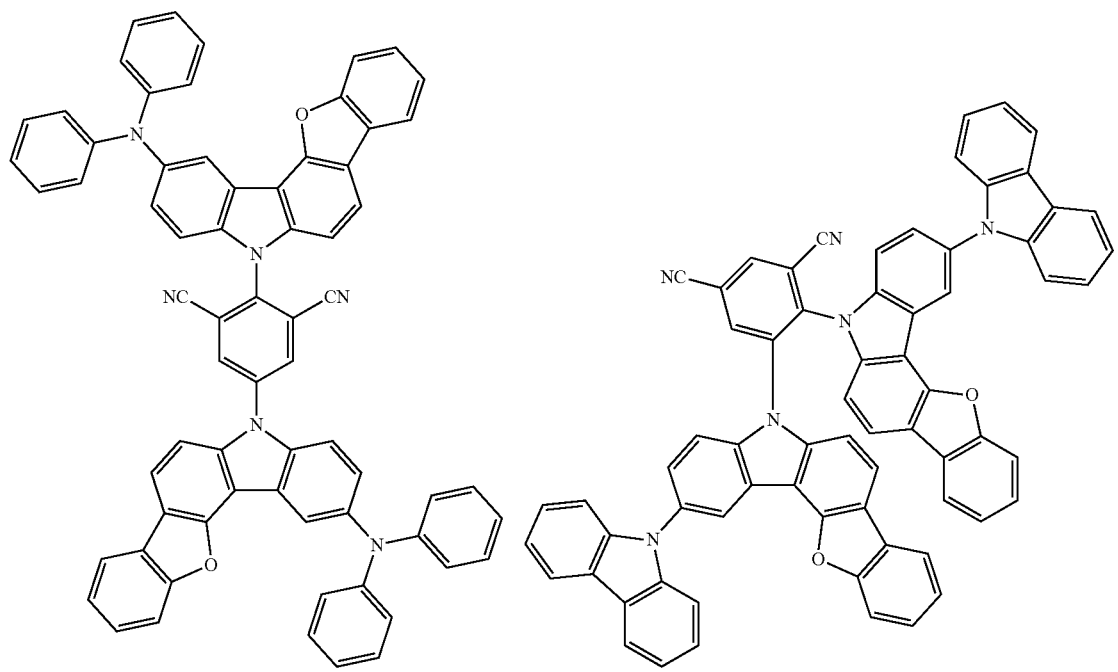

-continued
305
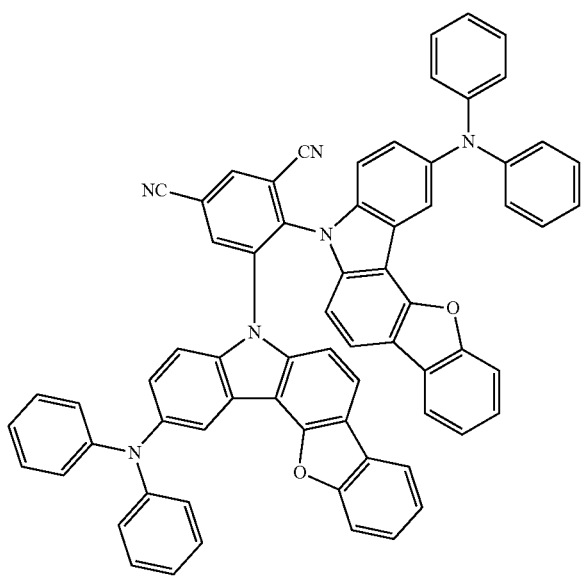
306
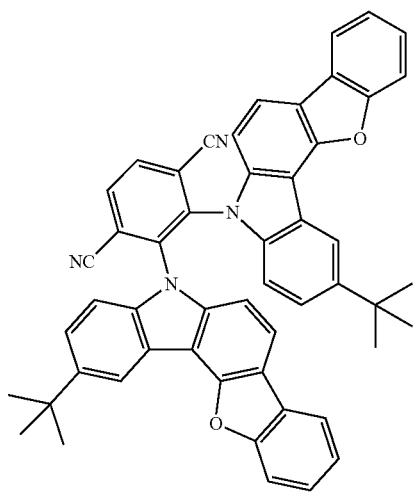
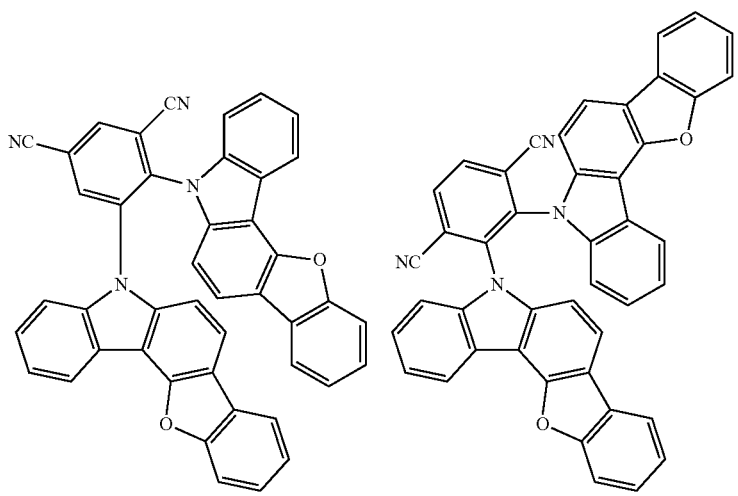
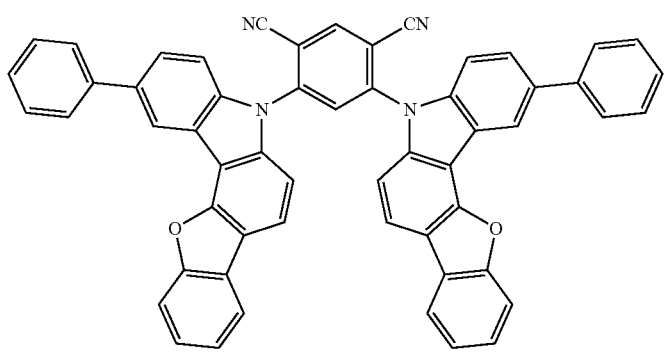

[Formula 149]
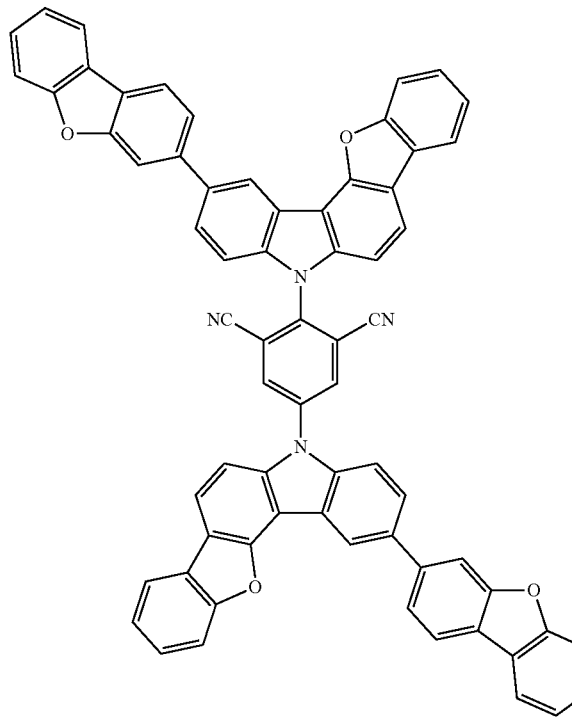
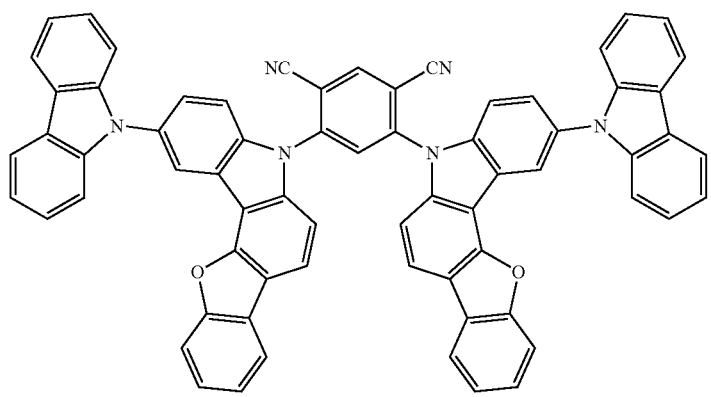
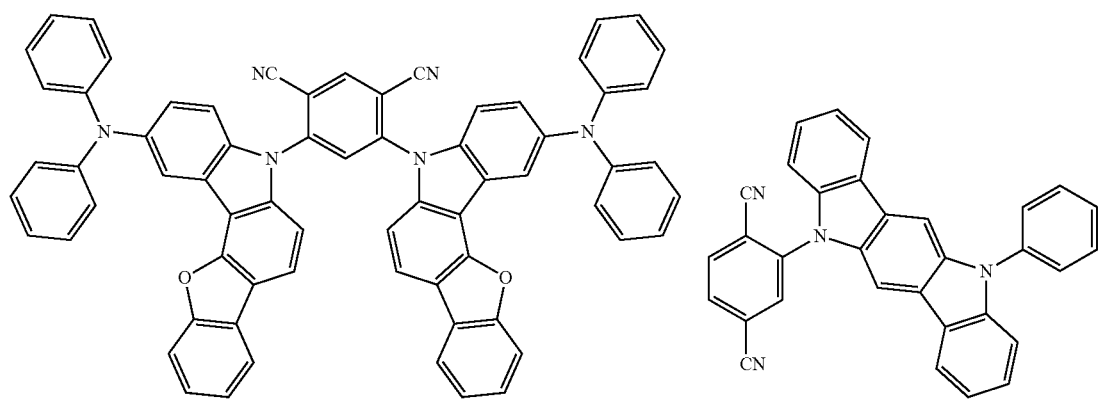

-continued
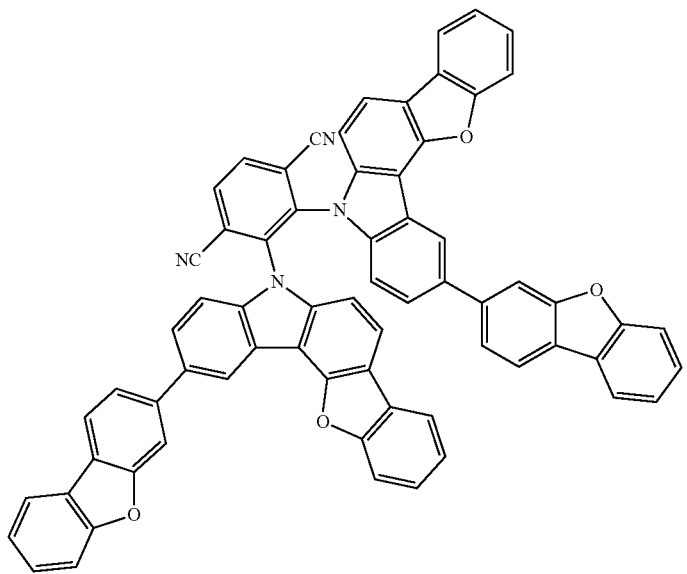
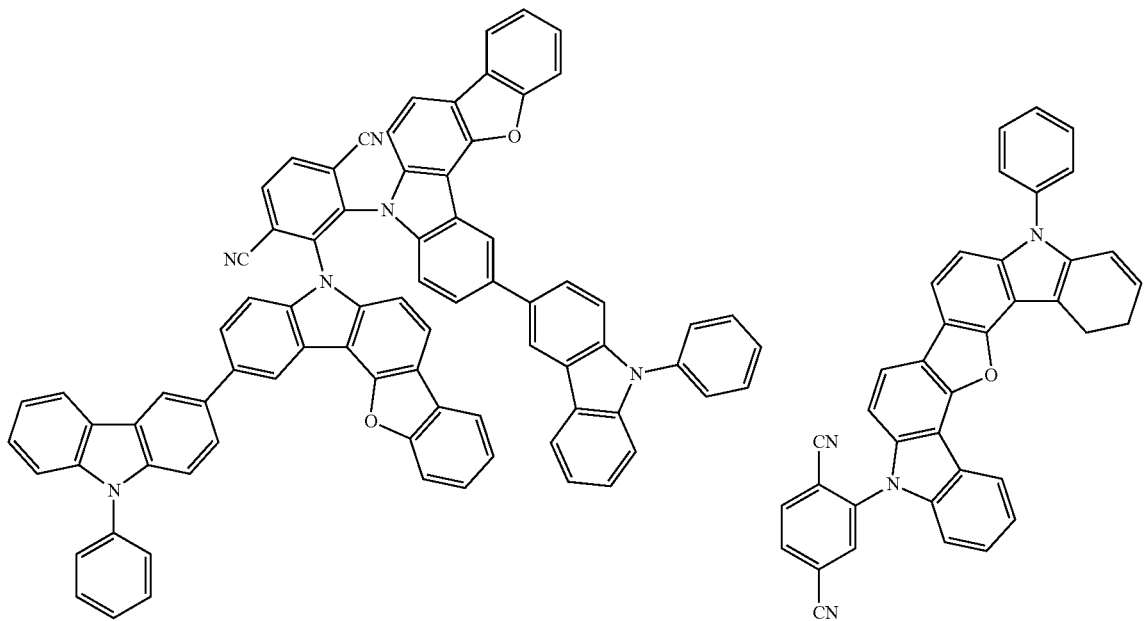
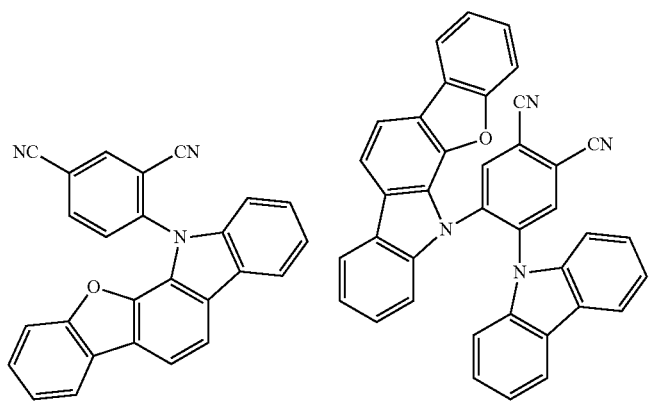

311    312
-continued
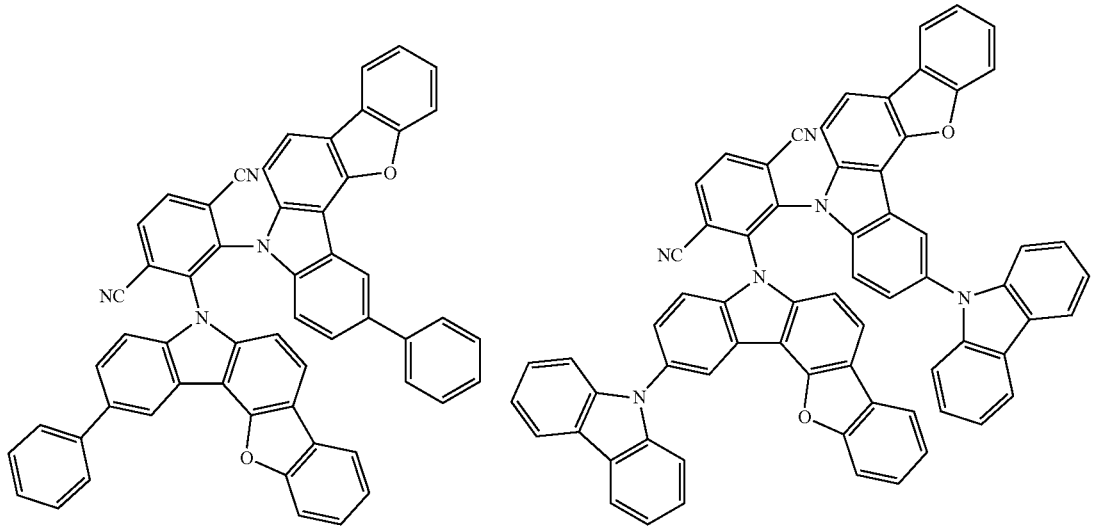
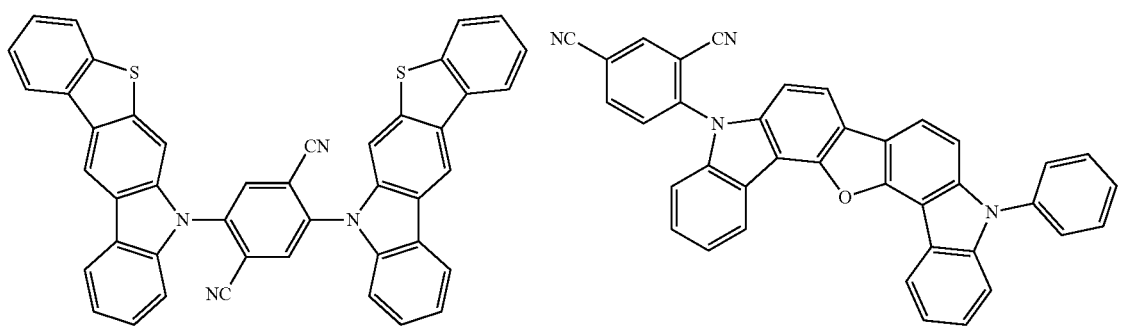
[Formula 150]
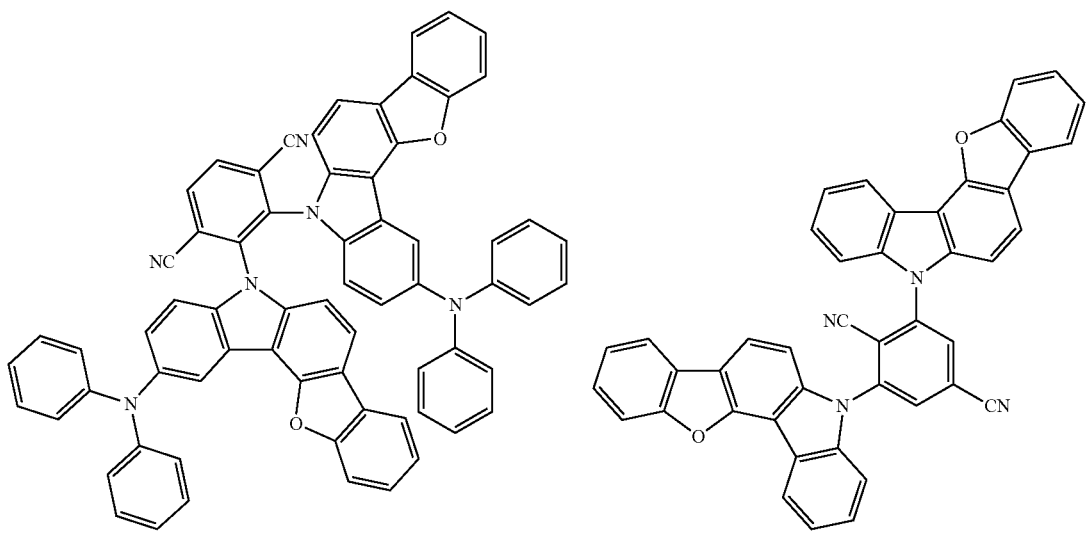

313
-continued
314
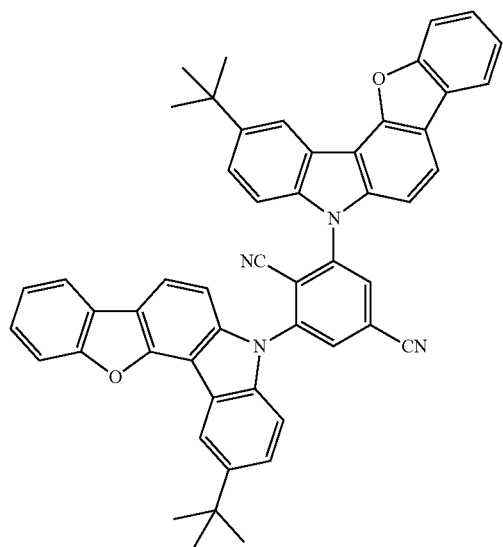
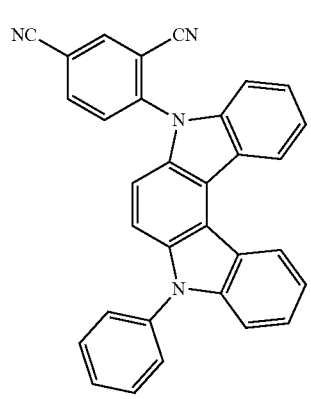
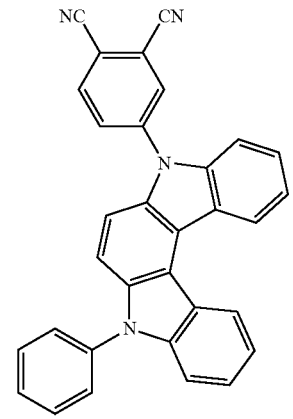
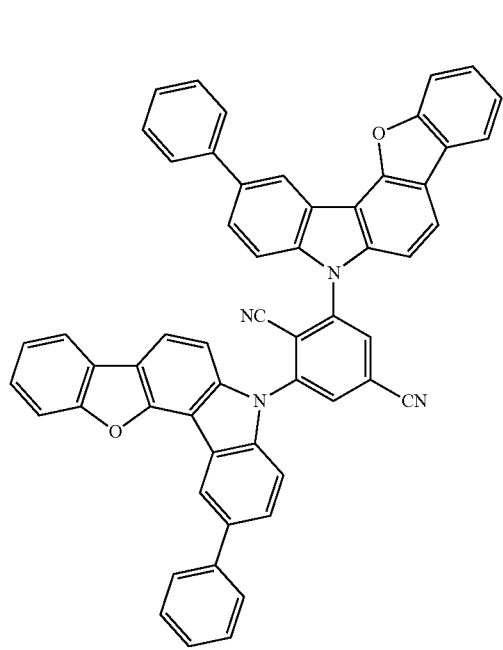
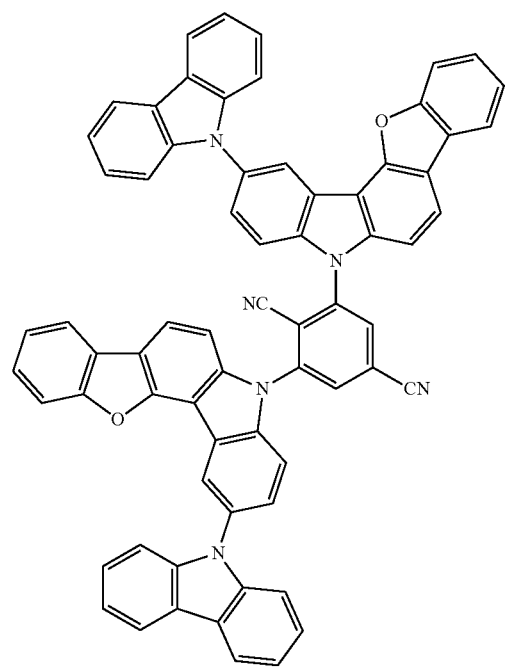

-continued
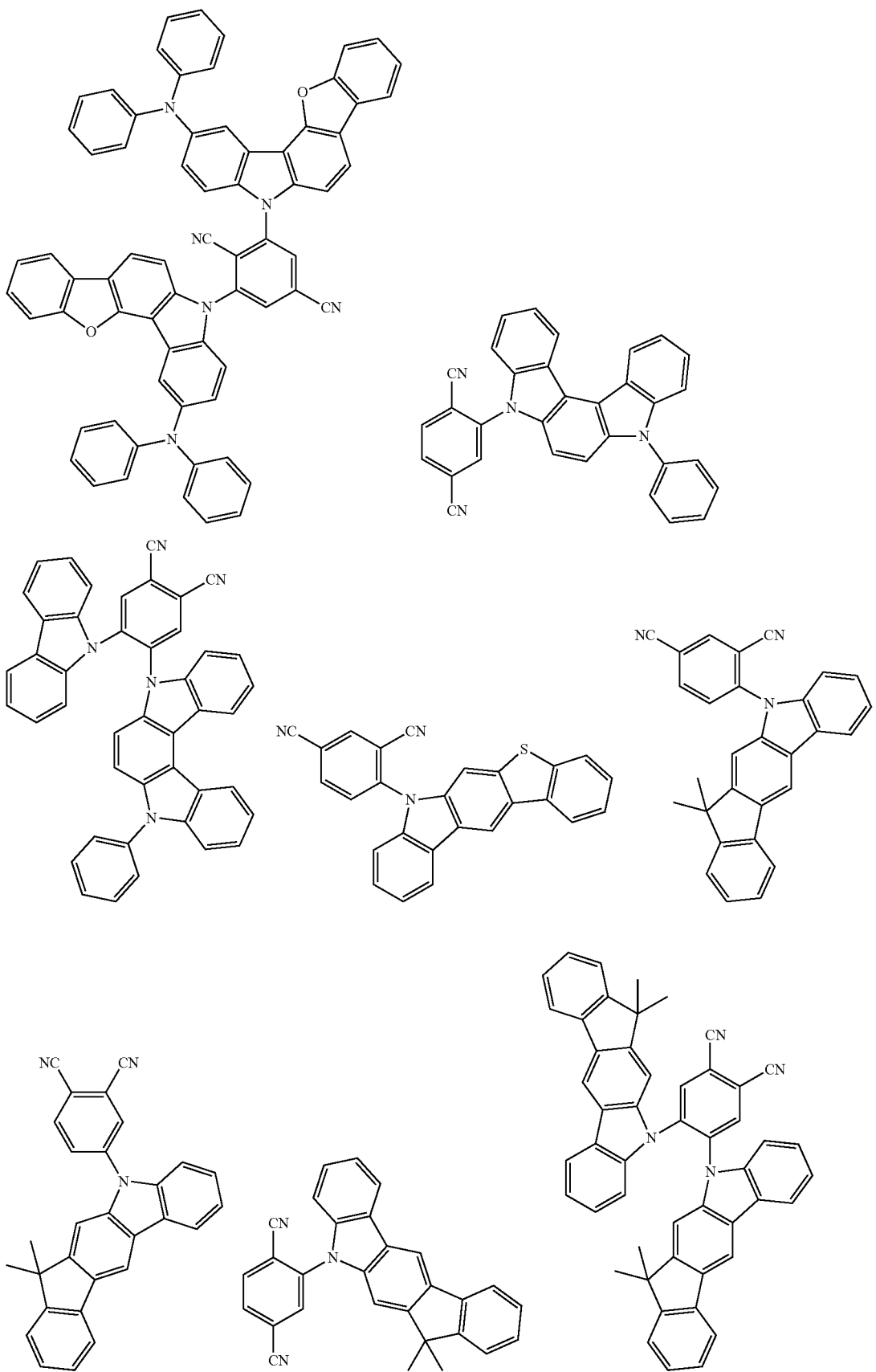

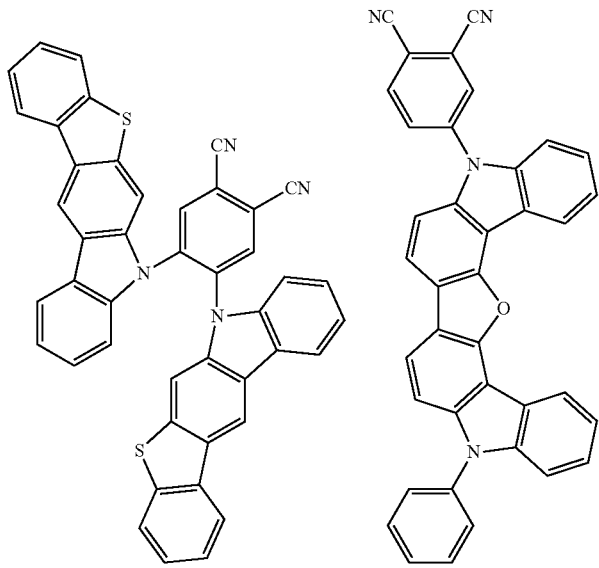
[Formula 151]
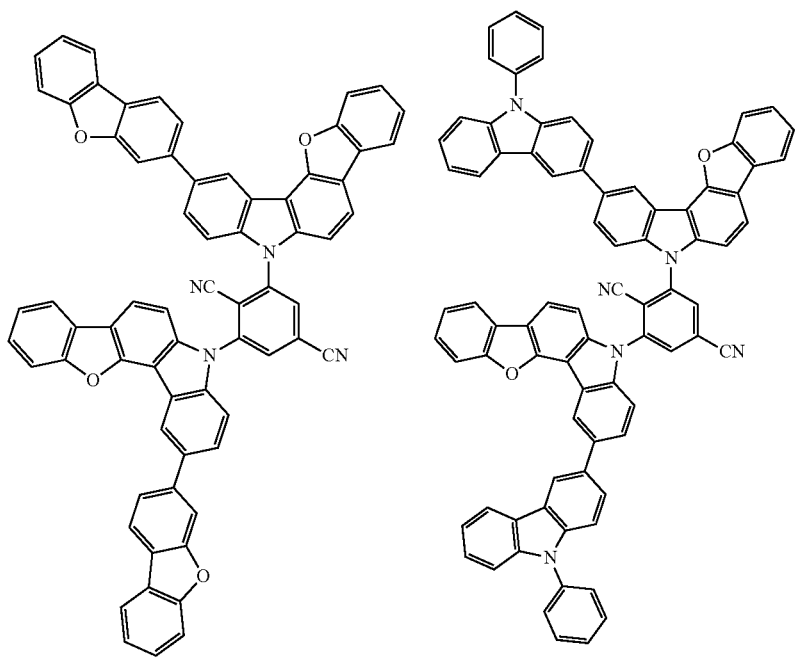

319 320
-continued
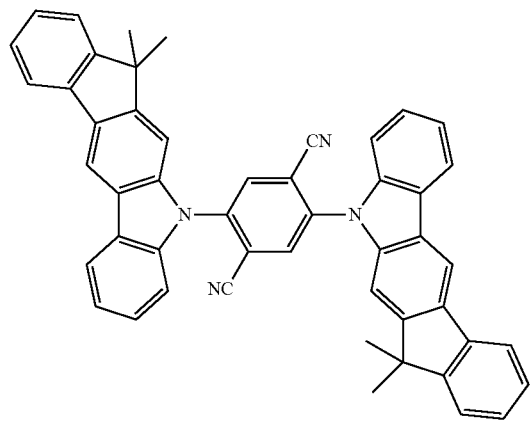
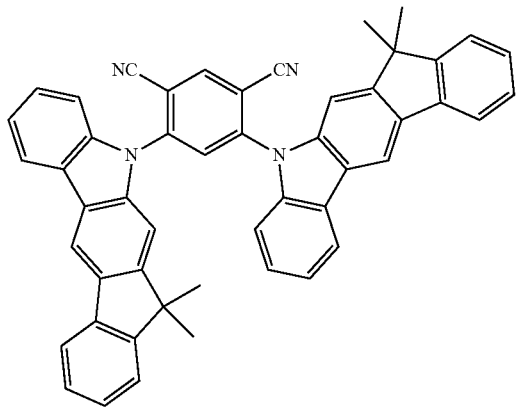
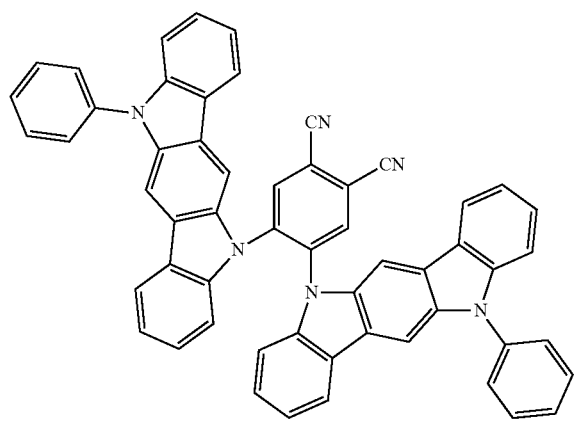
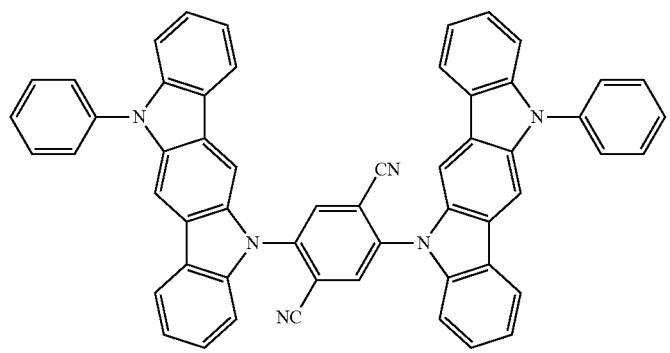
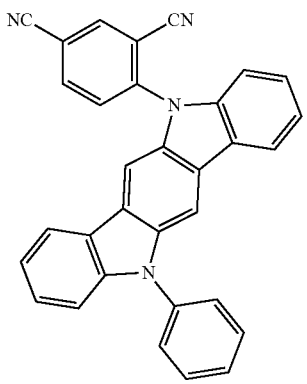
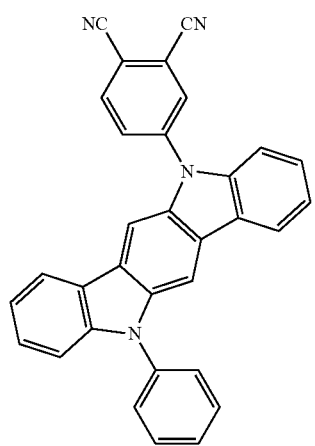
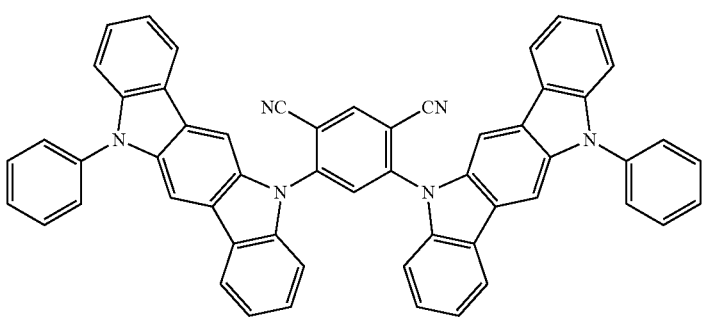

-continued
321
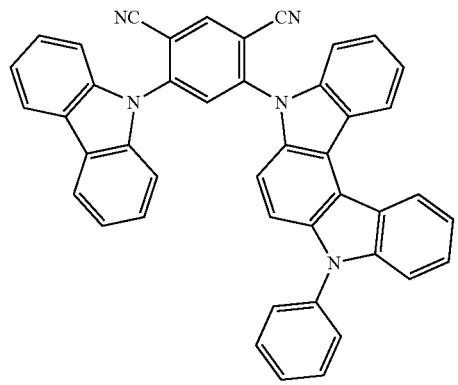
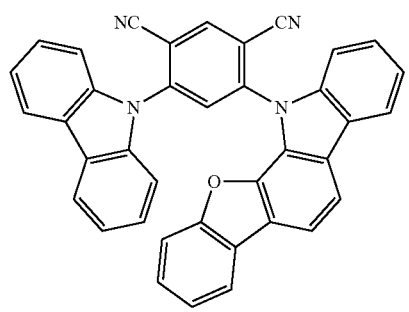
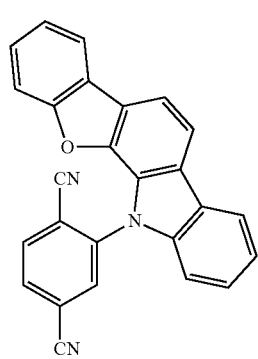
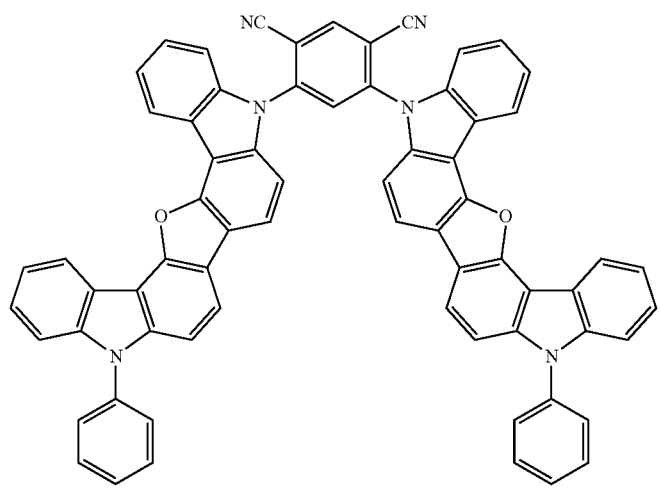
322
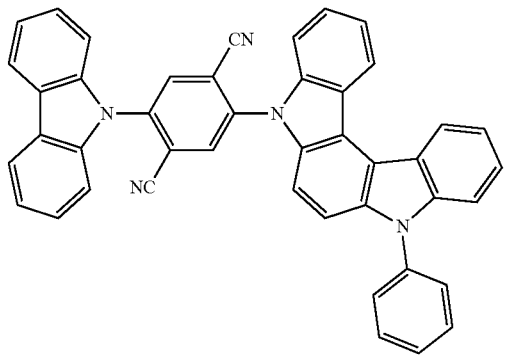
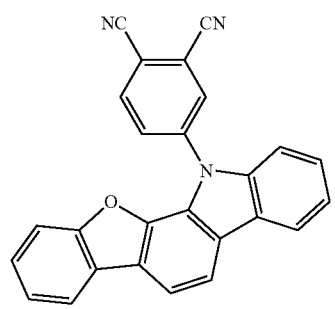
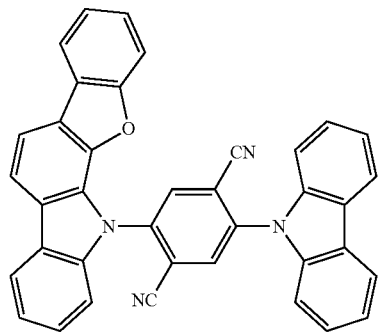

[Formula 152]
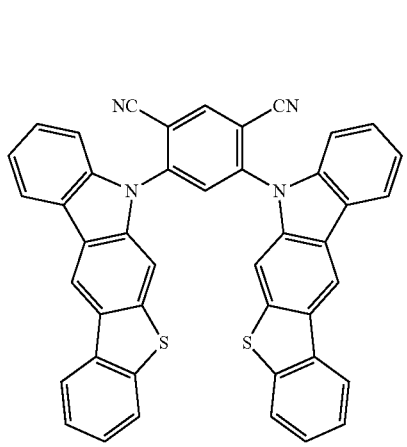
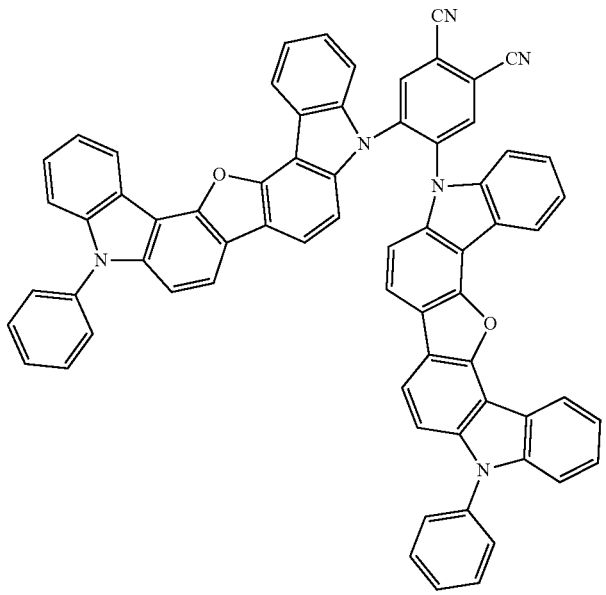
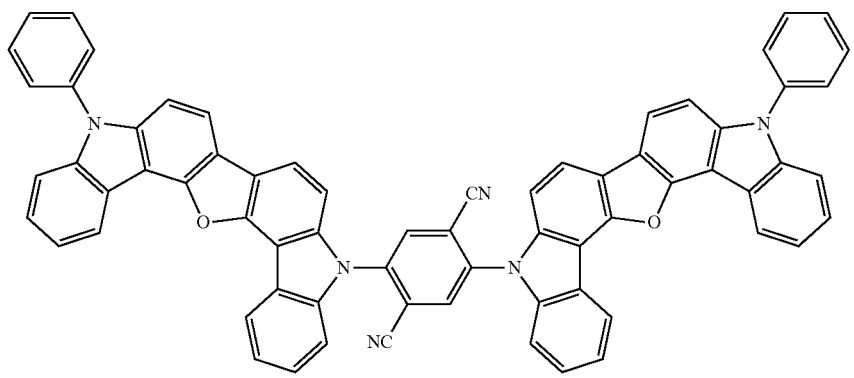
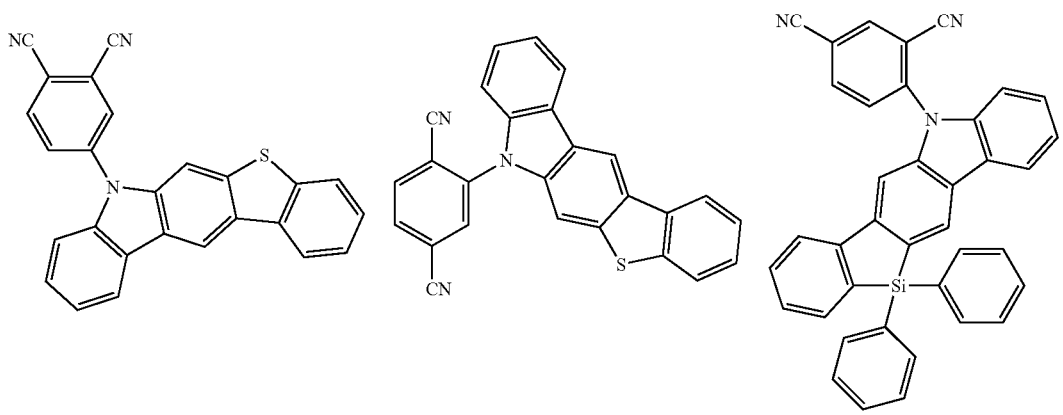

-continued
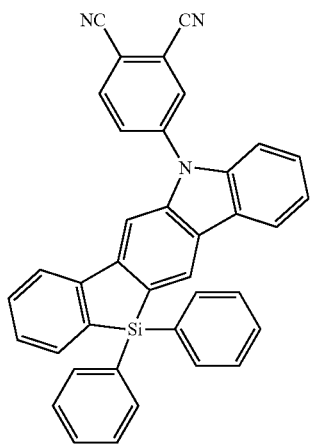
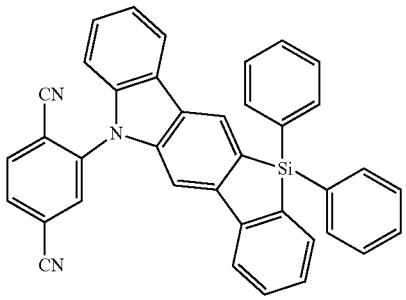
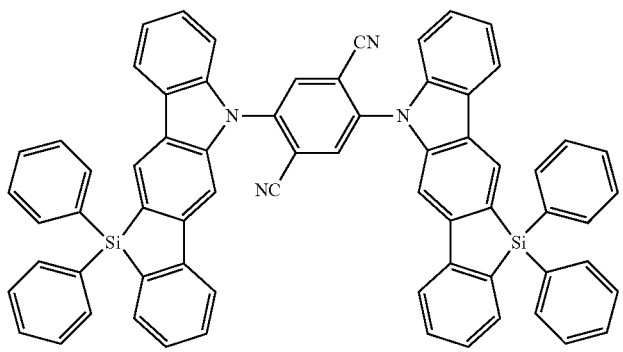
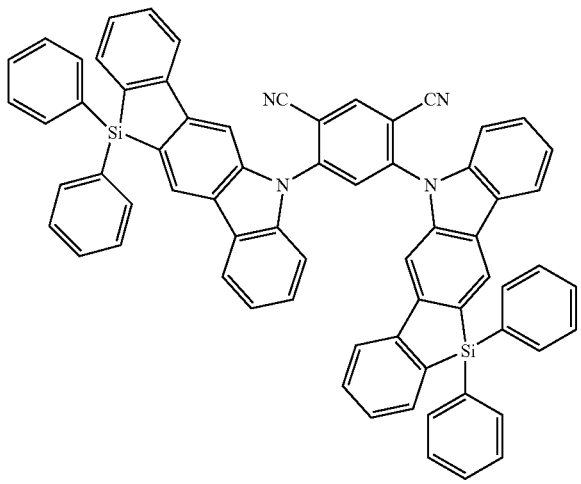
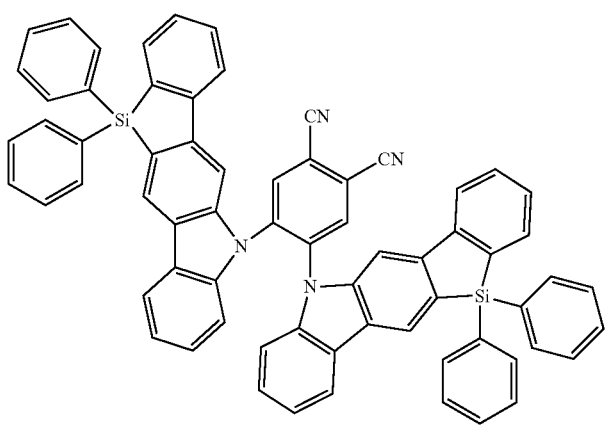

-continued
[Formula 153]
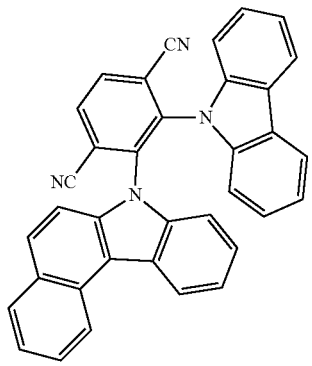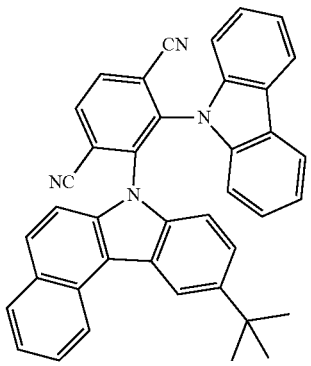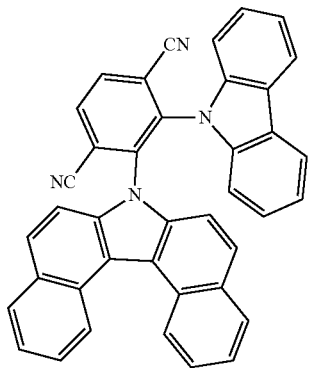
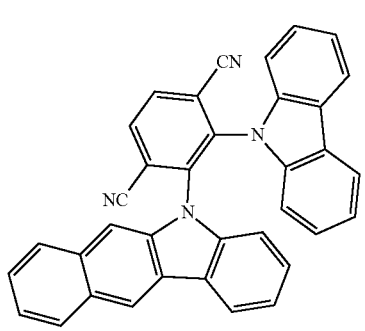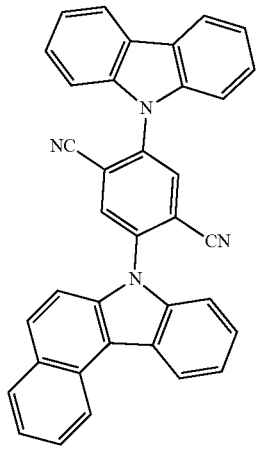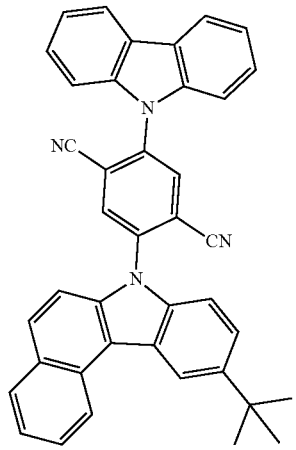
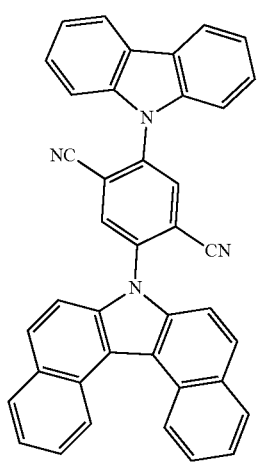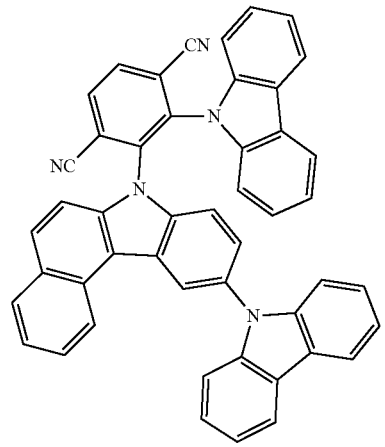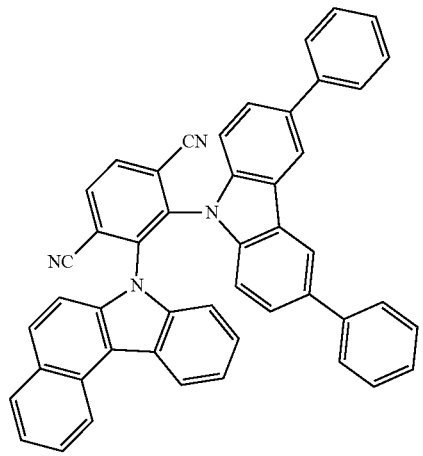

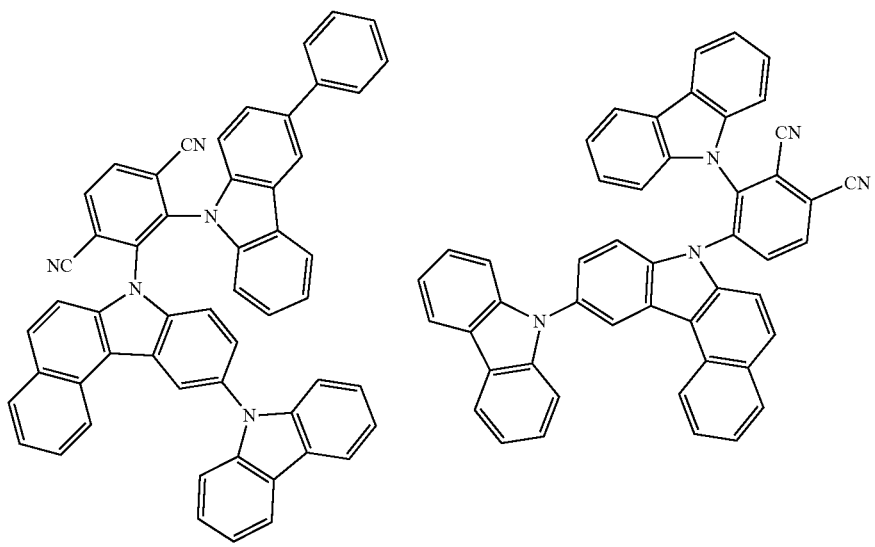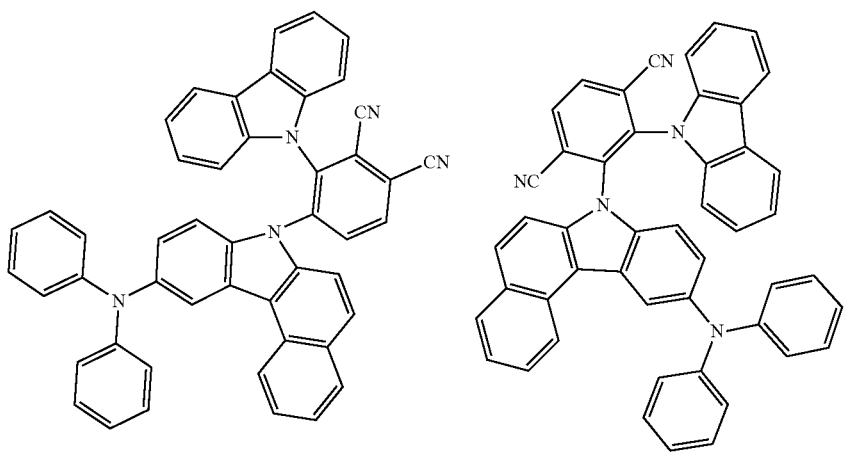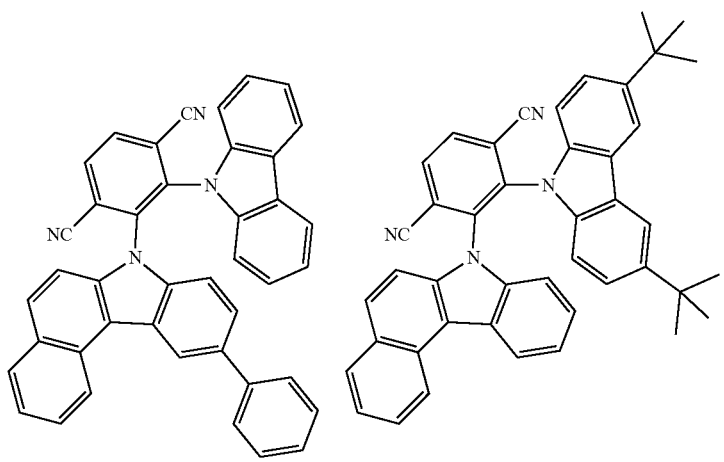

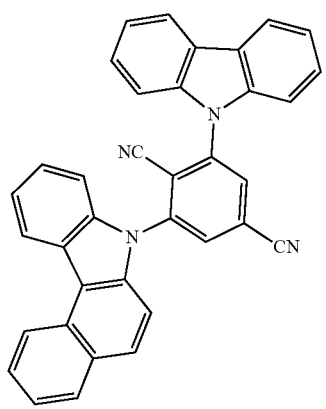
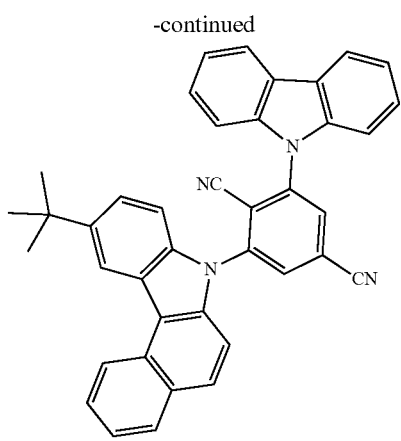
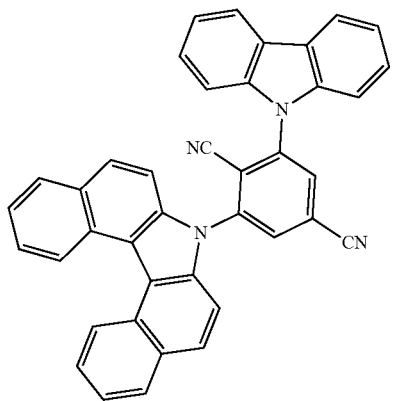
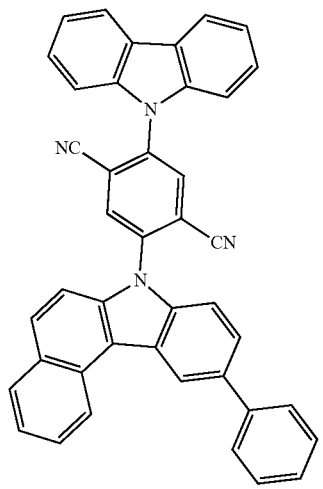
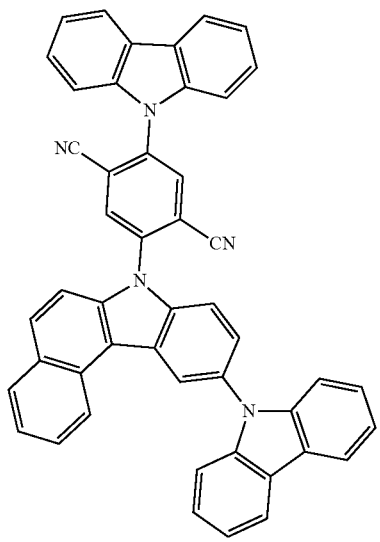
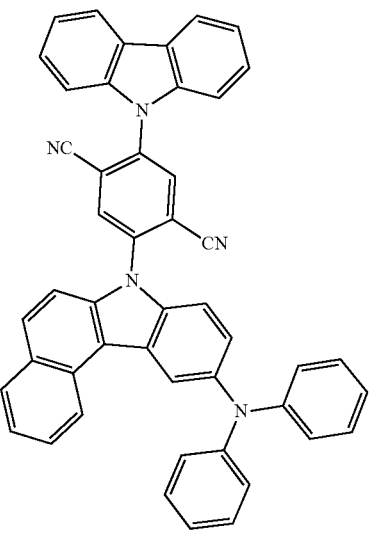

[Formula 154]
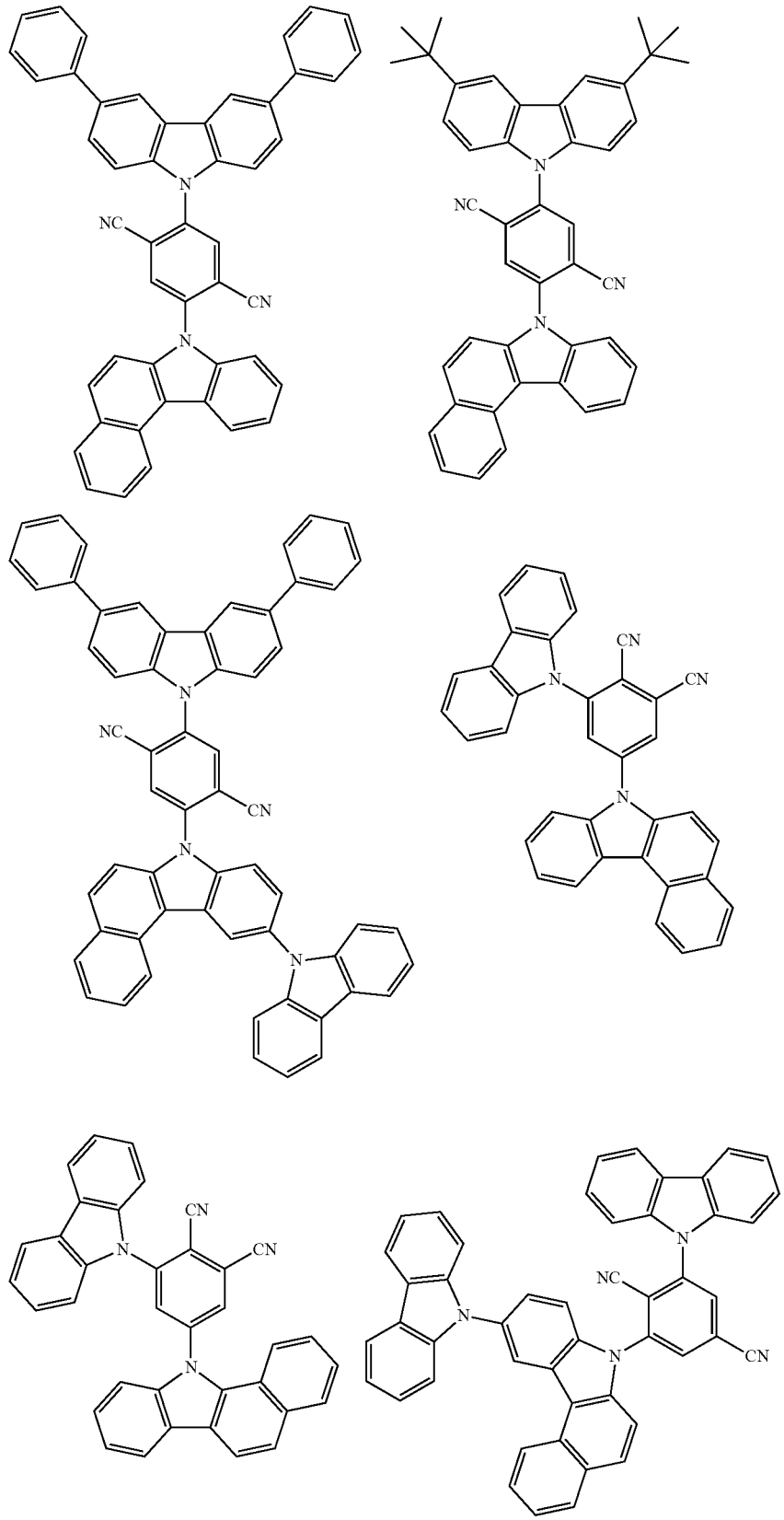

335
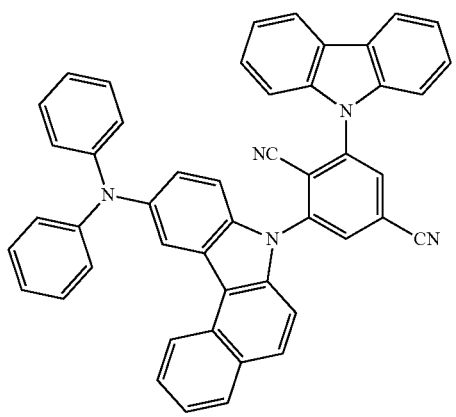
336
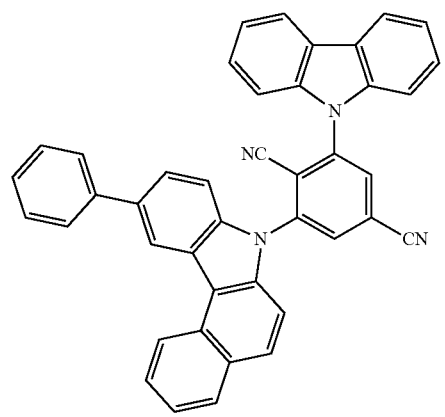
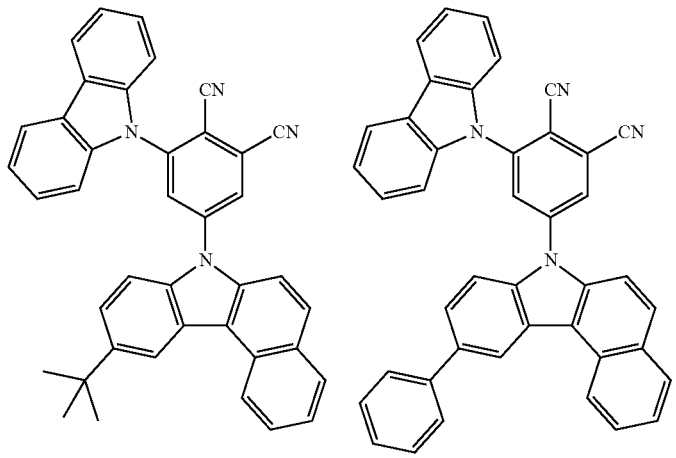
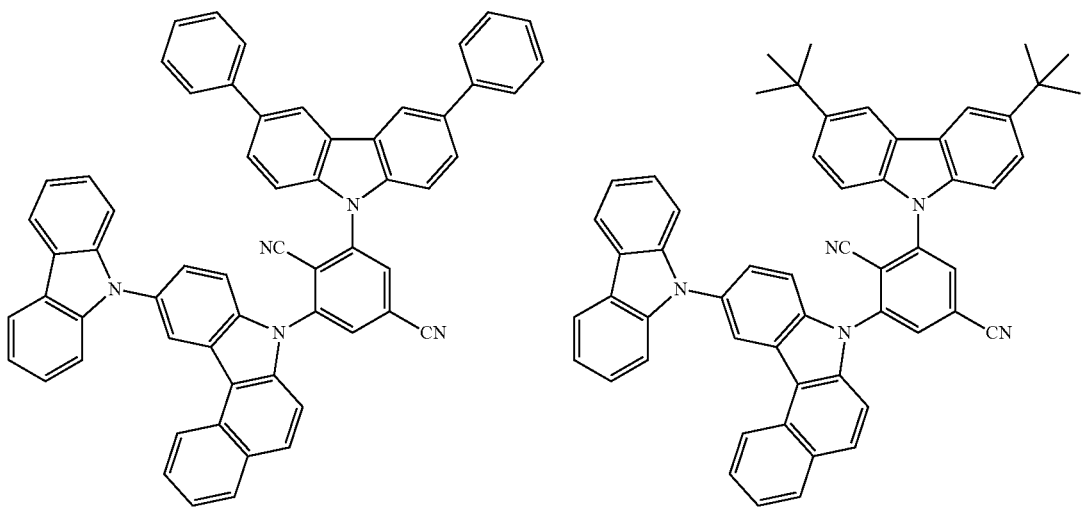

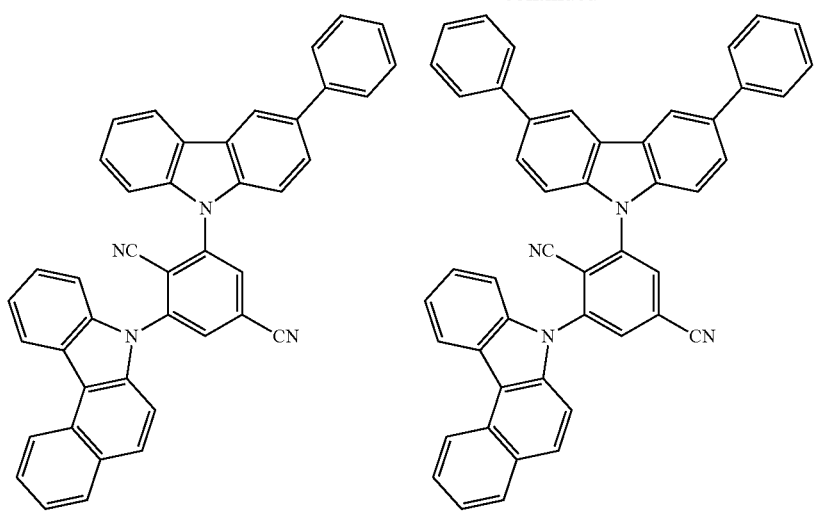
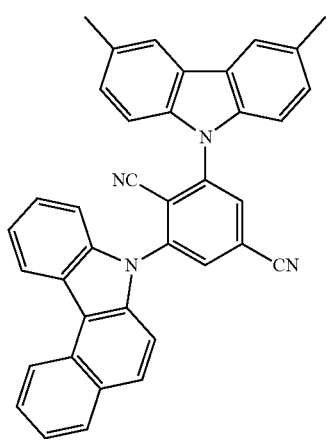
[Formula 155]
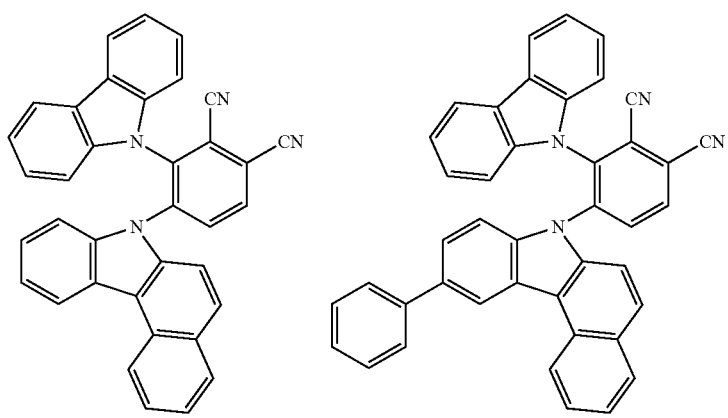

-continued
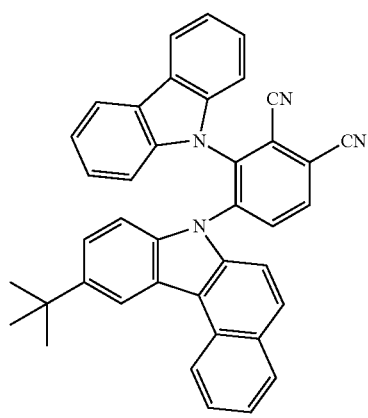
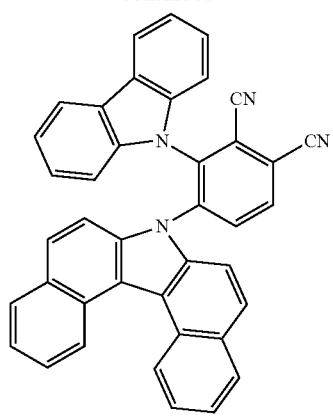
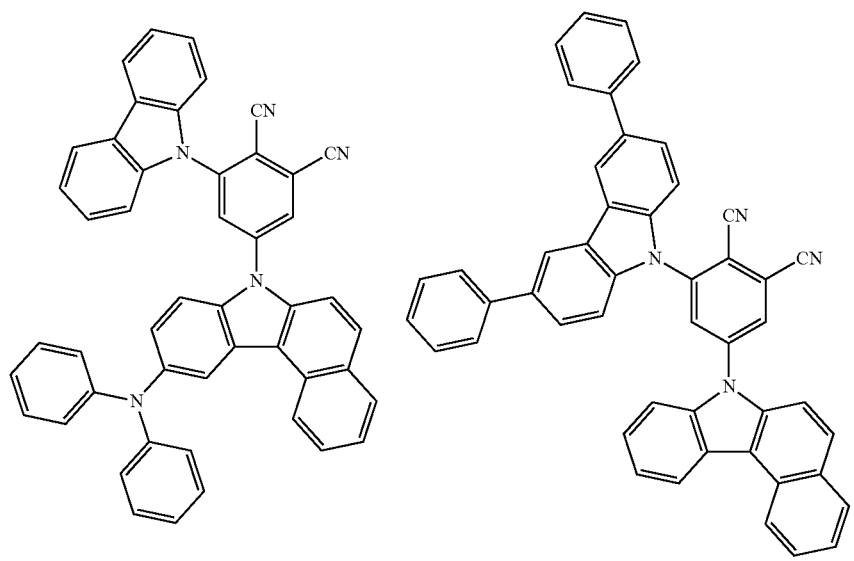
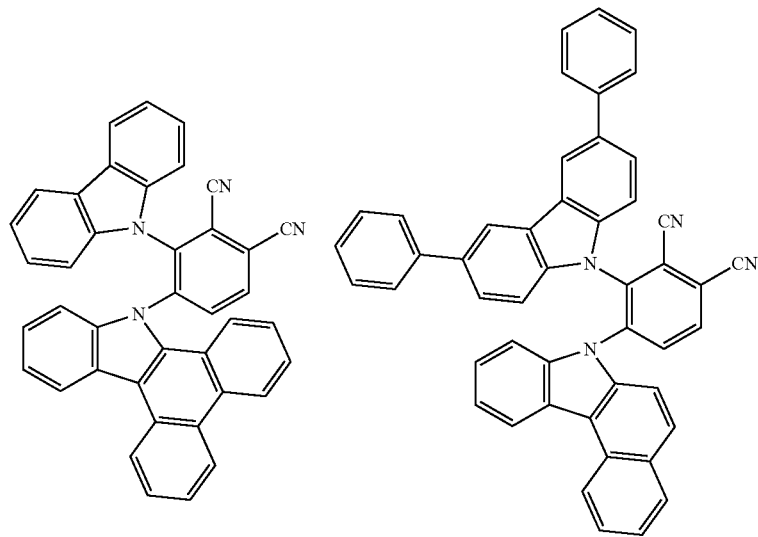

-continued
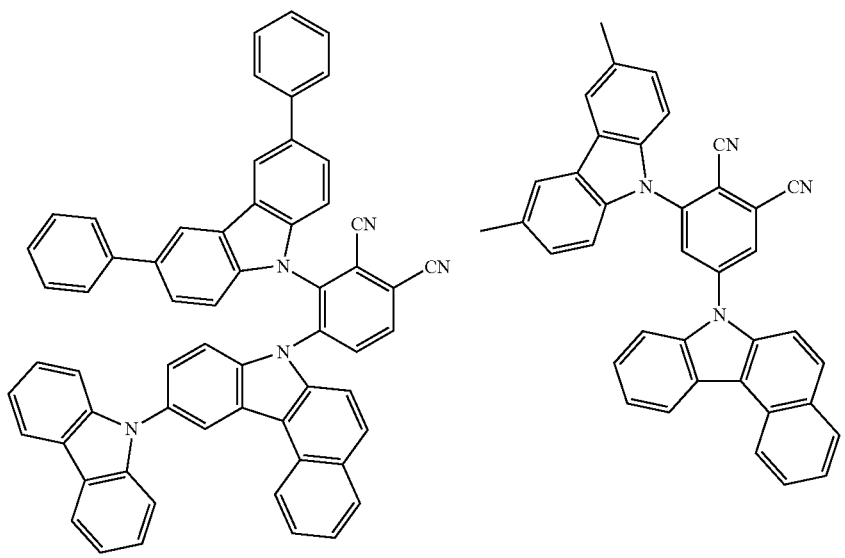
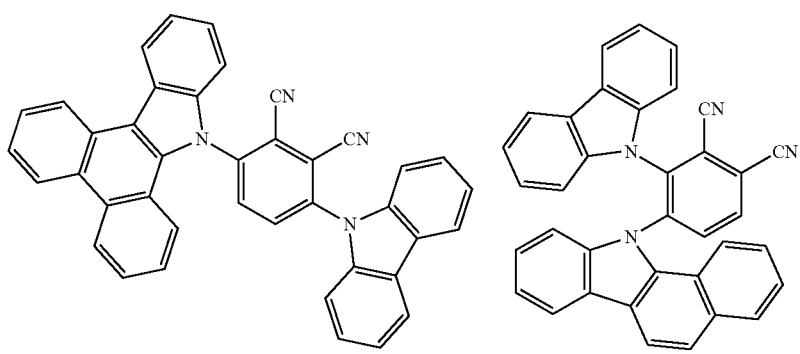
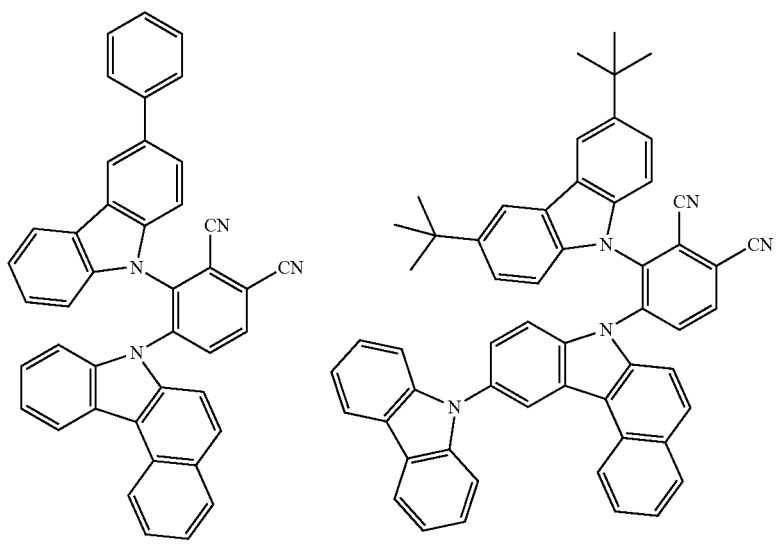

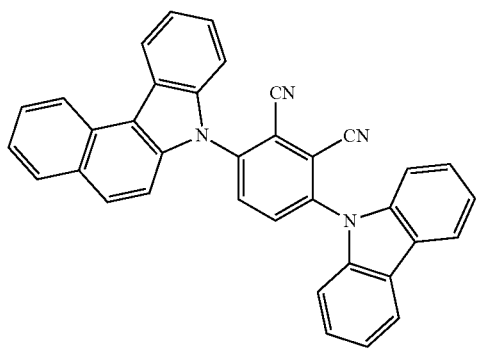
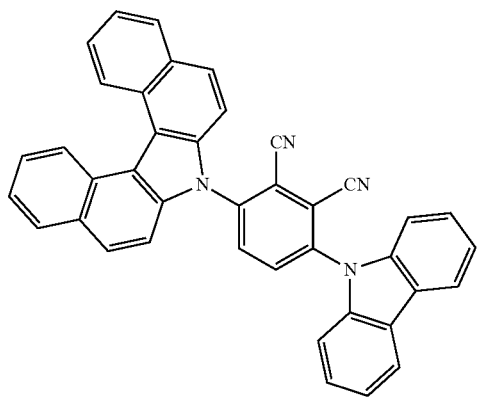
[Formula 156]
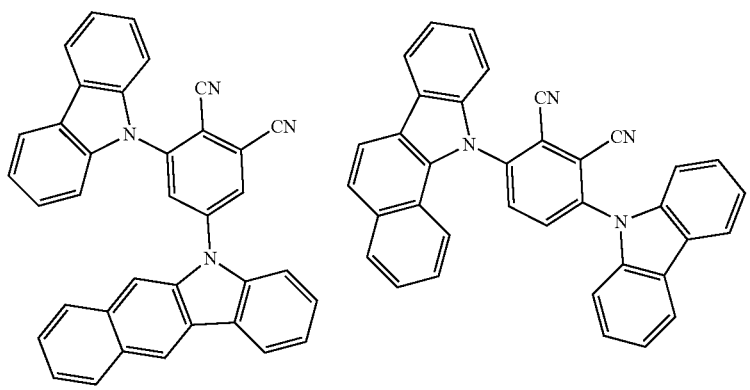
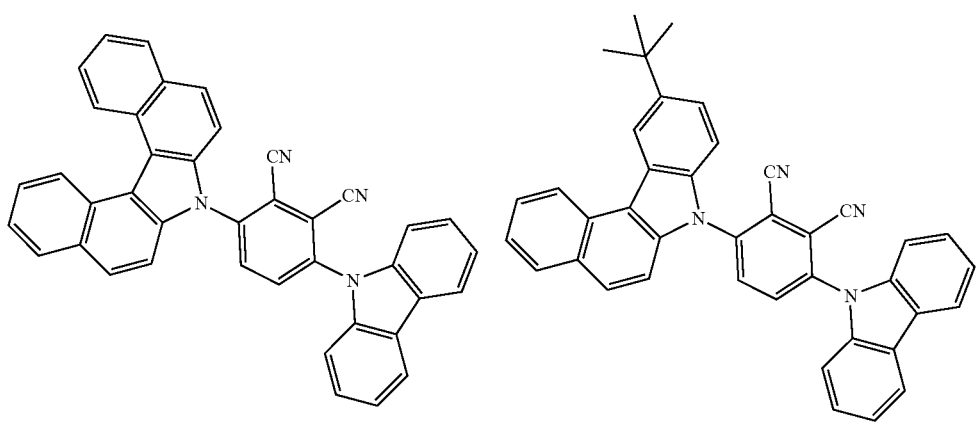

-continued
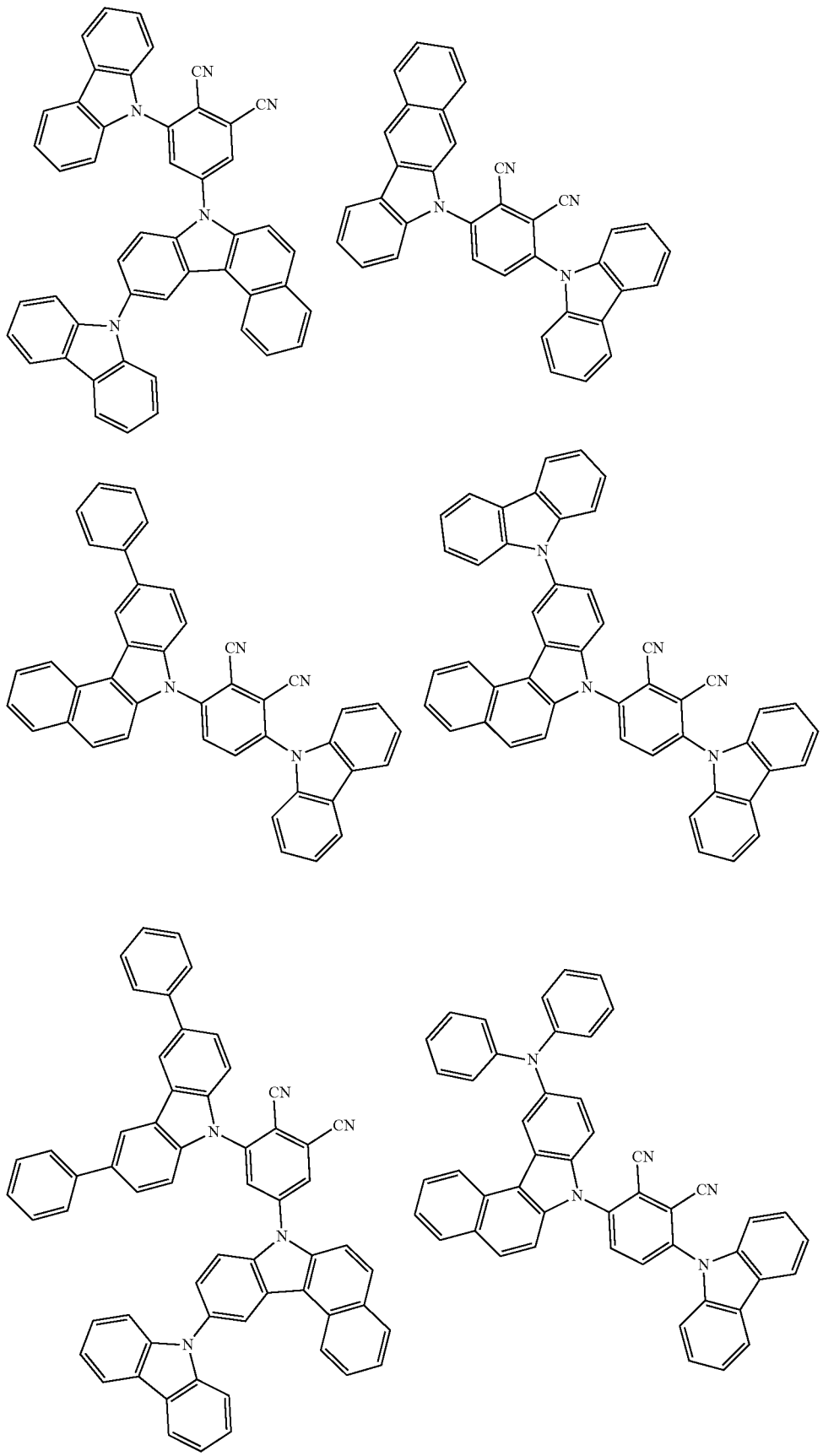

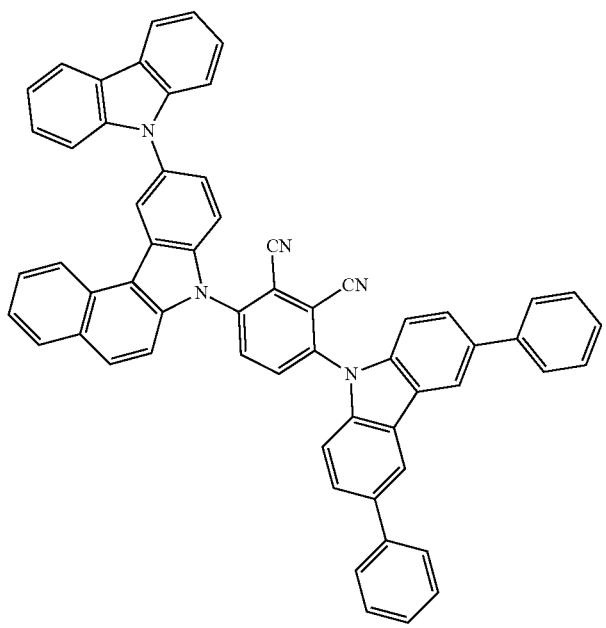
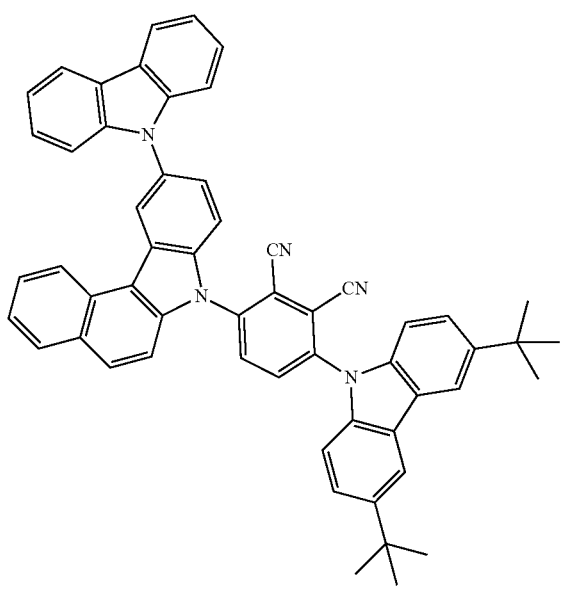
[Formula 157]
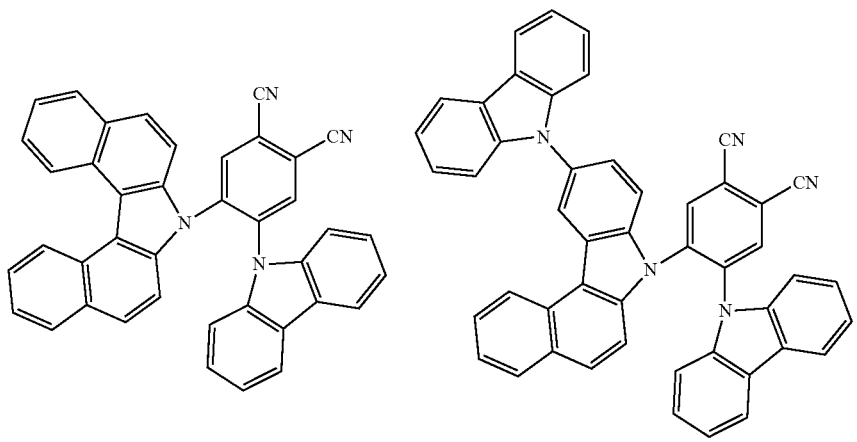

-continued
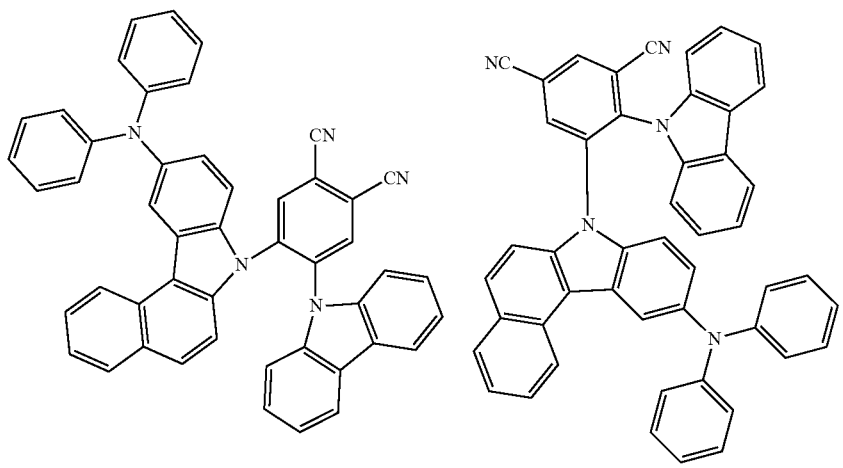
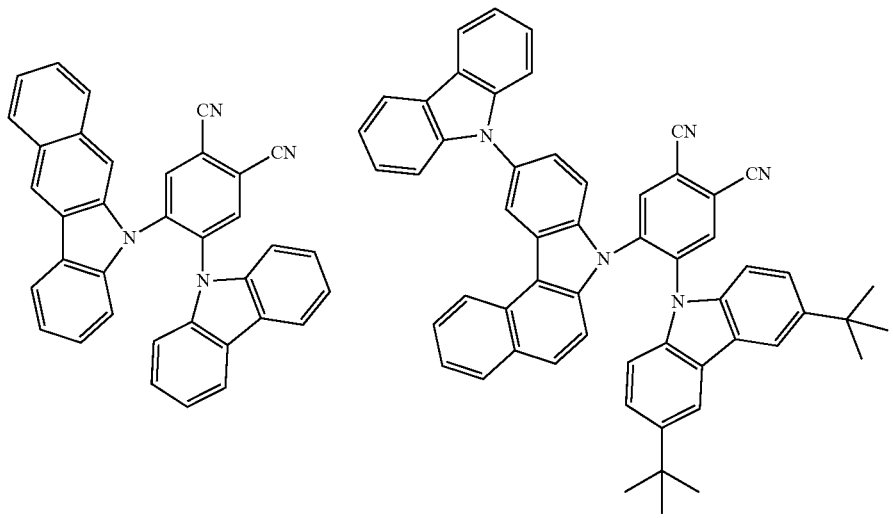
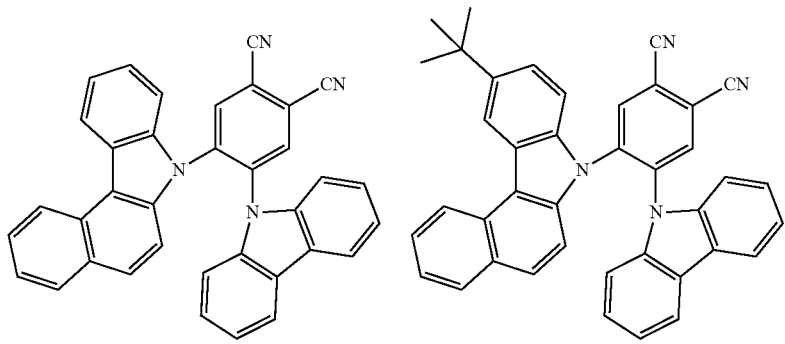
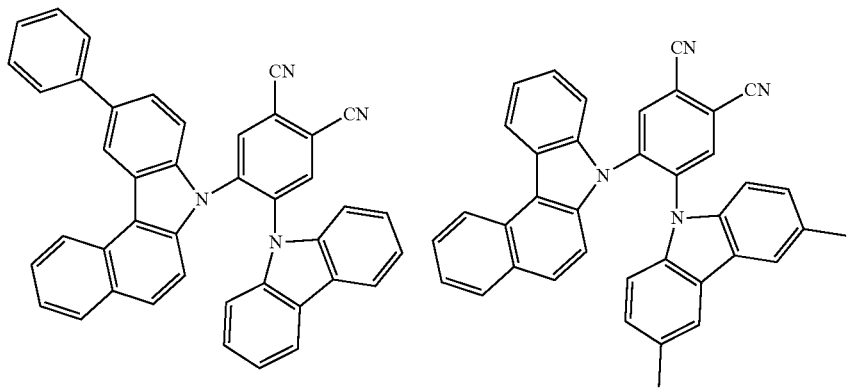

351 352
-continued
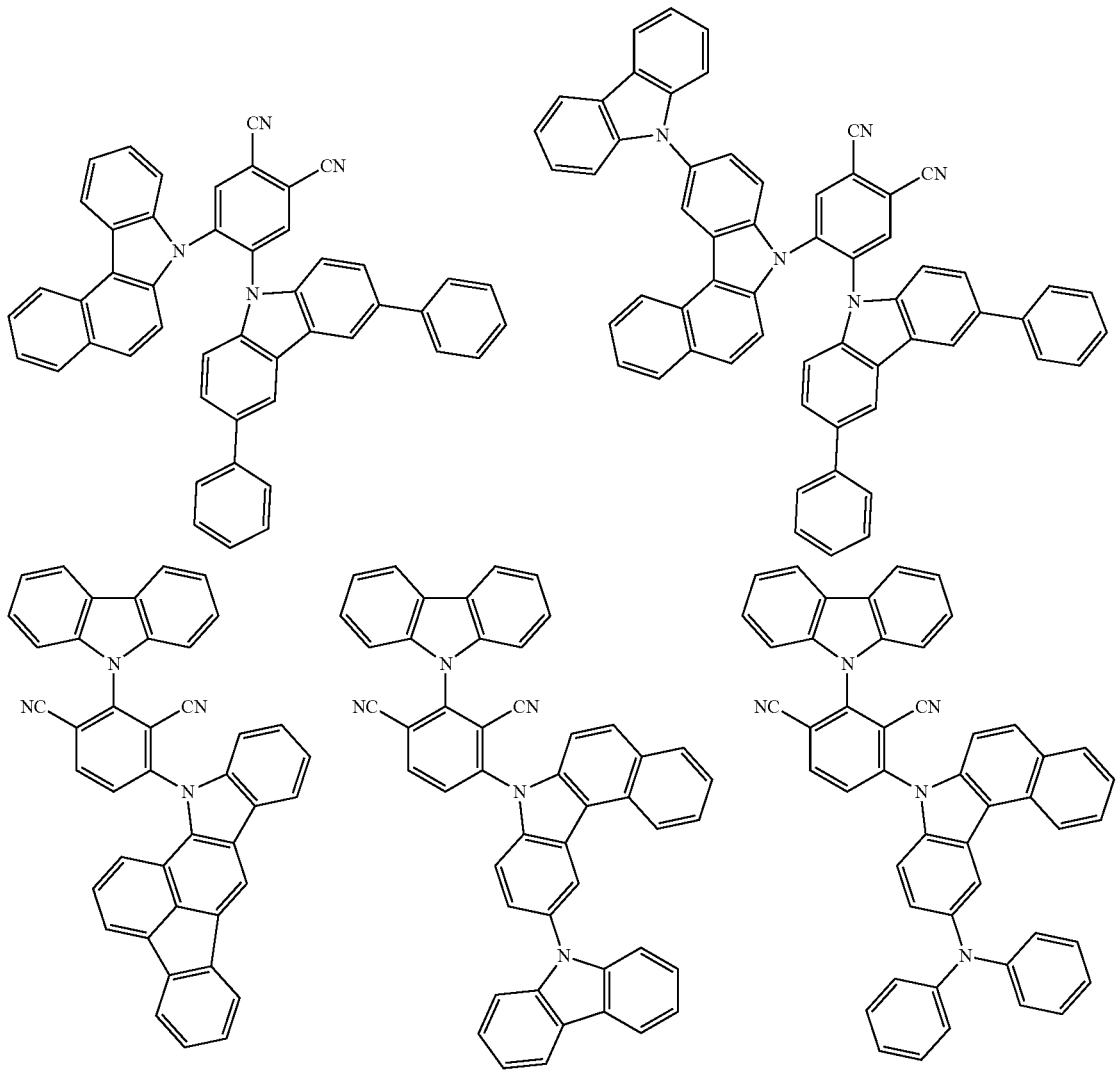
[Formula 158]
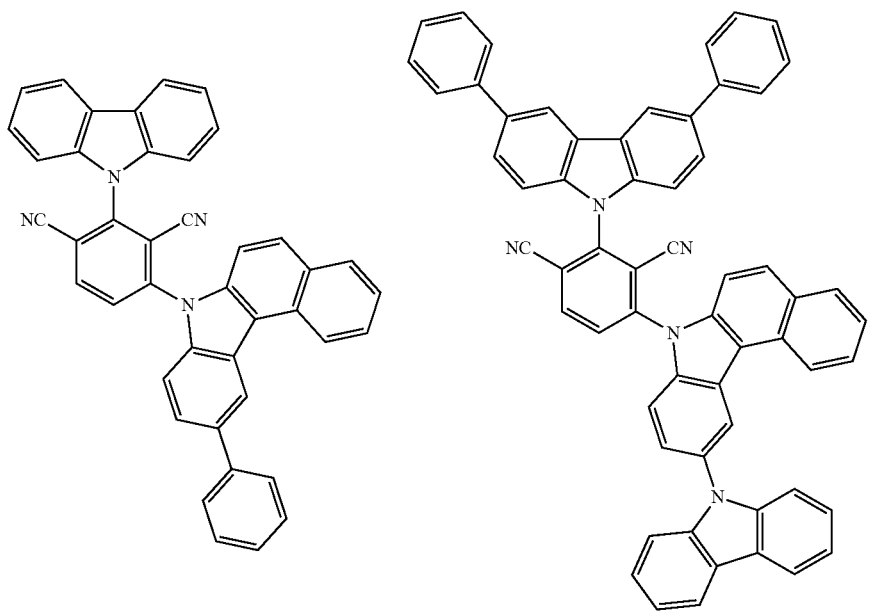

-continued
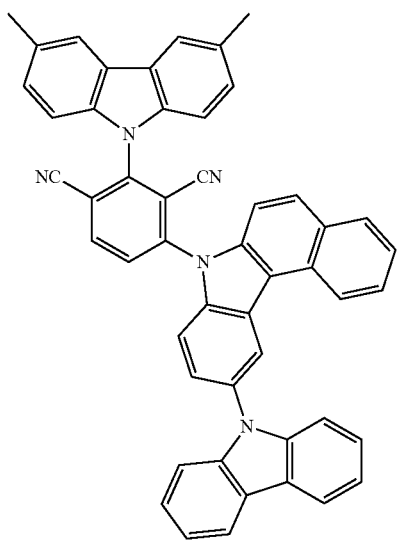
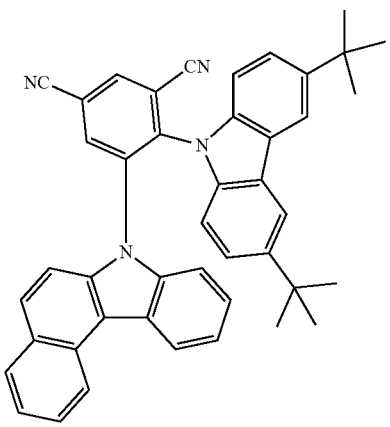
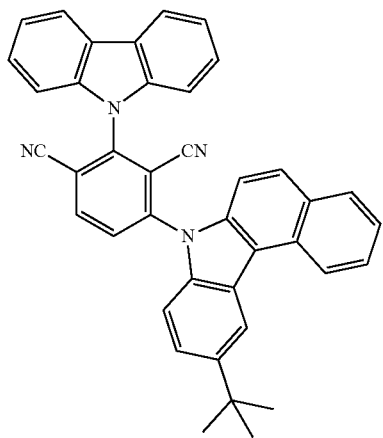
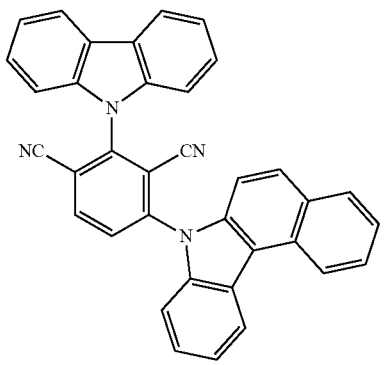
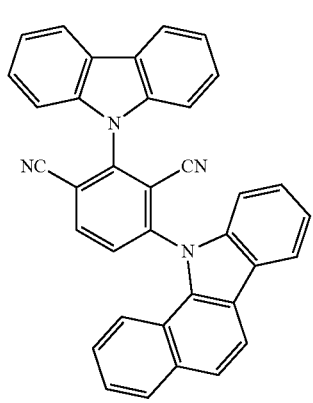
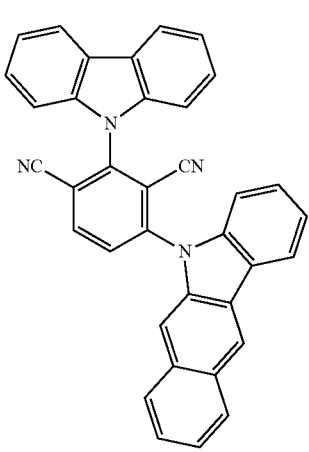
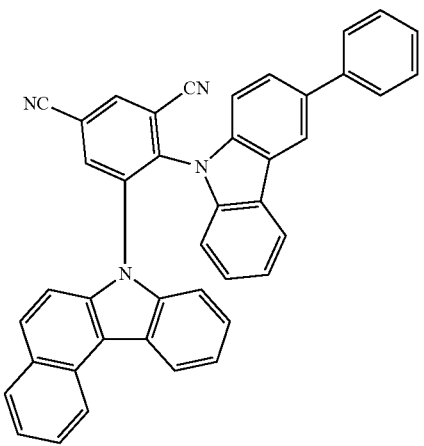

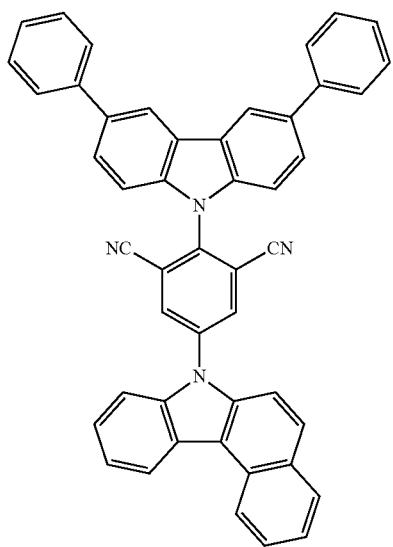
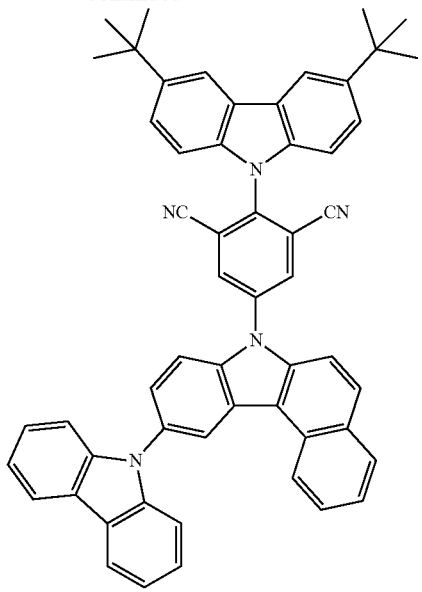
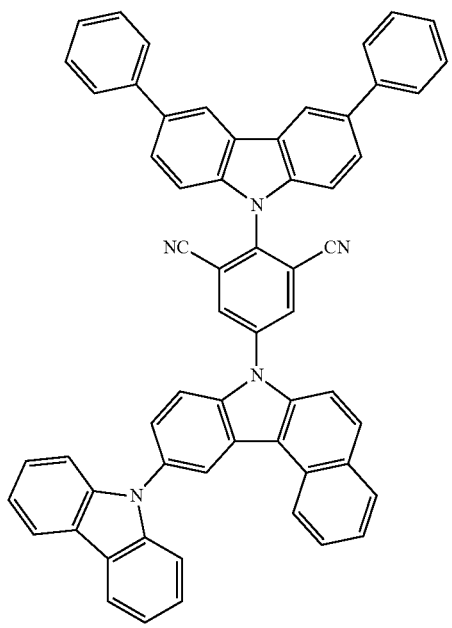
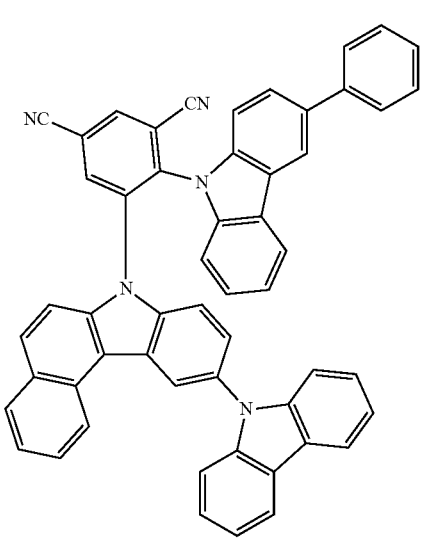
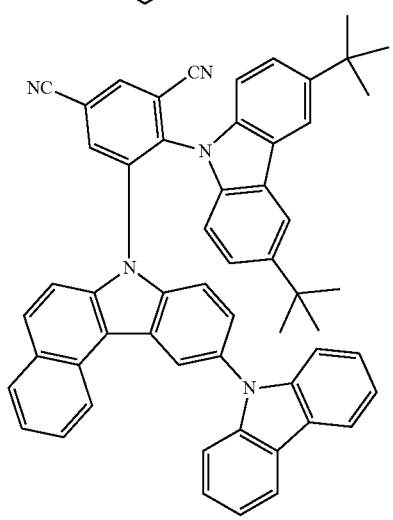

[Formula 159]
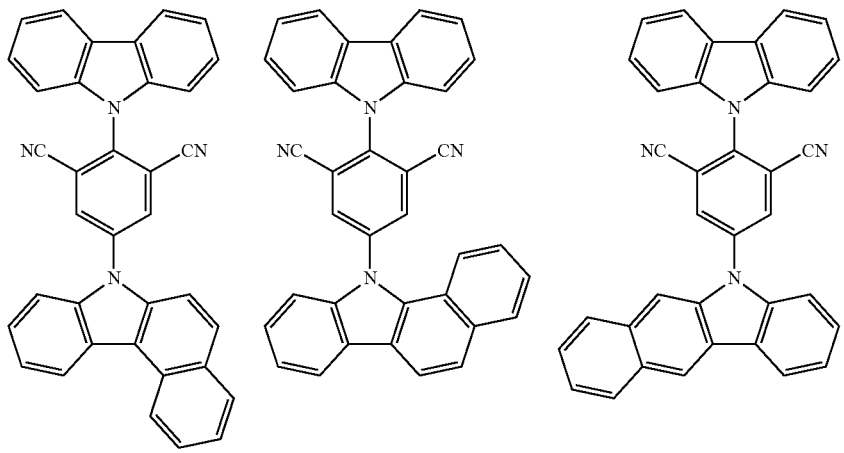
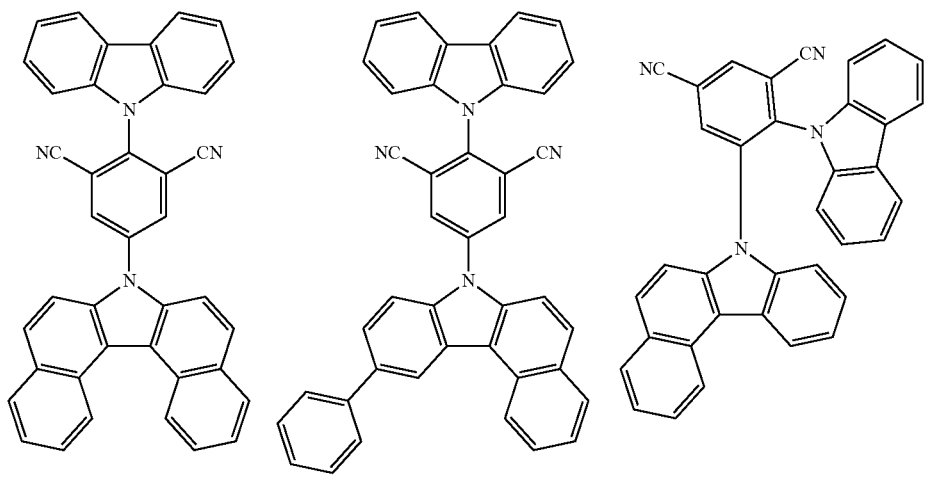
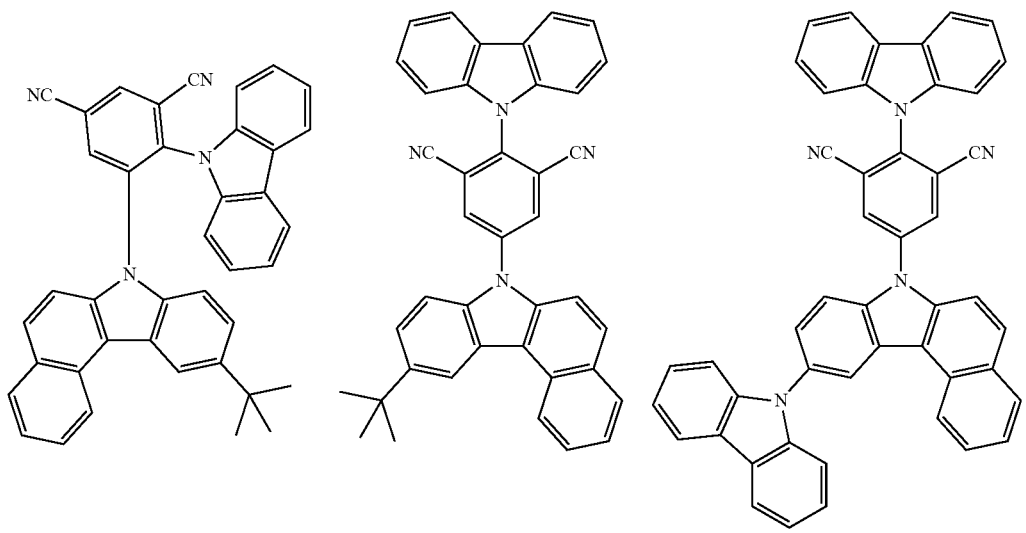

-continued
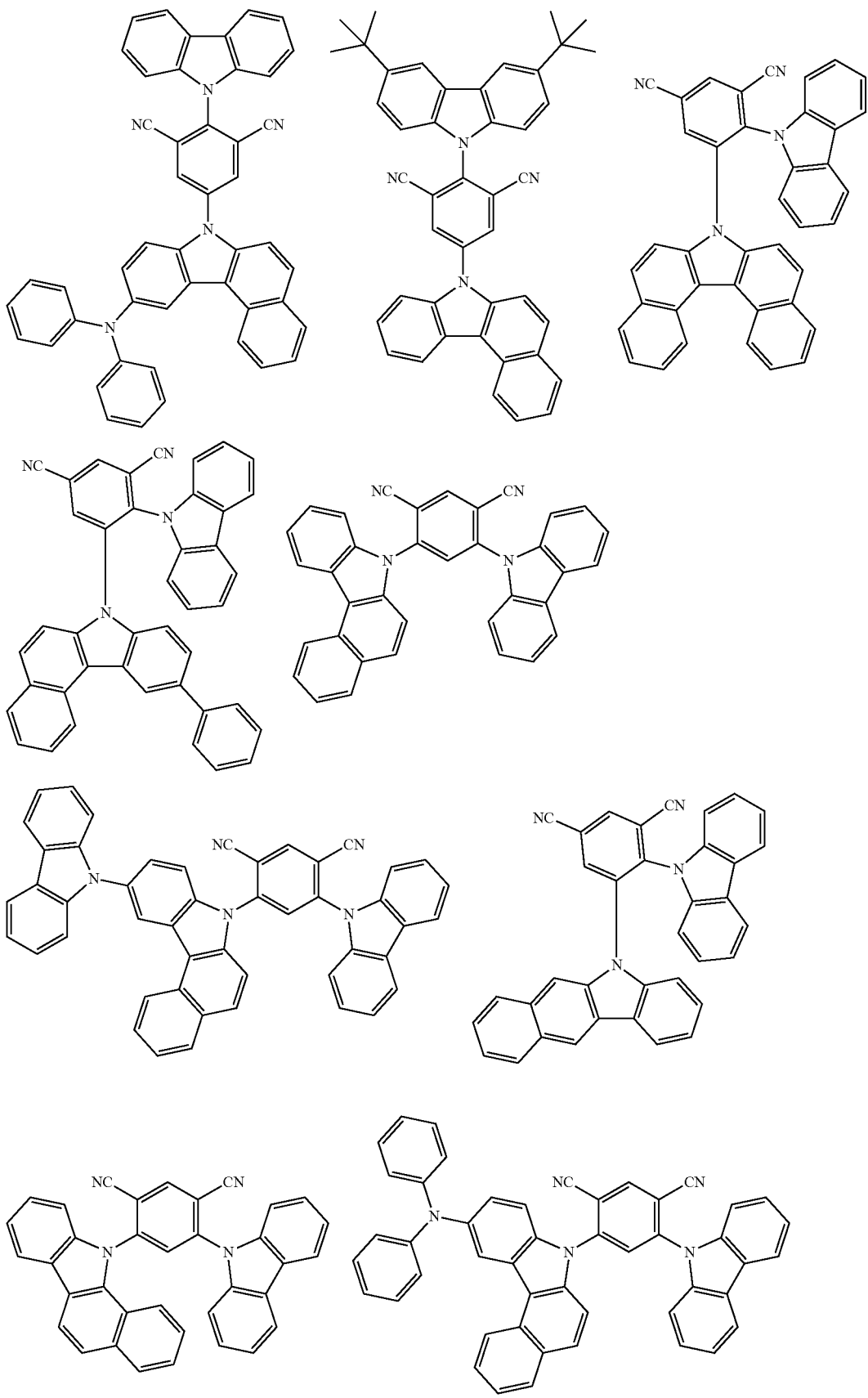

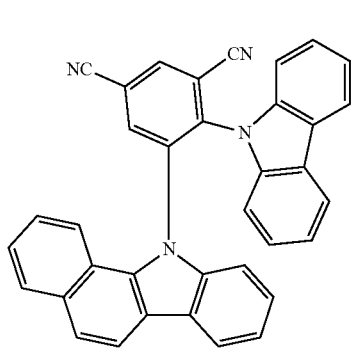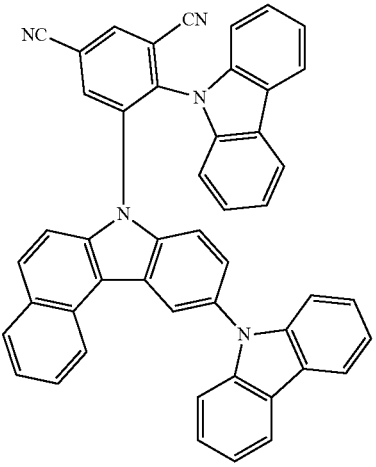
[Formula 160]
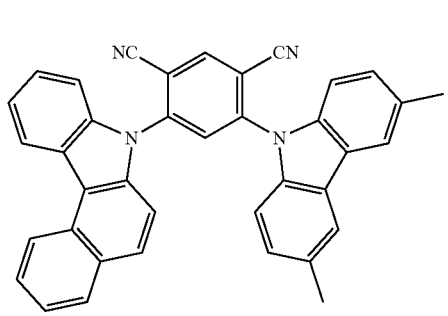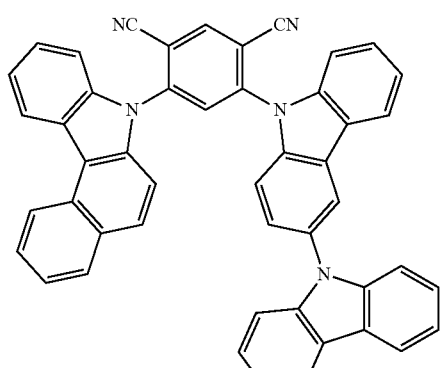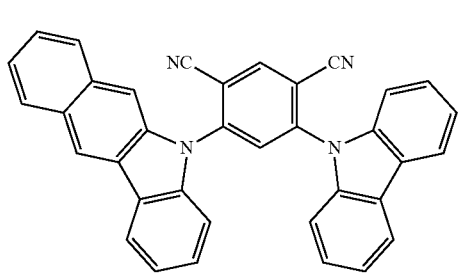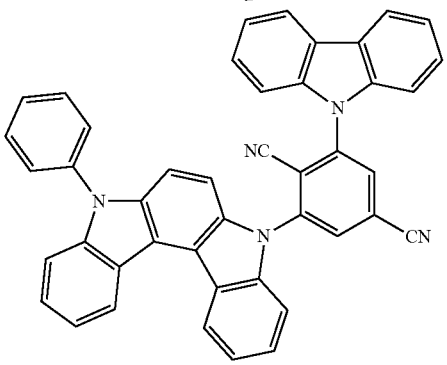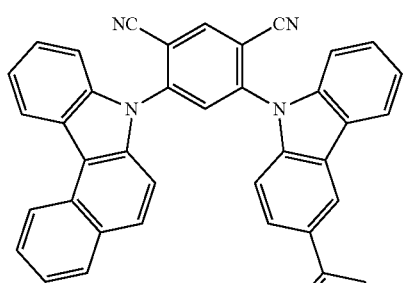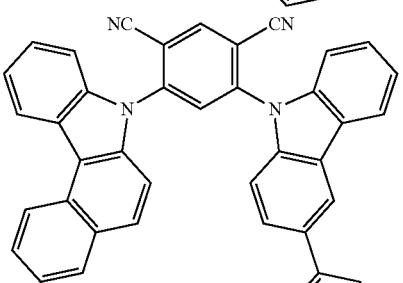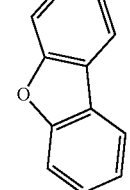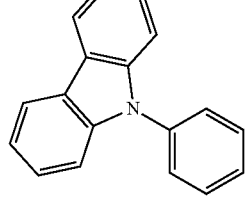

363
364
-continued
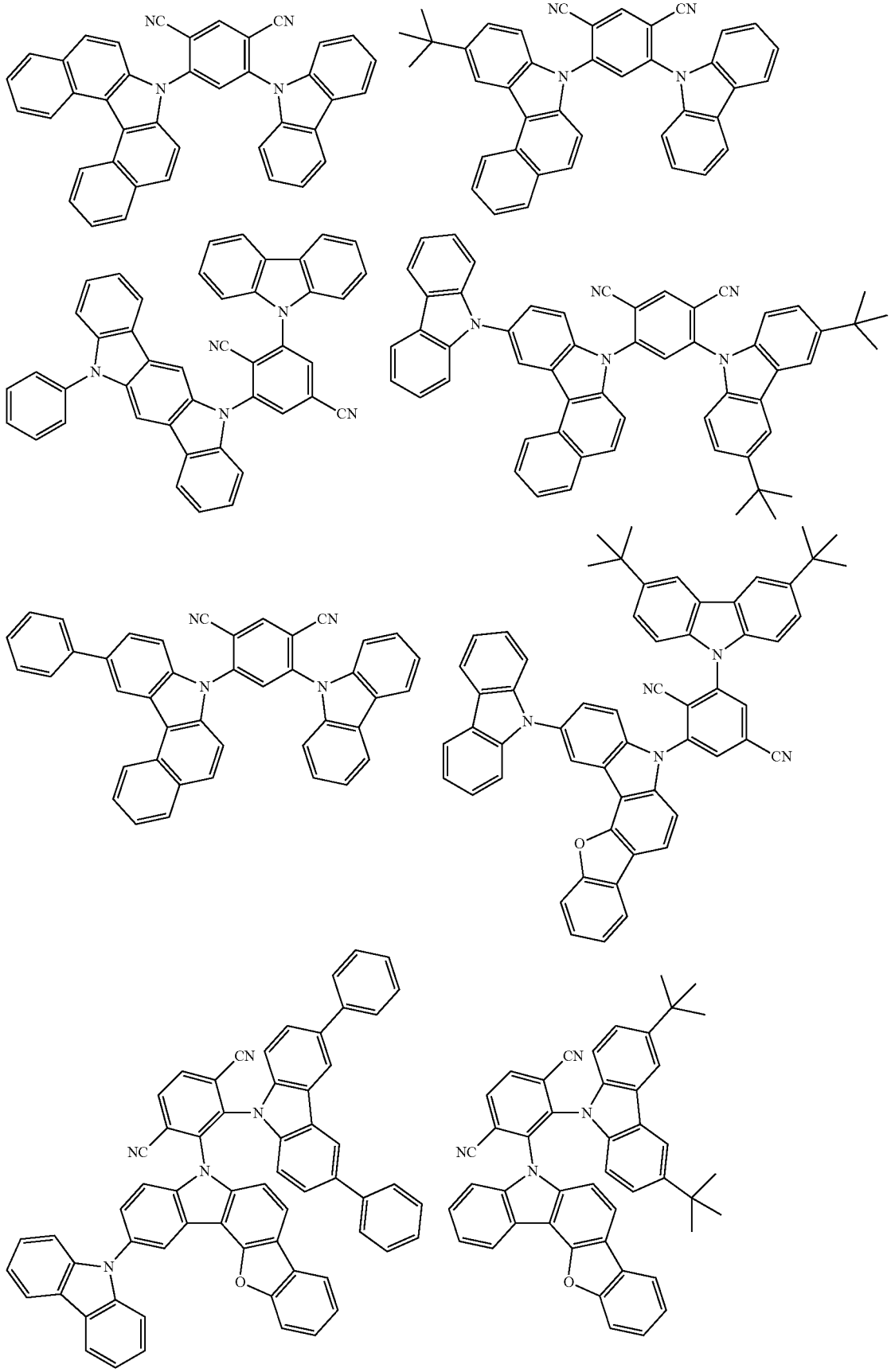

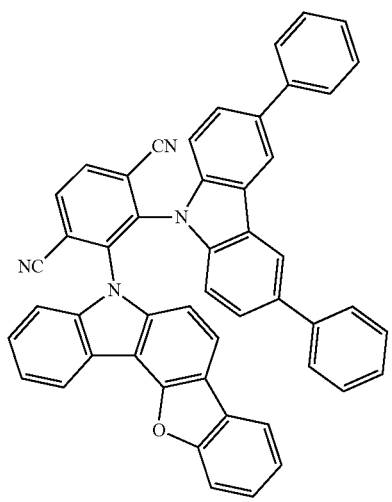
[Formula 161]
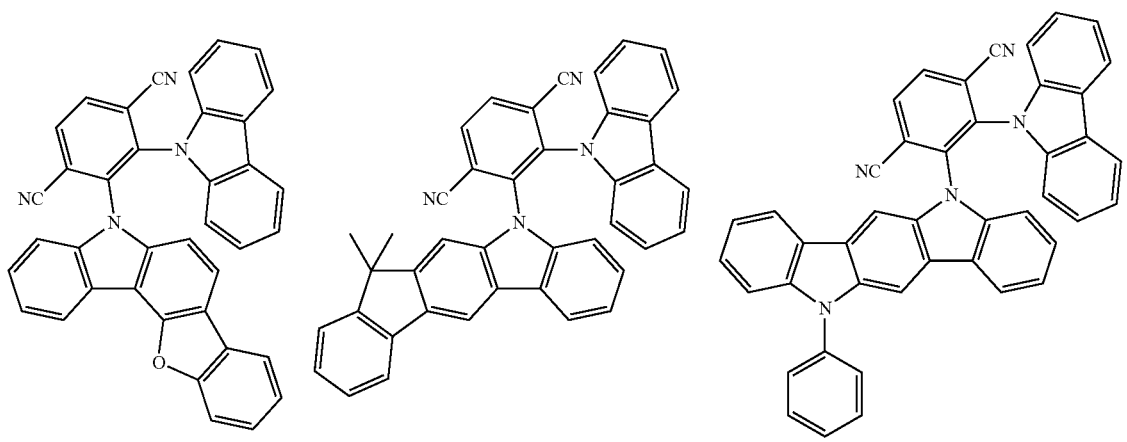
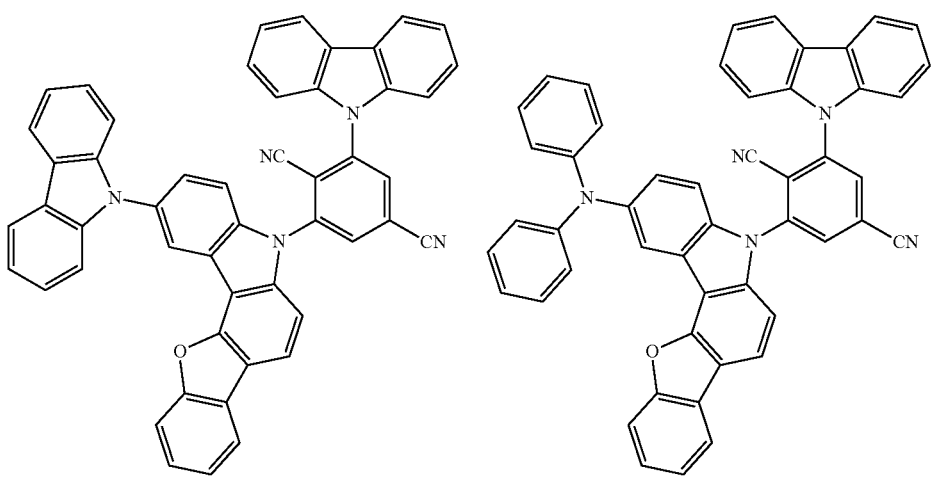

-continued
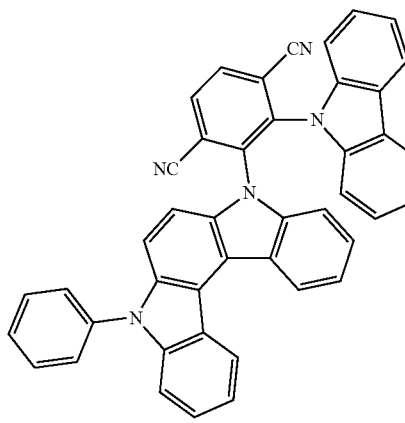
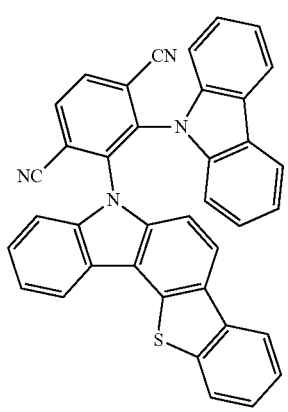
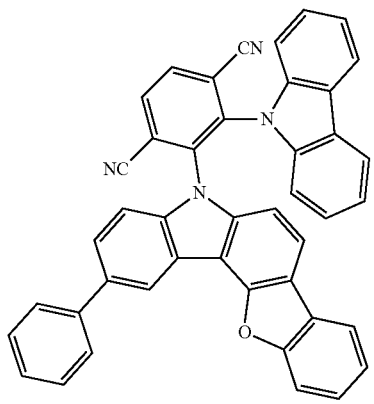
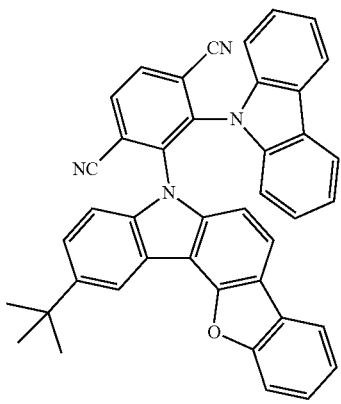
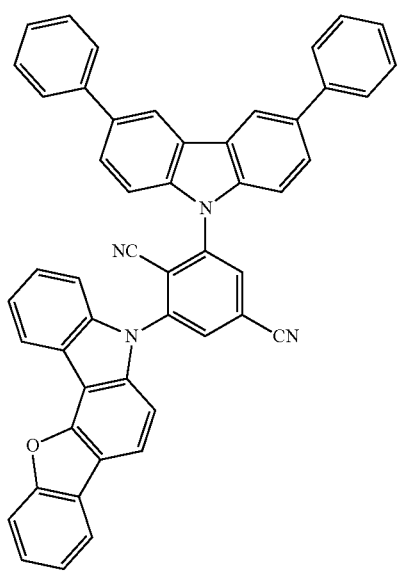
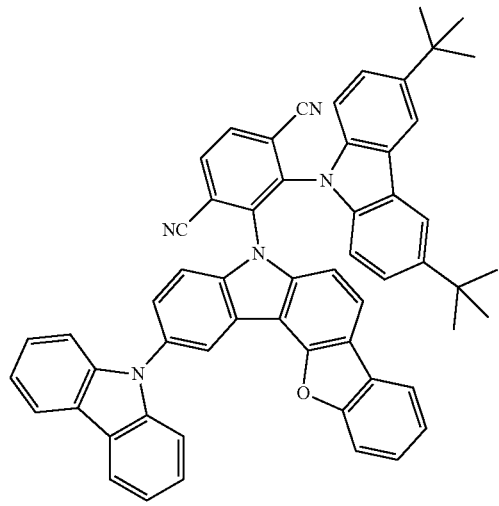

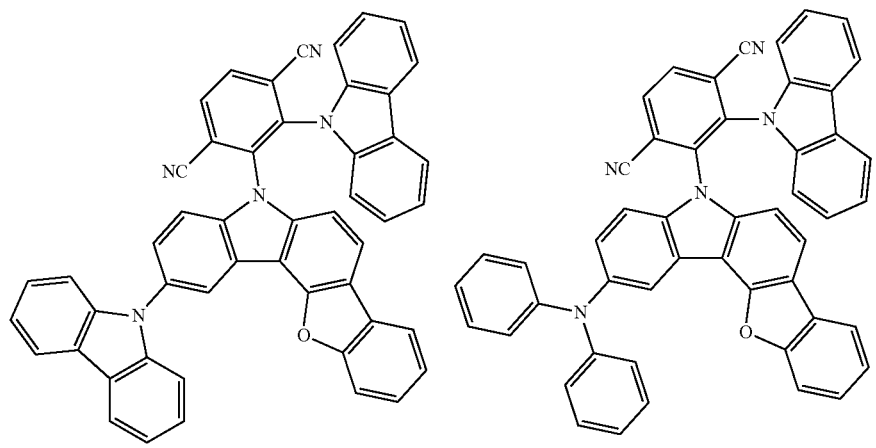
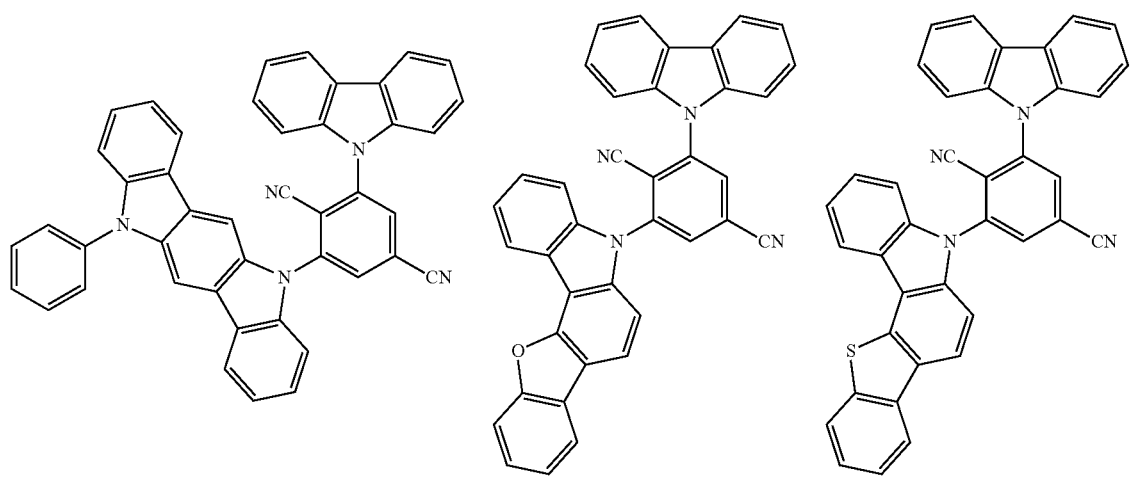
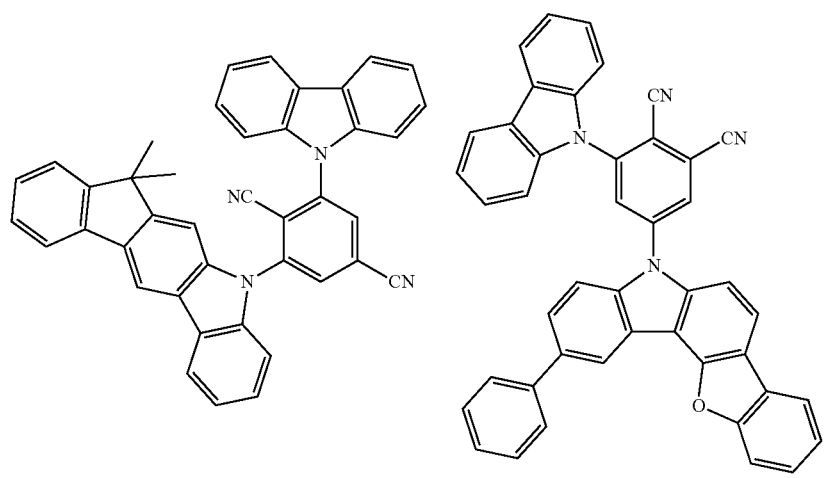

-continued
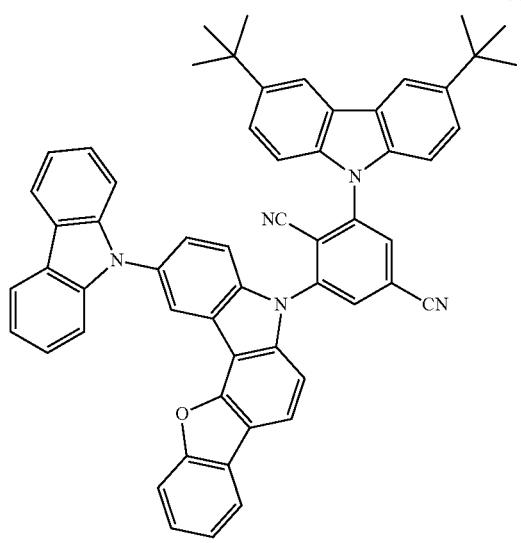
[Formula 162]
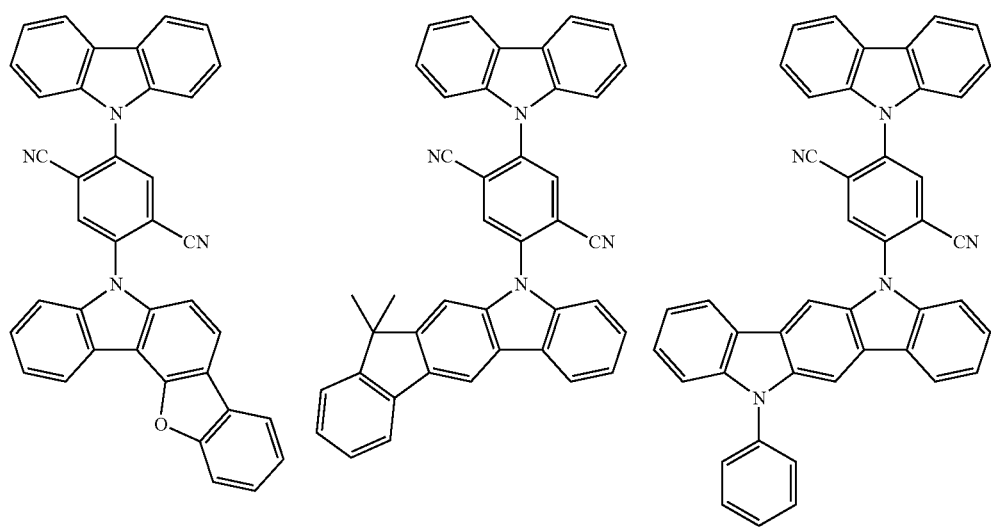
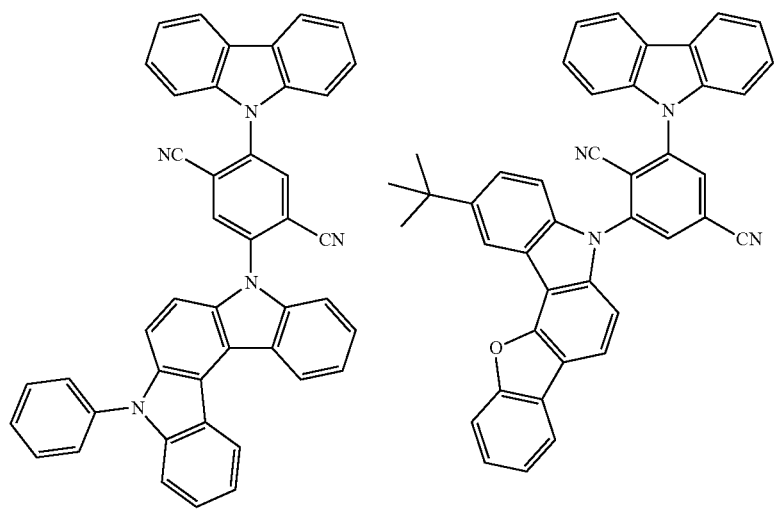

-continued
| 373 | | 374 |
|---|---|---|
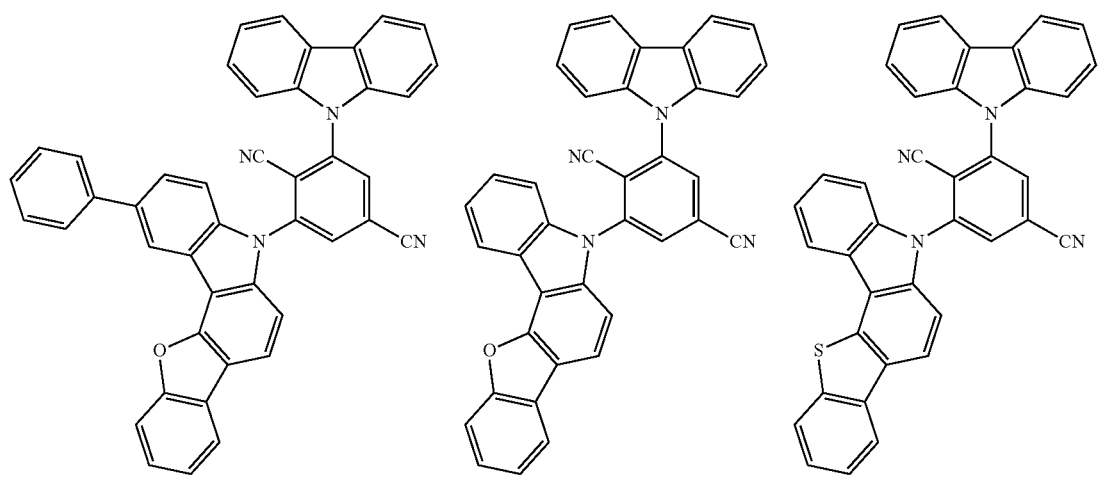
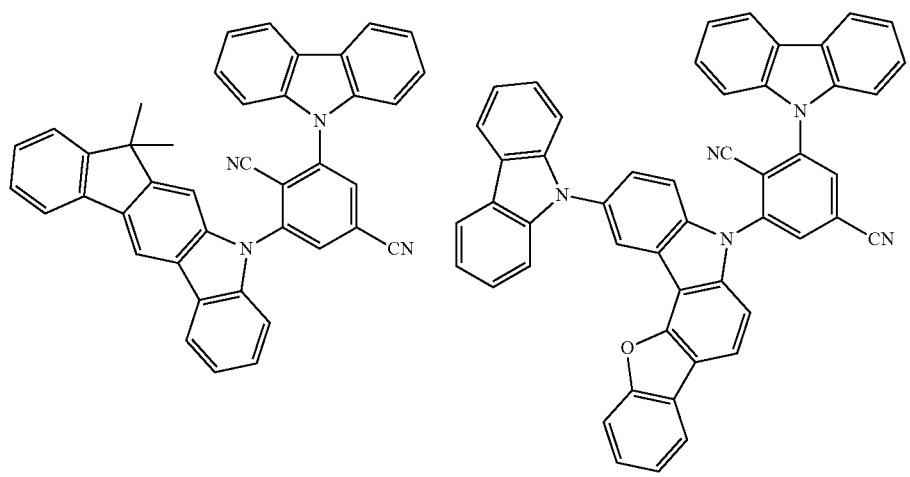
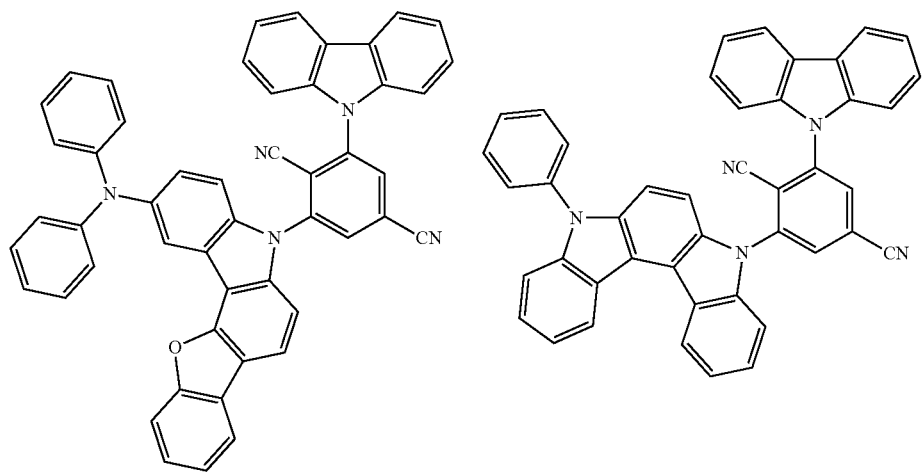

-continued
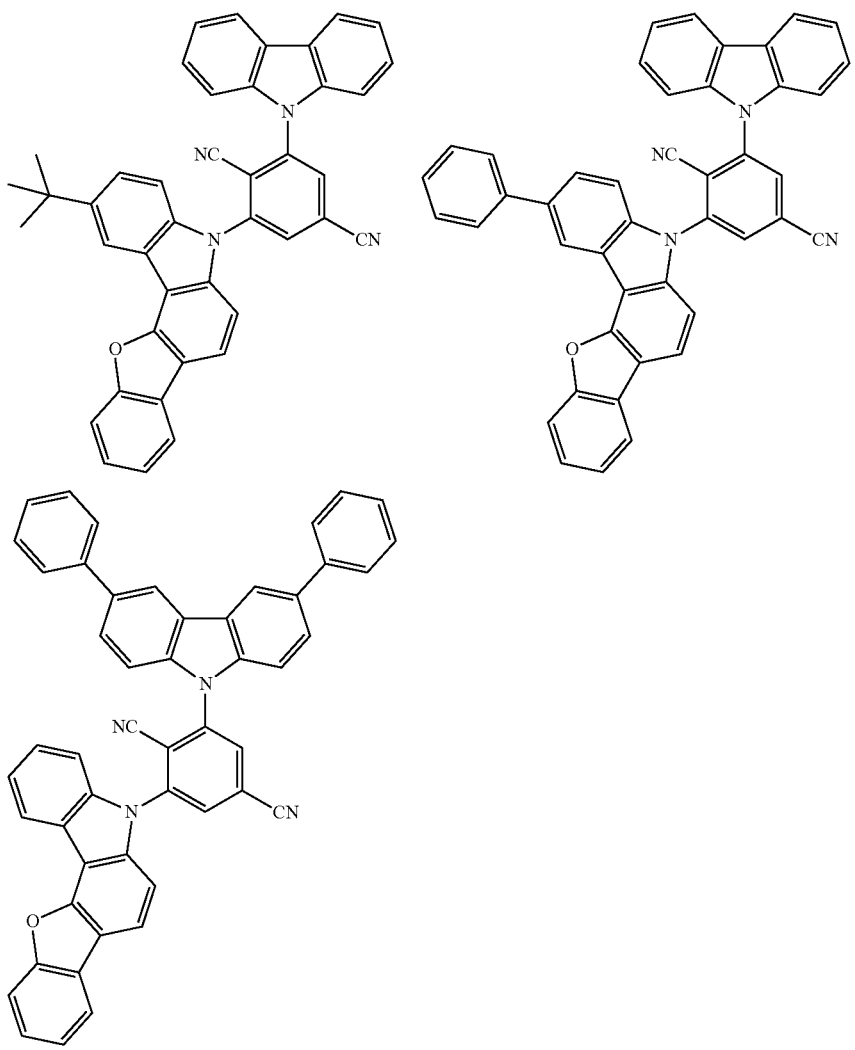
[Formula 163]
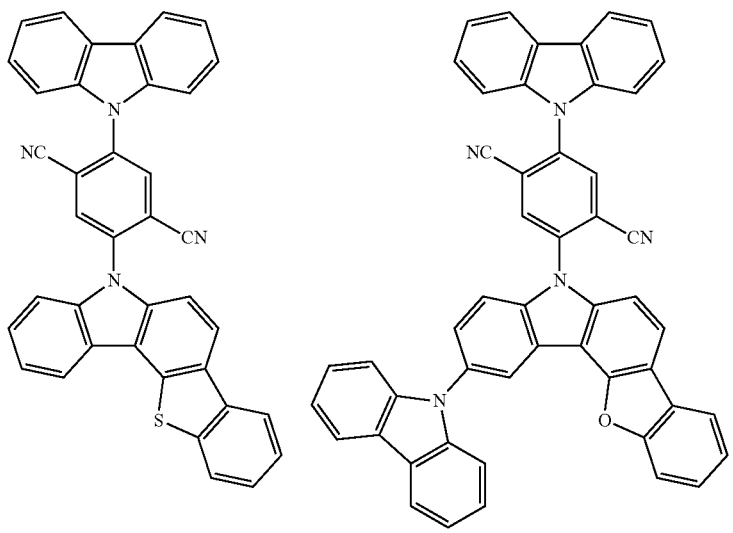

-continued
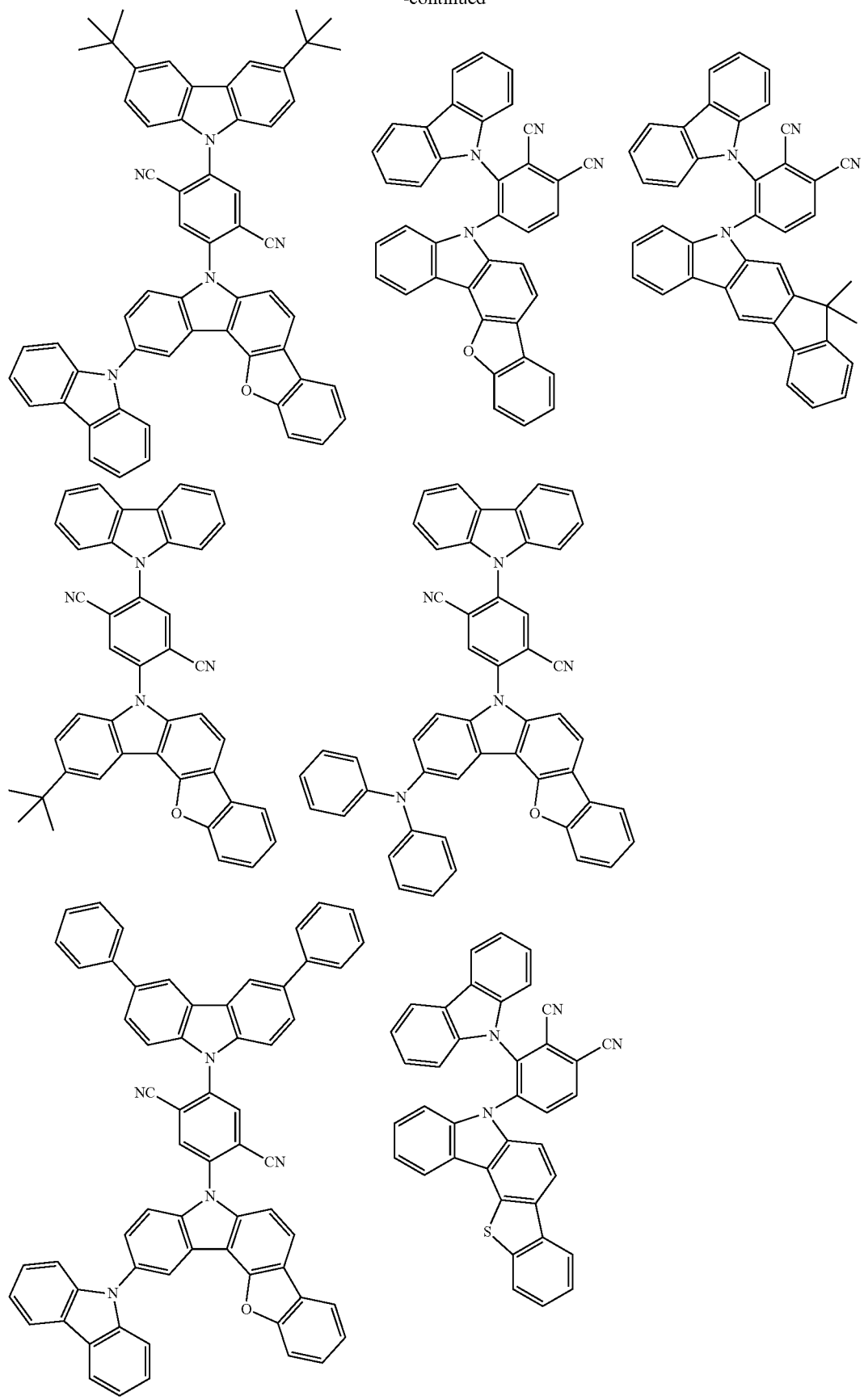

-continued
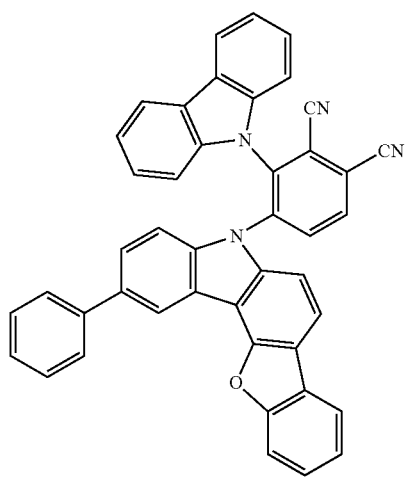
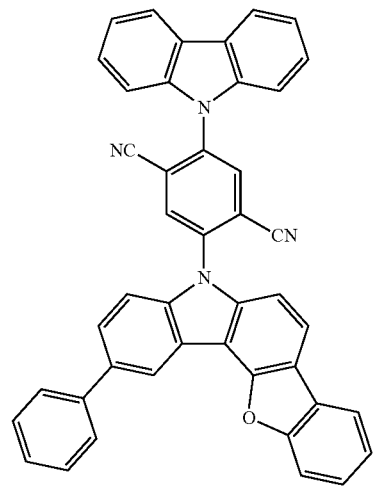
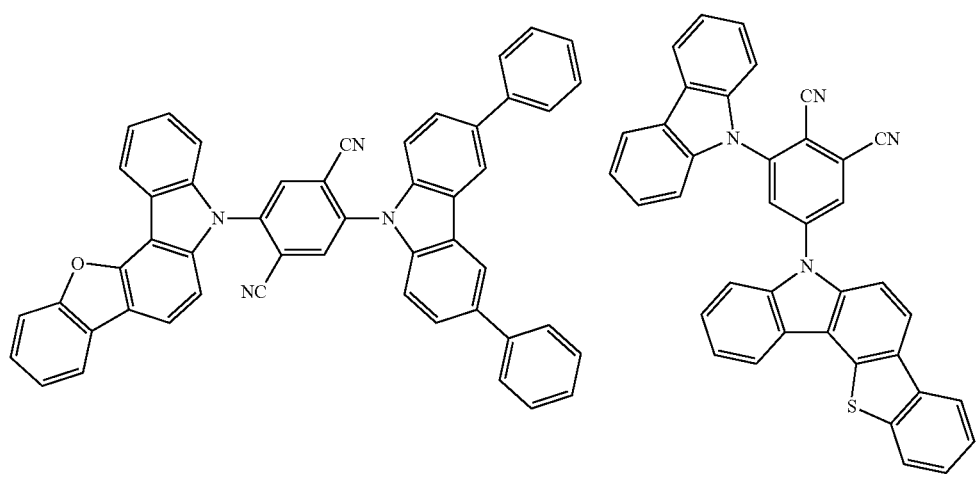
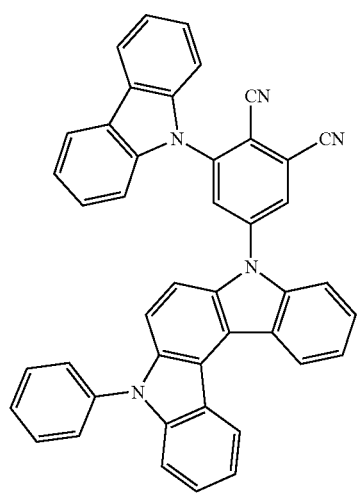

[Formula 164]
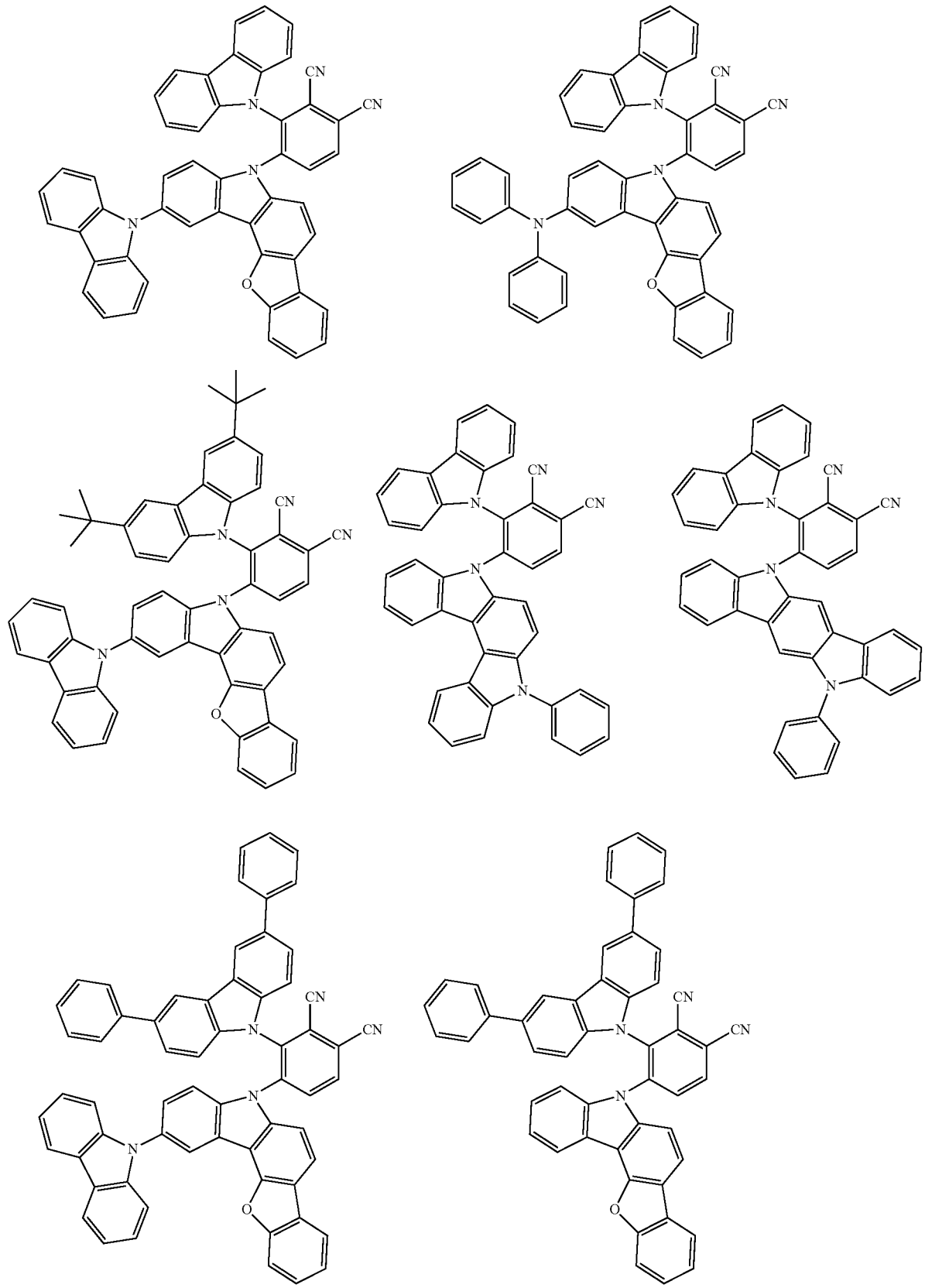

-continued
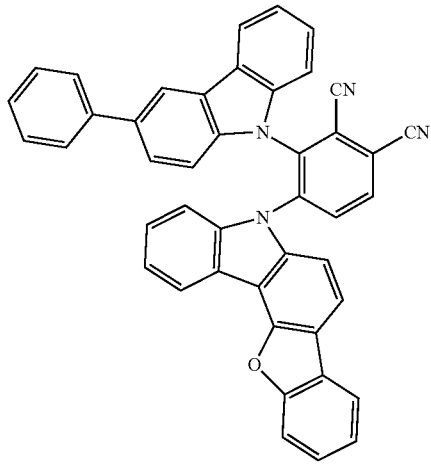
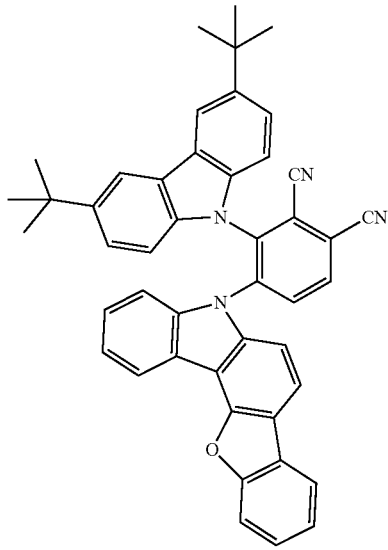
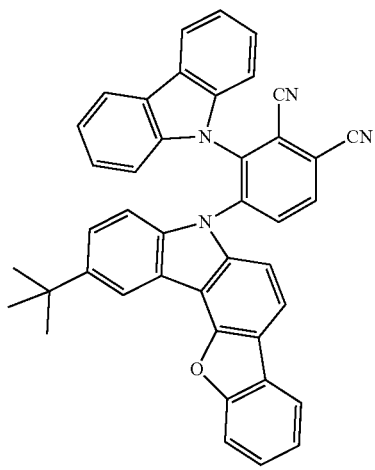
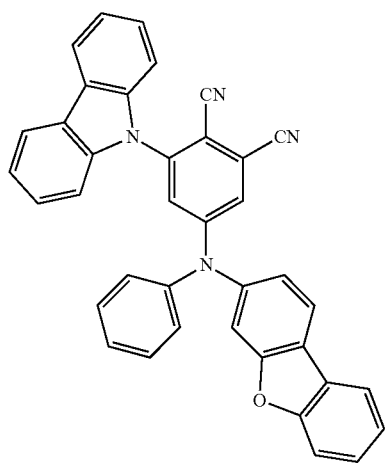
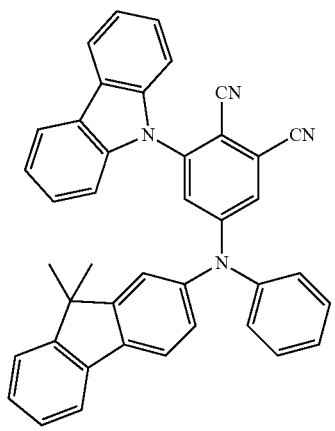
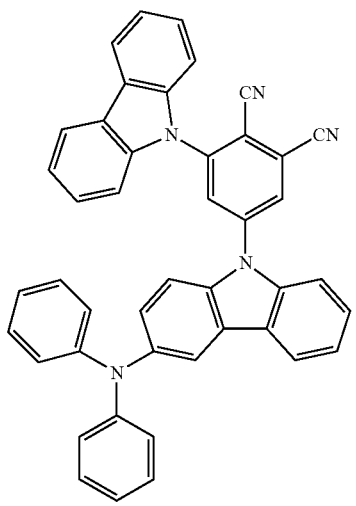

385
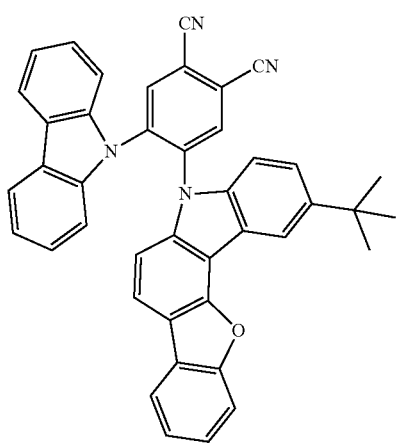
-continued
386
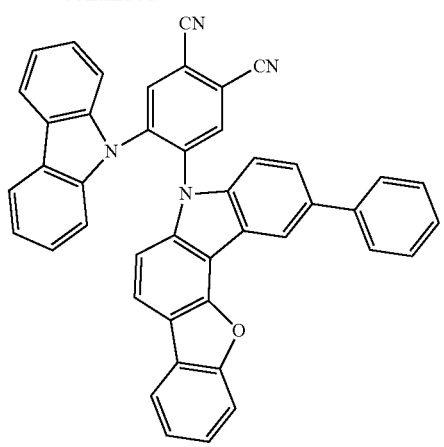
[Formula 165]
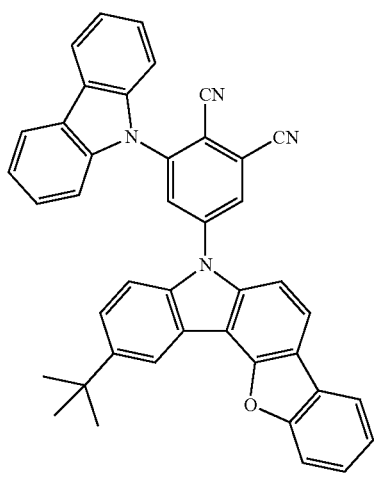
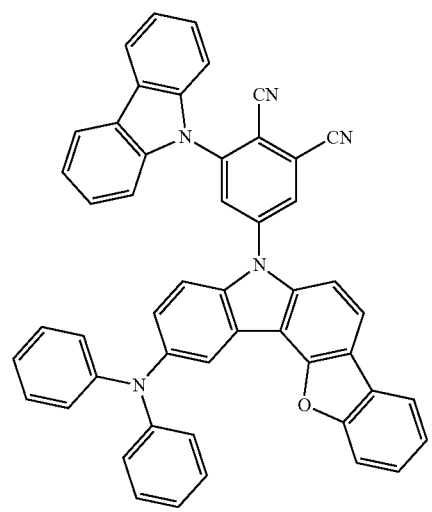
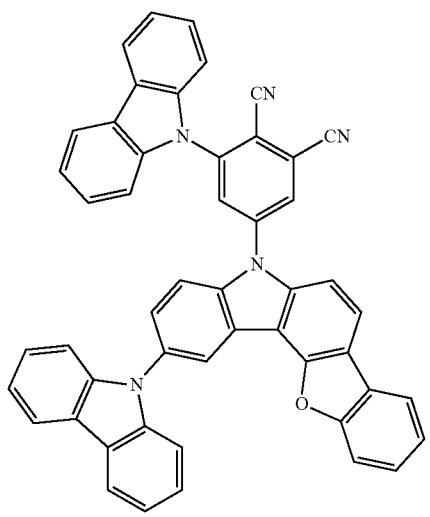
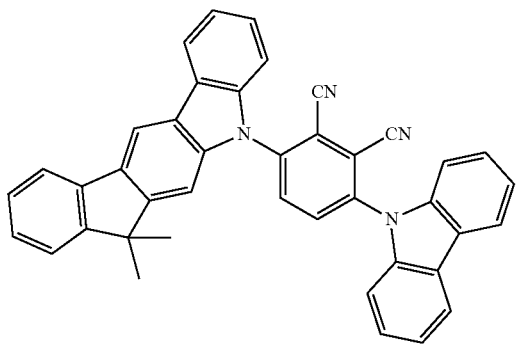

-continued
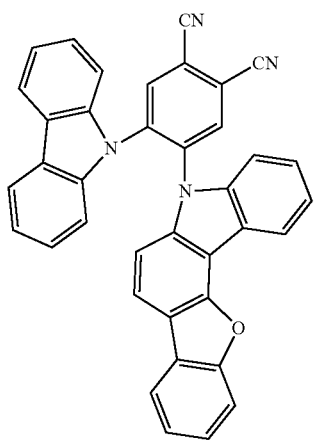
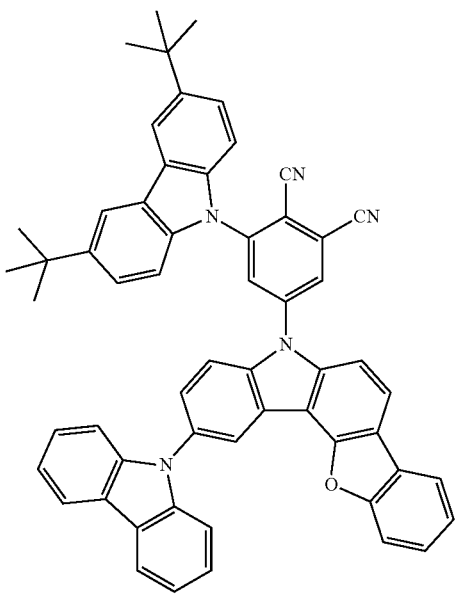
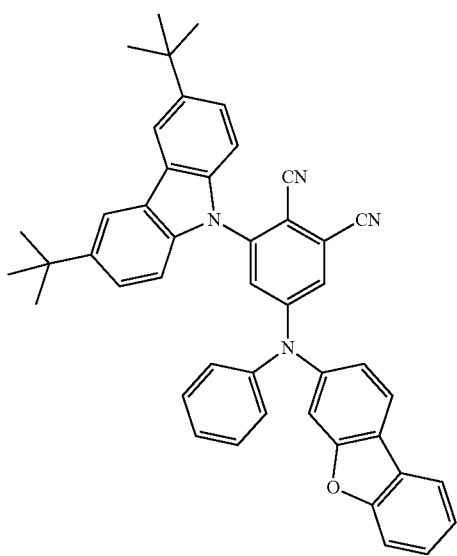
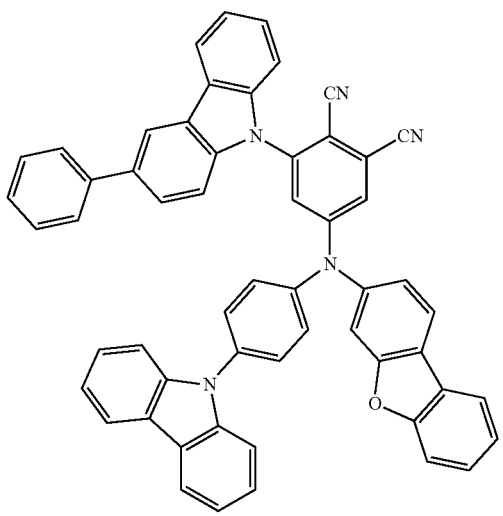
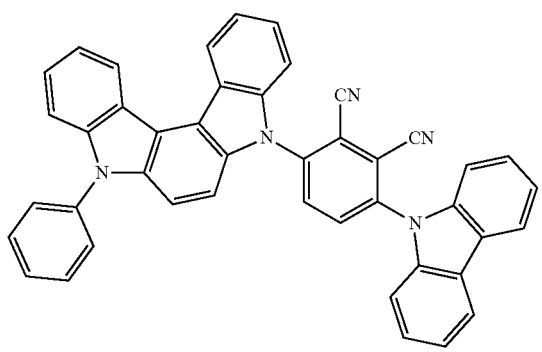
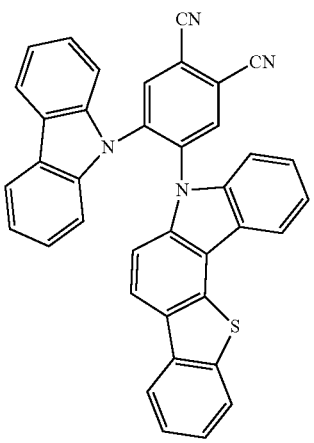

-continued
389
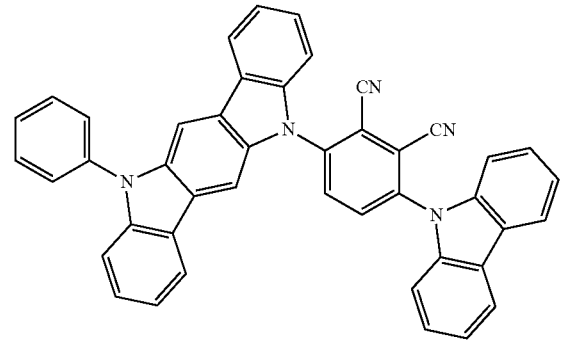
390
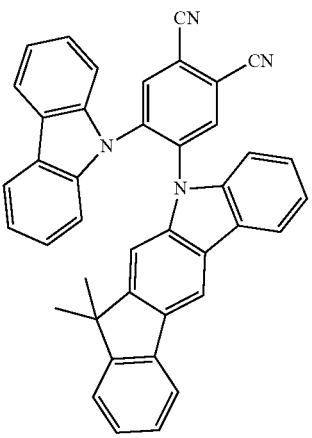
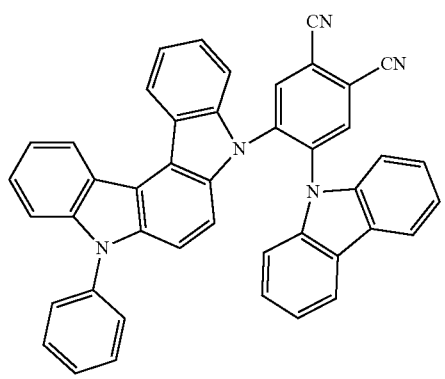
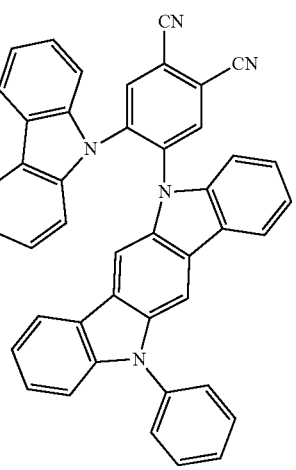
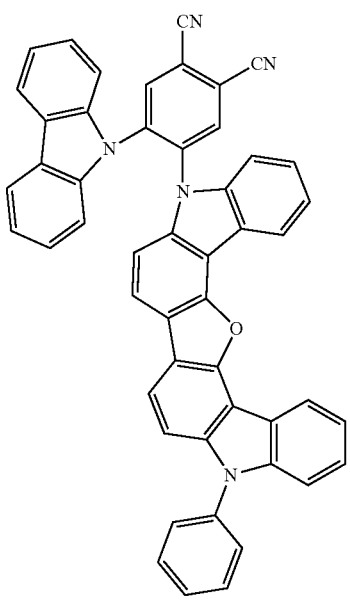
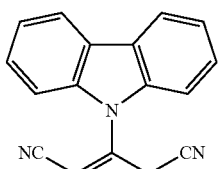
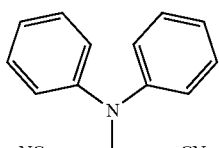
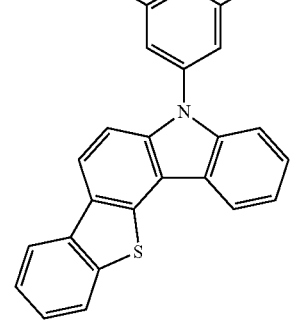
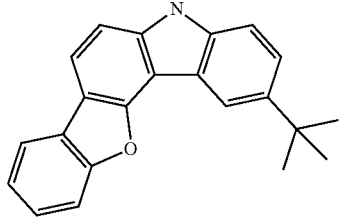

[Formula 166]
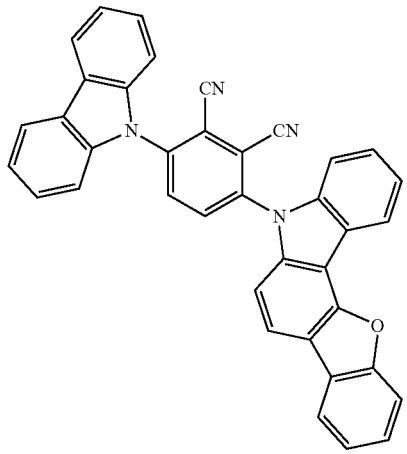 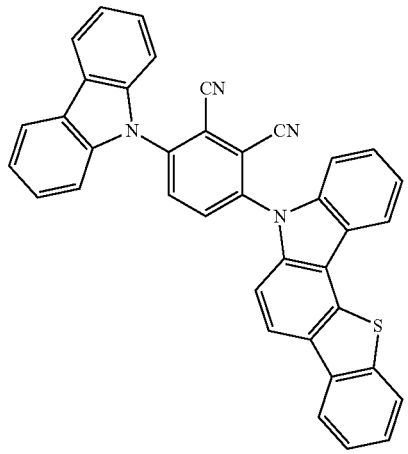
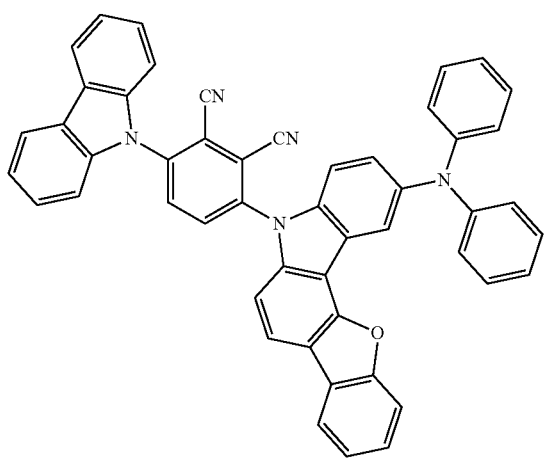 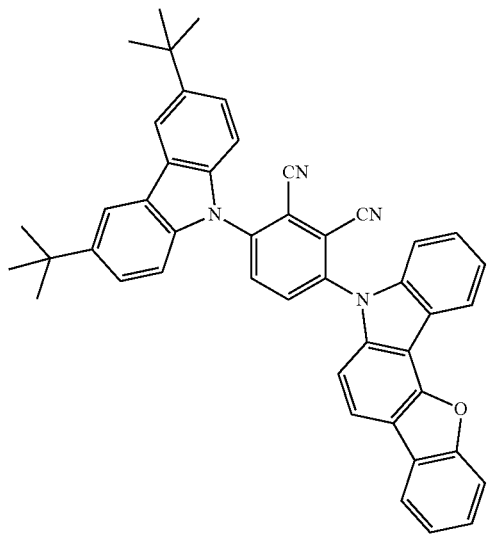
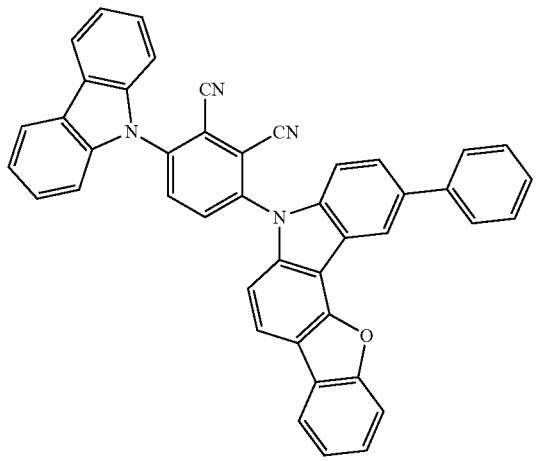 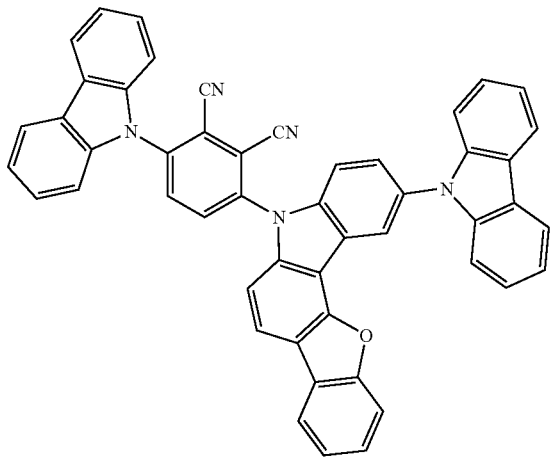

393 394
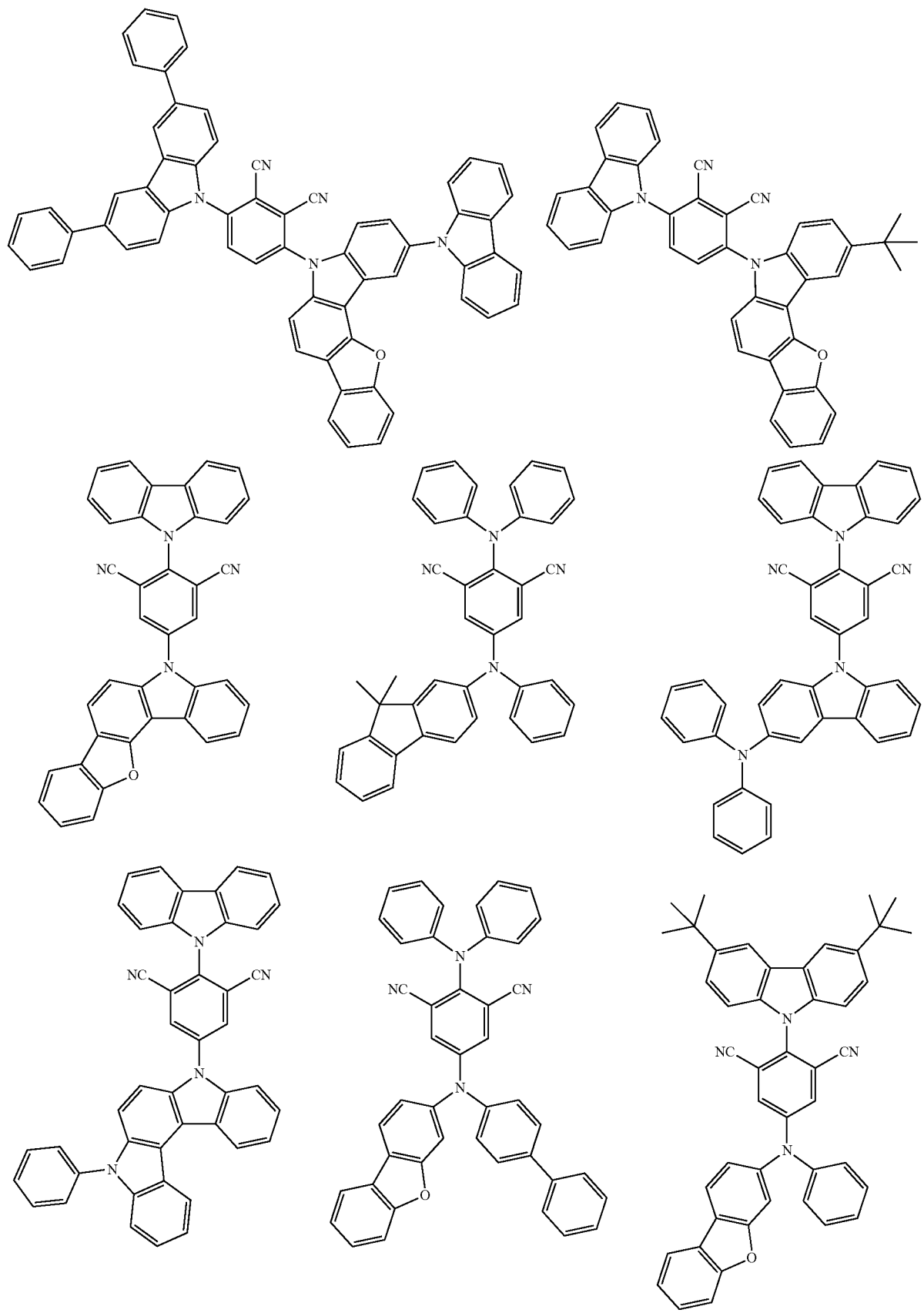
-continued

[Formula 167]
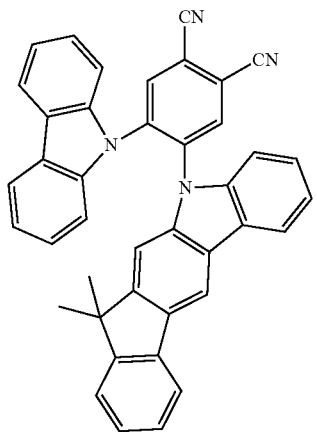 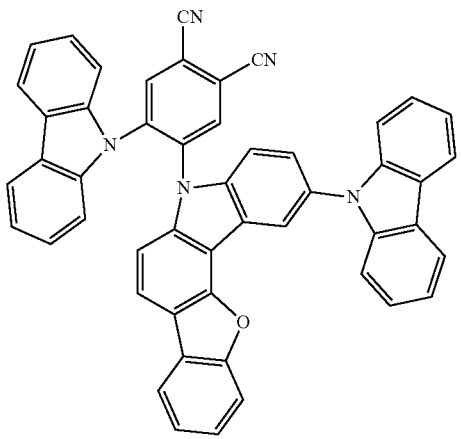
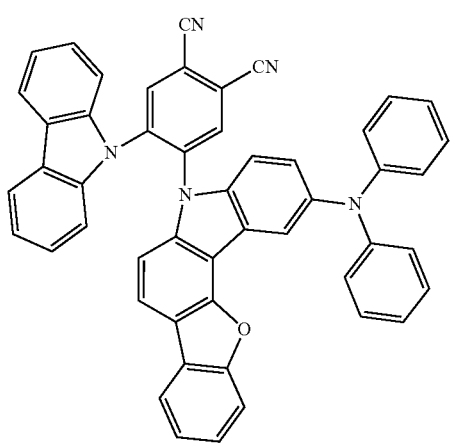 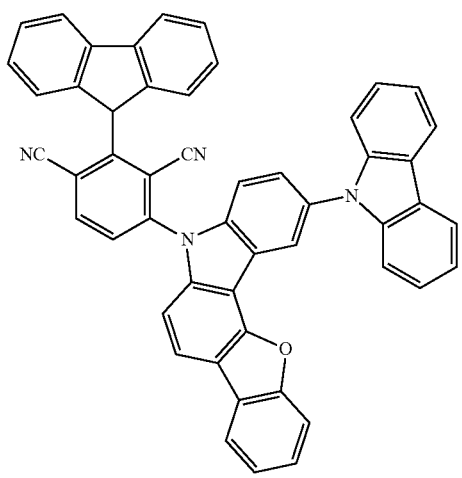
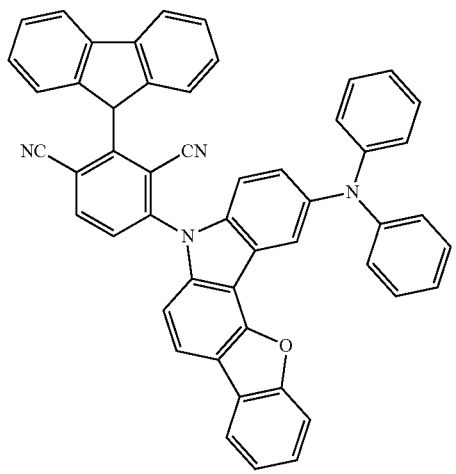 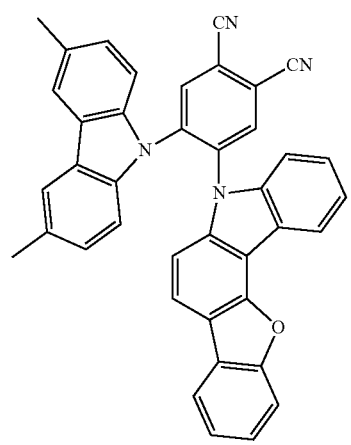

-continued
397
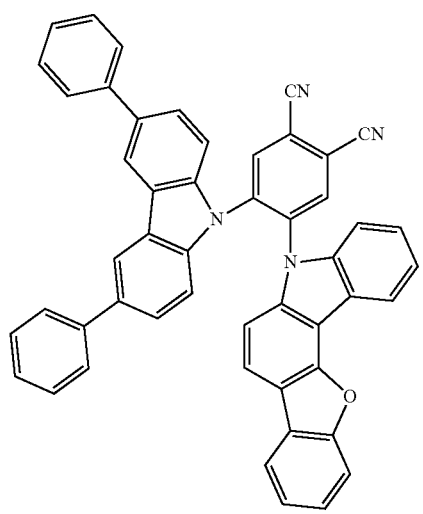
398
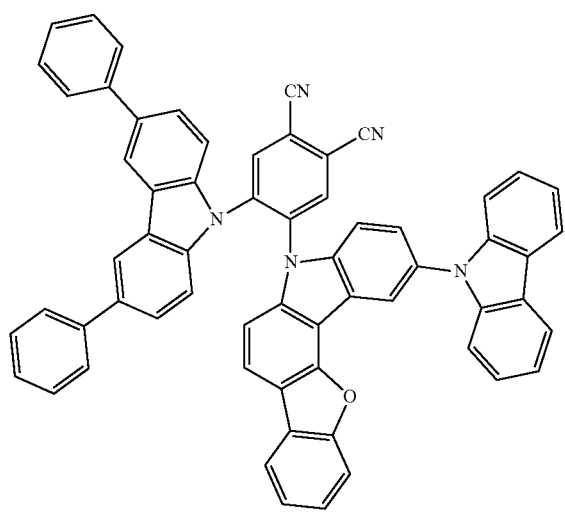
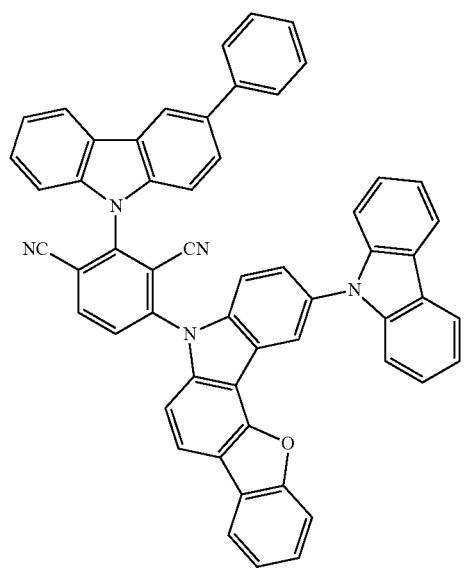
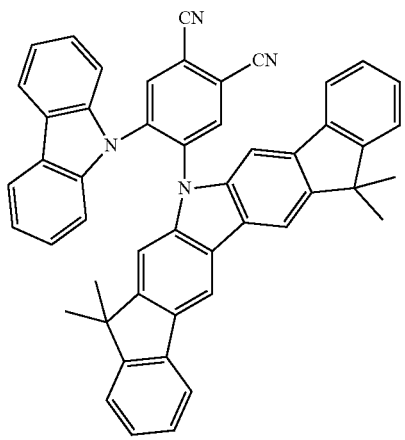
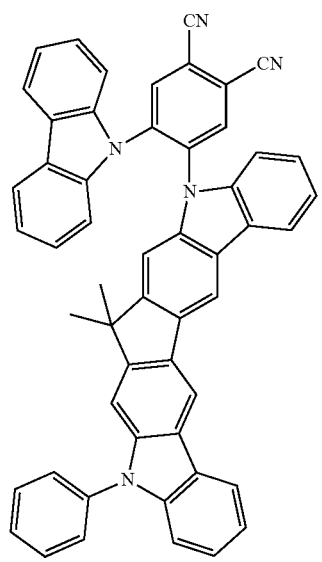
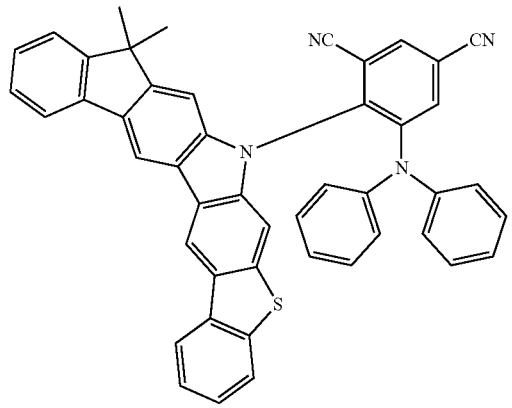

-continued
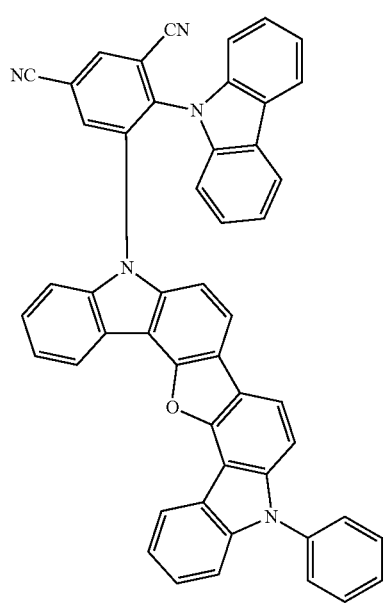
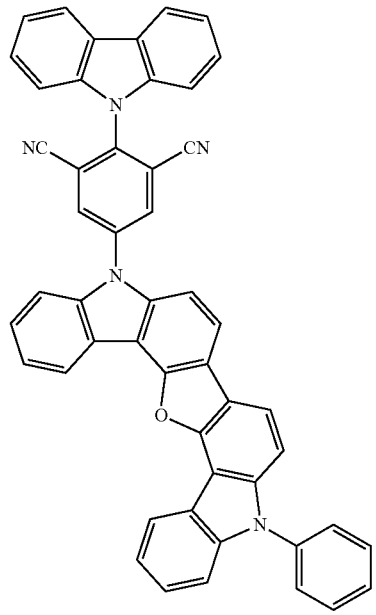
[Formula 168]
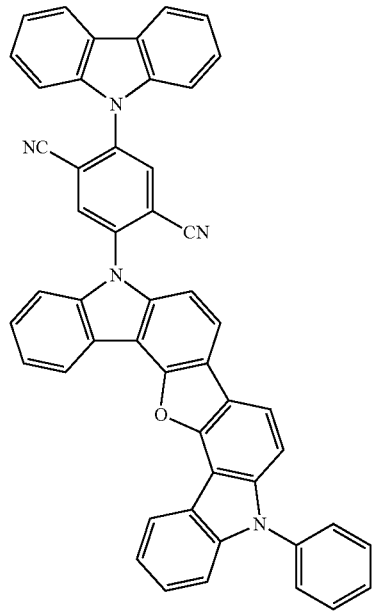
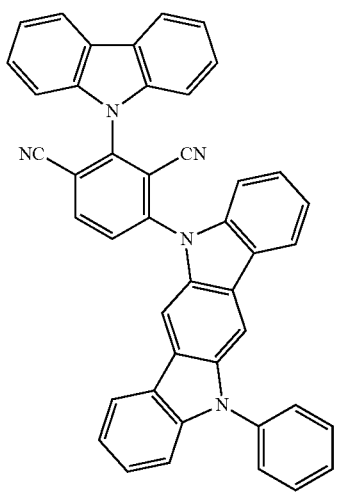
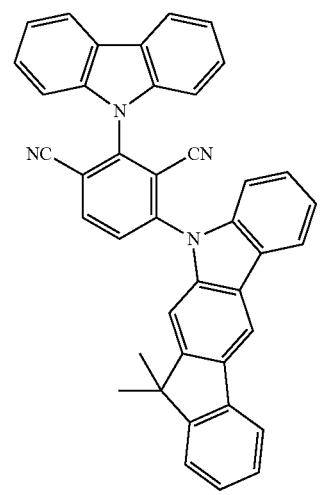

-continued
401
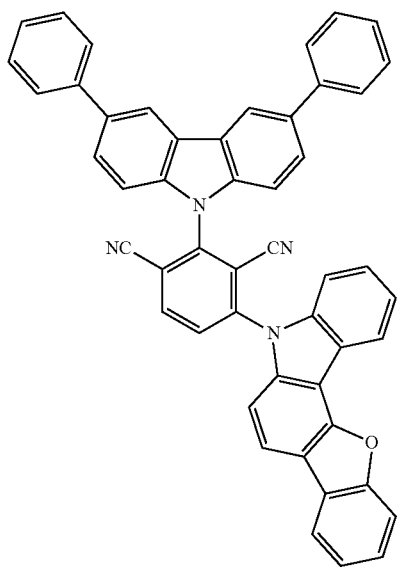
402
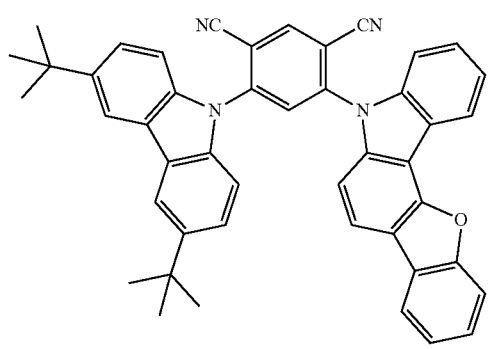
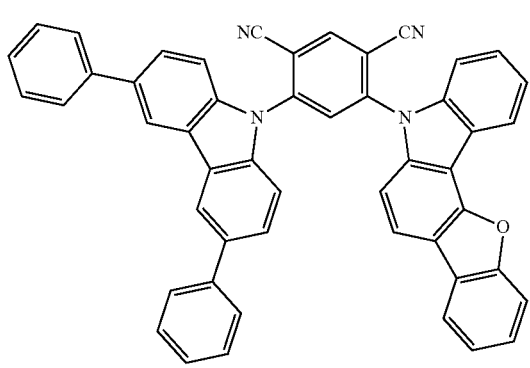
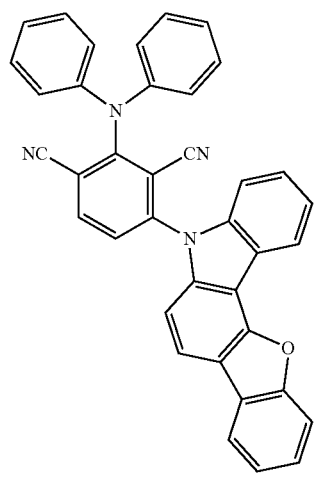
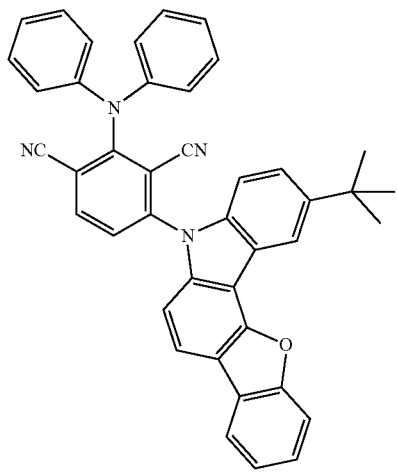
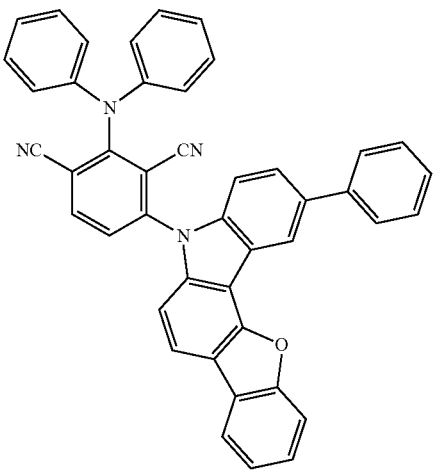

-continued
403
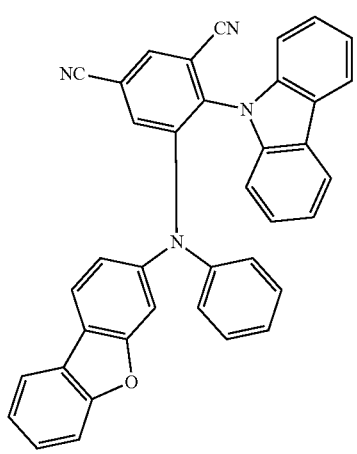
404
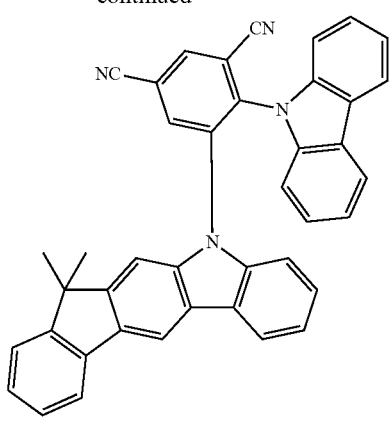
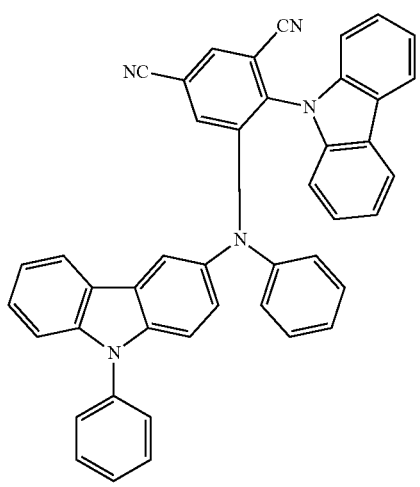
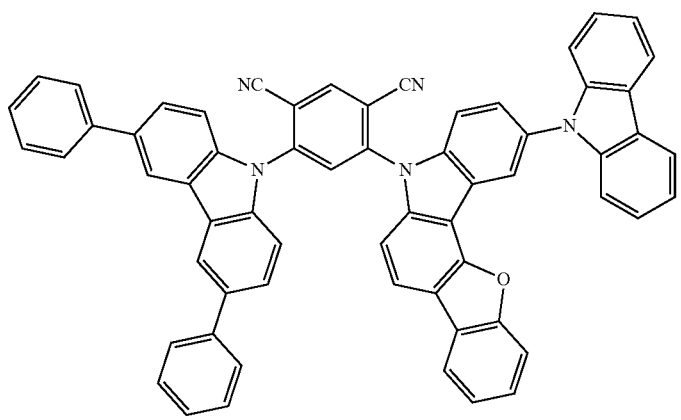
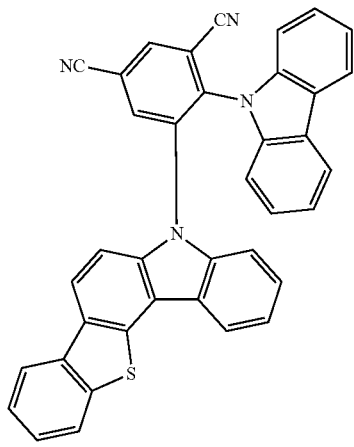
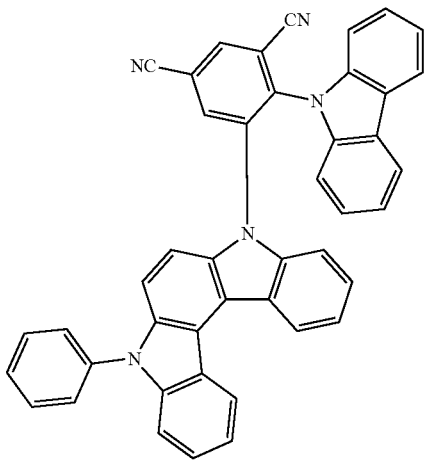

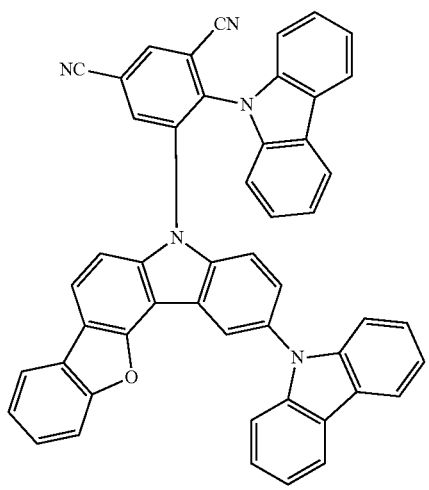
[Formula 169]
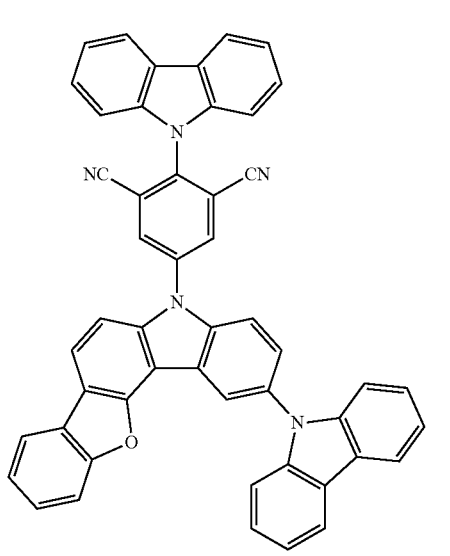
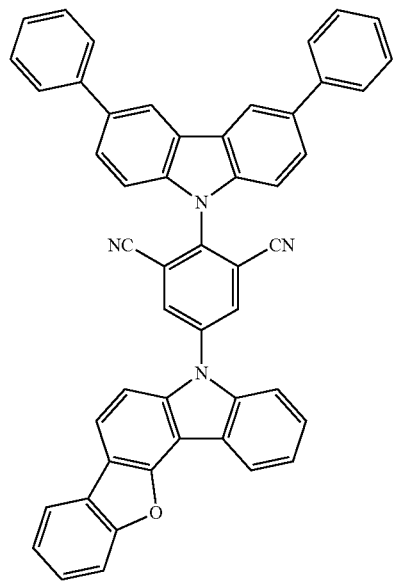
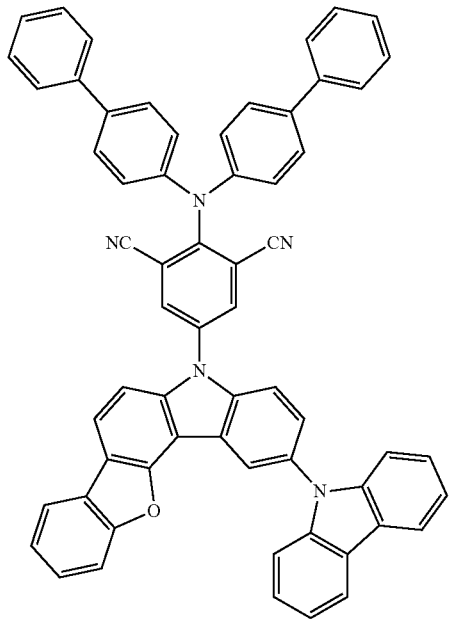
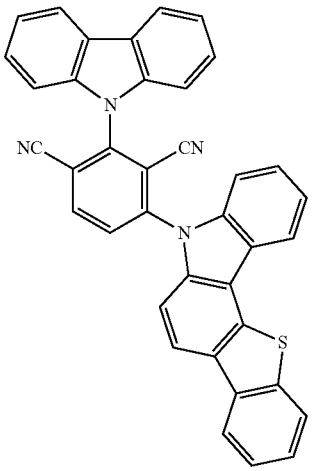

-continued
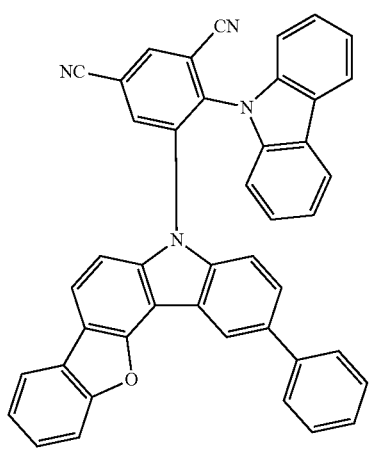
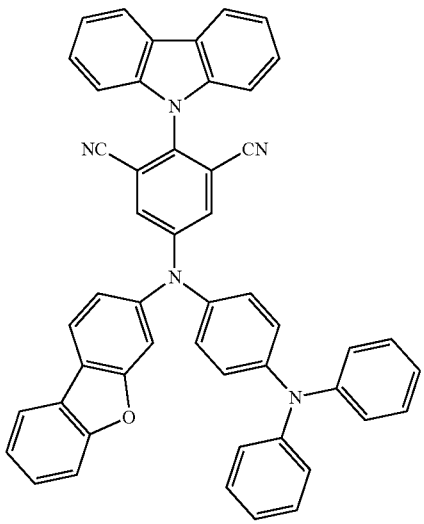
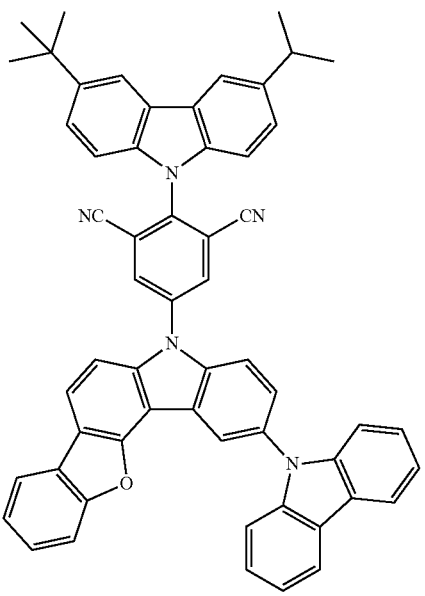
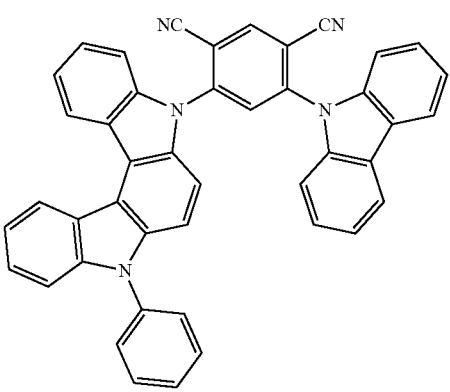
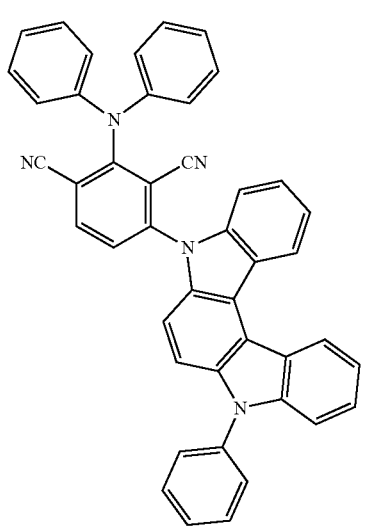
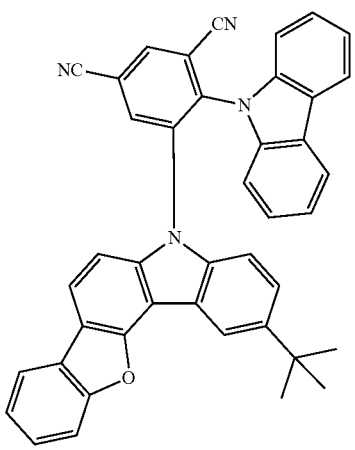

409
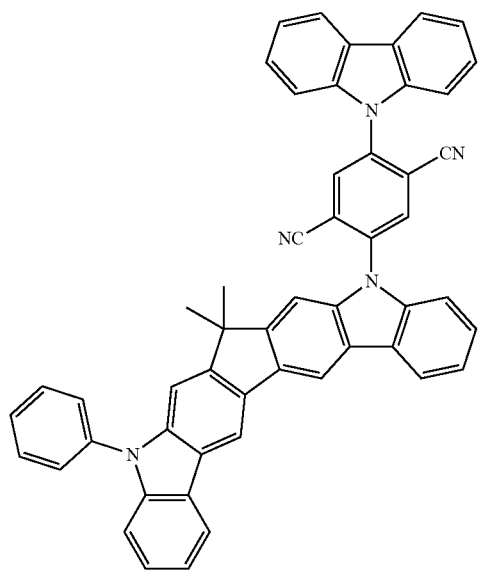
410
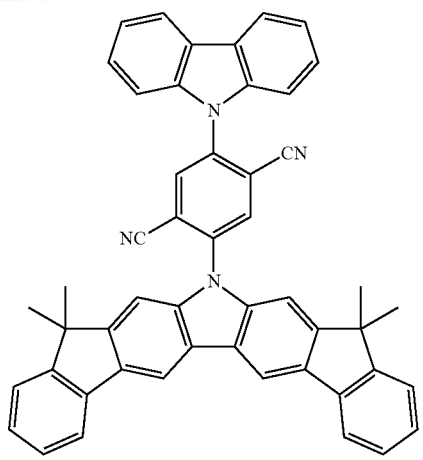
-continued
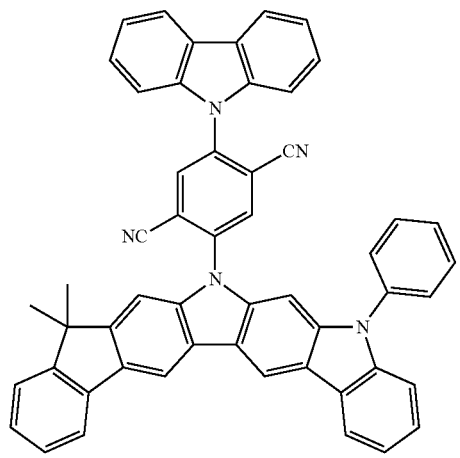
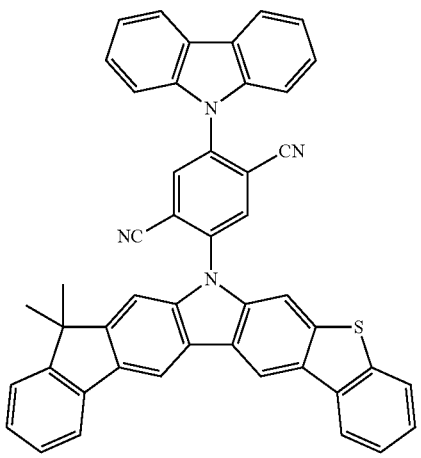
[Formula 170]
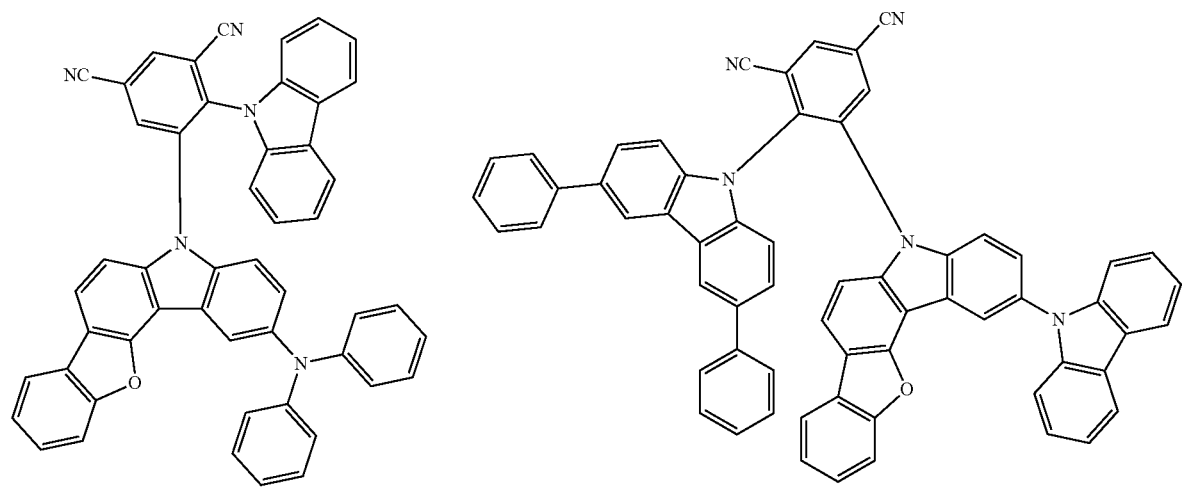

411
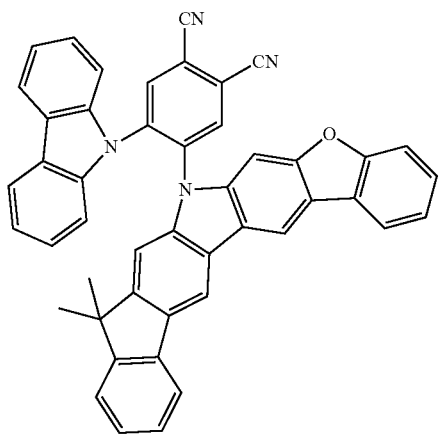
412
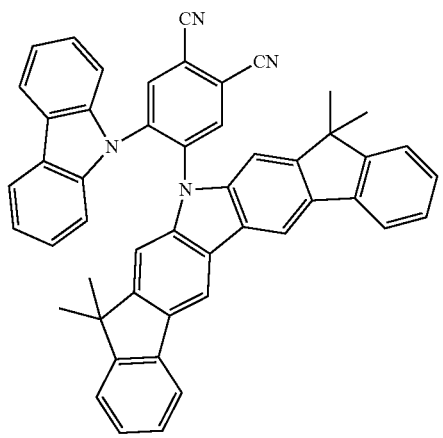
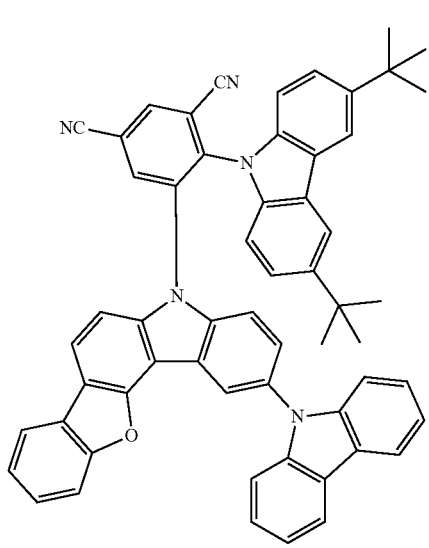
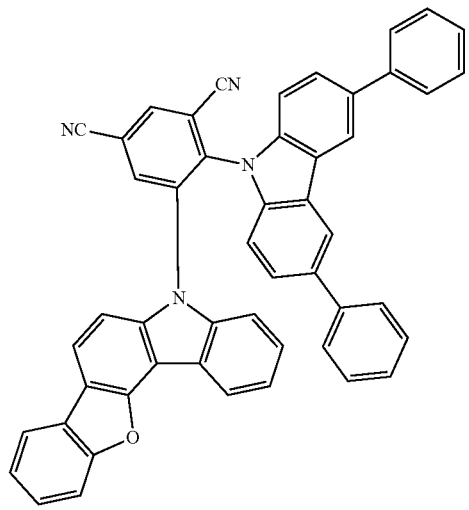
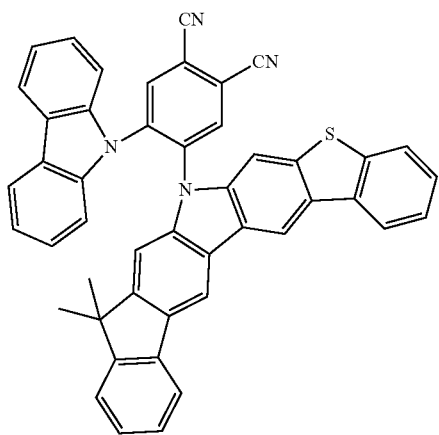
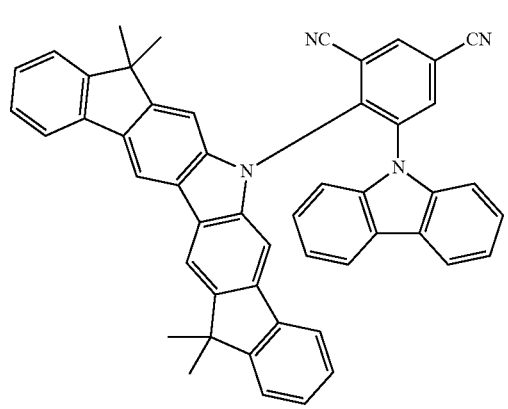

-continued
| 413 | 414 |
|---|---|
| 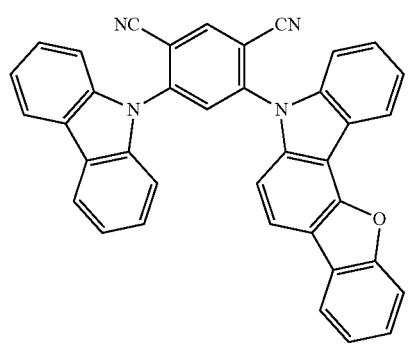 | 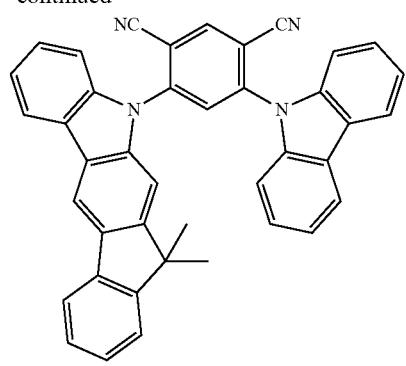 |
| 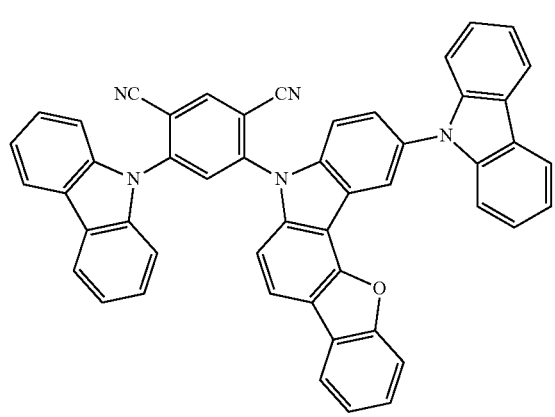 | 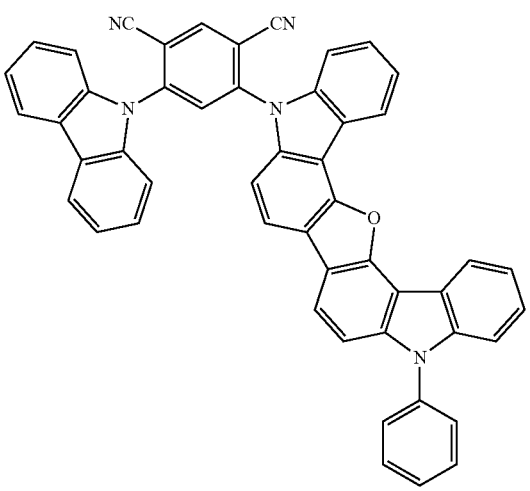 |
| 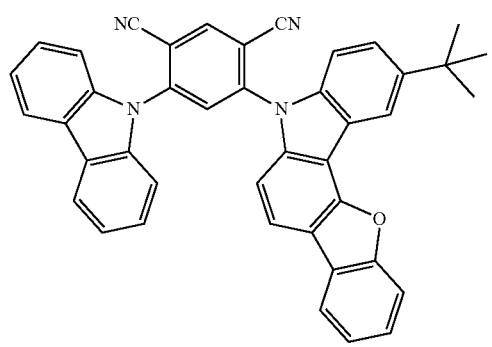 | 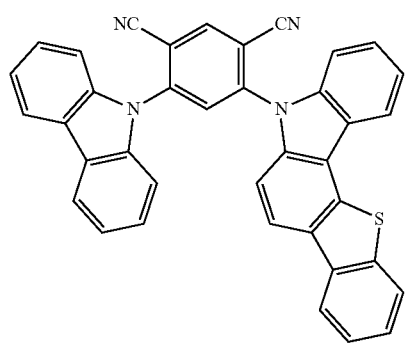 |
| 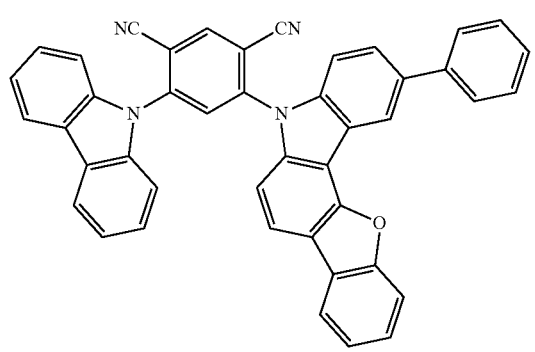 | 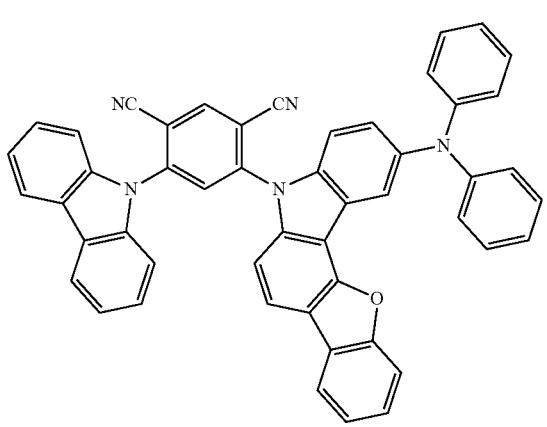 |

-continued
415 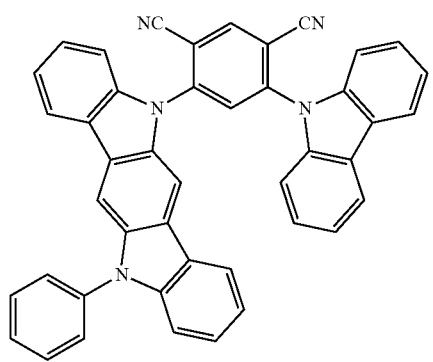
416 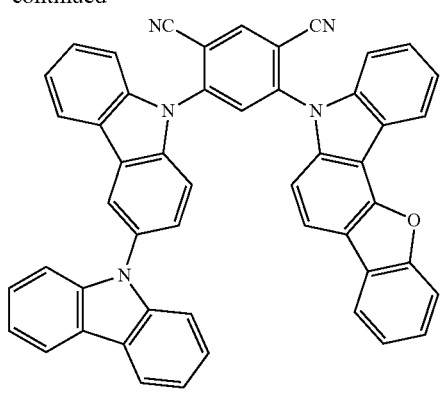
[Formula 171]
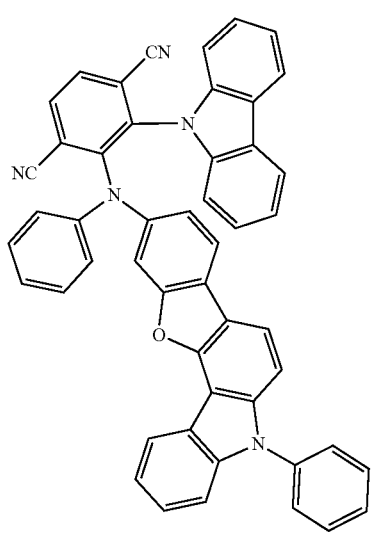
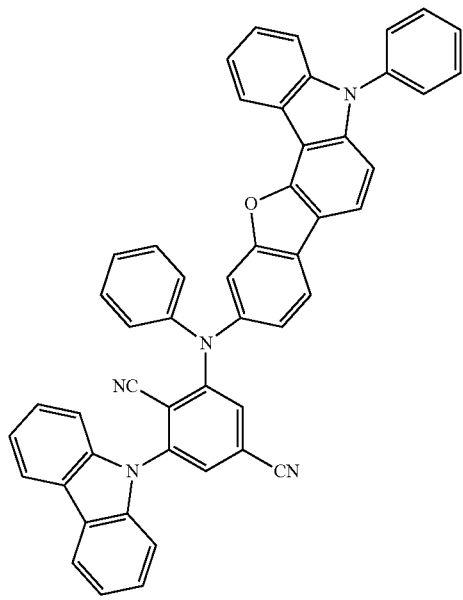
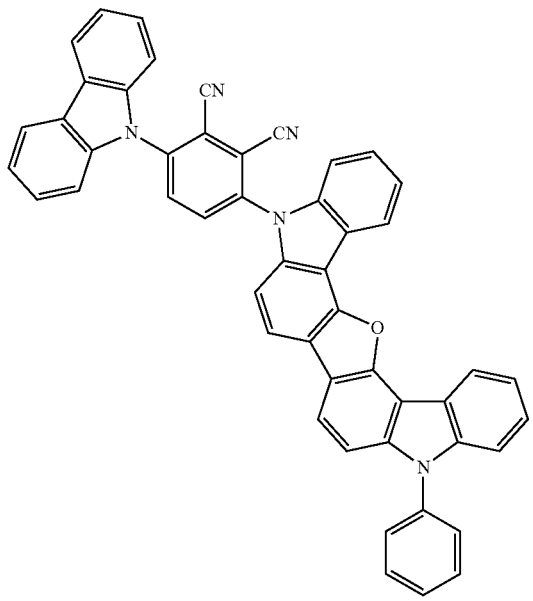
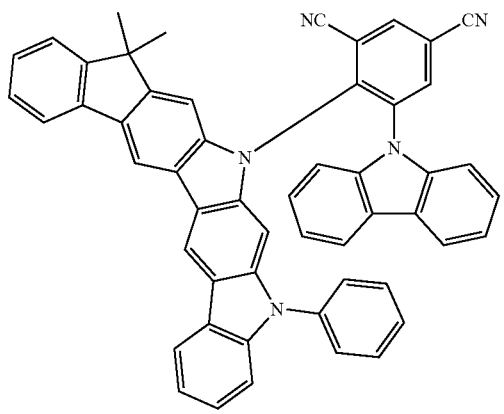

-continued
417
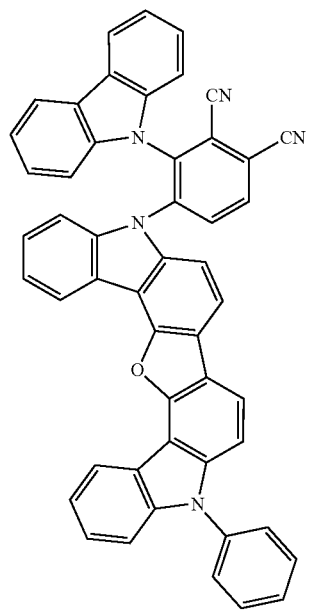 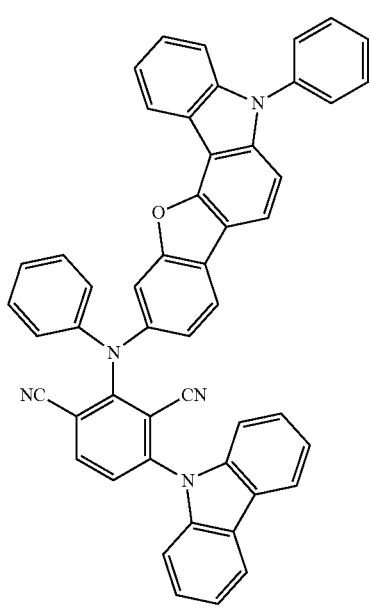
418
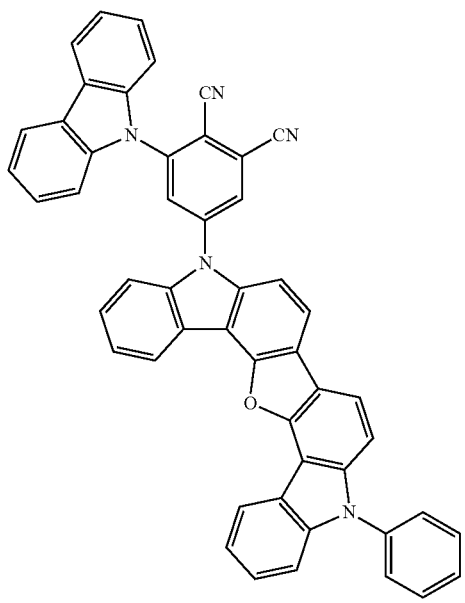
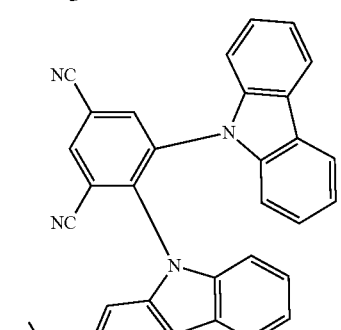 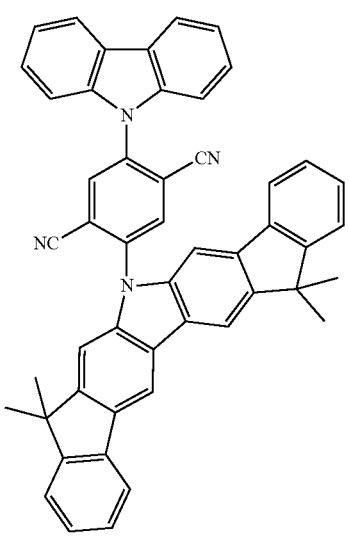
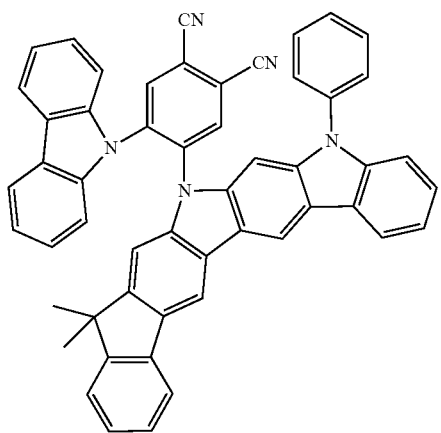 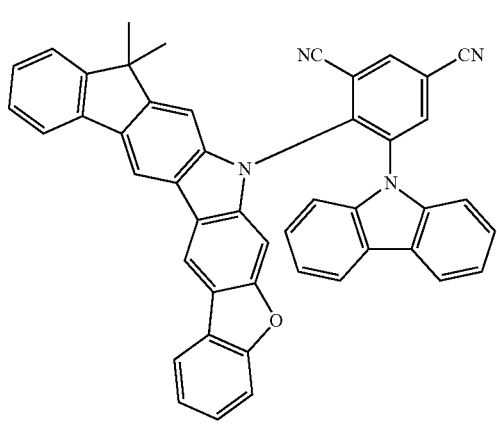

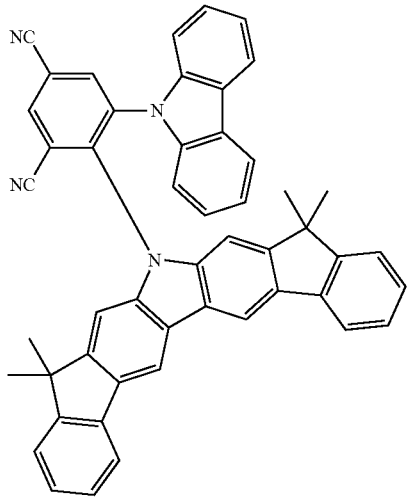
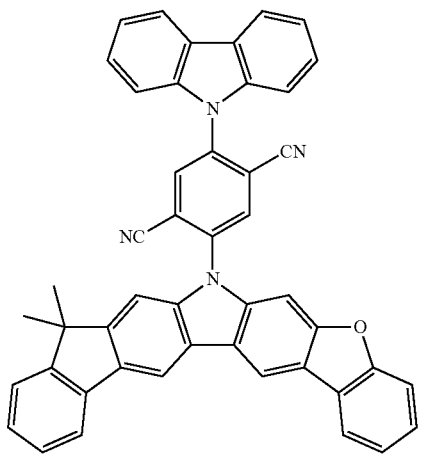
[Formula 172]
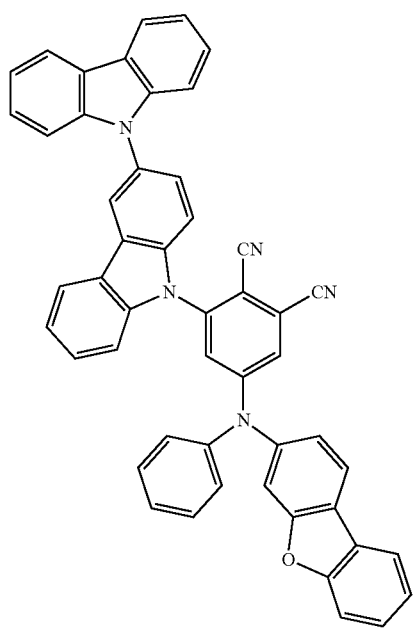
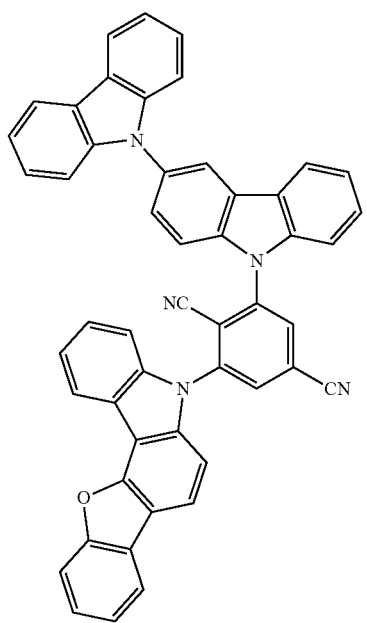

-continued
421
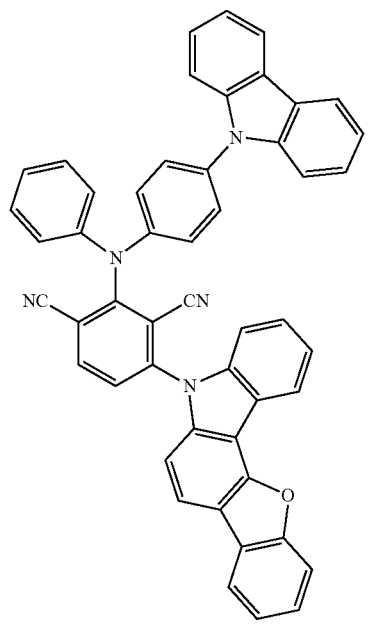
422
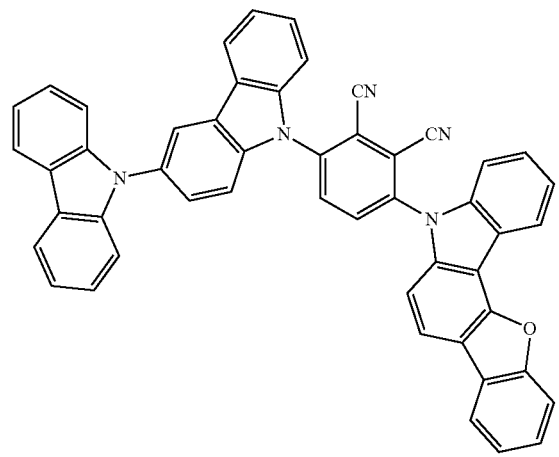
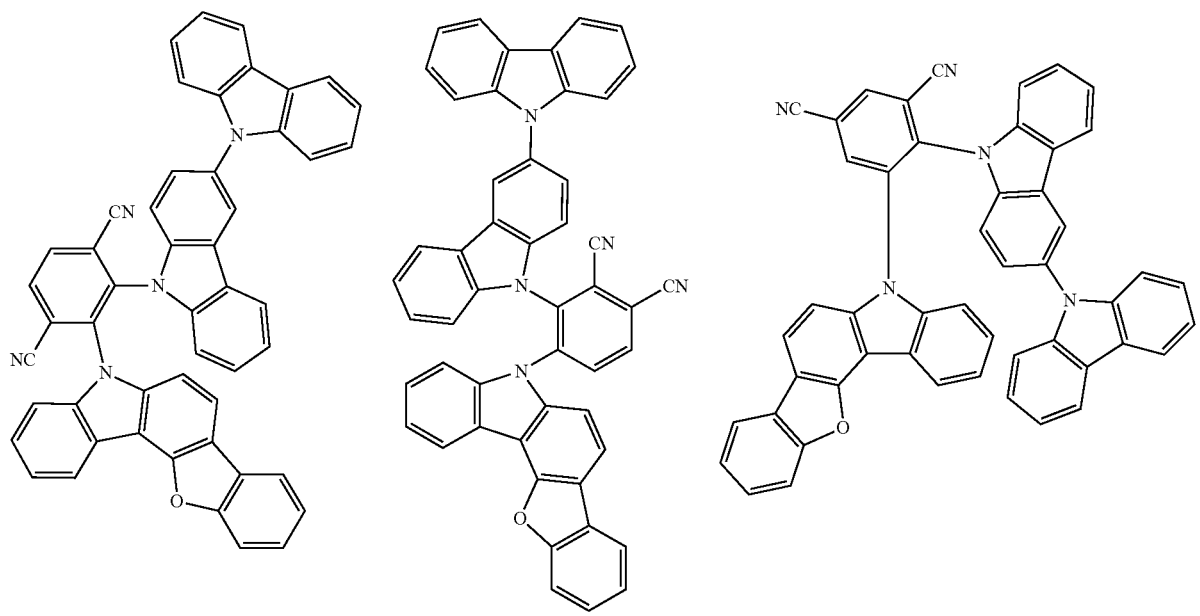

423 424
-continued
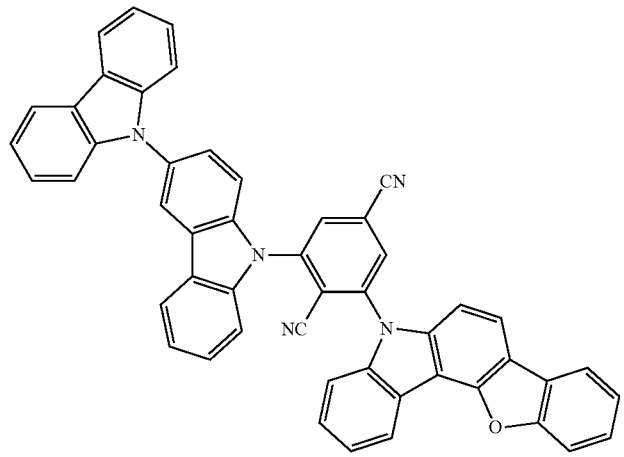
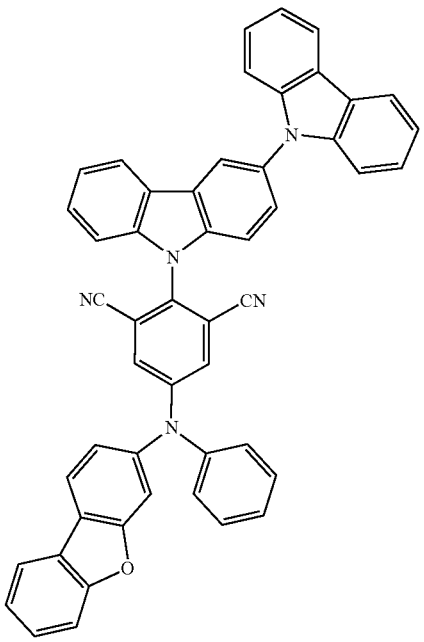
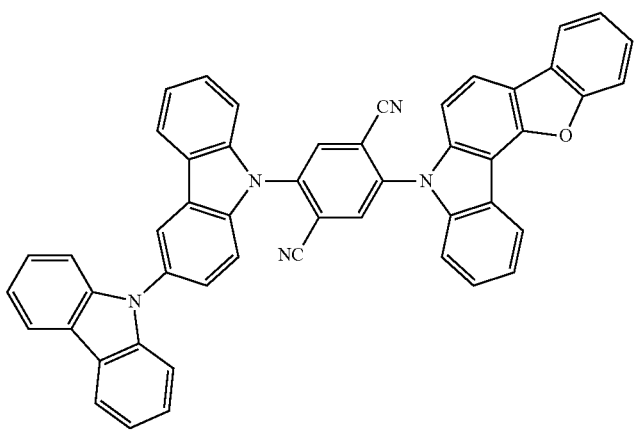
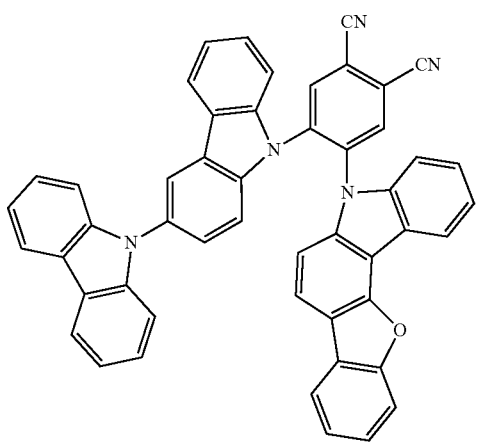
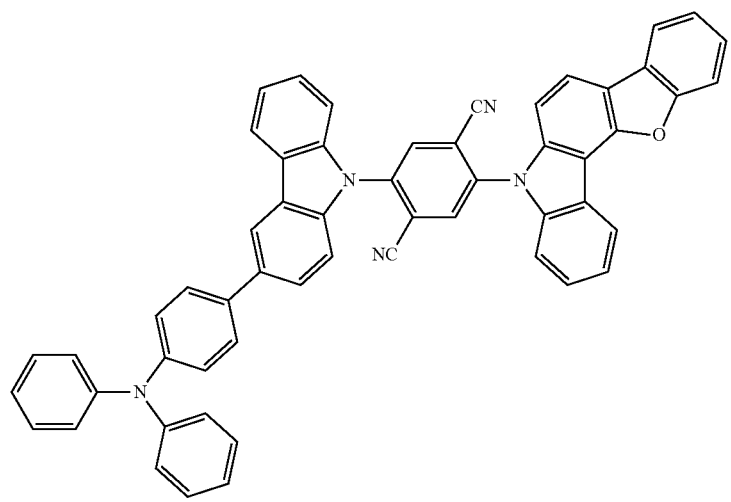

-continued
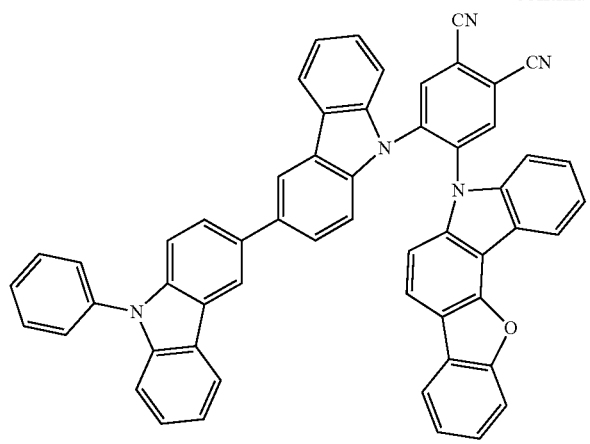
[Formula 173]
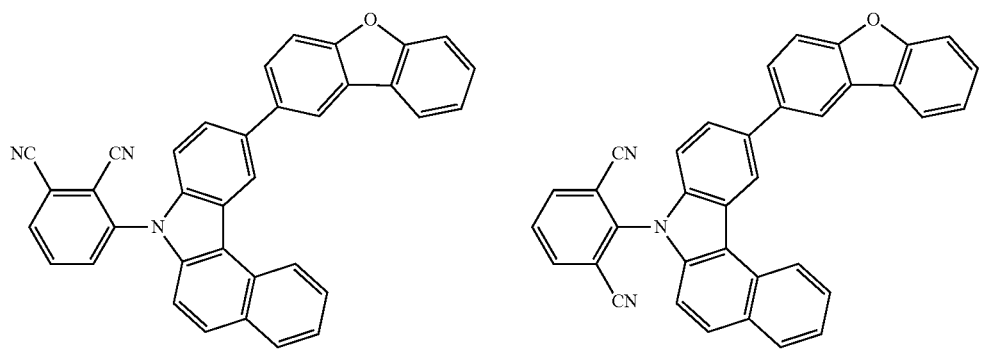
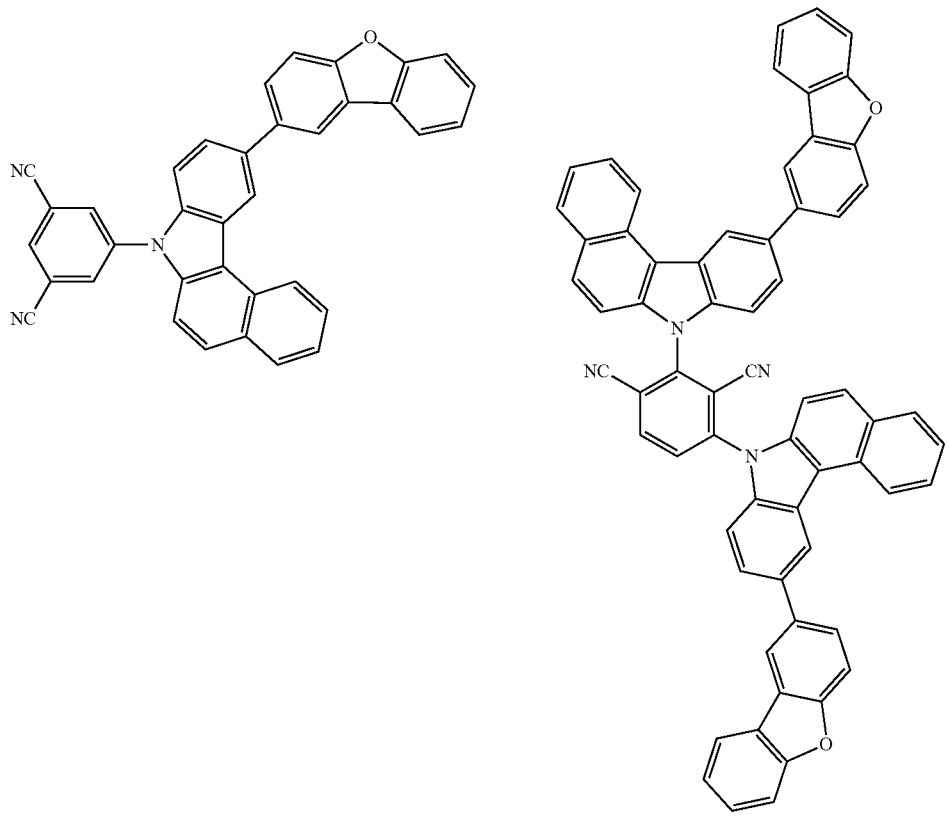

-continued
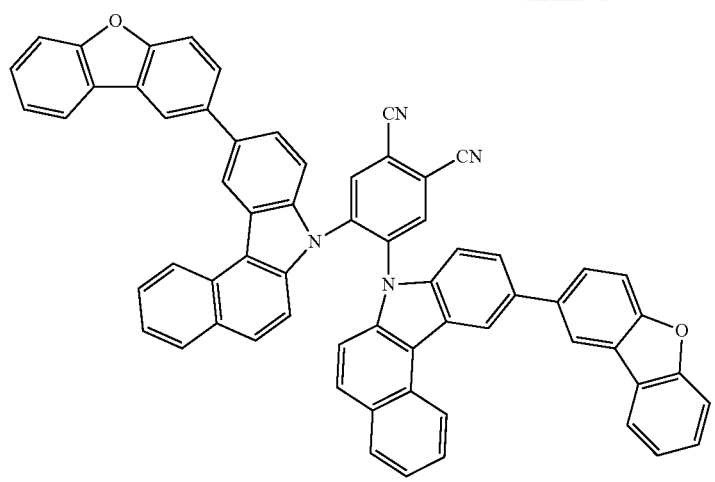
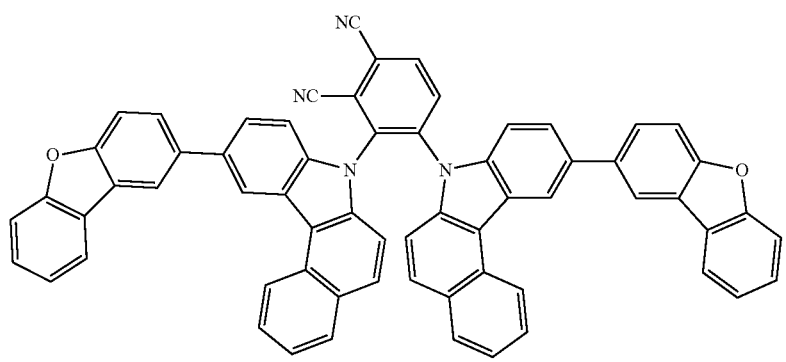
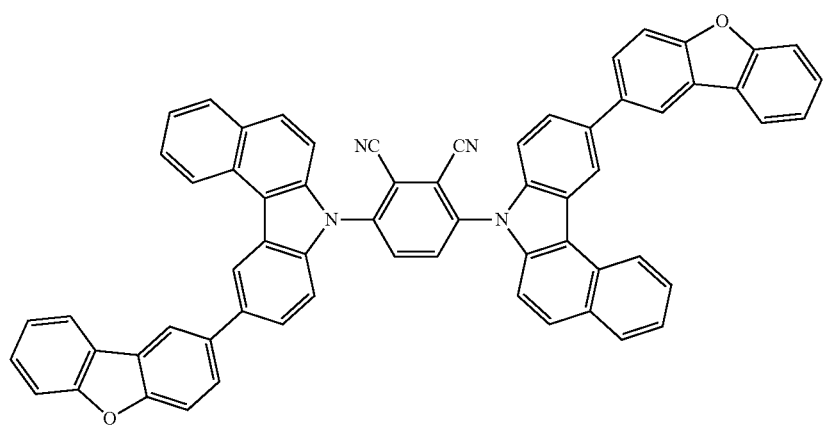

429
430
-continued
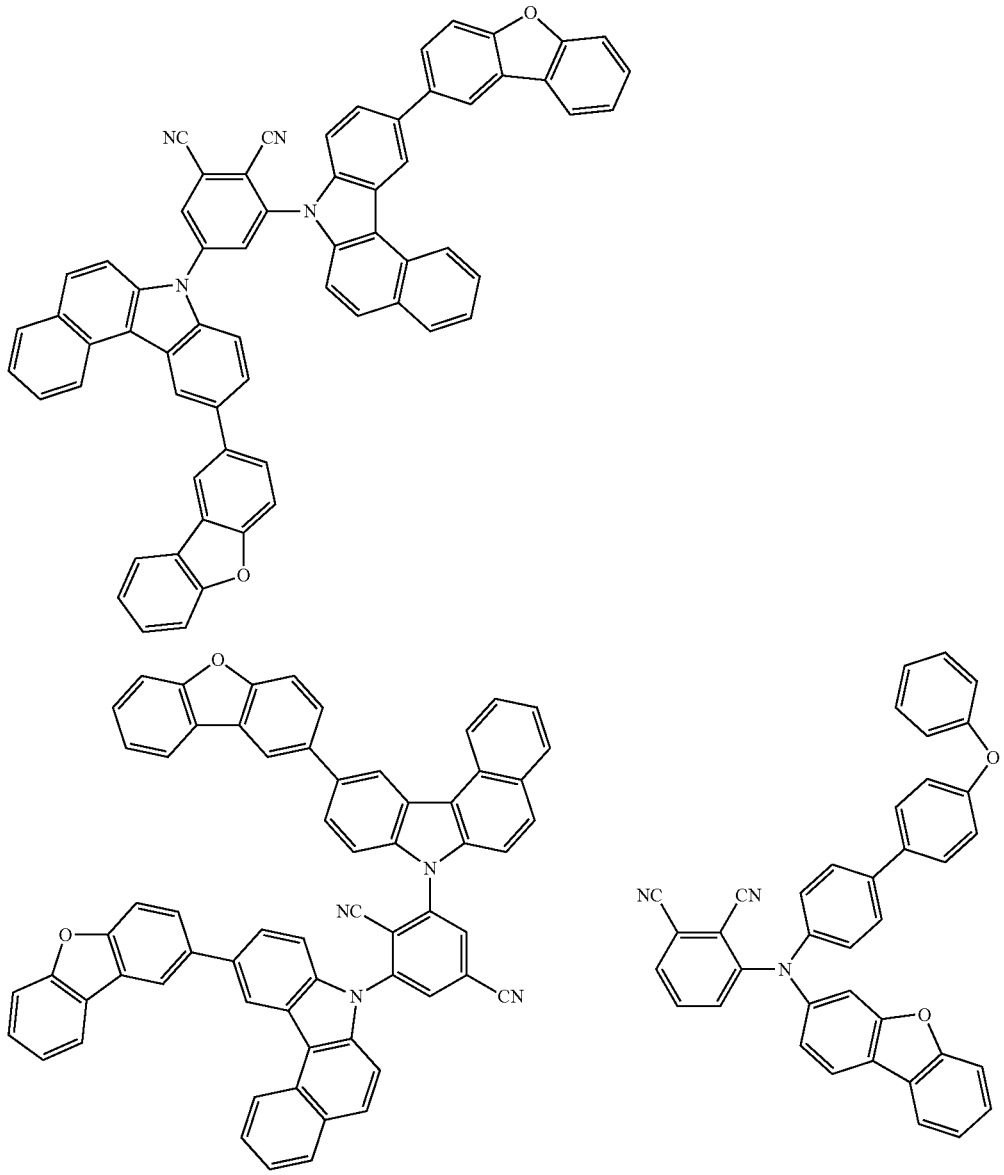
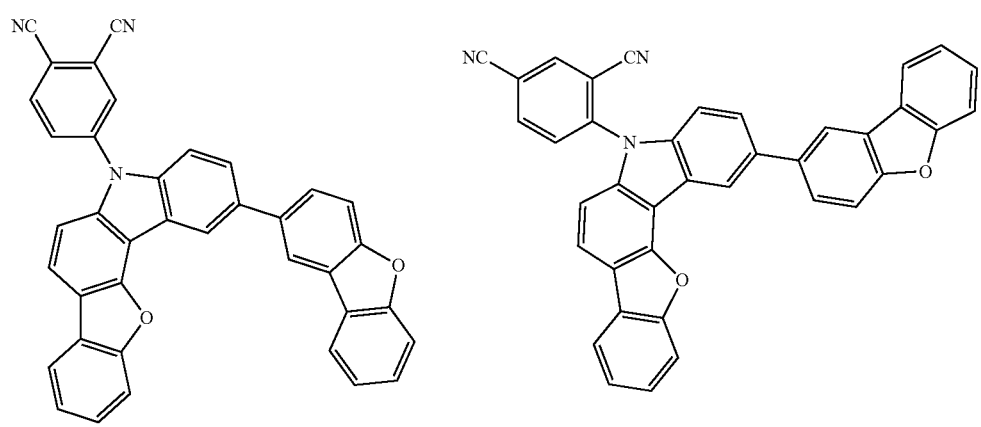

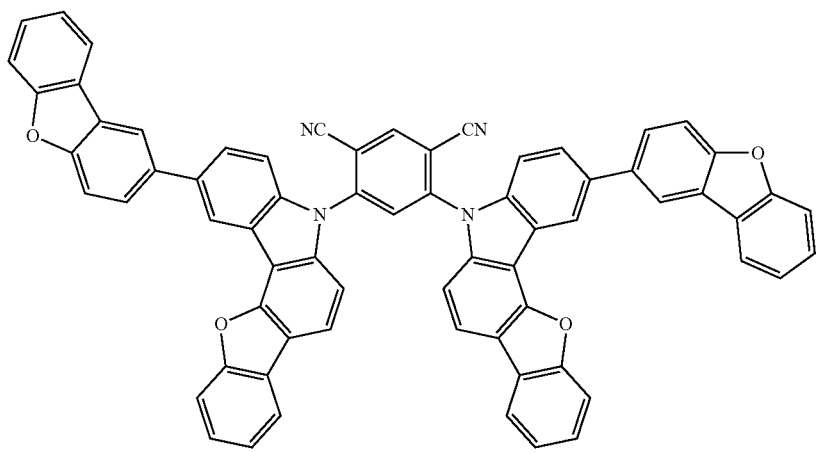
[Formula 174]
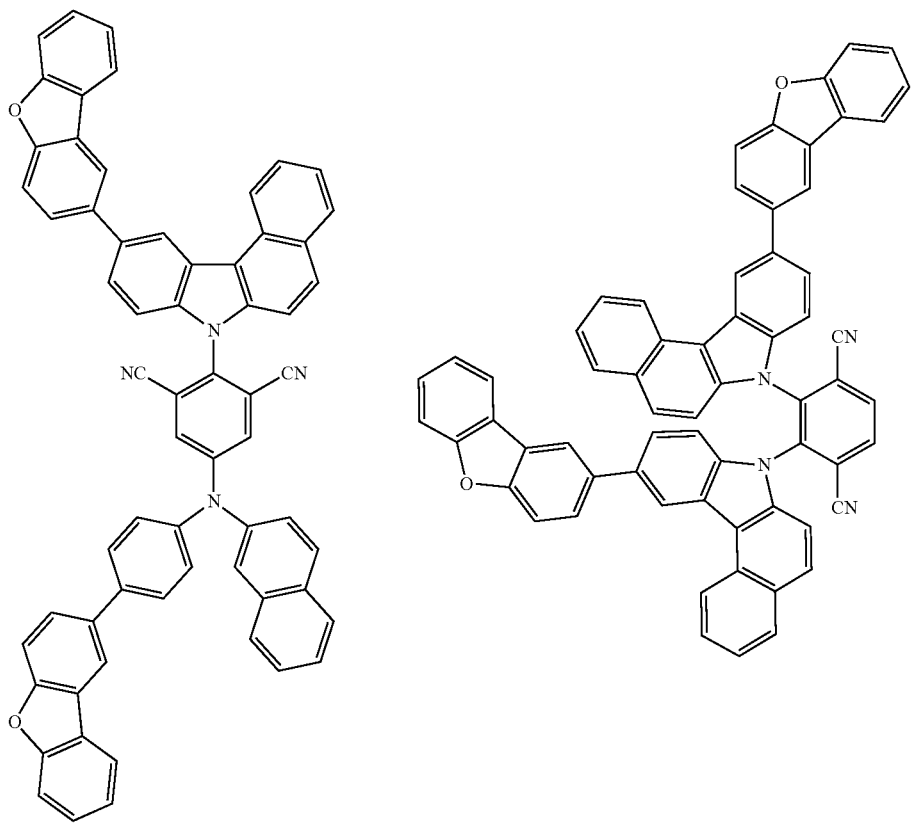

-continued
433
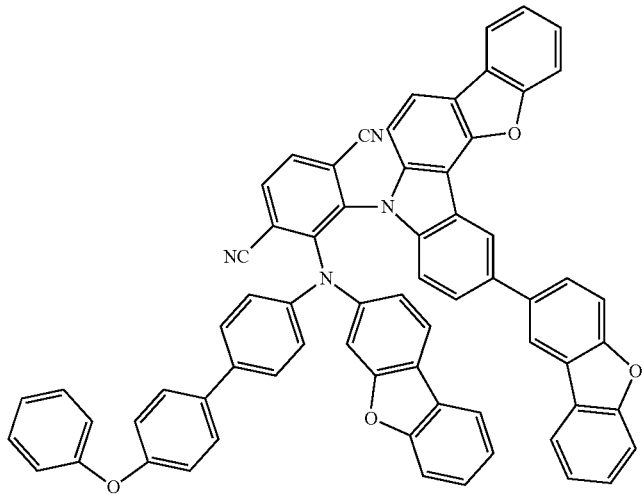
434
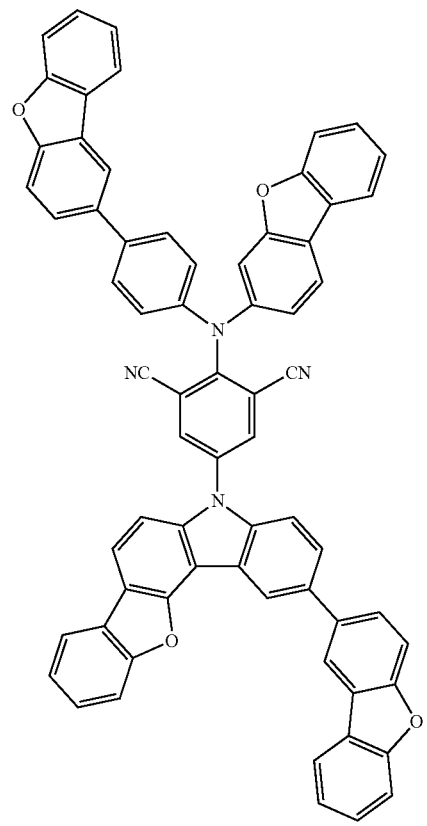
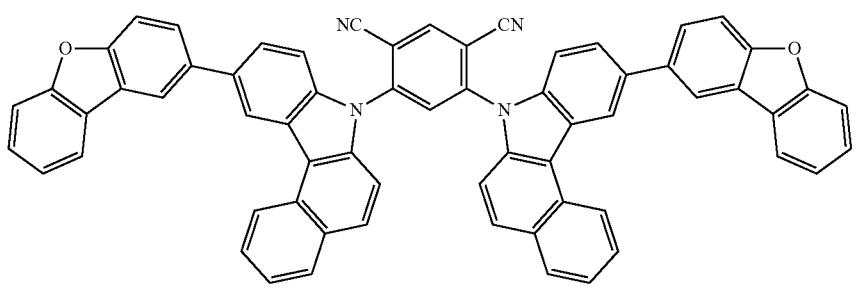

435
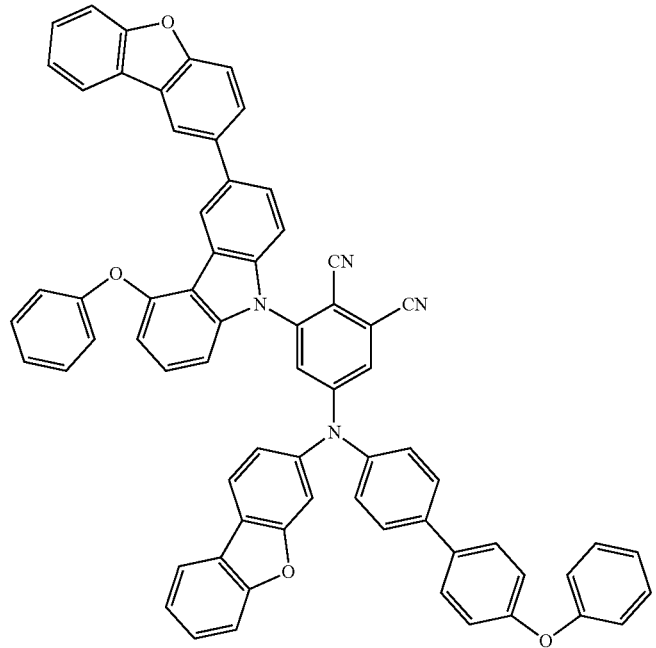
436
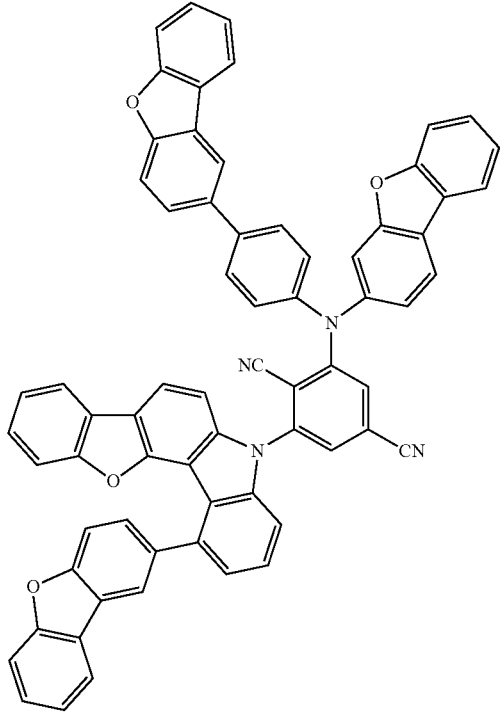
-continued
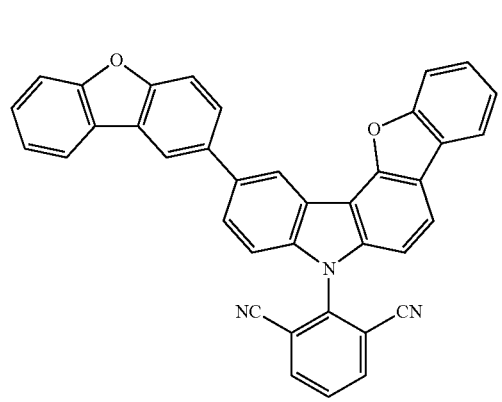
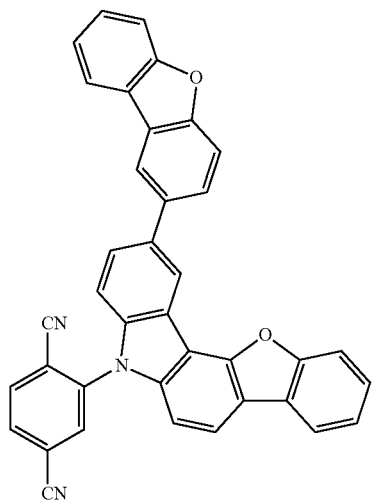

[Formula 175]
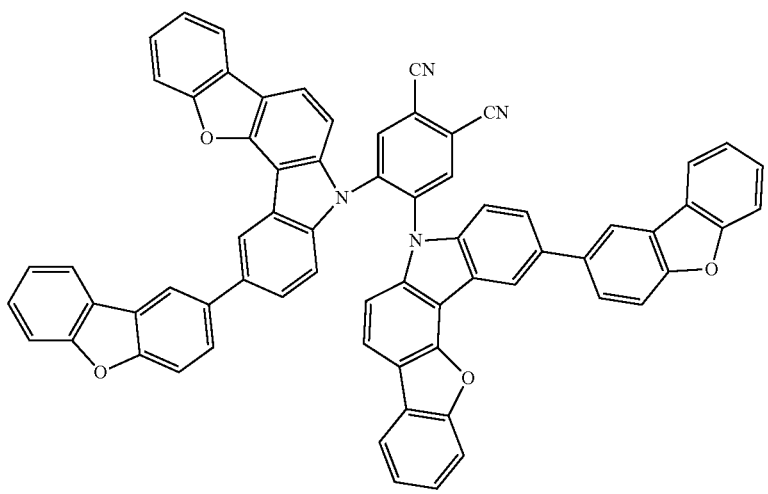
437
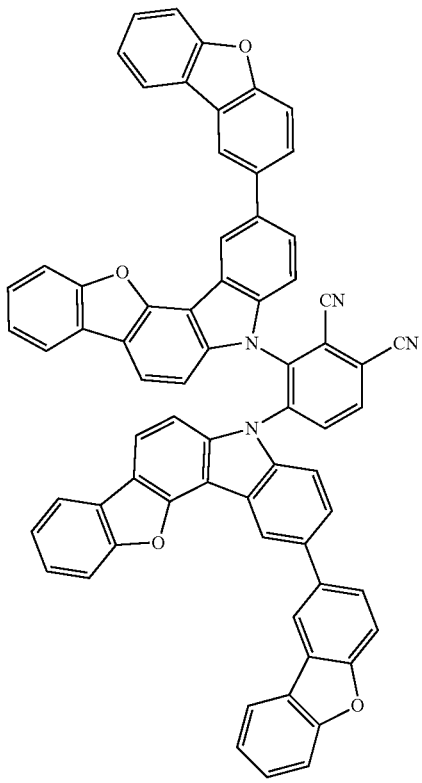
438
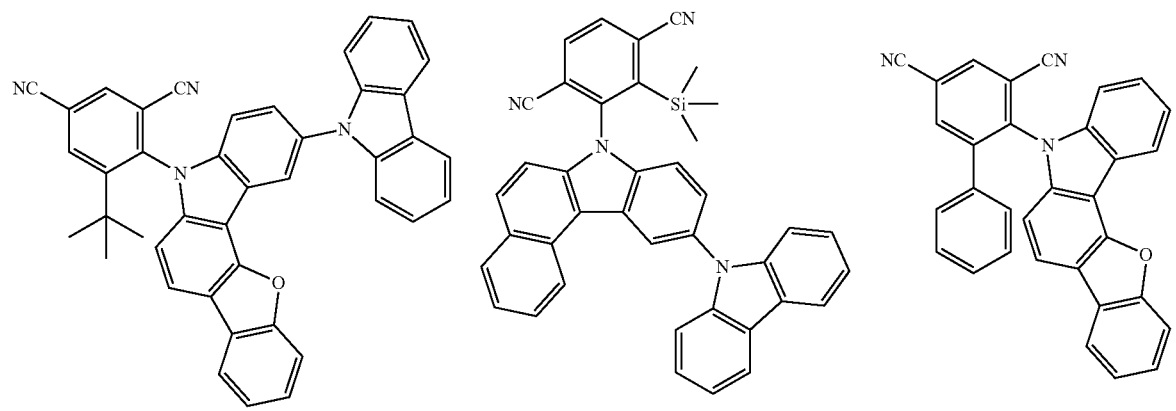

-continued
439
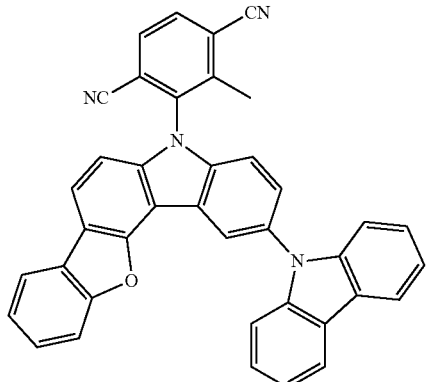
440
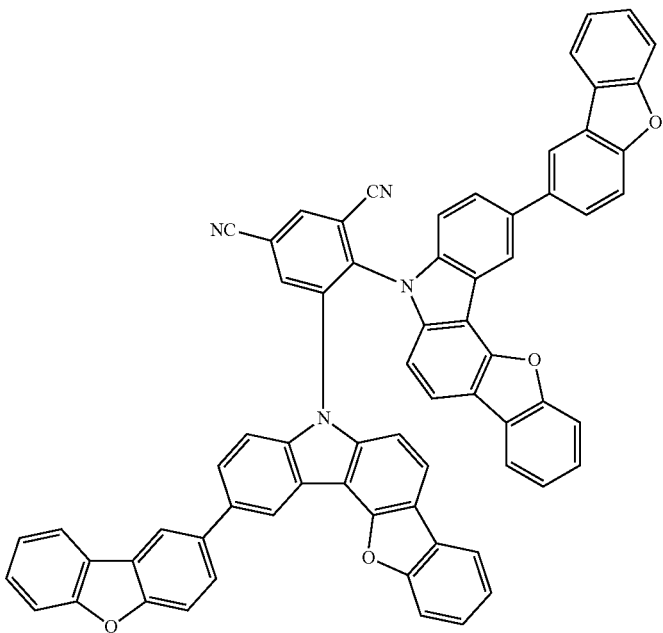
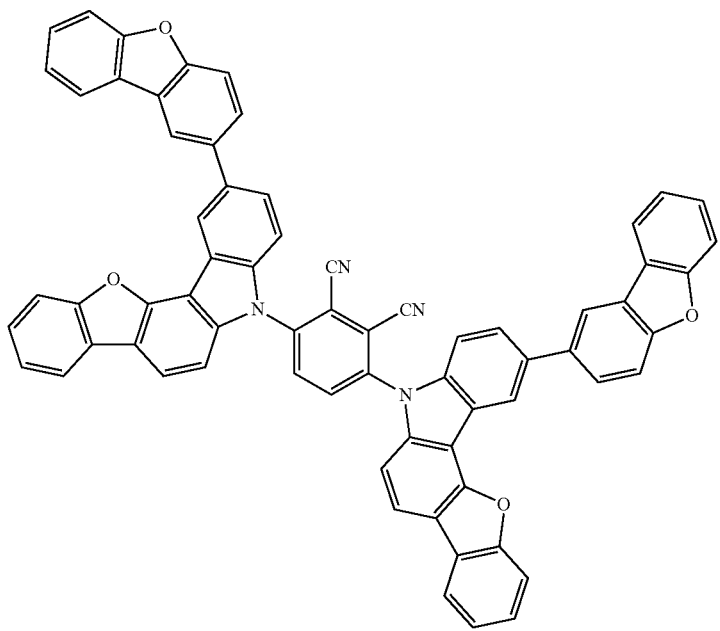

441
442
-continued
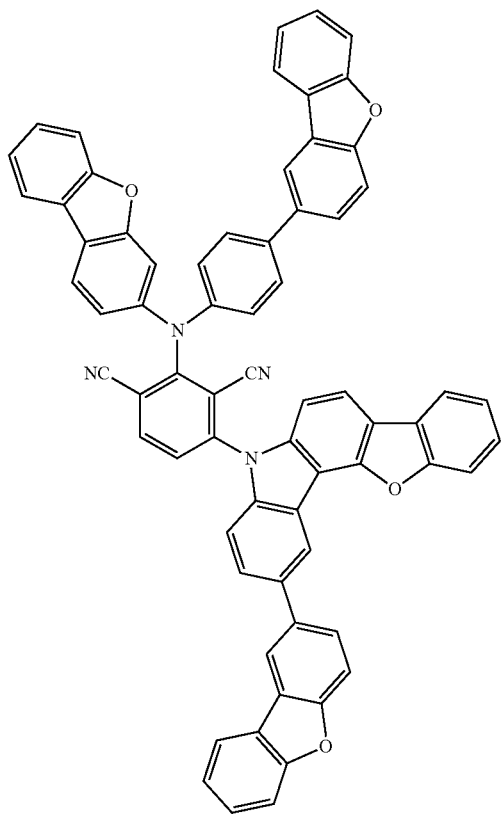
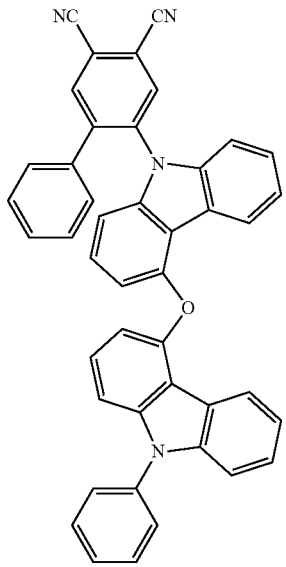
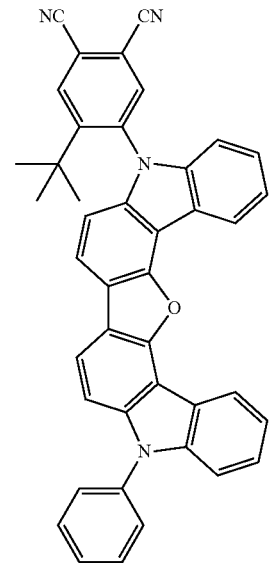
[Formula 176]
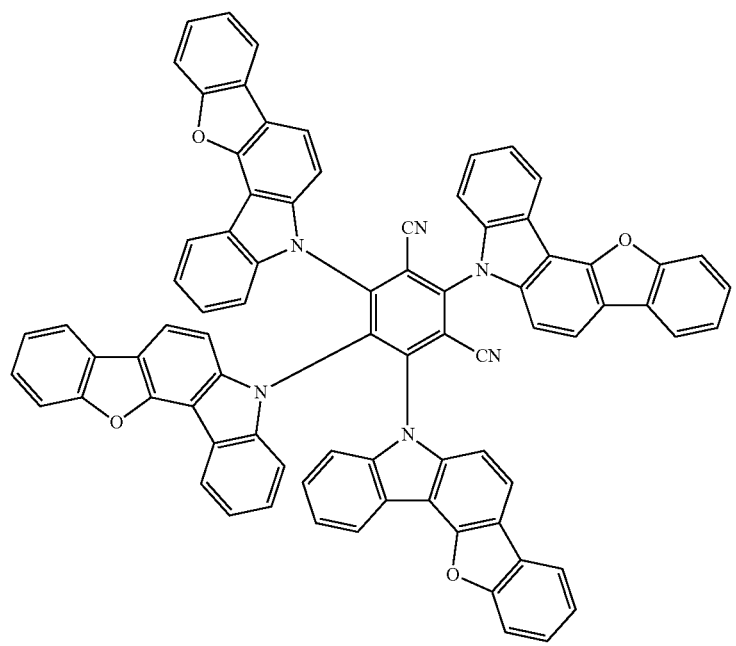

-continued
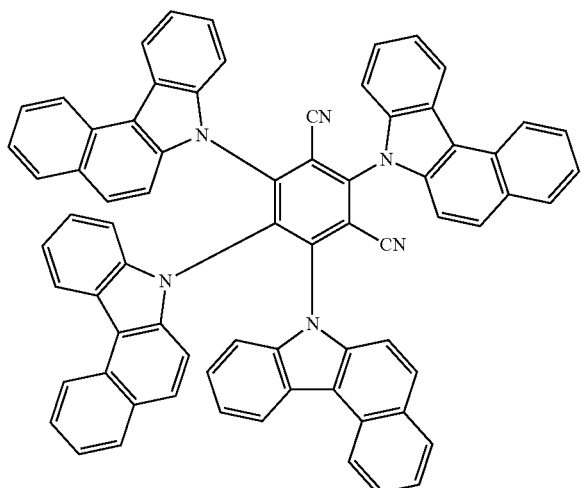
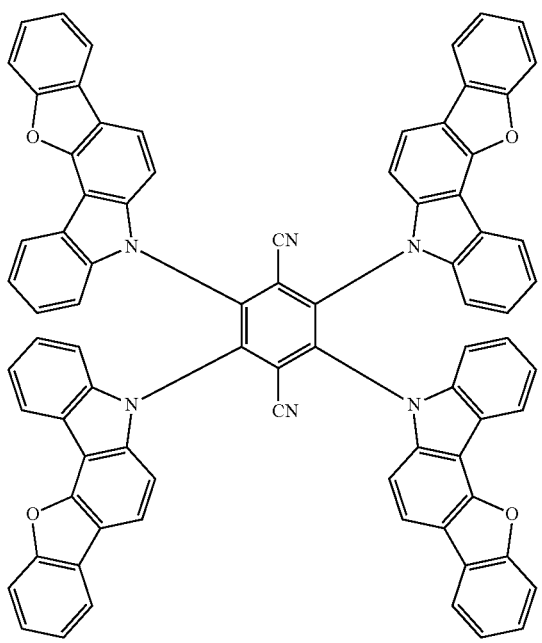
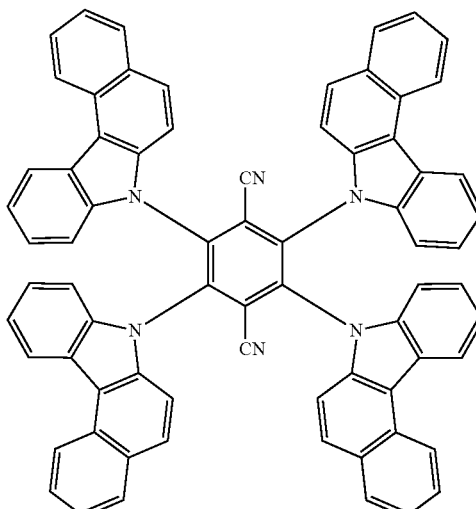
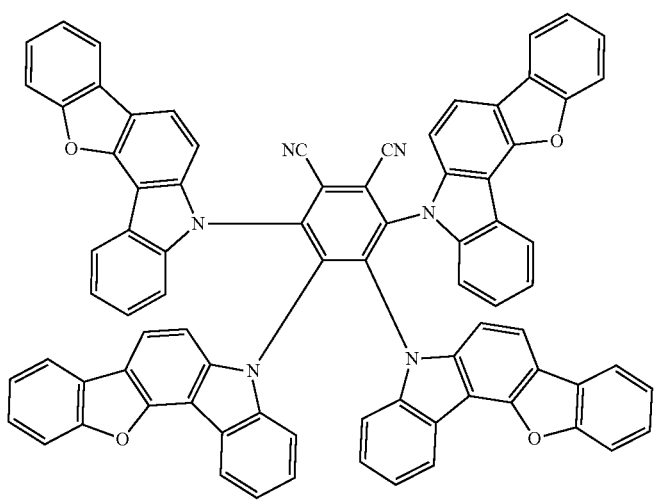

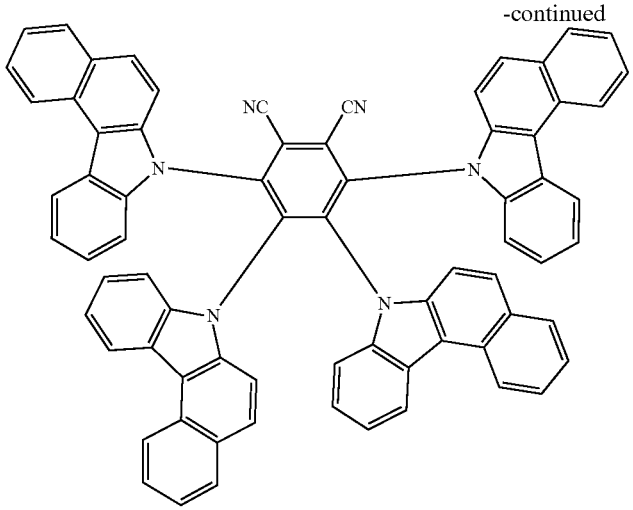

-continued

Material for Organic Electroluminescence Device

A material for an organic electroluminescence device (occasionally referred to as an organic EL device material) according to the first exemplary embodiment contains the compound according to the first exemplary embodiment. The organic EL device material may contain only the compound according to the first exemplary embodiment or may contain another compound.

In the organic EL device material of the first exemplary embodiment, the compound of the first exemplary embodiment to be contained is preferably a dopant material. In this arrangement, the organic EL device material may contain the compound of the first exemplary embodiment as the dopant material and another compound such as a host material.

In the organic EL device material of the first exemplary embodiment, the compound of the first exemplary embodiment to be contained is preferably a delayed fluorescence material.

Organic Electroluminescence Device

An organic EL device according to the first exemplary embodiment will be described.

The organic EL device includes a pair of electrodes and an organic layer between the pair of electrodes. The organic layer includes a layer formed of an organic compound. The organic EL device according to the exemplary embodiment includes at least one organic layer. The organic compound layer may further include an inorganic compound.

In the exemplary embodiment, at least one layer of the organic compound layer is an emitting layer. Accordingly, for instance, the organic layer may be provided by a single emitting layer. Alternatively, the organic layer may be provided by layers applied in an organic EL device such as a hole injecting layer, a hole transporting layer, an electron injecting layer, an electron transporting layer, a hole blocking layer and an electron blocking layer. In the first exemplary embodiment, at least one layer of the organic layer contains the above-described compound of the first exemplary embodiment.

The following are representative structure examples of an organic EL device:

(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode;
(e) anode/hole injecting•transporting layer/first emitting layer/second emitting layer/electron injecting•transporting layer/cathode; and
(f) anode/hole injecting•transporting layer/emitting layer/blocking layer/electron injecting•transporting layer/cathode.

While the arrangement (d) is preferably used among the above arrangements, the arrangement of the invention is not limited to the above arrangements.

It should be noted that the above-described "emitting layer" is an organic layer generally employing a doping system and including a first material and a second material. In general, the first material promotes recombination of electrons and holes and transmits excitation energy generated by recombination to the second material. The first material is often referred to as a host material. Accordingly, the first material is referred to as the host material in descriptions hereinafter. In general, the second material receives the excitation energy from the host material (the first material) to exhibit a high luminescent performance. The second material is often referred to as a dopant material or a guest material. Accordingly, the second material is referred to as the dopant material in descriptions hereinafter. The dopant material is preferably a compound having a high quantum efficiency.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

The "hole injecting•transporting layer (hole injecting/transporting layer)" means "at least one of a hole injecting layer and a hole transporting layer" while the "electron injecting•transporting layer (electron injecting/transporting layer)" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. Each of the hole injecting layer, hole transporting layer, electron transporting layer and electron injecting layer may be provided by a single layer or a plurality of layers.

In the first exemplary embodiment, when the compound of the first exemplary embodiment is contained in an emitting layer 5, the emitting layer 5 preferably contains no phosphorescent metal complex, more preferably contains no metal complex other than a phosphorescent metal complex.

ΔST

In the first exemplary embodiment, it is preferable that a difference ΔST(D) between singlet energy S(D) of the compound and an energy gap $T_{77K}(D)$ at 77K of the compound satisfies a numerical formula (Numerical Formula 1) below.

$$\Delta ST(D)=S(D)-T_{77K}(D)<0.3 \text{ [eV]} \qquad \text{(Numerical Formula 1)}.$$

ΔST(D) is preferably less than 0.2 [eV].

In the organic EL device material of the first exemplary embodiment, the compound of the first exemplary embodiment that satisfies the above ΔST(D) is preferably used.

Here, ΔST will be described.

In the organic EL device of the first exemplary embodiment, the above-described compound of the first exemplary embodiment is used as the dopant material. When a compound having a small energy difference (ΔST) between the singlet energy S and the triplet energy T is used as the dopant material, the organic EL device emits light at a high efficiency in a high current density region.

From quantum chemical viewpoint, a decrease in the energy difference (ΔST) between the singlet energy S and the triplet energy T can be achieved by a small exchange interaction therebetween. Physical details of the relationship between ΔST and the exchange interaction are described, for instance, in Reference Document 1 and Reference Document 2 below.

Reference Document 1: Organic EL Symposium, proceeding for the tenth meeting edited by Chihaya Adachi et al., S2-5, pp. 11-12

Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST to be used as the dopant material in the first exemplary embodiment are compounds in which a donor element is bonded to an acceptor element in a molecule and ΔST is in a range of 0 eV or more and less than 0.3 eV in terms of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV.

TADF Mechanism

As described above, when ΔST(D) of the compound is small, inverse intersystem crossing from the triplet level of the compound to the singlet level thereof is easily caused by heat energy given from the outside. An energy state conversion mechanism to perform spin exchange from the triplet state of electrically excited excitons within the organic EL device to the singlet state by inverse intersystem crossing is referred to as a TADF mechanism.

Currently, various arrangements of an organic EL device for emission by the TADF mechanism has been proposed. For instance, use of a compound having a small ΔST(D) as the host material and use of a compound having a small ΔST(D) as the dopant material have been proposed.

In the organic EL device material of the first exemplary embodiment, it is preferable to use the compound having a small ΔST(D) as the host material or the dopant material. Inverse intersystem crossing from the triplet energy level of the compound to the singlet energy level thereof is easily caused by heat energy given from the outside.

FIG. 2 shows a relationship in energy level between the host material and the dopant material in the emitting layer in the use of the compound having a small ΔST(D) as the dopant material. In FIG. 2, S0 represents a ground state, $S1_H$ represents the lowest singlet state of the host material, $T1_H$ represents the lowest triplet state of the host material, $S1_D$ represents the lowest singlet state of the dopant material, and $T1_D$ represents the lowest triplet state of the dopant material. A dashed arrow represents energy transfer between the states. As shown in FIG. 2, by using the compound having a small ΔST(D) as the dopant material, energy is transferred from the lowest triplet state $T1_H$ of the host material to the lowest singlet state $S1_D$ or the lowest triplet state $T1_D$ of the dopant material by Dexter transfer. Further, inverse intersystem crossing from the lowest triplet state $T1_D$ to the lowest singlet state $S1_D$ of the dopant material is possible by heat energy. As a result, fluorescent emission from the lowest singlet state $S1_D$ of the dopant material can be observed. It is inferred that the internal quantum efficiency can be theoretically raised up to 100% also by using delayed fluorescence by the TADF mechanism.

Relationship Between Triplet Energy T and $T_{77K}$

The above-described triplet energy T is different from a typically defined triplet energy. Such a difference will be described below.

The triplet energy is measured as follows. Firstly, a compound (a measurement target) is deposited on a quartz substrate to prepare a sample. As for this sample, the triplet energy is obtained by measuring this sample at a low temperature (77K) in terms of phosphorescence spectrum expressed in coordinates of which the ordinate axis indicates the phosphorescence intensity and of which the abscissa axis indicates the wavelength, drawing a tangent to the rise of the phosphorescence spectrum on the shorter wavelength side, and calculating from a predetermined conversion equation based on a wavelength value at an intersection of the tangent and the abscissa axis.

Here, the compound used for the dopant material in the exemplary embodiment is preferably the compound having a small ΔST(D) as described above. When ΔST(D) is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the first exemplary embodiment, the spectrum is measured by the same method as that for measuring a typical triplet energy T, but an amount of the triplet energy measured in the following manner is referred to as an energy gap $Eg_{77K}$ in order to differentiate the measured energy from a typical triplet energy T in a strict meaning. A compound (a measurement target) is deposited at a 100-nm film thickness on a quartz substrate to prepare a sample. The energy gap $T_{77K}$ of this sample is obtained by measuring this sample at a low temperature (77K) in terms of phosphorescence spectrum expressed in coordinates of which the ordinate axis indicates the phosphorescence intensity and of which the abscissa axis indicates the wavelength, drawing a tangent to the rise of the phosphorescence spectrum on the shorter wavelength side, and calculating from the following conversion equation 1 based on a wavelength value $\lambda_{edge}$[nm] at an intersection of the tangent and the abscissa axis.

$$T_{77K}[eV]=1239.85/\lambda_{edge} \qquad \text{Conversion Equation 1:}$$

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Singlet Energy S

The singlet energy S is measured as follows.

A compound (a measurement target) is deposited at a 100-nm film thickness on a quartz substrate to prepare a sample. An emission spectrum of the sample is measured at a normal temperature (300K), the spectrum being expressed in coordinates of which the ordinate axis indicates luminous intensity and of which the abscissa axis indicates the wavelength. A tangent is drawn to the rise of the emission spectrum on the short-wavelength side. The singlet energy S is calculated from the following conversion equation 2 based on a wavelength value $\lambda_{edge}$[nm] at an intersection of the tangent and the abscissa axis.

$$S\ [eV]=1239.85/\lambda_{edge} \qquad \text{Conversion Equation 2:}$$

Absorption spectrum is measured by a spectrophotometer. For instance, a spectrophotometer (product name: U3310) manufactured by Hitachi, Ltd. is usable.

The tangent to the rise of the emission spectrum on the short-wavelength side is drawn as follows. While moving on a curve of the emission spectrum from the short-wavelength side to the maximum spectral value closest to the short-wavelength side among the maximum spectral values, a tangent is checked at each point on the curve toward the long-wavelength of the emission spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the emission spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the emission spectrum on the short-wavelength side.

In the first exemplary embodiment, a difference between the singlet energy S and the energy gap $T_{77K}$ is defined as $\Delta ST$. Accordingly, in the first exemplary embodiment, $\Delta ST$ (D) of the dopant material is preferably represented by Numerical Formula (1) above.

Host Material in Emitting Layer

When the compound of the first exemplary embodiment is used as the dopant material, the host material preferably has a larger triplet level than that of the compound of the first exemplary embodiment. Examples of the compound suitable for the host material include an aromatic hydrocarbon derivative, heterocyclic derivative, arylamine derivative, porphyrin compound, various metal complexes, phosphorus compound and high-molecular compound. Specific examples of the compound suitable for the host material include compounds below.

Examples of the aromatic hydrocarbon derivative include compounds having a high triplet level such as benzene, naphthalene, phenanthrene, triphenylene and fluorene.

Examples of the heterocyclic derivative include: a pyrrole derivative, indole derivative, carbazole derivative, furan derivative, benzofuran derivative, dibenzofuran derivative, thiophene derivative, benzothiophene derivative, dibenzothiophene derivative, triazole derivative, oxazole derivative, oxadiazole derivative, imidazole derivative, benzimidazole derivative, imidazopyridine derivative, and indolizine derivative.

Examples of the porphyrin compound include a compound such as a phthalocyanine derivative.

Examples of the metal complexes include a metal complex of a quinolinol derivative and a metal complex having phthalocyanine, benzoxazole and benzothiazole as a ligand.

Examples of the phosphorus compound include a compound such as phosphine oxide.

Examples of the high-molecular compound include a poly(N-vinylcarbazole) derivative, aniline copolymer, thiophene oligomer, conductive polymer oligomer such as polythiophene, polythiophene derivative, polyphenylene derivative, polyphenylenevinylene derivative, and polyfluorene derivative.

As the host material, one of the various compounds may be used alone, or alternatively, two or more thereof may be used in combination.

Dopant Material in Emitting Layer

When the compound of the first exemplary embodiment is used as the host material, for instance, the following fluorescent material is usable as the dopant material.

An aromatic amine derivative and the like are usable as a green fluorescent material. Specific examples of the green fluorescent material include N-(9,10-diphenyl-2-anthryl)-N, 9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9, 10-diphenyl-2-anthryl)-N,N',N'-triphenyl-1,4-phenylene diamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

A tetracene derivative, diamine derivative and the like are usable as a red fluorescent material. Specific examples of the red fluorescent material include N,N,N',N'-tetrakis(4-methylphenyl)tetracene-5,11-diamine (abbreviation: p-mPhTD), and 7,14-diphenyl-N,N,N',N'-tetrakis(4-methylphenyl)acenaphtho[1,2-a]fluoranthene-3,10-diamine (abbreviation: p-mPhAFD).

In the first exemplary embodiment, the energy gap $T_{77K}$ (H1) at 77K of the compound usable as the host material is preferably larger than the energy gap $T_{77K}$(D) at 77K of the compound usable as the dopant material.

The thickness of the emitting layer is preferably in a range from 5 nm to 50 nm, more preferably from 7 nm to 50 nm, further preferably from 10 nm to 50 nm. The thickness of less than 5 nm may cause difficulty in forming the emitting layer and in controlling chromaticity, while the thickness of more than 50 nm may raise drive voltage.

In the emitting layer, a ratio of the host material and the dopant material is preferably in a range of 99:1 to 50:50 at a mass ratio.

Substrate

A substrate is used as a support for the organic EL device. For instance, glass, quartz, plastics and the like are usable as the substrate. A flexible substrate is also usable. The flexible substrate is a bendable substrate, which is exemplified by a plastic substrate formed of polycarbonate, polyarylate, polyethersulfone, polypropylene, polyester, polyvinyl fluoride, and polyvinyl chloride. Moreover, an inorganic vapor deposition film is also usable.

Anode

Metal, alloy, an electrically conductive compound and a mixture thereof, which have a large work function, specifically, of 4.0 eV or more, is preferably usable as the anode formed on the substrate. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vapor deposition, coating, ink jet printing, spin coating and the like may be used for forming a film.

Among EL layers formed on the anode, a hole injecting layer formed adjacent to the anode is formed of a composite material that facilitates injection of holes irrespective of the work function of the anode. Accordingly, a material usable as an electrode material (e.g., metal, alloy, an electrically conductive compound, a mixture thereof, and elements belonging to Groups 1 and 2 of the periodic table of the elements) is usable as the material for the anode.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), alloy thereof (e.g., MgAg, AlLi), a rare earth metal such as europium (Eu) and ytterbium (Yb), and alloy thereof are also usable as the material for the anode. When the anode is formed of the alkali metal, alkaline earth metal and alloy thereof, vapor deposition and sputtering are usable. Further, when the anode is formed of silver paste and the like, coating, ink jet printing and the like are usable.

Cathode

Metal, alloy, an electrically conductive compound, a mixture thereof and the like, which have a small work function, specifically, of 3.8 eV or less, is preferably usable as a material for the cathode. Specific examples of the material for the cathode include: the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr); alloy thereof (e.g., MgAg, AlLi); a rare earth metal such as europium (Eu) and ytterbium (Yb); and alloy thereof.

When the cathode is formed of the alkali metal, alkaline earth metal and alloy thereof, vapor deposition and sputtering are usable. Moreover, when the anode is formed of silver paste and the like, coating, ink jet printing and the like are usable.

By providing an electron injecting layer, various conductive materials such as Al, Ag, ITO, graphene and indium tin oxide containing silicon or silicon oxide are usable for forming the cathode irrespective of the magnitude of the work function. The conductive materials can be deposited as a film by sputtering, ink jet printing, spin coating and the like.

Hole Injecting Layer

A hole injecting layer is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include an aromatic amine compound that is a low-molecular compound such 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

Moreover, a high-molecular compound (e.g., an oligomer, dendrimer and polymer) is also usable as the highly hole-injectable substance. Examples of the high-molecular compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamido] (abbreviation: PTPDMA), and poly[N,N'-bis(4-butylphenyl)-N,N'-bis(phenyl)benzidine] (abbreviation: Poly-TPD). Furthermore, the examples of the high-molecular compound include a high-molecular compound added with an acid such as poly (3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer is a layer containing a highly hole-transportable substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/Vs or more.

A carbazole derivative such as CBP, CzPA and PCzPA and an anthracene derivative such as t-BuDNA, DNA, DPAnth may be used for the hole transporting layer. Moreover, a high-molecular compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used in addition to the above substances. A a highly hole-transportable substance may be provided by a single layer or a laminated layer of two layers or more formed of the above substance.

Electron Transporting Layer

An electron transporting layer is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecular compound are usable. Specifically, as a low-molecular organic compound, a metal complex such as Alq, tris(4-methyl-8-quinolinato)aluminum (abbreviation: Almq$_3$), bis(10-hydroxybenzo[h]quinolinato)beryllium (abbreviation: BeBq$_2$), BAlq, Znq, ZnPBO and ZnBTZ are usable. In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. The above-described substances mostly have an electron mobility of $10^{-6}$ cm$^2$/Vs or more. However, any substance having an electron transporting performance higher than a hole transporting performance may be used for the electron transporting layer in addition to the above substances. The electron transporting layer may be provided by a single layer or a laminated layer of two layers or more formed of the above substances.

Moreover, a high-molecular compound is also usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

An electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode.

Alternatively, a composite material provided by mixing an organic compound with an electron donor may be used for the electron injecting layer. The composite material exhibits excellent electron injecting performance and electron transporting performance since the electron donor generates electrons in the organic compound. In this arrangement, the organic compound is preferably a material exhibiting an excellent transporting performance of the generated electrons. Specifically, for instance, the above-described substance for the electron transporting layer (e.g., the metal complex and heteroaromatic compound) is usable. The electron donor may be any substance exhibiting an electron donating performance to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Layer Formation Method(s)

A method for forming each layer of the organic EL device is subject to no limitation except for the above particular description. However, known methods of dry film-forming such as vacuum deposition, sputtering, plasma or ion plating and wet film-forming such as spin coating, dipping, flow coating or ink-jet are applicable.

Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Modifications of Embodiment(s)

It should be noted that the invention is not limited to the above exemplary embodiment but may include any modification and improvement as long as such modification and improvement are compatible with the invention.

The emitting layer is not limited to a single layer, but may be provided as laminate by a plurality of emitting layers. When the organic EL device includes a plurality of emitting layers, it is only required that at least one of the emitting layers includes the compound represented by the formula (1). The others of the emitting layers may be a fluorescent emitting layer or a phosphorescent emitting layer.

When the organic EL device includes the plurality of emitting layers, the plurality of emitting layers may be adjacent to each other or a so-called tandem organic EL device in which a plurality of emitting units are laminated through an intermediate layer.

An arrangement in which the plurality of emitting layers are laminated is exemplified by an organic EL device 1A shown in FIG. 3. The organic EL device 1A includes an organic layer 10A. The organic layer 10A is different from the organic EL device 1 shown in FIG. 1 in including a first emitting layer 51 and a second emitting layer 52 between a hole injecting/transporting layer 6 and an electron injecting/transporting layer 7. At least one of the first emitting layer 51 and the second emitting layer 52 contains the compound represented by the formula (1). Except for the above point, the organic EL device 1A is arranged in the same manner as the organic EL device 1.

For instance, an electron blocking layer may be provided adjacent to a side of the emitting layer near the anode and a hole blocking layer may be provided adjacent to a side of the emitting layer near the cathode. With this arrangement, electrons and holes can be confined in the emitting layer, thereby enhancing probability of exciton generation in the emitting layer.

The organic EL device according to the first exemplary embodiment is usable for a display unit and electronic equipment such as a light-emitting unit. Examples of the display unit include a display component (e.g., en organic EL panel module), TV, mobile phone, tablet and personal computer. Examples of the light-emitting unit include an illuminator and a vehicle light.

Further, specific arrangements and configurations for practicing the invention may be altered to other arrangements and configurations as long as such other arrangements and configurations are compatible with the invention.

EXAMPLES

Examples of the invention will be described below. However, the invention is not limited by these Examples.

Example 1: Synthesis of Compound 1

A synthesis scheme of a compound 1 is shown below.

[Formula 177]

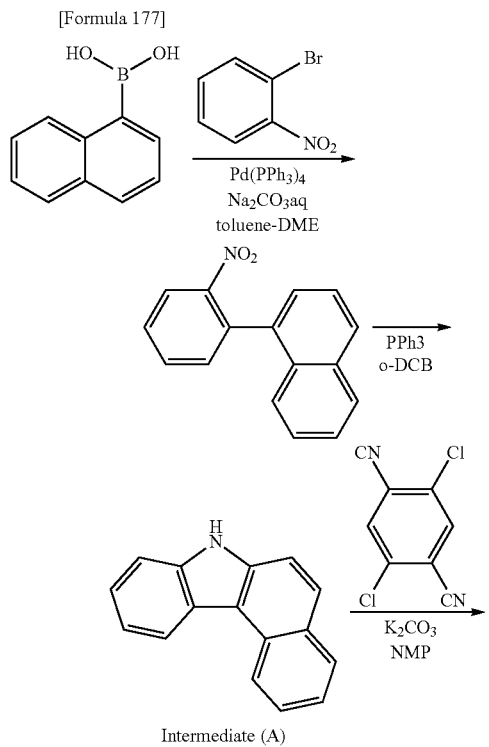

Intermediate (A)

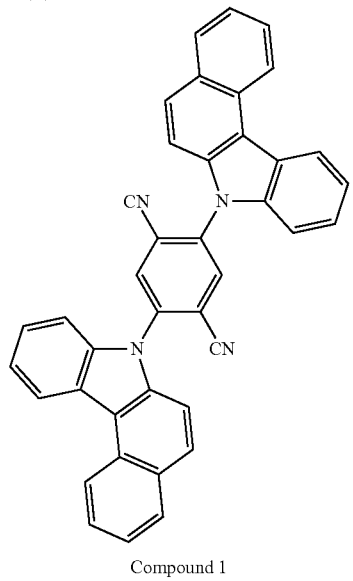

Compound 1

(1-1) Synthesis of 1-(2-nitrophenyl)naphthalene

Under nitrogen atmosphere, 18.5 g of 1-naphthaleneboronic acid, 18.2 g of 1-bromo-2-nitrobenzene, 3.12 g of tetrakis(triphenylphosphine)palladium(0), 144 mL of toluene, 144 mL of 1,2-dimethoxyethane, and 150 mL of 2M sodium carbonate aqueous solution were put into a flask and heated to reflux for nine hours while being stirred. After cooled down to the room temperature, the reaction solution was filtered and a solvent was distilled away under reduced pressure. The obtained residue was refined by silica-gel column chromatography, whereby 19.9 g (yield 89%) of a light yellow solid of 1-(2-nitrophenyl)naphthalene was obtained. It should be noted that 1,2-dimethoxyethane is occasionally abbreviated as DME.

(1-2) Synthesis of Intermediate (A)

Under nitrogen atmosphere, 19.9 g of 1-(2-nitrophenyl)naphthalene, 52.2 g of triphenylphosphine, and 163 mL of ortho-dichlorobenzene were put into a flask and heated to reflux for 32 hours while being stirred. After cooled down to the room temperature, the reaction solution was filtered and a solvent was distilled away under reduced pressure. The obtained residue was refined by silica-gel column chromatography, whereby 15.4 g (yield 90%) of a yellow solid of an intermediate (A) was obtained. It should be noted that ortho-dichlorobenzene is occasionally abbreviated as o-DCB.

(1-3) Synthesis of Compound 1

Under nitrogen atmosphere, 15.4 g of the intermediate (A), 6.64 g of 2,5-dichloroterephthalonitrile, 10.2 g of potassium carbonate, 112 mL of N-methyl-2-pyrrolidinone were put into a flask and stirred at 100 degrees C. for six hours and subsequently at 150 degrees C. for nine hours. After cooled down to the room temperature, the reaction solution was extracted with toluene. After an aqueous layer was removed, an organic layer was washed with a saturated ammonium chloride aqueous solution. After dried with magnesium sulfate, the organic layer was concentrated. The obtained residue was refined by silica-gel column chromatography, whereby 5.27 g (yield 28%) of a yellow solid of a compound 1 was obtained. It should be noted that N-methyl-2-pyrrolidinone is occasionally abbreviated as NMP.

Example 2: Synthesis of Compound 2

A synthesis scheme of a compound 2 is shown below.

[Formula 178]

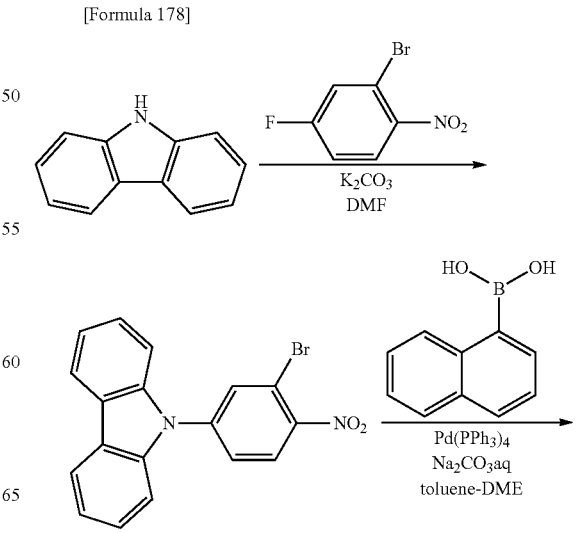

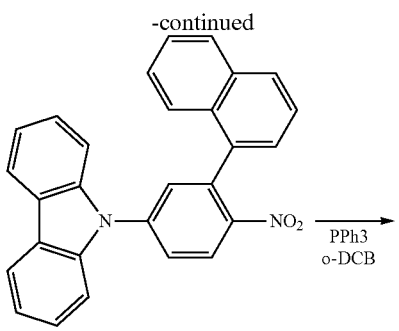

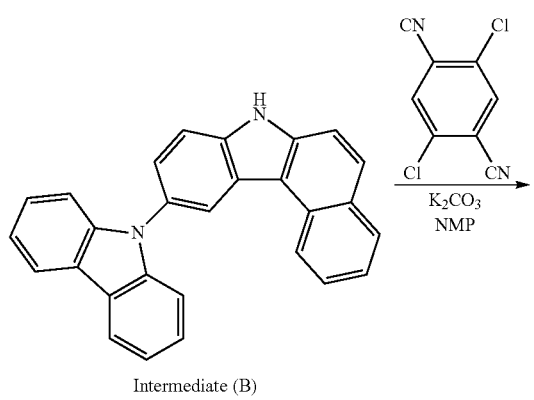

Intermediate (B)

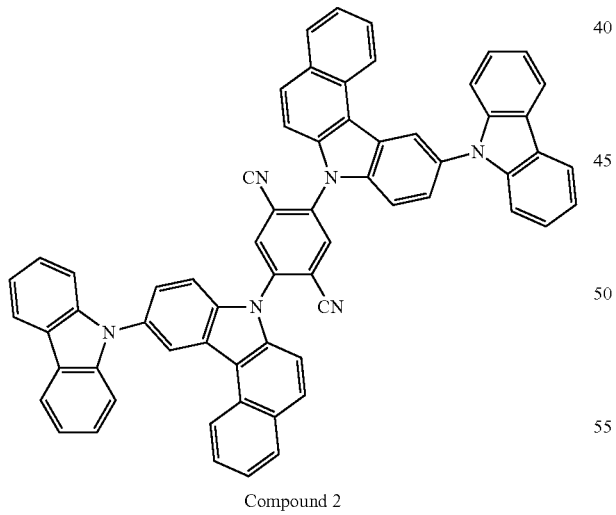

Compound 2

(2-1) Synthesis of 2-bromo-4-(9-carbazolyl)-1-nitrobenzene

Under nitrogen atmosphere, 7.52 g of carbazole, 11.8 g of 2-bromo-4-fluoro-1-nitrobenzen, 15.0 g of potassium carbonate and 150 mL of N,N-dimethylformamide were put into a flask and heated to reflux for 24 hours while being stirred. After cooled down to the room temperature, the reaction solution was extracted with toluene. After an aqueous layer was removed, an organic layer was washed with a saturated ammonium chloride aqueous solution. After dried with magnesium sulfate, the organic layer was concentrated and washed with methanol, whereby 14.2 g (yield 86%) of a yellow orange solid of 2-bromo-4-(9-carbazolyl)-1-nitrobenzene was obtained. It should be noted that N,N-dimethylformamide is occasionally abbreviated as DMF.

(2-2) Synthesis of 1-[2-nitro-5-(9-carbazolyl)phenyl]naphthalene

1-[2-nitro-5-(9-carbazolyl)phenyl]naphthalene was synthesized in the same manner as in the synthesis (1-1) of 1-(2-nitrophenyl)naphthalene, except for using 2-bromo-4-(9-carbazolyl)-1-nitrobenzene in place of 1-bromo-2-nitrobenzene.

(2-3) Synthesis of Intermediate (B)

An intermediate (B) was synthesized in the same manner as in the synthesis (1-2) of the intermediate (A), except for using 1-[2-nitro-5-(9-carb azolyl)phenyl]naphthalene in place of 1-(2-nitrophenyl]naphthalene.

(2-4) Synthesis of Compound 2

A compound 2 was synthesized in the same manner as in the synthesis (1-3) of the compound 1, except for using the intermediate (B) in place of the intermediate (A).

Example 3: Synthesis of Compound 3

A synthesis scheme of a compound 3 is shown below.

[Formula 179]

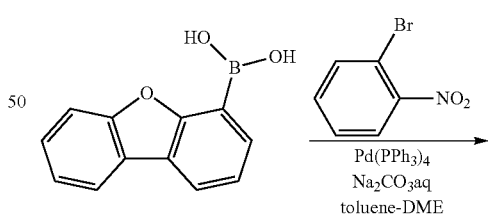

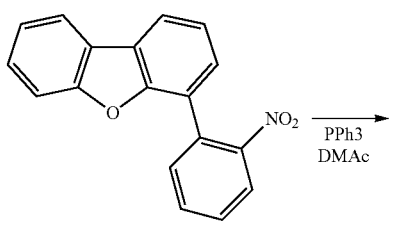

-continued

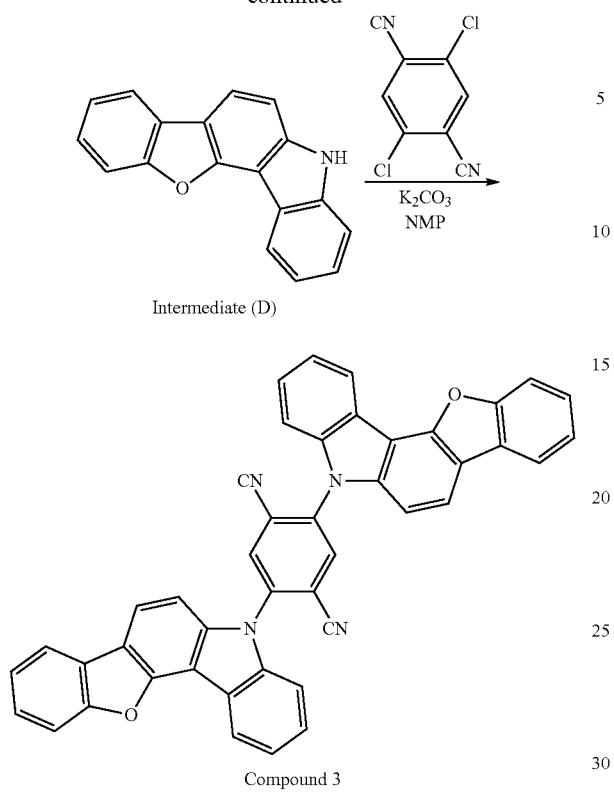

Intermediate (D)

Compound 3

(3-1) Synthesis of 2-dibenzofuranyl-1-nitrobenzene 2-dibenzofuranyl-1-nitrobenzene was synthesized in the same manner as in the synthesis (1-1) of 1-(2-nitrophenyl) naphthalene, except for using 4-dibenzofuran boronic acid in place of 1-naphthaleneboronic acid.

(3-2) Synthesis of Intermediate (D)

Under nitrogen atmosphere, 2-dibenzofuranyl-1-nitrobenzene of 24.0 g, triphenyl phosphine of 54.4 g and N,N-dimethylacetamide of 166 mL were put into a flask and heated to reflux for 20 hours while being stirred. After cooled down to the room temperature, the reaction solution was extracted with dichloromethane. After an aqueous layer was removed, an organic layer was washed with a saturated ammonium chloride aqueous solution. After dried with magnesium sulfate, the organic layer was concentrated. The obtained residue was refined by silica-gel column chromatography, whereby 14.5 g (yield 68%) of a white solid of an intermediate (D) was obtained. It should be noted that N,N-dimethylacetamide is occasionally abbreviated as DMAc.

(3-3) Synthesis of Compound 3

A compound 3 was synthesized in the same manner as in the synthesis (1-3) of the compound 1, except for using the intermediate (D) in place of the intermediate (A).
Evaluation of Compounds Next, fluorescence spectra of the compounds used in Example were measured. The target compounds are the compound 1 and a reference compound 1 shown below. A measurement method or a calculation method is described below. Measurement results or calculation results are shown in Table 1.

[Formula 180]

Reference Compound 1

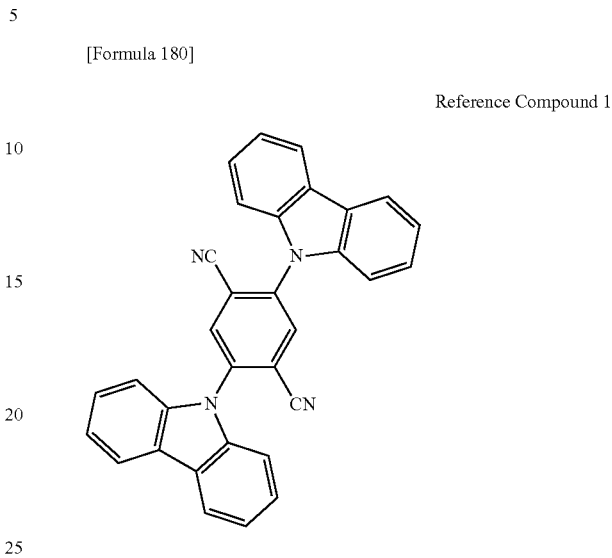

Each of the compounds was dissolved in a solvent to prepare a sample for measuring fluorescence spectra. The solvent was toluene in a spectroscopic grade. A concentration of each of the compounds for measuring fluorescence spectra was set at 5.0 [μmol/liter].

Each of the samples for measuring fluorescence spectra was put into a quartz cell and irradiated with excitation light at a room temperature (300 K), thereby measuring fluorescence intensity. The compound 1 was irradiated with excitation light having a 350-nm wavelength. The reference compound 1 was irradiated with excitation light having a 360-nm wavelength.

The fluorescence spectra were expressed in coordinates of which ordinate axis indicated the fluorescence intensity and of which abscissa axis indicated the wavelength.

For fluorescence spectra measurement, a spectrophotofluorometer body F-4500 (manufactured by Hitachi High-Technologies Corporation) was used.

A wavelength in which the fluorescence intensity was at the maximum (referred to as a main peak wavelength in the invention) $\lambda_F$ was calculated based on the obtained fluorescence spectra. The results are shown in Table 1.

As a result, it is revealed that the compound 1 forming a cyclic structure emits light in longer wavelength regions as compared with the reference compound 1.

TABLE 1

|  | Compound 1 | Reference Compound 1 |
| --- | --- | --- |
| $\lambda_F$ (nm) | 512 | 473 |

Transitional PL Measurement

A transitional PL measurement sample 1 and a transitional PL measurement sample 2 were prepared. Specifically, a co-deposition film was formed on a quartz substrate using a vapor deposition apparatus so as to have a composition and film thickness described below.

Transitional PL Measurement Sample 1
Composition: The transitional PL measurement sample 1 was provided by doping a compound PB with 12 mass % of the compound 1.
Film Thickness: 100 nm
Transitional PL Measurement Sample 2
Composition: The transitional PL measurement sample 2 was provided by doping the compound PB with 12 mass % of the reference compound 1.
Film Thickness: 100 nm

[Formula 181]

Compound PB

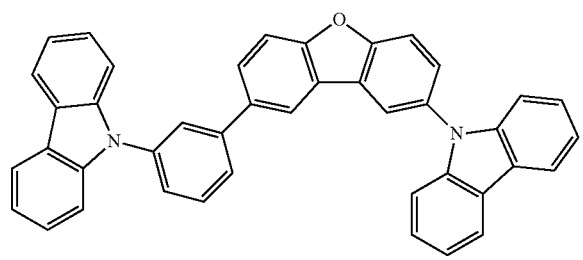

Emission lifetime of each of the compound 1 of the transitional PL measurement sample 1 and the reference compound 1 of the transitional PL measurement sample 2 was measured using a transitional fluorescence life-time measuring instrument and a picosecond pulse laser instrument. A fluorescence life-time measuring instrument C4780 (manufactured by Hamamatsu Photonics K.K.) was used as the transitional fluorescence life-time measuring instrument. Using a nitrogen laser MNL 200 (manufactured by LTB Lasertechnik Berlin GmbH) as the picosecond pulse laser instrument, picosecon pulse laser with a wavelength of 337 nm, an output of 2 mJ/pulse and a pulse width of about 700 ps was emitted.

As a result of the measurement, it is revealed that a delayed emission component with a microsecond lifetime exists in emission obtained from each of the compound 1 and the reference compound 1.

Accordingly, it is revealed from the above results that the compound 1 forming a cyclic structure emits light by the TADF mechanism in longer wavelength regions as compared with the reference compound 1.

Example 4: Synthesis of Compound 4

A synthesis scheme of a compound 4 is shown below.

[Formula 182]

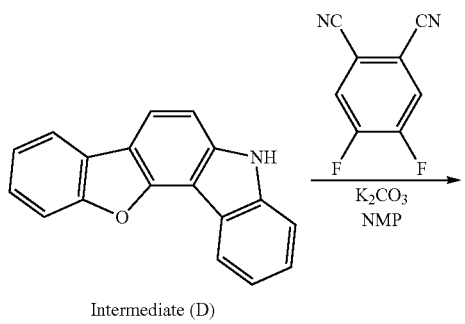

Intermediate (D)

Compound 4

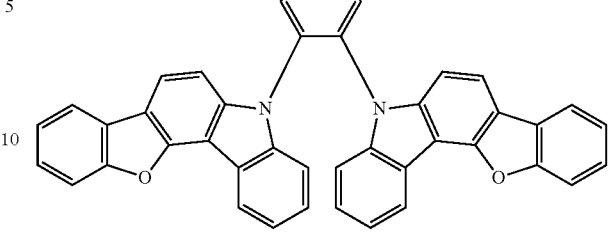

Under nitrogen atmosphere, 16.2 g of the intermediate (D), 4.92 g of 4.5-difluorophthalonitrile, 9.12 g of potassium carbonate, 120 mL of N-methyl-2-pyrrolidinone were put into a flask and stirred at the room temperature for 10 hours. Water was added to the reaction solution. The obtained solution was filtered to obtain a deposited solid. The obtained deposited solid was washed with toluene, whereby 3.25 g (yield 17%) of a yellow solid of the compound 4 was obtained.

Example 5: Synthesis of Compound 5

A synthesis scheme of a compound 5 is shown below.

[Formula 183]

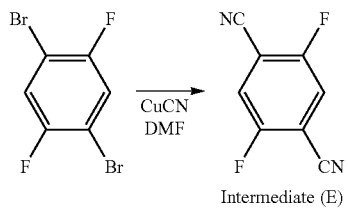

Intermediate (E)

[Formula 184]

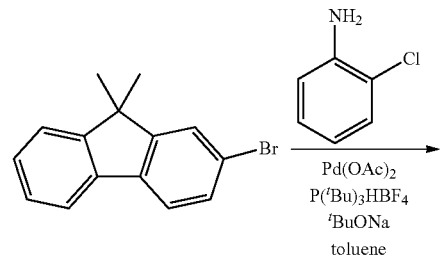

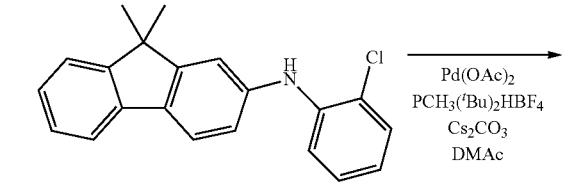

465

-continued

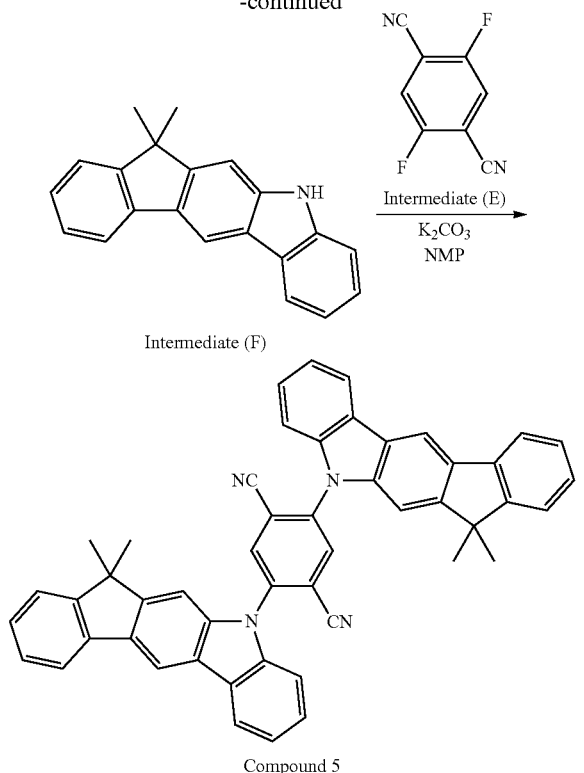

Intermediate (F)

Compound 5

(5-1) Synthesis of Intermediate (E)

Under nitrogen atmosphere, 119 g of 1,4-dibromo-2,5-difluorobenzene, 117 g of copper cyanide (I) and 730 mL of N,N-dimethylformamide were put into a flask and heated to reflux for 16 hours while being stirred. After cooled down to the room temperature, the reaction solution was added to ammonia water and extracted with dichloromethane. The organic layer was concentrated. The obtained residue was refined by silica-gel column chromatography and washing with heptane, whereby 46.0 g (yield 64%) of a white solid of an intermediate (E) was obtained.

(5-2) Synthesis of N-(2-chlorophenyl)-9,9-dimethyl-fluorene-2-amine

Under nitrogen atmosphere, 30.0 g of 2-dibromo-9,9-dimethylfluorene, 15.0 mL of 2-chloroaniline, 0.300 g of palladium(II) acetate, 0.478 g of tri-tert-butylphosphoniumtetrafluoroborate, 27.0 g of sodium-tert-butoxide, and 1.00 L of toluene were put into a flask and heated to reflux for eight hours while being stirred. Under nitrogen atmosphere, 0.100 g of palladium(II) acetate and 0.300 g of 1,1'-bis(diphenylphosphino)ferrocene were added and heated to reflux for three hours while being stirred. After cooled down to the room temperature, the reaction solution was extracted with toluene. After an aqueous layer was removed, an organic layer was washed with a saturated saline solution. After dried with sodium sulfate, the organic layer was concentrated. The obtained residue was refined by silica-gel column chromatography and recrystallization, whereby 25.0 g (yield 71%) of a white solid of N-(2-chlorophenyl)-9,9-dimethyl-fluorene-2-amine was obtained.

466

(5-3) Synthesis of Intermediate (F)

Under nitrogen atmosphere, 25.0 g of N-(2-chlorophenyl)-9,9-dimethyl-fluorene-2-amine, 3.50 g of palladium(II) acetate, 7.70 g of di-tert-butyl(methyl)phosphoniumtetrafluoroborate, 127 g of cesium carbonate, and 600 mL of N,N-dimethylacetoamide were put into a flask and heated to reflux for seven hours while being stirred. After cooled down to the room temperature, the reaction solution was extracted with ethyl acetate. After an aqueous layer was removed, an organic layer was washed with a saturated saline solution. After dried with sodium sulfate, the organic layer was concentrated. The obtained residue was refined by silica-gel column chromatography and recrystallization, whereby 16.3 g (yield 73%) of a brown solid of an intermediate (F) was obtained.

(5-4) Synthesis of Compound 5

Under nitrogen atmosphere, 0.755 g of the intermediate (E), 2.75 g of the intermediate (F), 1.40 g of potassium carbonate, 18 mL of N-methyl-2-pyrrolidinone were put into a flask and stirred at the room temperature for 10 hours. The reaction solution was added with water. The deposited solid was the organic layer was concentrated. The obtained residue was refined by silica-gel column chromatography and washed with toluene, whereby 1.60 g (yield 50%) of a yellow solid of a compound 5 was obtained.

Example 6: Synthesis of Compound 6

A synthesis scheme of a compound 6 is shown below.

[Formula 185]

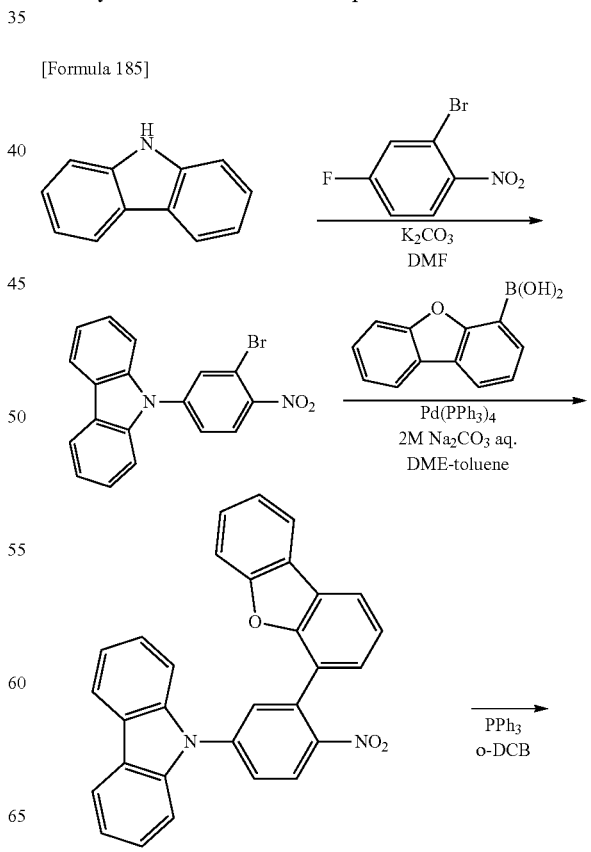

-continued

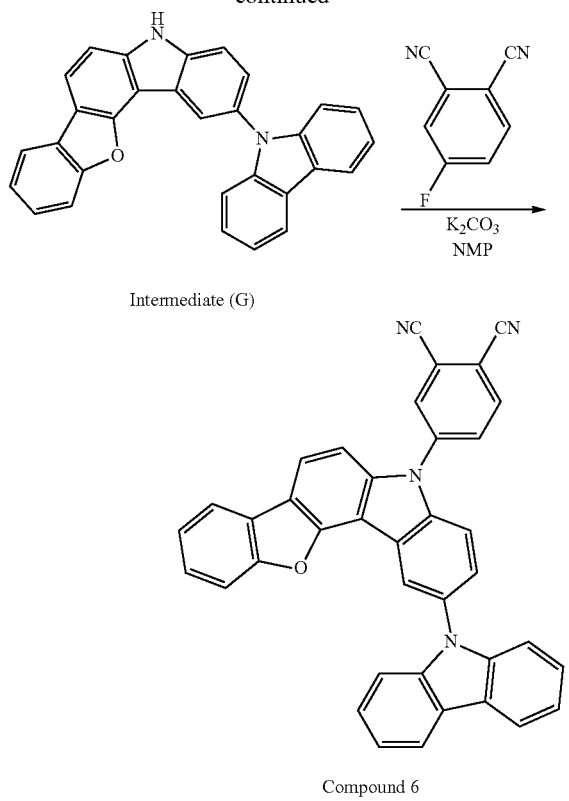

Compound 6

(6-1) Synthesis of 2-bromo-4-(9-carbazolyl)-1-nitrobenzene 2-bromo-4-(9-carbazolyl)-1-nitrobenzene was synthesized in the same manner as in the synthesis (2-1).

(6-2) Synthesis of 4-[2-nitro-5-(9-carbazolyl)phenyl]dibenzofuran

4-[2-nitro-5-(9-carbazolyl)phenyl]dibenzofuran was synthesized in the same manner as in the synthesis (1-1) of 1-(2-nitrophenyl)naphthalene, except for using 4-dibenzofuranboronic acid in place of 1-naphthaleneboronic acid and using 2-bromo-4-(9-carbazolyl)-1-nitrobenzene in place of 1-bromo-2-nitrobenzene.

(6-3) Synthesis of Intermediate (G)

An intermediate (G) was synthesized in the same manner as in the synthesis (1-2) of the intermediate (A), except for using 4-[2-nitro-5-(9-carbazolyl)phenyl]dibenzofuran in place of 1-(2-nitrophenyl)naphthalene.

(6-4) Synthesis of Compound 6

A compound 6 was synthesized in the same manner as in the synthesis (5-4) of the compound 5, except for using 4-fluorophthalonitrile in place of the intermediate (E) and using the intermediate (G) in place of the intermediate (F).

Example 7: Synthesis of Compound 7

A synthesis scheme of a compound 7 is shown below.

[Formula 186]

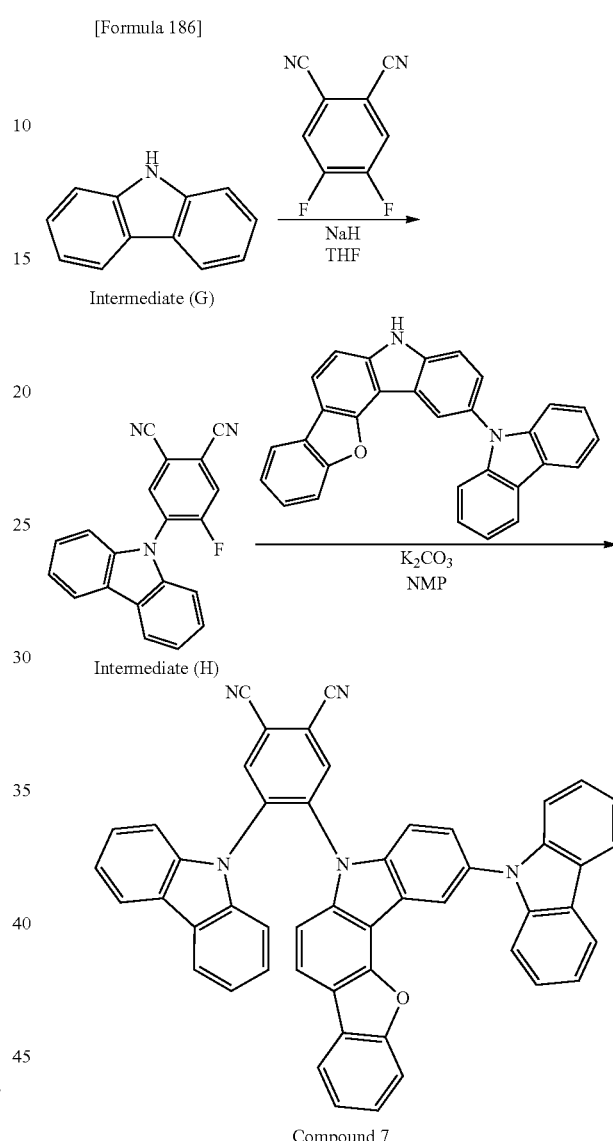

(7-1) Synthesis of Intermediate (H)

Under nitrogen atmosphere, 1.08 g of sodium hydride, 72 mL of THF (tetrahydrofuran), and 2.10 g of carbazole were put into a flask and stirred at the room temperature for one hour. The obtained reaction solution was dropped into a flask containing 2.07 g of 4,5-difluorophthalonitrile, and 36 mL of THF and was stirred at the room temperature for six hours. The reaction solution was extracted with toluene. After an aqueous layer was removed, an organic layer was washed with a saturated ammonium chloride aqueous solution. After dried with magnesium sulfate, the organic layer was concentrated. The obtained residue was refined by silica-gel column chromatography, whereby 1.43 g (yield 51%) of a white solid of an intermediate (H) was obtained.

(7-2) Synthesis of Compound 7

A compound 7 was synthesized in the same manner as in the synthesis (5-4) of the compound 5, except for using the intermediate (H) in place of the intermediate (E) and using the intermediate (G) in place of the intermediate (F).

Example 8: Synthesis of Compound 8

A synthesis scheme of a compound 8 is shown below.

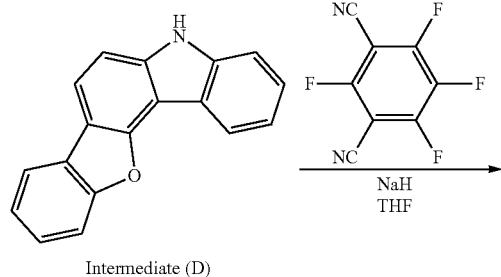

Example 9: Synthesis of Compound 9

A synthesis scheme of a compound 9 is shown below.

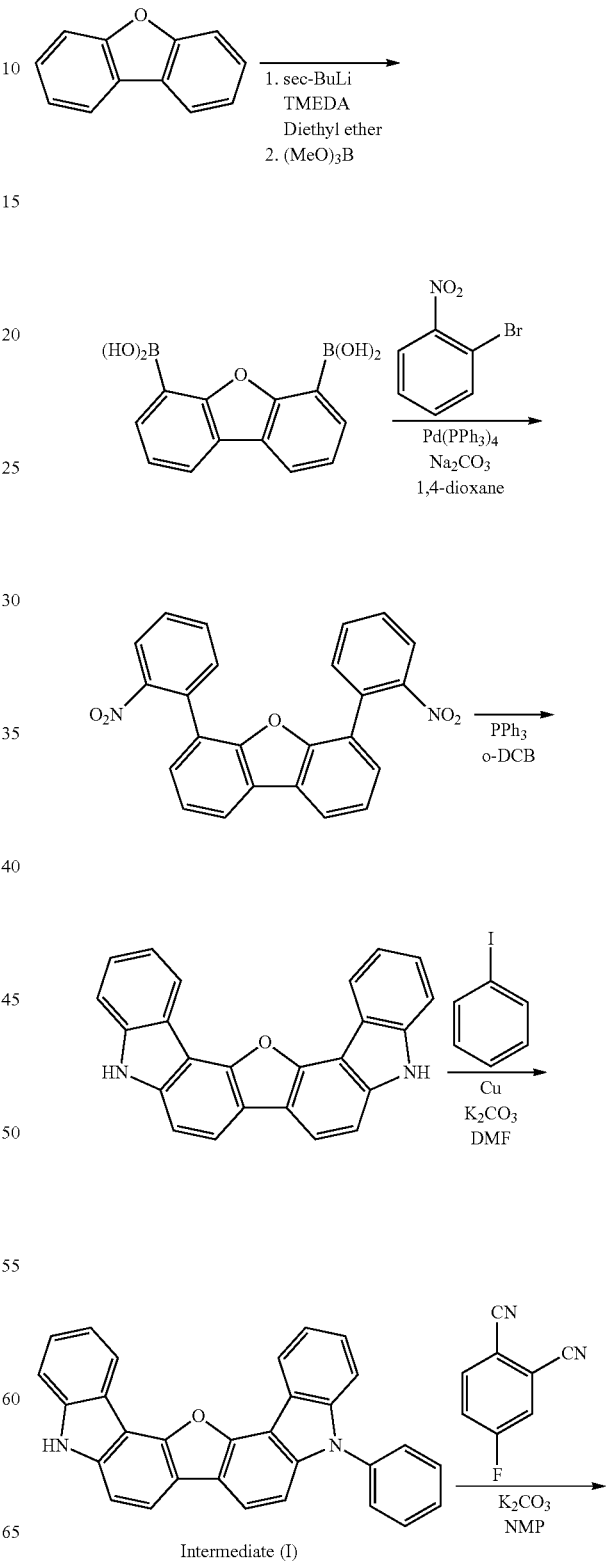

(8-1) Synthesis of Compound 8

A compound 8 was synthesized in the same manner as in the synthesis (7-1) of the intermediate (H), except for using the intermediate (D) in place of carbazole and using tere-fluoroisophthalonitrile in place of 4,5-difluorophthalonitrile.

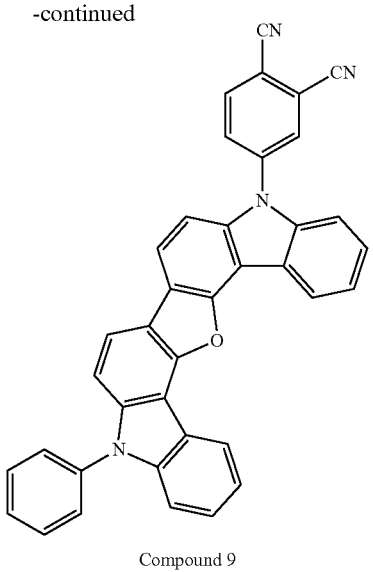

Compound 9

(9-1) Synthesis of dibenzofuran-4,6-diboronic acid

Under argon atmosphere, 30.0 g of dibenzofuran, 81.0 mL of N,N,N',N'-tetramethylethylenediamine, and 105 mL of diethylether were put into a flask and cooled to minus 78 degrees C. After the cooling, 417 mL of sec-butyllithium was dropped in the flask and stirred at the room temperature for 24 hours. After the stirring, the reaction solution was again cooled to minus 78 degrees C. Subsequently, 181 mL of trimelyl borate was dropped in the flask and stirred at the room temperature for 12 hours. After the stirring, 6N-hydrochloric acid was added to the flask. Subsequently, suction filtration was performed. The obtained substance by filtration and an organic layer of the filtrate were mixed. 6N-aqueous sodium hydroxide was added to the mixture. After the 6N-aqueous sodium hydroxide was added, the obtained aqueous layer was washed with diethylether and added with concentrated hydrochloric acid to obtain deposit. The obtained deposit was subjected to suction filtration. The filtrated deposit was washed with water, dried with sodium sulfate, concentrated and washed with ethyl acetate. The obtained residue was refined by recrystallization, whereby 22.0 g (yield 48%) of a white solid of dibenzofuran-4,6-diboronic acid was obtained. It should be noted that N,N,N',N'-tetramethylethylenediamine is occasionally abbreviated as TMEDA.

(9-2) Synthesis of 4,6-di(2-nitrophenyl)dibenzofuran

Under argon atmosphere, 38.2 g of 1-bromo-2-nitrobenzene, 22.0 g of dibenzofuran-4,6-diboronic acid, 3.96 g of tetrakis(triphenylphosphine)palladium(0), 26.4 mL of 2M-sodium hydrogen carbonate aqueous solution, and 31.0 mL of 1,4-dioxane were put into a flask and heated at 80 degrees C. for 39 hours while being stirred. After cooled down to the room temperature, the reaction solution was refined by silica-gel column chromatography and further by recrystallization, whereby 23.5 g (yield 67%) of a white solid of 4.6-di(2-nitrophenyl)dibenzofuran was obtained.

(9-3) Synthesis of 5,10-dihydrofuro[3,2-c:4,5-c'] dicarbazole 5,10-dihydrofuro[3,2-c:4,5-c']dicarbazole was synthesized in the same manner as in the synthesis (1-2) of the intermediate (A), except for using 4,6-di(2-nitrophenyl)dibenzofuran in place of 1-(2-nitrophenyl]naphthalene.

(9-4) Synthesis of Intermediate (I)

Under argon atmosphere, 7.27 g of 5,10-dihydrofuro[3,2-c:4,5-c']dicarbazole, 4.28 g of iodobenzene, 1.25 g of copper powder, 4.07 g of potassium carbonate and 29.4 mL of N,N-dimethylformamide were put into a flask and heated for 18 hours while being stirred. After cooled down to the room temperature, the reaction solution was refined by silica-gel column chromatography, further by recrystallization, still further by suspension and washing, whereby 1.02 g (yield 25%) of an intermediate (I) was obtained.

(9-5) Synthesis of Compound 9

A compound 6 was synthesized in the same manner as in the synthesis (5-4) of the compound 5, except for using 4-fluorophthalonitrile in place of the intermediate (E) and using the intermediate (I) in place of the intermediate (F).

Example 10: Synthesis of Compound 10

A synthesis scheme of a compound 10 is shown below.

[Formula 189]

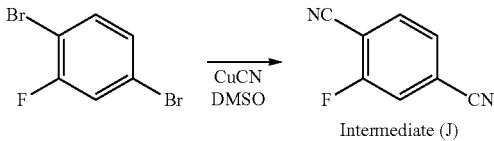

Intermediate (J)

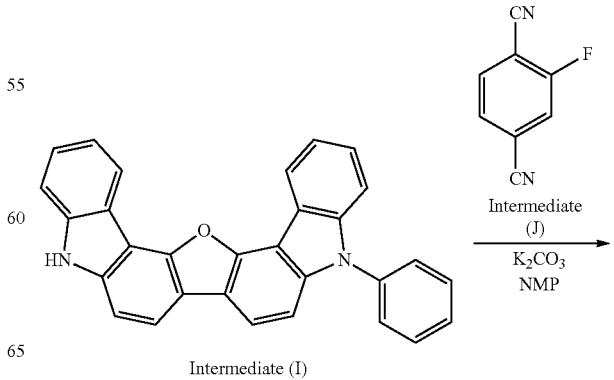

Intermediate (I)

-continued

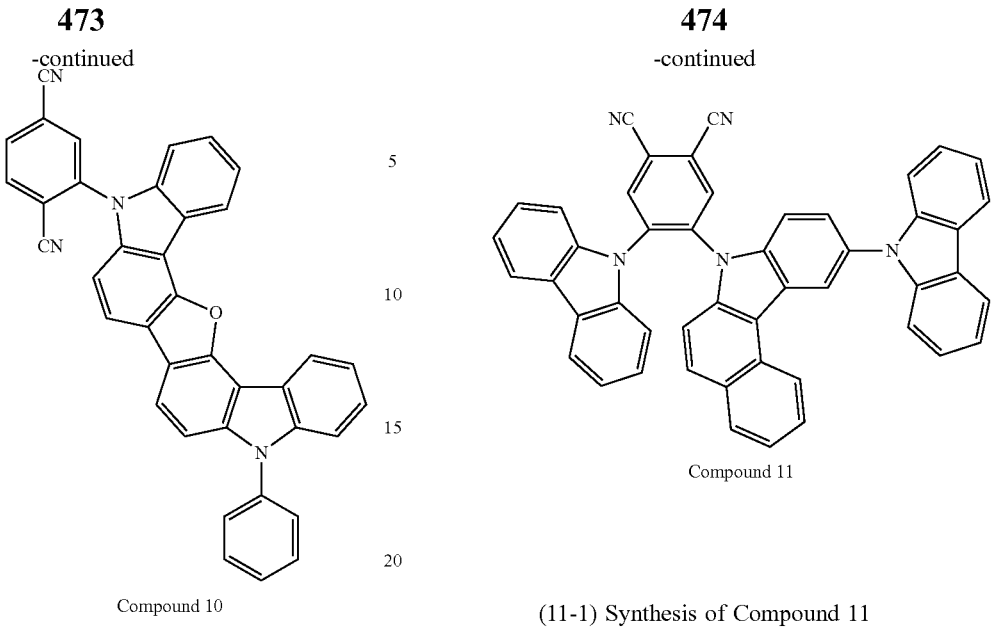

Compound 10

Compound 11

(10-1) Synthesis of Intermediate (J)

Under argon atmosphere, 56.3 g of 1,4-dibromo-2-fluorobenzene, 43.8 g of copper cyanide (I) and 500 mL of dimethylsulphoxide were put into a flask and heated at 115 degrees C. for 19 hours while being stirred. After cooled down to the room temperature, the reaction solution was added with ethyl acetate and water to be extracted. After an aqueous layer was removed, an organic layer was washed with ammonia water. After dried with sodium sulfate, the organic layer was concentrated. The obtained residue was refined by silica-gel column chromatography and further by recrystallization, whereby 16.3 g (yield 50%) of a white solid of an intermediate (J) was obtained. It should be noted that dimethylsulphoxide is occasionally abbreviated as DMSO.

(10-2) Synthesis of Compound 10

A compound 10 was synthesized in the same manner as in the synthesis (1-3) of the compound 1, except for using the intermediate (I) in place of the intermediate (A) and using the intermediate (J) in place of 2,5-dichloroterephthalonitrile.

Example 11: Synthesis of Compound 11

A synthesis scheme of a compound 11 is shown below.

[Formula 190]

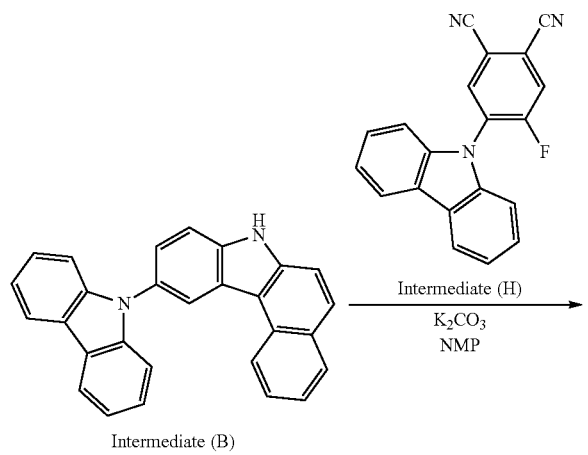

(11-1) Synthesis of Compound 11

A compound 11 was synthesized in the same manner as in the synthesis (1-3) of the compound 1, except for using the intermediate (B) in place of the intermediate (A) and using the intermediate (H) in place of 2,5-dichloroterephthalonitrile.

Second Evaluation of Compounds

Next, fluorescence spectra of the compounds 3 to 8 were measured to obtain a main peak wavelength $\lambda_F$. A measurement method or calculation method was the same as the above. The measurement results or calculation results are shown in Table 2.

As a result, it is revealed that the compounds 3 to 8 forming a cyclic structure emits light in longer wavelength regions as compared with the reference compound 1 described above.

TABLE 2

| | $\lambda_F$ (nm) |
|---|---|
| Compound 1 | 512 |
| Compound 2 | 541 |
| Compound 3 | 509 |
| Compound 4 | 495 |
| Compound 5 | 526 |
| Compound 6 | 479 |
| Compound 7 | 511 |
| Compound 8 | 536 |
| Compound 9 | 500 |
| Compound 10 | 536 |
| Compound 11 | 505 |
| Reference Compound 1 | 473 |

Device Evaluation

Next, an organic el device was prepared and evaluated.

In addition to the above compounds, compounds used for preparing the organic EL device were shown below.

[Formula 191]

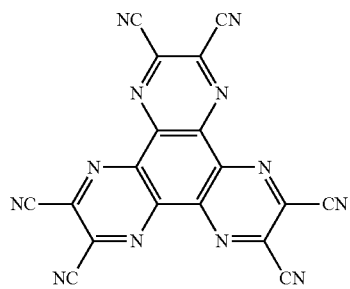
HI

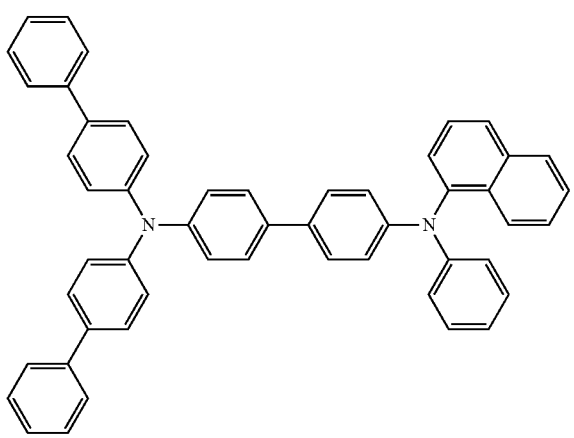
HT-1

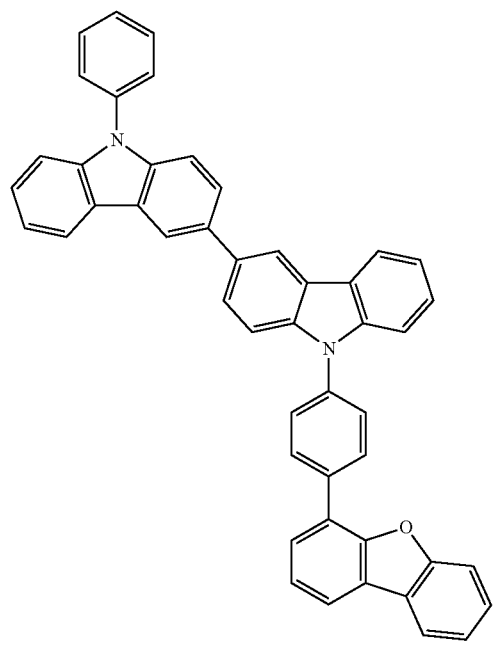
HT-2

[Formula 192]

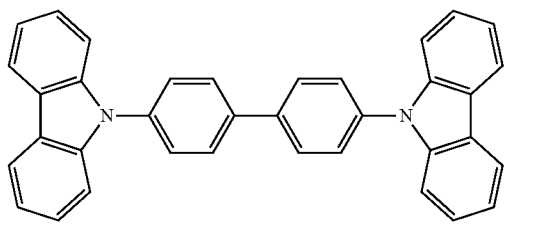
CBP

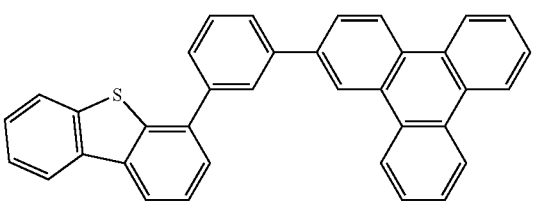
PG-1

EB-1

ET-1

Example 12: Preparation of Organic EL Device

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having an ITO transparent electrode was cleaned, the glass substrate was mounted on a substrate holder of a vacuum evaporation apparatus. Initially, a compound HI was deposited on a surface of the glass substrate where the transparent electrode line was provided in a manner to cover the transparent electrode, thereby forming a 5-nm thick film of the compound HI. The HI film serves as a hole injecting layer.

After the film formation of the HI film, a compound HT-1 was deposited on the HI film to form a 20-nm thick HT-1 film. The HT-1 film serves as a hole transporting layer.

After the formation of the HT-1 film, a compound HT-2 was deposited on the HT-1 film to form a 5-nm thick HT-2 film on the HT-1 film. The HT-2 film also serves as a hole transporting layer.

After the formation of the HT-2 film, a compound CBP was deposited on the HT-2 film to form a 5-nm thick CBP film on the HT-2 film. The CBP film also serves as a hole transporting layer.

Next, a compound PG-1 and the compound 1 were co-deposited to form a 25-nm thick emitting layer on the CBP film. A mass ratio between the compound PG-1 and the compound 1 was set at 76 mass %:24 mass %.

A compound EB-1 was deposited on the emitting layer to form a 5-nm thick hole blocking layer.

Further, a compound ET-1 was deposited on the EB-1 film to form a 50-nm thick ET-1 film. The ET-1 film serves as an electron transporting layer.

LiF was deposited on the electron transporting layer to form a 1-nm thick LiF film.

A metal Al was deposited on the LiF film to form an 80-nm thick metal cathode.

A device arrangement of the organic EL device in Example 12 is roughly shown as follows.

ITO(130)/HI(5)/HT-1(20)/HT-2(5)/CBP(5)/PG-1: Compound 1(25, 76%:24%)/EB-1(5)/ET-1(50)/LiF (1)/Al(80)

Numerals in parentheses represent a film thickness (unit: nm). The numerals represented by percentage in parentheses indicate a ratio (mass %) of the compound in the layer. The same applies below.

Example 13: Preparation of Organic EL Device

An organic EL device in Example 13 was prepared in the same manner as in Example 12 except that the mass ratio between the compound PG-1 and the compound 1 in the emitting layer of Example 12 was changed to 50 mass %: 50 mass %.

A device arrangement of the organic EL device in Example 13 is roughly shown as follows.

ITO(130)/HI(5)/HT-1(20)/HT-2(5)/CBP(5)/PG-1: Compound 1 (25, 50%:50%)/EB-1(5)/ET-1(50)/LiF(1)/Al(80)

Example 14: Preparation of Organic EL Device

An organic EL device in Example 14 was prepared in the same manner as in Example 12 except that the compound 1 in the emitting layer of Example 12 was changed to the compound 2.

A device arrangement of the organic EL device in Example 14 is roughly shown as follows.

ITO(130)/HI(5)/HT-1(20)/HT-2(5)/CBP(5)/PG-1: Compound 2(25, 76%:24%)/EB-1(5)/ET-1(50)/LiF (1)/Al(80)

Example 15: Preparation of Organic EL Device

An organic EL device in Example 15 was prepared in the same manner as in Example 13 except that the compound 1 in the emitting layer of Example 13 was changed to the compound 2.

A device arrangement of the organic EL device in Example 15 is roughly shown as follows.

ITO(130)/HI(5)/HT-1(20)/HT-2(5)/CBP(5)/PG-1: Compound 2 (25, 50%:50%)/EB-1(5)/ET-1(50)/LiF(1)/Al(80)

Example 16: Preparation of Organic EL Device

An organic EL device in Example 16 was prepared in the same manner as in Example 12 except that the compound 1 in the emitting layer of Example 12 was changed to the compound 3.

A device arrangement of the organic EL device in Example 16 is roughly shown as follows.

ITO(130)/HI(5)/HT-1(20)/HT-2(5)/CBP(5)/PG-1: Compound 3(25, 76%:24%)/EB-1(5)/ET-1(50)/LiF(1)/Al(80)

Example 17: Preparation of Organic EL Device

An organic EL device in Example 17 was prepared in the same manner as in Example 13 except that the compound 1 in the emitting layer of Example 13 was changed to the compound 3.

A device arrangement of the organic EL device in Example 17 is roughly shown as follows.

ITO(130)/HI(5)/HT-1(20)/HT-2(5)/CBP(5)/PG-1: Compound 3 (25, 50%:50%)/EB-1(5)/ET-1(50)/LiF(1)/Al(80)

Example 18: Preparation of Organic EL Device

An organic EL device in Example 18 was prepared in the same manner as in Example 12 except that the compound 1 in the emitting layer of Example 12 was changed to the compound 4.

A device arrangement of the organic EL device in Example 18 is roughly shown as follows.

ITO(130)/HI(5)/HT-1(20)/HT-2(5)/CBP(5)/PG-1: Compound 4 (25, 76%:24%)/EB-1(5)/ET-1(50)/LiF(1)/Al(80)

Example 19: Preparation of Organic EL Device

An organic EL device in Example 19 was prepared in the same manner as in Example 13 except that the compound 1 in the emitting layer of Example 13 was changed to the compound 4.

A device arrangement of the organic EL device in Example 19 is roughly shown as follows.

ITO(130)/HI(5)/HT-1(20)/HT-2(5)/CBP(5)/PG-1: Compound 4 (25, 50%:50%)/EB-1(5)/ET-1(50)/LiF(1)/Al(80)

Example 20: Preparation of Organic EL Device

An organic EL device in Example 20 was prepared in the same manner as in Example 12 except that the compound 1 in the emitting layer of Example 12 was changed to the compound 5.

A device arrangement of the organic EL device in Example 20 is roughly shown as follows.

ITO(130)/HI(5)/HT-1(20)/HT-2(5)/CBP(5)/PG-1: Compound 5 (25, 76%:24%)/EB-1(5)/ET-1(50)/LiF(1)/Al(80)

Example 21: Preparation of Organic EL Device

An organic EL device in Example 21 was prepared in the same manner as in Example 13 except that the compound 1 in the emitting layer of Example 13 was changed to the compound 5.

A device arrangement of the organic EL device in Example 21 is roughly shown as follows.

ITO(130)/HI(5)/HT-1(20)/HT-2(5)/CBP(5)/PG-1: Compound 5 (25, 50%:50%)/EB-1(5)/ET-1(50)/LiF(1)/Al(80)

Example 22: Preparation of Organic EL Device

An organic EL device in Example 22 was prepared in the same manner as in Example 12 except that the compound 1 in the emitting layer of Example 12 was changed to the compound 6.
A device arrangement of the organic EL device in Example 22 is roughly shown as follows.
ITO(130)/HI(5)/HT-1(20)/HT-2(5)/CBP(5)/PG-1: Compound 6 (25, 76%:24%)/EB-1(5)/ET-1(50)/LiF(1)/Al(80)

Example 23: Preparation of Organic EL Device

An organic EL device in Example 23 was prepared in the same manner as in Example 13 except that the compound 1 in the emitting layer of Example 13 was changed to the compound 6.
A device arrangement of the organic EL device in Example 23 is roughly shown as follows.
ITO(130)/HI(5)/HT-1(20)/HT-2(5)/CBP(5)/PG-1: Compound 6 (25, 50%:50%)/EB-1(5)/ET-1(50)/LiF(1)/Al(80)

Example 24: Preparation of Organic EL Device

An organic EL device in Example 24 was prepared in the same manner as in Example 12 except that the compound 1 in the emitting layer of Example 12 was changed to the compound 7.
A device arrangement of the organic EL device in Example 24 is roughly shown as follows.
ITO(130)/HI(5)/HT-1(20)/HT-2(5)/CBP(5)/PG-1: Compound 7 (25, 76%:24%)/EB-1(5)/ET-1(50)/LiF(1)/Al(80)

Example 25: Preparation of Organic EL Device

An organic EL device in Example 25 was prepared in the same manner as in Example 13 except that the compound 1 in the emitting layer of Example 13 was changed to the compound 7.
A device arrangement of the organic EL device in Example 25 is roughly shown as follows.
ITO(130)/HI(5)/HT-1(20)/HT-2(5)/CBP(5)/PG-1: Compound 7 (25, 50%:50%)/EB-1(5)/ET-1(50)/LiF(1)/Al(80)

Example 26: Preparation of Organic EL Device

An organic EL device in Example 26 was prepared in the same manner as in Example 12 except that the compound 1 in the emitting layer of Example 12 was changed to the compound 8.
A device arrangement of the organic EL device in Example 26 is roughly shown as follows.
ITO(130)/HI(5)/HT-1(20)/HT-2(5)/CBP(5)/PG-1: Compound 8 (25, 76%:24%)/EB-1(5)/ET-1(50)/LiF(1)/Al(80)

Example 27: Preparation of Organic EL Device

An organic EL device in Example 27 was prepared in the same manner as in Example 13 except that the compound 1 in the emitting layer of Example 13 was changed to the compound 8.
A device arrangement of the organic EL device in Example 27 is roughly shown as follows.

ITO(130)/HI(5)/HT-1(20)/HT-2(5)/CBP(5)/PG-1: Compound 8 (25, 50%:50%)/EB-1(5)/ET-1(50)/LiF(1)/Al(80)

Example 28: Preparation of Organic EL Device

An organic EL device in Example 28 was prepared in the same manner as in Example 12 except that the compound 1 in the emitting layer of Example 12 was changed to the compound 9.
A device arrangement of the organic EL device in Example 28 is roughly shown as follows.
ITO(130)/HI(5)/HT-1(20)/HT-2(5)/CBP(5)/PG-1: Compound 9 (25, 76%:24%)/EB-1(5)/ET-1(50)/LiF(1)/Al(80)

Example 29: Preparation of Organic EL Device

An organic EL device in Example 29 was prepared in the same manner as in Example 13 except that the compound 1 in the emitting layer of Example 13 was changed to the compound 9.
A device arrangement of the organic EL device in Example 29 is roughly shown as follows.
ITO(130)/HI(5)/HT-1(20)/HT-2(5)/CBP(5)/PG-1: Compound 9 (25, 50%:50%)/EB-1(5)/ET-1(50)/LiF(1)/Al(80)

Example 30: Preparation of Organic EL Device

An organic EL device in Example 30 was prepared in the same manner as in Example 12 except that the compound 1 in the emitting layer of Example 12 was changed to the compound 10.
A device arrangement of the organic EL device in Example 30 is roughly shown as follows.
ITO(130)/HI(5)/HT-1(20)/HT-2(5)/CBP(5)/PG-1: Compound 10 (25, 76%:24%)/EB-1(5)/ET-1(50)/LiF(1)/Al(80)

Example 31: Preparation of Organic EL Device

An organic EL device in Example 31 was prepared in the same manner as in Example 13 except that the compound 1 in the emitting layer of Example 13 was changed to the compound 10.
A device arrangement of the organic EL device in Example 31 is roughly shown as follows.
ITO(130)/HI(5)/HT-1(20)/HT-2(5)/CBP(5)/PG-1: Compound 10 (25, 50%:50%)/EB-1(5)/ET-1(50)/LiF(1)/Al(80)

Example 32: Preparation of Organic EL Device

An organic EL device in Example 32 was prepared in the same manner as in Example 12 except that the compound 1 in the emitting layer of Example 12 was changed to the compound 11.
A device arrangement of the organic EL device in Example 32 is roughly shown as follows.
ITO(130)/HI(5)/HT-1(20)/HT-2(5)/CBP(5)/PG-1: Compound 11 (25, 76%:24%)/EB-1(5)/ET-1(50)/LiF(1)/Al(80)

Example 33: Preparation of Organic EL Device

An organic EL device in Example 33 was prepared in the same manner as in Example 13 except that the compound 1 in the emitting layer of Example 13 was changed to the compound 11.
A device arrangement of the organic EL device in Example 33 is roughly shown as follows.

ITO(130)/HI(5)/HT-1(20)/HT-2(5)/CBP(5)/PG-1: Compound 11 (25, 50%:50%)/EB-1(5)/ET-1(50)/LiF(1)/Al(80)

Comparative 1: Preparation of Organic EL Device

An organic EL device in Comparative 1 was prepared in the same manner as in Example 12 except that the compound 1 in the emitting layer of Example 12 was changed to the compound 1.
A device arrangement of the organic EL device in Comparative 1 is roughly shown as follows.
ITO(130)/HI(5)/HT-1(20)/HT-2(5)/CBP(5)/PG-1: Reference Compound 1 (25, 76%:24%)/EB-1(5)/ET-1(50)/LiF(1)/Al(80)

Comparative 2: Preparation of Organic EL Device

An organic EL device in Comparative 2 was prepared in the same manner as in Example 13 except that the compound 1 in the emitting layer of Example 13 was changed to the compound 1.
A device arrangement of the organic EL device in Comparative 2 is roughly shown as follows.

ITO(130)/HI(5)/HT-1(20)/HT-2(5)/CBP(5)/PG-1: Reference Compound 1 (25, 50%:50%)/EB-1(5)/ET-1(50)/LiF(1)/Al(80)

Evaluation of Organic EL Devices

The prepared organic EL devices of Examples 12 to 33 and Comparatives 1 to 2 were evaluated as follows. The results are shown in Table 3.

Luminous Intensity

Voltage was applied on each of the organic EL devices such that the current density was 10.0 mA/cm², where a luminous intensity was measured using a spectroradiometer CS-1000 (manufactured by Konica Minolta, Inc.).

Main Peak Wavelength $\lambda_p$

Voltage was applied on each of the organic EL devices such that the current density was 10.0 mA/cm², where spectral radiance spectra were measured by a spectroradiometer CS-1000 (manufactured by Konica Minolta, Inc). Based on the obtained spectral radiance spectra, a main peak wavelength $\lambda_p$ was calculated. The main peak wavelength $\lambda_p$ is a peak wavelength at which the luminous intensity in the spectra reaches the maximum.

Delayed Fluorescence Lifetime

Delayed fluorescence lifetime was measured and calculated using a fluorescence lifetime spectrofluorometer (TemPro: manufactured HORIBA, Ltd). The prepared organic EL devices of Examples 12 to 33 and Comparatives 1 to 2 were used as measurement samples.

A semiconductor pulse LED light source NanoLED-340 or a semiconductor pulse LED light source SpectralLED-355 were used as an excitation light source. The excitation light source was selectively used depending on the delayed fluorescence lifetime. A spectral wavelength obtained by a detector PPD-850 of the fluorescence lifetime spectrofluorometer was defined as the main peak wavelength $\lambda_p$ of each of the organic EL devices of Examples 12 to 33 and Comparatives 1 to 2. The measurement was conducted at the room temperature.

TABLE 3

| | Emitting layer | | Luminous Intensicy | Main peak wavelength | Delayed fluorescence |
|---|---|---|---|---|---|
| | Compound | Mass ratio | (nit) | $\lambda_P$ (nm) | lifetime (µs) |
| Example 12 | PG-1:Compound 1 | 76%:24% | 1164.1 | 569 | 2.82 |
| Example 13 | PG-1:Compound 1 | 50%:50% | 670.6 | 581 | 2.31 |
| Example 14 | PG-1:Compound 2 | 76%:24% | 1004.6 | 575 | 2.26 |
| Example 15 | PG-1:Compound 2 | 50%:50% | 552.4 | 586 | 1.50 |
| Example 16 | PG-1:Compound 3 | 76%:24% | 1914.2 | 560 | 7.72 |
| Example 17 | PG-1:Compound 3 | 50%:50% | 1390.0 | 567 | 6.94 |
| Example 18 | PG-1:Compound 4 | 76%:24% | 3437.6 | 545 | 13.50 |
| Example 19 | PG-1:Compound 4 | 50%:50% | 3368.3 | 550 | 12.00 |
| Example 20 | PG-1:Compound 5 | 76%:24% | 876.3 | 567 | 5.20 |
| Example 21 | PG-1:Compound 5 | 50%:50% | 680.8 | 581 | 6.55 |
| Example 22 | PG-1:Compound 6 | 76%:24% | 2464.4 | 529 | 23.10 |
| Example 23 | PG-1:Compound 6 | 50%:50% | 3202.0 | 538 | 26.30 |
| Example 24 | PG-1:Compound 7 | 76%:24% | 3938.5 | 551 | 10.10 |
| Example 25 | PG-1:Compound 7 | 50%:50% | 3337.5 | 556 | 8.29 |
| Example 26 | PG-1:Compound 8 | 76%:24% | 1817.9 | 587 | 1.17 |
| Example 27 | PG-1:Compound 8 | 50%:50% | 1068.1 | 599 | 1.06 |
| Example 28 | PG-1:Compound 9 | 76%:24% | 2252.0 | 564 | 12.30 |
| Example 29 | PG-1:Compound 9 | 50%:50% | 2046.7 | 569 | 10.00 |
| Example 30 | PG-1:Compound 10 | 76%:24% | 704.2 | 577 | 3.22 |
| Example 31 | PG-1:Compound 10 | 50%:50% | 440.3 | 586 | 2.12 |
| Example 32 | PG-1:Compound 11 | 76%:24% | 2215.0 | 546 | 22.50 |
| Example 33 | PG-1:Compound 11 | 50%:50% | 1941.3 | 555 | 9.70 |
| Comp. 1 | PG-1:Reference Compound 1 | 76%:24% | 2613.5 | 520 | 58.60 |
| Comp. 2 | PG-1:Reference Compound 1 | 50%:50% | 1950.9 | 529 | 48.30 |

As shown in the above Table, it is found that the organic EL devices using the compounds 1 to 11 have main peak wavelengths in a longer wavelength as compared with the organic EL device using the reference compound 1.

As shown in the above Table, it is confirmed from the values of the delayed fluorescence lifetime of the organic EL devices in Examples 12 to 33 that the compounds 1 to 11 are compounds emitting delayed fluorescence.

EXPLANATION OF CODE(S)

1 . . . organic EL device, 2 . . . substrate, 3 . . . anode, . . . cathode, 5 . . . emitting layer, 6 . . . holes injecting/transporting layer, 7 . . . electrons injecting/transporting layer, 10 . . . organic layer.

The invention claimed is:
1. A compound represented by a formula (40):

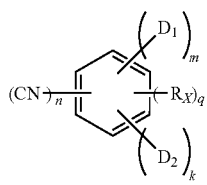
(40)

where: k is an integer of 0 to 2, m is an integer of 2 to 4, n is an integer of 2 to 4, q is an integer of 0 to 2, and k+m+n+q=6, and CN is a cyano group, and $R_x$ each independently is a hydrogen atom, a substituted or unsubstituted aryl group having 6 to 30 ring carbon atoms, a substituted or unsubstituted heterocyclic group having 6 to 30 ring atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms, and $D_1$ is represented by one of formulae (3) and (3x) below, $D_2$ is represented by one of the formulae (3), (3x) below and formulae (33) to (38) below, $D_1$ and $D_2$ being optionally the same or different, a plurality of $D_1$ being optionally the same or different, a plurality of $D_2$ being optionally the same or different,

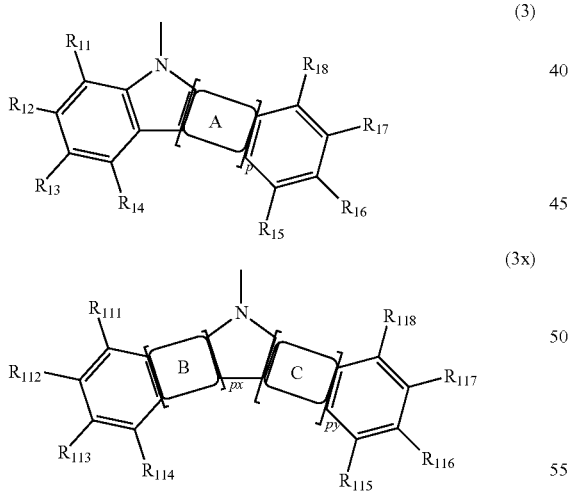

$R_{11}$ to $R_{18}$ of the formula (3), and $R_{111}$ to $R_{118}$ of the formula (3x) each independently represent a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms, in the formula (3), at least one of combinations of substituents selected from $R_{11}$ to $R_{18}$ is optionally mutually bonded to form a cyclic structure, in the formula (3x), at least one of combinations of substituents selected from $R_{111}$ to $R_{118}$ is optionally mutually bonded to form a cyclic structure, in the formulae (3) and (3x): A, B and C each independently represent a cyclic structure represented by one of a formula (31) and a formula (32) below, each of the cyclic structure A, cyclic structure B, and cyclic structure C being fused with its adjacent cyclic structures at any positions, p is 4, and four cyclic structures A include two cyclic structures represented by the formula (31) and two cyclic structures represented by the formula (32), and px and py are each 2, two cyclic structures B include one cyclic structure represented by the formula (31) and one cyclic structure represented by the formula (32), and two cyclic structures C include one cyclic structure represented by the formula (31) and one cyclic structure represented by the formula (32),

(31)

(32)

in the formula (31), $R_{19}$ and $R_{20}$ each independently represent the same as $R_{11}$ to $R_{18}$ and are optionally mutually bonded to form a cyclic structure, and in the formula (32): $X_1$ represents a sulfur atom, or an oxygen atom, and at least one $X_1$ in the formulae (3) and (3x) for $D_1$ is a sulfur atom,

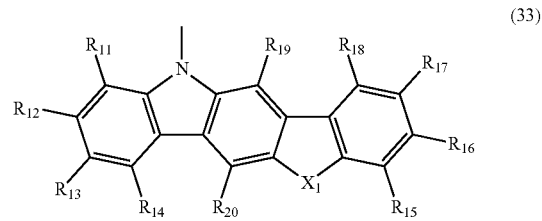
(33)

(34)
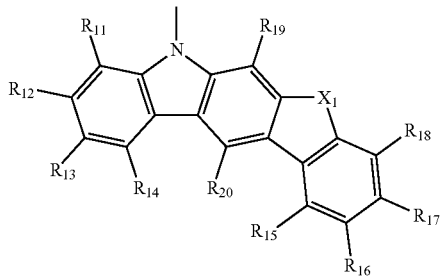

(35)
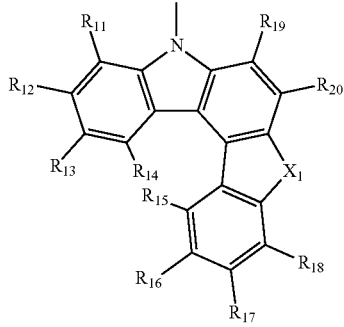

(36)
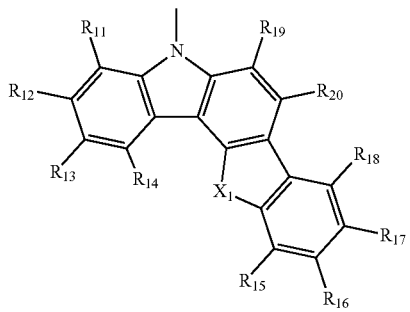

(37)
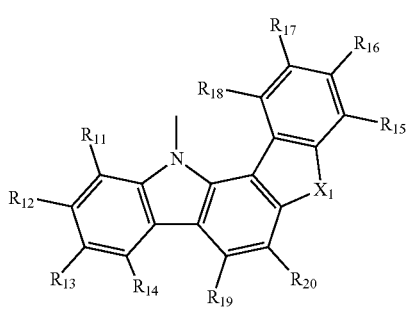

(38)
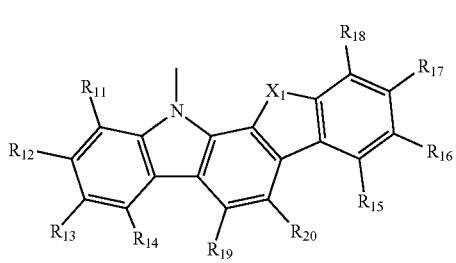

in the formulae (33) to (38), $R_{11}$ to $R_{20}$ each independently represent a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms; and at least one of combinations of substituents selected from $R_{11}$ to $R_{20}$ are optionally mutually bonded to form a cyclic structure, and $X_1$ in the formulae (33) to (38) represents a sulfur atom or an oxygen atom.

2. The compound according to claim 1, wherein $D_1$ is represented by the formula (3).

3. The compound according to claim 1, wherein $D_1$ is represented by the formula (3x).

4. The compound according to claim 1, wherein the formula (3x) is represented by a formula (3y) below, (3y)
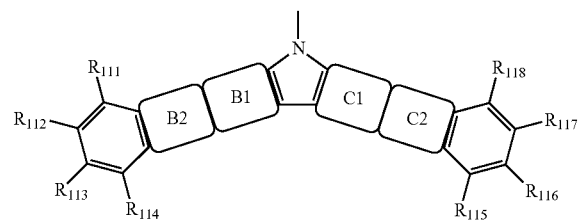

in the formula (3y), $R_{111}$ to $R_{118}$ each independently represent the same as $R_{111}$ to $R_{118}$ described in the formula (3x), one of a cyclic structure B1 and a cyclic structure B2 is the cyclic structure represented by the formula (31), and the other of the cyclic structure B1 and the cyclic structure B2 is the cyclic structure represented by the formula (32), and one of a cyclic structure C1 and a cyclic structure C2 is the cyclic structure represented by the formula (31), and the other of the cyclic structure C1 and the cyclic structure C2 is the cyclic structure represented by the formula (32).

5. The compound according to claim 4, wherein in the formula (3y), the cyclic structure B1 and the cyclic structure C1 are each independently the cyclic structure represented by the formula (31) and the cyclic structure B2 and the cyclic structure C2 are each independently the cyclic structure represented by the formula (32).

6. The compound according to claim 1, wherein $R_X$, $R_{11}$ to $R_{20}$ and $R_{111}$ to $R_{118}$ are each independently selected from the group consisting of a hydrogen atom, a substituted or unsubstituted aryl group having 6 to 20 ring carbon atoms, a substituted or unsubstituted heterocyclic group having 5 to 14 ring atoms, a substituted or unsubstituted alkyl group having 1 to 6 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms, any substituents of the substituent(s) are selected from the group consisting of a hydrogen atom, an aryl group having 6 to 20 ring carbon atoms, a heterocyclic group having 5 to 14 ring atoms, an alkyl group having 1 to 6 carbon atoms, an alkylsilyl group having 3 to 30 carbon atoms, an arylsilyl group having 6 to 60 ring carbon atoms, an alkoxy group having 1 to 30 carbon atoms, an aryloxy group having 6 to 30 ring carbon atoms, an alkylamino group having 2 to 30 carbon atoms, an arylamino group having 6 to 60 ring carbon atoms, an alkylthio group having 1 to 30 carbon atoms, and an arylthio group having 6 to 30 ring carbon atoms.

7. The compound according to claim 1, wherein $R_{11}$ to $R_{20}$ are not mutually bonded to form a cyclic structure, $R_{111}$ to $R_{118}$ are not mutually bonded to form a cyclic structure, and $R_{11}$ to $R_{20}$ and $R_{111}$ to $R_{118}$ are each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms.

8. The compound according to claim 1, wherein the compound is represented by a formula (4) below:

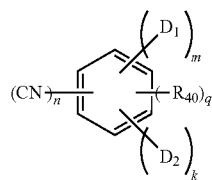

(4)

where: k is an integer of 0 to 2, m is an integer of 2 to 4, n is an integer of 2 to 4, q is an integer of 0 to 2, and k+m+n+q=6;

$R_{40}$ is each independently a hydrogen atom, a substituted or unsubstituted aryl group having 6 to 30 ring carbon atoms, a substituted or unsubstituted alkyl group having 1 to 30 carbon atoms, a substituted or unsubstituted alkylsilyl group having 3 to 30 carbon atoms, or a substituted or unsubstituted arylsilyl group having 6 to 60 ring carbon atoms, a plurality of $R_{40}$ being optionally mutually the same or different;

$D_1$ and $D_2$ each independently represent the same as $D_1$ and $D_2$ of the formula (40), a plurality of $D_1$ being optionally mutually the same or different, a plurality of $D_2$ being optionally mutually the same or different; and $R_{40}$, $D_1$, $D_2$ and CN are respectively bonded to carbon atoms forming a benzene ring.

9. The compound according to claim 8, wherein the compound is represented by one of formulae (41) to (43) below:

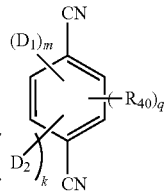

(41)

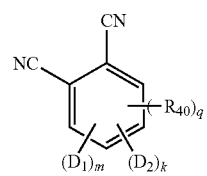

(42)

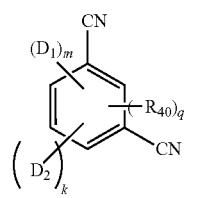

(43)

where: k is an integer of 0 to 2, m is an integer of 2 to 4, q is an integer of 0 to 2, and k+m+q=4, and $D_1$, $D_2$ and $R_{40}$ are as defined in claim 8.

10. The compound according to claim 9, wherein the compound is represented by the formula (43).

11. The compound according to claim 8, wherein $R_{40}$, $R_{11}$ to $R_{20}$ and $R_{111}$ to $R_{118}$ are each independently selected from the group consisting of a hydrogen atom, a substituted or unsubstituted aryl group having 6 to 20 ring carbon atoms, a substituted or unsubstituted alkyl group having 1 to 6 carbon atoms, a substituted or unsubstituted alkylsilyl group having 3 to 30 carbon atoms, and a substituted or unsubstituted arylsilyl group having 6 to 60 ring carbon atoms, and any substituents of said substituent(s) are selected from the group consisting of a hydrogen atom, an aryl group having 6 to 20 ring carbon atoms, a heterocyclic group having 5 to 14 ring atoms, an alkyl group having 1 to 6 carbon atoms, an alkylsilyl group having 3 to 30 carbon atoms, an arylsilyl group having 6 to 60 ring carbon atoms, an alkoxy group having 1 to 30 carbon atoms, an aryloxy group having 6 to 30 ring carbon atoms, an alkylamino group having 2 to 30 carbon atoms, an arylamino group having 6 to 60 ring carbon atoms, an alkylthio group having 1 to 30 carbon atoms, and an arylthio group having 6 to 30 ring carbon atoms.

12. The compound according to claim 8, wherein $R_{11}$ to $R_{20}$ are not mutually bonded to form a cyclic structure;

$R_{111}$ to $R_{118}$ are not mutually bonded to form a cyclic structure; and $R_{11}$ to $R_{20}$ and $R_{111}$ to $R_{118}$ are each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms.

13. An organic-electroluminescence-device material comprising the compound according to claim 1.

14. An organic electroluminescence device comprising:
 an anode;
 a cathode; and
 one or more organic layers interposed between the anode and the cathode, wherein at least one of the organic layers comprises the compound according to claim 1.

15. Electronic equipment comprising the organic electroluminescence device according to claim 14.

* * * * *